(12) United States Patent
Berthelot et al.

(10) Patent No.: US 8,614,201 B2
(45) Date of Patent: Dec. 24, 2013

(54) HETEROCYCLIC AMIDES AS MODULATORS OF TRPA1

(75) Inventors: Didier Jean-Calude Berthelot, Antwerp (BE); Henricus Jacobus Maria Gijsen, Breda (NL); Mirko Zaja, München (DE); Jason Rech, San Diego, CA (US); Alec Lebsack, San Diego, CA (US); Bryan Branstetter, Oceanside, CA (US); Wei Xiao, San Diego, CA (US); J. Guy Breitenbucher, Escondido, CA (US)

(73) Assignee: Janssen Pharmaceutica NV, Beerse (BE)

( * ) Notice: Subject to any disclaimer, the term of this patent is extended or adjusted under 35 U.S.C. 154(b) by 151 days.

(21) Appl. No.: 13/375,833

(22) PCT Filed: Jun. 4, 2010

(86) PCT No.: PCT/US2010/037381
§ 371 (c)(1),
(2), (4) Date: Dec. 2, 2011

(87) PCT Pub. No.: WO2010/141805
PCT Pub. Date: Dec. 9, 2010

(65) Prior Publication Data
US 2012/0083474 A1 Apr. 5, 2012

Related U.S. Application Data

(60) Provisional application No. 61/184,589, filed on Jun. 5, 2009.

(51) Int. Cl.
| | | |
|---|---|---|
| A01N 57/00 | (2006.01) | |
| A61K 31/66 | (2006.01) | |
| A01N 43/36 | (2006.01) | |
| A61K 31/40 | (2006.01) | |
| A01N 43/66 | (2006.01) | |
| A61K 31/53 | (2006.01) | |
| A01N 43/40 | (2006.01) | |
| A61K 31/435 | (2006.01) | |
| A01N 43/54 | (2006.01) | |
| C07D 239/42 | (2006.01) | |
| C07D 401/04 | (2006.01) | |
| C07D 239/00 | (2006.01) | |
| C07D 239/02 | (2006.01) | |
| C07D 213/00 | (2006.01) | |
| C07C 303/00 | (2006.01) | |
| C07C 307/00 | (2006.01) | |
| C07C 309/00 | (2006.01) | |
| C07C 311/00 | (2006.01) | |

(52) U.S. Cl.
USPC ........... 514/117; 514/408; 514/241; 514/247; 514/277; 514/256; 544/242; 546/1; 564/80

(58) Field of Classification Search
USPC ............... 514/117, 408, 241, 247, 277, 256; 544/242; 546/1; 564/80
See application file for complete search history.

(56) References Cited

U.S. PATENT DOCUMENTS

| | | | |
|---|---|---|---|
| 4,788,196 | A | 11/1988 | Cross et al. |
| 4,806,536 | A | 2/1989 | Cross et al. |
| 6,645,939 | B1 | 11/2003 | Durette et al. |

FOREIGN PATENT DOCUMENTS

| | | |
|---|---|---|
| WO | WO 91 09849 A1 | 7/1991 |
| WO | WO 99 26921 A1 | 6/1999 |
| WO | WO 2006 063718 A1 | 6/2006 |

OTHER PUBLICATIONS

Agopyan et al "TRPV1 Receptors Mediate Particulate Matter-Induced Apoptosis" Am J Physiol Lung Cell Mol Physiol 2004 vol. 286 pp. L563-L572.
Agopyan et al "Vanilloid Receptor Activation by 2- and 10-μM Particles Induces Responses Leading to Apoptosis in Human Airway Epithelial Cells" Toxicol Appl Pharmacol 2003 vol. 192 pp. 21-35.
Andersson et al "Transient Receptor Potential A1 Is A Sencory Receptor for Multiple Products of Oxidative Stress" J Neurosci 2008 vol. 28 pp. 2485-2494.
Andrade et al Contractile Mechanisms Coupled to TRPA1 Receptor Activation in Rat Urinary Bladder Biochem Pharmacol 2006 vol. 72 pp. 104-114.
Andre et al "Cigarette Smoke-Induced Neurogenic Inflammation Is Mediated by α,β-Unsaturated Aldehydes and the TRPA1 Receptor in Rodents" J Clin Invest 2008 vol. 118 pp. 2574-2582.
Asai et al "Heat and Mechanical Hyperalgesia in Mice Model of Cancer Pain" Pain 2005 vol. 117 pp. 19-29.
Bagshawe et al "Antibody-Directed Enzyme Prodrug Therapy: A Review" Drug Dev Res 1995 vol. 34 pp. 220-230.
Bandell et al "Noxious Cold Ion Channel TRPA1 Is Activated by Pungentcompounds and Bradykinin" Neuron 2004 vol. 41 pp. 849-857.
Bang et al "Transient Receptor Potential A1 Mediates Acetaldehyde-Evoked Pain Sensation" Eur J Neurosci 2007 vol. 26 pp. 2516-2523.

(Continued)

Primary Examiner — Kendra D Carter

(57) ABSTRACT

Certain heterocyclic amide compounds are described. The compounds may be used in pharmaceutical compositions and methods for treating disease states, disorders, and conditions mediated by TRPA1 activity, such as pain, arthritis, itch, cough, asthma, or inflammatory bowel disease.

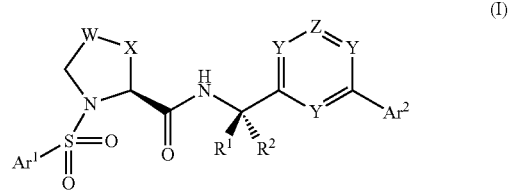

(I)

17 Claims, No Drawings

(56) References Cited

OTHER PUBLICATIONS

Barton et al "Attenuation of Experimental Arthritis in TRPV1R Knockout Mice" Exp Mol Pathol 2006 vol. 81(2) pp. 166-170.
Bautista et al "TRPA1 Mediates the Inflammatory Actions of Environmental Irritants and Proalgesic Agents" Cell 2006 vol. 124 pp. 1269-1282.
Bautista et al "Pungent Products From Garlic Activate the Sensory Ion Channel TRPA1" PNAS 2005 vol. 102(34) pp. 12248-12252.
Berge et al "Pharmaceutical Salts" Journal of Pharmaceutical Sciences 1977 vol. 66(1) pp. 1-19.
Bertolini et al "A New Rational Hypothesis for the Pharmacophore of the Active Metabolite of Leflunomide, A Potent Immunosuppressive Drug" J Med Chem 19976 vol. 40 pp. 2011-2016.
Bessac et al "Breathtaking TRP Channels: TRPA1 and TRPV1 in Airway Chemosensation and Reflex Control" Physiology 2008 vol. 23 pp. 360-370.
Bessac et al "Transient Receptor Potential Ankyrin 1 Antagonists Blocks the Noxious Effects of Toxic Industrial Isocyanates and Tear Gases" FASEB J 2008 vol. 23 pp. 1102-1114 Published Ahead of Print Nov. 26, 2008 E-Pub.
Bodor et al "Novel Approaches to the Design of Safer Drugs: Soft Drugs and Site-Specific Chemical Delivery Systems" Adv Drug Res 1984 vol. 13 pp. 224-.
Bolcskei et al "Investigation of the Role of TRPV1 Receptors in Acute and Chronic Nociceptive Processes Using Gene-Deficient Mice" Pain 2005 vol. 117(3) pp. 368-376.
Brone etal "Tear Gasses Cn, Cr, and Cs Are Potent Activators of the Human TRPA1 Recepto" Toxicol & Appl Pharmacol 2008 vol. 231 pp. 150-156.
Bundgaard et al Design of Prodrugs Ed. H Bundgaard Elsevier 1985.
Chan et al "Sensory Fibres Expressing Capsaicin Receptor TRPV1 in Patients With Rectal Hypersensitivity and Faecal Urgency" Lancet 2003 vol. 361 pp. 385-391.
Corey et al "TRPA1 Is a Candidate for the Mechanosensitive Transduction Channel of Vertebrate Hair Cells" Nature 2004 vol. 432 pp. 723-730.
Dinis et al "Anandamide-Evoked Activation of Vanilloid Receptor 1 Contributes to the Development of Bladder Hyperreflexia and Nociceptive Transmission to Spinal Dorsal Horn Neurons in Cystitis" J Neurosci 2004 vol. 24(50) pp. 11253-11263.
Diogenes et al "NGF Up-Regulates TRPA1: Implications for Orofacial Pain" J Dent Res 2007 vol. 86(6) pp. 550-555.
Du et al "Differential Expression Profile of Cold (TRPA1) and Cool (TRPM8) Receptors in Human Urogenital Organ" Urology 2008 vol. 72 pp. 450-455.
Escalera et al "TRPA1 Mediates the Noxious Effects of Natural Sesquiterpene Deterrents" JBC 2008 vol. 283(85) pp. 24136-24144.
Fleisher etal "Improved Oral Drug Delivery: Solubility Limitations Overcome by the Use of Prodrug" Adv Drug Delivery Rev 1996 vol. 19 pp. 115-130.
Frederick et al "Incresed TRPA1, TRPM8, and TRPV2 Expression in Dorsal Root Ganglia by Nerve Injury" Biochem Biophys Res Commun 2007 vol. 358 pp. 1058-1064.
Fujita et al "Methyl P-Hydroxybenzoate Causes Pain Sensation Through Activation of TRPA1 Channels" Br J Pharmacol 2007 vol. 151 pp. 153-160.
Garcia-Anoveros et al "TRPA1" Handbook of Experimental Pharmacology Springer Verlag Berlin DE 2007 vol. 179 pp. 347-362.
Geppetti et al "Activation and Sensitisation of the Vanilloid Receptor: Role in Gastrointestinal Inflammation and Function" Br J Pharmacol 2004 vol. 141 pp. 1313-1320.
Ghilardi et al "Selective Blockade of the Capsaicin Receptor TRPV1 Attenuates Bone Cancer Pain" J Neurosci 2005 vol. 25(12) pp. 3126-3131.
Goadsby et al "Post-Triptan Era for the Treatment of Acute Migraine" Curr Pain Headache Reports 2004 vol. 8 pp. 393-398.
Gratzke et al "Transient Receptor Potential A1 (TRPA1) Activity in the Human Urethra—Evidence for a Functional Role of TRPA1 in the Outflow Region" Eur Urology 2009 vol. 44 pp. 696-704 EPUB Apr. 30, 2008.

Honore et al "A-425619 [1-Isoquinolin-5-Yl-3-(4-Trifluoromethyl-Benzyl)-Urea], A Novel Transient Receptor Potential Type V1 Receptor Antagonist, Relieves Pathophysiological Pain Associates With Inflammation and Tissue Injury in Rats" J Pharmacol Exp Ther 2005 vol. 314 pp. 410-421.
Jaquemar et al "An Ankyrin-Like Protein With Transmembrane Domains Is Speficically Lost After Oncogenic Transformation of Human Fibroblasts" J Bjol Chem 1999 vol. 274(11) pp. 7325-7333.
Jordt et al "Mustard Oils and Cannabinoids Excite Sensory Nerve Fibres Through the TRP Channel ANKTM1" Nature 2004 vol. 427 pp. 260-265.
Kimball et al "Vanilloid Receptor 1 Antagonists Attenuate Disease Severity in Dextran Sulphae Sodium-Induced Colitis in Mice" Neurogastroenterol Motil 2004 vol. 16 pp. 811-818.
Kwan et al "TRPA1 Contributes to Cold, Mechanical and Chemical Nociception But Is Not Essential for Hair-Cell Transduction" Neuron 2006 vol. 50 pp. 277-289.
Lalloo et al "Capsazepine Inhibits Cough Induced by Capsaicin and Citric Acid But Not by Hypertonic Saline in Guinea Pig" J App Physiol 1995 vol. 79(4) pp. 1082-1087.
Larsen et al Design and Application of Prodrugs Drug Design and Development Krogsgaard-Larsen et al. Eds. Harwood Academic Publishers 1991.
Matta et al "General Anesthetics Activate a Nociceptive Ion Channel to Enhance Pain and Inflammation" PNAS 2008 vol. 105(25) pp. 8784-8789.
McNamara et al "TRPA1 Mediates Formalin-Induced Pain" PNAS 2007 vol. 104(33) pp. 13525-13530.
Menendez et al #5826 Zileuton Improves Quality of Life in Moderante and Severe Asthmatics Neurosci Lett 2005 vol. 393(1) pp. 70-73.
Nagata et al "Nociceptor and Hair Cell Transducer Properties of TRPA1, A Channel for Pain and Hearing" J Neurosci 2005 vol. 25(16) pp. 4052-4061.
Namer et al "TRAPA1 and TRPMB Activation in Humans: Effects of Cinnameldehyde and Menthol" Neuroreport 2005 vol. 16(9) pp. 955-959.
Obata et al "TRPA1 Induced in Sensory Neurons Contributes to Cold Hyperalgesia After Inflammation and Nerve Injury" J Clin Invest 2005 vol. 115(9) pp. 2393-2401.
Pomonis et al "N-(4-Tertiarybutylphenyl)-4-(3-Cholorphyridin-2-Yl)Tetrahydropyrazine-1(2H)-Carbox-Amide (BCTC), A Novel, Orally Effective Vanilloid Receptor 1 Antagonist With Analgesic Properties: II. In Vivo Characterization in Rat Models of Inflammatory and Neuropathic Pain" J Pharmacol Exp Ther 2003 vol. 306(1) pp. 387-393.
Robinson et al "Discovery of the Hemifumarate and (A-$_L$-Alanyloxy)Methyl Ether as Prodrugs of an Antirheumatic Oxindole: Prodrugs for the Enolic OH Group" J Med Chem 1996 vol. 39 pp. 10-18.
Sanchez et al "Expression of the Transient Receptor Potential Vanilloid 1 (TRPV1) in LNC$_A$P and PC-3 Prostate Cancer Cells and in Human Prostate Tissue" Eur J Pharmacol 2005 vol. 515 pp. 20-27.
Sculptoreanu et al "Protein Kinase C Contributes to Abnormal Capsaicin Response in Drg Neurons From Cats With Feline Interstitial Cystitis" Neurosci Lett 2005 vol. 381 pp. 42-46.
Shan et al "Prodrug Strategies Based on Intramolecular Cyclization Reactions" J Pharm Sci 1997 vol. 86(7) pp. 765-767.
Stahl et al Handbook of Pharmaceutical Salts Propeties Selection and Use Stahl and Wermuth Eds Wiley-VCH-VCHA Zurich 2002.
Story et al "ANKTM1, A TRP-Like Channel Expressed in Nociceptive Neurons, Is Activated by Cold Temperatures" Cell 2003 vol. 112 pp. 819-829.
Streng et al "Distribution and Function of the Hydrogen Sulfide-Sensitive TRPA1 Ion Channel in Rat Urinary Bladder" Eur Urology 2008 vol. 53 pp. 391-400.
Szabo et al "Role of Transient Receptor Potential Vanilloid 1 Receptors in Adjuvant-Induced Chronic Arthritis: In Vivo Study Using Gene-Deficient Mice" J Pharmacol Exp Ther 2005 vol. 314 pp. 111-119.

(56) References Cited

OTHER PUBLICATIONS

Taylor Clark et al "Relative Contributions of TRPA1 and TRPV1 Channels in the Activation of Vagal Bronchopulmonary C-Fibres by the Endogenous Autacoid 4-Oxononenal" J Physiol 2008 vol. 586 pp. 3447-3459.

Trevisani et al "4-Hydroxynonenal, An Endogenous Aldehyde, Causes Pain and Neurogenic Inflammation Through Activation of the Irritant Receptor TRPA1" PNA 2007 vol. 104 (33) 13519-13524.

Wade et al "Synthesis of Imidazo[1,5-C]Pyrimidine Derivatives [1]" J Heterocycli Chem 1986 vol. 23 pp. 981-986.

Walker et al "The VR1 Antagonist Capsazepine Reverses Mechanical Hyperalgesia in Models of Inflammatory and Neuropathic Pain" J Pharmacol Exp Ther 2003 vol. 304(1) pp. 56-62.

Yang et al "Transient Receptor Potential Anjyrin-1 Participates in Visceral Hyperalgesia Following Experimental Colitis" Neurosci Lett 2008 vol. 440 pp. 237-241.

Yiangou et al "Vanilloid Receptor 1 Immunoreactivity in Inflamed Human Bowel" Lancet 2001 vol. 357 pp. 1338-1339.

International Search Report for Corresponding PCT/US2010/037381 Mailed on Sep. 28, 2010.

US 8,614,201 B2

HETEROCYCLIC AMIDES AS MODULATORS OF TRPA1

CROSS-REFERENCE TO RELATED APPLICATIONS

This application is a national phase of International Application No. PCT/US2010/037381 filed Jun. 4, 2010 and claims benefit of priority under 35 U.S.C. §119(e) of U.S. Provisional Application No. 61/184,589 filed on Jun. 5, 2009.

FIELD OF THE INVENTION

The present invention relates to certain heterocyclic amide compounds, pharmaceutical compositions containing them, methods of making them, and methods of using them for the modulation of the TRPA1 receptor and for the treatment of disease states, disorders, and conditions mediated by TRPA1 receptor activity.

BACKGROUND OF THE INVENTION

TRPA1 (ANKTM1, p120) is a non-selective cation channel that belongs to the Transient Receptor Potential (TRP) superfamily. TRPA1 was first identified as a transformation sensitive mRNA in cultured human lung fibroblasts (Jaquemar et al., *J Biol. Chem.*, 1999, 274, 7325-7333). Subsequent studies indicated that TRPA1 was also highly expressed in sensory neurons of the dorsal root, trigeminal and nodose ganglia, and in hair cells of the inner ear (Story et al., *Cell*, 2003, 112, 819-829; Corey et al., *Nature*, 2004, 432, 723-730; Nagata et al., *J. Neurosci.*, 2005, 25, 4052-4061; Diogenes et al., *J Dent Res.*, 2007, 86, 550-555). In sensory neurons, TRPA1 expression is most prevalent in small diameter neurons where it co-localizes with markers of peptidergic nociceptors such as TRPV1, CGRP and substance P (Story et al., supra; Bautista et al., *PNAS*, 2005, 102, 12248-12252; Nagata et al., *J Neurosci.*, 2005, 25, 4052-4061; Diogenes et al., *J Dent Res.*, 2007, 86, 550-555).

The finding that TRPA1 is expressed in small diameter nociceptors has led to the suggestion that this channel may be involved in pain sensation. Indeed a number of additional observations support this suggestion. For example, TRPA1 expression can be increased by inflammatory mediators such as NGF (Diogenes et al., *J Dent Res.*, 2007, 86, 550-555) and following nerve injury or inflammation (Obata et al., *J Clin Invest.* 2005, 115, 2393-2401; Frederick et al., *Biochem Biophys Res Commun.*, 2007, 358, 1058-1064). Bradykinin, a potent algogenic peptide released at sites of injury and inflammation, can activate TRPA1 via G-protein coupled BK2 receptors (Bandell et al., *Neuron*, 2004, 41, 849-857). In addition, TRPA1 can be activated by a range of pungent or irritant compounds that can elicit pain in animals and humans, such as mustard oil (AITC), cinnamaldehyde, acreolin, allicin, and formalin (Bandell et al., supra; Namer et al., *Neuroreport*, 2005, 16, 955-959; Bautista et al., *Cell*, 2006, 124, 1269-1282; Fujita et al., *Br J. Pharmacol.*, 2007, 151, 153-160; McNamara et al., *PNAS*, 2007, 104, 13525-13530). TRPA1 may also be activated by noxious cold (Bandell et al., *Neuron*, 2004, 41, 849-857; Jordt et al., *Nature*, 2004, 427, 260-265; Nagata et al., *J Neurosci.*, 2005, 25, 4052-4061). In behavioral studies, intra-thecal TRPA1 anti-sense oligodeoxynucleotide suppressed inflammation and nerve injury-induced cold allodynia (Obata et al., *J Clin Invest.*, 2005, 115, 2393-2401) and mustard oil induced pain behaviors and bradykinin-induced acute pain and hyperalgesia are abolished in TRPA1−/− mice (Bautista et al., supra; Kwan et al., *Neuron*, 2006, 50, 277-289).

In a formalin-induced pain model, TRPA1 has been shown to be the principal site of formalin's pain-producing action in vivo, and activation of TRPA1 underlies the physiological and behavioral responses associated with this model of pain. Formalin induced activation of the TRPA1 channel has been shown to be attenuated by TRPA1 antagonists (McNamara et al., *PNAS*, 2007, 104, 13525-13530).

Treatment with cigarette smoke extracts (CSE) increased $Ca^{2+}$ influx in TRPA1-transfected cells, and promoted neuropeptide release from isolated guinea pig airway tissue. Furthermore, the effect of CSE on $Ca^{2+}$ influx in dorsal root ganglion neurons was abolished in TRPA1-deficient mice. These data suggest a role for TRPA1 in the pathogenesis of CSE-induced diseases such as Chronic obstructive pulmonary disease, or COPD (André et al., *J Clin Invest.*, 2008, 118, 2574-2582).

In addition, TRPA1 activation by various oxidants and products of lipid peroxidation, such as 4-hydroxynonenal and 4-oxononenal, is suggested to be a key mechanism that links oxidative stress to nocifensive responses in the airway (Taylor-Clark et al., *J. Physiol.*, 2008, 586, 3447-3459; Trevisani et al., *PNAS*, 2007, 104, 13519-13524; Andersson et al., *J. Neurosci.*, 2008, 28, 2485-2494). TRPA1 is discussed to represent a new target for the development of drugs that suppress neuronal hypersensitivity in individuals with airway disease such as asthma, chronic cough and reactive airway dysfunction syndrome (Bessac and Jordt, *Physiology*, 2008, 23, 360-370).

A recent study showed that a variety of the known electrophilic tear gasses used in the past and present as riot control or incapacitating agents, are potent activators of the human TRPA1 channel (Brone et al., *Toxicol & Appl Pharmacol.*, 2008, 231, 150-156; Bessac et al., *FASEB J.*, 2008, Nov. 26 e-pub). Thus antagonism of the TRPA1 channel could have use for military and police applications as defense against such agents.

TRPA1 is also expressed in bladder and urethra urothelium, epithelium and nerve fibers of the urothelium, suburothelial space, muscle layers and around blood vessels (Du et al., *Urology*, 2008, 72, 450-455; Andrade et al., *Biochem Pharmacol.*, 2006, 72, 104-114; Gratzke et al., *Eur Urology*, 2008, Apr. 30 e-pub; Streng et al., *Eur Urology*, 2008, 53, 391-400). TRPA1 expression is increased in bladder mucosa from patients with bladder outlet obstruction (Du et al., *Urology*, 2008, 72, 450-455). Activation of TRPA1 causes increased micturition frequency and reduced voiding volume (Streng et al., supra). Activation of TRPA1 in the bladder by reactive metabolites of cyclophosphamide (e.g., acrolein) may be responsible for cystitis that sometimes accompanies the use of chemotherapeutic agents (Bautista et al., supra). TRPA1 is also expressed in colonic afferents, is upregulated following induction of experimental colitis, and TRPA1 anti-sense oligonucleotides suppressed colitis-induced hyperalgesia to colonic distension (Yang et al., *Neurosci Lett.*, 2008, 440, 237-241). These data suggest a role for TRPA1 in the pathogenesis of visceral pain and dysfunction, such as bladder instability, urinary incontinence, cystitis and colitis.

TRPA1 may also be activated by general anesthetics such as isoflurane (Matta et al., *PNAS*, 2008, 105, 8784-8789), suggesting a possible role for TRPA1 antagonists in post-surgical pain. In addition, TRPA1 can be activated by a variety of skin sensitizers, natural products (Escalera et al., *JBC*, 2008, 283, 24136-24144) and ethanol metabolites (Bang et al., *Eur J. Neurosci.*, 2007, 26, 2516-2523), suggesting roles for TRPA1 antagonists in the treatment of contact dermatitis, and the symptoms of "hangover" (i.e., headache, nasal congestion, facial flushing).

Certain diamine-substituted pyridines are described in the following publications: Intl. Pat. Appl. Publ. WO 1991/09849 (Upjohn, Jul. 11, 1991); Intl. Pat. Appl. Publ. WO 2006/063718 (Hoffmann La Roche, Jun. 22, 2006); U.S. Pat. No. 4,788,196 (Pfizer, Nov. 29, 1988); and U.S. Pat. No. 4,806,536 (Pfizer, Feb. 21, 1989). Certain β-Alanine derivatives are disclosed in U.S. Pat. No. 6,645,939 (Merck & Co., Inc.).

Still further, certain compounds were obtained from a third party. The compounds are identified herein as Examples 189 to 225 and 286 to 316.

However, there remains a need for potent histamine TRPA1 receptor modulators with desirable pharmaceutical properties. Certain heterocyclic amide derivatives have been found in the context of this invention to have TRPA1 receptor-modulating activity.

SUMMARY OF INVENTION

Certain heterocyclic amides have now been found to have TRPA1-modulating activity. In particular, the invention is directed to the general and preferred embodiments defined, respectively, by the independent and dependent claims appended hereto, which are incorporated by reference herein.

Thus, in one general aspect, the invention relates to compounds of Formula (I):

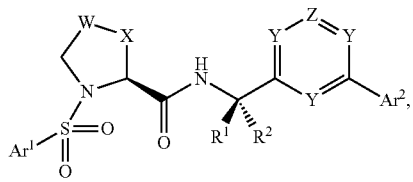

(I)

wherein,
$Ar^1$ is:
  i) phenyl substituted with 0, 1, 2 or 3 substituents $R^a$; or
  ii) a 5- or 6-membered monocyclic aromatic heterocycle ring optionally substituted with one or two substituents $R^a$;
    where each $R^a$ is independently halo, —$C_{1-4}$alkyl, —$OC_{1-4}$alkyl, —CN, —$CF_3$, —$OCF_3$, —$NO_2$, —$C(O)C_{1-4}$alkyl or —$CO_2H$;
$Ar^2$ is:
  i) phenyl substituted with 0, 1, 2 or 3 substituents $R^b$;
    where each $R^b$ is independently halo, —$C_{1-4}$alkyl, —$C(O)NR^cR^d$, —$OC_{1-4}$alkyl, —$OC_{0-4}$alkylCF$_3$, —CN, —$CF_3$, —$OCF_2H$, —$NO_2$, —$NR^cR^d$, —$S(O)_{0-2}C_{1-4}$alkyl, —$C(O)C_{1-4}$alkyl, —$S(O)(O)NH_2$, —$(CH_2)_{0-2}$-morpholinyl, piperidin-1-yl or piperazinyl, said piperazinyl optionally substituted with a methyl;
  ii) pyridyl substituted with 0, 1 or 2 substituents $R^e$,
    where each $R^e$ is independently selected from halo, —$C_{1-4}$alkyl, —$OC_{1-4}$alkyl, —$CF_3$, —$NR^cR^d$ or 4-morpholinyl; or
  iii) a bicyclic 9- or 10-membered aromatic heterocycle optionally substituted with 1 substituent $R^f$;
    where $R^f$ is —$C_{1-4}$alkyl;
$R^c$ and $R^d$ are each independently selected from H or —$C_{1-4}$alkyl;
W is —$CR''H$— or —$CF_2$—;

X is —$CR''H$—;
or W and X may each be a CH group linked together by a double bond;
$R''$ is H or —OH; or
two adjacent $R''$ moieties taken together form —$CH_2$—;
$R^1$ and $R^2$ are each independently H or —$C_{1-4}$alkyl;
each Y is independently CH or N;
Z is $CR^g$;
$R^g$ is
  i) H, —$C_{1-4}$alkyl, —$CF_3$, —$OR^z$, —$N(CH_3)_2$ or —$NR^hR^i$;
    where $R^h$ is selected from H, 2-hydroxy-propyl, 2-hydroxy-2-methyl-propyl, —$C_{1-4}$alkyl-N(CH$_3$)$_2$, —$C_{1-4}$alkyl-pyridyl, —$C_{1-4}$alkyl-phenyl, 1-pyridinyl-ethyl, 1-methyl-pyrrolidin-3-ylmethyl or —$C_{1-4}$alkyl-piperidinyl, said piperidinyl optionally substituted with —$C_{1-4}$alkyl;
      where $R^z$ is —$C_{1-4}$alkyl, —$C_{1-4}$alkylCF$_3$ or —$C_{1-4}$alkyl-heterocycloalkyl;
  ii) 1-pyrrolidinyl optionally substituted with —$C_{1-4}$alkyl or —$NR^kR^1$;
  iii) piperazinyl optionally substituted with —$C_{2-5}$alkyl, —$OC_{1-4}$alkyl, —$C_{1-4}$alkyl-pyridyl, —$C_{0-4}$alkyl-1-methyl-piperidin-4-yl, —$C_{0-4}$alkylNR$^k$R$^i$ or —$C_{0-4}$alkyl-phenyl, said phenyl optionally substituted with one or two substituents selected from the group consisting of Cl, Br, I, —$OCF_3$, and —$C_{1-4}$alkyl or said one substituent is F bound at the 2-position;
  iv) phenyl optionally substituted with —$CF_3$; or
  v) pyridyl;
  vi) 1-piperidinyl;
$R^k$ is H, —$C_{1-4}$alkyl or —$C(O)_{1-2}C_{1-4}$alkyl; and
$R^i$ is H or $CH_3$;
with the proviso that when
$Ar^1$ is 4-fluoro-phenyl;
$Ar^2$ is 4-trifluoromethyl-phenyl;
$R^1$ and $R^2$ are each H;
W and X are each —$CH_2$—;
and the two Y's adjacent to Z are N with the third being C;
then $R^g$ cannot be [4-(2-fluoro-phenyl)-piperazin-1-yl].

The invention also relates to pharmaceutically acceptable salts of compounds of Formula (I), pharmaceutically acceptable prodrugs of compounds of Formula (I) and pharmaceutically active metabolites of compounds of Formula (I). In certain preferred embodiments, the compound of Formula (I) is a compound selected from those species described or exemplified in the detailed description below.

In a further general aspect, the invention relates to pharmaceutical compositions each comprising: (a) a therapeutically effective amount of at least one chemical entity selected from compounds of Formula (II), pharmaceutically acceptable salts of compounds of Formula (II), pharmaceutically acceptable prodrugs of compounds of Formula (II), and pharmaceutically active metabolites of compounds of Formula (II):

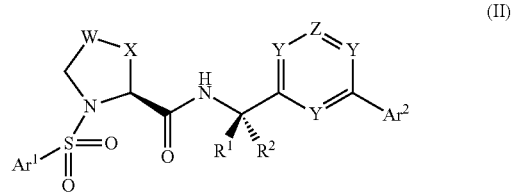

(II)

wherein,

Ar$^1$ is:
  i) phenyl substituted with 0, 1, 2 or 3 substituents R$^a$; or
  ii) a 5- or 6-membered monocyclic aromatic heterocycle ring optionally substituted with one or two substituents R$^a$;
    where each R$^a$ is independently halo, —C$_{1-4}$alkyl, —OC$_{1-4}$alkyl, —CN, —CF$_3$, —OCF$_3$, —NO$_2$, —C(O)C$_{1-4}$alkyl or —CO$_2$H;

Ar$^2$ is:
  i) phenyl substituted with 0, 1, 2 or 3 substituents R$^b$;
    where each R$^b$ is independently halo, —C$_{1-4}$alkyl, —C(O)NR$^c$R$^d$, —OC$_{1-4}$alkyl, —OC$_{0-4}$alkylCF$_3$, —CN, —CF$_3$, —OCF$_2$H, —NO$_2$, —NR$^c$R$^d$, —S(O)$_{0-2}$C$_{1-4}$alkyl, —C(O)C$_{1-4}$alkyl, S(O)(O)NH$_2$, —(CH$_2$)$_{0-2}$-morpholinyl, piperidin-1-yl, piperazinyl, said piperazinyl optionally substituted with a methyl, or two R$^b$ substituents on adjacent carbon atoms taken together form —O(CH$_2$)$_{1-2}$O—;
  ii) pyridyl substituted with 0, 1 or 2 substituents R$^e$;
    where each R$^e$ is independently selected from halo, —C$_{1-4}$alkyl, —OC$_{1-4}$alkyl, —CF$_3$, —NR$^c$R$^d$ or 4-morpholinyl; or
  iii) a bicyclic 9- or 10-membered aromatic heterocycle optionally substituted with 1 substituent R$^f$;
    where R$^f$ is —C$_{1-4}$alkyl;

R$^c$ and R$^d$ are each independently selected from H or —C$_{1-4}$alkyl;
W is —CR″H— or —CF$_2$—;
X is —CR″H—;
or W and X may each be a CH group linked together by a double bond;
R″ is H or —OH; or
two adjacent R″ moieties taken together form —CH$_2$—;
R$^1$ and R$^2$ are each independently H or —C$_{1-4}$alkyl;
each Y is independently CH or N;
Z is CR$^g$;
R$^g$ is
  i) H, —C$_{1-4}$alkyl, —CF$_3$, —OR$^z$ or —NR$^h$R$^i$;
    where R$^h$ is selected from
      a) H, —C$_{0-4}$alkylCF$_3$, —C$_{1-4}$alkyl-N(CH$_3$)$_2$, 1-hydroxymethyl-2-phenyl-ethyl, —C$_{1-4}$alkyl-3H-indol-3yl, indan-1yl, saturated cycloalkyl or —C$_{1-4}$alkyl-monocyclic heteroaryl ring;
      b) —C$_{1-5}$alkyl optionally substituted with OH;
      c) —C$_{1-4}$alkyl-heterocycloalkyl, said heterocycloalkyl optionally substituted with —C$_{1-4}$alkyl; or
      d) —C$_{0-4}$alkyl-phenyl, said phenyl optionally substituted with one or two R$^j$ moieties;
        where each R$^j$ is independently halo, —OC$_{1-4}$alkyl, —S(O)(O)NH$_2$ or 4-methyl-piperazine-1-carbonyl;
    R$^z$ is —C$_{1-4}$alkyl, —C$_{1-4}$alkylCF$_3$ or —C$_{1-4}$alkyl-heterocycloalkyl;
  ii) 1-pyrrolidinyl optionally substituted with a moiety selected from the group consisting of —NR$^k$R$^i$ and —C$_{1-4}$alkyl, said —C$_{1-4}$alkyl optionally substituted with —OH;
  iii) 1-piperidinyl optionally substituted with —C$_{1-4}$alkyl, —C(O)NH$_2$, —CO$_2$C$_{1-4}$alkyl or —C$_{0-4}$alkyl-phenyl;
  iv) piperazinyl optionally substituted with —C$_{1-5}$alkyl, —OC$_{1-4}$alkyl, —C$_{0-4}$-alkylpyridyl, —C$_{0-4}$alkyl-1-methyl-piperidin-4-yl, —C$_{0-4}$alkylNR$^k$R$^i$ or —C$_{0-4}$-alkyl-phenyl, said phenyl optionally substituted with one or two R$^T$ substituents;
    where each R$^T$ substituent is selected from the group consisting of halo, —OCF$_3$, —CO$_2$C$_{1-4}$alkyl, —C(O)CH$_3$ and —C$_{0-4}$alkylNR$^k$R$^i$, or two R$^T$ substituents on adjacent carbon atoms taken together form —O(CH$_2$)$_{1-2}$O—;
  v) phenyl optionally substituted with CF$_3$, pyridyl or 3,4-dihydro-1H-isoquinolin-2-yl;
  vi) pyridyl;
  vii) 3,4-dihydro-1H-isoquinolin-2-yl;
  viii) [1,4]diazepane-yl optionally substituted with —C$_{1-4}$alkyl; or
  ix) morpholin-yl;

R$^k$ is H, —C$_{1-4}$alkyl or —C(O)$_{1-2}$C$_{1-4}$alkyl;
R$^i$ is H or C$_{1-4}$alkyl; and
pharmaceutically acceptable salts of compounds of Formula (II), and
pharmaceutically acceptable prodrugs of compounds of Formula (II);
and (b) a pharmaceutically acceptable excipient.

In another aspect, embodiments of the invention are useful as TRPA1 modulators. Thus, the invention is directed to a method for modulating TRPA1 activity, comprising exposing TRPA1 to a therapeutically effective amount of at least one chemical entity selected from compounds of Formula (II), pharmaceutically acceptable salts of compounds of Formula (II), pharmaceutically acceptable prodrugs of compounds of Formula (II), and pharmaceutically active metabolites of compounds of Formula (II). Embodiments of this invention modulate TRPA1 activity.

In another general aspect, the invention is directed to a method of treating a subject suffering from or diagnosed with a disease, disorder, or medical condition (collectively, "indications") mediated by TRPA1 activity, comprising administering to the subject in need of such treatment a therapeutically effective amount of a compound of Formula (II), a pharmaceutically acceptable salt of a compound of Formula (II), pharmaceutically acceptable prodrug of a compound of Formula (II), or pharmaceutically active metabolite of a compound of Formula (II). In certain preferred embodiments of the inventive method, the disease, disorder, or medical condition is selected from: pain (acute, chronic, inflammatory, or neuropathic pain); itch or various inflammatory disorders; inner ear disorders; fever and other conditions or disorders of thermoregulation; tracheobronchial and diaphragmatic dysfunction; gastrointestinal and urinary tract disorders; chronic obstructive pulmonary disease; incontinence; and disorders associated with reduced blood flow to the CNS or CNS hypoxia.

Preferred embodiments, features, and advantages of the invention will be apparent from the following detailed description and through practice of the invention.

DETAILED DESCRIPTION OF INVENTION AND ITS PREFERRED EMBODIMENTS

For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Such groups may contain saturated or unsaturated Carbon atoms within the chain. Examples of alkyl groups include methyl (Me, which also may be structurally depicted by / symbol), ethyl (Et), n-propyl, isopropyl, butyl, isobutyl, sec-butyl, tert-butyl (tBu), pentyl, isopentyl, tert-pentyl, hexyl, isohexyl, prop-2-enyl, prop-2-ynyl, and groups that in light of the ordinary skill in the art and the teachings provided herein would be considered equivalent to any one of the foregoing examples.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

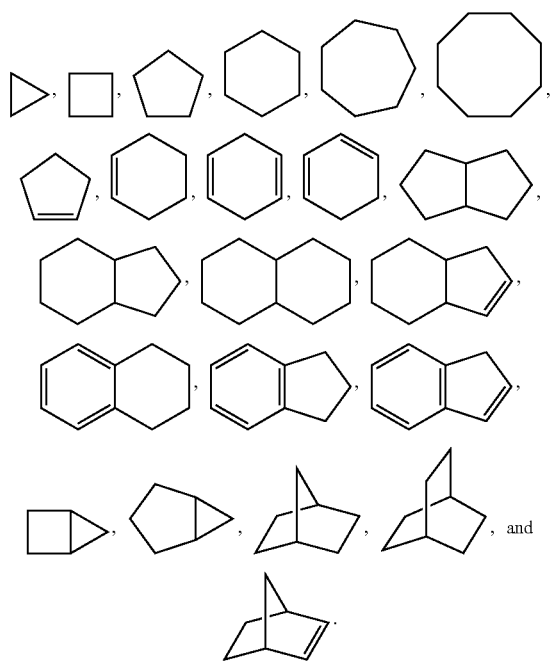

A "heterocycloalkyl" refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members. Illustrative entities, in the form of properly bonded moieties, include:

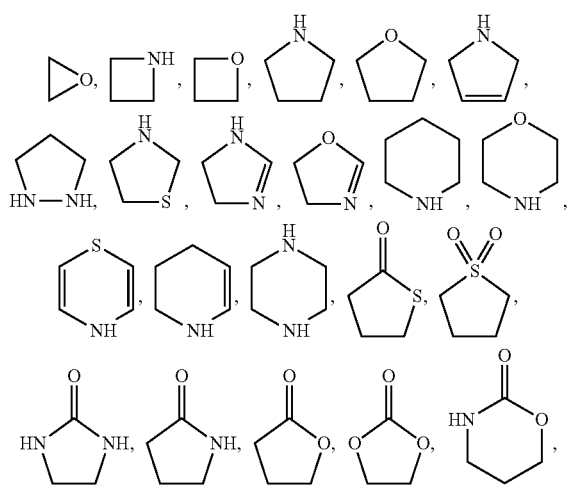

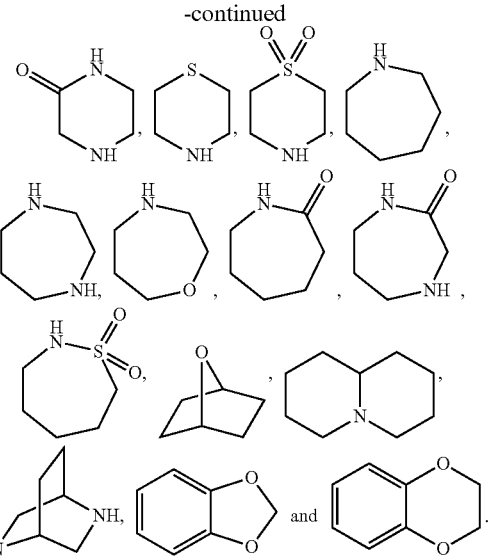

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

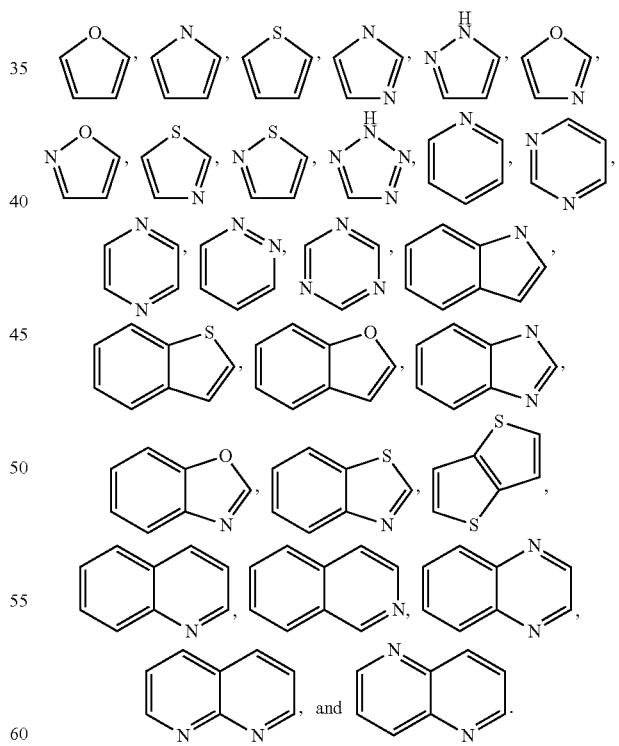

Those skilled in the art will recognize that the species of cycloalkyl, heterocycloalkyl, and heteroaryl groups listed or illustrated above are not exhaustive, and that additional species within the scope of these defined terms may also be selected.

The term "halogen" represents chlorine, fluorine, bromine, or iodine. The term "halo" represents chloro, fluoro, bromo, or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

Additionally, any formula given herein is intended to refer also to hydrates, solvates, and polymorphs of such compounds, and mixtures thereof, even if such forms are not listed explicitly. Certain compounds of Formulas (I) and (II), or pharmaceutically acceptable salts of compounds of Formulas (I) and (II), may be obtained as solvates. Solvates include those formed from the interaction or complexation of compounds of the invention with one or more solvents, either in solution or as a solid or crystalline form. In some embodiments, the solvent is water and then the solvates are hydrates. In addition, certain crystalline forms of compounds of Formulas (I) and (II), or pharmaceutically acceptable salts of compounds of Formulas (I) and (II), may be obtained as co-crystals. In certain embodiments of the invention, compounds of Formulas (I) or (II) may be obtained in a crystalline form. In other embodiments, pharmaceutically acceptable salts of compounds of Formulas (I) or (II) may be obtained in a crystalline form. In still other embodiments, compounds of Formulas (I) or (II) may be obtained as a polymorphic form, in one of several polymorphic forms, as a mixture of crystalline forms, or as an amorphous form. In other embodiments, compounds of Formulas (I) or (II) convert in solution between one or more crystalline forms and/or polymorphic forms.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Reference to a chemical entity herein stands for a reference to any one of: (a) the actually recited form of such chemical entity, and (b) any of the forms of such chemical entity in the medium in which the compound is being considered when named. For example, reference herein to a compound such as R—COOH, encompasses reference to any one of, for example, R—COOH$_{(s)}$, R—COOH$_{(sol)}$, and R—COO$^-_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO$^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI:27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $^+H_3NCH_2COO^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2H$, $^3H$, $^{11}C$, $^{13}C$, $^{14}C$, $^{15}N$, $^{18}O$, $^{17}O$, $^{32}P$, $^{33}P$, $^{35}S$, $^{18}F$, $^{36}Cl$, and $^{125}I$, respectively. Such isotopically labelled compounds are useful in metabolic studies (preferably with $^{14}C$), reaction kinetic studies (with, for example $^2H$ or $^3H$), detection or imaging techniques, such as positron emission tomography (PET) or single-photon emission computed tomography (SPECT), including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $Ar^1$, $Ar^2$, $R^a$, $R^b$, $R^c$, $R^d$, and $R^f$, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $Ar^1$, $Ar^2$, $R^a$, $R^b$, $R^c$, $R^d$, and $R^f$ and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies n≤N≤m, with m>n.

Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

In some embodiments of Formulas (I) and (II), each instance of Y and Z is CH. In some embodiments, Z is $CR^g$ and two instances of Y are N. In some embodiments, Z is $CR^g$, two instances of Y are N, and $R^g$ is $NR^hR^i$. In further embodiments, Z is $CR^g$ and one instance of Y is N. In yet further embodiments, Z is $CR^g$, one instance of Y is N, and $R^g$ is $NR^hR^i$.

In some embodiments of Formulas (I) and (II), W and X are each CH. In some embodiments, W is —$CF_2$—. In some embodiments, W and X are each —$CH_2$—.

In some embodiments of Formulas (I) and (II), $R^1$ and $R^2$ are H.

In some embodiments of Formulas (I) and (II), $R^g$ is $NR^hR^1$.

In some embodiments of Formulas (I) and (II), $R^b$ is selected from —$CF_3$, —$OCF_3$, F, Cl, Br, —$NO_2$, —$SO_2Me$, —$SCH_3$, —$OCH_3$, —$N(CH_3)_2$, —$SO_2NH_2$, —CN, —$CONH_2$, —$OCH_2CF_3$, —$(CH_2)_{0-1}$-morpholinyl, piperazinyl or N-methylpiperazinyl.

In some embodiments of Formulas (I) and (II), $Ar^1$ is phenyl with zero, one, two or three $R^a$ substituents. In some embodiments, $Ar^1$ is phenyl with one $R^a$ substituent. In some embodiments, $Ar^1$ is phenyl with two $R^a$ substituents. In some embodiments, $Ar^1$ is phenyl substituted with halo. In some embodiments, $Ar^1$ is phenyl substituted at the 4-position. In some embodiments, $Ar^1$ is thiophen-yl with zero, one or two $R^a$ substituents. In some embodiments, $Ar^1$ is thiophen-yl with one $R^a$ substituent. In some embodiments, $Ar^1$ is thiophen-yl with two $R^a$ substituents. In some embodiments, $Ar^1$ is thiophen-yl substituted with halo. In some embodiments, $Ar^1$ is thiophen-yl substituted with halo. In some embodiments, $Ar^1$ is thiophen-yl substituted at the 5-position.

In some embodiments of Formulas (I) and (II), $Ar^2$ is phenyl with zero, one, two or three $R^b$ substituents. In some embodiments, $Ar^2$ is phenyl with one $R^b$ substituent. In some embodiments, $Ar^2$ is phenyl with two $R^b$ substituents. In some embodiments, $Ar^2$ is phenyl substituted with —$CF_3$. In some embodiments, $Ar^2$ is phenyl substituted with —$OCF_3$. In some embodiments, $Ar^2$ is phenyl substituted at the 4-position. In some embodiments, $Ar^2$ is pyridyl.

In some embodiments of Formulas (I) and (II), $Ar^1$ is phenyl with zero, one, two or three $R^a$ substituents and $Ar^2$ is phenyl with zero, one, two or three $R^b$ substituents. In some embodiments, $Ar^1$ is phenyl with zero, one, two or three $R^a$ substituents and $Ar^2$ is pyridyl. In some embodiments, $Ar^1$ is thiophen-yl with zero, one or two $R^a$ substituents and $Ar^2$ is phenyl with zero, one, two or three $R^b$ substituents. In some embodiments, $Ar^1$ is thiophen-yl with zero, one or two $R^a$ substituents and $Ar^2$ is pyridyl. In some embodiments, $Ar^1$ is phenyl with one $R^a$ substituent and $Ar^2$ is phenyl with one $R^b$ substituent. In some embodiments, $Ar^1$ is phenyl substituted with halo and $Ar^2$ is phenyl substituted with —$CF_3$.

In some embodiments of Formulas (I) and (II), $Ar^1$ is phenyl with zero, one, two or three $R^a$ substituents, $Ar^2$ is phenyl with zero, one, two or three $R^b$ substituents and each instance of Y and Z are CH. In some embodiments, $Ar^1$ is phenyl with zero, one, two or three $R^a$ substituents, $Ar^2$ is pyridyl and each instance of Y and Z are CH. In some embodiments, $Ar^1$ is thiophen-yl with zero, one or two $R^a$ substituents, $Ar^2$ is phenyl with zero, one, two or three $R^b$ substituents and each instance of Y and Z are CH. In some embodiments, $Ar^1$ is thiophen-yl with zero, one or two $R^a$ substituents, $Ar^2$ is pyridyl and each instance of Y and Z are CH. In some embodiments, $Ar^1$ is phenyl with one $R^a$ substituent, $Ar^2$ is phenyl with one $R^b$ substituent and each instance of Y and Z are CH. In some embodiments, $Ar^1$ is phenyl substituted with halo, $Ar^2$ is phenyl substituted with —$CF_3$ and each instance of Y and Z are CH.

In some embodiments of Formulas (I) and (II), $Ar^1$ is phenyl with zero, one, two or three $R^a$ substituents, $Ar^2$ is phenyl with zero, one, two or three $R^b$ substituents and Z is $CR^9$ and two instances of Y are N. In some embodiments, $Ar^1$ is phenyl with zero, one, two or three $R^a$ substituents, $Ar^2$ is pyridyl and Z is $CR^9$ and two instances of Y are N. In some embodiments, $Ar^1$ is thiophen-yl with zero, one or two $R^a$ substituents, $Ar^2$ is phenyl with zero, one, two or three $R^b$ substituents and Z is $CR^9$ and two instances of Y are N. In some embodiments, $Ar^1$ is thiophen-yl with zero, one or two $R^a$ substituents, $Ar^2$ is pyridyl and Z is $CR^9$ and two instances of Y are N. In some embodiments, $Ar^1$ is phenyl with one $R^a$ substituent, $Ar^2$ is phenyl with one $R^b$ substituent and Z is $CR^9$ and two instances of Y are N. In some embodiments, $Ar^1$ is phenyl substituted with halo, $Ar^2$ is phenyl substituted with —$CF_3$ and Z is $CR^9$ and two instances of Y are N.

In some embodiments of Formulas (I) and (II), $Ar^1$ is phenyl with zero, one, two or three $R^a$ substituents, $Ar^2$ is phenyl with zero, one, two or three $R^b$ substituents and Z is $CR^g$ and one instance of Y is N. In some embodiments, $Ar^1$ is phenyl with zero, one, two or three $R^a$ substituents, $Ar^2$ is pyridyl and Z is $CR^9$ and one instance of Y is N. In some embodiments, $Ar^1$ is thiophen-yl with zero, one or two $R^a$ substituents, $Ar^2$ is phenyl with zero, one, two or three $R^b$ substituents and Z is $CR^9$ and one instance of Y is N. In some embodiments, $Ar^1$ is thiophen-yl with zero, one or two $R^a$ substituents, $Ar^2$ is pyridyl and Z is $CR^9$ and one instance of Y is N. In some embodiments, $Ar^1$ is phenyl with one $R^a$ substituent, $Ar^2$ is phenyl with one $R^b$ substituent and Z is $CR^9$ and one instance of Y is N. In some embodiments, $Ar^1$ is phenyl substituted with halo, $Ar^2$ is phenyl substituted with —$CF_3$ and Z is $CR^9$ and one instance of Y is N.

In another general aspect, the present invention relates to compounds of Formula (I) and (II) as presented above, wherein when $Ar^1$ is phenyl substituted with zero, one, two, or three substituents $R^a$, wherein each $R^a$ is independently halo, —$C_{1-4}$alkyl, —$OC_{1-4}$alkyl, —CN, —$CF_3$, —$OCF_3$, —$NO_2$, —$C(O)C_{1-4}$alkyl or —$CO_2H$.

In another general aspect, the present invention relates to compounds of Formula (I) and (II) as presented above, wherein when $Ar^2$ is phenyl optionally substituted with one, two or three substituents $R^b$, each $R^b$ is independently halo, —$C_{1-4}$alkyl, —$C(O)NR^cR^d$, —$OC_{1-4}$alkyl, —$OC_{0-4}$alkylCF$_3$, —CN, —$OCF_2H$, —$NO_2$, —$NR^cR^d$, —$S(O)_{0-2}C_{1-4}$alkyl, —$C(O)C_{1-4}$alkyl, —$S(O)(O)NH_2$, —$(CH_2)_{0-2}$-morpholinyl, piperidin-1-yl or piperazinyl, said piperazinyl optionally substituted with a methyl. In further embodiments, $Ar^2$ is pyridyl substituted with zero, one or two substituents $R^e$, where each $R^e$ is independently selected from halo, —$C_{1-4}$alkyl, —$OC_{1-4}$alkyl, —$CF_3$, —$NR^cR^d$ or 4-morpholinyl.

In another general aspect, the present invention relates to compounds of Formula (I) and (II) as presented above, wherein when $Ar^1$ is phenyl substituted with zero, one, two or three substituents $R^a$, wherein each $R^a$ is independently halo, —$C_{1-4}$alkyl, —$OC_{1-4}$alkyl, —CN, —$CF_3$, —$OCF_3$, —$NO_2$, —$C(O)C_{1-4}$alkyl or —$CO_2H$; and $Ar^2$ is phenyl optionally substituted with 1, 2 or 3 substituents $R^b$, each $R^b$ is independently —$C_{1-4}$alkyl, —$C(O)NR^cR^d$, —$OC_{1-4}$alkyl, —$OC_{0-4}$alkylCF$_3$, —CN, —$OCF_2H$, —$NO_2$, —$NR^cR^d$, —$S(O)_{0-2}C_{1-4}$alkyl, —$C(O)C_{1-4}$alkyl, —$S(O)(O)NH_2$, —$(CH_{0-2})$-morpholinyl, piperazinyl optionally substituted with a methyl or piperidin-1-yl; pyridyl optionally substituted with 1 or 2 substituents $R^e$, where each $R^e$ is independently selected from halo, —$C_{1-4}$alkyl, —$OC_{1-4}$alkyl, —$CF_3$, —$NR^cR^d$ or 4-morpholinyl.

The invention includes also pharmaceutically acceptable salts of the compounds represented by Formulas (I) and (II). Pharmaceutically acceptable salts of the specific compound salts exemplified herein are preferred. The invention also includes methods of using such salts.

A "pharmaceutically acceptable salt" is intended to mean a salt of a free acid or base of a compound represented by Formulas (I) or (II) that is non-toxic, biologically tolerable, or otherwise biologically suitable for administration to the subject. See, generally, S. M. Berge, et al., "Pharmaceutical Salts", *J Pharm Sci.*, 1977, 66:1-19, and *Handbook of Pharmaceutical Salts, Properties, Selection, and Use*, Stahl and Wermuth, Eds., Wiley-VCH and VHCA, Zurich, 2002. Preferred pharmaceutically acceptable salts are those that are pharmacologically effective and suitable for contact with the tissues of patients without undue toxicity, irritation, or allergic response.

A compound of Formulas (I) and (II) may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound of Formulas (I) or (II) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

If the compound of Formulas (I) or (II) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

In some embodiments, pharmaceutically acceptable salts of compounds of Formulas (I) or (II) were hydrochloride and trifluoroacetic acid salts. In preferred embodiments, compounds of Formulas (I) or (II) were obtained as trifluoroacetic acid salts.

The invention also relates to pharmaceutically acceptable prodrugs of the compounds of Formulas (I) and (II), and methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formulas (I) or (II)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Examples of prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formulas (I) and (II). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of compounds of Formulas (I) or (II) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{6-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in *Adv. Drug Delivery Rev.* 1996, 19, 115. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in *J. Med. Chem.* 1996, 39, 10. Free amines can also be derivatized as amides, sulfonamides or phosphonamides. All of these prodrug moieties may incorporate groups including ether, amine, and carboxylic acid functionalities.

The present invention also relates to pharmaceutically active metabolites of compounds of Formulas (I) and (II), and uses of such metabolites in the methods of the invention. A "pharmaceutically active metabolite" means a pharmacologically active product of metabolism in the body of a compound of Formulas (I) or (II) or salts thereof. Prodrugs and active metabolites of a compound may be determined using routine techniques known or available in the art. See, e.g., Bertolini, et al., *J. Med. Chem.* 1997, 40, 2011-2016; Shan, et al., *J. Pharm. Sci.* 1997, 86 (7), 765-767; Bagshawe, *Drug Dev. Res.* 1995, 34, 220-230; Bodor, *Adv. Drug Res.* 1984, 13, 224-331; Bundgaard, Design of Prodrugs (Elsevier Press, 1985); and Larsen, Design and Application of Prodrugs, Drug Design and Development (Krogsgaard-Larsen, et al., eds., Harwood Academic Publishers, 1991).

The compounds of Formulas (I) and (II), and their pharmaceutically acceptable salts, pharmaceutically acceptable prodrugs, and pharmaceutically active metabolites (collectively, "agents") of the present invention are useful as TRPA1 modulators in the methods of the invention. The agents may be used in the inventive methods for the treatment of medical conditions, diseases, or disorders, including symptoms or disease states, mediated through modulation of TRPA1, such as those described herein.

Accordingly, the invention relates to methods of using the agents to treat subjects diagnosed with or suffering from a disease, disorder, or condition mediated through TRPA1 activity, such as: i) pain (acute, chronic, inflammatory, or neuropathic pain); ii) itch or various inflammatory disorders; iii) inner ear disorders; iv) fever or other disorders of thermoregulation; v) tracheobronchial or diaphragmatic dysfunction; vi) gastrointestinal or urinary tract disorders; vii) chronic obstructive pulmonary disease; viii) incontinence; or ix) disorders associated with reduced blood flow to the CNS or CNS hypoxia.

In a preferred embodiment, an agent of the present invention is administered to treat pain. Certain types of pain may be considered a disease or disorder, while other types may be considered symptoms of various diseases or disorders, and pain may include various etiologies. Exemplary types of pain treatable with a TRPA1-modulating agent according to the invention include pain associated with, arising from, or caused by: osteoarthritis, rotator cuff disorders, arthritis (e.g., rheumatoid arthritis or inflammatory arthritis; see, Barton et al. *Exp. Mol. Pathol.* 2006, 81(2), 166-170), fibromyalgia, migraine and headache (e.g. cluster headache, sinus headache, or tension headache; see, Goadsby *Curr. Pain Headache Reports* 2004, 8, 393), sinusitis, oral mucositis, toothache, dental trauma, dental extractions, dental infections, burn (Bölcskei et al., *Pain* 2005, 117(3), 368-376), sunburn, dermatitis, psoriasis, eczema, insect sting or bite, musculoskeletal disorders, bony fractures, ligamentous sprains, plantar fasciitis, costochondritis, tendonitis, bursitis, tennis elbow, pitcher's elbow, patellar tendonitis, repetitive strain injury, myofascial syndrome, muscle strain, myositis, temporomandibular joint disorder, amputation, low back pain, spinal cord injury, neck pain, whiplash, bladder spasms, GI tract disorders, cystitis, interstitial cystitis, cholecystitis, urinary tract infection, urethral colic, renal colic, pharyngitis, cold sores, stomatitis, external otitis, otitis media (Chan et al., *Lancet*, 2003, 361, 385), burning mouth syndrome, mucositis, esophageal pain, esophageal spasms, abdominal disorders, gastroesophageal reflux disease, pancreatitis, enteritis, irritable bowel disorder, inflammatory bowel disease, Crohn's disease, ulcerative colitis, colon distension, abdominal constriction, diverticulosis, diverticulitis, intestinal gas, hemorrhoids, anal fissures, anorectal disorders, prostatitis, epididymitis, testicular pain, proctitis, rectal pain, labor, childbirth, endometriosis, menstrual cramps, pelvic pain, vulvodynia, vaginitis, orolabial and genital infections (e.g. herpes simplex), pleurisy, pericarditis, non-cardiac chest pain, contusions, abrasions, skin incision (Honore, P. et al., *J Pharmacol Exp Ther.*, 2005, 314, 410-21), postoperative pain, peripheral neuropathy, central neuropathy, diabetic neuropathy, acute herpetic neuralgia, post-herpetic neuralgia, trigeminal neuralgia, glossopharyngeal neuralgia, atypical facial pain, gradiculopathy, HIV associated neuropathy, physical nerve damage, causalgia, reflex sympathetic dystrophy, sciatica, cervical, thoracic or lumbar radiculopathy, brachial plexopathy, lumbar plexopathy, neurodegenerative disorders, occipital neuralgia, intercostal neuralgia, supraorbital neuralgia, inguinal neuralgia, meralgia paresthetica, genitofemoral neuralgia, carpal tunnel syndrome, Morton's neuroma, post-mastectomy syndrome, post-thoracotomy syndrome, post-polio syndrome, Guillain-Barré syndrome, Raynaud's syndrome, coronary artery spasm (Printzmetal's or variant angina), visceral hyperalgesia (Pomonis, J. D. et al. *J. Pharmacol. Exp. Ther.* 2003, 306, 387; Walker, K. M. et al., *J. Pharmacol. Exp. Ther.* 2003, 304(1), 56-62), thalamic pain, cancer (e.g. pain caused by cancer, including osteolytic sarcoma, by treatment of cancer by radiation or chemotherapy, or by nerve or bone lesions associated with cancer (see, Menendez, L. et al., *Neurosci. Lett.* 2005, 393 (1), 70-73; Asai, H. et al., *Pain* 2005, 117, 19-29), or bone destruction pain (see, Ghilardi, J. R. et al., *J. Neurosci.* 2005, 25, 3126-31)), infection, or metabolic disease. Additionally, the compounds may be used to treat pain indications such as visceral pain, ocular pain, thermal pain, dental pain, capsaicin-induced pain (as well as other symptomatic conditions induced by capsaicin such as cough, lachrymation, and bronchospasm).

In another preferred embodiment, inventive agents are administered to treat: itch, which may arise from various sources, such as dermatological or inflammatory disorders; or inflammatory disorders selected from the group consisting of: renal or hepatobiliary disorders, immunological disorders, medication reactions and unknown/idiopathic conditions. Inflammatory disorders treatable with an inventive agent include, for example, inflammatory bowel disease (IBD), Crohn's disease, and ulcerative colitis (Geppetti, P. et al., *Br. J. Pharmacol.* 2004, 141, 1313-20; Yiangou, Y. et al., *Lancet* 2001, 357, 1338-39; Kimball, E. S. et al., *Neurogastroenterol. Motil.,* 2004, 16, 811), osteoarthritis (Szabo, A. et al., *J. Pharmacol. Exp. Ther.* 2005, 314, 111-119), psoriasis, psoriatic arthritis, rheumatoid arthritis, myasthenia gravis, multiple sclerosis, scleroderma, glomerulonephritis, pancreatitis, inflammatory hepatitis, asthma, chronic obstructive pulmonary disease, allergic rhinitis, uveitis, and cardiovascular manifestations of inflammation including atherosclerosis, myocarditis, pericarditis, and vasculitis.

In another preferred embodiment, inner ear disorders are treated with an inventive agent. Such disorders include, for example, hyperacusis, tinnitus, vestibular hypersensitivity, and episodic vertigo.

In another preferred embodiment, tracheobronchial and diaphragmatic dysfunctions are treated with an inventive agent, including, for example, asthma and allergy-related immune responses (Agopyan, N. et al., *Am. J. Physiol. Lung Cell Mol. Physiol.* 2004, 286, L563-72; Agopyan, N. et al., *Toxicol. Appl. Pharmacol.* 2003, 192, 21-35), cough (e.g., acute or chronic cough, or cough caused by irritation from gastroesophageal reflux disease; see, Lalloo, U. G. et al., *J. Appl. Physiol.* 1995, 79(4), 1082-7), bronchospasm, chronic obstructive pulmonary disease, chronic bronchitis, emphysema, and hiccups (hiccoughs, singultus).

In yet another preferred embodiment, gastrointestinal and urinary tract disorders are treated with an inventive agent, such as, bladder overactivity, inflammatory hyperalgesia, visceral hyperreflexia of the urinary bladder, hemorrhagic cystitis (Dinis, P. et al., *J. Neurosci.,* 2004, 24, 11253-11263), interstitial cystitis (Sculptoreanu, A. et al., *Neurosci Lett.,* 2005, 381, 42-46), inflammatory prostate disease, prostatitis (Sanchez, M. et al., *Eur J. Pharmacol.,* 2005, 515, 20-27), nausea, vomiting, intestinal cramping, intestinal bloating, bladder spasms, urinary urgency, defecation urgency and urge incontinence.

In another preferred embodiment, disorders associated with reduced blood flow to the CNS or CNS hypoxia are treated with an inventive agent. Such disorders include, for example, head trauma, spinal injury, thromboembolic or hemorrhagic stroke, transient ischaemic attacks, cerebral vasospasm, hypoglycaemia, cardiac arrest, status epilepticus, perinatal asphyxia, Alzheimer's disease, and Huntington's Disease.

In other embodiments, inventive agents are administered to treat other diseases, disorders, or conditions mediated through TRPA1 activity, such as: anxiety; learning or memory disorders; eye-related disorders (such as glaucoma, vision loss, increased intraocular pressure, and conjunctivitis); baldness (e.g., by stimulating hair growth); diabetes (including insulin-resistant diabetes or diabetic conditions mediated by insulin sensitivity or secretion); obesity (e.g., through appetite suppression); dyspepsia; biliary colic; renal colic; painful bladder syndrome; inflamed esophagus; upper airway disease; urinary incontinence; acute cystitis; and envenomations (such as marine, snake, or insect stings or bites, including jellyfish, spider, or stingray envenomations).

In especially preferred embodiments of the therapeutic methods of the invention, effective amounts of the TRPA1 modulators of the present invention are administered to treat pain, arthritis, itch, cough, asthma, or inflammatory bowel disease.

The term "treat" or "treating" as used herein is intended to refer to administration of an inventive agent or composition of matter of the invention to a subject to effect a therapeutic or prophylactic benefit through modulation of TRPA1 activity. Treating includes reversing, ameliorating, alleviating, inhibiting the progress of, lessening the severity of, or preventing a disease, disorder, or condition (or one or more symptoms of such disease, disorder or condition) mediated through modulation of TRPA1 activity. The term "subject" refers to a mammalian patient in need of such treatment, such as a human. "Modulators" include both inhibitors and activators, where "inhibitors" refer to compounds that decrease, prevent, inactivate, desensitize or down-regulate TRPA1 expression or activity, and "activators" are compounds that increase, activate, facilitate, sensitize, or up-regulate TRPA1 expression or activity.

In treatment methods according to the invention, an effective amount of at least one agent according to the invention is administered to a subject suffering from or diagnosed as having such a disease, disorder, or condition. An "effective amount" means an amount or dose generally sufficient to bring about the desired therapeutic or prophylactic benefit in patients in need of such treatment for the designated disease, disorder, or condition. Effective amounts or doses of the agents of the present invention may be ascertained by routine methods such as modeling, dose escalation studies, or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status, and response to drugs, and the judgment of the treating physician. An exemplary dose is in the range of from about 0.001 to about 200 mg of inventive agent per kg of subject's body weight per day, preferably about 0.05 to 100 mg/kg/day, or about 1 to 35 mg/kg/day, or about 0.1 to 10 mg/kg daily in single or divided dosage units (e.g., BID, TID, or QID). For a 70-kg human, an illustrative range for a suitable dosage amount is from about 0.05 to about 7 g/day, or about 0.2 to about 2.5 g/day. Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the pharmaceutical agents of the invention may be used in combination with additional active ingredients in the treatment methods described above. The additional active ingredients may be coadministered separately with an inventive agent or included with such an agent in a pharmaceutical composition according to the invention. In an exemplary embodiment, additional active ingredients are those that are known or discovered to be effective in the treatment of conditions, disorders, or diseases mediated by TRPA1 activity, such as another TRPA1 modulator or a compound active against another target associated with the particular condition, disorder, or disease. The combination may serve to increase efficacy (e.g., by including in the combination a compound potentiating the potency or effectiveness of an agent according to the invention), decrease one or more side effects, or decrease the required dose of the agent according to the invention. In one illustrative embodiment, a composition for treating pain according to the invention may contain one or more additional active ingredients selected from opioids, NSAIDs (e.g., ibuprofen, cyclooxygenase-2 (COX-2) inhibitors, and naproxen), gabapentin, pregabalin, tramadol, acetaminophen, aspirin, and alpha-2 adrenergic agonists (e.g., brimonidine, clonidine, dexmedetomidine, mivazerol, guanabenz, guanfacine, or methyldopa).

The agents of the invention are used, alone or in combination with one or more other active ingredients, to formulate pharmaceutical compositions of the invention. A pharmaceutical composition of the invention comprises: (a) an effective amount of a pharmaceutical agent in accordance with the invention; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an inventive agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the pharmaceutical agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the agents may be formulated to yield a dosage of, e.g., from about 0.05 to about 50 mg/kg daily, or from about 0.05 to about 20 mg/kg daily, or from about 0.1 to about 10 mg/kg daily.

Oral tablets may include the inventive agent and any other active ingredients mixed with compatible pharmaceutically acceptable excipients such as diluents, disintegrators, binders, lubricants, sweeteners, flavors, colors, and preservatives. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrators. Binders may include starch and gelatin. The lubricator, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, the inventive agent may be mixed with a solid, semi-solid, or liquid diluent. Soft gelatin capsules may be prepared by mixing the inventive agent with water, an oil such as peanut oil, sesame oil, or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspenders (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The agents of this invention may also be administered by non-oral routes. For example, compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For topical administration, the agents may be mixed with a pharmaceutical carrier at a concentration of about 0.1% to about 10% of drug to vehicle. Another mode of administering the agents of the invention may utilize a patch formulation to effect transdermal delivery.

Inventive agents may alternatively be administered in methods of this invention by inhalation, via the nasal or oral routes, e.g., in a spray formulation also containing a suitable carrier.

List of abbreviations: Ac=acetyl, AcOH=acetic acid, AIBN=azobisisobutyronitrile, BBr$_3$=boron tribromide, Boc=tert-butylcarbamoyl, BOP=(benzotriazol-1-yloxy)tris(dimethylamino)phosphonium hexafluorophosphate, m-CPBA=meta-chloroperoxybenzoic acid, DCE=dichloroethane, DCM=dichloromethane, DEAD=diethyldiazodicarboxylate, DIBALH=diisobutyl aluminum hydride, DIEA=N,N-diisopropylethylamine, DMA=N,N-dimethylacetamide, DME=dimethyl ether, DMF=dimethylformamide, DMSO=dimethyl sulfoxide, EDC=1-ethyl-3-(3-dimethylaminopropyl) carbodiimide hydrochloride, Et$_3$N=triethylamine, Et$_2$O=diethyl ether, EtOAc=ethyl acetate, FCC=flash column chromatography, HOBt=1-hydroxybenzotriazole, IPA=isopropanol, LAH=lithium aluminum hydride, MeCN=acetonitrile, MeOH=methanol, Ms$_2$O=methane sulfonic anhydride, MsCl=methanesulfonyl chloride, NMP=N-methyl-pyrrolidine, Rochelle's Salt=potassium sodium tartrate, RT=room temperature, TBDMS=tert-butyldimethylsilyl, TEA=triethylamine, TFA=trifluoroacetic acid, TFAA=trifluoroacetic acid anhydride, THF=tetrahydrofuran, TLC=thin layer chromatography, Q-Phos=1,2,3,4,5-pentaphenyl-1-(di-tert-butylphosphino)ferrocene.

Exemplary chemical entities useful in methods of the invention will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables in the formulas depicted in the schemes below are as defined above in reference to Formulas (I) and (II).

EXAMPLES

Chemistry Methods

In obtaining the compounds described in the examples below and the corresponding analytical data, the following experimental and analytical protocols were followed unless otherwise indicated.

Unless otherwise stated, reaction mixtures were magnetically stirred at room temperature (rt). Where solutions were "dried," they were generally dried over a drying agent such as Na$_2$SO$_4$ or MgSO$_4$. Where mixtures, solutions, and extracts were "concentrated", they were typically concentrated on a rotary evaporator under reduced pressure. Column chromatography was typically conducted on disposable silica gel columns for flash chromatography (Teledyne Isco, Inc.).

Analytical reversed-phase high performance liquid chromatography (HPLC) was performed on an Agilent 1100 Series instrument using one of the following gradients: 1 to 99% acetonitrile/water (0.05% trifluoroacetic acid) over 5.0 min or 7.0 min with a flow rate of 1 mL/min (Waters XTerra MS C18 (5 µm, 4.6×100 mm) column or Phenomenex Synergi max-RP (4 µm, 4.6×150 mm) column) or 1 to 99% acetonitrile/water (20 mM NH$_4$OH) over 5.0 min or 7.0 min with a flow rate of 1.5 mL/min (Phenomenex Gemini C18 (5 µm, 3.0×150 mm) column). Analytical reversed phase LC/MS was performed either on an Agilent 1100 Series instrument using 5 to 99% acetonitrile/water (0.05% trifluoroacetic acid) over 5.0 min or 7.0 min with a flow rate of 0.6 mL/min (Waters XTerra RP18 (5 µm, 3.0×100 mm) column) or on a Waters 2790 instrument using 5 to 99% acetonitrile/water (0.1% formic acid) over 5.0 min with a flow rate of 0.6 mL/min (Waters XTerra RP18 (5 µm, 3.0×100 mm) column).

Preparative reversed phase HPLC was performed on a Dionex APS2000 LC/MS or HPLC with a Phenomenex Gemini C18 (5 µm, 30×100 mm) column or a Waters XBridge C18 (5 µm, 30×100 mm) column and variable gradients of acetonitrile/water (20 mM NH$_4$OH) at a flow rate of 30 mL/min. Alternatively, the purification was performed with a Phenomenex Gemini C18 (5 µm, 50×100 mm) column or a Waters XBridge C18 (5 µm, 50×100 mm) column and variable gradients of acetonitrile/water (20 mM NH$_4$OH) at a flow rate of 80 mL/min. Formate salts of desired compounds were obtained when purifications were performed using an Inertsil ODS-3 C18 (3 µm, 30×100 mm) column at 46° C.

with variable gradients of acetonitrile/water (0.1% formic acid) at a flow rate of 90 mL/min.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. The format of the $^1$H NMR data below is: chemical shift in ppm downfield of the tetramethylsilane reference (multiplicity, coupling constant J in Hz, integration). NMR interpretation was performed using MestReC or MestReNova software to assign chemical shift and multiplicity. In cases where two adjacent peaks of equal or unequal height were observed, these two peaks may be labeled either as a multiplet or as a doublet. In the case of a doublet a coupling constant using this software may be assigned. In any given example, one or more protons may not be reported due to obscurity by water and/or solvent peaks.

Chemical names were typically generated using CS ChemDraw Ultra with the stereochemistry added manually (Cambridgesoft, Cambridge, Mass., U.S.A.).

In utilization of method A, intermediates (IV) and (V) were converted to intermediates (VIII) through an amide bond formation. Suitable conditions included mixing of intermediate (IV), (benzotriazol-1-yloxy)tris(dimethylamino)phosphonium hexafluorophosphate, and triethylamine in dichloromethane followed by addition of intermediate (V). In alternative methods, intermediate (VIII) formation was achieved by mixing intermediate (IV), N-(3-dimethylaminopropyl)-pyrrolidine-2-carbodiimide hydrochloride, triethylamine, and 1-hydroxybenzotriazole in dimethylformamide followed by addition of intermediate (V). Intermediates (V) are commercially available or were prepared according to the following schemes or methods known to one skilled in the art.

In alternative methods, Intermediates (VIII) were also formed by method B. In this method, intermediates (VI) were generated from intermediates (V) and the appropriate commercially available di-tert-butyl dicarbonate (Boc) protected amino acid through an amide bond formation, as described in method A. The Boc-moiety was removed by treatment of intermediates (VI) in dichloromethane with 4M HCl in dioxane. Treatment of intermediate (VII) in dichloromethane with Scheme A

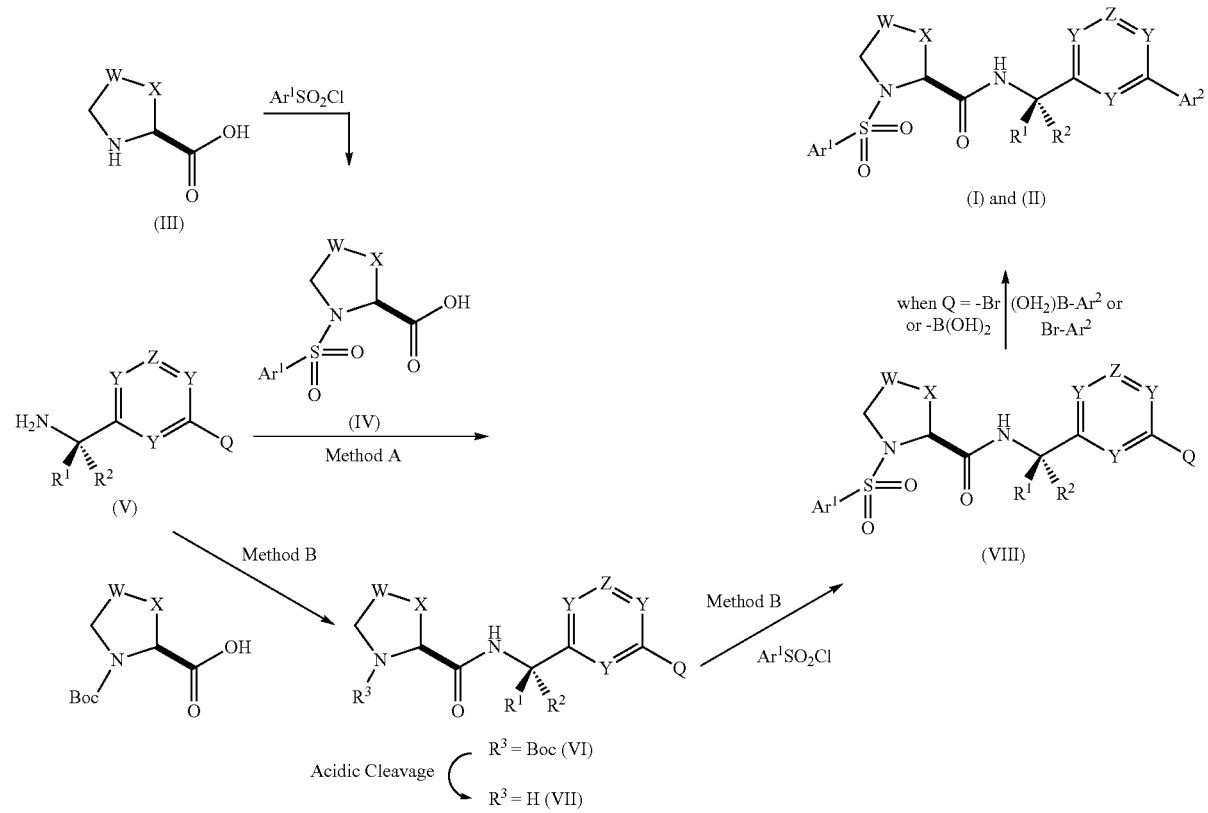

Referring to Scheme A, embodiments of Formula (I) and (II) were prepared from intermediates (V), where Q is Ar$^2$ or a suitable group for general palladium mediated coupling conditions, such as —Br or —B(OH)$_2$, by methods A or B. Intermediates (IV) were prepared from the appropriate intermediate (III), which were either commercially available or prepared according to methods known in the art, by treatment with sodium hydroxide and the appropriate sulfonyl chloride, which were either commercially available or prepared according to methods known in the art, in tetrahydrofuran.

commercially available aryl sulfonyl chloride and triethylamine generated intermediate (VIII). In certain embodiments, N,N-dimethylaminopyridine was added to enhance the rate of sulfonamide formation.

When Q is —Br or —B(OH)$_2$, intermediates (VIII) can be converted to a compound of Formula (I) or (II) under standard palladium mediated coupling conditions in the presence of the appropriate aryl bromide or aryl boronic acid. Suitable conditions included tetrakis(triphenylphosphine)palladium and potassium phosphate in dimethoxyethane and water at 85° C.

Scheme B

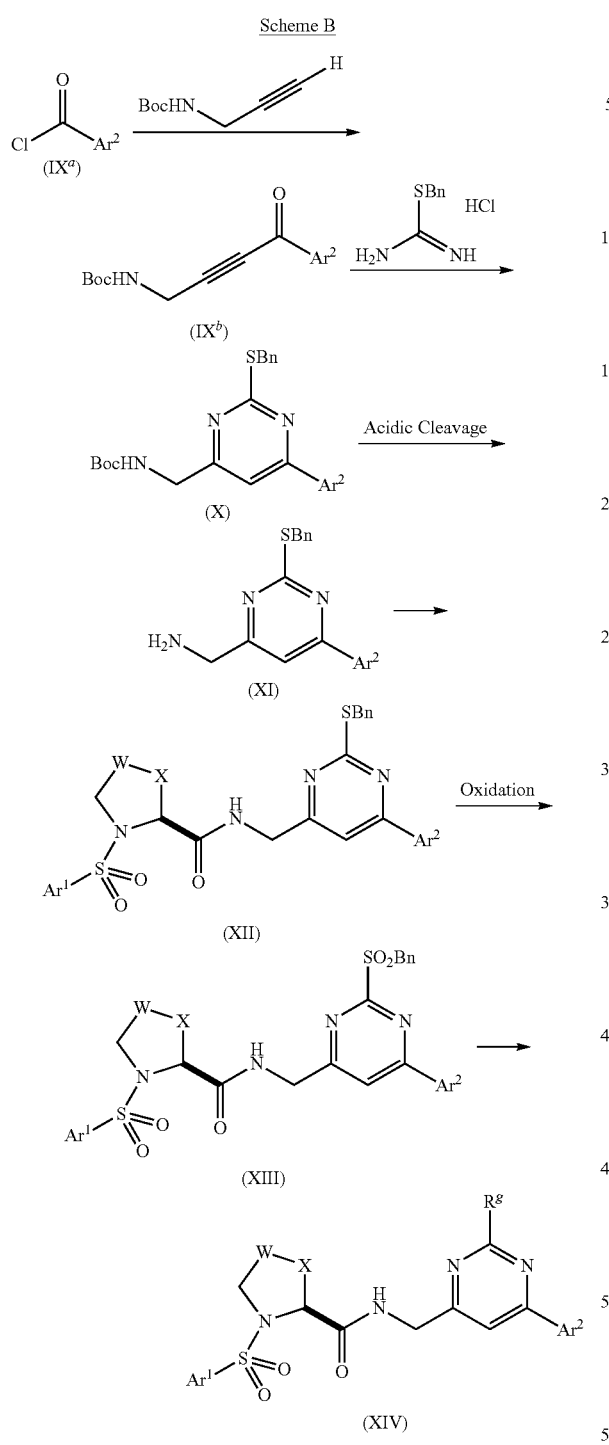

Referring to Scheme B, embodiments of Formulas (I) and (II) were prepared from the appropriate acyl chloride (IX$^a$), which were either commercially available or prepared according to methods known in the art, and commercially available N-Boc-propargyl amine. Intermediates (IX$^b$) were generated by treating acyl chlorides (IX$^a$) and N-Boc-propargyl amine in tetrahydrofuran with PdCl$_2$(PPh$_3$)$_2$, copper(I) iodide, and triethylamine at room temperature. Intermediates (X) were generated by treating intermediates (IX$^b$) in acetonitrile with 2-benzyl-2-thiopseudourea hydrochloride and potassium carbonate. Removal of the Boc-moiety from intermediates (X) and subsequent amide bond formation were achieved by following analogous procedures to those described in Scheme A. Oxidation of intermediates (XII) with m-chloroperbenzoic acid in dichloromethane generated intermediates (XIII). Nucleophilic displacement of the pyrimidine attached sulfone resulted in the generation of intermediates (XIV). One of routine skill in the art would recognize that intermediates (XIV) are certain embodiments of Formulas (I) and (II).

In cases where an amine served as the nucleophile, suitable conditions included the treatment of intermediates (XIII) with the desired amine in t-amyl alcohol at 110° C. In cases where the desired nucleophile is a commercially available alcohol, suitable conditions included adding intermediates (XIII) in tetrahydrofuran to a mixture of the desired alcohol and sodium hydride in methanol or tetrahydrofuran.

Scheme C

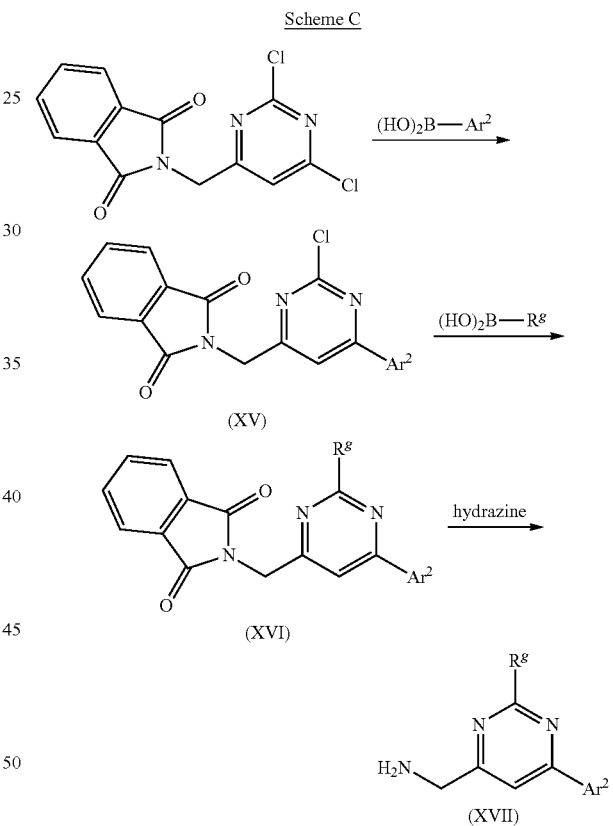

Referring to Scheme C, intermediates (XVII) were prepared from 2-(2,6-dichloropyrimidin-4-yl)isoindole-1,3-dione (*J Heterocyclic Chem.*, 1986, 23, 981-986). Intermediates (XVI) were generated by sequential palladium mediated coupling reactions. Suitable conditions included the treatment of intermediate (XV) with tetrakis(triphenylphosphine) palladium, a desired boronic acid, and potassium phosphate in dimethoxyethane and water at 85° C. Treatment of intermediates (XVI) with hydrazine in ethanol at 90° C. afforded intermediates (XVII). One skilled in the art would recognize that intermediates (XVII) represent certain embodiments of intermediates (V) in Scheme A.

Scheme D

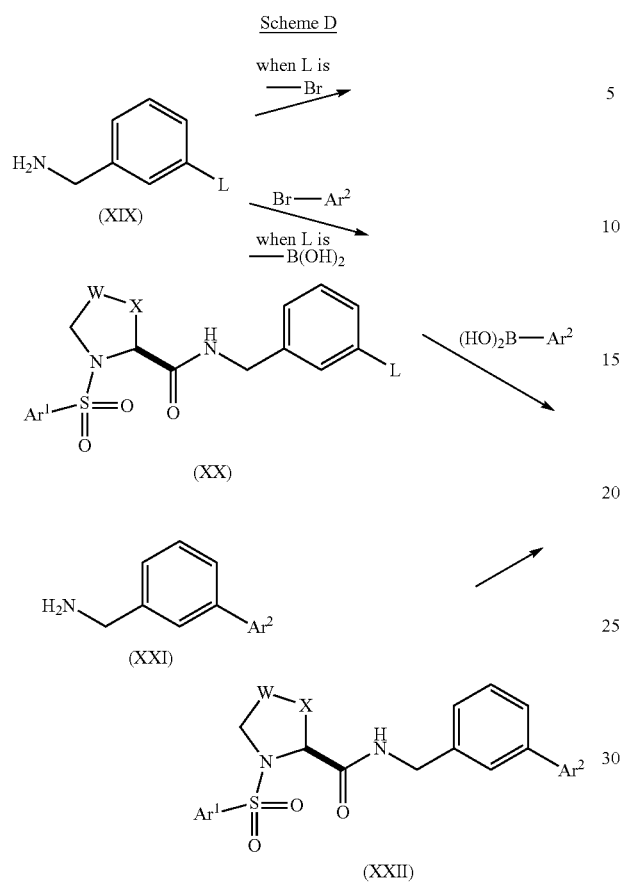

Referring to Scheme D, embodiments of Formulas (I) and (II) were prepared from intermediates (XIX). When L of intermediates (XIX) is —Br, intermediates (XX) were generated by a procedure analogous to that described in method A or B of Scheme A. The conversion of intermediates (XX) to intermediates (XXII) was accomplished by a procedure analogous to that described for the formation of compounds of Formulas (I) and (II) from intermediates (VII), Scheme A. Alternatively, when L is —B(OH)$_2$, intermediates (XXI) were generated by a procedure analogous to that described for the formation of compounds of Formulas (I) and (II) from intermediate (VIII). Intermediate (XXI) was converted to intermediate (XXII) by method A or B as described in Scheme A. One of routine skill in the art would recognize that intermediates (XXII) are certain embodiments of Formulas (I) and (II).

Scheme E

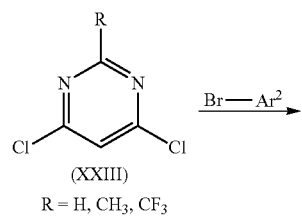

R = H, CH$_3$, CF$_3$

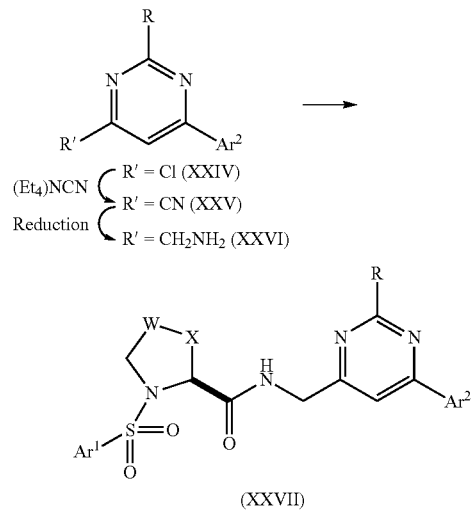

Referring to Scheme E, embodiments of Formulas (I) and (II) were prepared from intermediates (XXIII), which were either commercially available or prepared according to methods known in the art. The conversion of intermediates (XXIII) to intermediates (XXIV) was accomplished by a procedure analogous to that described for the formation of compounds of Formulas (I) and (II) from intermediate (VIII). Installation of the nitrile to generate intermediates (XXV) was accomplished by treating intermediates (XXIV) with tetraethylammonium cyanide and triethylamine in acetonitrile at 80° C. Nitrile reduction to generate intermediates (XXVI) was accomplished by treating intermediates (XXV) in ethanol with 10% Pd/C under a 55 psi hydrogen atmosphere. Further elaboration of intermediates (XXVI) to intermediates (XXVII) was accomplished by following method A or B as described in Scheme A. One of routine skill in the art would recognize that intermediates (XXVII) are certain embodiments of Formulas (I) and (II).

Scheme F

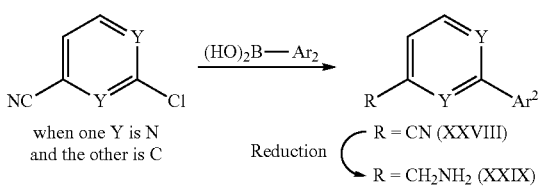

Referring to Scheme F, intermediates (XXIX) may be prepared from cyanopyridines, which were either commercially available or prepared according to methods known in the art. Intermediates (XXVIII) were prepared by treating a desired cyanopyridine compound with commercially available boronic acid in the presence of palladium acetate, 2-dicyclohexylphosphino-2',4',6'-triisopropylbiphenyl and cesium carbonate in dioxane at 100° C. Reduction of the nitrile was accomplished by treating intermediates (XXVIII) in ethanol with Pd/C and HCl or in methanol with NH$_3$ and Raney nickel under a 55 psi hydrogen atmosphere. One skilled in the art will recognize that intermediates (XXIX) are certain embodiments of intermediates (V) in Scheme A.

Scheme H

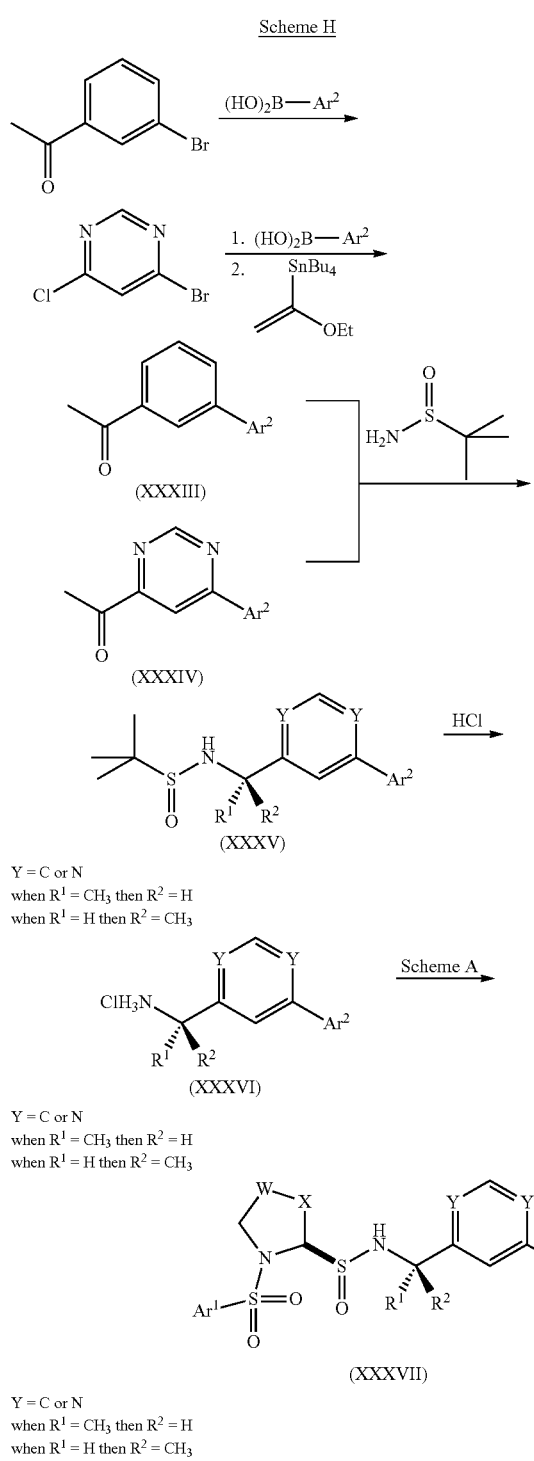

(XXXIII)

(XXXIV)

(XXXV)
Y = C or N
when R¹ = CH₃ then R² = H
when R¹ = H then R² = CH₃

(XXXVI)
Y = C or N
when R¹ = CH₃ then R² = H
when R¹ = H then R² = CH₃

(XXXVII)
Y = C or N
when R¹ = CH₃ then R² = H
when R¹ = H then R² = CH₃

Referring to Scheme H, embodiments of Formulas (I) and (II) were prepared from commercially available 3-bromoacetophenone and 3,5-dichloropyrimidine. 3-Bromoacetophenone was converted to intermediate (XXXIII) by a procedure analogous to that described for the formation of compounds of Formulas (I) and (II) from intermediates (VIII) in Scheme A.

Intermediates (XXXIV) were prepared from 3,5-dichloropyrimidine. 3,5-dichloropyrimidine was converted to intermediate (XXXIV) by sequential palladium mediated cross couplings as described in Scheme A. The —Ar² was first installed by a procedure similar to that described in the formation of compounds of Formulas (I) or (II) from intermediates (VIII) in Scheme A. In a subsequent step, the ketone was installed by treatment with tributyl-(1-ethoxy-vinyl)-stannane and trans-dichlorobis(triphenylphosphine)palladium (II) in dimethylformamide at 80° C. followed by the acid mediated hydrolysis of the enol ether by treatment with HCl in tetrahydrofuran.

Intermediate (XXXIII) and intermediate (XXXIV) in tetrahydrofuran were treated with the desired commercially available 2-methyl-2-propanesulfinamide and titanium(IV) ethoxide followed by sodium borohydride to form intermediate (XXXV). Acid cleavage of the sulfinamide moiety by treatment with 4 M HCl in dioxane provided intermediate (XXXVI) which was subsequently converted to intermediate (XXXVII) by following the procedure provided in method A or B in Scheme A. One skilled in the art will recognize that intermediates (XXXVII) are certain embodiments of Formulas (I) and (II).

Scheme I

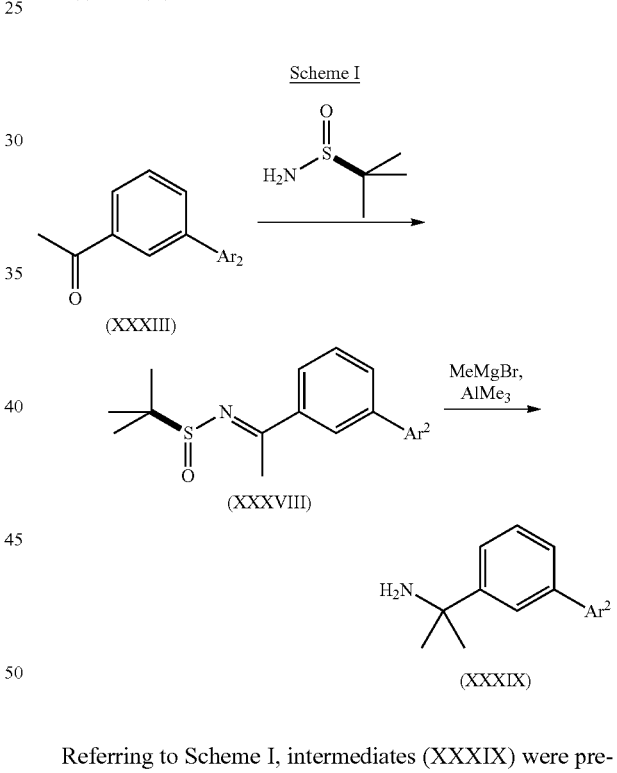

(XXXIII)

(XXXVIII)

(XXXIX)

Referring to Scheme I, intermediates (XXXIX) were prepared from intermediates (XXXIII). Intermediates (XXXIII) were converted to intermediates (XXXVIII) by treatment with (S)-(−)-2-methyl-propanesulfinamide and titanium(IV) ethoxide in THF. Intermediates (XXXIX) were generated from the treatment of intermediate (XXXVIII) with methylmagnesium bromide and trimethylaluminium in THF followed by treatment of the resulting product in methanol with 4 M HCl in dioxane. Intermediate (XXXIX) was converted to intermediate (XXXX) by method A or B described in Scheme A. One skilled in the art will recognize that intermediates (XXXIX) are certain embodiments of intermediates (V) in Scheme A.

Scheme J

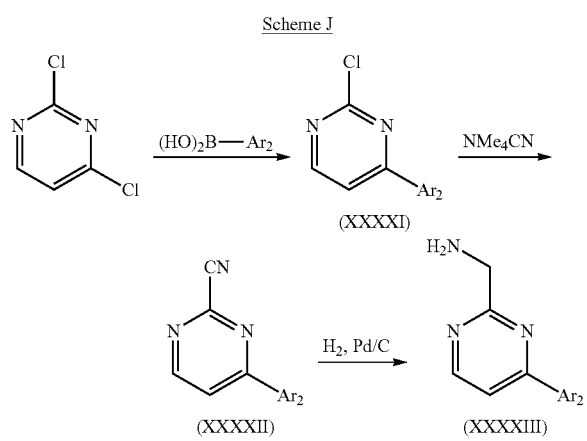

Referring to Scheme J, intermediates (XXXXIII) were prepared from commercially available 2,4-dichloropyrimidine. Intermediates (XXXXI) were generated from 2,4-dichloropyrimidine by a procedure analogous to that described for the formation of compounds of Formulas (I) and (II) from intermediate (VIII) in Scheme A. Conversion of intermediates (XXXXI) to intermediates (XXXXII) was accomplished by treatment with tetramethylammonium cyanide and diisopropylamine in acetonitrile. Treatment of intermediates (XXXXII) in ethanol with Pd/C under a 50 psi atmosphere of hydrogen resulted in the reduction of the nitrile to generate intermediates (XXXXIII). One skilled in the art will recognize that intermediates (XXXXIII) are certain embodiments of intermediates (V) in Scheme A.

Scheme K

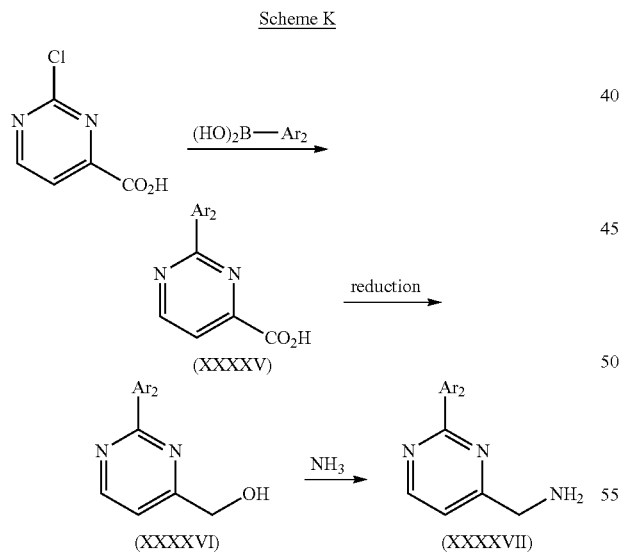

Referring to Scheme K, intermediates (XXXXVIII) were prepared from commercially available 2-chloropyrimidine-4-carboxcyclic acid. Intermediates (XXXXV) were formed by a procedure analogous to that described for the generation of compounds of Formulas (I) and (II) from intermediates (VIII) in Scheme A. Intermediates (XXXXVI) were generated by treating intermediates (XXXXV) in THF with isobutyl chloroformate and triethylamine followed by the addition of sodium borohydride. Intermediates (XXXXVII) were generated by treating intermediates (XXXXVI) in dichlochloromethane with methanesulfonyl chloride and triethylamine followed by treatment with 4 N ammonia in methanol. One skilled in the art will recognize that intermediates (XXXXVIII) are certain embodiments of intermediates (V) in Scheme A.

Where the above schemes produce compounds of Formulas (I) and (II) in a protected form, such as where an amine is protected with a suitable protecting group (such as tert-butyl-carbamoyl group), such intermediates are converted to compounds of Formulas (I) or (II) using generally known methods. For example, where the protecting group is a Boc group, deprotection is accomplished using an acid such as HCl or trifluoroacetic acid (TFA), in a solvent such as diethyl ether, dioxane, or $CH_2Cl_2$. Additional substituents on the —$NR^1R^2$ group are then installed by acylation or carbamoylation protocols using methods known in the art.

Compounds of Formulas (I) and (II) may be converted to their corresponding salts using methods described in the art. For example, an amine of Formulas (I) or (II) is treated with TFA, HCl, or citric acid in a solvent such as diethyl ether, $CH_2Cl_2$, THF, MeOH, or isopropanol to provide the corresponding salt form.

Compounds prepared according to the schemes described above may be obtained as single enantiomers, diastereomers, or regioisomers, by enantio-, diastero-, or regiospecific synthesis, or by resolution. Compounds prepared according to the schemes above may alternately be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation methods known to one skilled in the art, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

The following specific examples are provided to further illustrate the invention and various preferred embodiments.

Intermediate 1: [4-Oxo-4-(4-trifluoromethyl-phenyl)but-2-ynyl]-carbamic acid tert-butyl ester

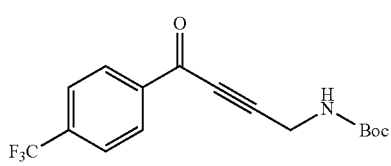 [SMILES: CC(C)(C)OC(=O)NCC#CC(=O)c1ccc(C(F)(F)F)cc1]

To a solution of N-boc-propargylamine (5.0 g, 32.2 mmol) in THF (100 mL) was added 4-trifluoromethylbenzoyl chloride (4.3 mL, 29.3 mmol), $PdCl_2(PPh_3)_2$ (0.18 g, 0.264 mmol), and CuI (0.17 g, 0.879 mmol). The mixture was allowed to stir for 5 min at rt, at which time freshly distilled triethylamine (5.1 mL, 36.6 mmol) was added. After 30 min the resulting mixture was filtered, concentrated, and purified by flash column chromatography, or FCC, to afford the title compound as a colorless solid (3.6 g, 35%). MS (ESI): mass calcd. for $C_{16}H_{16}F_3NO_3$, 327.1; m/z found, 328.2 $[M+H]^+$. $^1$H NMR (500 MHz, (DMSO) δ 8.26 (d, J=8.04 Hz, 2H), 7.96 (d, J=8.12 Hz, 2H), 7.62-7.54 (m, 1H), 4.14 (d, J=5.53 Hz, 2H), 1.42 (s, 9H).

Intermediate 2: [2-Benzylsulfanyl-6-(4-trifluoromethyl-phenyl)-pyrimidin-4-ylmethyl]-carbamic acid tert-butyl ester

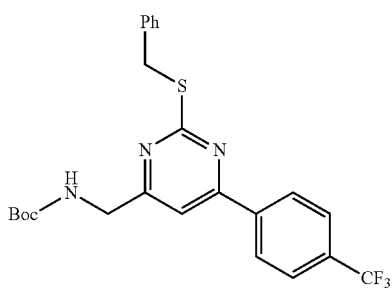 [SMILES: CC(C)(C)OC(=O)NCc1cc(-c2ccc(C(F)(F)F)cc2)nc(SCc2ccccc2)n1]

To a solution of [4-oxo-4-(4-trifluoromethyl-phenyl)but-2-ynyl]-carbamic acid tert-butyl ester (3.0 g, 9.17 mmol) and 2-benzyl-2-thiopseudo-urea hydrochloride (2.1 g, 10.1 mmol) in freshly distilled $CH_3CN$ (100 mL) was added $K_2CO_3$ (1.9 g, 13.8 mmol) at rt. After 12 h the resulting mixture was partitioned between $H_2O$ (75 mL) and DCM (50 mL). The layers were separated and the aqueous layer was extracted with DCM (2×50 mL). The combined organic layers were dried over $Na_2SO_4$, filtered and concentrated. The resulting solid was used without purification. MS (ESI): mass calcd. for $C_{24}H_{24}F_3N_3O_2S$, 475.2; m/z found, 476.3 $[M+H]^+$. $^1$H NMR ($CDCl_3$) δ 8.15 (d, J=8.14 Hz, 2H), 7.75 (d, J=8.28 Hz, 2H), 7.51-7.47 (m, 2H), 7.39-7.31 (m, 4H), 5.52 (s, 1H), 4.51 (s, 2H), 4.43 (d, J=5.48 Hz, 2H), 1.51 (s, 9H).

Intermediate 3: C-[2-Benzylsulfanyl-6-(4-trifluoromethyl-phenyl)-pyrimidin-4-yl]-methylamine

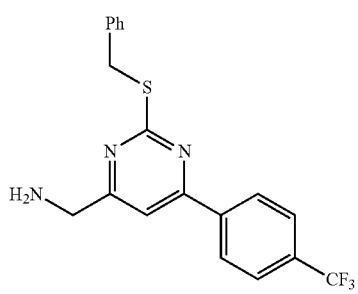 [SMILES: NCc1cc(-c2ccc(C(F)(F)F)cc2)nc(SCc2ccccc2)n1]

[2-benzylsulfanyl-6-(4-trifluoromethyl-phenyl)-pyrimidin-4-ylmethyl]-carbamic acid tert-butyl ester was diluted with 4N HCl in dioxane (20 mL) at rt. After 30 min. the mixture was concentrated and the resulting solid was used without further purification. MS (ESI): mass calcd. for $C_{19}H_{16}F_3N_3S$, 373.2; m/z found, 374.2 $[M+H]^+$.

Intermediate 4: 1-(4-Fluoro-benzenesulfonyl)-pyrrolidine-2S-carboxylic acid

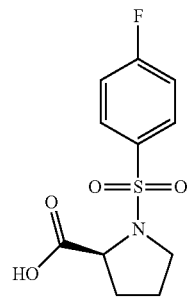 [SMILES: O=C(O)[C@@H]1CCCN1S(=O)(=O)c1ccc(F)cc1]

To a solution of L-proline (5.0 g, 43.4 mmol) in saturated aqueous sodium hydroxide (30 mL) at rt was added 4-fluorophenylsulfonyl chloride (10.1 g, 52.1 mmol) in THF (30 mL). The reaction mixture was stirred at rt for 16 hours at which point the pH of the reaction mixture was adjusted to about pH 2 with 2N HCl. The resulting mixture was extracted with EtOAc (3×50 mL). The organic layers were combined, washed with brine (2×10 mL), dried with $Na_2SO_4$, filtered and concentrated to provide the desired product as a white solid (11.3 g, 95%) that was used without further purification. $^1$H NMR (400 MHz, DMSO) δ 12.73 (s, 1H), 7.97-7.86 (m, 2H), 7.52-7.38 (m, 2H), 4.13 (dd, J=8.6, 4.1, 1H), 3.41-3.31 (m, 1H), 3.21-3.13 (m, 1H), 1.98-1.89 (m, 1H), 1.90-1.76 (m, 2H), 1.72-1.53 (m, 1H).

Intermediate 5 was prepared using methods analogous to those described for intermediate 4 using the appropriate sulfonyl chloride.

Intermediate 5: 1-(5-Chloro-thiophene-2-sulfonyl)-pyrrolidine-2S-carboxylic acid

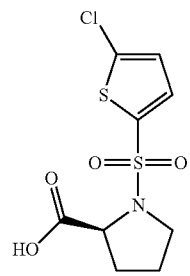 [SMILES: O=C(O)[C@@H]1CCCN1S(=O)(=O)c1ccc(Cl)s1]

$^1$H NMR (400 MHz, DMSO) δ 12.81 (s, 1H), 7.63 (d, J=4.1, 1H), 7.34-7.32 (m, 1H), 4.17-4.06 (m, 1H), 3.49-3.38 (m, 1H), 3.28-3.17 (m, 1H), 2.11-1.95 (m, 1H), 1.94-1.78 (m, 2H), 1.76-1.61 (m, 1H).

Intermediate 6: 1-(4-Fluoro-benzenesulfonyl)-pyrrolidine-2S-carboxylic acid [2-benzylsulfanyl-6-(4-trifluoromethyl-phenyl)-pyrimidin-4-ylmethyl]-amide

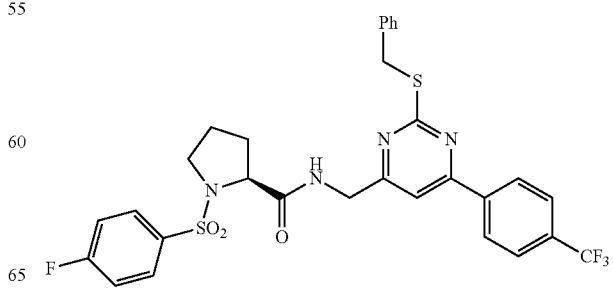

To a solution of C-[2-benzylsulfanyl-6-(4-trifluoromethyl-phenyl)-pyrimidin-4-yl]-methylamine (1.2 g, 3.19 mmol), 1-(4-Fluoro-benzenesulfonyl)-pyrrolidine-2S-carboxylic acid (0.88 g, 3.19 mmol), HOBt (0.87 g, 6.39 mmol), and EDC (1.2 g, 6.39 mmol) in DMF (30 mL) was added triethylamine (1.3 mL, 9.59 mmol) at rt. After 12 hours, the resulting mixture was partitioned between H$_2$O (30 mL) and EtOAc (30 mL). The layers were separated and the aqueous layer was extracted with EtOAc (2×30 mL). The combined organic layers were dried over Na$_2$SO$_4$, filtered, concentrated, and purified by FCC to afford the title compound as a colorless solid (1.3 g, 62%). MS (ESI): mass calcd. for C$_{30}$H$_{26}$F$_4$N$_4$O$_3$S$_2$, 630.1; m/z found, 631.2 [M+H]$^+$. $^1$H NMR (CDCl$_3$) δ 8.26 (d, J=8.16 Hz, 2H), 7.95-7.90 (m, 2H), 7.73 (d, J=8.28 Hz, 2H), 7.68-7.63 (m, 1H), 7.62 (s, 1H), 7.51-7.48 (m, 2H), 7.36-7.31 (m, 2H), 7.30-7.25 (m, 3H), 4.83 (dd, J=17.59, 7.08 Hz, 1H), 4.55 (s, 2H), 4.48 (dd, J=17.60, 5.06 Hz, 1H), 4.20-4.16 (m, 1H), 3.70-3.60 (m, 1H), 3.23-3.15 (m, 1H), 2.30-2.14 (m, 1H), 1.95-1.82 (m, 1H), 1.82-1.73 (m, 1H), 1.74-1.63 (m, 1H).

Intermediate 7: 1-(5-Chloro-thiophene-2-sulfonyl)-pyrrolidine-2S-carboxylic acid [2-benzylsulfanyl-6-(4-trifluoromethyl-phenyl)-pyrimidin-4-ylmethyl]-amide

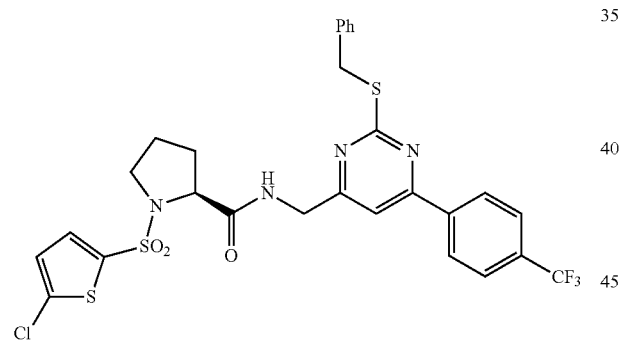

To a solution of C-[2-benzylsulfanyl-6-(4-trifluoromethyl-phenyl)-pyrimidin-4-yl]-methylamine (1.5 g, 3.99 mmol), 1-(5-Chloro-thiophene-2-sulfonyl)-pyrrolidine-2(S)-carboxylic acid (1.2 g, 3.99 mmol), HOBt (1.1 g, 7.99 mmol), and EDC (1.5 g, 7.99 mmol) in DMF (35 mL) was added triethylamine (1.6 mL, 11.9 mmol) at rt. After 12 hours, the resulting mixture was partitioned between H$_2$O (30 mL) and EtOAc (30 mL). The layers were separated and the aqueous layer was extracted with EtOAc (2×30 mL). The combined organic layers were dried over Na$_2$SO$_4$, filtered, concentrated, and purified by FCC to afford the title compound as a colorless solid (1.5 g, 57%). MS (ESI): mass calcd. for C$_{28}$H$_{24}$ClF$_3$N$_4$O$_3$S$_3$, 652.1; m/z found, 653.2 [M+H]$^+$.

Intermediate 8: 1-(4-Fluoro-benzenesulfonyl)-pyrrolidine-2S-carboxylic acid [2-phenylmethanesulfonyl-6-(4-trifluoromethyl-phenyl)-pyrimidin-4-ylmethyl]-amide

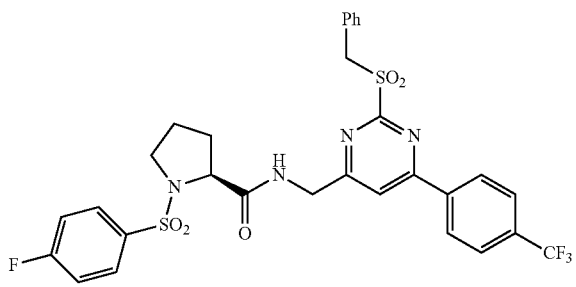 [SMILES: O=C(NCc1cc(-c2ccc(C(F)(F)F)cc2)nc(S(=O)(=O)Cc2ccccc2)n1)[C@@H]1CCCN1S(=O)(=O)c1ccc(F)cc1]

A solution of 1-(4-fluoro-benzenesulfonyl)-pyrrolidine-2S-carboxylic acid [2-benzylsulfanyl-6-(4-trifluoromethyl-phenyl)-pyrimidin-4-ylmethyl]-amide (1.3 g, 1.98 mmol) in DCM (20 mL) was cooled to 0° C. using an ice bath. Once at 0° C. m-CPBA (1.5 g, 6.94 mmol) was added and the resulting mixture was stirred for 12 hours while slowly warming to rt. The resulting mixture was poured over satd. aq. NaHCO$_3$ and extracted with DCM (2×25 mL). The combined organic layers were dried over NaSO$_4$, filtered, concentrated and purified by FCC to afford the title compound as a colorless solid (0.98 g, 75%). MS (ESI): mass calcd. for C$_{30}$H$_{26}$F$_4$N$_4$O$_5$S$_2$, 662.1; m/z found, 663.2 [M+H]$^+$. $^1$H NMR (CDCl$_3$) δ 8.36 (d, J=8.17 Hz, 2H), 8.19 (s, 1H), 8.07 (t, J=1.74, 1.74 Hz, 1H), 7.99-7.95 (m, 1H), 7.95-7.90 (m, 2H), 7.74 (d, J=8.31 Hz, 2H), 7.71-7.66 (m, 1H), 7.42-7.38 (m, 2H), 7.33-7.29 (m, 3H), 5.03 (dd, J=18.03, 7.75 Hz, 1H), 4.87 (d, J=1.94 Hz, 2H), 4.58 (dd, J=18.00, 5.02 Hz, 1H), 4.18 (dd, J=8.83, 3.58 Hz, 1H), 3.74-3.64 (m, 1H), 3.22-3.12 (m, 1H), 2.24-2.10 (m, 1H), 1.98-1.77 (m, 2H), 1.74-1.63 (m, 1H).

Intermediate 9: 1-(5-Chloro-thiophene-2-sulfonyl)-pyrrolidine-2S-carboxylic acid [2-phenylmethanesulfonyl-6-(4-trifluoromethyl-phenyl)-pyrimidin-4-ylmethyl]-amide

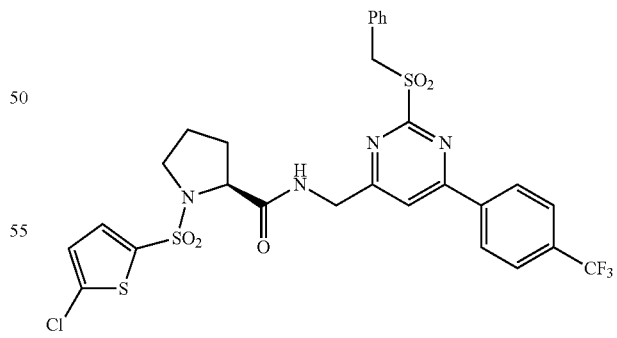

1-(5-chloro-thiophene-2-sulfonyl)-pyrrolidine-2S-carboxylic acid [2-benzylsulfanyl-6-(4-trifluoromethyl-phenyl)-pyrimidin-4-ylmethyl]-amide (1.5 g, 2.3 mmol) in DCM (25 mL) was cooled to 0° C. using an ice bath. Once at 0° C. m-CPBA (1.8 g, 8.05 mmol) was added and the resulting mixture was stirred for 12 hours while slowly warming to rt. The resulting mixture was poured over satd. aq. NaHCO$_3$ and extracted with DCM (2×25 mL). The combined organic layers were dried over NaSO$_4$, filtered, concentrated, and purified by FCC to afford the title compound as a colorless solid (1.5 g, 95%). MS (ESI): mass calcd. for C$_{28}$H$_{24}$ClF$_3$N$_4$O$_5$S$_3$, 684.1; m/z found, 685.2 [M+H]$^+$. $^1$H NMR (500 MHz, CDCl$_3$) δ 8.34 (d, J=8.20 Hz, 2H), 8.12 (s, 1H), 7.75 (d, J=8.33 Hz, 2H), 7.71-7.66 (m, 1H), 7.49 (d, J=4.02 Hz, 1H), 7.42-7.37 (m, 2H), 7.32-7.29 (m, 3H), 7.06 (d, J=4.02 Hz, 1H), 5.02 (dd, J=18.01, 7.70 Hz, 1H), 4.86 (d, J=3.23 Hz, 2H), 4.57 (dd, J=17.97, 4.98 Hz, 1H), 4.20 (dd, J=8.46, 3.47 Hz, 1H), 3.76-3.67 (m, 1H), 3.30-3.22 (m, 1H), 2.30-2.15 (m, 1H), 2.02-1.90 (m, 2H), 1.83-1.72 (m, 1H).

Intermediate 10: 2-[2-Chloro-6-(4-trifluoromethyl-phenyl)-pyrimidin-4-ylmethyl]-isoindole-1,3-dione

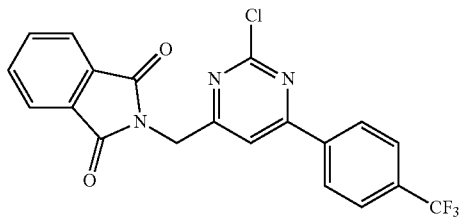 [SMILES: O=C1c2ccccc2C(=O)N1Cc1cc(-c2ccc(C(F)(F)F)cc2)nc(Cl)n1]

To a solution of 2-(2,6-dichloro-pyrimidin-4-ylmethyl)-isoindole-1,3-dione$^1$ (3.0 g, 9.7 mmol) in DME (40 mL) and H$_2$O (10 mL) was added 4-trifluoromethylboronic acid (1.8 g, 9.7 mmol), Pd(PPh$_3$)$_4$ (0.56 g, 0.48 mmol) and K$_3$PO$_4$ (3.1 g, 14.6 mmol). The mixture was allowed to stir for 12 hour at 90° C. The resulting mixture was cooled to rt then partitioned between H$_2$O (50 mL) and EtOAc (30 mL). The layers were separated and the aqueous layer was extracted with EtOAc (2×30 mL). The combined organic layers were dried over Na$_2$SO$_4$, filtered, concentrated, and purified by FCC to afford the title compound as a colorless solid (1.7 g, 43%). MS (ESI): mass calcd. for C$_{20}$H$_{11}$ClF$_3$N$_3$O$_2$, 417.0; m/z found, 418.1 [M+H]$^+$.

Intermediate 11: 2-[2-Pyridin-3-yl-6-(4-trifluoromethyl-phenyl)-pyrimidin-4-ylmethyl]-isoindole-1,3-dione

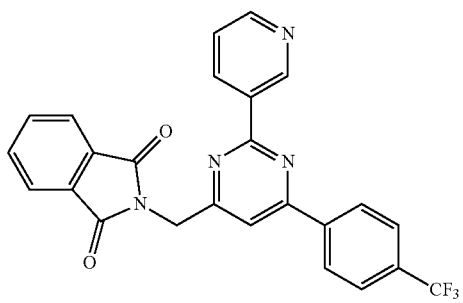 [SMILES: O=C1c2ccccc2C(=O)N1Cc1cc(-c2ccc(C(F)(F)F)cc2)nc(-c2cccnc2)n1]

To a solution of 2-[2-chloro-6-(4-trifluoromethyl-phenyl)-pyrimidin-4-ylmethyl]-isoindole-1,3-dione (0.30 g, 0.72 mmol) in DME (4 mL) and H$_2$O (1 mL) was added 3-pyridine boronic acid (0.09 g, 0.72 mmol), Pd(PPh$_3$)$_4$ (0.04 g, 0.04 mmol), and K$_3$PO$_4$ (0.21 g, 1.01 mmol). The resulting mixture was heated to 80° C. for 12 hours then allowed to cool to rt. At which time the mixture was partitioned between H$_2$O (5 mL) and EtOAc (5 mL). The layers were separated and the aqueous layer was extracted with EtOAc (2×5 mL). The organic layers were combined, dried over Na$_2$SO$_4$, filtered, concentrated and purified by FCC to afford the title compound as a colorless solid (0.11 g, 33%). MS (ESI): mass calcd. for C$_{25}$H$_{15}$F$_3$N$_4$O$_2$, 460.1; m/z found, 461.2 [M+H]$^+$.

Intermediate 12: C-[2-Pyridin-3-yl-6-(4-trifluoromethyl-phenyl)-pyrimidin-4-yl]-methylamine

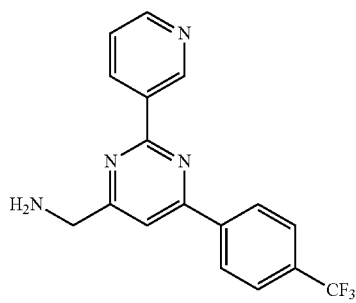 [SMILES: NCc1cc(-c2ccc(C(F)(F)F)cc2)nc(-c2cccnc2)n1]

To a solution of 2-[2-pyridin-3-yl-6-(4-trifluoromethyl-phenyl)-pyrimidin-4-ylmethyl]-isoindole-1,3-dione (0.1 g, 0.217 mmol) in ethanol (5 mL) was added hydrazine monohydrate (14 μl, 0.434 mmol) at rt. The resulting mixture was heated to 90° C. for 12 h then cooled to rt. The resulting mixture was concentrated and taken on crude to the next step. MS (ESI): mass calcd. for C$_{17}$H$_{13}$F$_3$N$_4$, 330.1; m/z found, 331.2 [M+H]$^+$.

Intermediate 13: 1-(4-Fluoro-benzenesulfonyl)-pyrrolidine-2S-carboxylic acid 3-bromo-benzylamide

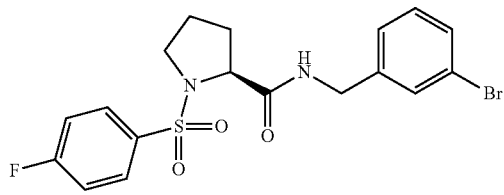 [SMILES: O=C(NCc1cccc(Br)c1)[C@@H]1CCCN1S(=O)(=O)c1ccc(F)cc1]

Intermediate 13 was prepared by a procedure similar to that described for the generation of intermediate 6 were in the appropriate commercially available amine and intermediate 4 were employed to provide the desired product. $^1$H NMR (400 MHz, CDCl$_3$) δ 7.91-7.84 (m, 2H), 7.46 (s, 1H), 7.43-7.39 (m, 1H), 7.29-7.19 (m, 4H), 4.56-4.41 (m, 2H), 4.18-4.06 (m, 1H), 3.57 (ddd, J=10.4, 7.2, 3.3, 1H), 3.17 (ddd, J=9.7, 6.4, 1H), 2.30-2.21 (m, 1H), 1.86-1.71 (m, 1H), 1.72-1.59 (m, 2H).

Intermediate 14: C-(4'-Trifluoromethyl-biphenyl-3-yl)-methylamine

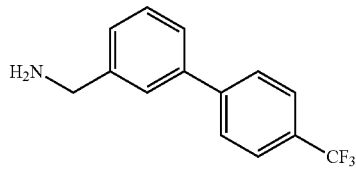

In a screw top flask 3-aminoethylphenylboronic acid hydrochloride (10.0 g, 53.4 mmol), 4-bromobenzotrifluoride (12.0, 53.4 mmol) and potassium phosphate (34.0 g, 160.2 mmol) were combined in dimethoxyethane (50 mL) and water (10 mL). The flask was flushed with $N_2$ and tetrakis (triphenylphosphine)palladium (3.10 g, 2.67 mmol) was added. The flask was sealed and heated to 120° C. for 12 hours. The reaction mixture was cooled to rt and $H_2O$ (100 mL) was added and the resulting mixture was extracted with EtOAc (3×25 mL). The organic phases were combined, washed with brine (20 mL), dried with $Na_2SO_4$, filtered, concentrated and purified by flash column chromatography (0%-20% of a 10% $NH_3$ in $CH_2Cl_2$ in $CH_2Cl_2$) providing the desired product as a brown oil (8.7 g, 69%). MS (ESI): mass calcd. for $C_{14}H_{12}F_3N$, 251.25; m/z found 252.1 [M+H]$^+$. $^1$H NMR (500 MHz, DMSO) δ 7.90 (d, J=8.1, 2H), 7.82 (d, J=8.2, 2H), 7.71 (s, 1H), 7.56 (d, J=7.5, 1H), 7.44 (t, J=7.5, 1H), 7.39 (d, J=7.5, 1H), 3.79 (s, 2H), 1.86 (s, 2H).

Intermediate 15: 2S-[(4'-Trifluoromethyl-biphenyl-3-ylmethyl)-carbamoyl]-pyrrolidine-1-carboxylic acid tert-butyl ester

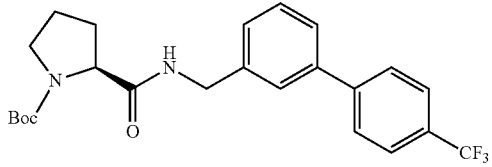 [SMILES: CC(C)(C)OC(=O)N1CCC[C@H]1C(=O)NCc1cccc(-c2ccc(C(F)(F)F)cc2)c1]

To a solution of N-(tert-butoxycarbonyl)-L-proline (86 mg, 0.40 mmol) in $CH_2Cl_2$ (5 mL) was added (Benzotriazol-1-yloxy)tris(dimethylamino)phosphonium hexafluorophosphate (177 mg, 0.40 mmol) and the reaction mixture was cooled to 0° C. Triethylamine (121 mg, 1.20 mmol) was added and the reaction mixture was stirred at 0° C. for 0.5 hours. C-(4'-trifluoromethyl-biphenyl-3-yl)-methylamine (100 mg, 0.40 mmol) was added, the reaction mixture was warmed to rt and stirred for 8 hours. $H_2O$ (10 mL) was added and the resulting mixture was extracted with $CH_2Cl_2$ (2×10 mL). The organic layers were combined, washed with brine (5 mL), dried with $Na_2SO_4$, filtered, concentrated and purified by flash column chromatography (0%-70% EtOAc) to provided the desired product (93 mg, 54%). MS (ESI): mass calcd. for $C_{24}H_{27}F_3N_2O_3$, 448.48; m/z found 471.2 [M+Na]. $^1$H NMR (400 MHz, DMSO) δ 8.43 (s, 1H), 7.85 (t, J=19.7, 4H), 7.63 (dd, J=20.8, 10.7, 2H), 7.44 (d, J=6.9, 1H), 7.33 (s, 1H), 4.36 (d, J=17.7, 2H), 4.12 (d, J=20.6, 1H), 3.50-3.35 (m, 1H), 3.35-3.21 (m, 1H), 2.21-2.03 (m, 1H), 1.92-1.69 (m, 3H), 1.42-1.12 (m, 9H).

Intermediates 16 to 17 were prepared using methods analogous to those described for intermediate 15, wherein the appropriate acids were employed to provide the desired products.

Intermediate 16: 2S-[(4'-Trifluoromethyl-biphenyl-3-ylmethyl)-carbamoyl]-3-aza-1S,5R-bicyclo[3.1.0]hexane-3-carboxylic acid tert-butyl ester

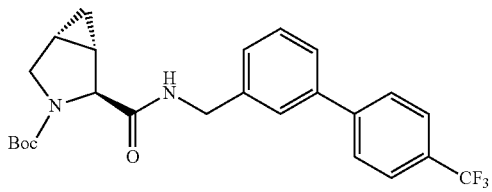 [SMILES: CC(C)(C)OC(=O)N1C[C@@H]2C[C@@H]2[C@H]1C(=O)NCc1cccc(-c2ccc(C(F)(F)F)cc2)c1]

MS (ESI): mass calcd. for $C_{25}H_{27}F_3N_2O_3$, 460.49; m/z found 483.2 [M+Na]. $^1$H NMR (400 MHz, DMSO) δ 8.48-8.27 (m, 1H), 8.04-7.54 (m, 6H), 7.51-7.40 (m, 1H), 7.40-7.28 (m, 1H), 4.31 (d, J=65.0, 3H), 3.47 (s, 1H), 3.43-3.35 (m, 1H), 1.92-1.78 (m, 1H), 1.67-1.52 (m, 1H), 1.42-1.11 (m, 9H), 0.79-0.64 (m, 1H), 0.64-0.46 (m, 1H).

Intermediate 17: 2S-[(4'-Trifluoromethyl-biphenyl-3-ylmethyl)-carbamoyl]-2,5-dihydro-pyrrole-1-carboxylic acid tert-butyl ester

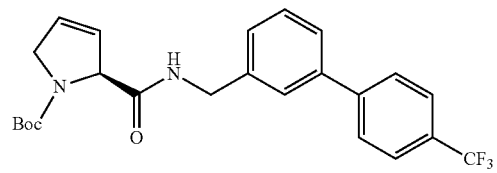 [SMILES: CC(C)(C)OC(=O)N1CC=C[C@H]1C(=O)NCc1cccc(-c2ccc(C(F)(F)F)cc2)c1]

MS (ESI): mass calcd. for $C_{24}H_{25}F_3N_2O_3$, 446.46; m/z found 469.2 [M+Na]. $^1$H NMR (500 MHz, DMSO) δ 8.60-8.52 (m, 1H), 7.95-7.78 (m, 4H), 7.68-7.55 (m, 2H), 7.50-7.40 (m, 1H), 7.39-7.28 (m, 1H), 6.03-5.96 (m, 1H), 5.83-5.71 (m, 1H), 4.93-4.77 (m, J=36.4, 1H), 4.47-4.25 (m, 2H), 4.21-4.04 (m, 2H), 1.42-1.17 (m, 9H).

Intermediate 18: 1-(4'-Trifluoromethyl-biphenyl-3-yl)-ethanone

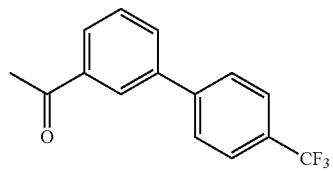 [SMILES: CC(=O)c1cccc(-c2ccc(C(F)(F)F)cc2)c1]

A mixture of 1-(3-bromo-phenyl)-ethanone (4.9 g, 24 mmol), 4-trifluoromethyl phenyl boronic acid (4.6 g, 24 mmol), tetrakis(triphenylphosphine)palladium(0) (1.4 g, 1.2 mmol), potassium phosphate (10 g, 49 mmol), 1,2-dimethoxyethane (50 mL) and water (10 mL) was heated to 80° C. under a blanket of nitrogen in a sealed tube. After 5 h, the mixture was partitioned between water (50 mL) and ethyl acetate (50 mL). The aqueous layer was extracted with ethyl acetate (3×50 mL). The combined organic layers were dried ($MgSO_4$), filtered, and concentrated. The residue was purified directly by FCC to afford a clear oil (5.6 g, 87%). MS (ESI): mass calcd. for $C_{15}H_{11}F_3O$, 264.0; m/z found, 265.1 [M+H]$^+$. $^1$H NMR (500 MHz, $CDCl_3$) δ 8.21 (t, J=1.6, 1H), 8.04-7.98 (m, 1H), 7.85-7.78 (m, 1H), 7.76-7.69 (m, 4H), 7.60 (t, J=7.7, 1H), 2.68 (s, 3H).

Intermediate 19: (2S)-2-Methyl-propane-2-sulfinic acid [1-(4'-trifluoromethyl-biphenyl-3-yl)-ethylidene]-amide

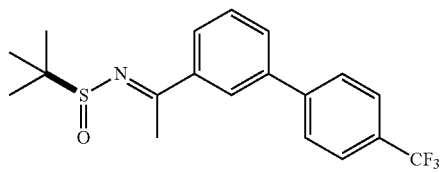 [SMILES: C/C(=N\[S@@](=O)C(C)(C)C)c1cccc(-c2ccc(C(F)(F)F)cc2)c1]

To a solution of 1-(4'-trifluoromethyl-biphenyl-3-yl)-ethanone (1.2 g, 4.7 mmol), (S)-(−)-2-methyl-2-propanesulfinamide (570 mg, 4.70 mmol), and THF (10 mL) was added titanium(IV) ethoxide (1.9 mL, 9.4 mmol). The resulting solution was heated to 75° C. in a sealed tube. After 12 h, the solution was cooled to rt and MeOH was added dropwise until gas evolution was no longer observed. The crude reaction mixture was poured into an equal volume of brine while being rapidly stirred. The resulting suspension was filtered through a plug of celite, and the filter cake was washed with ethyl acetate (20 mL). The filtrate was washed with brine, and brine layer was extracted with ethyl acetate (3×20 mL). The combined organic layers were dried (MgSO$_4$), filtered, and concentrated. The residue was purified directly by FCC to afford a white solid (1.1 g, 65%). MS (ESI): mass calcd. for $C_{19}H_{20}F_3NOS$, 367.1; m/z found, 368.1 $[M+H]^+$. $^1$H NMR (500 MHz, CDCl$_3$) δ 8.12 (s, 1H), 7.92 (d, J=7.8, 1H), 7.79-7.68 (m, 5H), 7.56 (t, J=7.8, 1H), 2.85 (s, 3H), 1.36 (s, 9H).

Intermediate 20: (1S,2S)-2-Methyl-propane-2-sulfinic acid [1-(4'-trifluoromethyl-biphenyl-3-yl)-ethyl]-amide

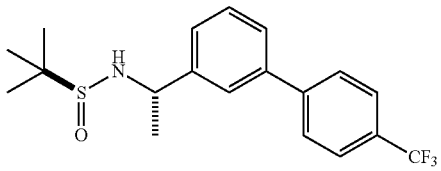 [SMILES: C[C@H](N[S@@](=O)C(C)(C)C)c1cccc(-c2ccc(C(F)(F)F)cc2)c1]

To a solution of 1-(4'-trifluoromethyl-biphenyl-3-yl)-ethanone (381 mg, 1.44 mmol), (S)-(−)-2-methyl-2-propanesulfinamide (175 mg, 1.44 mmol), and THF (3 mL) was added titanium(IV) ethoxide (0.6 mL, 2.88 mmol). The resulting solution was heated to 75° C. in a sealed tube. After 12 h, the solution was cooled to −50° C. and sodium borohydride was added in a single portion (163 mg, 4.32 mmol). The resulting mixture was allowed to warm to rt. After 12 h, MeOH was added dropwise until gas evolution was no longer observed. The crude reaction mixture was poured into an equal volume of brine while being rapidly stirred. The resulting suspension was filtered through a plug of celite, and the filter cake was washed with ethyl acetate (20 mL). The filtrate was washed with brine, and brine layer was extracted with ethyl acetate (3×20 mL). The combined organic layers were dried (MgSO$_4$), filtered, and concentrated. The residue was purified directly by FCC to afford a white solid (310 mg, 58%). MS (ESI): mass calcd. for $C_{19}H_{22}F_3NOS$, 369.1; m/z found, 370.1 $[M+H]^+$. $^1$H NMR (500 MHz, CDCl$_3$) δ 7.76-7.67 (m, 4H), 7.59 (t, J=1.7, 1H), 7.56-7.52 (m, 1H), 7.48 (t, J=7.6, 1H), 7.42 (d, J=7.6, 1H), 4.65 (qd, J=6.5, 3.1, 1H), 3.48 (d, J=2.7, 1H), 1.59 (d, J=6.6, 3H), 1.27 (s, 9H).

Intermediate 21 was prepared using methods analogous to those described for intermediate 20 substituting (R)-(−)-2-methyl-2-propanesulfinamide to provide the desired product.

Intermediate 21: (1R,2R)-2-Methyl-propane-2-sulfinic acid [1-(4'-trifluoromethyl-biphenyl-3-yl)-ethyl]-amide

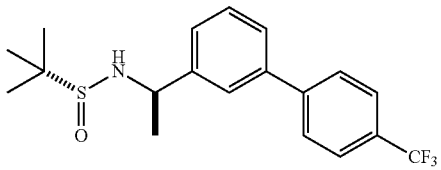 [SMILES: C[C@@H](N[S@](=O)C(C)(C)C)c1cccc(-c2ccc(C(F)(F)F)cc2)c1]

MS (ESI): mass calcd. for $C_{19}H_{22}F_3NOS$, 369.1; m/z found, 370.1 $[M+H]^+$. $^1$H NMR (500 MHz, CDCl$_3$) δ 7.75-7.68 (m, 4H), 7.59 (t, J=1.7, 1H), 7.56-7.52 (m, 1H), 7.48 (t, J=7.6, 1H), 7.44-7.39 (m, 1H), 4.65 (qd, J=6.5, 3.1, 1H), 3.49 (d, J=2.6, 1H), 1.59 (d, J=6.6, 3H), 1.27 (s, 9H).

Intermediate 22: 1-Methyl-1-(4'-trifluoromethyl-biphenyl-3-yl)-ethylamine trifluoromethyl acetic acid

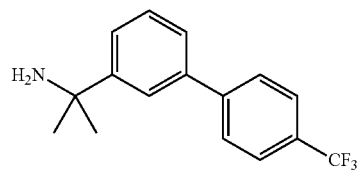 [SMILES: CC(C)(N)c1cccc(-c2ccc(C(F)(F)F)cc2)c1]

To a solution of (S)-2-methyl-propane-2-sulfinic acid [1-(4'-trifluoromethyl-biphenyl-3-yl)-ethylidene]-amide (346 mg, 0.94 mmol) and toluene (4 mL) was added trimethylaluminum (0.5 mL, 1.0 mmol; 2M in toluene) at −78° C. After 20 min, methylmagnesium bromide (0.7 mL, 2.1 mmol; 3M solution in diethyl ether) was added dropwise and resulting solution was allowed to warm to rt. After 12 h, the mixture was quenched with aqueous saturated sodium bicarbonate (10 mL) and the solids were removed by filtration. The resulting filtrate was concentrated and the residue was re-dissolved in MeOH (10 mL) and treated with 4N HCl in dioxane (0.5 mL, 2.1 mmol). After 1 h, the solution was concentrated and purified by preparative reverse-phase HPLC to afford a white solid (150 mg, 41%). MS (ESI): mass calcd. for $C_{16}H_{16}F_3N$, 279.1; m/z found, 280.1 $[M+H]^+$.

Intermediate 23: (2S)-4,4-Difluoro-pyrrolidine-2-carboxylic acid (4'-trifluoromethyl-biphenyl-3-ylmethyl)-amide hydrochloride

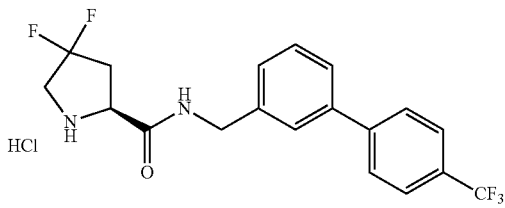 [SMILES: Cl ; O=C(NCc1cccc(-c2ccc(C(F)(F)F)cc2)c1)[C@@H]1CC(F)(F)CN1]

To a mixture of (2S)-4,4-difluoro-pyrrolidine-1,2-dicarboxylic acid 1-tert-butyl ester (1.8 g, 7.3 mmol), C-(4'-trifluoromethyl-biphenyl-3-yl)-methylamine (1.8 g, 7.3 mmol), N-(3-dimethylamniopropyl)-N'-ethylcarbodiimide hydrochloride (2.1 g, 11 mmol), 1-hydroxybenzotriazole (1.5 g, 11 mmol), and DMF (10 mL) was added Et$_3$N (2 mL, 15 mmol). After 12 h, the mixture was partitioned between water (50 mL) and ethyl acetate (50 mL). The aqueous layer was extracted with ethyl acetate (3×50 mL). The combined organic layers were dried (MgSO$_4$), filtered, and concentrated. The residue was purified directly by FCC to afford a clear oil (3.0 g, 86%). MS (ESI): mass calcd. for $C_{24}H_{25}F_5N_2O_3$, 484.1; m/z found, 485.2 $[M+H]^+$.

To the clear oil (3.0 g, 6.2 mmol) was added 4N HCl in dioxane (20 mL). After 15 min the resulting solution was concentrated and the resulting crude residue was used for further studies (2.3 g, 97%). MS (ESI): mass calcd. for $C_{19}H_{17}F_5N_2O$, 384.1; m/z found, 385.1 [M+H]$^+$.

Intermediate 24:
2-(4-Trifluoromethyl-phenyl)-isonicotinonitrile

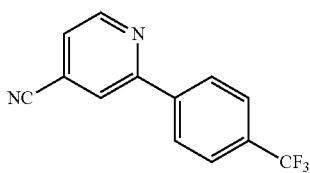

To a suspension of 2-chloro-4-pyridinecarbonitrile (0.50 g, 3.61 mmol), $Cs_2CO_3$ (1.70 g, 7.22 mmol) and 4-(trifluoromethyl)phenylboronic acid (0.82 g, 3.61 mmol) in dioxane (18 mL) was added palladium acetate (0.02 g, 0.07 mmol) and 2-dicyclohexylphosphino-2',4',6'-triisopropylbiphenyl (0.07 g, 0.14 mmol). The reaction vessel was sealed and heated to 100° C. for 4 hours and cooled to rt. The reaction mixture was filtered through a pad of celite, concentrated and purified by FCC (0%-100% EtOAc in hexane) to provide the desired product (0.69 g, 78%). MS (ESI): mass calcd. for $C_{13}H_7F_3N_2$, 248.2; m/z found 249.1 [M+H]$^+$. $^1$H NMR (400 MHz, DMSO) δ 9.00-8.92 (m, 1H), 8.63-8.57 (m, 1H), 8.38 (d, J=8.1, 2H), 7.94-7.85 (m, 3H).

Intermediate 25:
2-(4-Trifluoromethoxy-phenyl)-isonicotinonitrile

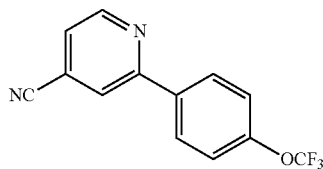 [SMILES: N#Cc1ccnc(-c2ccc(OC(F)(F)F)cc2)c1]

Intermediate 25 was prepared using methods analogous to that described for intermediate 24 substituting 4-(trifluoromethoxy)phenylboronic acid as a reagent. MS (ESI): mass calcd. for $C_{13}H_7F_3N_2O$, 264.2; m/z found 265.1 [M+H]$^+$. $^1$H NMR (400 MHz, DMSO) δ 8.93 (dd, J=5.0, 0.9, 1H), 8.58-8.51 (m, 1H), 8.33-8.25 (m, 2H), 7.86 (dd, J=5.0, 1.4, 1H), 7.52 (dd, J=8.9, 0.9, 2H).

Intermediate 26: [2-(4-Trifluoromethyl-phenyl)-pyridin-4-ylmethyl]-carbamic acid tert-butyl ester

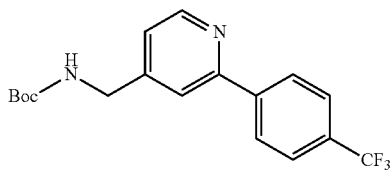 [SMILES: CC(C)(C)OC(=O)NCc1ccnc(-c2ccc(C(F)(F)F)cc2)c1]

To a solution of 2-(4-trifluoromethyl-phenyl)-isonicotinonitrile (1.40 g, 5.64 mmol) in ethanol (40 mL) was added 1.25 M HCl in ethanol (4.5 mL, 5.64 mmol) and Pd/C (0.14 g) and the reaction mixture was placed under a 50 psi hydrogen atmosphere for 12 hours. The reaction mixture was filtered through a pad of celite and concentrated. The resulting residue was re-dissolved in THF (10 mL) followed by addition of di-tert-butyl dicarbonate (1.85 g, 8.46 mmol) and triethylamine (1.6 mL, 11.28 mmol). The reaction mixture was stirred for 8 hours and water was added. The resulting mixture was extracted with EtOAc. The organic layers were combined, concentrated and purified by FCC (0-100% EtOAc in hexane) to provide the desired product (1.30 g, 65%). MS (ESI): mass calcd. for $C_{18}H_{19}F_3N_2O_2$, 352.35; m/z found 353.2 [M+H]$^+$. $^1$H NMR (500 MHz, CDCl3) δ 8.66 (d, J=5.0, 1H), 8.10 (d, J=8.0, 2H), 7.72 (d, J=8.1, 2H), 7.66 (s, 1H), 7.21 (d, J=5.0, 1H), 4.41 (s, 2H), 1.49 (s, 9H).

Intermediate 27 was prepared using methods analogous to those described for intermediate 26

Intermediate 27: [2-(4-Trifluoromethoxy-phenyl)-pyridin-4-ylmethyl]-carbamic acid tert-butyl ester

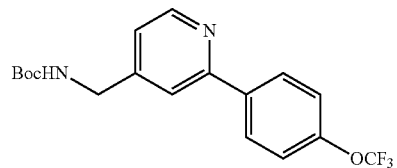 [SMILES: CC(C)(C)OC(=O)NCc1ccnc(-c2ccc(OC(F)(F)F)cc2)c1]

MS (ESI): mass calcd. for $C_{18}H_{19}F_3N_2O_3$, 368.35; m/z found 369.2 [M+H]$^+$. $^1$H NMR (500 MHz, EtOD) δ 8.61 (d, J=4.8, 1H), 8.17 (d, J=8.8, 2H), 7.84 (s, 1H), 7.58-7.52 (m, 1H), 7.49 (d, J=8.7, 2H), 7.23 (d, J=4.8, 1H), 4.24 (d, J=5.8, 2H), 1.41 (s, 9H).

Intermediate 28: 2S-{[2-(4-Trifluoromethyl-phenyl)-pyridin-4-ylmethyl]-carbamoyl}-pyrrolidine-1-carboxylic acid tert-butyl ester

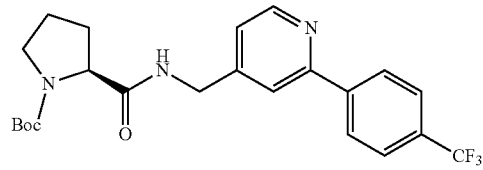 [SMILES: CC(C)(C)OC(=O)N1CCC[C@H]1C(=O)NCc1ccnc(-c2ccc(C(F)(F)F)cc2)c1]

To a solution of [2-(4-Trifluoromethyl-phenyl)-pyridin-4-ylmethyl]-carbamic acid tert-butyl ester (134 mg, 0.40 mmol) in DCM (6 mL) was added 4 M HCl in dioxane (2 mL). The reaction mixture was stirred for 4 hours and concentrated. The resulting residue was taken up in DCM (5 mL) and added to a solution of (benzotriazol-1-yloxy)tris(dimethylamino) phosphonium hexafluorophosphate (175 mg, 0.40 mmol), triethylamine (240 mg, 2.38 mmol) and N-boc-L-proline (85 mg, 0.40 mmol) in DCM (5 mL) and the reaction mixture was stirred for 12 hours. Water was added and the reaction mixture was extracted with DCM. The organic layers were combined, dried with Na2SO4, filtered, concentrated and purified by FCC (0-100% EtOAc in hexane) to provide the desired product (143 mg, 80%). MS (ESI): mass calcd. for $C_{23}H_{26}F_3N_3O_3$, 449.47; m/z found 450.2 [M+H]$^+$. $^1$H NMR (400 MHz, DMSO) δ 8.70-8.52 (m, 2H), 8.36 (d, J=8.1, 1H), 8.25 (d, J=8.2, 1H), 7.97 (d, J=16.6, 1H), 7.88 (d, J=8.3, 1H), 7.83 (d, J=8.3, 1H), 7.37-7.26 (m, 1H), 4.52-4.29 (m, 2H), 4.23-4.06 (m, 1H), 3.51-3.38 (m, 1H), 3.38-3.23 (m, 1H), 2.27-2.05 (m, 1H), 1.97-1.69 (m, 3H), 1.44-1.21 (m, 9H).

Intermediates 29 to 33 were synthesized using methods analogous to those described for intermediate 28 substituting the appropriate acids to provide the desired products.

Intermediate 29: 4,4-Difluoro-2S-{[2-(4-trifluoromethyl-phenyl)-pyridin-4-ylmethyl]-carbamoyl}-pyrrolidine-1-carboxylic acid tert-butyl ester

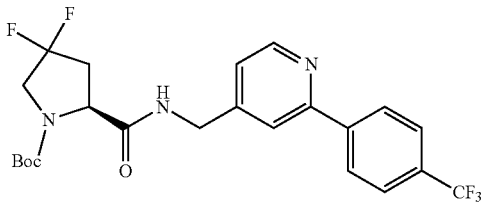 [SMILES: CC(C)(C)OC(=O)N1CC(F)(F)C[C@H]1C(=O)NCc1ccnc(-c2ccc(C(F)(F)F)cc2)c1]

MS (ESI): mass calcd. for $C_{23}H_{24}F_5N_3O_3$, 485.45; m/z found 486.2 [M+H]$^+$. $^1$H NMR (500 MHz, DMSO) δ 8.84-8.73 (m, 1H), 8.68-8.56 (m, 1H), 8.37-8.20 (m, 2H), 8.01-7.85 (m, 2H), 7.85-7.78 (m, 1H), 7.35-7.28 (m, 1H), 4.57-4.25 (m, 3H), 3.94-3.64 (m, 2H), 2.95-2.76 (m, 1H), 2.45-2.29 (m, 1H), 1.58-1.19 (m, 9H).

Intermediate 30: 2S-{[2-(4-Trifluoromethyl-phenyl)-pyridin-4-ylmethyl]-carbamoyl}-2,5-dihydro-pyrrole-1-carboxylic acid tert-butyl ester

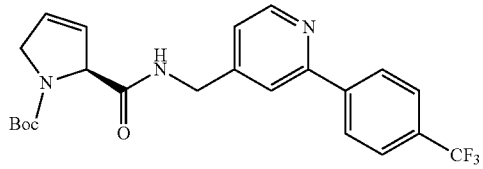

MS (ESI): mass calcd. for $C_{23}H_{24}F_3N_3O_3$, 447.54; m/z found 448.2 [M+H]$^+$. $^1$H NMR (400 MHz, DMSO) δ 8.73-8.58 (m, 2H), 8.40-8.20 (m, 2H), 8.01-7.91 (m, 1H), 7.91-7.80 (m, 2H), 7.36-7.27 (m, 1H), 6.10-5.96 (m, 1H), 5.88-5.72 (m, 1H), 4.95-4.76 (m, 1H), 4.51-4.26 (m, 2H), 4.29-4.07 (m, 2H), 1.47-1.22 (m, 9H).

Intermediate 31: 2S-{[2-(4-Trifluoromethoxy-phenyl)-pyridin-4-ylmethyl]-carbamoyl}-pyrrolidine-1-carboxylic acid tert-butyl ester

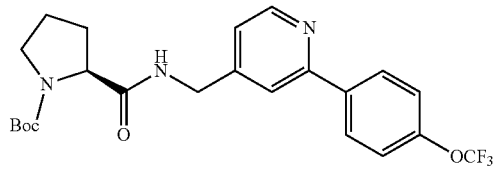 [SMILES: CC(C)(C)OC(=O)N1CCC[C@H]1C(=O)NCc1ccnc(-c2ccc(OC(F)(F)F)cc2)c1]

MS (ESI): mass calcd. for $C_{23}H_{26}F_3N_3O_4$, 465.47; m/z found 466.2 [M+H]$^+$. $^1$H NMR (400 MHz, DMSO) δ 8.65-8.51 (m, 2H), 8.27 (d, J=8.8, 1H), 8.15 (d, J=8.8, 1H), 7.97-7.84 (m, 1H), 7.50 (d, J=8.3, 1H), 7.45 (d, J=8.2, 1H), 7.32-7.22 (m, 1H), 4.52-4.25 (m, 2H), 4.23-4.06 (m, 1H), 3.50-3.22 (m, 2H), 2.26-2.05 (m, 1H), 1.93-1.71 (m, 3H), 1.44-1.19 (m, 9H).

Intermediate 32: 4,4-Difluoro-2S-{[2-(4-trifluoromethoxy-phenyl)-pyridin-4-ylmethyl]-carbamoyl}-pyrrolidine-1-carboxylic acid tert-butyl ester

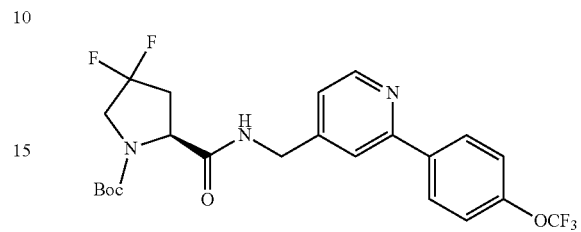

MS (ESI): mass calcd. for $C_{23}H_{24}F_5N_3O_4$, 501.45; m/z found 502.2 [M+H]$^+$. $^1$H NMR (600 MHz, DMSO) δ 8.83-8.73 (m, 1H), 8.60 (dd, J=19.8, 5.0, 1H), 8.24 (d, J=8.7, 1H), 8.16 (d, J=8.7, 1H), 7.90 (d, J=18.0, 1H), 7.50 (d, J=8.4, 1H), 7.45 (d, J=8.3, 1H), 7.28 (d, J=5.0, 1H), 4.51-4.26 (m, 3H), 3.89-3.68 (m, 2H), 2.73 (m, 1H), 2.31 (m, 1H), 1.44-1.19 (m, 9H).

Intermediate 33: 2S-{[2-(4-Trifluoromethoxy-phenyl)-pyridin-4-ylmethyl]-carbamoyl}-2,5-dihydro-pyrrole-1-carboxylic acid tert-butyl ester

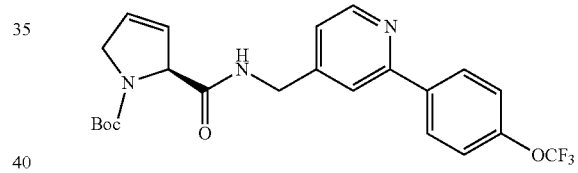

MS (ESI): mass calcd. for $C_{23}H_{24}F_3N_3O_4$, 463.45; m/z found 464.2 [M+H]. $^1$H NMR (600 MHz, DMSO) δ 8.66 (t, J=5.6, 1H), 8.59 (dd, J=22.0, 5.0, 1H), 8.27 (d, J=8.8, 1H), 8.15 (d, J=8.8, 1H), 7.89 (d, J=27.4, 1H), 7.50 (d, J=8.2, 1H), 7.45 (d, J=8.2, 1H), 7.29-7.23 (m, 1H), 6.07-5.96 (m, 1H), 5.87-5.80 (m, 1H), 4.96-4.81 (m, 1H), 4.45-4.29 (m, 2H), 4.24-4.06 (m, 2H), 1.45-1.21 (m, 9H).

Intermediate 34: 2-[(4-Chloro-pyridin-2-ylmethyl)-carbamoyl]-pyrrolidine-1-carboxylic acid tert-butyl ester

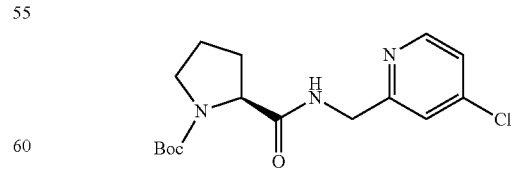

To a solution of N-boc-L-proline (0.50 g, 2.3 mmol) and (benzotriazol-1-yloxy)tris(dimethylamino)phosphonium hexafluorophosphate (1.02 g, 2.3 mmol) in DCM was added triethylamine (1.40 g, 13.8 mmol) and the reaction mixture was stirred for 30 minutes. C-(4-Chloro-pyridin-2-yl)-methylamine dihydrogenchloride (0.50 g, 2.30 mmol) was added and the reaction mixture was stirred for 12 hours. Water was added and the reaction mixture was extracted with DCM. The organic layers were combined, dried with $Na_2SO_4$, filtered, concentrated and purified by FCC (0-60% EtOAc in hexane) to provide the desired product (0.93 g, 93%). $^1H$ NMR (400 MHz, DMSO) δ 8.62-8.51 (m, 1H), 8.47 (dd, J=9.8, 5.3, 1H), 7.56-7.31 (m, 2H), 4.45-4.27 (m, 2H), 4.20-4.09 (m, 1H), 3.51-3.24 (m, 2H), 2.26-2.05 (m, 1H), 1.95-1.69 (m, 3H), 1.48-1.24 (m, 9H).

Intermediates 35 to 36 were prepared using methods analogous to those described for intermediate 34.

Intermediate 35: 2-[(4-Chloro-pyridin-2-ylmethyl)-carbamoyl]-2,5-dihydro-pyrrole-1-carboxylic acid tert-butyl ester

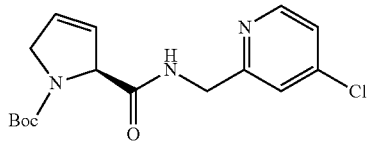 [SMILES: CC(C)(C)OC(=O)N1CC=C[C@H]1C(=O)NCc1cc(Cl)ccn1]

$^1H$ NMR (400 MHz, DMSO) δ 8.70-8.62 (m, 1H), 8.47 (dd, J=9.5, 5.3, 1H), 7.52-7.31 (m, 2H), 6.06-5.95 (m, 1H), 5.85-5.71 (m, 1H), 4.92-4.80 (m, 1H), 4.48-4.25 (m, 2H), 4.24-4.06 (m, 2H), 1.51-1.25 (m, 9H).

Intermediate 36: 2-[(4-Chloro-pyridin-2-ylmethyl)-carbamoyl]-4,4-difluoro-pyrrolidine-1-carboxylic acid tert-butyl ester

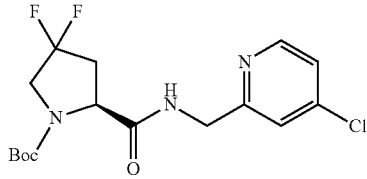 [SMILES: CC(C)(C)OC(=O)N1CC(F)(F)C[C@H]1C(=O)NCc1cc(Cl)ccn1]

$^1H$ NMR (400 MHz, DMSO) δ 8.78 (dd, J=10.1, 5.0, 1H), 8.48 (dd, J=7.9, 5.5, 1H), 7.55-7.30 (m, 2H), 4.48-4.29 (m, 3H), 3.92-3.66 (m, 2H), 2.98-2.73 (m, 1H), 2.38 (qd, J=14.1, 5.1, 1H), 1.49-1.25 (m, 9H).

Intermediates 37 to 43 were prepared using methods analogous to those described for intermediate 24 substituting the appropriate boronic acid to provide the desired product.

Intermediate 37: 2S-{[4-(4-Trifluoromethyl-phenyl)-pyridin-2-ylmethyl]-carbamoyl}-pyrrolidine-1-carboxylic acid tert-butyl ester

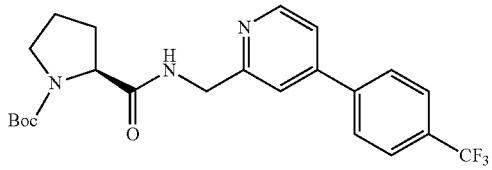

MS (ESI): mass calcd. for $C_{23}H_{26}F_3N_3O_3$, 449.47; m/z found 450.2 $[M+H]^+$. $^1H$ NMR (400 MHz, DMSO) δ 8.71-8.43 (m, 2H), 8.13-7.59 (m, 6H), 4.58-4.31 (m, 2H), 4.25-4.08 (m, 1H), 3.50-3.19 (m, 2H), 2.24-2.04 (m, 1H), 1.95-1.68 (m, 3H), 1.39-1.09 (m, 9H).

Intermediate 38: 2S-{[4-(4-Trifluoromethoxy-phenyl)-pyridin-2-ylmethyl]-carbamoyl}-pyrrolidine-1-carboxylic acid tert-butyl ester

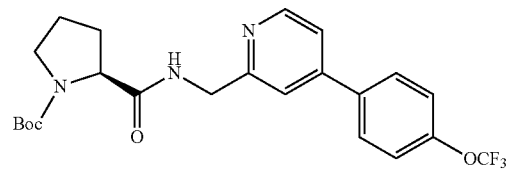 [SMILES: CC(C)(C)OC(=O)N1CCC[C@H]1C(=O)NCc1cc(-c2ccc(OC(F)(F)F)cc2)ccn1]

MS (ESI): mass calcd. for $C_{23}H_{26}F_3N_3O_4$, 465.47; m/z found 466.2 $[M+H]^+$. $^1H$ NMR (400 MHz, DMSO) δ 8.65-8.46 (m, 2H), 8.04-7.81 (m, 2H), 7.78-7.57 (m, 2H), 7.57-7.44 (m, 2H), 4.58-4.28 (m, 2H), 4.24-4.06 (m, 1H), 3.49-3.20 (m, 2H), 2.23-2.05 (m, 1H), 1.95-1.66 (m, 3H), 1.44-1.10 (m, 9H).

Intermediate 39: 2S-{[4-(4-Trifluoromethoxy-phenyl)-pyridin-2-ylmethyl]-carbamoyl}-2,5-dihydro-pyrrole-1-carboxylic acid tert-butyl ester

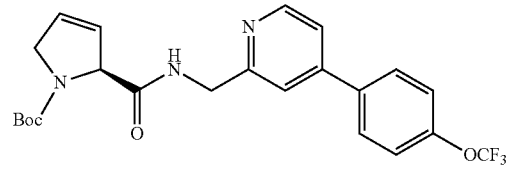 [SMILES: CC(C)(C)OC(=O)N1CC=C[C@H]1C(=O)NCc1cc(-c2ccc(OC(F)(F)F)cc2)ccn1]

MS (ESI): mass calcd. for $C_{23}H_{24}F_3N_3O_4$, 463.45; m/z found 464.2 $[M+H]^+$. $^1H$ NMR (400 MHz, DMSO) δ 8.77-8.51 (m, 2H), 8.05-7.28 (m, 6H), 6.11-5.95 (m, 1H), 5.92-5.70 (m, 1H), 5.03-4.77 (m, 1H), 4.53-4.32 (m, 2H), 4.29-3.98 (m, 2H), 1.43-1.09 (m, 9H).

Intermediate 40: 4,4-Difluoro-2S-{[4-(4-trifluoromethyl-phenyl)-pyridin-2-ylmethyl]-carbamoyl}-pyrrolidine-1-carboxylic acid tert-butyl ester

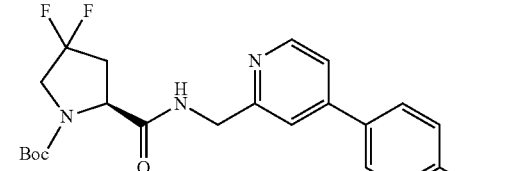

MS (ESI): mass calcd. for $C_{23}H_{24}F_5N_3O_3$, 485.45; m/z found 486.2 $[M+H]^+$. $^1H$ NMR (400 MHz, DMSO) δ 8.93-

8.56 (m, 2H), 8.09-7.61 (m, 6H), 4.63-4.32 (m, 3H), 3.92-3.67 (m, 2H), 2.98-2.73 (m, 1H), 2.48-2.28 (m, 1H), 1.42-1.12 (m, 9H).

Intermediate 41: 4,4-Difluoro-2S-{[4-(4-trifluoromethoxy-phenyl)-pyridin-2-ylmethyl]-carbamoyl}-pyrrolidine-1-carboxylic acid tert-butyl ester

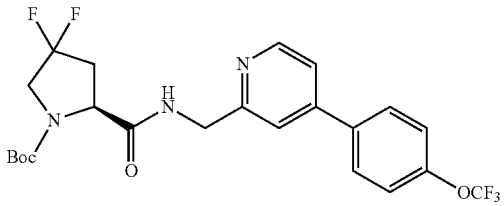 [SMILES: CC(C)(C)OC(=O)N1CC(F)(F)C[C@H]1C(=O)NCc1cc(-c2ccc(OC(F)(F)F)cc2)ccn1]

MS (ESI): mass calcd. for $C_{23}H_{24}F_5N_3O_4$, 501.45; m/z found 502.2 [M+H]+. 1H NMR (400 MHz, DMSO) δ 8.90-8.49 (m, 2H), 8.05-7.36 (m, 6H), 4.60-4.32 (m, 3H), 3.95-3.67 (m, 2H), 2.94-2.71 (m, 1H), 2.48-2.30 (m, 1H), 1.42-1.09 (m, 9H).

Intermediate 42: 2S-{[4-(4-Trifluoromethyl-phenyl)-pyridin-2-ylmethyl]-carbamoyl}-2,5-dihydro-pyrrole-1-carboxylic acid tert-butyl ester

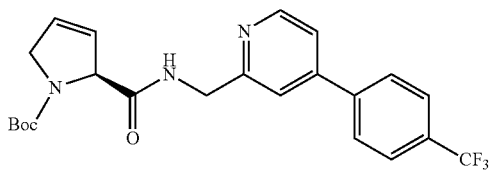

MS (ESI): mass calcd. for $C_{23}H_{24}F_3N_3O_3$, 447.45; m/z found 448.2 [M+H]+. 1H NMR (400 MHz, DMSO) δ 8.79-8.57 (m, 2H), 8.11-7.59 (m, 5H), 6.08-5.95 (m, 1H), 5.88-5.75 (m, 1H), 5.02-4.74 (m, 1H), 4.54-4.36 (m, 2H), 4.27-4.07 (m, 2H), 1.42-1.13 (m, 9H).

Intermediate 43: 2S-{[4-(4-Trifluoromethoxy-phenyl)-pyridin-2-ylmethyl]-carbamoyl}-2,5-dihydro-pyrrole-1-carboxylic acid tert-butyl ester

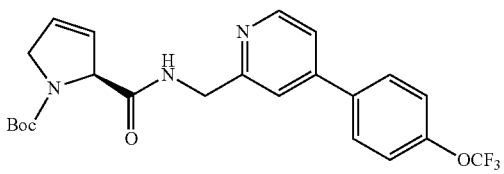 [SMILES: CC(C)(C)OC(=O)N1CC=C[C@H]1C(=O)NCc1cc(-c2ccc(OC(F)(F)F)cc2)ccn1]

MS (ESI): mass calcd. for $C_{23}H_{24}F_3N_3O_4$, 463.45; m/z found 464.2 [M+H]+. 1H NMR (400 MHz, DMSO) δ 8.77-8.51 (m, 2H), 8.05-7.28 (m, 5H), 6.11-5.95 (m, 1H), 5.92-5.70 (m, 1H), 5.03-4.77 (m, 1H), 4.53-4.32 (m, 2H), 4.29-3.98 (m, 2H), 1.43-1.09 (m, 9H).

Intermediate 44: 6-(4-Trifluoromethyl-phenyl)-pyrimidine-4-carbonitrile

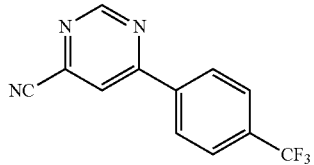

Nitrogen gas was bubbled through a suspension of 4,6-dichloropyrimidine (10.0 g, 67.1 mmol), 4-(trifluoromethyl)phenylboronic acid (12.7 g, 67.1 mmol) and $K_3PO_4$ (28.5 g, 134.2 mmol) in dimethoxyethane (280 mL) and $H_2O$ (70 mL) for 30 minutes. Tetrakis(triphenylphosphine)-palladium (3.99 g, 3.4 mmol) was added and the reaction mixture was heated to 90° C. for 24 hours. The reaction mixture was cooled to rt, $H_2O$ (200 mL) was added and the resulting mixture was extracted with EtOAc (2×100 mL). The organic layers were combined, washed with brine (2×50 mL), dried with $Na_2SO_4$, filtered and purified by flash column chromatography (100% $CH_2Cl_2$) to provide the desire product as an inseparable ~3:1 mixture of the desired and bisarylated products (10.37 g, 60%). This mixture material was advanced without further purification. The mixture (1.4 g, 3.9 mmol (corrected for impurity) was taken up in acetonitrile (15 mL) and tetraethylammonium cyanide (1.2 g, 7.7 mmol) and triethylamine (0.78 g, 7.7 mmol) were added and the reaction mixture was heated to 80° C. for 1 hr. The reaction mixture was cooled to rt, taken up in $CH_2Cl_2$ (100 mL), washed with $H_2O$ (2×20 mL), dried with $Na_2SO_4$, filtered, concentrated and the resulting oil was purified by flash column chromatography (100% $CH_2Cl_2$) to provide the desired product (0.49 g, 50%). 1H NMR (500 MHz, $CDCl_3$) δ 9.44 (d, J=1.4, 1H), 8.27 (d, J=8.1, 2H), 8.10 (d, J=1.4, 1H), 7.84 (d, J=10.2, 2H).

Intermediate 45: C-[6-(4-Trifluoromethyl-phenyl)-pyrimidin-4-yl]-methylamine

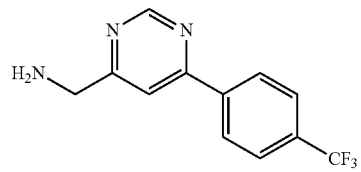 [SMILES: NCc1cc(-c2ccc(C(F)(F)F)cc2)ncn1]

To a solution of solution of 6-(4-trifluoromethyl-phenyl)-pyrimidine-4-carbonitrile (1.34 g, 5.37 mmol) in ethanol (40 mL) was added 10% Pd/C (700 mg) and the reaction mixture was placed under a $H_2$ atmosphere (55 psi) for 3 hours. The reaction mixture was filtered through a pad of celite and concentrated to provide the desired product (1.3 g, 97%). 1H NMR (400 MHz, CDCl3) δ 9.23 (d, J=1.2, 1H), 8.23 (d, J=8.1, 2H), 7.83 (s, 1H), 7.77 (d, J=8.2, 2H), 4.08 (s, 2H), 1.59 (s, 2H).

Intermediate 46 was prepared using methods analogous to those described for intermediate 15.

Intermediate 46: 2S-{[6-(4-Trifluoromethyl-phenyl)-pyrimidin-4-ylmethyl]-carbamoyl}-pyrrolidine-1-carboxylic acid tert-butyl ester

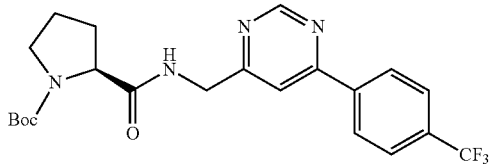 [SMILES: CC(C)(C)OC(=O)N1CCC[C@H]1C(=O)NCc1cc(-c2ccc(C(F)(F)F)cc2)ncn1]

¹H NMR (400 MHz, CDCl3) δ 9.20 (s, 1H), 8.38-8.12 (m, 2H), 7.91-7.78 (m, 1H), 7.76 (d, J=8.3, 2H), 7.48-7.31 (m, 1H), 4.74-4.64 (m, 1H), 4.64-4.54 (m, 1H), 4.48-4.30 (m, 1H), 3.58-3.36 (m, 2H), 2.40-2.03 (m, 2H), 2.03-1.85 (m, 2H), 1.51-1.30 (m, 9H).

Intermediate 47: 4-Chloro-6-(4-trifluoromethyl-phenyl)-pyrimidine

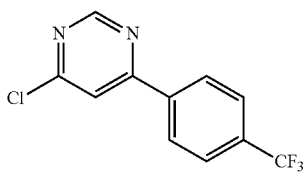 [SMILES: FC(F)(F)c1ccc(-c2cc(Cl)ncn2)cc1]

In a screw top flask, 4,6-dichloropyrimidine (3.1 g, 21 mmol), 4-trifluoromethyl-phenyl boronic acid (3.9 g, 21 mmol) and potassium phosphate (8.8 g, 42 mmol) were combined in dimethoxyethane (60 mL) and water (12 mL). The flask was flushed with $N_2$ and tetrakis(triphenylphosphine)palladium (1.2 g, 1.0 mmol) was added. The flask was sealed and heated to 90° C. for 12 hours. The reaction mixture was cooled to rt and $H_2O$ (50 mL) was added and resulting mixture was extracted with EtOAc (3×50 mL). The organic phases were combined, washed with brine (50 mL), dried with $Na_2SO_4$, filtered, and concentrated. The resulting residue was purified by flash column chromatography using ethyl acetate-hexanes (0%-20%) to provide a clear oil (2.6 g, 48%). MS (ESI): mass calcd. for $C_{11}H_6ClF_3N_2$, 258.0; m/z found 259.1 [M+H]⁺.

Intermediate 48: 1-[6-(4-Trifluoromethyl-phenyl)-pyrimidin-4-yl]-ethanone

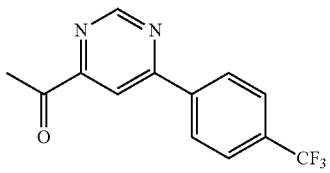 [SMILES: CC(=O)c1cc(-c2ccc(C(F)(F)F)cc2)ncn1]

In a screw top flask 4-chloro-6-(4-trifluoromethyl-phenyl)-pyrimidine (1.6 g, 6.1 mmol), tributyl-(1-ethoxy-vinyl)-stannane (1.8 g, 4.8 mmol) and trans-dichlorobis(triphenylphosphine)palladium(II) (212 mg, 0.30 mmol) were combined in DMF (10 mL). Under nitrogen the flask was sealed and heated to 80° C. for 12 hours. The reaction mixture was cooled to rt, concentrated, and purified by flash column chromatography using ethyl acetate-hexanes (0%-20%) to provide the desired product as a clear oil (1.3 g, 73%). MS (ESI): mass calcd. for $C_{15}H_{13}F_3N_2O$, 294.0; m/z found 295.1 [M+H]⁺. The resulting clear oil was diluted with THF (60 mL) and 2N HCl (10 mL) and stirred. After 12 h, the resulting solution was partitioned between saturated aqueous sodium bicarbonate (50 mL) and ethyl acetate (50 mL). The organic layer was separated and the aqueous layer was extracted with ethyl acetate (2×50 mL). The organic phases were combined, dried with $Na_2SO_4$, filtered, and concentrated. The resulting residue was purified by flash column chromatography using ethyl acetate-hexanes (0%-20%) to provide the desired product as a clear oil (1.1 g, 93%). MS (ESI): mass calcd. for $C_{13}H_9F_3N_2O$, 266.0; m/z found 267.1 [M+H]⁺. ¹H NMR (CDCl₃) δ 9.45 (d, J=1.3 Hz, 1H), 8.37 (d, J=1.3 Hz, 1H), 8.31 (d, J=8.1 Hz, 2H), 7.82 (d, J=8.2 Hz, 2H), 2.81 (s, 3H).

Intermediate 49: 2-Chloro-4-(4-trifluoromethyl-phenyl)-pyrimidine

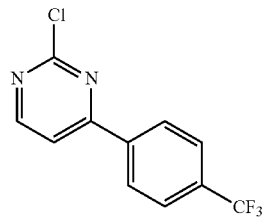

A mixture of 2,4-dichloro-pyrimidine (4.0 g, 27 mmol), 4-trifluoromethyl phenyl boronic acid (5.1 g, 27 mmol), tetrakis(triphenylphosphine)palladium(0) (1.5 g, 1.3 mmol), potassium phosphate (11 g, 54 mmol), 1,2-dimethoxyethane (50 mL) and water (10 mL) was heated to 80° C. under a blanket of nitrogen in a sealed tube. After 5 h, the mixture was partitioned between water (50 mL) and ethyl acetate (50 mL). The aqueous layer was extracted with ethyl acetate (3×50 mL). The combined organic layers were dried (MgSO₄), filtered, and concentrated. The residue was purified directly by FCC to afford a white solid (5.0 g, 72%). MS (ESI): mass calcd. for $C_{11}H_6ClF_3N_2$, 258.0; m/z found, 259.0 [M+H]⁺. ¹H NMR (500 MHz, CDCl₃) δ 8.74 (d, J=5.2, 1H), 8.23 (d, J=8.1, 2H), 7.80 (d, J=8.2, 2H), 7.71 (d, J=5.2, 1H).

Intermediate 50: 2-Chloro-4-(4-trifluoromethyl-phenyl)-pyrimidine

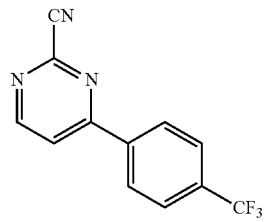 [SMILES: N#Cc1nccc(-c2ccc(C(F)(F)F)cc2)n1]

A mixture of 2-chloro-4-(4-trifluoromethyl-phenyl)-pyrimidine (1.0 g, 3.9 mmol), tetraethylammonium cyanide (2.4 g, 16 mmol), diisopropylethylamine (3.9 mmol, 0.7 mL), and CH₃CN (10 mL) was heated to 80° C. After 1 h, reaction mixture was cooled and concentrated. The residue was purified directly by FCC to afford a white solid (0.5 mg, 51%). MS (ESI): mass calcd. for C$_{12}$H$_6$F$_3$N$_3$, 249.0; m/z found, 250.1 [M+H]$^+$. $^1$H NMR (500 MHz, CDCl$_3$) δ 8.95 (d, J=5.4, 1H), 8.27 (d, J=8.2, 2H), 7.98 (d, J=5.4, 1H), 7.83 (d, J=8.2, 2H).

Intermediate 51: C-[4-(4-Trifluoromethyl-phenyl)-pyrimidin-2-yl]-methylamine

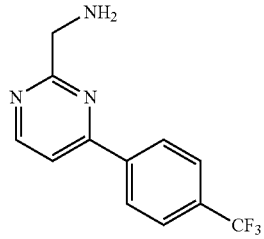 [SMILES: NCc1nccc(-c2ccc(C(F)(F)F)cc2)n1]

A mixture of 2-chloro-4-(4-trifluoromethyl-phenyl)-pyrimidine (0.4 g, 1.6 mmol), Pd/C (10% wt., 0.2 g), and EtOH (20 mL) was hydrogenated under 50 psi H$_2$ in a parr shaker. After 4 h, the resulting mixture was filtered through Celite. The Celite was washed with ethyl acetate (100 mL) and combine organics were concentrated. The resulting residue was a clear oil (350 mg, 86%). MS (ESI): mass calcd. for C$_{12}$H$_{10}$F$_3$N$_3$, 253.0; m/z found, 254.1 [M+H]$^+$.

Intermediate 52: 2-(4-Trifluoromethyl-phenyl)-pyrimidine-4-carboxylic acid

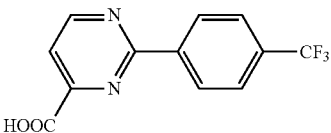 [SMILES: O=C(O)c1ccnc(-c2ccc(C(F)(F)F)cc2)n1]

A mixture of 2-chloro-pyrimidine-4-carboxylic acid (2.0 g, 13 mmol), 4-trifluoromethyl phenyl boronic acid (2.4 g, 13 mmol), tetrakis(triphenylphosphine)palladium(0) (0.7 g, 0.6 mmol), potassium phosphate (5.3 g, 25 mmol), 1,2-dimethoxyethane (40 mL) and water (8 mL) was heated to 80° C. under a blanket of nitrogen in a sealed tube. After 5 h, the mixture was partitioned between water (50 mL) and ethyl acetate (50 mL). The aqueous layer was extracted with ethyl acetate (2×50 mL). The combined organic layers were discarded, and the aqueous layer was acidified with concentrated HCl to pH 2. The aqueous layer was extracted with ethyl acetate (2×50 mL). The combined organic layers were dried (MgSO$_4$), filtered, and concentrated. The residue was purified directly by FCC to afford a white solid (1.4 g, 42%). MS (ESI): mass calcd. for C$_{12}$H$_7$F$_3$N$_2$O$_2$, 268.0 m/z found, 269.0 [M+H]$^+$.

Intermediate 53: [2-(4-Trifluoromethyl-phenyl)-pyrimidin-4-yl]-methanol

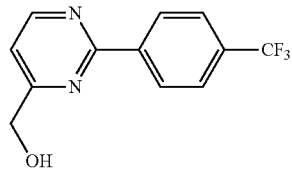 [SMILES: OCc1ccnc(-c2ccc(C(F)(F)F)cc2)n1]

To a solution of 2-(4-trifluoromethyl-phenyl)-pyrimidine-4-carboxylic acid (435 mg, 1.60 mmol), Et$_3$N (0.34 mL, 2.40 mmol) and THF (10 mL) was added isobutyl chloroformate (333 mg, 2.40 mmol). After 1 h, the resulting mixture was filtered through a fritted funnel and washed with THF (30 mL). The filtrate was concentrated to approximately 10 mL and MeOH (1 mL) was added followed by sodium borohydride (121 mg, 3.20 mmol). After 12 h, the mixture was partitioned between saturated aqueous NaHCO$_3$ (30 mL) and ethyl acetate (30 mL). The aqueous layer was extracted with ethyl acetate (2×30 mL). The combined organic layers were dried (MgSO$_4$), filtered, and concentrated. The residue was purified directly by FCC to afford a white solid (120 mg, 27%). MS (ESI): mass calcd. for C$_{12}$H$_9$F$_3$N$_2$O; 254.0 m/z found, 255.1 [M+H]$^+$. $^1$H NMR (500 MHz, CDCl$_3$) δ 8.80 (d, J=5.1, 1H), 8.57 (d, J=8.1, 2H), 7.75 (d, J=8.2, 2H), 7.30 (d, J=5.1, 1H), 4.85 (s, 2H).

Intermediate 54: C-[2-(4-Trifluoromethyl-phenyl)-pyrimidin-4-yl]-methylamine

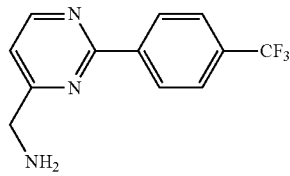 [SMILES: NCc1ccnc(-c2ccc(C(F)(F)F)cc2)n1]

To a solution of [2-(4-trifluoromethyl-phenyl)-pyrimidin-4-yl]-methanol (110 mg, 0.43 mmol), diisopropylethylamine (0.10 mL, 0.52 mmol), and CH$_2$Cl$_2$ (5 mL) was added methanesulfonyl chloride (37 µL, 0.47 mmol). After 1 h, the resulting solution was concentrated. The residue was re-dissolved in 7N NH$_3$ in MeOH (10 mL) and heated to 70° C. in a sealed tube. After 1 h, the resulting solution was cooled, concentrated, and the residue was used crude (110 mg, 100%). MS (ESI): mass calcd. for C$_{12}$H$_{10}$F$_3$N$_3$, 253.0; m/z found, 254.1 [M+H]$^+$.

Intermediate 55: 2-Chloro-6-pyrrolidin-1-yl-isonicotinonitrile

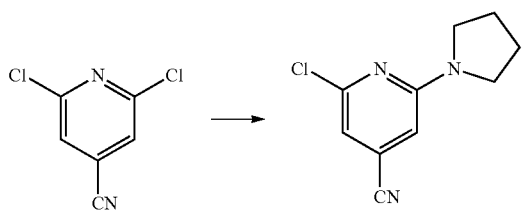 [SMILES: N#Cc1cc(Cl)nc(Cl)c1 ; N#Cc1cc(Cl)nc(N2CCCC2)c1]

To a solution of 2,6-dichloroisoniconitrile (0.20 g, 1.16 mmol) in 1-methyl-2-pyrrolidinone (3 mL) was added triethylamine (161 µL, 1.16 mmol) and pyrrolidine (96 µL, 1.16 mmol). The reaction mixture was heated to 70° C. via oil bath for 4 hours. The reaction mixture was cooled to rt, diluted with EtOAc (10 mL), washed with water (2×10 mL), dried with Na$_2$SO$_4$, filtered, concentrated under reduced pressure and purified by flash column chromatography (0%-60% EtOAc in hexane) to provide the desired product (0.18 g, 73%). ¹H NMR (600 MHz, CDCl₃) δ 6.66 (d, J=0.9 Hz, 1H), 6.41 (d, J=1.0 Hz, 1H), 3.45 (s, 4H), 2.00 (d, J=40.5 Hz, 4H).

Intermediate 56: 2-Pyrrolidin-1-yl-6-(4-trifluoromethyl-phenyl)-isonicotinonitrile

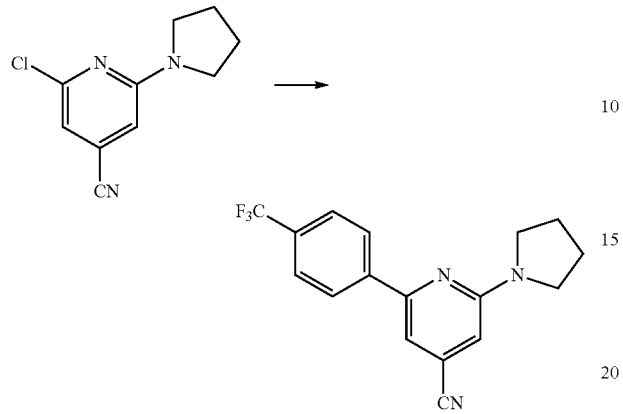

2-Chloro-6-pyrrolidin-1-yl-isonicotinonitrile (0.18 g, 0.87 mmol), 4-trifluoromethylphenylboronic acid (0.18 g, 0.95 mmol), palladium acetate (3.9 mg, 0.02 mmol), cesium carbonate (0.56 g, 1.73 mmol), and XPhos (17 mg, 0.04 mmol) were combined, placed under a nitrogen atmosphere and dioxane (1.0 mL) was added. The reaction vessel was sealed and heated to 100° C. for 2 hours. The reaction mixture was cooled to rt, filtered through celite, concentrated under reduced pressure and purified by flash column chromatography (0%-80% EtOAc in hexane) to provide the desired product (253 mg, 92%). ¹H NMR (400 MHz, CDCl₃) δ 8.11 (d, J=8.1 Hz, 2H), 7.70 (d, J=8.2 Hz, 2H), 7.15 (d, J=0.8 Hz, 1H), 6.54 (d, J=0.9 Hz, 1H), 3.55 (bs, 4H), 2.13-1.99 (m, 4H).

Intermediate 57: C-[2-Pyrrolidin-1-yl-6-(4-trifluoromethyl-phenyl)-pyridin-4-yl]-methylamine

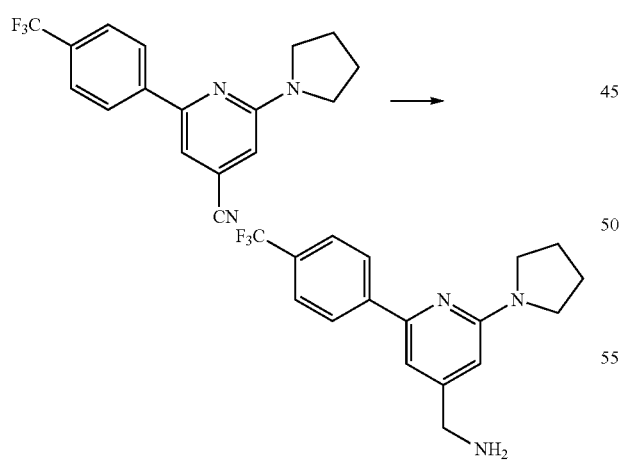

To a solution of 2-pyrrolidin-1-yl-6-(4-trifluoromethyl-phenyl)-isonicotinonitrile (0.20 g, 0.61 mmol) in ethanol (20 mL) was added 1.25 M HCl in ethanol (0.50 mL, 0.63 mmol) and Pd/C (20 mg, 10 wt. %) and the system was placed under H₂ atmosphere (50 atm) for 72 hours. The reaction mixture was filtered through Celite and concentrated under reduced pressure to provide the desired product (200 mg, 99%).

Example 1

1-(4-Fluoro-benzenesulfonyl)-pyrrolidine-2S-carboxylic acid [2-(4-isobutyl-piperazin-1-yl)-6-(4-trifluoromethyl-phenyl)-pyrimidin-4-ylmethyl]-amide

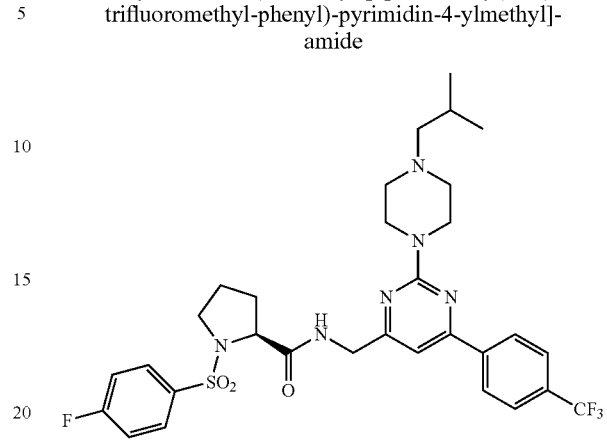

To a solution of 1-(4-fluoro-benzenesulfonyl)-pyrrolidine-2S-carboxylic acid [2-phenylmethanesulfonyl-6-(4-trifluoromethyl-phenyl)-pyrimidin-4-ylmethyl]-amide (0.65 g, 0.982 mmol) in t-amyl alcohol (10 mL) was added isobutylpiperazine (0.42 g, 2.95 mmol). The resulting mixture was heated to 110° C. for 4 hours then allowed to cool to rt. The resulting mixture was concentrated and purified by preparative reverse-phase HPLC to afford the title compound as a colorless solid (0.37 g, 58%). MS (ESI): mass calcd. for $C_{31}H_{36}F_4N_6O_3S$, 648.2; m/z found, 649.5 [M+H]⁺. ¹H NMR (CDCl₃) δ 8.17 (d, J=8.33 Hz, 2H), 8.07 (t, J=4.76, 4.76 Hz, 1H), 7.93-7.88 (m, 2H), 7.72-7.68 (m, 1H), 7.28-7.22 (m, 2H), 6.95 (s, 1H), 4.59 (dd, J=17.56, 5.19 Hz, 1H), 4.42 (dd, J=17.56, 4.80 Hz, 1H), 4.18 (dd, J=8.79, 2.39 Hz, 1H), 4.03-3.96 (m, 4H), 3.67-3.57 (m, 1H), 3.25-3.15 (m, 1H), 2.57-2.45 (m, 4H), 2.30-2.22 (m, 1H), 2.14 (d, J=7.32 Hz, 2H), 1.91-1.75 (m, 2H), 1.74-1.51 (m, 3H), 0.94 (d, J=6.57 Hz, 6H).

Example 2

1-(4-Fluoro-benzenesulfonyl)-pyrrolidine-2S-carboxylic acid [2-methoxy-6-(4-trifluoromethyl-phenyl)-pyrimidin-4-ylmethyl]-amide

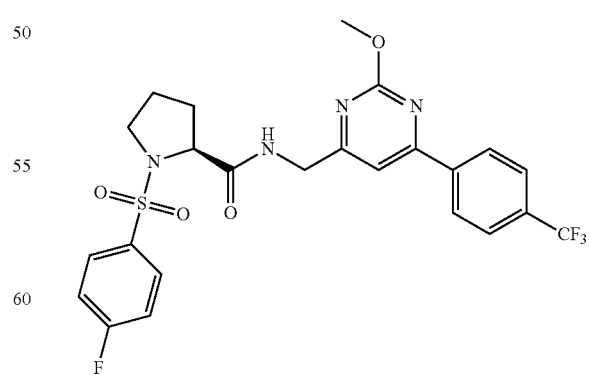

To a solution of sodium methoxide (0.02 mg, 0.36 mmol) in MeOH (1.5 mL) was added 1-(4-fluoro-benzenesulfonyl)-pyrrolidine-2-carboxylic acid [2-phenylmethanesulfonyl-6-

(4-trifluoromethyl-phenyl)-pyrimidin-4-ylmethyl]-amide (0.04 mg, 0.061 mmol) at rt. After 12 hours the resulting mixture was concentrated and purified by preparative reverse-phase HPLC to afford the title compound as a colorless solid (25 mg, 76%). MS (ESI): mass calcd. for $C_{24}H_{22}F_4N_4O_4S$, 538.1; m/z found, 539.2 [M+H]$^+$. $^1$H NMR (500 MHz, CDCl$_3$) δ 8.30 (d, J=8.31 Hz, 2H), 7.93 (dd, J=8.08, 5.05 Hz, 2H), 7.83-7.78 (m, 1H), 7.73 (d, J=8.27 Hz, 2H), 7.61 (s, 1H), 7.28 (t, J=8.52, 8.52 Hz, 2H), 4.86 (dd, J=17.51, 7.03 Hz, 1H), 4.47 (dd, J=17.54, 4.80 Hz, 1H), 4.22 (dd, J=8.87, 3.01 Hz, 1H), 4.15 (s, 3H), 3.70-3.62 (m, 1H), 3.23-3.14 (m, 1H), 2.25-2.16 (m, 1H), 1.92-1.82 (m, 1H), 1.83-1.73 (m, 1H), 1.73-1.66 (m, 1H).

Example 3

1-(4-Fluoro-benzenesulfonyl)-pyrrolidine-2S-carboxylic acid [2-pyridin-3-yl-6-(4-trifluoromethyl-phenyl)-pyrimidin-4-ylmethyl]-amide

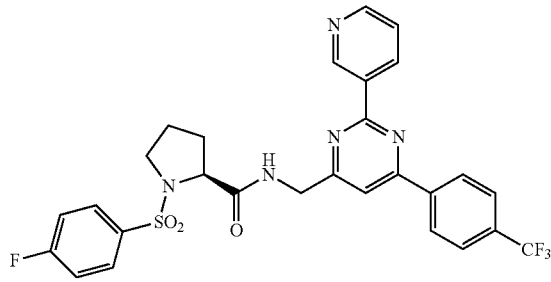 [SMILES: O=C(NCc1cc(-c2ccc(C(F)(F)F)cc2)nc(-c2cccnc2)n1)[C@@H]1CCCN1S(=O)(=O)c1ccc(F)cc1]

The title compound was generated from Intermediate 12 by a similar procedure to that described in the formation of Intermediate 6. MS (ESI): mass calcd. for $C_{28}H_{23}F_4N_5O_3S$, 585.1; m/z found, 586.5 [M+H]$^+$. $^1$H NMR (500 MHz, DMSO) δ 9.84 (s, 1H), 9.33-9.27 (m, 1H), 9.04-8.98 (m, 1H), 8.64 (t, J=5.92, 5.92 Hz, 1H), 8.54 (d, J=8.24 Hz, 2H), 8.20 (s, 1H), 8.16-8.11 (m, 2H), 8.04 (dd, J=7.92, 5.34 Hz, 1H), 7.81 (d, J=8.41 Hz, 2H), 7.49-7.44 (m, 2H), 4.89 (dd, J=17.48, 5.87 Hz, 1H), 4.65 (dd, J=17.70, 4.01 Hz, 1H), 4.38-4.32 (m, 1H), 3.73-3.66 (m, 1H), 3.35-3.32 (1H, m), 2.16-2.09 (m, 1H), 2.04-1.88 (m, 2H), 1.77-1.68 (m, 1H).

Examples 4 to 7 were prepared using methods analogous to those described for Example 3 wherein the appropriate boronic acid was employed to yield the desired outcome.

Example 4

1-(4-Fluoro-benzenesulfonyl)-pyrrolidine-2S-carboxylic acid [2,6-bis-(4-trifluoromethyl-phenyl)-pyrimidin-4-ylmethyl]-amide

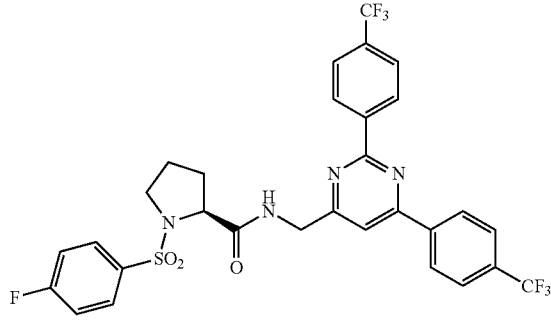 [SMILES: O=C(NCc1cc(-c2ccc(C(F)(F)F)cc2)nc(-c2ccc(C(F)(F)F)cc2)n1)[C@@H]1CCCN1S(=O)(=O)c1ccc(F)cc1]

MS (ESI): mass calcd. for $C_{30}H_{23}F_7N_4O_3S$, 652.1; m/z found, 653.2 [M+H]$^+$. $^1$H NMR (DMSO) δ 8.99 (t, J=5.95, 5.95 Hz, 1H), 8.75 (d, J=8.09 Hz, 2H), 8.54 (d, J=8.16 Hz, 2H), 8.12 (s, 1H), 8.06-8.01 (m, 2H), 7.97-7.91 (m, 4H), 7.54-7.46 (m, 2H), 4.66 (dd, J=17.30, 6.15 Hz, 1H), 4.57 (dd, J=17.27, 5.74 Hz, 1H), 4.22-4.16 (m, 1H), 3.57-3.49 (m, 1H), 3.27-3.18 (m, 1H), 1.94-1.80 (m, 3H), 1.63-1.51 (m, 1H).

Example 5

1-(4-Fluoro-benzenesulfonyl)-pyrrolidine-2S-carboxylic acid [2-(3-trifluoromethyl-phenyl)-6-(4-trifluoromethyl-phenyl)-pyrimidin-4-ylmethyl]-amide

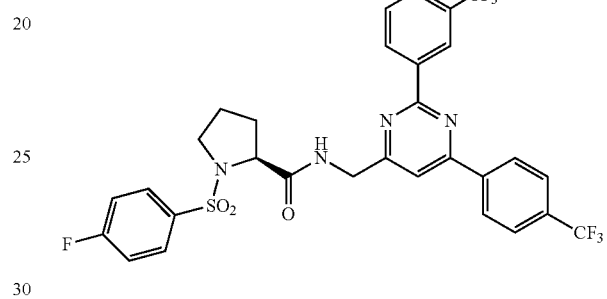

MS (ESI): mass calcd. for $C_{30}H_{23}F_7N_4O_3S$, 652.1; m/z found, 653.2 [M+H]$^+$. $^1$H NMR (500 MHz, CDCl$_3$) δ 8.80 (d, J=8.08 Hz, 2H), 8.59-8.51 (m, 1H), 8.43 (d, J=8.13 Hz, 2H), 8.15-8.07 (m, 1H), 8.00-7.94 (m, 2H), 7.84-7.78 (m, 4H), 7.35-7.29 (m, 2H), 5.04-4.62 (m, 2H), 4.36-4.27 (m, 1H), 3.78-3.69 (m, 1H), 3.30-3.19 (m, 1H), 2.31-2.18 (m, 1H), 1.97-1.76 (m, 2H), 1.77-1.68 (m, 1H).

Example 6

1-(4-Fluoro-benzenesulfonyl)-pyrrolidine-2S-carboxylic acid [2-(2-trifluoromethyl-phenyl)-6-(4-trifluoromethyl-phenyl)-pyrimidin-4-ylmethyl]-amide

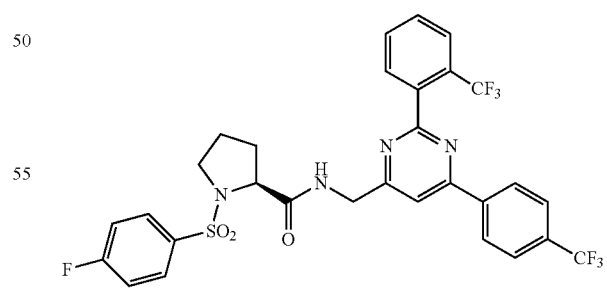

MS (ESI): mass calcd. for $C_{30}H_{23}F_7N_4O_3S$, 652.1; m/z found, 653.2 [M+H]$^+$. $^1$H NMR (500 MHz, CDCl$_3$) δ 8.78 (d, J=8.07 Hz, 2H), 8.41 (d, J=8.11 Hz, 2H), 8.29 (t, J=5.37, 5.37 Hz, 1H), 8.00-7.94 (m, 2H), 7.84 (s, 1H), 7.82-7.79 (m, 4H), 7.33-7.29 (m, 2H), 4.98 (dd, J=17.77, 6.33 Hz, 1H), 4.65 (dd, J=17.79, 4.69 Hz, 1H), 4.32 (dd, J=8.82, 3.06 Hz, 1H), 3.76-

3.69 (m, 1H), 3.28-3.20 (m, 1H), 2.29-2.21 (m, 1H), 1.94-1.76 (m, 2H), 1.76-1.67 (m, 1H).

Example 7

1-(4-Fluoro-benzenesulfonyl)-pyrrolidine-2S-carboxylic acid [2-pyridin-4-yl-6-(4-trifluoromethyl-phenyl)-pyrimidin-4-ylmethyl]-amide

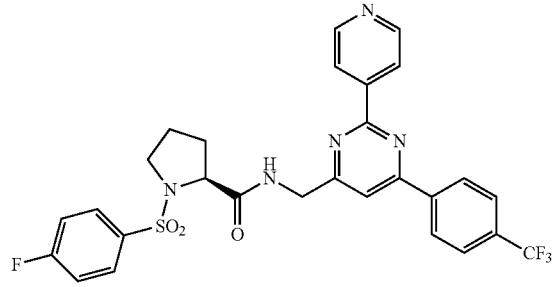 [SMILES: O=C(NCc1cc(-c2ccc(C(F)(F)F)cc2)nc(-c2ccncc2)n1)[C@@H]1CCCN1S(=O)(=O)c1ccc(F)cc1]

MS (ESI): mass calcd. for $C_{28}H_{23}F_4N_5O_3S$, 585.1; m/z found, 586.5 [M+H]$^+$. $^1$H NMR (500 MHz, (CD$_3$)$_2$CO) δ 9.07 (d, J=4.61 Hz, 2H), 8.97-8.91 (m, 2H), 8.66 (d, J=8.15 Hz, 2H), 8.35 (s, 1H), 8.15-8.10 (m, 2H), 7.91 (d, J=8.28 Hz, 2H), 7.51-7.45 (m, 2H), 4.95 (dd, J=17.56, 5.32 Hz, 1H), 4.71 (dd, J=17.56, 3.32 Hz, 1H), 4.30 (dd, J=8.68, 3.63 Hz, 1H), 3.72-3.64 (m, 1H), 3.40-3.31 (m, 1H), 2.15-2.07 (m, 1H), 2.03-1.85 (m, 2H), 1.79-1.66 (m, 1H).

Examples 8 to 10 were prepared using methods analogous to those described for Example 1 wherein the appropriate amine was employed to yield the desired product.

Example 8

1-(4-Fluoro-benzenesulfonyl)-pyrrolidine-2S-carboxylic acid [2-amino-6-(4-trifluoromethyl-phenyl)-pyrimidin-4-ylmethyl]-amide

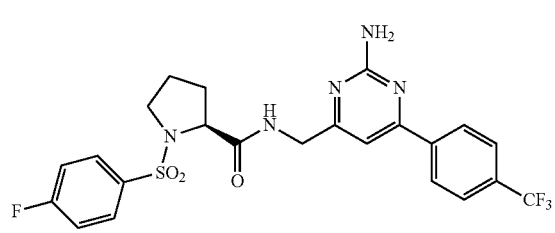 [SMILES: Nc1nc(CNC(=O)[C@@H]2CCCN2S(=O)(=O)c2ccc(F)cc2)cc(-c2ccc(C(F)(F)F)cc2)n1]

MS (ESI): mass calcd. for $C_{23}H_{21}F_4N_5O_3S$, 523.1; m/z found, 524.5 [M+H]$^+$. $^1$H NMR (500 MHz, CDCl$_3$) δ 8.23 (d, J=8.22 Hz, 2H), 7.96-7.91 (m, 2H), 7.91-7.86 (m, 1H), 7.71 (d, J=8.36 Hz, 2H), 7.52 (s, 1H), 7.33-7.29 (m, 2H), 4.99 (dd, J=17.80, 7.86 Hz, 1H), 4.40 (dd, J=17.78, 4.80 Hz, 1H), 4.14-4.10 (m, 1H), 3.80-3.72 (m, 1H), 3.20-3.10 (m, 1H), 2.15-2.06 (m, 1H), 1.99-1.85 (m, 2H), 1.75-1.66 (m, 1H).

Example 9

1-(4-Fluoro-benzenesulfonyl)-pyrrolidine-2S-carboxylic acid [2-(4-isopropyl-piperazin-1-yl)-6-(4-trifluoromethyl-phenyl)-pyrimidin-4-ylmethyl]-amide

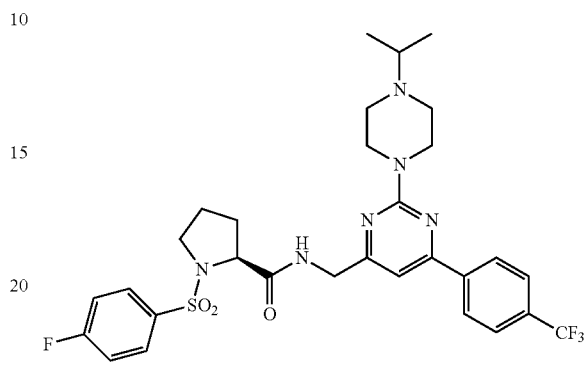

MS (ESI): mass calcd. for $C_{30}H_{34}F_4N_6O_3S$, 634.2; m/z found, 635.7 [M+H]$^+$. $^1$H NMR (500 MHz, DMSO) δ 8.79 (t, J=6.01, 6.01 Hz, 1H), 8.35 (d, J=8.16 Hz, 2H), 8.03-7.99 (m, 2H), 7.86 (d, J=8.28 Hz, 2H), 7.53-7.47 (m, 2H), 7.41 (s, 1H), 4.98 (d, J=13.74 Hz, 2H), 4.39 (dd, J=17.29, 6.14 Hz, 1H), 4.31 (dd, J=17.29, 6.14 Hz, 1H), 4.19-4.13 (m, 1H), 3.61-3.45 (m, 4H), 3.37-3.27 (m, 2H), 3.25-3.05 (m, 3H), 1.91-1.74 (m, 3H), 1.61-1.50 (m, 1H), 1.29 (d, J=6.63 Hz, 6H).

Example 10

1-(4-Fluoro-benzenesulfonyl)-pyrrolidine-2S-carboxylic acid [2-dimethylamino-6-(4-trifluoromethyl-phenyl)-pyrimidin-4-ylmethyl]-amide

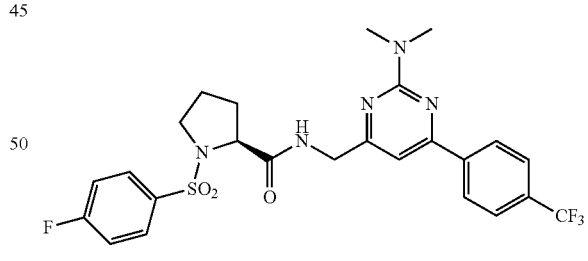

MS (ESI): mass calcd. for $C_{25}H_{25}F_4N_5O_3S$, 551.1; m/z found, 552.5 [M+H]$^+$. $^1$H NMR (500 MHz, DMSO) δ 8.74 (t, J=5.94, 5.94 Hz, 1H), 8.33 (d, J=8.13 Hz, 2H), 8.03-7.97 (m, 2H), 7.84 (d, J=8.28 Hz, 2H), 7.52-7.46 (m, 2H), 7.25 (s, 1H), 4.31 (m, 2H), 4.18-4.13 (m, 1H), 3.53-3.46 (m, 1H), 3.23 (s, 6H), 3.21-3.16 (m, 1H), 1.91-1.74 (m, 3H), 1.61-1.49 (m, 1H).

Example 11 was prepared using methods analogous to those described for intermediate 6.

Example 11

1-(4-Fluoro-benzenesulfonyl)-pyrrolidine-2S-carboxylic acid [6-(4-trifluoromethyl-phenyl)-pyrimidin-4-ylmethyl]-amide

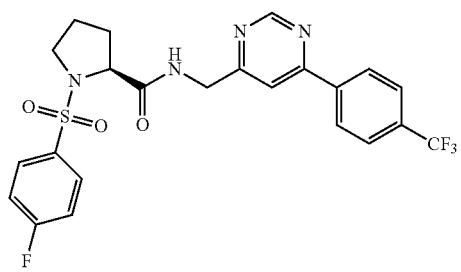 [SMILES: O=C(NCc1cc(-c2ccc(C(F)(F)F)cc2)ncn1)[C@@H]1CCCN1S(=O)(=O)c1ccc(F)cc1]

MS (ESI): Mass calcd. for $C_{23}H_{20}F_4N_4O_3S$, 508.12; m/z found 509.5 [M+H]$^+$. $^1$H NMR (400 MHz, CDCl$_3$) δ 9.23 (d, J=1.3, 1H), 8.31 (d, J=8.2, 2H), 7.98-7.95 (m, 1H), 7.95-7.90 (m, 2H), 7.77-7.72 (m, 2H), 7.67-7.59 (m, 1H), 7.31-7.28 (m, 1H), 4.91 (dd, J=17.5, 7.2, 1H), 4.52 (dd, J=17.5, 5.0, 1H), 4.19 (dd, J=8.7, 3.2, 1H), 3.67 (ddd, J=10.2, 6.7, 3.6, 1H), 3.20 (ddd, J=9.3, 6.6, 1H), 2.21 (ddd, J=12.1, 5.9, 3.0, 1H), 1.96-1.83 (m, 1H), 1.79 (ddd, J=13.0, 6.5, 3.0, 1H), 1.75-1.64 (m, 1H).

Examples 12 to 38 were prepared using methods analogous to those described for Example 1 wherein the appropriate amine was employed to yield the desired product.

Example 12

1-(4-Fluoro-benzenesulfonyl)-pyrrolidine-2S-carboxylic acid [2-[(1-methyl-pyrrolidin-3-ylmethyl)-amino]-6-(4-trifluoromethyl-phenyl)-pyrimidin-4-ylmethyl]-amide

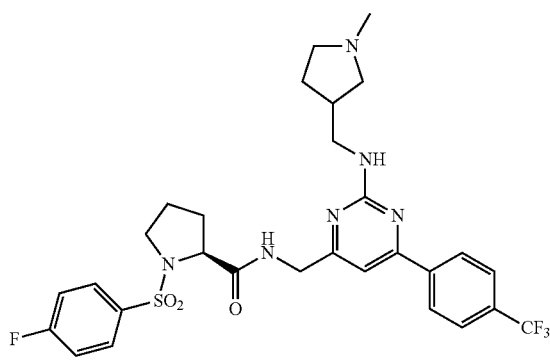 [SMILES: CN1CCC(CNc2nc(CNC(=O)[C@@H]3CCCN3S(=O)(=O)c3ccc(F)cc3)cc(-c3ccc(C(F)(F)F)cc3)n2)C1]

MS (ESI): mass calcd. for $C_{29}H_{32}F_4N_6O_3S$, 620.2; m/z found, 621.6 [M+H]$^+$. $^1$H NMR (400 MHz, CDCl$_3$) δ 8.46-8.33 (m, 1H), 8.17 (d, J=8.28 Hz, 2H), 7.91-7.85 (m, 2H), 7.74 (d, J=8.34 Hz, 2H), 7.34-7.27 (m, 2H), 7.03 (s, 1H), 4.67 (dd, J=17.20, 5.04 Hz, 1H), 4.43 (dd, J=17.21, 4.21 Hz, 1H), 4.24-4.15 (m, 1H), 3.95-3.83 (m, 1H), 3.83-3.56 (m, 2H), 3.54-3.40 (m, 1H), 3.28 (d, J=6.00 Hz, 3H), 3.25-3.05 (m, 2H), 3.04-2.87 (m, 3H), 2.59-2.36 (m, 2H), 2.36-2.24 (m, 1H), 1.93-1.73 (m, 1H), 1.74-1.48 (m, 2H).

Example 13

1-(4-Fluoro-benzenesulfonyl)-pyrrolidine-2S-carboxylic acid [2-[4-(1-ethyl-propyl)-piperazin-1-yl]-6-(4-trifluoromethyl-phenyl)-pyrimidin-4-ylmethyl]-amide

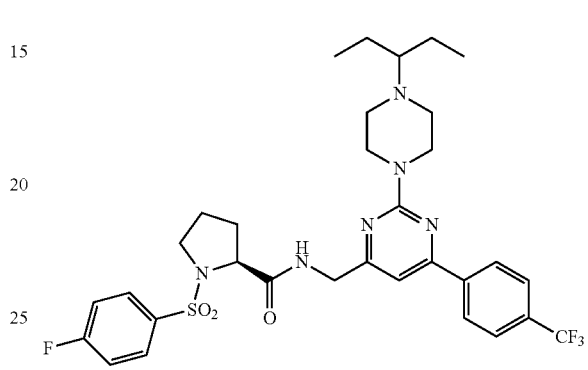

MS (ESI): mass calcd. for $C_{32}H_{38}F_4N_6O_3S$, 662.2; m/z found, 663.3 [M+H]$^+$. $^1$H NMR (400 MHz, CDCl$_3$) δ 8.37-8.20 (m, 1H), 8.13 (d, J=8.13 Hz, 2H), 7.92-7.84 (m, 2H), 7.71 (d, J=8.25 Hz, 2H), 7.58 (d, J=7.87 Hz, 2H), 7.08 (s, 1H), 5.27-5.05 (m, 2H), 4.69 (dd, J=17.98, 5.49 Hz, 1H), 4.40 (dd, J=17.97, 4.12 Hz, 1H), 4.18 (dd, J=8.76, 2.95 Hz, 1H), 3.73-3.54 (m, 5H), 3.24-2.91 (m, 4H), 2.32-2.14 (m, 1H), 1.98-1.74 (m, 3H), 1.74-1.59 (m, 4H), 1.05 (t, J=7.49, 7.49 Hz, 6H).

Example 14

1-(4-Fluoro-benzenesulfonyl)-pyrrolidine-2S-carboxylic acid [2-methylamino-6-(4-trifluoromethyl-phenyl)-pyrimidin-4-ylmethyl]-amide

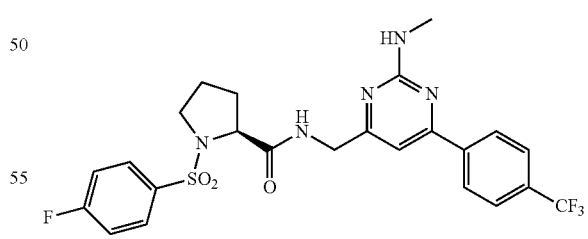

MS (ESI): mass calcd. for $C_{24}H_{23}F_4N_5O_3S$, 537.1; m/z found, 538.2 [M+H]$^+$. $^1$H NMR (500 MHz, CDCl$_3$) δ 9.94 (s, 1H), 8.45-8.20 (m, 2H), 7.96-7.89 (m, 2H), 7.88-7.82 (m, 1H), 7.76 (d, J=8.33 Hz, 2H), 7.44 (s, 1H), 7.32-7.26 (m, 2H), 4.92 (dd, J=17.20, 7.16 Hz, 1H), 4.42 (dd, J=17.57, 4.78 Hz, 1H), 4.14-4.08 (m, 1H), 3.75-3.66 (m, 1H), 3.19 (s, 3H), 3.18-3.13 (m, 1H), 2.17-2.04 (m, 1H), 1.96-1.82 (m, 2H), 1.74-1.63 (m, 1H).

Example 15

1-(4-Fluoro-benzenesulfonyl)-pyrrolidine-2S-carboxylic acid [2-(4-ethyl-piperain-1-yl)-6-(4-trifluoromethyl-phenyl)-pyrimidin-4-ylmethyl]-amide

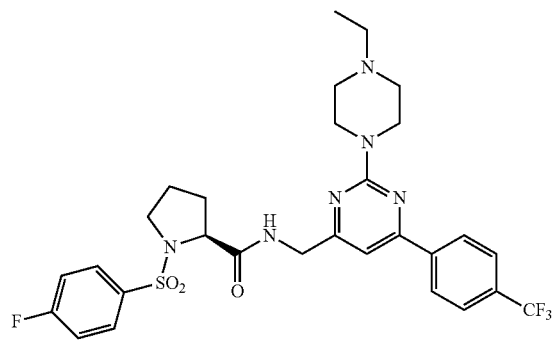 [SMILES: CCN1CCN(c2nc(CNC(=O)[C@@H]3CCCN3S(=O)(=O)c3ccc(F)cc3)cc(-c3ccc(C(F)(F)F)cc3)n2)CC1]

MS (ESI): mass calcd. for $C_{29}H_{32}F_4N_6O_3S$, 620.2; m/z found, 621.3 [M+H]$^+$. $^1$H NMR (500 MHz, CDCl$_3$) δ 8.36-8.23 (m, 1H), 8.15 (d, J=8.13 Hz, 2H), 7.93-7.87 (m, 2H), 7.73 (d, J=8.25 Hz, 2H), 7.32-7.26 (m, 2H), 7.12 (s, 1H), 5.10-5.20 (m, 2H), 4.72 (dd, J=17.97, 5.53 Hz, 1H), 4.41 (dd, J=17.95, 4.05 Hz, 1H), 4.21 (dd, J=8.81, 2.87 Hz, 1H), 3.70-3.81 (m, 2H), 3.69-3.53 (m, 3H), 3.24-3.11 (m, 3H), 2.94-2.80 (m, 2H), 2.31-2.17 (m, 1H), 1.89-1.76 (m, 1H), 1.72-1.62 (m, 2H), 1.42 (t, J=7.32, 7.32 Hz, 3H).

Example 16

1-(4-Fluoro-benzenesulfonyl)-pyrrolidine-2S-carboxylic acid [2-(1-pyridin-2-yl-ethylamino)-6-(4-trifluoromethyl-phenyl)-pyrimidin-4-ylmethyl]-amide

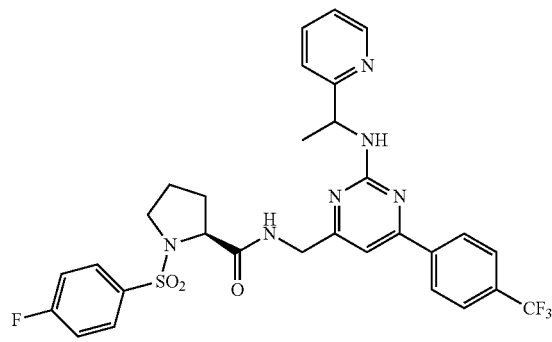 [SMILES: CC(Nc1nc(CNC(=O)[C@@H]2CCCN2S(=O)(=O)c2ccc(F)cc2)cc(-c2ccc(C(F)(F)F)cc2)n1)c1ccccn1]

MS (ESI): mass calcd. for $C_{30}H_{28}F_4N_6O_3S$, 628.2; m/z found, 629.2 [M+H]$^+$. $^1$H NMR (500 MHz, CDCl$_3$) δ 8.92-8.80 (m, 1H), 8.21-8.13 (m, 2H), 7.96-7.84 (m, 4H), 7.70 (d, J=6.46 Hz, 2H), 7.66-7.55 (m, 1H), 7.52-7.40 (m, 1H), 7.32-7.24 (m, 2H), 5.88-5.74 (m, 1H), 4.98-4.72 (m, 1H), 4.50-4.28 (m, 1H), 4.21-4.00 (m, 1H), 3.75-3.60 (m, 1H), 3.20-3.10 (m, 1H), 2.19-2.09 (m, 1H), 1.97-1.83 (m, 2H), 1.81 (d, J=7.06 Hz, 3H), 1.73-1.64 (m, 1H).

Example 17

1-(4-Fluoro-benzenesulfonyl)-pyrrolidine-2S-carboxylic acid [2-[4-(2-dimethylamino-ethyl)-piperazin-1-yl]-6-(4-trifluoromethyl-phenyl)-pyrimidin-4-ylmethyl]-amide

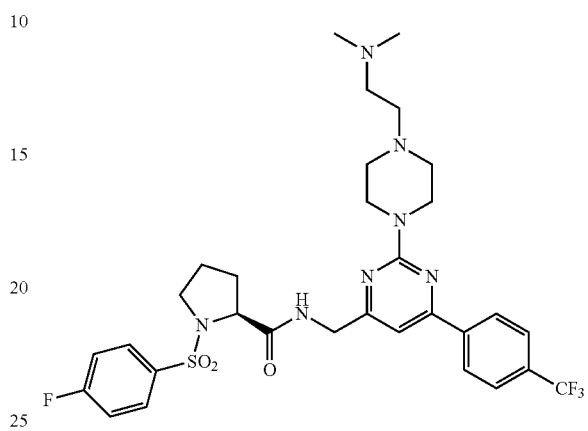

MS (ESI): mass calcd. for $C_{31}H_{37}F_4N_7O_3S$, 663.3; m/z found, 664.3 [M+H]$^+$. $^1$H NMR (500 MHz, CDCl$_3$) δ 8.25 (t, J=4.62, 4.62 Hz, 1H), 8.15 (d, J=8.14 Hz, 2H), 7.92-7.87 (m, 2H), 7.74 (d, J=8.28 Hz, 2H), 7.32-7.28 (m, 1H), 7.13 (s, 1H), 4.73 (dd, J=17.91, 5.46 Hz, 1H), 4.47-4.25 (m, 4H), 4.20 (dd, J=8.79, 2.47 Hz, 1H), 3.76-3.68 (m, 1H), 3.67-3.58 (m, 4H), 3.50 (s, 1H), 3.43-3.32 (m, 4H), 3.21-3.11 (m, 1H), 2.93 (s, 6H), 2.32-2.24 (m, 1H), 1.88-1.76 (m, 1H), 1.72-1.56 (m, 2H).

Example 18

1-(4-Fluoro-benzenesulfonyl)-pyrrolidine-2S-carboxylic acid [2-[(2-dimethylamino-ethyl)-methylamino]-6-(4-trifluoromethyl-phenyl)-pyrimidin-4-ylmethyl]-amide

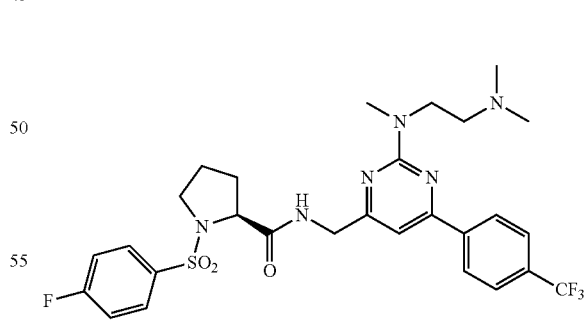

MS (ESI): mass calcd. for $C_{28}H_{32}F_4N_6O_3S$, 608.2; m/z found, 609.3 [M+H]$^+$. $^1$H NMR (500 MHz, CDCl$_3$) δ 8.17 (d, J=7.70 Hz, 2H), 8.09-8.15 (m, 1H), 7.90-7.85 (m, 2H), 7.71 (d, J=8.36 Hz, 2H), 7.20-7.29 (m, 2H), 7.13 (s, 1H), 4.62 (dd, J=16.68, 5.76 Hz, 1H), 4.39 (dd, J=16.72, 4.74 Hz, 1H), 4.23-4.11 (m, 3H), 3.66-3.58 (m, 1H), 3.48-3.35 (m, 2H), 3.33 (s, 3H), 3.20-3.12 (m, 1H), 2.98 (s, 6H), 2.25-2.14 (m, 1H), 1.92-1.80 (m, 1H), 1.77-1.58 (m, 2H).

Example 19

1-(4-Fluoro-benzenesulfonyl)-pyrrolidine-2S-carboxylic acid [2-(4-pyridin-3-ylmethyl-piperazin-1-yl)-6-(4-trifluoromethyl-phenyl)-pyrimidin-4-ylmethyl]-amide

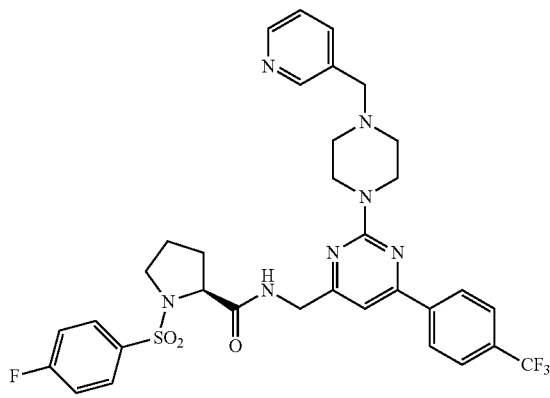 [SMILES: O=C(NCc1cc(-c2ccc(C(F)(F)F)cc2)nc(N2CCN(Cc3cccnc3)CC2)n1)[C@@H]1CCCN1S(=O)(=O)c1ccc(F)cc1]

MS (ESI): mass calcd. for $C_{33}H_{33}F_4N_7O_3S$, 683.2; m/z found, 684.3 [M+H]$^+$. $^1$H NMR (500 MHz, CDCl$_3$) δ 8.85 (s, 1H), 8.77-8.71 (m, 1H), 8.33 (d, J=8.00 Hz, 1H), 8.18 (t, J=4.64, 4.64 Hz, 1H), 8.13 (d, J=8.18 Hz, 2H), 7.90-7.84 (m, 2H), 7.71 (d, J=8.34 Hz, 2H), 7.69-7.64 (m, 1H), 7.28 (t, J=8.47, 8.47 Hz, 2H), 7.10 (s, 1H), 4.70 (dd, J=17.76, 5.59 Hz, 1H), 4.42-4.37 (m, 2H), 4.37-4.33 (m, 4H), 4.15 (dd, J=8.62, 2.52 Hz, 1H), 3.63-3.55 (m, 1H), 3.36-3.22 (m, 4H), 3.17-3.09 (m, 1H), 2.29-2.20 (m, 1H), 2.10-1.95 (m, 1H), 1.88-1.73 (m, 1H), 1.71-1.56 (m, 2H).

Example 20

1-(4-Fluoro-benzenesulfonyl)-pyrrolidine-2S-carboxylic acid [2-[4-(1-methyl-piperidin-4-ylmethyl)-piperazin-1-yl]-6-(4-trifluoromethyl-phenyl)-pyrimidin-4-ylmethyl]-amide

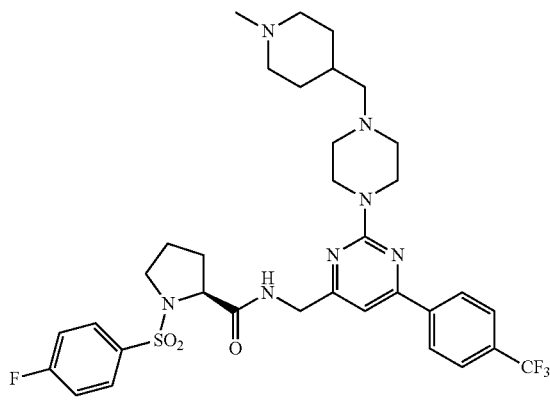 [SMILES: CN1CCC(CN2CCN(c3nc(CNC(=O)[C@@H]4CCCN4S(=O)(=O)c4ccc(F)cc4)cc(-c4ccc(C(F)(F)F)cc4)n3)CC2)CC1]

MS (ESI): mass calcd. for $C_{34}H_{41}F_4N_7O_3S$, 703.3; m/z found, 704.3 [M+H]$^+$. $^1$H NMR (600 MHz, DMSO) δ 8.76 (t, J=5.96, 5.96 Hz, 1H), 8.32 (d, J=8.20 Hz, 2H), 8.00-7.95 (m, 2H), 7.83 (d, J=8.37 Hz, 2H), 7.49-7.44 (m, 2H), 7.39 (s, 1H), 4.94-4.75 (m, 2H), 4.36 (dd, J=17.23, 6.12 Hz, 1H), 4.28 (dd, J=17.20, 5.73 Hz, 1H), 4.16-4.12 (m, 1H), 3.50-3.37 (m, 6H), 3.21-3.13 (m, 1H), 3.14-3.00 (m, 4H), 2.95-2.84 (m, 2H), 2.75 (d, J=4.32 Hz, 3H), 2.10-2.00 (m, 1H), 1.96 (d, J=13.65 Hz, 2H), 1.87-1.72 (m, 4H), 1.57-1.47 (m, 1H), 1.45-1.34 (m, 2H).

Example 21

1-(4-Fluoro-benzenesulfonyl)-pyrrolidine-2S-carboxylic acid [2-(4-pyridin-4-ylmethyl-piperazin-1-yl)-6-(4-trifluoromethyl-phenyl)-pyrimidin-4-ylmethyl]-amide

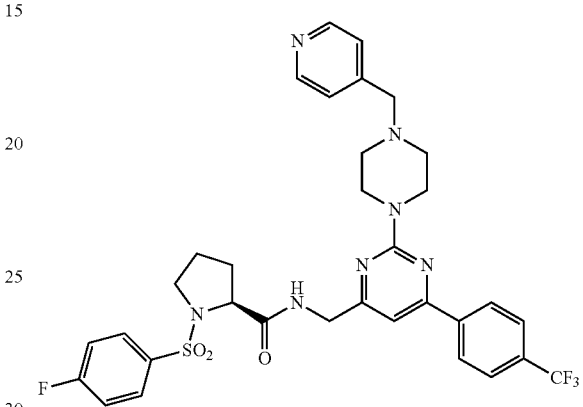

MS (ESI): mass calcd. for $C_{33}H_{33}F_4N_7O_3S$, 683.2; m/z found, 684.3 [M+H]$^+$. $^1$H NMR (500 MHz, CDCl$_3$) δ 8.76 (d, J=5.70 Hz, 2H), 8.24-8.19 (m, 1H), 8.13 (d, J=8.20 Hz, 2H), 7.88-7.83 (m, 2H), 7.76 (d, J=6.05 Hz, 1H), 7.73 (d, J=8.38 Hz, 2H), 7.30 (t, J=8.44, 8.44 Hz, 2H), 7.09 (s, 1H), 4.72 (dd, J=17.83, 5.60 Hz, 1H), 4.48-4.06 (m, 7H), 3.65-3.54 (m, 1H), 3.26-3.14 (m, 4H), 3.16-3.08 (m, 2H), 2.30-2.20 (m, 1H), 1.88-1.74 (m, 1H), 1.71-1.56 (m, 2H).

Example 22

1-(4-Fluoro-benzenesulfonyl)-pyrrolidine-2S-carboxylic acid [2-(4-pyridin-2-ylmethyl-piperazin-1-yl)-6-(4-trifluoromethyl-phenyl)-pyrimidin-4-ylmethyl]-amide

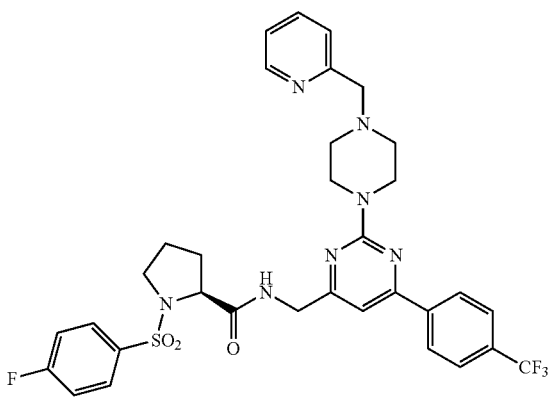 [SMILES: O=C(NCc1cc(-c2ccc(C(F)(F)F)cc2)nc(N2CCN(Cc3ccccn3)CC2)n1)[C@@H]1CCCN1S(=O)(=O)c1ccc(F)cc1]

MS (ESI): mass calcd. for $C_{33}H_{33}F_4N_7O_3S$, 683.2; m/z found, 684.3 [M+H]$^+$. $^1$H NMR (500 MHz, CDCl$_3$) δ 8.61-

8.57 (m, 1H), 8.17 (d, J=8.17 Hz, 2H), 8.06 (t, J=4.95, 4.95 Hz, 1H), 7.91-7.87 (m, 2H), 7.72-7.65 (m, 3H), 7.47 (d, J=7.79 Hz, 1H), 7.28-7.22 (m, 2H), 7.21-7.16 (m, 1H), 6.98 (s, 1H), 4.60 (dd, J=17.58, 5.37 Hz, 1H), 4.45-4.38 (m, 1H), 4.18 (dd, J=8.81, 2.43 Hz, 1H), 4.08-4.01 (m, 4H), 3.76-3.72 (m, 2H), 3.65-3.58 (m, 1H), 3.23-3.13 (m, 1H), 2.68-2.60 (m, 4H), 2.30-2.21 (m, 1H), 1.90-1.75 (m, 1H), 1.72-1.56 (m, 2H).

Example 23

1-(4-Fluoro-benzenesulfonyl)-pyrrolidine-2S-carboxylic acid [2-piperazin-1-yl-6-(4-trifluoromethyl-phenyl)-pyrimidin-4-ylmethyl]-amide

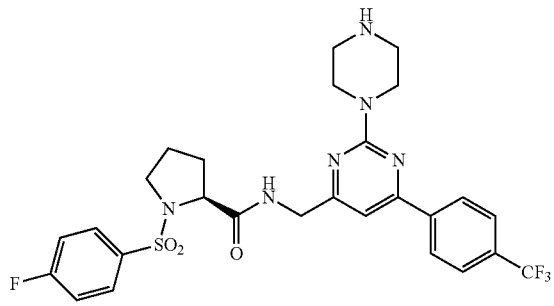 [SMILES: O=C(NCc1cc(-c2ccc(C(F)(F)F)cc2)nc(N2CCNCC2)n1)[C@@H]1CCCN1S(=O)(=O)c1ccc(F)cc1]

MS (ESI): mass calcd. for $C_{27}H_{28}F_4N_6O_3S$, 592.2; m/z found, 563.2 [M+H]$^+$. $^1$H NMR (500 MHz, CDCl$_3$) δ 8.15 (d, J=8.19 Hz, 2H), 8.09 (t, J=4.85, 4.85 Hz, 1H), 7.91-7.84 (m, 3H), 7.71 (d, J=8.33 Hz, 2H), 7.25 (t, J=8.45, 8.45 Hz, 2H), 7.02 (s, 1H), 4.64 (dd, J=17.70, 5.45 Hz, 1H), 4.40 (dd, J=17.73, 4.45 Hz, 1H), 4.19-4.15 (m, 1H), 4.15-4.09 (m, 4H), 3.63-3.56 (m, 1H), 3.19-3.08 (m, 5H), 2.32-2.21 (m, 1H), 1.87-1.72 (m, 1H), 1.70-1.54 (m, 2H).

Example 24

1-(5-Chloro-thiophene-2-sulfonyl)-pyrrolidine-2S-carboxylic acid [2-(4-isobutyl-piperazin-1-yl)-6-(4-trifluoromethyl-phenyl)-pyrimidin-4-ylmethyl]-amide

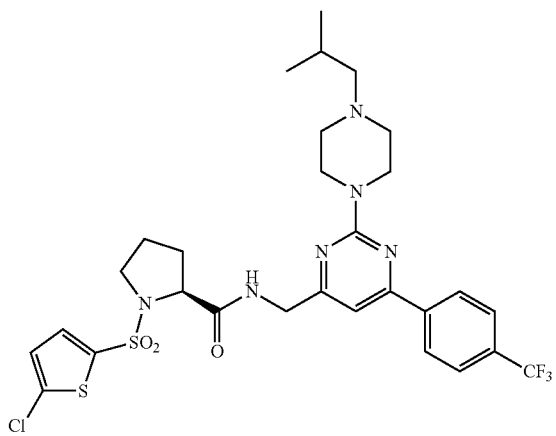 [SMILES: CC(C)CN1CCN(c2nc(CNC(=O)[C@@H]3CCCN3S(=O)(=O)c3ccc(Cl)s3)cc(-c3ccc(C(F)(F)F)cc3)n2)CC1]

MS (ESI): mass calcd. for $C_{29}H_{34}ClF_3N_6O_3S_2$, 670.2; m/z found, 671.2 [M+H]$^+$. $^1$H NMR (400 MHz, CDCl$_3$) δ 8.15 (d, J=8.11 Hz, 2H), 8.05 (t, J=4.72, 4.72 Hz, 1H), 7.70 (d, J=8.26 Hz, 2H), 7.46 (d, J=4.00 Hz, 1H), 7.03 (d, J=4.02 Hz, 1H), 6.91 (s, 1H), 4.58 (dd, J=17.65, 5.13 Hz, 1H), 4.42 (dd, J=17.65, 4.75 Hz, 1H), 4.24-4.18 (m, 1H), 4.01-3.95 (m, 4H), 3.68-3.60 (m, 1H), 3.33-3.23 (m, 1H), 2.53-2.46 (m, 4H), 2.39-2.29 (m, 1H), 2.14 (d, J=7.33 Hz, 2H), 1.93-1.67 (m, 4H), 0.94 (d, J=6.57 Hz, 6H).

Example 25

1-(4-Fluoro-benzenesulfonyl)-pyrrolidine-2S-carboxylic acid [2-(2-methyl-pyrrolidin-1-yl)-6-(4-trifluoromethyl-phenyl)-pyrimidin-4-ylmethyl]-amide MS (ESI): mass calcd. for $C_{28}H_{29}F_4N_5O_3S$, 591.2; m/z found, 592.6 [M+H]$^+$. $^1$H NMR (400 MHz, CDCl3) δ 8.80-8.54 (m, 1H), 8.24 (d, J=8.3, 2H), 7.94-7.87 (m, 2H), 7.74 (d, J=8.3, 2H), 7.26-7.20 (m, 3H), 4.75-4.62 (m, 2H), 4.14-4.07 (m, 1H), 3.96-3.84 (m, 1H), 3.84-3.70 (m, 1H), 3.70-3.60 (m, 1H), 3.21-3.11 (m, 1H), 2.22-2.03 (m, 4H), 1.98-1.89 (m, 1H), 1.86-1.75 (m, 2H), 1.70-1.59 (m, 1H), 1.36 (dd, J=6.4, 0.9, 3H).

Example 26

1-(4-Fluoro-benzenesulfonyl)-pyrrolidine-2S-carboxylic acid [2-(2S-methyl-pyrrolidin-1-yl)-6-(4-trifluoromethyl-phenyl)-pyrimidin-4-ylmethyl]-amide

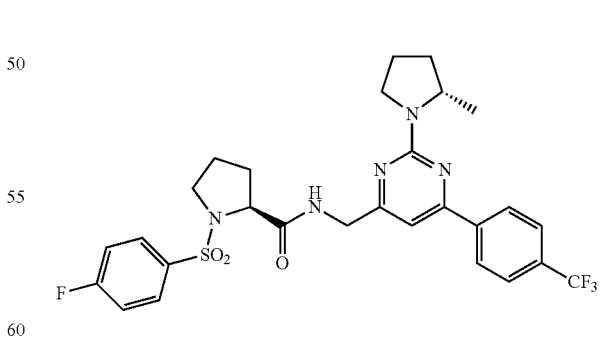

MS (ESI): mass calcd. for $C_{28}H_{29}F_4N_5O_3S$, 591.2; m/z found, 592.2 [M+H]$^+$. $^1$H NMR (500 MHz, CDCl$_3$) δ 8.89-8.61 (m, 1H), 8.27 (d, J=8.33 Hz, 2H), 7.94-7.87 (m, 2H), 7.76 (d, J=8.35 Hz, 2H), 7.32 (s, 1H), 7.26-7.21 (m, 2H), 4.75 (dd, J=16.68, 6.61 Hz, 1H), 4.64-4.53 (m, 2H), 4.12-4.04 (m, 1H), 3.96-3.88 (m, 1H), 3.84-3.75 (m, 1H), 3.71-3.64 (m, 1H), 3.20-3.08 (m, 1H), 2.26-2.02 (m, 4H), 2.03-1.74 (m, 3H), 1.72-1.57 (m, 1H), 1.37 (d, J=6.37 Hz, 3H).

Example 27

1-(4-Fluoro-benzenesulfonyl)-pyrrolidine-2S-carboxylic acid [2-(2R-methyl-pyrrolidin-1-yl)-6-(4-trifluoromethyl-phenyl)-pyrimidin-4-ylmethyl]-amide

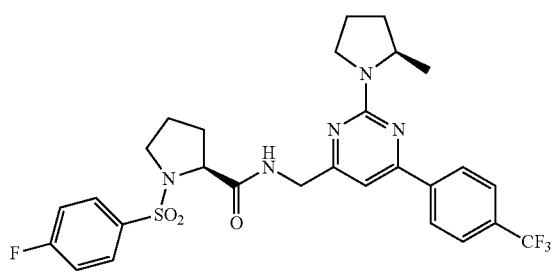 [SMILES: C[C@@H]1CCCN1c1nc(CNC(=O)[C@@H]2CCCN2S(=O)(=O)c2ccc(F)cc2)cc(-c2ccc(C(F)(F)F)cc2)n1]

MS (ESI): mass calcd. for $C_{28}H_{29}F_4N_5O_3S$, 592.2; m/z found, 593.2 [M+H]$^+$. $^1$H NMR (500 MHz, CDCl$_3$) δ 8.92-8.74 (m, 1H), 8.27 (d, J=8.21 Hz, 2H), 7.94-7.89 (m, 2H), 7.76 (d, J=8.32 Hz, 2H), 7.37 (s, 1H), 7.26-7.22 (m, 2H), 4.73 (dd, J=16.70, 6.51 Hz, 1H), 4.65-4.58 (m, 2H), 4.09 (dd, J=8.58, 4.22 Hz, 1H), 3.98-3.90 (m, 1H), 3.81-3.71 (m, 1H), 3.70-3.63 (m, 1H), 3.18-3.09 (m, 1H), 2.28-2.03 (m, 4H), 2.03-1.77 (m, 3H), 1.69-1.58 (m, 1H), 1.37 (d, J=6.38 Hz, 3H).

Example 28

1-(5-Chloro-thiophene-2-sulfonyl)-pyrrolidine-2S-carboxylic acid [2-methylamino-6-(4-trifluoromethyl-phenyl)-pyrimidin-4-ylmethyl]-amide

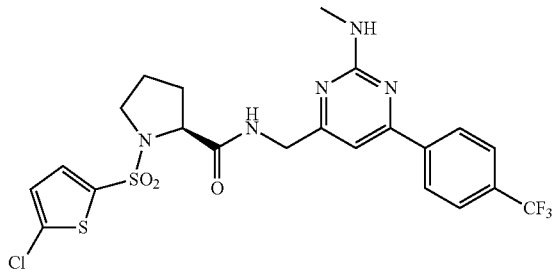 [SMILES: CNc1nc(CNC(=O)[C@@H]2CCCN2S(=O)(=O)c2ccc(Cl)s2)cc(-c2ccc(C(F)(F)F)cc2)n1]

MS (ESI): mass calcd. for $C_{22}H_{21}ClF_3N_5O_3S_2$, 559.0; m/z found, 560.1 [M+H]$^+$. $^1$H NMR (500 MHz, CDCl$_3$) δ 9.96-9.74 (m, 1H), 8.39-8.21 (m, 2H), 7.85-7.79 (m, 1H), 7.77 (d, J=8.34 Hz, 2H), 7.48 (d, J=4.02 Hz, 1H), 7.40-7.33 (m, 1H), 7.05 (d, J=4.02 Hz, 1H), 4.90 (dd, J=17.38, 7.57 Hz, 1H), 4.41 (dd, J=17.47, 4.80 Hz, 1H), 4.16-4.10 (m, 1H), 3.74-3.67 (m, 1H), 3.30-3.21 (m, 1H), 3.19 (s, 3H), 2.19-2.10 (m, 1H), 2.06-1.88 (m, 2H), 1.82-1.73 (m, 1H).

Example 29

1-(5-Chloro-thiophene-2-sulfonyl)-pyrrolidine-2S-carboxylic acid [2-dimethylamino-6-(4-trifluoromethyl-phenyl)-pyrimidin-4-ylmethyl]-amide

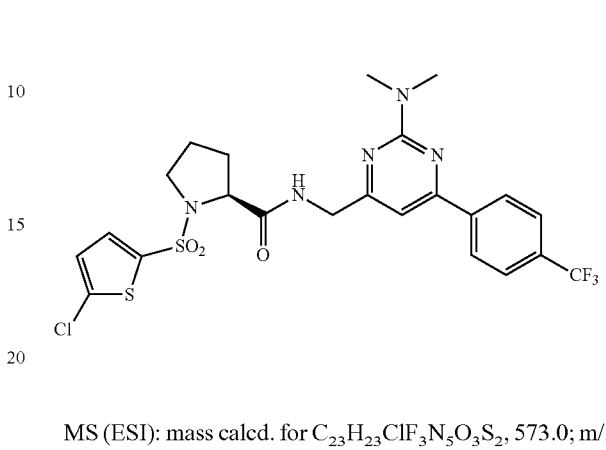

MS (ESI): mass calcd. for $C_{23}H_{23}ClF_3N_5O_3S_2$, 573.0; m/z found, 574.1 [M+H]$^+$. $^1$H NMR (500 MHz, CDCl$_3$) δ 8.79-8.71 (m, 1H), 8.24 (d, J=8.21 Hz, 2H), 7.76 (d, J=8.39 Hz, 2H), 7.48 (d, J=4.02 Hz, 1H), 7.25 (s, 1H), 7.02 (d, J=4.01 Hz, 1H), 4.71 (dd, J=16.73, 6.35 Hz, 1H), 4.55 (dd, J=16.73, 5.08 Hz, 1H), 4.15-4.09 (m, 1H), 3.73-3.67 (m, 1H), 3.42 (s, 6H), 3.29-3.21 (m, 1H), 2.25-2.12 (m, 1H), 2.03-1.91 (m, 2H), 1.80-1.69 (m, 1H).

Example 30

1-(5-Chloro-thiophene-2-sulfonyl)-pyrrolidine-2(S)-carboxylic acid [2-(2R-methyl-pyrrolidin-1-yl)-6-(4-trifluoromethyl-phenyl)-pyrimidin-4-ylmethyl]-amide

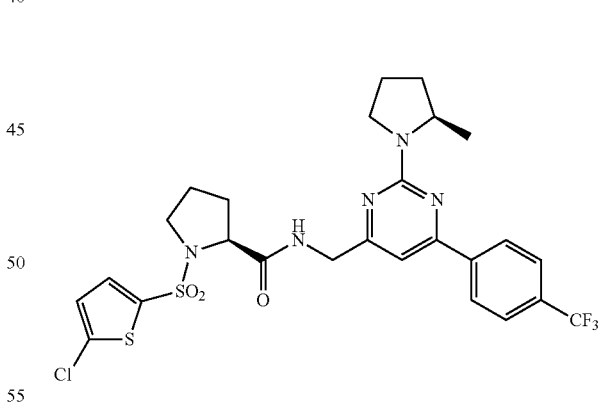

MS (ESI): mass calcd. for $C_{26}H_{27}ClF_3N_5O_3S_2$, 613.1; m/z found, 614.2 [M+H]$^+$. $^1$H NMR (500 MHz, CDCl$_3$) δ 8.82-8.63 (m, 1H), 8.25 (d, J=8.19 Hz, 2H), 7.76 (d, J=8.28 Hz, 2H), 7.49 (d, J=4.01 Hz, 1H), 7.30 (s, 1H), 7.01 (d, J=4.02 Hz, 1H), 4.71 (dd, J=16.61, 6.23 Hz, 1H), 4.65-4.54 (m, 2H), 4.16-4.05 (m, 1H), 3.98-3.87 (m, 1H), 3.81-3.64 (m, 2H), 3.31-3.19 (m, 1H), 2.26-2.04 (m, 4H), 2.04-1.93 (m, 2H), 1.88-1.78 (m, 1H), 1.78-1.69 (m, 1H), 1.36 (d, J=6.35 Hz, 3H).

Example 31

1-(5-Chloro-thiophene-2-sulfonyl)-pyrrolidine-2S-carboxylic acid [2-(2S-methyl-pyrrolidin-1-yl)-6-(4-trifluoromethyl-phenyl)-pyrimidin-4-ylmethyl]-amide

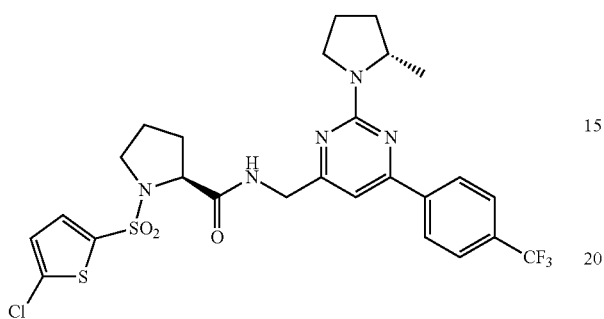

MS (ESI): mass calcd. for $C_{26}H_{27}ClF_3N_5O_3S_2$, 613.1; m/z found, 614.2 [M+H]$^+$. $^1$H NMR (500 MHz, CDCl$_3$) δ 8.90-8.65 (m, 1H), 8.25 (d, J=8.28 Hz, 2H), 7.76 (d, J=8.33 Hz, 2H), 7.48 (d, J=3.97 Hz, 1H), 7.27-7.26 (m, 1H), 7.01 (d, J=3.98 Hz, 1H), 4.75 (dd, J=16.62, 6.43 Hz, 1H), 4.62-4.51 (m, 1H), 4.10 (dd, J=7.91, 3.92 Hz, 1H), 3.95-3.85 (m, 1H), 3.82-3.74 (m, 1H), 3.74-3.67 (m, 1H), 3.29-3.20 (m, 1H), 2.25-2.06 (m, 4H), 2.04-1.91 (m, 1H), 1.85-1.79 (m, 1H), 1.78-1.70 (m, 1H), 1.36 (d, J=6.35 Hz, 3H).

Example 32

1-(5-Chloro-thiophene-2-sulfonyl)-pyrrolidine-2S-carboxylic acid [2-(3R-dimethylamino-pyrrolidin-1-yl)-6-(4-trifluoromethyl-phenyl)-pyrimidin-4-ylmethyl]-amide

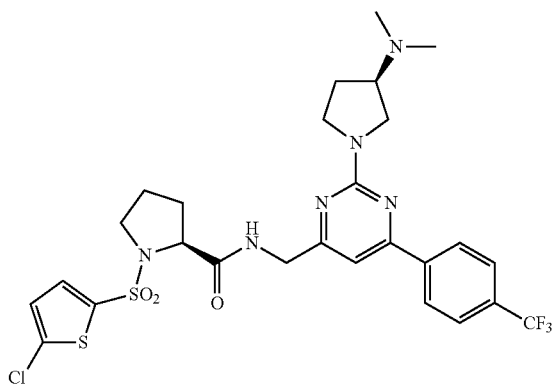 [SMILES: CN(C)[C@@H]1CCN(c2nc(CNC(=O)[C@@H]3CCCN3S(=O)(=O)c3ccc(Cl)s3)cc(-c3ccc(C(F)(F)F)cc3)n2)C1]

MS (ESI): mass calcd. for $C_{27}H_{30}ClF_3N_6O_3S_2$, 642.1; m/z found, 643.2 [M+H]$^+$. $^1$H NMR (500 MHz, CDCl$_3$) δ 8.17 (d, J=8.04 Hz, 2H), 7.71 (d, J=8.29 Hz, 2H), 7.44 (d, J=3.74 Hz, 1H), 7.02 (d, J=4.00 Hz, 1H), 6.94 (s, 1H), 4.58 (dd, J=17.72, 4.84 Hz, 1H), 4.44 (dd, J=17.69, 4.28 Hz, 1H), 4.24-4.10 (m, 2H), 4.08-3.99 (m, 1H), 3.72-3.49 (m, 3H), 3.33-3.19 (m, 1H), 3.19-2.98 (m, 1H), 2.51 (s, 6H), 2.39-2.26 (m, 2H), 2.20-2.06 (m, 1H), 1.93-1.81 (m, 1H), 1.81-1.69 (m, 2H).

Example 33

1-(5-Chloro-thiophene-2-sulfonyl)-pyrrolidine-2S-carboxylic acid [2-(3S-dimethylamino-pyrrolidin-1-yl)-6-(4-trifluoromethyl-phenyl)-pyrimidin-4-ylmethyl]-amide

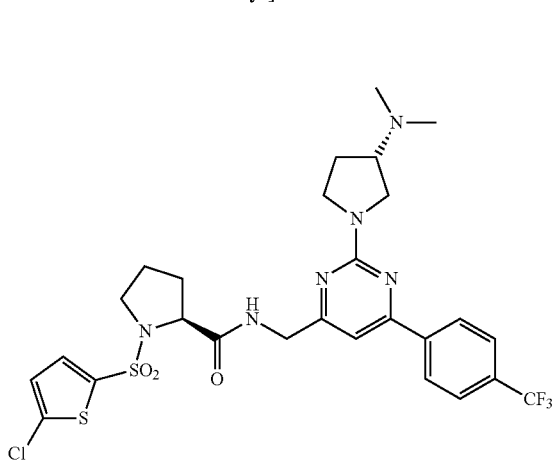

MS (ESI): mass calcd. for $C_{27}H_{30}ClF_3N_6O_3S_2$, 642.1; m/z found, 643.2 [M+H]$^+$. $^1$H NMR (500 MHz, CDCl$_3$) δ 8.18 (d, J=8.16 Hz, 2H), 7.71 (d, J=8.28 Hz, 2H), 7.45 (d, J=4.00 Hz, 1H), 7.02 (d, J=3.98 Hz, 1H), 6.94 (s, 1H), 4.60 (dd, J=17.76, 4.65 Hz, 1H), 4.42 (dd, J=17.70, 4.55 Hz, 1H), 4.21 (dd, J=8.66, 2.25 Hz, 2H), 4.14-4.08 (m, 1H), 4.03-3.93 (m, 1H), 3.79-3.45 (m, 3H), 3.33-3.20 (m, 1H), 3.19-2.86 (m, 1H), 2.46 (s, 6H), 2.40-2.25 (m, 2H), 2.16-2.04 (m, 1H), 1.94-1.81 (m, 1H), 1.82-1.67 (m, 2H).

Example 34

{1-[4-({[1-(5-Chloro-thiophene-2-sulfonyl)-pyrrolidine-2S-carbonyl]-amino}-methyl)-6-(4-trifluoromethyl-phenyl)-pyrimidin-2-yl]-pyrrolidin-3S-yl}-carbamic acid tert-butyl ester

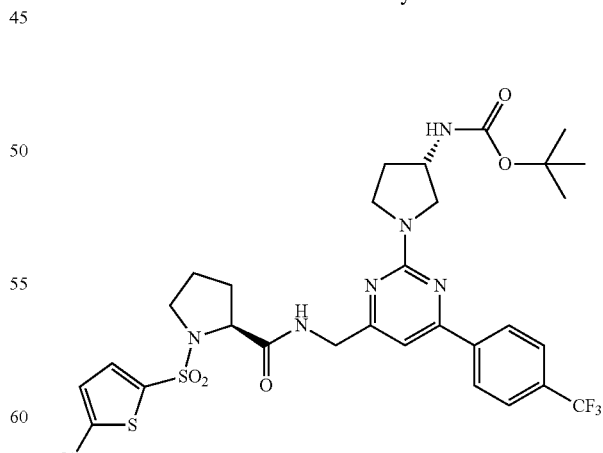

MS (ESI): mass calcd. for $C_{30}H_{34}ClF_3N_6O_5S_2$, 714.1; m/z found, 715.2 [M+H]$^+$. $^1$H NMR (500 MHz, CDCl$_3$) δ 8.57 (s, 1H), 8.18 (d, J=8.20 Hz, 2H), 7.87-7.71 (m, 1H), 7.70 (d, J=8.35 Hz, 2H), 7.44 (d, J=4.01 Hz, 1H), 7.14 (s, 1H), 6.99 (d, J=4.01 Hz, 1H), 4.65 (dd, J=17.10, 5.92 Hz, 1H), 4.44 (dd, J=17.12, 4.74 Hz, 1H), 4.39-4.29 (m, 1H), 4.15-4.08 (m, 1H), 3.95 (dd, J=12.00, 6.07 Hz, 1H), 3.90-3.80 (m, 2H), 3.76-3.62 (m, 2H), 3.28-3.17 (m, 1H), 2.36-2.24 (m, 1H), 2.22-2.15 (m, 1H), 2.09-1.98 (m, 1H), 1.99-1.80 (m, 2H), 1.78-1.69 (m, 1H), 1.41 (s, 9H).

Example 35

{1-[4-({[1-(5-Chloro-thiophene-2-sulfonyl)-pyrrolidine-2S-carbonyl]-amino}-methyl)-6-(4-trifluoromethyl-phenyl)-pyrimidin-2-yl]-pyrrolidin-3R-yl}-carbamic acid tert-butyl ester

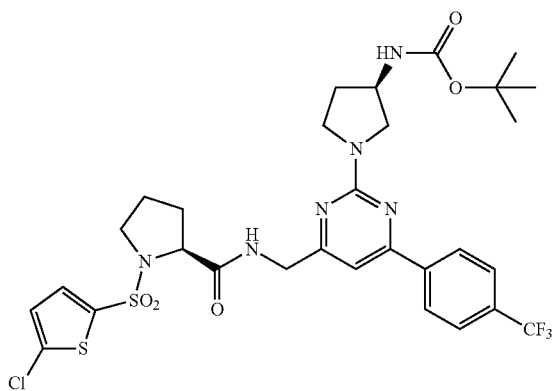 [SMILES: CC(C)(C)OC(=O)N[C@@H]1CCN(c2nc(CNC(=O)[C@@H]3CCCN3S(=O)(=O)c3ccc(Cl)s3)cc(-c3ccc(C(F)(F)F)cc3)n2)C1]

MS (ESI): mass calcd. for $C_{30}H_{34}ClF_3N_6O_5S_2$, 714.1; m/z found, 715.2 [M+H]$^+$. $^1$H NMR (500 MHz, CDCl$_3$) δ 8.61 (s, 1H), 8.22 (d, J=8.23 Hz, 2H), 7.74 (d, J=8.43 Hz, 2H), 7.63-7.50 (m, 1H), 7.47 (d, J=4.01 Hz, 1H), 7.18 (s, 1H), 7.02 (d, J=4.01 Hz, 1H), 4.67 (dd, J=16.94, 5.50 Hz, 1H), 4.49 (dd, J=17.06, 4.94 Hz, 1H), 4.43-4.33 (m, 1H), 4.18-4.11 (m, 1H), 4.05-3.97 (m, 1H), 3.97-3.89 (m, 1H), 3.89-3.81 (m, 1H), 3.80-3.64 (m, 2H), 3.31-3.21 (m, 1H), 2.40-2.26 (m, 1H), 2.25-2.18 (m, 1H), 2.13-2.03 (m, 1H), 2.01-1.84 (m, 2H), 1.81-1.71 (m, 1H), 1.43 (s, 9H).

Example 36

1-(5-Chloro-thiophene-2-sulfonyl)-pyrrolidine-2S-carboxylic acid [2-(1-pyridin-2-yl-ethylamino)-6-(4-trifluoromethyl-phenyl)-pyrimidin-4S-ylmethyl]-amide

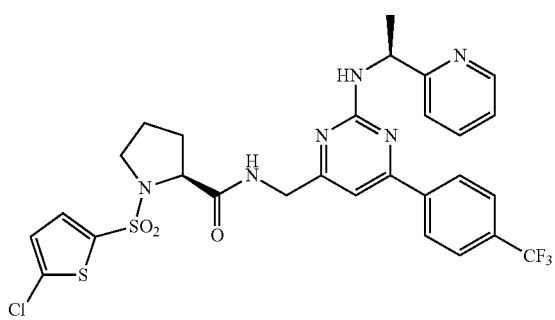 [SMILES: C[C@H](Nc1nc(CNC(=O)[C@@H]2CCCN2S(=O)(=O)c2ccc(Cl)s2)cc(-c2ccc(C(F)(F)F)cc2)n1)c1ccccn1]

MS (ESI): mass calcd. for $C_{28}H_{26}ClF_3N_6O_3S_2$, 650.1; m/z found, 651.2 [M+H]$^+$. $^1$H NMR (500 MHz, CDCl$_3$) δ 10.31-10.01 (m, 1H), 8.88 (d, J=5.39 Hz, 1H), 8.23-8.15 (m, 1H), 8.12 (d, J=7.99 Hz, 2H), 7.93 (d, J=7.73 Hz, 2H), 7.89-7.80 (m, 1H), 7.68 (d, J=8.04 Hz, 2H), 7.66-7.60 (m, 1H), 7.47 (d, J=4.00 Hz, 1H), 7.38 (t, J=7.89, 7.89 Hz, 1H), 7.04 (d, J=3.97 Hz, 1H), 5.87-5.76 (m, 1H), 4.95-4.73 (m, 1H), 4.50-4.32 (m, 1H), 4.18-4.09 (m, 1H), 3.74-3.65 (m, 1H), 3.30-3.20 (m, 1H), 2.22-2.11 (m, 1H), 2.03-1.88 (m, 2H), 1.80 (d, J=7.10 Hz, 3H), 1.79-1.73 (m, 1H).

Example 37

1-(5-Chloro-thiophene-2-sulfonyl)-pyrrolidine-2S-carboxylic acid [2-(1-pyridin-2-yl-ethylamino)-6-(4-trifluoromethyl-phenyl)-pyrimidin-4R-ylmethyl]-amide

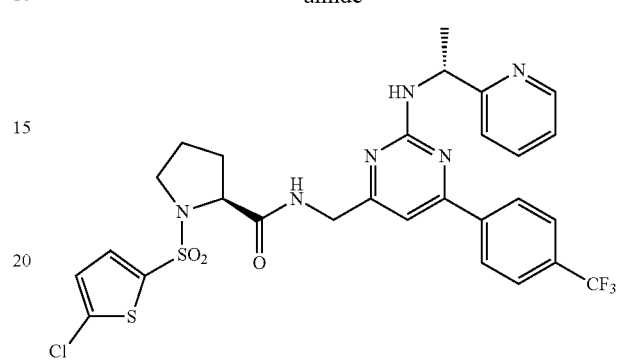

MS (ESI): mass calcd. for $C_{28}H_{26}ClF_3N_6O_3S_2$, 650.1; m/z found, 651.2 [M+H]$^+$. $^1$H NMR (500 MHz, CDCl$_3$) δ 10.38 (s, 1H), 8.91-8.83 (m, 1H), 8.28-8.05 (m, 3H), 8.02-7.86 (m, 2H), 7.69 (d, J=7.39 Hz, 2H), 7.67-7.58 (m, 1H), 7.45 (d, J=4.02 Hz, 1H), 7.42-7.35 (m, 1H), 7.03 (d, J=4.01 Hz, 1H), 5.90-5.82 (m, 1H), 4.96-4.78 (m, 1H), 4.47-4.30 (m, 1H), 4.16-4.03 (m, 1H), 3.75-3.64 (m, 1H), 3.30-3.19 (m, 1H), 2.23-2.09 (m, 1H), 2.05-1.88 (m, 2H), 1.81 (d, J=7.03 Hz, 3H), 1.79-1.72 (m, 1H).

Example 38

{1-[4-({[1-(5-Chloro-thiophene-2-sulfonyl)-pyrrolidine-2S-carbonyl]-amino}-methyl)-6-(4-trifluoromethyl-phenyl)-pyrimidin-2-yl]-pyrrolidin-3-yl}-methyl-carbamic acid tert-butyl ester

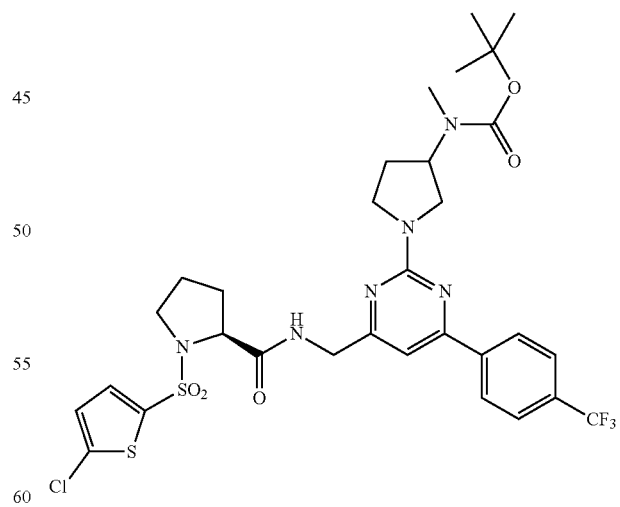

MS (ESI): mass calcd. for $C_{31}H_{36}ClF_3N_6O_5S_2$, 728.2; m/z found, 729.2 [M+H]$^+$. $^1$H NMR (500 MHz, CDCl$_3$) δ 8.80-8.66 (m, 1H), 8.25 (d, J=8.21 Hz, 2H), 7.76 (d, J=8.41 Hz, 2H), 7.50-7.45 (m, 1H), 7.32-7.29 (m, 1H), 7.02 (dd, J=3.99, 0.93 Hz, 1H), 5.04-4.83 (m, 2H), 4.79-4.67 (m, 1H), 4.59-4.49 (m, 1H), 4.17-3.99 (m, 1H), 3.84-3.61 (m, 3H), 3.29-

3.19 (m, 1H), 2.83 (d, J=6.31 Hz, 3H), 2.36-2.10 (m, 3H), 2.01-1.91 (m, 2H), 1.80-1.69 (m, 1H), 1.48 (s, 9H).

Example 39

1-(5-Chloro-thiophene-2-sulfonyl)-pyrrolidine-2S-carboxylic acid [2-(3S-amino-pyrrolidin-1-yl)-6-(4-trifluoromethyl-phenyl)-pyrimidin-4-ylmethyl]-amide

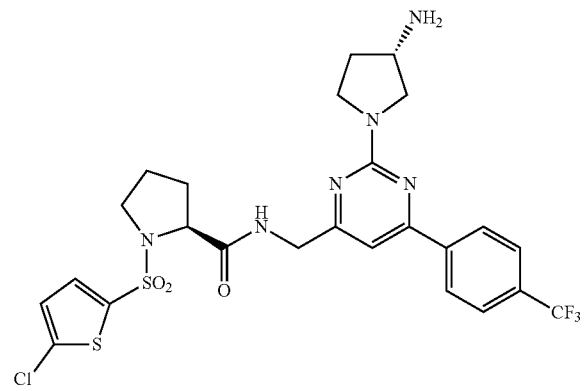 [SMILES: N[C@H]1CCN(c2nc(CNC(=O)[C@@H]3CCCN3S(=O)(=O)c3ccc(Cl)s3)cc(-c3ccc(C(F)(F)F)cc3)n2)C1]

A solution of {1-[4-({[1-(5-Chloro-thiophene-2-sulfonyl)-pyrrolidine-2-carbonyl]-amino}-methyl)-6-(4-trifluoromethyl-phenyl)-pyrimidin-2-yl]-pyrrolidin-3-yl}-carbamic acid tert-butyl ester (0.06 g, 0.08 mmol) in 4N HCl and dioxane (3 mL) was stirred at rt. After 3 h, the resulting mixture was concentrated and purified by preparative reverse-phase HPLC to afford the title compound as a colorless solid (0.05 g, 97%). MS (ESI): mass calcd. for $C_{25}H_{26}ClF_3N_6O_3S_2$, 614.1; m/z found, 615.1 [M+H]$^+$. $^1$H NMR (500 MHz, CDCl$_3$) δ 8.45-8.32 (m, 1H), 8.23 (d, J=8.06 Hz, 2H), 7.69 (d, J=8.27 Hz, 2H), 7.45 (d, J=3.94 Hz, 1H), 7.37 (s, 1H), 6.97 (d, J=4.00 Hz, 1H), 4.76 (dd, J=17.26, 6.26 Hz, 1H), 4.44 (dd, J=16.87, 3.29 Hz, 1H), 4.21-4.09 (m, 2H), 4.09-4.02 (m, 1H), 4.03-3.98 (m, 1H), 3.93-3.84 (m, 1H), 3.68-3.59 (m, 1H), 3.25-3.16 (m, 1H), 2.52-2.31 (m, 2H), 2.13-2.02 (m, 1H), 2.01-1.82 (m, 2H), 1.73-1.64 (m, 1H).

Examples 40 to 41 were prepared using methods analogous to those described for Example 39.

Example 40

1-(5-Chloro-thiophene-2-sulfonyl)-pyrrolidine-2S-carboxylic acid [2-(3R-amino-pyrrolidin-1-yl)-6-(4-trifluoromethyl-phenyl)-pyrimidin-4-ylmethyl]-amide

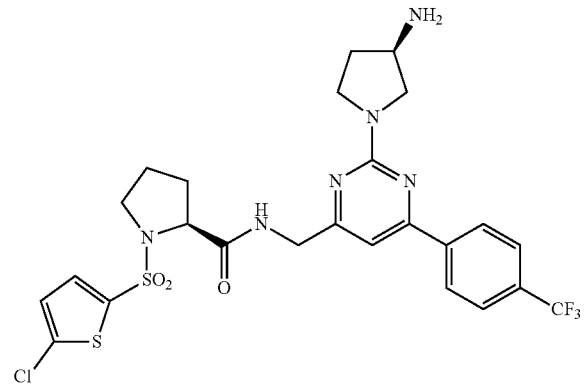 [SMILES: N[C@@H]1CCN(c2nc(CNC(=O)[C@@H]3CCCN3S(=O)(=O)c3ccc(Cl)s3)cc(-c3ccc(C(F)(F)F)cc3)n2)C1]

MS (ESI): mass calcd. for $C_{25}H_{26}ClF_3N_6O_3S_2$, 614.1; m/z found, 615.1 [M+H]$^+$. $^1$H NMR (500 MHz, CDCl$_3$) δ 8.39 (t, J=5.15, 5.15 Hz, 1H), 8.24 (d, J=8.20 Hz, 2H), 7.68 (d, J=8.12 Hz, 2H), 7.45 (d, J=4.00 Hz, 1H), 7.42 (s, 1H), 6.99 (d, J=3.97 Hz, 1H), 4.84-4.71 (m, 1H), 4.53-4.39 (m, 1H), 4.30-4.14 (m, 2H), 4.14-3.98 (m, 3H), 3.94-3.81 (m, 1H), 3.68-3.58 (m, 1H), 3.25-3.15 (m, 1H), 2.51-2.32 (m, 1H), 2.11-2.01 (m, 1H), 2.01-1.83 (m, 2H), 1.75-1.62 (m, 1H).

Example 41

1-(5-Chloro-thiophene-2-sulfonyl)-pyrrolidine-2S-carboxylic acid [2-(3-methylamino-pyrrolidin-1-yl)-6-(4-trifluoromethyl-phenyl)-pyrimidin-4-ylmethyl]-amide

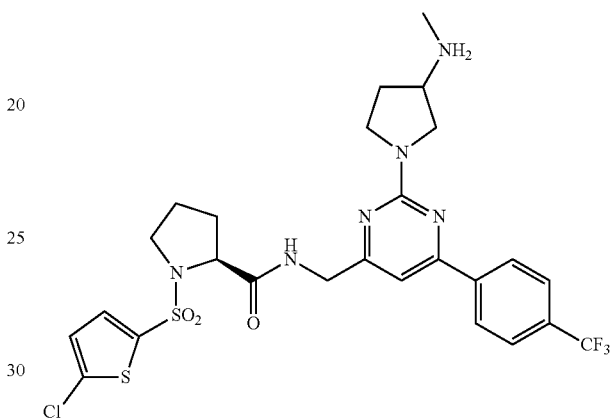

MS (ESI): mass calcd. for $C_{26}H_{28}ClF_3N_6O_3S_2$, 628.1; m/z found, 629.1 [M+H]$^+$. $^1$H NMR (500 MHz, CDCl$_3$) δ 8.49 (t, J=5.37, 5.37 Hz, 1H), 8.20 (d, J=8.06 Hz, 2H), 7.71 (d, J=8.12 Hz, 2H), 7.45 (dd, J=3.84, 2.73 Hz, 1H), 7.27 (s, 1H), 7.01 (t, J=4.32, 4.32 Hz, 1H), 4.73 (dd, J=17.34, 6.26 Hz, 1H), 4.49-4.39 (m, 1H), 4.27-4.19 (m, 1H), 4.19-4.03 (m, 3H), 3.97-3.79 (m, 2H), 3.70-3.61 (m, 1H), 3.27-3.17 (m, 1H), 2.79 (d, J=6.11 Hz, 3H), 2.53-2.41 (m, 2H), 2.21-2.11 (m, 1H), 1.97-1.84 (m, 2H), 1.79-1.68 (m, 1H).

Example 42

1-(4-Fluoro-benzenesulfonyl)-pyrrolidine-2-carboxylic acid [2-isobutoxy-6-(4-trifluoromethyl-phenyl)-pyrimidin-4-ylmethyl]-amide

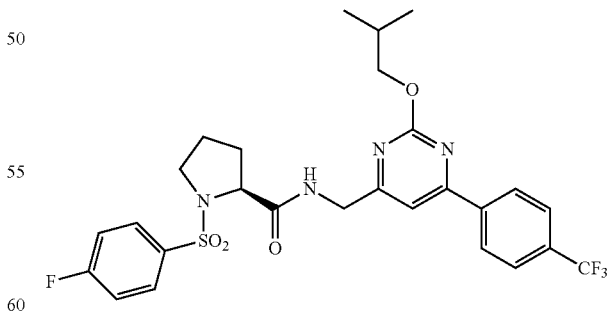

To a solution of sodium hydride (0.02 g, 0.54 mmol) in isobutanol (1.0 mL) was added 1-(4-fluoro-benzenesulfonyl)-pyrrolidine-2S-carboxylic acid [2-phenylmethanesulfonyl-6-(4-trifluoromethyl-phenyl)-pyrimidin-4-ylmethyl]-amide (0.06 g, 0.10 mmol) at rt. After 1 h, the resulting mixture was concentrated and purified by preparative reverse-phase HPLC to afford the title compound as a colorless solid (0.03 g, 48%). MS (ESI): mass calcd. for $C_{27}H_{28}F_4N_4O_4S$, 580.1; m/z found, 581.2 [M+H]$^+$. $^1$H NMR (500 MHz, CDCl$_3$) δ 8.29 (d, J=8.17 Hz, 2H), 7.95-7.88 (m, 3H), 7.73 (d, J=8.29 Hz, 2H), 7.65 (s, 1H), 7.31-7.27 (m, 2H), 4.89 (dd, J=17.46, 7.28 Hz, 1H), 4.50 (dd, J=17.45, 4.90 Hz, 1H), 4.33-4.29 (m, 2H), 4.23 (dd, J=8.82, 3.46 Hz, 1H), 3.71-3.63 (m, 1H), 3.22-3.12 (m, 1H), 2.27-2.11 (m, 2H), 1.95-1.76 (m, 2H), 1.73-1.65 (m, 1H), 1.08 (d, J=6.73 Hz, 6H).

Example 43 was prepared using methods analogous to those described for Example 42.

Example 43

1-(5-Chloro-thiophene-2-sulfonyl)-pyrrolidine-2S-carboxylic acid [2-isobutoxy-6-(4-trifluoromethyl-phenyl)-pyrimidin-4-ylmethyl]-amide

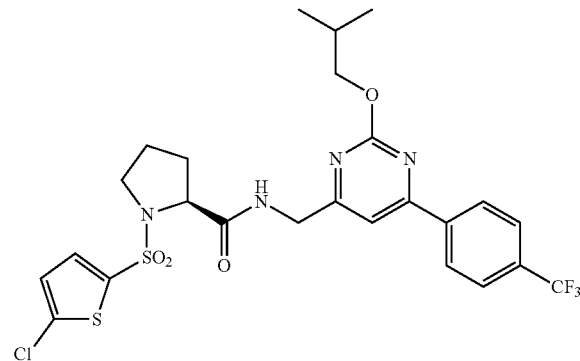 [SMILES: CC(C)COc1nc(CNC(=O)[C@@H]2CCCN2S(=O)(=O)c2ccc(Cl)s2)cc(-c2ccc(C(F)(F)F)cc2)n1]

MS (ESI): mass calcd. for $C_{25}H_{26}ClF_3N_4O_4S_2$, 602.1; m/z found, 603.1 [M+H]$^+$. $^1$H NMR (500 MHz, CDCl$_3$) δ 8.27 (d, J=8.22 Hz, 2H), 7.92-7.85 (m, 1H), 7.75 (d, J=8.40 Hz, 2H), 7.61 (s, 1H), 7.50 (d, J=4.02 Hz, 1H), 7.06 (d, J=4.01 Hz, 1H), 4.89 (dd, J=17.41, 7.24 Hz, 1H), 4.51 (dd, J=17.41, 4.91 Hz, 1H), 4.32-4.29 (m, 2H), 4.24 (dd, J=8.41, 3.42 Hz, 1H), 3.73-3.66 (m, 1H), 3.33-3.23 (m, 1H), 2.27-2.13 (m, 2H), 2.01-1.87 (m, 2H), 1.84-1.75 (m, 1H), 1.08 (d, J=6.73 Hz, 6H).

Examples 44 to 46 were prepared using methods analogous to those described for Example 1.

Example 44

1-(5-Chloro-thiophene-2-sulfonyl)-pyrrolidine-2S-carboxylic acid [2-(2-isopropyl-pyrrolidin-1-yl)-6-(4-trifluoromethyl-phenyl)-pyrimidin-4-ylmethyl]-amide

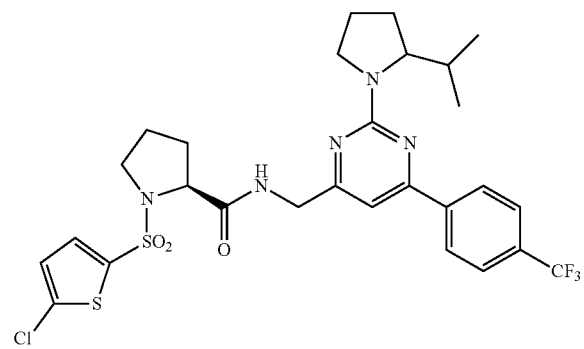 [SMILES: CC(C)C1CCCN1c1nc(CNC(=O)[C@@H]2CCCN2S(=O)(=O)c2ccc(Cl)s2)cc(-c2ccc(C(F)(F)F)cc2)n1]

MS (ESI): mass calcd. for $C_{28}H_{31}ClF_3N_5O_3S_2$, 641.1; m/z found, 642.2 [M+H]$^+$. $^1$H NMR (500 MHz, CDCl$_3$) δ 9.02-8.76 (m, 1H), 8.24 (dd, J=7.70, 5.65 Hz, 2H), 7.78 (d, J=8.28 Hz, 2H), 7.48 (dd, J=4.00, 2.76 Hz, 1H), 7.33 (d, J=10.64 Hz, 1H), 7.01 (d, J=4.01 Hz, 1H), 4.80-4.68 (m, 1H), 4.65-4.53 (m, 1H), 4.50-4.43 (m, 1H), 4.13-4.03 (m, 1H), 4.01-3.85 (m, 1H), 3.85-3.75 (m, 1H), 3.75-3.67 (m, 1H), 3.29-3.20 (m, 1H), 2.51-2.37 (m, 1H), 2.20-2.09 (m, 2H), 2.09-1.94 (m, 5H), 1.80-1.68 (m, 1H), 0.94 (d, J=6.84 Hz, 6H).

Example 45

1-(5-Chloro-thiophene-2-sulfonyl)-pyrrolidine-2S-carboxylic acid [2-(2-hydroxy-propylamino)-6-(4-trifluoromethyl-phenyl)-pyrimidin-4-ylmethyl]-amide

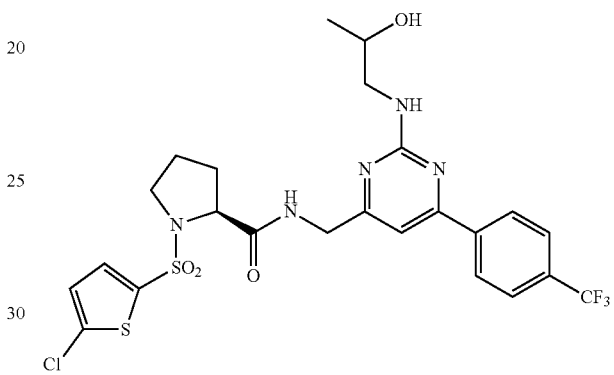

MS (ESI): mass calcd. for $C_{24}H_{25}ClF_3N_5O_4S_2$, 603.1; m/z found, 604.1 [M+H]$^+$. $^1$H NMR (500 MHz, CDCl$_3$) δ 9.93 (s, 1H), 8.33-8.18 (m, 2H), 7.88-7.79 (m, 1H), 7.77 (d, J=8.39 Hz, 2H), 7.47 (d, J=4.03 Hz, 1H), 7.39-7.32 (m, 1H), 7.05 (d, J=4.02 Hz, 1H), 5.00-4.77 (m, 1H), 4.40 (dd, J=17.42, 4.70 Hz, 1H), 4.19-4.07 (m, 2H), 3.79-3.66 (m, 2H), 3.65-3.53 (m, 1H), 3.29-3.21 (m, 1H), 2.23-2.08 (m, 1H), 2.06-1.86 (m, 2H), 1.82-1.72 (m, 1H), 1.30 (d, J=6.33 Hz, 3H).

Example 46

1-(5-Chloro-thiophene-2-sulfonyl)-pyrrolidine-2S-carboxylic acid [2-(2-hydroxy-2-methyl-propylamino)-6-(4-trifluoromethyl-phenyl)-pyrimidin-4-ylmethyl]-amide

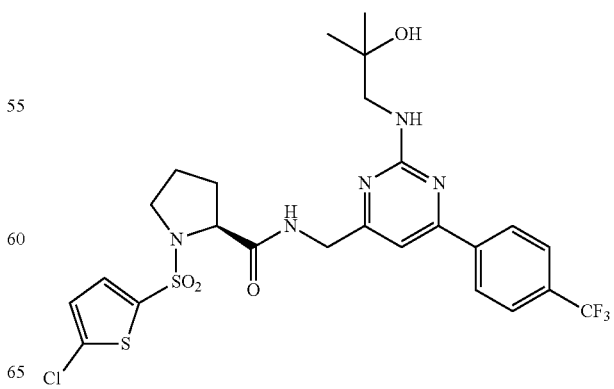

MS (ESI): mass calcd. for $C_{25}H_{27}ClF_3N_5O_4S_2$, 617.1; m/z found, 618.1 [M+H]⁺. ¹H NMR (500 MHz, CDCl₃) δ 9.87-9.64 (m, 1H), 8.38-8.12 (m, 2H), 7.91-7.80 (m, 1H), 7.77 (d, J=8.43 Hz, 2H), 7.47 (d, J=4.02 Hz, 1H), 7.39-7.31 (m, 1H), 7.04 (d, J=4.03 Hz, 1H), 4.95-4.81 (m, 1H), 4.41 (dd, J=17.41, 4.90 Hz, 1H), 4.17-4.04 (m, 1H), 3.77-3.61 (m, 3H), 3.30-3.21 (m, 1H), 2.27-2.09 (m, 1H), 2.06-1.86 (m, 2H), 1.83-1.72 (m, 1H), 1.34 (d, J=1.28 Hz, 6H).

Example 47 was prepared using methods analogous to those described for Example 2.

Example 47

1-(5-Chloro-thiophene-2-sulfonyl)-pyrrolidine-2S-carboxylic acid [2-methoxy-6-(4-trifluoromethyl-phenyl)-pyrimidin-4-ylmethyl]-amide

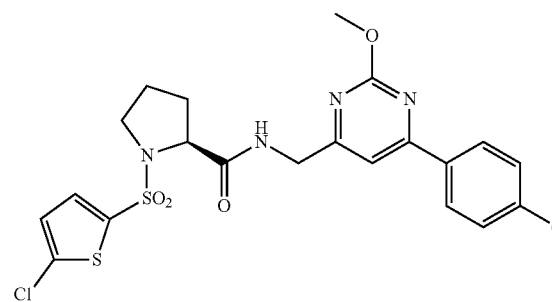

MS (ESI): mass calcd. for $C_{22}H_{20}ClF_3N_4O_4S_2$, 560.0; m/z found, 561.1 [M+H]⁺. ¹H NMR (500 MHz, CDCl₃) δ 8.28 (d, J=8.42 Hz, 2H), 7.85-7.79 (m, 1H), 7.74 (d, J=8.40 Hz, 2H), 7.56 (s, 1H), 7.49 (d, J=4.04 Hz, 1H), 7.05 (d, J=4.03 Hz, 1H), 4.85 (dd, J=17.44, 7.00 Hz, 1H), 4.49 (dd, J=17.44, 4.90 Hz, 1H), 4.25 (dd, J=8.20, 3.17 Hz, 1H), 4.15 (s, 3H), 3.73-3.65 (m, 1H), 3.34-3.24 (m, 1H), 2.32-2.19 (m, 1H), 1.98-1.87 (m, 2H), 1.85-1.74 (m, 1H).

Example 48 was prepared using methods analogous to those described for example 1.

Example 48

1-(5-Chloro-thiophene-2-sulfonyl)-pyrrolidine-2S-carboxylic acid [2-(2-methyl-pyrrolidin-1-yl)-6-(4-trifluoromethyl-phenyl)-pyrimidin-4-ylmethyl]-amide

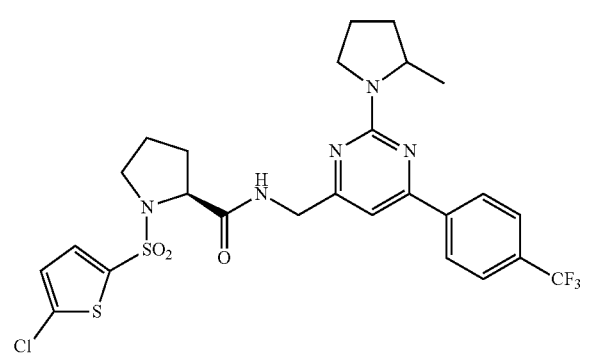 [SMILES: CC1CCCN1c1nc(CNC(=O)[C@@H]2CCCN2S(=O)(=O)c2ccc(Cl)s2)cc(-c2ccc(C(F)(F)F)cc2)n1]

MS (ESI): mass calcd. for $C_{26}H_{27}ClF_3N_5O_3S_2$, 613.1; m/z found, 614.1 [M+H]⁺. ¹H NMR (500 MHz, CDCl₃) δ 8.18 (d, J=8.02 Hz, 2H), 8.16-8.13 (m, 1H), 7.71 (d, J=8.28 Hz, 2H), 7.47-7.44 (m, 1H), 7.02 (d, J=4.00 Hz, 1H), 6.89 (d, J=5.96 Hz, 1H), 4.60-4.51 (m, 1H), 4.50-4.39 (m, 2H), 4.23-4.18 (m, 1H), 3.87-3.60 (m, 3H), 3.29 (dt, J=9.98, 9.89, 6.64 Hz, 1H), 2.38-2.28 (m, 1H), 2.20-2.05 (m, 2H), 2.03-1.94 (m, 1H), 1.93-1.83 (m, 1H), 1.83-1.72 (m, 3H), 1.35 (d, J=6.29 Hz, 3H).

Example 49 was prepared using methods analogous to those described for Example 2.

Example 49

1-(5-Chloro-thiophene-2-sulfonyl)-pyrrolidine-2S-carboxylic acid [2-ethoxy-6-(4-trifluoromethyl-phenyl)-pyrimidin-4-ylmethyl]-amide

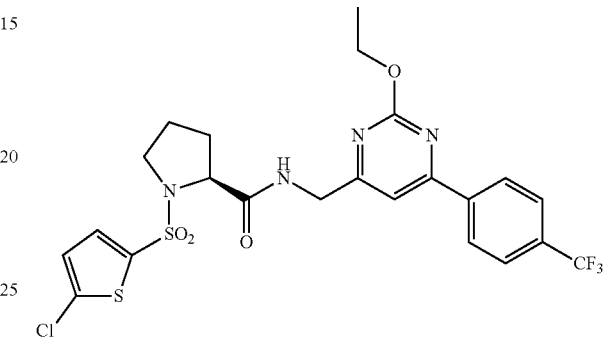

MS (ESI): mass calcd. for $C_{23}H_{22}ClF_3N_4O_4S_2$, 574.0; m/z found, 575.1 [M+H]⁺. ¹H NMR (500 MHz, CDCl₃) δ 8.27 (d, J=8.25 Hz, 2H), 7.86-7.79 (m, 1H), 7.74 (d, J=8.45 Hz, 2H), 7.56 (s, 1H), 7.50 (d, J=4.04 Hz, 1H), 7.06 (d, J=4.02 Hz, 1H), 4.85 (dd, J=17.50, 7.03 Hz, 1H), 4.63-4.55 (m, 2H), 4.48 (dd, J=17.51, 4.84 Hz, 1H), 4.25 (dd, J=8.31, 3.19 Hz, 1H), 3.72-3.65 (m, 1H), 3.33-3.23 (m, 1H), 2.32-2.19 (m, 1H), 1.99-1.85 (m, 2H), 1.85-1.74 (m, 1H), 1.50 (t, J=7.08, 7.08 Hz, 3H).

Examples 50 to 57 were prepared using methods analogous to those described for Example 1.

Example 50

1-(4-Fluoro-benzenesulfonyl)-pyrrolidine-2S-carboxylic acid [2-[4-(2-chloro-benzyl)-piperazin-1-yl]-6-(4-trifluoromethyl-phenyl)-pyrimidin-4-ylmethyl]-amide

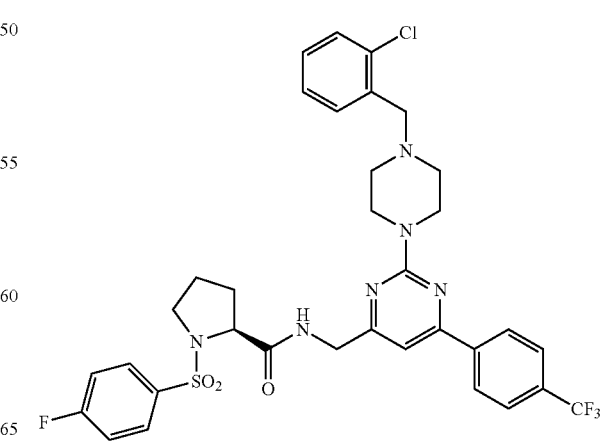

MS (ESI): mass calcd. for C$_{34}$H$_{33}$ClF$_4$N$_6$O$_3$S, 716.2; m/z found, 717.2 [M+H]$^+$. $^1$H NMR (500 MHz, CDCl$_3$) δ 8.23-8.15 (m, 1H), 8.13 (d, J=8.14 Hz, 2H), 7.91-7.85 (m, 2H), 7.73-7.69 (m, 3H), 7.44-7.40 (m, 1H), 7.39-7.36 (m, 2H), 7.31-7.27 (m, 2H), 7.10 (s, 1H), 5.31-4.96 (m, 2H), 4.71 (dd, J=17.87, 5.78 Hz, 1H), 4.49 (q, J=13.17, 13.16, 13.16 Hz, 2H), 4.38 (dd, J=17.85, 4.15 Hz, 1H), 4.19 (dd, J=8.78, 2.81 Hz, 1H), 3.85-3.42 (m, 5H), 3.19-3.11 (m, 1H), 3.10-2.87 (m, 2H), 2.33-2.18 (m, 1H), 1.90-1.73 (m, 1H), 1.71-1.58 (m, 2H).

Example 51

1-(4-Fluoro-benzenesulfonyl)-pyrrolidine-2S-carboxylic acid [2-[4-(2-trifluoromethoxy-benzyl)-piperazin-1-yl]-6-(4-trifluoromethyl-phenyl)-pyrimidin-4-ylmethyl]-amide

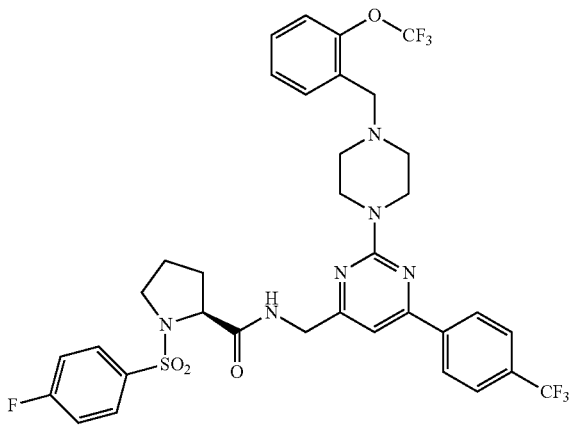 [SMILES: O=C(NCc1cc(-c2ccc(C(F)(F)F)cc2)nc(N2CCN(Cc3ccccc3OC(F)(F)F)CC2)n1)[C@@H]1CCCN1S(=O)(=O)c1ccc(F)cc1]

MS (ESI): mass calcd. for C$_{35}$H$_{33}$F$_7$N$_6$O$_4$S, 766.2; m/z found, 767.2 [M+H]$^+$. $^1$H NMR (500 MHz, CDCl$_3$) δ 8.23-8.15 (m, 1H), 8.13 (d, J=8.17 Hz, 2H), 7.90-7.86 (m, 2H), 7.74-7.70 (m, 3H), 7.53-7.47 (m, 1H), 7.33-7.42 (m, 1H), 7.33-7.29 (m, 1H), 7.31-7.27 (m, 2H), 7.09 (s, 1H), 5.40-4.91 (m, 1H), 4.71 (dd, J=17.91, 5.73 Hz, 1H), 4.42-4.32 (m, 3H), 4.18 (dd, J=8.73, 2.62 Hz, 1H), 3.84-3.35 (m, 5H), 3.19-3.09 (m, 1H), 3.06-2.75 (m, 2H), 2.32-2.18 (m, 1H), 1.87-1.75 (m, 1H), 1.71-1.58 (m, 2H).

Example 52

1-(4-Fluoro-benzenesulfonyl)-pyrrolidine-2S-carboxylic acid [2-[4-(2-ethyl-benzyl)-piperazin-1-yl]-6-(4-trifluoromethyl-phenyl)-pyrimidin-4-ylmethyl]-amide

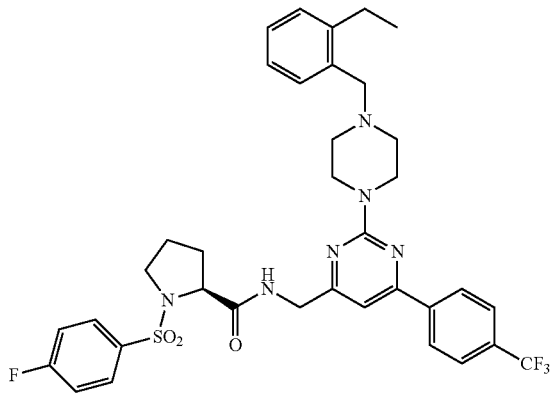 [SMILES: CCc1ccccc1CN1CCN(c2nc(CNC(=O)[C@@H]3CCCN3S(=O)(=O)c3ccc(F)cc3)cc(-c3ccc(C(F)(F)F)cc3)n2)CC1]

MS (ESI): mass calcd. for C$_{36}$H$_{38}$F$_4$N$_6$O$_3$S, 710.2; m/z found, 711.3 [M+H]$^+$. $^1$H NMR (500 MHz, CDCl$_3$) δ 8.23-8.15 (m, 1H), 8.13 (d, J=8.26 Hz, 2H), 7.90-7.85 (m, 2H), 7.71 (d, J=8.42 Hz, 2H), 7.47 (d, J=7.76 Hz, 1H), 7.38-7.33 (m, 1H), 7.31-7.27 (m, 2H), 7.26-7.22 (m, 2H), 7.08 (s, 1H), 5.31-4.93 (m, 2H), 4.70 (dd, J=17.88, 5.69 Hz, 1H), 4.41-4.27 (m, 2H), 4.17 (dd, J=8.74, 2.70 Hz, 1H), 3.81-3.54 (m, 4H), 3.19-3.07 (m, 1H), 3.04-2.76 (m, 2H), 2.71 (q, J=7.53, 7.53, 7.53 Hz, 2H), 2.30-2.19 (m, 2H), 1.89-1.75 (m, 1H), 1.71-1.58 (m, 2H), 1.17 (t, J=7.53, 7.53 Hz, 3H).

Example 53

1-(5-Chloro-thiophene-2-sulfonyl)-pyrrolidine-2S-carboxylic acid [2-[3-(acetyl-methyl-amino)-pyrrolidin-1-yl]-6-(4-trifluoromethyl-phenyl)-pyrimidin-4-ylmethyl]-amide

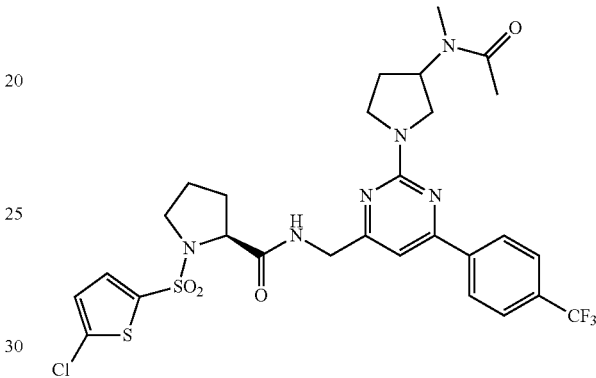

MS (ESI): mass calcd. for C$_{28}$H$_{30}$ClF$_3$N$_6$O$_4$S$_2$, 670.1; m/z found, 671.2 [M+H]$^+$. $^1$H NMR (400 MHz, CDCl$_3$) δ 8.64-8.49 (m, 1H), 8.26-8.15 (m, 2H), 7.74 (d, J=8.34 Hz, 2H), 7.48-7.44 (m, 1H), 7.21-7.07 (m, 1H), 7.02 (d, J=4.02 Hz, 1H), 5.48-5.27 (m, 1H), 4.76-4.59 (m, 1H), 4.49 (dd, J=17.07, 4.57 Hz, 1H), 4.26-3.93 (m, 3H), 3.88-3.57 (m, 3H), 3.25 (dd, J=17.38, 7.70 Hz, 1H), 2.99 (d, J=3.91 Hz, 2H), 2.97-2.93 (m, 1H), 2.39-2.22 (m, 3H), 2.18 (d, J=8.77 Hz, 3H), 2.00-1.82 (m, 2H), 1.82-1.67 (m, 1H).

Example 54

1-(5-Chloro-thiophene-2-sulfonyl)-pyrrolidine-2S-carboxylic acid [2-(3-diethylamino-pyrrolidin-1-yl)-6-(4-trifluoromethyl-phenyl)-pyrimidin-4-ylmethyl]-amide

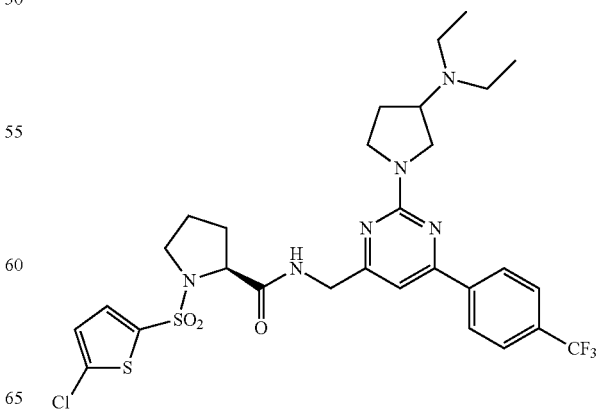

MS (ESI): mass calcd. for $C_{29}H_{34}ClF_3N_6O_3S_2$, 670.1; m/z found, 671.2 [M+H]$^+$. $^1$H NMR (400 MHz, CDCl$_3$) δ 8.56-8.42 (m, 1H), 8.21-8.13 (m, 2H), 7.73 (d, J=8.39 Hz, 2H), 7.45 (dd, J=11.62, 4.03 Hz, 1H), 7.12 (s, 1H), 7.03 (d, J=4.01 Hz, 1H), 4.73-4.61 (m, 1H), 4.51-4.28 (m, 2H), 4.24-4.16 (m, 1H), 4.16-3.89 (m, 3H), 3.84-3.60 (m, 2H), 3.58-3.33 (m, 2H), 3.32-3.11 (m, 3H), 2.68-2.41 (m, 2H), 2.35-2.19 (m, 1H), 1.98-1.69 (m, 3H), 1.37 (t, J=7.19, 7.19 Hz, 6H).

Example 55

1-(5-Chloro-thiophene-2S-sulfonyl)-pyrrolidine-2S-carboxylic acid [2-[(1-isopropyl-piperidin-4-ylmethyl)-methyl-amino]-6-(4-trifluoromethyl-phenyl)-pyrimidin-4-ylmethyl]-amide

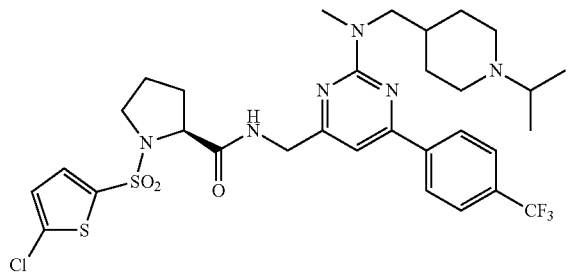 [SMILES: CC(C)N1CCC(CN(C)c2nc(CNC(=O)[C@@H]3CCCN3S(=O)(=O)c3ccc(Cl)s3)cc(-c3ccc(C(F)(F)F)cc3)n2)CC1]

MS (ESI): mass calcd. for $C_{29}H_{34}ClF_3N_6O_3S_2$, 698.2; m/z found, 699.2 [M+H]$^+$. $^1$H NMR (400 MHz, CDCl$_3$) δ 8.78-8.51 (m, 1H), 8.19 (d, J=8.03 Hz, 2H), 7.76 (d, J=8.31 Hz, 2H), 7.45 (d, J=3.98 Hz, 1H), 7.17 (s, 1H), 7.02 (d, J=4.03 Hz, 1H), 4.65 (dd, J=16.50, 6.21 Hz, 1H), 4.51-4.38 (m, 1H), 4.14 (dd, J=8.29, 3.57 Hz, 1H), 3.84 (dd, J=14.24, 6.83 Hz, 1H), 3.71-3.61 (m, 2H), 3.57-3.43 (m, 3H), 3.37 (s, 3H), 3.27-3.21 (m, 1H), 2.96-2.62 (m, 2H), 2.26-2.10 (m, 2H), 2.05-1.82 (m, 6H), 1.82-1.67 (m, 1H), 1.31 (m, 2H).

Example 56

1-(5-Chloro-thiophene-2-sulfonyl)-2,5-dihydro-1H-pyrrole-2S-carboxylic acid [2-(4-isobutyl-piperazin-1-yl)-6-(4-trifluoromethyl-phenyl)-pyrimidin-4-ylmethyl]-amide

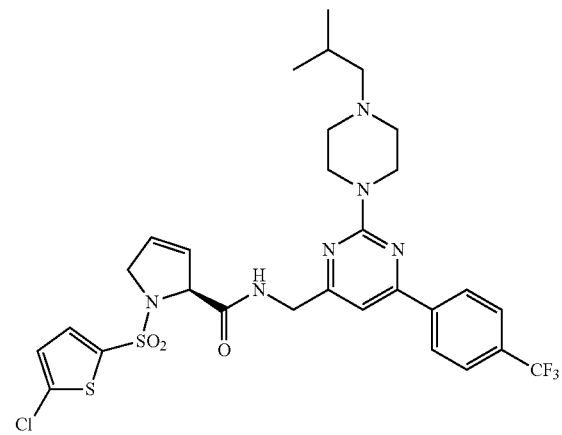 [SMILES: CC(C)CN1CCN(c2nc(CNC(=O)[C@@H]3C=CCN3S(=O)(=O)c3ccc(Cl)s3)cc(-c3ccc(C(F)(F)F)cc3)n2)CC1]

MS (ESI): mass calcd. for $C_{29}H_{32}ClF_3N_6O_3S_2$, 668.2; m/z found, 669.2 [M+H]$^+$. $^1$H NMR (500 MHz, CDCl$_3$) δ 8.13 (d, J=8.11 Hz, 2H), 8.10-8.02 (m, 1H), 7.72 (d, J=8.21 Hz, 2H), 7.47 (d, J=4.01 Hz, 1H), 7.09 (s, 1H), 7.04 (d, J=4.01 Hz, 1H), 5.92-5.88 (m, 1H), 5.83-5.79 (m, 1H), 5.08 (d, J=13.60 Hz, 2H), 4.97-4.93 (m, 1H), 4.72 (dd, J=17.88, 5.80 Hz, 1H), 4.43-4.29 (m, 2H), 4.29-4.22 (m, 1H), 3.84-3.74 (m, 2H), 3.74-3.62 (m, 2H), 2.99-2.74 (m, 4H), 2.27-2.12 (m, 1H), 1.10-1.06 (m, 6H).

Example 57

1-(5-Chloro-thiophene-2-sulfonyl)-4,4-difluoro-pyrrolidine-2S-carboxylic acid [2-(4-isobutyl-piperazin-1-yl)-6-(4-trifluoromethyl-phenyl)-pyrimidin-4-ylmethyl]-amide

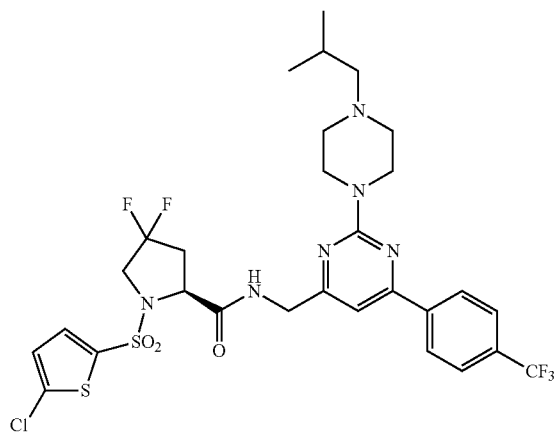 [SMILES: CC(C)CN1CCN(c2nc(CNC(=O)[C@@H]3CC(F)(F)CN3S(=O)(=O)c3ccc(Cl)s3)cc(-c3ccc(C(F)(F)F)cc3)n2)CC1]

MS (ESI): mass calcd. for $C_{29}H_{32}ClF_5N_6O_3S_2$, 706.1; m/z found, 707.2 [M+H]$^+$. $^1$H NMR (500 MHz, CDCl$_3$) δ 8.20-8.07 (m, 3H), 7.73 (d, J=8.15 Hz, 2H), 7.51 (d, J=3.99 Hz, 1H), 7.09 (d, J=4.00 Hz, 1H), 7.06 (s, 1H), 5.13-4.99 (m, 2H), 4.65 (dd, J=17.84, 5.17 Hz, 1H), 4.46 (dd, J=18.04, 3.99 Hz, 1H), 4.42 (d, J=3.92 Hz, 1H), 3.94-3.82 (m, 1H), 3.79 (d, J=11.05 Hz, 2H), 3.74-3.63 (m, 3H), 2.93 (d, J=6.93 Hz, 2H), 2.88-2.78 (m, 3H), 2.50-2.33 (m, 1H), 2.24-2.12 (m, 1H), 1.08 (dd, J=6.34, 2.47 Hz, 6H).

Example 58 was prepared using methods analogous to those described for Example 42.

Example 58

1-(5-Chloro-thiophene-2-sulfonyl)-pyrrolidine-2S-carboxylic acid [2-(2,2,2-trifluoro-ethoxy)-6-(4-trifluoromethyl-phenyl)-pyrimidin-4-ylmethyl]-amide

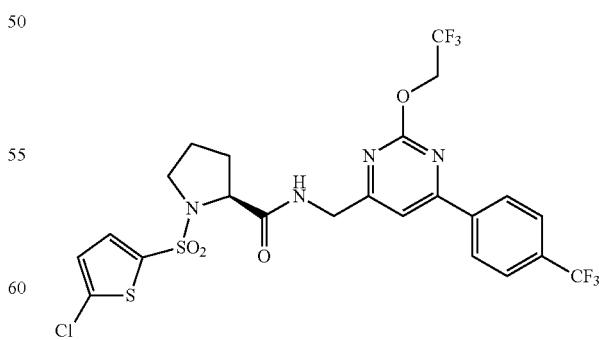

MS (ESI): mass calcd. for $C_{23}H_{19}ClF_6N_4O_4S_2$, 628.0; m/z found, 629.1 [M+H]$^+$. $^1$H NMR (500 MHz, CDCl$_3$) δ 8.26 (d, J=8.06 Hz, 2H), 7.80-7.76 (m, 1H), 7.73 (d, J=8.17 Hz, 2H), 7.66 (s, 1H), 7.51-7.48 (m, 1H), 7.08-7.04 (m, 1H), 5.01-4.79

(m, 3H), 4.45 (dd, J=17.60, 4.62 Hz, 1H), 4.27-4.22 (m, 1H), 3.73-3.65 (m, 1H), 3.33-3.24 (m, 1H), 2.31-2.19 (m, 1H), 1.98-1.87 (m, 2H), 1.85-1.73 (m, 1H).

Examples 59 to 60 were prepared using methods analogous to those described for Example 1 substituting the appropriate amine to provide the desired product.

Example 59

1-(5-Chloro-thiophene-2-sulfonyl)-pyrrolidine-2S-carboxylic acid [2-dimethylamino-6-(4-trifluoromethyl-phenyl)-pyrimidin-4-ylmethyl]-amide

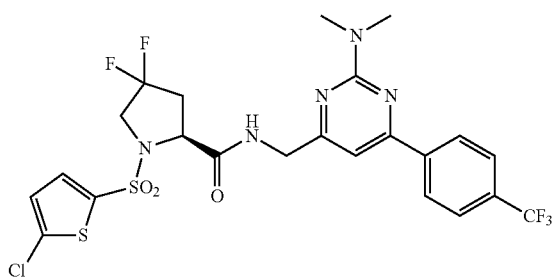 [SMILES: CN(C)c1nc(CNC(=O)[C@@H]2CC(F)(F)CN2S(=O)(=O)c2ccc(Cl)s2)cc(-c2ccc(C(F)(F)F)cc2)n1]

MS (ESI): mass calcd. for $C_{23}H_{21}ClF_5N_5O_3S_2$, 609.1; m/z found, 610.1 [M+H]+. $^1$H NMR (CDCl$_3$) δ 8.23 (d, J=8.17 Hz, 2H), 7.79 (d, J=8.30 Hz, 2H), 7.54 (d, J=4.07 Hz, 1H), 7.31 (s, 1H), 7.03 (d, J=4.07 Hz, 1H), 4.63 (d, J=5.89 Hz, 2H), 4.30 (t, J=7.96, 7.96 Hz, 1H), 3.99-3.88 (m, 1H), 3.73-3.61 (m, 1H), 3.46-3.41 (m, 6H), 2.74-2.46 (m, 2H).

Example 60

1-(5-Chloro-thiophene-2-sulfonyl)-pyrrolidine-4,4-difluoro-pyrrolidine-2S-carboxylic acid [2-(2-methyl-pyrrolidin-1-yl)-6-(4-trifluoromethyl-phenyl)-pyrimidin-4-ylmethyl]-amide

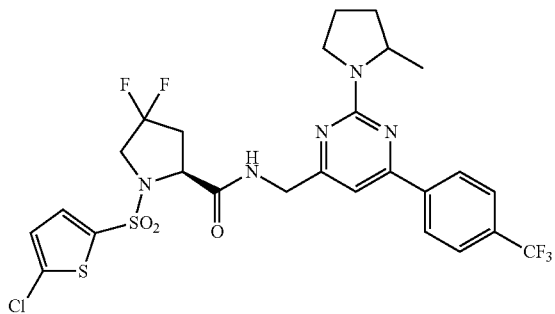 [SMILES: CC1CCCN1c1nc(CNC(=O)[C@@H]2CC(F)(F)CN2S(=O)(=O)c2ccc(Cl)s2)cc(-c2ccc(C(F)(F)F)cc2)n1]

MS (ESI): mass calcd. for $C_{26}H_{25}ClF_5N_5O_3S_2$, 649.1; m/z found, 650.1 [M+H]+. $^1$H NMR (CDCl$_3$) δ 8.25 (d, J=8.23 Hz, 2H), 7.80 (d, J=8.43 Hz, 2H), 7.54 (d, J=4.06 Hz, 1H), 7.35 (s, 1H), 7.02 (d, J=4.06 Hz, 1H), 4.72-4.58 (m, 2H), 4.29 (t, J=8.08, 8.08 Hz, 1H), 4.02-3.84 (m, 2H), 3.83-3.70 (m, 1H), 3.70-3.60 (m, 1H), 2.71-2.48 (m, 2H), 2.29-2.01 (m, 4H), 1.95-1.73 (m, 1H), 1.37 (d, J=6.22 Hz, 3H).

Example 61 was prepared using methods analogous to those described for Example 42.

Example 61

1-(5-Chloro-thiophene-2-sulfonyl)-4,4-difluoro-pyrrolidine-2S-carboxylic acid [2-(2,2,2-trifluoro-ethoxy)-6-(4-trifluoromethyl-phenyl)-pyrimidin-4-ylmethyl]-amide

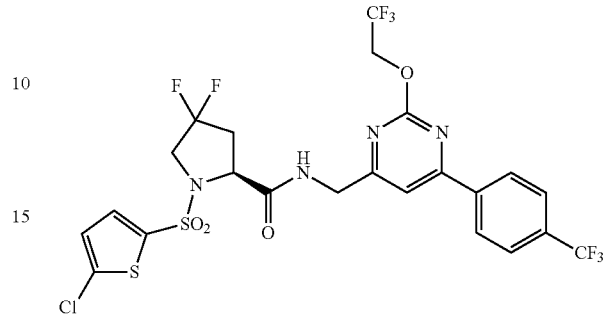

MS (ESI): mass calcd. for $C_{23}H_{17}ClF_8N_4O_4S_2$, 664.0; m/z found, 665.1 [M+H]+. $^1$H NMR (CDCl$_3$) δ 8.23 (d, J=8.17 Hz, 1H), 7.74 (d, J=8.26 Hz, 2H), 7.69 (t, J=5.83, 5.83 Hz, 1H), 7.59 (s, 1H), 7.53 (d, J=4.06 Hz, 1H), 7.09 (d, J=4.06 Hz, 1H), 4.94 (q, J=8.32, 8.31, 8.31 Hz, 2H), 4.79 (dd, J=17.61, 6.67 Hz, 1H), 4.56 (dd, J=17.63, 5.23 Hz, 1H), 4.44 (dd, J=9.96, 4.41 Hz, 1H), 4.00-3.83 (m, 1H), 3.75-3.62 (m, 1H), 2.87-2.70 (m, 1H), 2.56-2.41 (m, 1H).

Example 62

1-(5-Chloro-thiophene-2-sulfonyl)-pyrrolidine-2S-carboxylic acid [2-(2-pyrrolidin-1-yl-ethoxy)-6-(4-trifluoromethyl-phenyl)-pyrimidin-4-ylmethyl]-amide

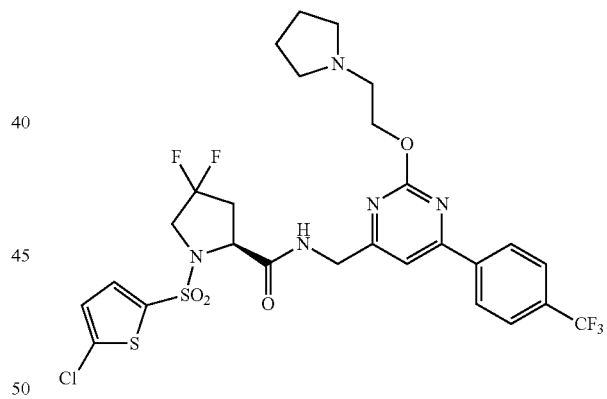

To a solution of 1-(5-chloro-thiophene-2-sulfonyl)-pyrrolidine-2S-carboxylic acid [2-phenylmethanesulfonyl-6-(4-trifluoromethyl-phenyl)-pyrimidin-4-ylmethyl]-amide (0.04 g, 0.06 mmol) in THF (2 mL) was added hydroxyethylpyrrolidine (0.04 g, 0.35 mmol) and N,N-diisopropylethylamine (0.05 g, 0.35 mmol). The resulting mixture was stirred for 24 h at rt at which time the mixture was concentrated, diluted in MeOH (2 mL), filtered and purified directly by preparative reverse-phase HPLC to afford the title compound as a colorless solid (0.03 g, 63%). MS (ESI): mass calcd. for $C_{27}H_{29}ClF_3N_5O_4S_2$, 643.1; m/z found, 644.2 [M+H]+. $^1$H NMR (CDCl$_3$) δ 8.22 (d, J=8.16 Hz, 2H), 7.95-7.90 (m, 1H), 7.74 (d, J=8.28 Hz, 2H), 7.56 (s, 1H), 7.47 (d, J=4.03 Hz, 1H), 7.05 (d, J=4.02 Hz, 1H), 4.94-4.89 (m, 2H), 4.83 (dd, J=17.65, 6.72 Hz, 1H), 4.44 (dd, J=17.64, 4.44 Hz, 1H), 4.21 (dd, J=8.49, 3.05 Hz, 1H), 4.05-3.94 (m, 2H), 3.76-3.66 (m, 2H), 3.66-3.58 (m, 1H), 3.31-3.20 (m, 1H), 3.14-2.97 (m, 2H), 2.34-2.21 (m, 1H), 2.23-2.07 (m, 4H), 1.98-1.74 (m, 3H).

Examples 63 to 64 were prepared using methods analogous to those described for Example 62 substituting the appropriate alcohols to provide the desired product.

Example 63

1-(5-Chloro-thiophene-2-sulfonyl)-pyrrolidine-2S-carboxylic acid [2-(2-piperidin-1-yl-ethoxy)-6-(4-trifluoromethyl-phenyl)-pyrimidin-4-ylmethyl]-amide

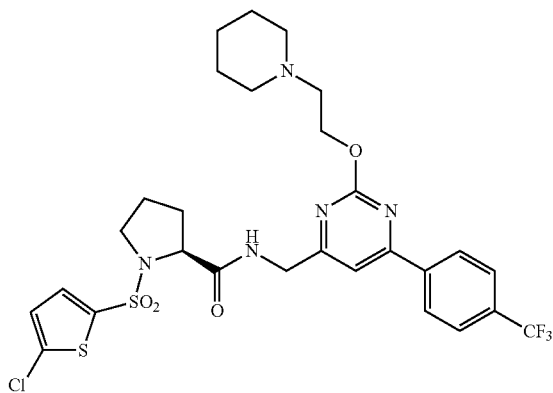 [SMILES: O=C(NCc1cc(-c2ccc(C(F)(F)F)cc2)nc(OCCN2CCCCC2)n1)[C@@H]1CCCN1S(=O)(=O)c1ccc(Cl)s1]

MS (ESI): mass calcd. for $C_{28}H_{31}ClF_3N_5O_4S_2$, 657.1; m/z found, 658.2 [M+H]$^+$. $^1$H NMR (CDCl$_3$) δ 8.22 (d, J=8.19 Hz, 2H), 7.88-7.83 (m, 1H), 7.74 (d, J=8.27 Hz, 2H), 7.56 (s, 1H), 7.48 (d, J=4.02 Hz, 1H), 7.05 (d, J=4.02 Hz, 1H), 4.95-4.91 (m, 2H), 4.84 (dd, J=17.72, 6.77 Hz, 1H), 4.43 (dd, J=17.67, 4.45 Hz, 1H), 4.20 (dd, J=8.47, 3.03 Hz, 1H), 3.86-3.77 (m, 2H), 3.73-3.66 (m, 1H), 3.65-3.51 (m, 2H), 3.31-3.20 (m, 1H), 2.93-2.80 (m, 2H), 2.32-2.21 (m, 1H), 2.10-1.71 (m, 8H), 1.51-1.34 (m, 1H).

Example 64

1-(5-Chloro-thiophene-2-sulfonyl)-pyrrolidine-2S-carboxylic acid [2-(2-morpholin-4-yl-ethoxy)-6-(4-trifluoromethyl-phenyl)-pyrimidin-4-ylmethyl]-amide

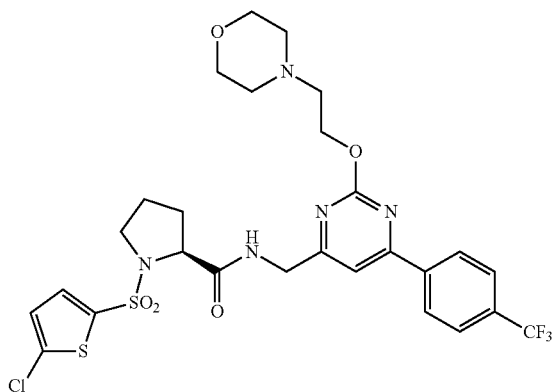 [SMILES: O=C(NCc1cc(-c2ccc(C(F)(F)F)cc2)nc(OCCN2CCOCC2)n1)[C@@H]1CCCN1S(=O)(=O)c1ccc(Cl)s1]

MS (ESI): mass calcd. for $C_{27}H_{29}ClF_3N_5O_5S_2$, 659.1; m/z found, 660.2 [M+H]$^+$. $^1$H NMR (CDCl$_3$) δ 8.21 (d, J=8.16 Hz, 2H), 7.97-7.90 (m, 1H), 7.74 (d, J=8.28 Hz, 2H), 7.55 (s, 1H), 7.47 (d, J=4.03 Hz, 1H), 7.04 (d, J=4.03 Hz, 1H), 4.98-4.91 (m, 2H), 4.84 (dd, J=17.71, 6.67 Hz, 1H), 4.43 (dd, J=17.70, 4.40 Hz, 1H), 4.21 (dd, J=8.28, 2.98 Hz, 1H), 4.04-3.97 (m, 4H), 3.88-3.71 (m, 1H), 3.71-3.53 (m, 4H), 3.32-3.19 (m, 1H), 3.20-3.01 (m, 2H), 2.33-2.19 (m, 1H), 1.98-1.71 (m, 3H).

Example 65

1-(4-Fluorobenzenesulfonyl)-pyrrolidine-2S-carboxylic acid (4'-trifluoromethylbiphenyl-3-ylmethyl)-amide

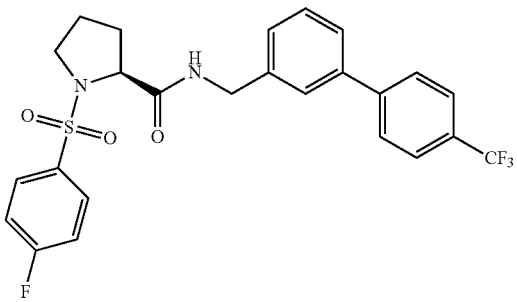

To a solution of 2S-[(4'-trifluoromethyl-biphenyl-3-ylmethyl)-carbamoyl]-pyrrolidine-1-carboxylic acid tert-butyl ester (22.6 mg, 0.05 mmol) in CH$_2$Cl$_2$ (5 mL) was added 4 M HCl in dioxane (1 mL) and the reaction mixture was stirred at rt for 3 hours. The reaction mixture was concentrated, dissolved in CH$_2$Cl$_2$ (3 mL) and triethylamine (40.5 mg, 0.40 mmol) and 4-fluorobenzenesulfonyl chloride (19.6 mg, 0.10 mmol) and a catalytic amount of N,N-dimethylaminopyridine were added. The reaction mixture was stirred for 12 hours, concentrated and purified by preparative reverse-phase HPLC to provide the desired product (20.0 mg, 80%). MS (ESI): Mass calcd. for $C_{25}H_{22}F_4N_2O_3S$, 506.51; m/z found 507.5 [M+H]$^+$. $^1$H NMR (500 MHz, CDCl$_3$) δ 7.94-7.86 (m, 2H), 7.75 (d, J=8.2, 2H), 7.70 (d, J=8.3, 2H), 7.60 (s, 1H), 7.54 (d, J=7.8, 1H), 7.51-7.45 (m, 1H), 7.37 (d, J=7.6, 1H), 7.32 (s, 1H), 7.28-7.23 (m, 2H), 4.69 (dd, J=15.2, 6.4, 1H), 4.54 (dd, J=15.2, 5.6, 1H), 4.17-4.14 (m, 1H), 3.60 (ddd, J=10.2, 7.0, 3.4, 1H), 3.18 (ddd, J=10.0, 9.9, 6.5, 1H), 2.32-2.23 (m, 1H), 1.88-1.75 (m, 1H), 1.74-1.63 (m, 2H).

Example 66

1-(4-Fluorobenzenesulfonyl)-pyrrolidine-2S-carboxylic acid (3'-trifluoromethylbiphenyl-3-ylmethyl)-amide

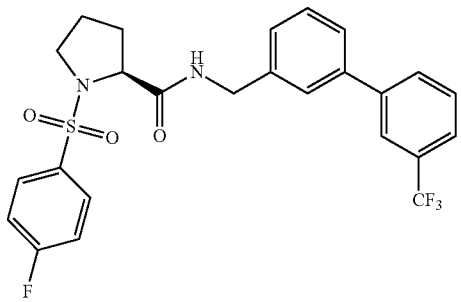 [SMILES: O=C(NCc1cccc(-c2cccc(C(F)(F)F)c2)c1)[C@@H]1CCCN1S(=O)(=O)c1ccc(F)cc1]

To a solution of 1-(4-fluoro-benzenesulfonyl)-pyrrolidine-2S-carboxylic acid 3-bromo-benzylamide (100 mg, 0.23 mmol) in DME (4 mL) and water (1 mL) was added K$_3$PO$_4$ (98 mg, 0.46 mmol), 3-trifluoromethylphenylboronic acid (52 mg, 0.27 mmol) and Pd(PPh3)$_4$ (8 mg, 0.01 mmol). The reaction vessel was sealed and the reaction mixture was heated to 85° C. for 16 hours. The reaction mixture was filtered, concentrated and purified by FCC (10-100% EtOAc in hexanes) to provide the desired product (93 mg, 80%). MS (ESI): Mass calcd. for $C_{25}H_{22}F_4N_2O_3S$, 506.51; m/z found 507.5 [M+H]$^+$. $^1$H NMR (500 MHz, CDCl$_3$) δ 7.93-7.85 (m, 3H), 7.85-7.79 (m, 1H), 7.64-7.51 (m, 4H), 7.47 (t, J=7.6, 1H), 7.39-7.30 (m, 2H), 7.28-7.23 (m, 2H), 4.69 (dd, J=15.2, 6.5, 1H), 4.56 (dd, J=15.2, 5.6, 1H), 4.19-4.10 (m, 1H), 3.66-3.57 (m, 1H), 3.23-3.14 (m 1H), 2.33-2.23 (m, 1H), 1.88-1.76 (m, 1H), 1.74-1.62 (m, 2H).

Examples 67 to 108 were prepared using methods analogous to those described for example 66 substituting the appropriate boronic acid to provide the desired product.

Example 67

1-(4-Fluorobenzenesulfonyl)-pyrrolidine-2S-carboxylic acid (2'-trifluoromethylbiphenyl-3-ylmethyl)-amide

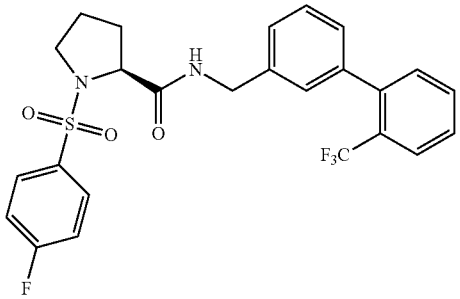 [SMILES: O=C(NCc1cccc(-c2ccccc2C(F)(F)F)c1)[C@@H]1CCCN1S(=O)(=O)c1ccc(F)cc1]

MS (ESI): Mass calcd. for $C_{25}H_{22}F_4N_2O_3S$, 506.51; m/z found 507.5 [M+H]$^+$. $^1$H NMR (500 MHz, CDCl$_3$) δ 7.92-7.84 (m, 2H), 7.79-7.72 (m, 1H), 7.61-7.54 (m, 1H), 7.52-7.45 (m, 1H), 7.44-7.33 (m, 3H), 7.27-7.19 (m, 4H), 4.62 (dd, J=15.0, 6.3, 1H), 4.52 (dd, J=15.1, 5.7, 1H), 4.18-4.08 (m, 2H), 3.61-3.51 (m, 1H), 3.18 (ddd, J=9.9, 9.8, 6.5, 1H), 2.29-2.20 (m, 1H), 1.85-1.71 (m, 1H), 1.71-1.62 (m, 2H).

Example 68

1-(4-Fluorobenzenesulfonyl)-pyrrolidine-2S-carboxylic acid (4'-trifluoromethoxybiphenyl-3-ylmethyl)-amide

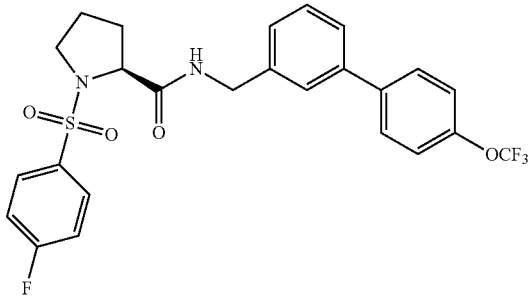

MS (ESI): Mass calcd. for $C_{25}H_{22}F_4N_2O_4S$, 522.51; m/z found 523.5 [M+H]$^+$. $^1$H NMR (400 MHz, CDCl$_3$) δ 7.92-7.84 (m, 3H), 7.66-7.56 (m, 2H), 7.53 (s, 1H), 7.51-7.39 (m, 2H), 7.35-7.16 (m, 5H), 4.64 (dd, J=15.2, 6.3, 1H), 4.58-4.44 (m, 1H), 4.17-4.07 (m, 1H), 3.57 (ddd, J=10.2, 7.0, 3.1, 1H), 3.26 (ddd, J=10.0, 6.5, 6.5, 1H), 2.31-2.19 (m, 1H), 1.86-1.72 (m, 1H), 1.72-1.60 (m, 2H).

Example 69

1-(4-Fluorobenzenesulfonyl)-pyrrolidine-2S-carboxylic acid (3'-trifluoromethoxybiphenyl-3-ylmethyl)-amide

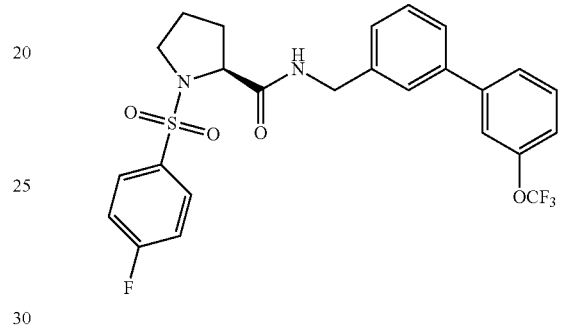

MS (ESI): Mass calcd. for $C_{25}H_{22}F_4N_2O_4S$, 522.51; m/z found 523.5 [M+H]$^+$. $^1$H NMR (400 MHz, CDCl$_3$) δ 7.93-7.82 (m, 2H), 7.58-7.40 (m, 6H), 7.36-7.16 (m, 5H), 4.64 (dd, J=15.2, 6.3, 1H), 4.53 (dd, J=15.2, 5.7, 1H), 4.14 (dd, J=8.8, 2.9, 1H), 3.57 (ddd, J=10.2, 6.7, 3.3, 1H), 3.17 (ddd, J=10.0, 6.5, 6.5, 1H), 2.31-2.21 (m, 1H), 1.86-1.74 (m, 1H), 1.72-1.61 (m, 2H).

Example 70

1-(4-Fluorobenzenesulfonyl)-pyrrolidine-2S-carboxylic acid (2'-trifluoromethoxybiphenyl-3-ylmethyl)-amide

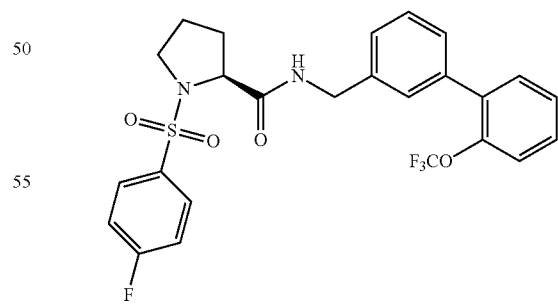

MS (ESI): Mass calcd. for $C_{25}H_{22}F_4N_2O_4S$, 522.51; m/z found 523.5 [M+H]$^+$. $^1$H NMR (400 MHz, CDCl$_3$) δ 7.91-7.82 (m, 2H), 7.48-7.30 (m, 8H), 7.26-7.16 (m, 3H), 4.64-4.48 (m, 2H), 4.13 (dd, J=8.8, 2.9, 1H), 3.55 (ddd, J=10.2, 6.8, 3.3, 1H), 3.24 (ddd, J=10.0, 6.5, 6.5, 1H), 2.30-2.19 (m, 1H), 1.85-1.71 (m, 1H), 1.70-1.59 (m, 2H).

Example 71

1-(4-Fluorobenzenesulfonyl)-pyrrolidine-2S-carboxylic acid (3'-fluoro-4'-trifluoromethylbiphenyl-3-ylmethyl)-amide

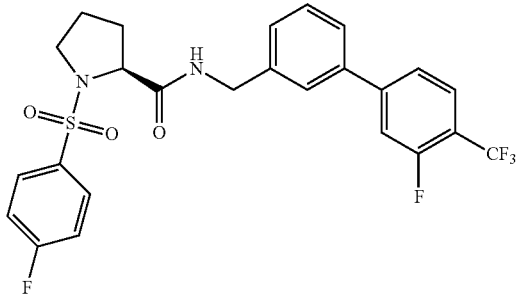 [SMILES: O=C(NCc1cccc(-c2ccc(C(F)(F)F)c(F)c2)c1)[C@@H]1CCCN1S(=O)(=O)c1ccc(F)cc1]

MS (ESI): Mass calcd. for $C_{25}H_{21}F_5N_2O_3S$, 524.50; m/z found 525.1 [M+H]$^+$. $^1$H NMR (400 MHz, CDCl$_3$) δ 7.94-7.82 (m, 2H), 7.69-7.61 (m, 1H), 7.58 (s, 1H), 7.53-7.42 (m, 4H), 7.40-7.28 (m, 2H), 7.29-7.20 (m, 2H), 4.71 (dd, J=15.3, 6.7, 1H), 4.49 (dd, J=15.3, 5.4, 1H), 4.15 (dd, J=8.6, 3.0, 1H), 3.62-3.55 (m, 1H), 3.21-3.11 (m, 1H), 2.30-2.20 (m, 1H), 1.85-1.60 (m, 3H).

Example 72

1-(4-Fluoro-benzenesulfonyl)-pyrrolidine-2S-carboxylic acid (3'-chloro-4'-trifluoromethyl-biphenyl-3-ylmethyl)-amide

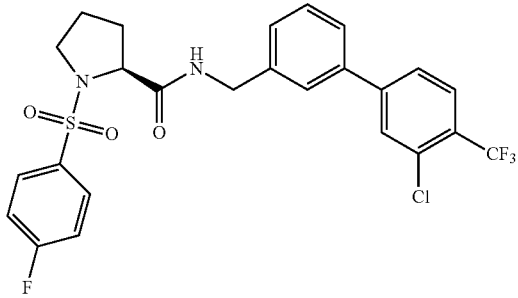 [SMILES: O=C(NCc1cccc(-c2ccc(C(F)(F)F)c(Cl)c2)c1)[C@@H]1CCCN1S(=O)(=O)c1ccc(F)cc1]

MS (ESI): Mass calcd. for $C_{25}H_{21}ClF_4N_2O_3S$, 540.96; m/z found 541.1 [M+H]$^+$. $^1$H NMR (400 MHz, CDCl$_3$) δ 7.93-7.84 (m, 2H), 7.81-7.70 (m, 2H), 7.63-7.55 (m, 2H), 7.53-7.42 (m, 2H), 7.41-7.30 (m, 2H), 7.29-7.21 (m, 2H), 4.71 (dd, J=15.3, 6.7, 1H), 4.49 (dd, J=15.3, 5.4, 1H), 4.16 (dd, J=8.6, 3.0, 1H), 3.59 (ddd, J=10.1, 6.7, 3.3, 1H), 3.18 (ddd, J=15.8, 7.9, 7.9, 1H), 2.31-2.20 (m, 1H), 1.88-1.60 (m, 3H).

Example 73

1-(4-Fluorobenzenesulfonyl)-pyrrolidine-2S-carboxylic acid (3'-fluoro-4'-trifluoromethoxybiphenyl-3-ylmethyl)-amide

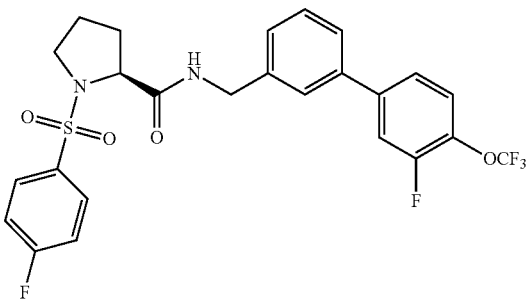 [SMILES: O=C(NCc1cccc(-c2ccc(OC(F)(F)F)c(F)c2)c1)[C@@H]1CCCN1S(=O)(=O)c1ccc(F)cc1]

MS (ESI): Mass calcd. for $C_{25}H_{21}F_5N_2O_4S$, 540.50; m/z found 541.1 [M+H]$^+$. $^1$H NMR (400 MHz, CDCl3) δ 7.93-7.83 (m, 2H), 7.53 (s, 1H), 7.50-7.21 (m, 9H), 4.68 (dd, J=15.2, 6.6, 1H), 4.49 (dd, J=15.3, 5.5, 1H), 4.14 (dd, J=8.7, 3.0, 1H), 3.58 (ddd, J=10.1, 6.8, 3.3, 1H), 3.17 (ddd, J=9.8, 6.4, 6.4, 1H), 2.31-2.18 (m, 1H), 1.88-1.60 (m, 3H).

Example 74

1-(4-Fluorobenzenesulfonyl)-pyrrolidine-2S-carboxylic acid (4'-difluoromethoxy-3',5'-difluorobiphenyl-3-ylmethyl)-amide

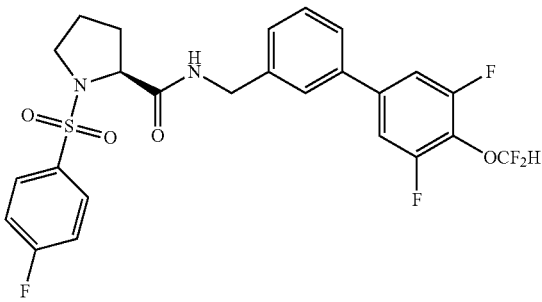

MS (ESI): Mass calcd. for $C_{25}H_{21}F_5N_2O_4S$, 540.50; m/z found 541.1 [M+H]$^+$. $^1$H NMR (400 MHz, CDCl3) δ 7.92-7.83 (m, 2H), 7.52 (s, 1H), 7.47-7.41 (m, 2H), 7.39-7.21 (m, 6H), 4.71 (dd, J=15.3, 6.8, 1H), 4.47 (dd, J=15.3, 5.4, 1H), 4.14 (dd, J=8.6, 3.0, 1H), 3.64-3.55 (m, 1H), 3.18 (ddd, J=15.9, 7.9, 7.9, 1H), 2.32-2.15 (m, 1H), 1.90-1.58 (m, 3H).

Example 75

1-(4-Fluorobenzenesulfonyl)-pyrrolidine-2S-carboxylic acid (4'-methanesulfonylbiphenyl-3-ylmethyl)-amide

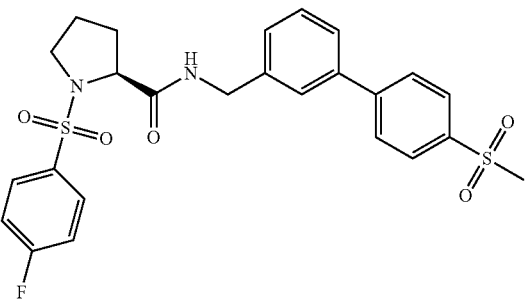 [SMILES: CS(=O)(=O)c1ccc(-c2cccc(CNC(=O)[C@@H]3CCCN3S(=O)(=O)c3ccc(F)cc3)c2)cc1]

MS (ESI): Mass calcd. for $C_{25}H_{25}FN_2O_5S_2$, 516.61; m/z found 517.1 [M+H]$^+$. $^1$H NMR (400 MHz, CDCl$_3$) δ 7.92-7.85 (m, 2H), 7.71-7.62 (m, 2H), 7.63-7.56 (m, 2H), 7.55-7.42 (m, 2H), 7.40-7.33 (m, 2H), 7.30-7.23 (m, 3H), 4.72 (dd, J=15.3, 6.7, 1H), 4.50 (dd, J=15.3, 5.4, 1H), 4.23-4.09 (m, 1H), 3.66-3.51 (m, 1H), 3.21-3.13 (m, 1H), 3.09 (s, 3H), 2.30-2.10 (m, 1H), 1.89-1.59 (m, 3H).

Example 76

1-(4-Fluorobenzenesulfonyl)-pyrrolidine-2S-carboxylic acid (4'-nitrobiphenyl-3-ylmethyl)-amide

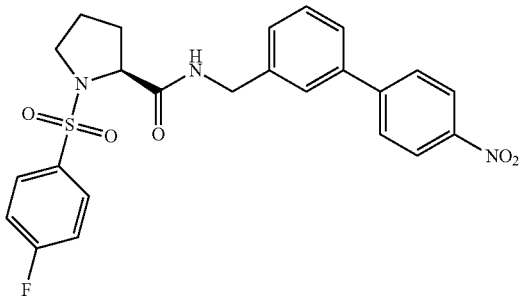 [SMILES: O=C(NCc1cccc(-c2ccc([N+](=O)[O-])cc2)c1)[C@@H]1CCCN1S(=O)(=O)c1ccc(F)cc1]

MS (ESI): Mass calcd. for $C_{24}H_{22}FN_3O_5S$, 483.51; m/z found 484.1 [M+H]$^+$. $^1$H NMR (400 MHz, CDCl$_3$) δ 8.32-8.24 (m, 2H), 7.92-7.85 (m, 2H), 7.82-7.73 (m, 2H), 7.66-7.62 (m, 1H), 7.58-7.51 (m, 1H), 7.51-7.45 (m, 1H), 7.41-7.36 (m, 1H), 7.28-7.23 (m, 2H), 7.35-7.28 (m, 1H), 4.73 (dd, J=15.4, 6.8, 1H), 4.49 (dd, J=15.3, 5.4, 1H), 4.15 (dd, J=8.6, 3.1, 1H), 3.63-3.53 (m, 1H), 3.22-3.10 (m, 1H), 2.32-2.16 (m, 1H), 1.90-1.74 (m, 1H), 1.73-1.62 (m, 2H).

Example 77

1-(4-Fluoro-benzenesulfonyl)-pyrrolidine-2S-carboxylic acid (4'-bromo-biphenyl-3-ylmethyl)-amide

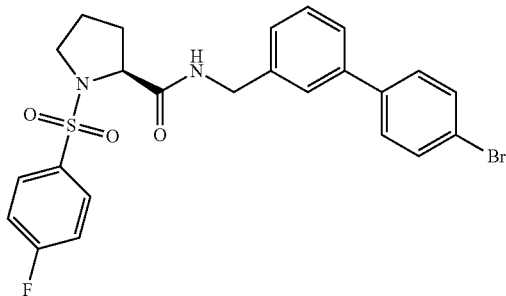 [SMILES: O=C(NCc1cccc(-c2ccc(Br)cc2)c1)[C@@H]1CCCN1S(=O)(=O)c1ccc(F)cc1]

MS (ESI): Mass calcd. for $C_{24}H_{22}BrFN_2O_3S$, 517.41; m/z found 517.1 [M$^+$]. $^1$H NMR (400 MHz, CDCl$_3$) δ 7.91-7.83 (m, 2H), 7.64-7.19 (m, 11H), 4.63 (dd, J=15.1, 6.2, 1H), 4.52 (dd, J=15.1, 5.6, 1H), 4.15 (dd, J=8.6, 3.1, 1H), 3.61-3.49 (m, 1H), 3.23-3.12 (m, 1H), 2.31-2.18 (m, 1H), 1.85-1.73 (m, 1H), 1.72-1.58 (m, 2H).

Example 78

1-(4-Fluorobenzenesulfonyl)-pyrrolidine-2S-carboxylic acid (4'-sulfamoyl-biphenyl-3-ylmethyl)-amide

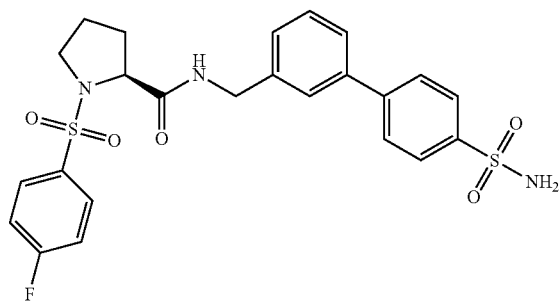 [SMILES: NS(=O)(=O)c1ccc(-c2cccc(CNC(=O)[C@@H]3CCCN3S(=O)(=O)c3ccc(F)cc3)c2)cc1]

MS (ESI): Mass calcd. for $C_{24}H_{24}FN_3O_5S_2$, 517.41; m/z found 518.1 [M+H]$^+$. $^1$H NMR (400 MHz, CDCl$_3$) δ 7.93-7.82 (m, 2H), 7.72-7.63 (m, 2H), 7.62-7.21 (m, 9H), 4.85 (bs, 2H), 4.76-4.62 (m, 1H), 4.57-4.44 (m, 1H), 4.23-4.11 (m, 1H), 3.63-3.50 (m, 1H), 3.25-3.13 (m, 1H), 2.32-2.15 (m, 1H), 1.89-1.56 (m, 3H).

Example 79

1-(4-Fluoro-benzenesulfonyl)-pyrrolidine-2S-carboxylic acid (4'-methyl-biphenyl-3-ylmethyl)-amide

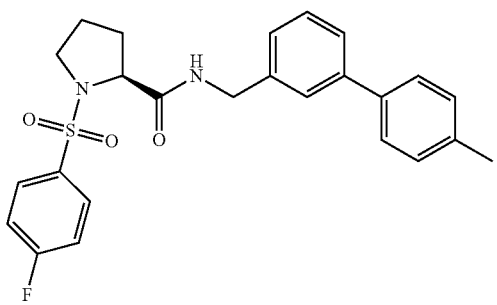 [SMILES: Cc1ccc(-c2cccc(CNC(=O)[C@@H]3CCCN3S(=O)(=O)c3ccc(F)cc3)c2)cc1]

MS (ESI): Mass calcd. for $C_{25}H_{25}FN_2O_3S$, 452.54; m/z found 453.2 [M+H]$^+$. $^1$H NMR (400 MHz, CDCl$_3$) δ 7.92-7.82 (m, 2H), 7.56-7.47 (m, 4H), 7.46-7.37 (m, 1H), 7.31-7.18 (m, 6H), 4.64-4.50 (m, 2H), 4.16 (dd, J=8.6, 3.1, 1H), 3.62-3.47 (m, 1H), 3.23-3.07 (m, 1H), 2.93 (s, 3H), 2.31-2.14 (m, 1H), 1.87-1.73 (m, 1H), 1.72-1.57 (m, 2H).

Example 80

1-(4-Fluorobenzenesulfonyl)-pyrrolidine-2S-carboxylic acid (4'-methoxybiphenyl-3-ylmethyl)-amide

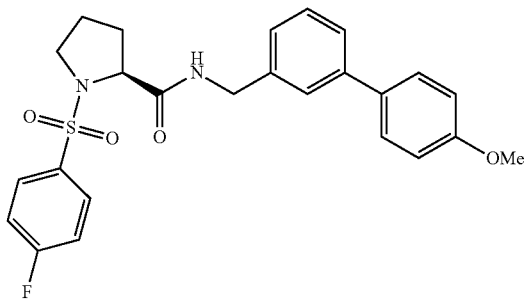 [SMILES: COc1ccc(-c2cccc(CNC(=O)[C@@H]3CCCN3S(=O)(=O)c3ccc(F)cc3)c2)cc1]

MS (ESI): Mass calcd. for $C_{25}H_{25}FN_2O_4S$, 468.54; m/z found 469.2 [M+H]$^+$. $^1$H NMR (400 MHz, CDCl$_3$) δ 7.91-7.83 (m, 2H), 7.58-7.50 (m, 1H), 7.52-7.36 (m, 3H), 7.30-7.18 (m, 6H), 7.01-6.92 (m, 1H), 4.60-4.53 (m, 1H), 4.53-4.41 (m, 1H), 4.22-4.07 (m, 1H), 3.85 (s, 3H), 3.63-3.47 (m, 1H), 3.25-3.09 (m, 1H), 2.30-2.14 (m, 1H), 1.78 (d, J=8.9, 1H), 1.73-1.56 (m, 2H).

Example 81

1-(4-Fluorobenzenesulfonyl)-pyrrolidine-2S-carboxylic acid [4'-(2,2,2-trifluoroethoxy)-biphenyl-3-ylmethyl]-amide

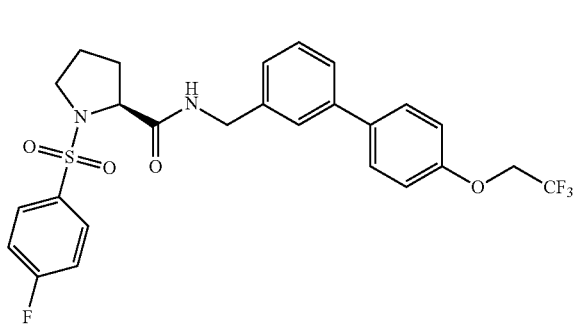 [SMILES: O=C(NCc1cccc(-c2ccc(OCC(F)(F)F)cc2)c1)[C@@H]1CCCN1S(=O)(=O)c1ccc(F)cc1]

MS (ESI): Mass calcd. for $C_{26}H_{24}F_4N_2O_4S$, 536.54; m/z found 537.2 [M+H]$^+$. $^1$H NMR (400 MHz, CDCl$_3$) δ 7.90-7.82 (m, 2H), 7.62-7.54 (m, 2H), 7.54-7.36 (m, 3H), 7.29-7.19 (m, 4H), 7.06-6.97 (m, 2H), 4.61 (dd, J=15.1, 6.1, 1H), 4.52 (dd, J=15.1, 5.7, 1H), 4.41 (q, J=8.1, 2H), 4.15 (dd, J=8.7, 3.0, 1H), 3.56 (ddd, J=10.2, 6.8, 3.4, 1H), 3.17 (ddd, J=9.9, 6.5, 6.5, 1H), 2.32-2.17 (m, 1H), 1.85-1.73 (m, 1H), 1.72-1.57 (m, 2H).

Example 82

1-(4-Fluoro-benzenesulfonyl)-pyrrolidine-2S-carboxylic acid (4'-methylsulfanyl-biphenyl-3-ylmethyl)-amide

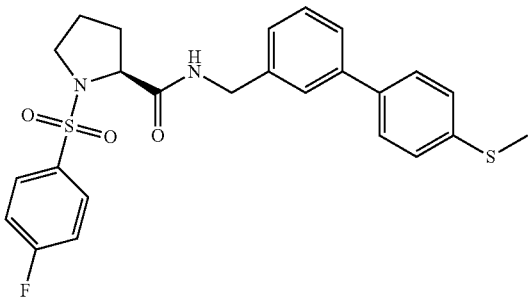

MS (ESI): Mass calcd. for $C_{25}H_{25}FN_2O_3S_2$, 484.61; m/z found 485.2 [M+H]$^+$. $^1$H NMR (400 MHz, CDCl$_3$) δ 7.90-7.81 (m, 2H), 7.57-7.46 (m, 3H), 7.44-7.38 (m, 1H), 7.36-7.30 (m, 2H), 7.30-7.18 (m, 5H), 4.66-4.46 (m, 2H), 4.15 (dd, J=8.7, 3.0, 1H), 3.56 (ddd, J=10.2, 7.0, 3.3, 1H), 3.17 (ddd, J=10.0, 6.5, 6.5, 1H), 2.52 (s, 3H), 2.30-2.18 (m, 1H), 1.85-1.71 (m, 1H), 1.73-1.58 (m, 2H).

Example 83

1-(4-Fluoro-benzenesulfonyl)-pyrrolidine-2S-carboxylic acid 3-(6-chloro-pyridin-3-yl)-benzylamide

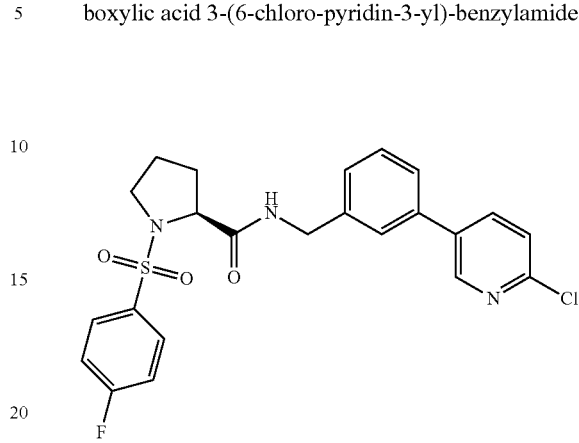

MS (ESI): Mass calcd. for $C_{23}H_{21}ClFN_3O_3S$, 473.95; m/z found 474.1 [M+H]$^+$. $^1$H NMR (600 MHz, CDCl$_3$) δ 8.63 (d, J=2.5, 1H), 7.94-7.83 (m, 3H), 7.55 (s, 1H), 7.49-7.43 (m, 2H), 7.43-7.30 (m, 3H), 7.29-7.19 (m, 2H), 4.70 (dd, J=15.3, 6.7, 1H), 4.49 (dd, J=15.3, 5.4, 1H), 4.18-4.11 (m, 1H), 3.59 (ddd, J=10.2, 7.2, 3.2, 1H), 3.16 (ddd, J=9.9, 6.5, 6.5, 1H), 2.31-2.19 (m, 1H), 1.87-1.72 (m, 1H), 1.70-1.59 (m, 2H).

Example 84

1-(4-Fluorobenzenesulfonyl)-pyrrolidine-2S-carboxylic acid 3-(6-methoxypyridin-3-yl)-benzylamide

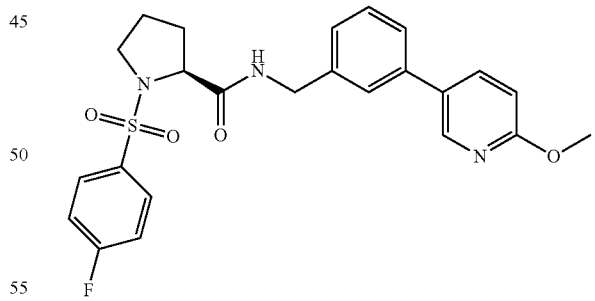

MS (ESI): Mass calcd. for $C_{24}H_{24}FN_3O_4S$, 469.53; m/z found 470.2 [M+H]$^+$. $^1$H NMR (600 MHz, CDCl$_3$) δ 8.39 (d, J=2.2, 1H), 7.90-7.85 (m, 2H), 7.83 (dd, J=8.6, 2.6, 1H), 7.48 (s, 1H), 7.47-7.39 (m, 2H), 7.32-7.21 (m, 4H), 6.81 (d, J=8.6, 1H), 4.62 (dd, J=15.1, 6.2, 1H), 4.53 (dd, J=15.1, 5.7, 1H), 4.15-4.11 (m, 1H), 3.96 (s, 3H), 3.57 (ddd, J=10.3, 7.2, 3.2, 1H), 3.16 (ddd, J=9.9, 6.5, 6.5, 1H), 2.29-2.19 (m, 1H), 1.87-1.72 (m, 1H), 1.71-1.57 (m, 2H).

Example 85

1-(4-Fluorobenzenesulfonyl)-pyrrolidine-2S-carboxylic acid (4'-carbamoylbiphenyl-3-ylmethyl)-amide

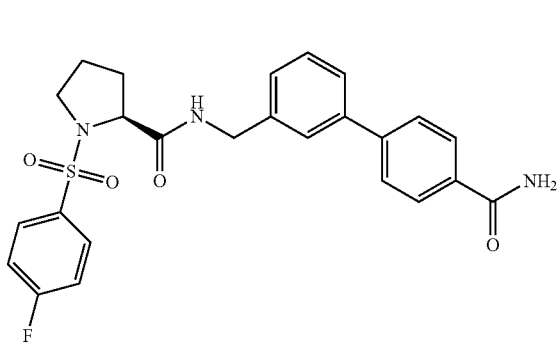 [SMILES: NC(=O)c1ccc(-c2cccc(CNC(=O)[C@@H]3CCCN3S(=O)(=O)c3ccc(F)cc3)c2)cc1]

MS (ESI): Mass calcd. for $C_{25}H_{24}FN_3O_4S$, 481.54; m/z found 482.2 [M+H]$^+$. $^1$H NMR (600 MHz, CDCl$_3$) δ 7.91-7.84 (m, 4H), 7.76-7.70 (m, 2H), 7.62-7.59 (m, 1H), 7.58-7.52 (m, 1H), 7.49-7.40 (m, 1H), 7.36-7.33 (m, 1H), 7.33-7.29 (m, 1H), 7.27-7.21 (m, 4H), 4.67 (dd, J=15.2, 6.4, 1H), 4.53 (dd, J=15.2, 5.6, 1H), 4.15 (dd, J=8.9, 3.0, 1H), 3.63-3.52 (m, 1H), 3.16 (ddd, J=10.0, 6.5, 6.5, 1H), 2.32-2.19 (m, 1H), 1.85-1.73 (m, 1H), 1.73-1.58 (m, 2H).

Example 86

1-(4-Fluoro-benzenesulfonyl)-pyrrolidine-2S-carboxylic acid (4'-cyano-biphenyl-3-ylmethyl)-amide

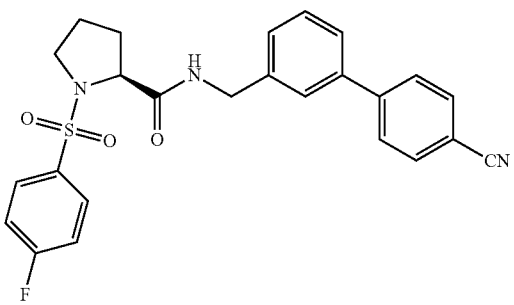 [SMILES: N#Cc1ccc(-c2cccc(CNC(=O)[C@@H]3CCCN3S(=O)(=O)c3ccc(F)cc3)c2)cc1]

MS (ESI): Mass calcd. for $C_{25}H_{22}FN_3O_3S$, 481.54; m/z found 482.2 [M+H]$^+$. $^1$H NMR (400 MHz, CD$_2$Cl$_2$) δ 7.91-7.82 (m, 2H), 7.80-7.69 (m, 4H), 7.61 (s, 1H), 7.57-7.50 (m, 1H), 7.51-7.43 (m, 1H), 7.40-7.35 (m, 1H), 7.34-7.21 (m, 3H), 4.67 (dd, J=15.4, 6.8, 1H), 4.46 (dd, J=15.4, 5.5, 1H), 4.11 (dd, J=8.7, 3.0, 1H), 3.56 (ddd, J=10.2, 7.0, 3.3, 1H), 3.20-3.08 (m, 1H), 2.22-2.11 (m, 1H), 1.89-1.54 (m, 3H).

Example 87

1-(4-Fluorobenzenesulfonyl)-pyrrolidine-2S-carboxylic acid 3-(6-methylpyridin-3-yl)-benzyl amide

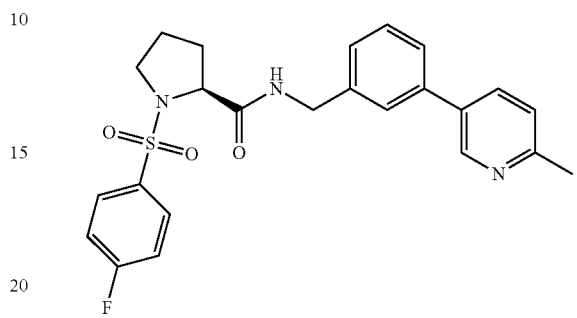

MS (ESI): Mass calcd. for $C_{24}H_{24}FN_3O_3S$, 453.53; m/z found 454.2 [M+H]$^+$. $^1$H NMR (500 MHz, CD$_2$Cl$_2$) δ 8.77 (d, J=2.0, 1H), 7.97-7.84 (m, 3H), 7.61 (s, 1H), 7.58-7.52 (m, 1H), 7.52-7.46 (m, 1H), 7.37 (d, J=7.9, 1H), 7.35-7.24 (m, 4H), 4.68 (dd, J=15.3, 6.7, 1H), 4.51 (dd, J=15.3, 5.5, 1H), 4.14 (dd, J=8.7, 2.9, 1H), 3.60 (ddd, J=10.2, 7.1, 3.2, 1H), 3.19 (ddd, J=9.6, 6.4, 1H), 2.61 (s, 3H), 2.27-2.12 (m, 1H), 1.91-1.76 (m, 1H), 1.76-1.63 (m, 2H).

Example 88

1-(4-Fluorobenzenesulfonyl)-pyrrolidine-2S-carboxylic acid 3-(6-trifluoromethylpyridin-3-yl)-benzyl amide

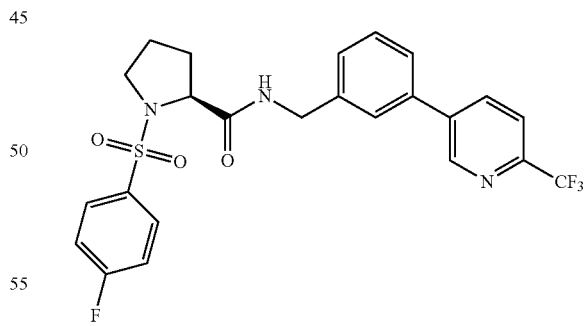

MS (ESI): Mass calcd. for $C_{24}H_{21}F_4N_3O_3S$, 507.5; m/z found 508.2 [M+H]$^+$. $^1$H NMR (600 MHz, CDCl$_3$) δ 9.18 (s, 1H), 8.22 (d, J=8.3, 2H), 7.81-7.71 (m, 3H), 7.43 (dd, J=8.4, 5.2, 2H), 7.11-7.03 (m, 2H), 4.75-4.57 (m, 3H), 4.55-4.45 (m, 1H), 4.41-4.27 (m, 1H), 3.63-3.46 (m, 1H), 3.37-3.25 (m, 1H), 2.65-2.49 (m, 1H), 2.41-2.28 (m, 1H), 2.25-2.09 (m, 2H).

Example 89

1-(4-Fluorobenzenesulfonyl)-pyrrolidine-2S-carboxylic acid (4'-acetylbiphenyl-3-ylmethyl)-amide

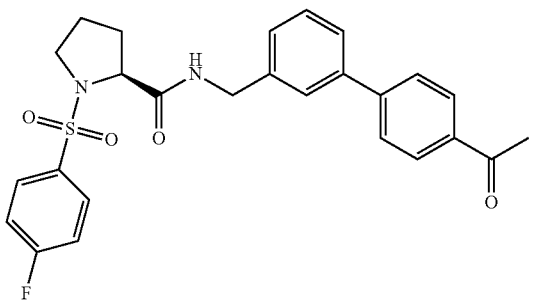 [SMILES: CC(=O)c1ccc(-c2cccc(CNC(=O)[C@@H]3CCCN3S(=O)(=O)c3ccc(F)cc3)c2)cc1]

MS (ESI): Mass calcd. for $C_{26}H_{25}FN_2O_4S$, 480.55; m/z found 481.2 [M+H]$^+$. $^1$H NMR (400 MHz, CD$_2$Cl$_2$) δ 8.06-7.98 (m, 2H), 7.91-7.83 (m, 2H), 7.79-7.72 (m, 2H), 7.63 (s, 1H), 7.61-7.53 (m, 1H), 7.50-7.43 (m, 1H), 7.39-7.32 (m, 1H), 7.30-7.22 (m, 3H), 4.65 (dd, J=15.3, 6.6, 1H), 4.48 (dd, J=15.3, 5.6, 1H), 4.11 (dd, J=8.6, 3.0, 1H), 3.56 (ddd, J=10.2, 7.1, 3.3, 1H), 3.24-3.11 (m, 1H), 2.60 (s, 3H), 2.23-2.10 (m, 1H), 1.87-1.59 (m, 3H).

Example 90

1-(4-Fluorobenzenesulfonyl)-pyrrolidine-2S-carboxylic acid 3-(5-methoxypyridin-2-yl)-benzylamide

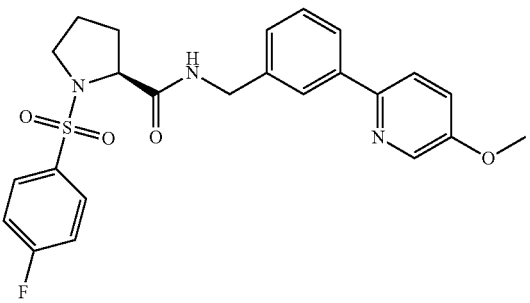

MS (ESI): Mass calcd. for $C_{24}H_{24}FN_3O_4S$, 469.53; m/z found 470.2 [M+H]$^+$. $^1$H NMR (600 MHz, CD$_2$Cl$_2$) δ 8.36 (d, J=2.9, 1H), 7.93 (s, 1H), 7.90-7.85 (m, 3H), 7.78 (d, J=8.7, 1H), 7.46-7.41 (m, 1H), 7.34-7.23 (m, 5H), 4.60 (dd, J=15.2, 6.4, 1H), 4.51 (dd, J=15.2, 5.8, 1H), 4.12 (dd, J=8.7, 2.9, 1H), 3.89 (s, 3H), 3.57 (ddd, J=10.2, 7.4, 3.3, 1H), 3.16 (ddd, J=9.7, 6.5, 6.5, 1H), 2.21-2.11 (m, 1H), 1.86-1.73 (m, 1H), 1.73-1.57 (m, 2H).

Example 91

1-(4-Fluorobenzenesulfonyl)-pyrrolidine-2S-carboxylic acid 3-(5-chloropyridin-2-yl)-benzylamide

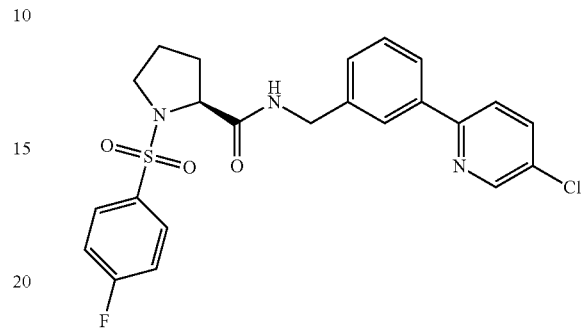

MS (ESI): Mass calcd. for $C_{23}H_{21}ClFN_3O_3S$, 473.95; m/z found 474.2 [M+H]$^+$. $^1$H NMR (500 MHz, CDCl$_3$) δ 8.62 (s, 1H), 7.92 (s, 1H), 7.90-7.84 (m, 3H), 7.78-7.68 (m, J=8.6, 2H), 7.49-7.35 (m, 2H), 7.32-7.20 (m, 3H), 4.64 (dd, J=15.1, 6.3, 1H), 4.59-4.48 (m, 1H), 4.19-4.11 (m, 1H), 3.63-3.50 (m, 1H), 3.21-3.06 (m, 1H), 2.30-2.18 (m, 1H), 1.88-1.72 (m, 1H), 1.73-1.56 (m, 2H).

Example 92

1-(4-Fluorobenzenesulfonyl)-pyrrolidine-2S-carboxylic acid 3-(5-trifluoromethylpyridin-2-yl)-benzylamide

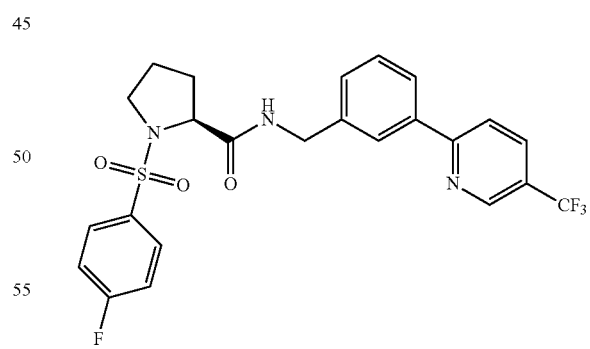

MS (ESI): Mass calcd. for $C_{24}H_{21}F_4N_3O_3S$, 507.50; m/z found 508.2 [M+H]$^+$. $^1$H NMR (500 MHz, CDCl$_3$) δ 8.93 (s, 1H), 8.05-7.84 (m, 6H), 7.54-7.19 (m, 5H), 4.69 (dd, J=15.3, 6.4, 1H), 4.55 (dd, J=15.3, 5.5, 1H), 4.25-4.08 (m, 1H), 3.70-3.48 (m, 1H), 3.27-3.02 (m, 1H), 2.31-2.18 (m, 1H), 1.95-1.76 (m, 1H), 1.75-1.55 (m, 2H).

Example 93

1-(4-Fluorobenzenesulfonyl)-pyrrolidine-2S-carboxylic acid (4'-dimethylaminobiphenyl-3-ylmethyl)-amide

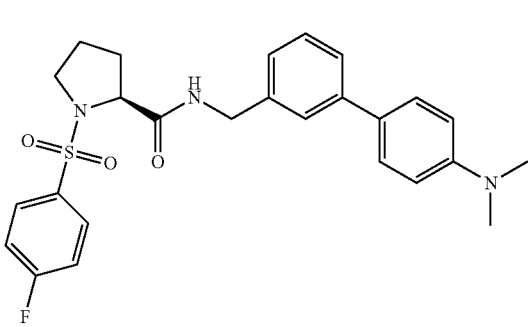

MS (ESI): Mass calcd. for $C_{26}H_{28}FN_3O_3S$, 481.58; m/z found 482.2 [M+H]$^+$. $^1$H NMR (500 MHz, CD$_2$Cl$_2$) δ 7.94-7.81 (m, 2H), 7.60-7.45 (m, J=20.6, 4H), 7.42-7.33 (m, 1H), 7.32-7.14 (m, 4H), 6.89-6.69 (m, 2H), 4.66-4.51 (m, 1H), 4.53-4.39 (m, 1H), 4.18-3.99 (m, 1H), 3.63-3.41 (m, 1H), 3.27-3.10 (m, 1H), 2.98 (s, 6H), 2.24-2.09 (m, 1H), 1.87-1.73 (m, 1H), 1.73-1.60 (m, 2H).

Example 94

1-(4-Fluorobenzenesulfonyl)-pyrrolidine-2S-carboxylic acid (4'-morpholin-4-yl-biphenyl-3-ylmethyl)-amide

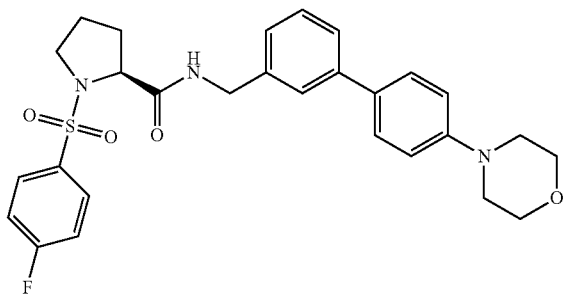 [SMILES: O=C(NCc1cccc(-c2ccc(N3CCOCC3)cc2)c1)[C@@H]1CCCN1S(=O)(=O)c1ccc(F)cc1]

MS (ESI): Mass calcd. for $C_{28}H_{30}FN_3O_4S$, 523.62; m/z found 524.2 [M+H]$^+$. $^1$H NMR (500 MHz, CD$_2$Cl$_2$) δ 7.92-7.83 (m, 2H), 7.71 (d, J=8.7, 2H), 7.69-7.60 (m, 2H), 7.57 (s, 1H), 7.56-7.50 (m, 2H), 7.41 (t, J=7.6, 1H), 7.41-7.23 (m, 3H), 4.72-4.60 (m, 1H), 4.55-4.43 (m, 1H), 4.19-4.10 (m, 1H), 4.07-3.97 (m, 4H), 3.63-3.50 (m, 1H), 3.50-3.31 (m, 4H), 3.22-3.08 (m, 1H), 2.23-2.03 (m, 1H), 1.88-1.55 (m, 3H).

Example 95

1-(4-Fluoro-benzenesulfonyl)-pyrrolidine-2S-carboxylic acid 3-(1H-indol-5-yl)-benzylamide

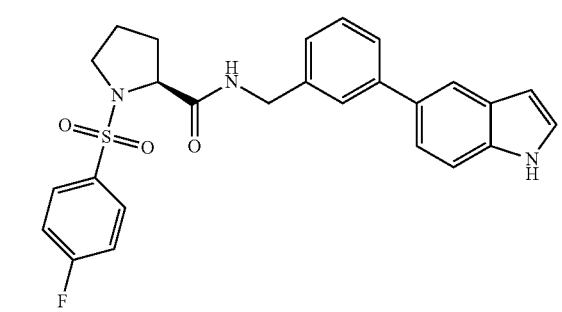 [SMILES: O=C(NCc1cccc(-c2ccc3[nH]ccc3c2)c1)[C@@H]1CCCN1S(=O)(=O)c1ccc(F)cc1]

MS (ESI): Mass calcd. for $C_{26}H_{24}FN_3O_3S$, 477.55; m/z found 478.2 [M+H]$^+$. $^1$H NMR (500 MHz, CD$_2$Cl$_2$) δ 8.37 (s, 1H), 7.92-7.75 (m, 3H), 7.68-7.53 (m, 2H), 7.51-7.45 (m, 2H), 7.45 (dd, J=7.6, 1H), 7.33-7.16 (m, 5H), 6.59 (d, J=2.1, 1H), 4.60 (dd, J=15.1, 6.2, 1H), 4.55-4.47 (m, 1H), 4.14-4.10 (m, 1H), 3.61-3.51 (m, 1H), 3.17 (m, 1H), 2.23-2.14 (m, 1H), 1.87-1.73 (m, 1H), 1.72-1.59 (m, J=10.3, 2H).

Example 96

1-(4-Fluoro-benzenesulfonyl)-pyrrolidine-2S-carboxylic acid 3-(1-methyl-1H-indol-5-yl)-benzylamide

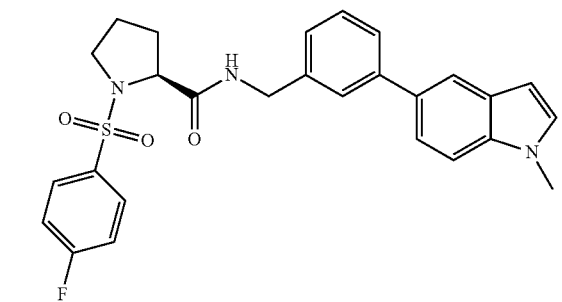 [SMILES: Cn1ccc2cc(-c3cccc(CNC(=O)[C@@H]4CCCN4S(=O)(=O)c4ccc(F)cc4)c3)ccc21]

MS (ESI): Mass calcd. for $C_{27}H_{26}FN_3O_3S$, 491.58; m/z found 492.2 [M+H]$^+$. $^1$H NMR (500 MHz, CD$_2$Cl$_2$) δ 7.98-7.80 (m, 3H), 7.61 (s, 1H), 7.60-7.55 (m, 1H), 7.54-7.48 (m, 1H), 7.46-7.35 (m, 2H), 7.32-7.19 (m, J=8.6, 4H), 7.11 (d, J=3.0, 1H), 6.51 (d, J=3.0, 1H), 4.65-4.56 (m, 1H), 4.56-4.45 (m, 1H), 4.18-4.09 (m, 1H), 3.81 (s, 3H), 3.61-3.51 (m, 1H), 3.27-3.11 (m, 1H), 2.25-2.12 (m, 1H), 1.88-1.74 (m, 1H), 1.72-1.60 (m, 2H).

Example 97

1-(4-Fluorobenzenesulfonyl)-pyrrolidine-2S-carboxylic acid 3-(6-morpholin-4-yl-pyridin-3-yl)-benzylamide

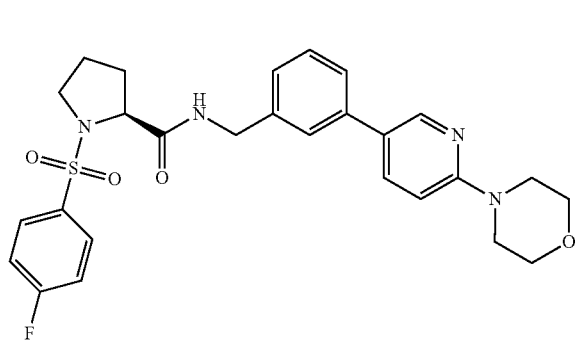 [SMILES: O=C(NCc1cccc(-c2ccc(N3CCOCC3)nc2)c1)[C@@H]1CCCN1S(=O)(=O)c1ccc(F)cc1]

MS (ESI): Mass calcd. for $C_{27}H_{29}FN_4O_4S$, 524.61; m/z found 525.2 [M+H]$^+$. $^1$H NMR (500 MHz, CD$_2$Cl$_2$) δ 8.45 (d, J=2.5, 1H), 7.88 (dd, J=8.8, 5.1, 2H), 7.85-7.76 (m, 1H), 7.52 (s, 1H), 7.49-7.44 (m, 1H), 7.41 (dd, J=7.6, 1H), 7.31-7.21 (m, 4H), 6.80-6.65 (m, 1H), 4.60 (dd, J=15.3, 6.7, 1H), 4.45 (dd, J=15.3, 5.5, 1H), 4.10 (dd, J=8.6, 2.8, 1H), 3.85-3.73 (m, 4H), 3.61-3.50 (m, 5H), 3.21-3.10 (m, 1H), 2.16 (s, 1H), 1.78 (s, 1H), 1.65 (s, 2H).

Example 98

1-(4-Fluorobenzenesulfonyl)-pyrrolidine-2S-carboxylic acid (biphenyl-3-ylmethyl)-amide

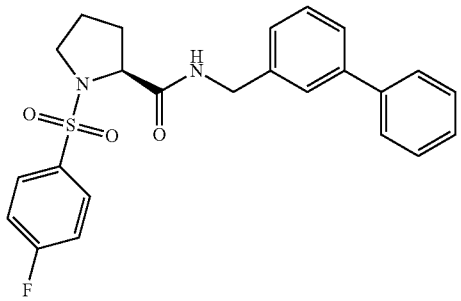 [SMILES: O=C(NCc1cccc(-c2ccccc2)c1)[C@@H]1CCCN1S(=O)(=O)c1ccc(F)cc1]

MS (ESI): Mass calcd. for $C_{24}H_{23}FN_2O_3S$, 438.52; m/z found 439.2 [M+H]$^+$. $^1$H NMR (500 MHz, CD$_2$Cl$_2$) δ 7.91-7.84 (m, 2H), 7.66-7.61 (m, 2H), 7.57 (s, 1H), 7.55-7.51 (m, 1H), 7.47-7.41 (m, 3H), 7.38-7.22 (m, 5H), 4.61 (dd, J=15.2, 6.5, 1H), 4.49 (dd, J=15.2, 5.7, 1H), 4.11 (dd, J=8.7, 3.0, 1H), 3.62-3.47 (m, 1H), 3.23-3.10 (m, 1H), 2.24-2.12 (m, 1H), 1.86-1.73 (m, 1H), 1.71-1.57 (m, 2H).

Example 99

1-(4-Fluorobenzenesulfonyl)-pyrrolidine-2S-carboxylic acid (4'-amino-biphenyl-3-ylmethyl)-amide

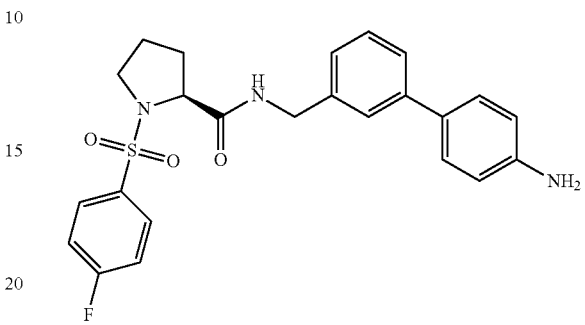

MS (ESI): Mass calcd. for $C_{24}H_{24}FN_3O_3S$, 453.53; m/z found 454.2 [M+H]$^+$. $^1$H NMR (500 MHz, CD$_2$Cl$_2$) δ 7.87 (dd, J=8.9, 5.1, 2H), 7.55-7.33 (m, 5H), 7.24 (dd, J=19.3, 10.6, 4H), 6.74 (d, J=8.6, 2H), 4.55 (dd, J=15.4, 6.0, 1H), 4.49 (dd, J=15.4, 5.8, 1H), 4.14-4.07 (m, 1H), 3.92-3.64 (m, 2H), 3.61-3.48 (m, 1H), 3.22-3.11 (m, 1H), 2.22-2.10 (m, 1H), 1.84-1.71 (m, 1H), 1.71-1.59 (m, 2H).

Example 100

1-(4-Fluorobenzenesulfonyl)-pyrrolidine-2S-carboxylic acid [4'-(4-methylpiperazin-1-yl)biphenyl-3-ylmethyl]-amide

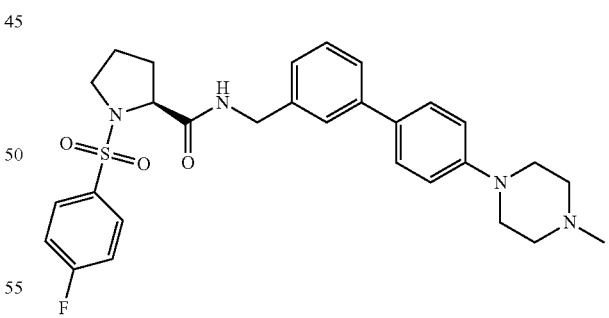

MS (ESI): Mass calcd. for $C_{29}H_{33}FN_4O_3S$, 536.66; m/z found 537.3 [M+H]$^+$. $^1$H NMR (500 MHz, CD$_2$Cl$_2$) δ 7.92-7.83 (m, 2H), 7.63-7.43 (m, 5H), 7.43-7.35 (m, 1H), 7.32-7.18 (m, 3H), 7.03-6.94 (m, 2H), 4.63-4.53 (m, 1H), 4.50 (m, 1H), 4.16-4.07 (m, 1H), 3.62-3.51 (m, 1H), 3.37-3.20 (m, 4H), 3.21-3.09 (m, 1H), 2.73-2.45 (m, 3H), 2.34 (s, 3H), 2.25-2.11 (m, 1H), 1.85-1.73 (m, 1H), 1.64 (m, 3H).

Example 101

1-(4-Fluorobenzenesulfonyl)-pyrrolidine-2S-carboxylic acid 3-(1H-indol-6-yl)-benzylamide

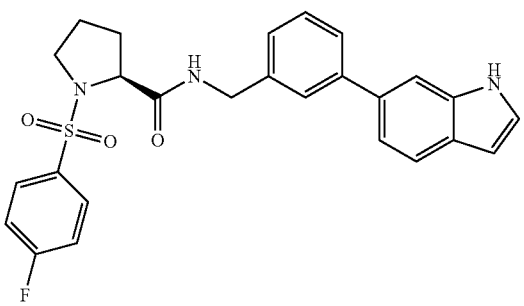 [SMILES: O=C(NCc1cccc(-c2ccc3cc[nH]c3c2)c1)[C@@H]1CCCN1S(=O)(=O)c1ccc(F)cc1]

MS (ESI): Mass calcd. for $C_{26}H_{24}FN_3O_3S$, 477.55; m/z found 478.2 [M+H]$^+$. $^1$H NMR (500 MHz, CD$_2$Cl$_2$) δ 8.43 (s, 1H), 7.88 (dd, J=8.8, 5.1, 2H), 7.71 (s, 1H), 7.69-7.61 (m, 2H), 7.61-7.57 (m, 1H), 7.47-7.37 (m, 2H), 7.33-7.22 (m, 4H), 6.55 (s, 1H), 4.61 (dd, J=15.3, 6.8, 1H), 4.55 (dd, J=6.4, 1H), 4.18-4.12 (m, 1H), 3.61-3.53 (m, 1H), 3.23-3.12 (m, 1H), 2.22-2.15 (m, 1H), 1.87-1.73 (m, 1H), 1.73-1.59 (m, 2H).

Example 102

1-(4-Fluorobenzenesulfonyl)-pyrrolidine-2S-carboxylic acid (4'-morpholin-4-ylmethylbiphenyl-3-ylmethyl)-amide

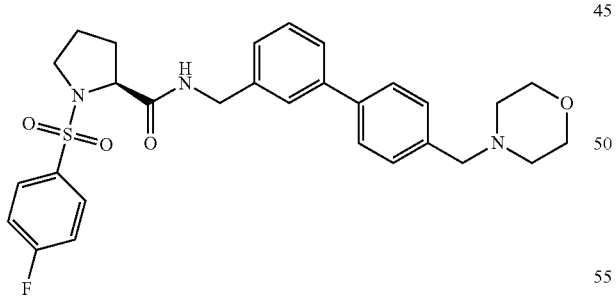

MS (ESI): Mass calcd. for $C_{29}H_{32}FN_3O_4S$, 537.65; m/z found 538.2 [M+H]$^+$. $^1$H NMR (500 MHz, CD$_2$Cl$_2$) δ 7.93-7.83 (m, 2H), 7.73 (d, J=8.2, 2H), 7.59 (s, 1H), 7.61-7.48 (m, 4H), 7.35 (d, J=7.5, 2H), 7.27 (t, J=8.6, 2H), 4.73-4.60 (m, 1H), 4.55-4.43 (m, 1H), 4.25 (s, 2H), 4.20-4.10 (m, 1H), 4.05-3.88 (m, 4H), 3.64-3.52 (m, 1H), 3.53-3.38 (m, 2H), 3.22-3.08 (m, 1H), 3.00-2.83 (m, 2H), 2.24-2.06 (m, 1H), 1.91-1.55 (m, 3H).

Example 103

1-(4-Fluoro-benzenesulfonyl)-pyrrolidine-2S-carboxylic acid (4'-piperidin-1-yl-biphenyl-3-ylmethyl)-amide

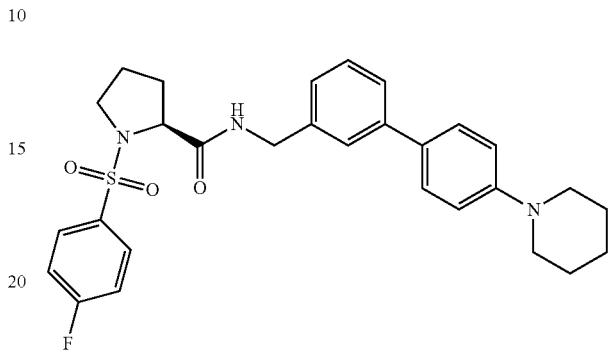

MS (ESI): Mass calcd. for $C_{29}H_{32}FN_3O_3S$, 521.65; m/z found 522.2 [M+H]$^+$. $^1$H NMR (500 MHz, CD$_2$Cl$_2$) δ 7.94-7.84 (m, 2H), 7.59-7.45 (m, 4H), 7.38 (s, 1H), 7.32-7.17 (m, 4H), 7.05-6.91 (m, 2H), 4.64-4.54 (m, 1H), 4.55-4.42 (m, 1H), 4.19-4.03 (m, 1H), 3.64-3.48 (m, 1H), 3.29-3.12 (m, 5H), 2.25-2.11 (m, 1H), 1.89-1.50 (m, 9H).

Example 104

1-(4-Fluorobenzenesulfonyl)-pyrrolidine-2S-carboxylic acid 3-(6-dimethylaminopyridin-3-yl)-benzylamide

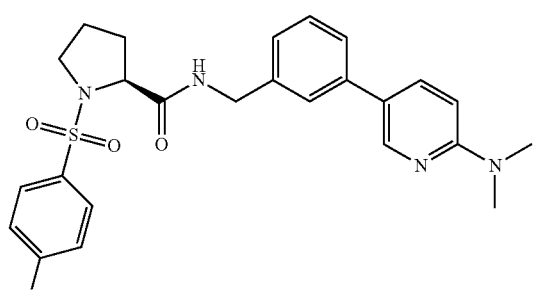

MS (ESI): Mass calcd. for $C_{25}H_{27}FN_4O_3S$, 482.57; m/z found 483.2 [M+H]$^+$. $^1$H NMR (500 MHz, CD$_2$Cl$_2$) δ 8.42 (s, 1H), 7.94-7.83 (m, 2H), 7.82-7.74 (m, 1H), 7.65 (s, 1H), 7.52-7.39 (m, 3H), 7.31-7.19 (m, 3H), 6.63 (s, 1H), 4.66-4.54 (m, 1H), 4.52-4.41 (m, 1H), 4.16-4.06 (m, 1H), 3.62-3.49 (m, 1H), 3.13 (s, 6H), 3.16 (m, 1H), 2.23-2.12 (m, 1H), 1.86-1.73 (m, 1H), 1.73-1.61 (m, 2H).

Example 105

1-(4-Fluorobenzenesulfonyl)-pyrrolidine-2S-carboxylic acid (2-methylene-4-quinolin-3-yl-pent-3-enyl)-amide

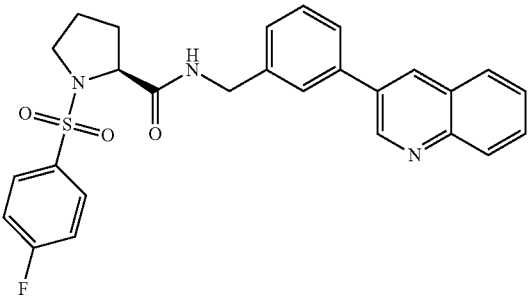 [SMILES: O=C(NCc1cccc(-c2cnc3ccccc3c2)c1)[C@@H]1CCCN1S(=O)(=O)c1ccc(F)cc1]

MS (ESI): Mass calcd. for $C_{27}H_{24}FN_3O_3S$, 489.56; m/z found 490.2 [M+H]$^+$. $^1$H NMR (500 MHz, CD$_2$Cl$_2$) δ 9.27-9.18 (m, 1H), 8.45 (s, 1H), 8.11 (d, J=8.3, 1H), 7.98-7.87 (m, 2H), 7.83-7.23 (m, 10H), 4.72 (dd, J=15.3, 6.8, 1H), 4.51 (dd, J=15.3, 5.8, 1H), 4.19-4.09 (m, 1H), 3.69-3.54 (m, 1H), 3.30-3.09 (m, 1H), 2.30-2.13 (m, 1H), 1.92-1.75 (m, 1H), 1.74-1.57 (m, 2H).

Example 106

1-(4-Fluoro-benzenesulfonyl)-pyrrolidine-2S-carboxylic acid 3-quinolin-6-yl-benzylamide

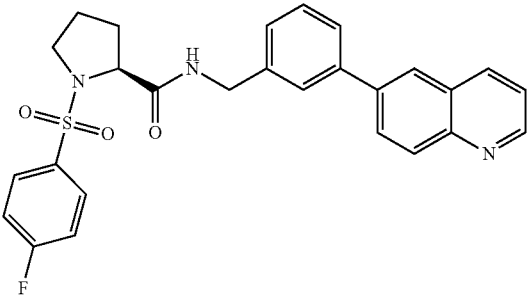 [SMILES: O=C(NCc1cccc(-c2ccc3ncccc3c2)c1)[C@@H]1CCCN1S(=O)(=O)c1ccc(F)cc1]

MS (ESI): Mass calcd. for $C_{27}H_{24}FN_3O_3S$, 489.56; m/z found 490.2 [M+H]$^+$. $^1$H NMR (500 MHz, CD$_2$Cl$_2$) δ 8.92-8.86 (m, 1H), 8.32-8.24 (m, 1H), 8.23-8.13 (m, 2H), 8.11-8.02 (m, 1H), 7.94-7.86 (m, 2H), 7.75 (s, 1H), 7.71-7.60 (m, 1H), 7.54-7.42 (m, 2H), 7.40-7.22 (m, 4H), 4.70 (dd, J=15.3, 6.6, 1H), 4.51 (dd, J=15.3, 5.4, 1H), 4.18-4.12 (m, 1H), 3.65-3.52 (m, 1H), 3.24-3.11 (m, 1H), 2.25-2.13 (m, 1H), 1.87-1.74 (m, 1H), 1.74-1.60 (m, 2H).

Example 107

1-(4-Fluoro-benzenesulfonyl)-pyrrolidine-2S-carboxylic acid 3-quinolin-2-yl-benzylamide

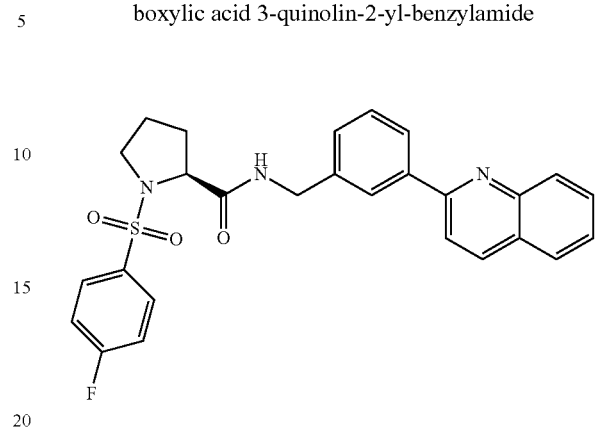

MS (ESI): Mass calcd. for $C_{27}H_{24}FN_3O_3S$, 489.56; m/z found 490.2 [M+H]$^+$. $^1$H NMR (500 MHz, CD$_2$Cl$_2$) δ 8.30 (d, J=8.6, 1H), 8.20 (d, J=8.3, 1H), 8.13 (s, 1H), 8.05 (d, J=7.7, 1H), 7.96 (d, J=8.6, 1H), 7.93-7.85 (m, 2H), 7.81-7.72 (m, 1H), 7.60-7.54 (m, 1H), 7.52-7.46 (m, 1H), 7.46-7.30 (m, 3H), 7.30-7.23 (m, 2H), 4.63 (dd, J=15.3, 6.4, 1H), 4.57 (dd, J=15.3, 5.8, 1H), 4.18-4.12 (m, 1H), 3.66-3.54 (m, 1H), 3.22-3.13 (m, 1H), 2.24-2.15 (m, 1H), 1.89-1.77 (m, 1H), 1.75-1.58 (m, 2H).

Example 108

1-(4-Fluorobenzenesulfonyl)-pyrrolidine-2S-carboxylic acid 3-(1-methyl-1H-indol-6-yl)-benzylamide

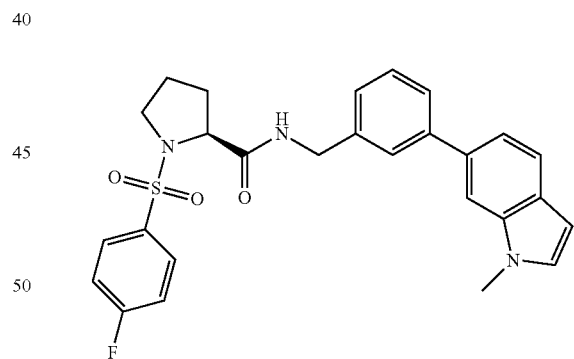

MS (ESI): Mass calcd. for $C_{27}H_{26}FN_3O_3S$, 491.58; m/z found 492.2 [M+H]$^+$. $^1$H NMR (500 MHz, CD$_2$Cl$_2$) δ 7.88 (dd, J=8.8, 5.1, 2H), 7.68 (s, 1H), 7.66-7.58 (m, 3H), 7.48-7.40 (m, 1H), 7.41-7.36 (m, 1H), 7.31-7.22 (m, 4H), 7.10 (d, J=3.0, 1H), 6.47 (d, J=3.0, 1H), 4.65 (dd, J=15.2, 6.5, 1H), 4.50 (dd, J=15.2, 5.4, 1H), 4.16-4.08 (m, 1H), 3.81 (s, 3H), 3.62-3.54 (m, 1H), 3.23-3.13 (m, 1H), 2.24-2.13 (m, 1H), 1.87-1.73 (m, 1H), 1.73-1.61 (m, 2H).

Examples 109 to 112 were prepared using methods analogous to those described for Example 65 substituting the appropriate sulfonyl chloride to provide the desired product.

Example 109

3-(4-Fluorobenzenesulfonyl)-3-aza-1S,5R-bicyclo[3.1.0]hexane-2S-carboxylic acid (4'-trifluoromethylbiphenyl-3-ylmethyl)-amide

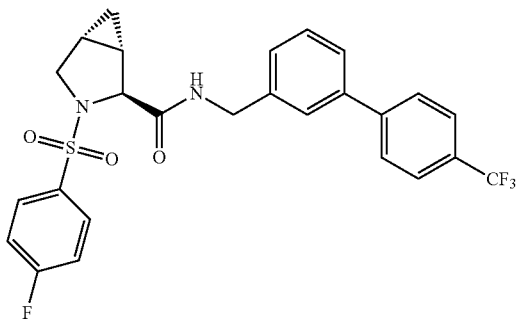 [SMILES: O=C(NCc1cccc(-c2ccc(C(F)(F)F)cc2)c1)[C@@H]1[C@H]2C[C@H]2CN1S(=O)(=O)c1ccc(F)cc1]

MS (ESI): mass calcd. for $C_{26}H_{22}F_4N_2O_3S$, 518.53. found 519.1 [M+H]$^+$. $^1$H NMR (600 MHz, DMSO) δ 8.60 (t, J=6.0, 1H), 7.96-7.92 (m, 2H), 7.89 (d, J=8.1, 2H), 7.78 (d, J=8.2, 2H), 7.72 (s, 1H), 7.62 (d, J=8.0, 1H), 7.54-7.45 (m, 3H), 7.40 (d, J=7.7, 1H), 4.51-4.39 (m, 2H), 4.10 (d, J=5.0, 1H), 3.41 (d, J=9.3, 1H), 3.21 (dd, J=9.3, 4.9, 1H), 1.85 (ddd, J=11.9, 7.8, 4.5, 1H), 1.62-1.55 (m, 1H), 1.02-0.95 (m, 1H), 0.60-0.49 (m, 1H).

Example 110

3-(5-Chlorothiophene-2-sulfonyl)-3-aza-1S,5R-bicyclo[3.1.0]hexane-2S-carboxylic acid (4'-trifluoromethylbiphenyl-3-ylmethyl)-amide

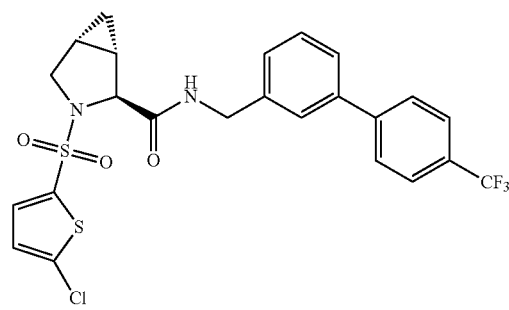 [SMILES: O=C(NCc1cccc(-c2ccc(C(F)(F)F)cc2)c1)[C@@H]1[C@H]2C[C@H]2CN1S(=O)(=O)c1ccc(Cl)s1]

MS (ESI): mass calcd. for $C_{24}H_{20}ClF_3N_2O_3S_2$, 541.01; m/z found 541.0 [M$^+$]. $^1$H NMR (600 MHz, DMSO) δ 8.61 (t, J=6.0, 1H), 7.89 (d, J=8.1, 2H), 7.80 (d, J=8.2, 2H), 7.69 (s, 1H), 7.64 (d, J=4.1, 1H), 7.62 (d, J=7.7, 1H), 7.47 (t, J=7.7, 1H), 7.40 (d, J=4.1, 1H), 7.38 (d, J=7.7, 1H), 4.49-4.39 (m, 2H), 4.13 (d, J=5.1, 1H), 3.50 (d, J=9.5, 1H), 3.34 (dd, J=9.4, 5.0, 1H), 1.91 (ddd, J=12.0, 7.8, 4.5, 1H), 1.65 (ddd, J=12.2, 7.8, 4.7, 1H), 1.03-0.94 (m, 1H), 0.62-0.54 (m, 1H).

Example 111

1-(4-Fluorobenzenesulfonyl)-2,5-dihydro-1H-pyrrole-2S-carboxylic acid (4'-trifluoromethylbiphenyl-3-ylmethyl)-amide

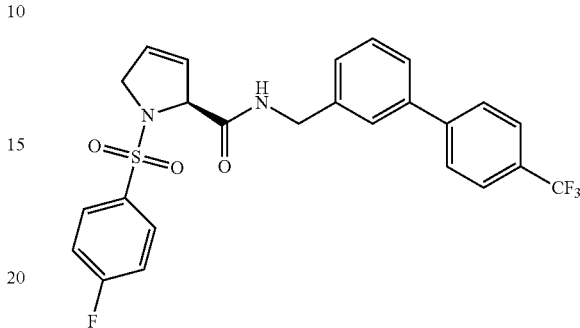

MS (ESI): mass calcd. for $C_{25}H_{20}F_4N_2O_3S$, 504.51; m/z found 505.1 [M+H]$^+$. $^1$H NMR (500 MHz, DMSO) δ 8.74 (s, 1H), 7.97 (dd, J=8.6, 5.2, 2H), 7.90 (d, J=8.4, 2H), 7.80 (d, J=8.4, 2H), 7.67 (s, 1H), 7.62 (d, J=7.8, 1H), 7.50-7.43 (m, 3H), 7.36 (d, J=7.6, 1H), 5.92-5.84 (m, 1H), 5.74-5.67 (m, 1H), 4.90 (s, 1H), 4.46 (dd, J=15.5, 6.2, 1H), 4.38 (dd, J=15.5, 5.8, 1H), 4.30-4.22 (m, 1H), 4.17-4.10 (m, 1H).

Example 112

1-(5-Chlorothiophene-2-sulfonyl)-2,5-dihydro-1H-pyrrole-2S-carboxylic acid (4'-trifluoromethylbiphenyl-3-ylmethyl)-amide

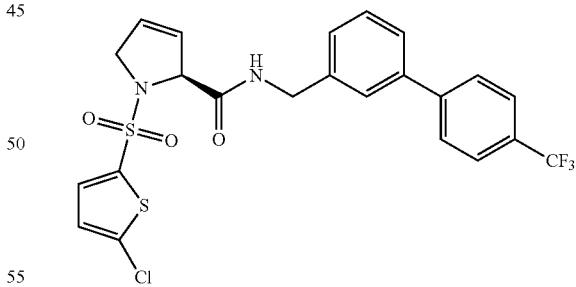

MS (ESI): mass calcd. for $C_{23}H_{18}ClF_3N_2O_3S_2$, 526.99; m/z found 527.0 [M$^+$]. $^1$H NMR (500 MHz, DMSO) δ 8.78 (t, J=6.0, 1H), 7.89 (d, J=8.4, 2H), 7.81 (d, J=8.5, 2H), 7.71 (d, J=4.1, 1H), 7.64 (s, 1H), 7.62 (d, J=7.9, 1H), 7.49-7.44 (m, 1H), 7.36 (d, J=4.1, 1H), 7.34 (d, J=7.7, 1H), 5.94 (dd, J=6.2, 1.9, 1H), 5.76 (dd, J=6.2, 2.2, 1H), 4.90 (dd, J=5.4, 2.3, 1H), 4.46 (dd, J=15.5, 6.3, 1H), 4.37 (dd, J=15.8, 6.1, 1H), 4.35-4.28 (m, 1H), 4.17 (dd, J=15.2, 2.1, 1H).

Example 113

(1S,2S)-1-(4-Fluoro-benzenesulfonyl)-pyrrolidine-2-carboxylic acid [1-(4'-trifluoromethyl-biphenyl-3-yl)-ethyl]-amide

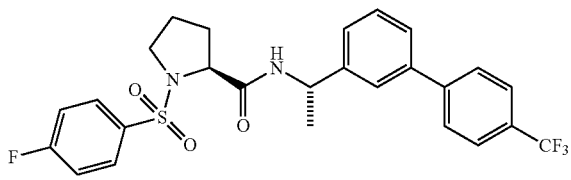 [SMILES: C[C@H](NC(=O)[C@@H]1CCCN1S(=O)(=O)c1ccc(F)cc1)c1cccc(-c2ccc(C(F)(F)F)cc2)c1]

To a solution of (1S,2S)-2-methyl-propane-2-sulfinic acid [1-(4'-trifluoromethyl-biphenyl-3-yl)-ethyl]-amide (310 mg, 0.83 mmol) and MeOH (10 mL) was added 4M HCl in dioxane (0.42 mL, 1.66 mmol). After 1 h, resulting solution was concentrated and the residue ((S)-1-(4'-trifluoromethyl-biphenyl-3-yl)-ethylamine hydrochloride) was used crude in next step.

A mixture of (5)-1-(4'-trifluoromethyl-biphenyl-3-yl) ethylamine hydrochloride (75 mg, 0.25 mmol), (S)-1-(4-fluoro-benzenesulfonyl)-pyrrolidine-2-carboxylic acid (68 mg, 0.25 mmol), N-(3-dimethylamniopropyl)-N'-ethylcarbodiimide hydrochloride (71 mg, 0.37 mmol), 1-hydroxybenzotriazole (50 mg, 0.37 mmol) and DMF (2 mL) was added Et₃N (0.10 mL, 0.75 mmol). After 12 h, MeOH (0.5 mL) was added to the reaction mixture and resulting solution was purified by preparative reverse-phase HPLC to afford (70 mg, 54%) of a white solid. MS (ESI): mass calcd. for $C_{26}H_{24}F_4N_2O_3S$, 520.1; m/z found, 521.1 [M+H]⁺. ¹H NMR (500 MHz, CDCl₃) δ 7.93-7.87 (m, 2H), 7.79 (d, J=8.0, 2H), 7.73-7.66 (m, 3H), 7.54 (d, J=7.6, 1H), 7.49 (t, J=7.6, 1H), 7.44 (d, J=7.6, 1H), 7.35 (d, J=8.0, 1H), 7.30-7.23 (m, J=8.7, 1H), 5.27-5.11 (m, 1H), 4.11 (dd, J=8.9, 3.1, 1H), 3.71-3.60 (m, 1H), 3.26-3.15 (m, 1H), 2.28-2.17 (m, 1H), 1.91-1.75 (m, 1H), 1.74-1.64 (m, 2H), 1.60 (d, J=7.0, 3H).

Examples 114 to 118 mere prepared using methods analogous to those described for example 113.

Example 114

(1R,2S)-1-(4-Fluoro-benzenesulfonyl)-pyrrolidine-2-carboxylic acid [1-(4'-trifluoromethyl-biphenyl-3-yl) ethyl]-amide

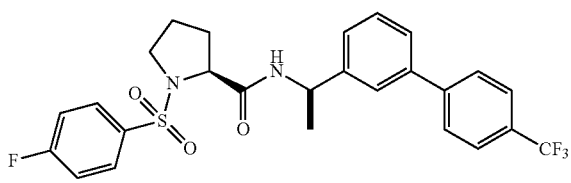 [SMILES: C[C@@H](NC(=O)[C@@H]1CCCN1S(=O)(=O)c1ccc(F)cc1)c1cccc(-c2ccc(C(F)(F)F)cc2)c1]

MS (ESI): mass calcd. for $C_{26}H_{24}F_4N_2O_3S$, 520.1; m/z found, 522.1 [M+H]⁺. ¹H NMR (500 MHz, CDCl₃) δ 7.93-7.86 (m, 2H), 7.71 (app s, 4H), 7.58-7.45 (m, 3H), 7.37 (d, J=7.6, 1H), 7.30-7.23 (m, 2H), 5.29-5.14 (m, 1H), 4.14 (dd, J=8.6, 3.1, 1H), 3.56 (dd, J=11.8, 5.0, 1H), 3.26-3.11 (m, 1H), 2.27-2.15 (m, 1H), 1.82-1.55 (m, 6H).

Example 115

(1S,2S)-1-(5-Chloro-thiophene-2-sulfonyl)-pyrrolidine-2-carboxylic acid [1-(4'-trifluoromethylbiphenyl-3-yl)ethyl]-amide

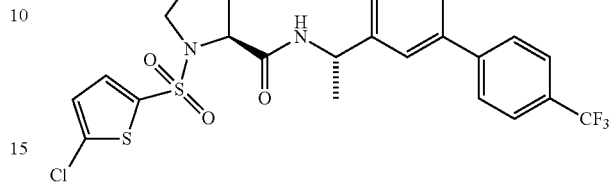

MS (ESI): mass calcd. for $C_{24}H_{22}ClF_3N_2O_3S_2$, 542.0; m/z found, 543.1 [M+H]⁺. ¹H NMR (500 MHz, CDCl₃) δ 7.77 (d, J=8.1, 2H), 7.70 (d, J=8.2, 2H), 7.64 (s, 1H), 7.55-7.50 (m, 1H), 7.51-7.44 (m, 2H), 7.41 (d, J=7.6, 1H), 7.32 (d, J=8.0, 1H), 7.05 (d, J=4.0, 1H), 5.30-5.10 (m, 1H), 4.21-4.12 (m, 1H), 3.68 (dd, J=8.5, 5.1, 1H), 3.36-3.20 (m, 1H), 2.37-2.22 (m, 1H), 1.96-1.73 (m, 3H), 1.59 (d, J=7.0, 3H).

Example 116

(1R,2S)-1-(5-Chloro-thiophene-2-sulfonyl)-pyrrolidine-2-carboxylic acid [1-(4'-trifluoromethylbiphenyl-3-yl)ethyl]-amide

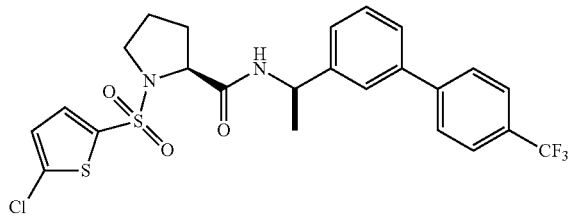 [SMILES: C[C@@H](NC(=O)[C@@H]1CCCN1S(=O)(=O)c1ccc(Cl)s1)c1cccc(-c2ccc(C(F)(F)F)cc2)c1]

MS (ESI): mass calcd. for $C_{24}H_{22}ClF_3N_2O_3S_2$, 542.0; m/z found, 543.1 [M+H]⁺. ¹H NMR (400 MHz, CDCl3) δ 7.69 (app s, 4H), 7.56-7.42 (m, 4H), 7.34 (d, J=7.5, 1H), 7.19 (d, J=7.9, 1H), 7.02 (d, J=4.0, 1H), 5.19 (p, J=7.1, 1H), 4.16 (dd, J=8.1, 2.6, 1H), 3.58 (dd, J=8.6, 4.7, 1H), 3.24 (dd, J=18.1, 8.1, 1H), 2.32-2.17 (m, 1H), 1.85-1.68 (m, 3H), 1.60 (d, J=6.9, 3H).

Example 117

(2S)-1-(4-Fluoro-benzenesulfonyl)-pyrrolidine-2-carboxylic acid [1-methyl-1-(4'-trifluoromethyl-biphenyl-3-yl)ethyl]-amide

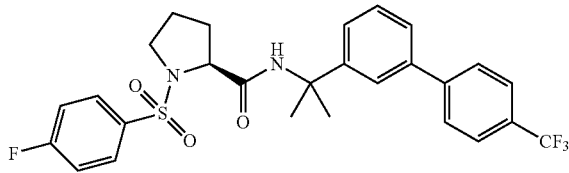 [SMILES: CC(C)(NC(=O)[C@@H]1CCCN1S(=O)(=O)c1ccc(F)cc1)c1cccc(-c2ccc(C(F)(F)F)cc2)c1]

MS (ESI): mass calcd. for $C_{27}H_{26}F_4N_2O_3S$, 534.1; m/z found, 535.2 [M+H]$^+$. $^1$H NMR (400 MHz, CDCl3) δ 7.92-7.85 (m, 2H), 7.74 (d, J=8.2, 2H), 7.71-7.64 (m, 3H), 7.52-7.43 (m, 3H), 7.40 (br s, 1H), 7.27-7.21 (m, 2H), 4.06 (dd, J=8.7, 3.3, 1H), 3.62 (ddd, J=10.1, 6.8, 3.4, 1H), 3.19 (dt, J=15.6, 7.7, 1H), 2.19-2.06 (m, 1H), 1.79 (d, J=9.1, 6H), 1.74-1.58 (m, 3H).

Example 118

(2S)-1-(5-Chloro-thiophene-2-sulfonyl)-pyrrolidine-2-carboxylic acid [1-methyl-1-(4'-trifluoromethyl-biphenyl-3-yl)ethyl]-amide

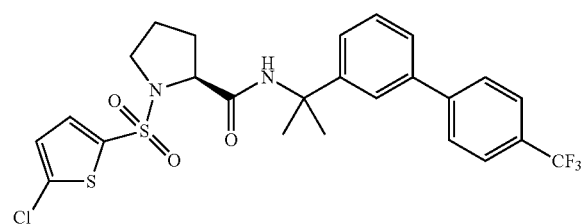 [SMILES: CC(C)(NC(=O)[C@@H]1CCCN1S(=O)(=O)c1ccc(Cl)s1)c1cccc(-c2ccc(C(F)(F)F)cc2)c1]

MS (ESI): mass calcd. for $C_{25}H_{24}ClF_3N_2O_3S_2$, 556.0; m/z found, 557.1 [M+H]$^+$. $^1$H NMR (400 MHz, CDCl$_3$) δ 7.77-7.64 (m, 5H), 7.51-7.41 (m, 4H), 7.32 (s, 1H), 7.03 (d, J=4.0, 1H), 4.10-4.03 (m, 1H), 3.70-3.61 (m, 1H), 3.32-3.20 (m, 1H), 2.28-2.14 (m, 1H), 1.90-1.70 (m, 9H).

Example 119

(2S)-4,4-Difluoro-1-(4-fluoro-benzenesulfonyl)-pyrrolidine-2-carboxylic acid (4'-trifluoromethyl-biphenyl-3-ylmethyl)-amide

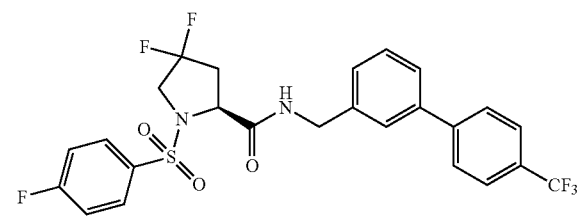 [SMILES: O=C(NCc1cccc(-c2ccc(C(F)(F)F)cc2)c1)[C@@H]1CC(F)(F)CN1S(=O)(=O)c1ccc(F)cc1]

To a solution of (2S)-4,4-difluoro-pyrrolidine-2-carboxylic acid (4'-trifluoromethyl-biphenyl-3-ylmethyl)-amide hydrochloride (149 mg, 0.38 mmol), Et$_3$N (0.1 mL, 0.76 mmol), and CH$_2$Cl$_2$ (2 mL) was added 4-fluoro-benzenesulfonyl chloride (75 mg, 0.38 mmol). After 1 h, the resulting mixture was concentrated, re-dissolved in MeOH (2 mL), and purified by preparative reverse-phase HPLC to afford (135 mg, 66%) of a white solid. MS (ESI): mass calcd. for $C_{25}H_{20}F_6N_2O_3S$, 542.1; m/z found, 543.1 [M+H]$^+$. $^1$H NMR (500 MHz, CDCl$_3$) δ 7.92-7.85 (m, 2H), 7.70 (q, J=8.6, 4H), 7.59-7.51 (m, 2H), 7.47 (t, J=7.6, 1H), 7.37-7.26 (m, 3H), 4.62 (qd, J=15.2, 6.0, 2H), 4.38 (dd, J=10.0, 4.4, 1H), 3.80 (dd, J=23.2, 11.5, 1H), 3.63 (dd, J=24.2, 11.6, 1H), 2.73 (d, J=12.1, 1H), 2.42-2.22 (m, 1H).

Examples 120 to 170 were prepared using methods analogous to those described for example 65 substituting the appropriate sulfonyl chloride to provide the desired product.

Example 120

(2S)-1-(5-Chloro-thiophene-2-sulfonyl)-4,4-difluoro-pyrrolidine-2-carboxylic acid (4'-trifluoromethyl-biphenyl-3-ylmethyl)-amide

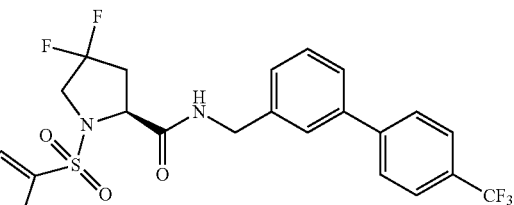

MS (ESI): mass calcd. for $C_{23}H_{18}ClF_5N_2O_3S_2$, 564.0; m/z found, 565.1 [M+H]$^+$. $^1$H NMR (500 MHz, CDCl$_3$) δ 7.75-7.66 (m, 4H), 7.57-7.51 (m, 2H), 7.50-7.44 (m, 2H), 7.33 (d, J=7.5, 1H), 7.22 (app s, 1H), 7.06 (d, J=4.0, 1H), 4.71-4.53 (m, 2H), 4.40 (dd, J=10.0, 4.0, 1H), 3.83 (app q, J=11.3, 1H), 3.67 (dd, J=25.8, 11.5, 1H), 2.89-2.77 (m, 1H), 2.49-2.36 (m, 1H).

Example 121

(2S,4S)-1-(4-Fluoro-benzenesulfonyl)-4-hydroxy-pyrrolidine-2-carboxylic acid (4'-trifluoromethyl-biphenyl-3-ylmethyl)-amide

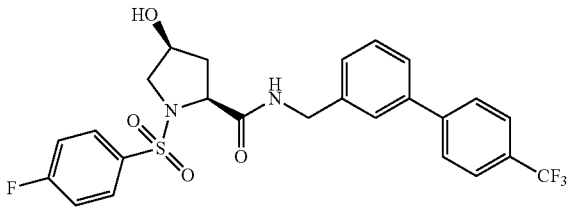 [SMILES: O=C(NCc1cccc(-c2ccc(C(F)(F)F)cc2)c1)[C@@H]1C[C@H](O)CN1S(=O)(=O)c1ccc(F)cc1]

MS (ESI): mass calcd. for $C_{25}H_{22}ClF_4N_2O_4S$, 522.1; m/z found, 523.1 [M+H]$^+$. $^1$H NMR (400 MHz, CD$_3$OD) δ 8.63-8.53 (m, 1H), 7.95 (dd, J=9.0, 5.1, 2H), 7.86 (d, J=8.1, 2H). 7.77-7.65 (m, 3H), 7.58 (d, J=7.4, 1H), 7.49-7.29 (m, 4H), 4.58-4.51 (m, 2H), 4.26-4.16 (m, 2H), 3.55-3.46 (m, 1H), 3.31-3.29 (m, 1H), 2.12-1.97 (m, 2H).

Example 122

(2S,4R)-1-(4-Fluoro-benzenesulfonyl)-4-hydroxy-pyrrolidine-2-carboxylic acid (4'-trifluoromethyl-biphenyl-3-ylmethyl)-amide

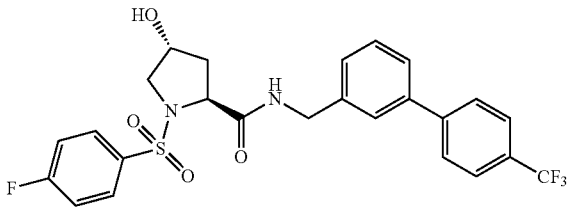 [SMILES: O=C(NCc1cccc(-c2ccc(C(F)(F)F)cc2)c1)[C@@H]1C[C@@H](O)CN1S(=O)(=O)c1ccc(F)cc1]

MS (ESI): mass calcd. for $C_{25}H_{22}ClF_4N_2O_4S$, 522.1; m/z found, 523.1 [M+H]$^+$. $^1$H NMR (400 MHz, CD$_3$OD) δ 8.85-8.77 (m, 1H), 7.98-7.88 (m, 2H), 7.86 (d, J=8.1, 2H), 7.76-7.65 (m, 3H), 7.58 (d, J=7.6, 1H), 7.49-7.36 (m, 2H), 7.28 (dd, J=12.2, 5.4, 2H), 4.51 (app br s, 2H), 4.30 (app br s, 1H), 4.23 (t, J=8.0, 1H), 3.66 (dd, J=11.4, 3.8, 1H), 3.37-3.32 (m, 1H), 2.15-1.96 (m, 2H).

Example 123

1-(4-Fluoro-benzenesulfonyl)-pyrrolidine-2S-carboxylic acid [2-(4-trifluoromethyl-phenyl)-pyridin-4-ylmethyl]-amide

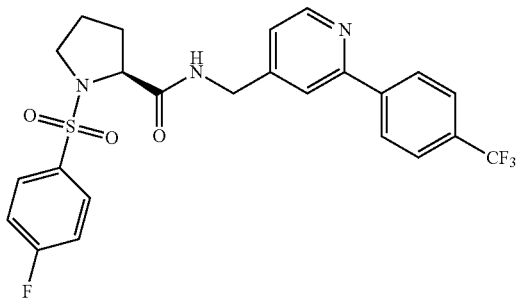 [SMILES: O=C(NCc1ccnc(-c2ccc(C(F)(F)F)cc2)c1)[C@@H]1CCCN1S(=O)(=O)c1ccc(F)cc1]

$^1$H NMR (360 MHz, DMSO-d$_6$) δ 1.48-1.60 (m, 1H), 1.75-1.89 (m, 3H), 3.15-3.25 (m, 1H), 3.46-3.54 (m, 1H), 4.07-4.14 (m, 1H), 4.41 (dd, J=16.5, 5.9 Hz, 1H), 4.49 (dd, J=16.5, 6.2 Hz, 1H), 7.35 (d, J=5.0 Hz, 1H), 7.50 (t, J=8.8 Hz, 2H), 7.84 (d, J=8.2 Hz, 2H), 8.00 (dd, J=8.8, 5.2 Hz, 2H), 8.00 (s, 1H), 8.32 (d, J=8.2 Hz, 2H), 8.65 (d, J=5.0 Hz, 1H), 8.83 (t, J=6.0 Hz, 1H).

Example 124

1-(5-Chlorothiophene-2-sulfonyl)pyrrolidine-2S-carboxylic acid [2-(4-trifluoromethylphenyl)-pyridin-4-ylmethyl]-amide

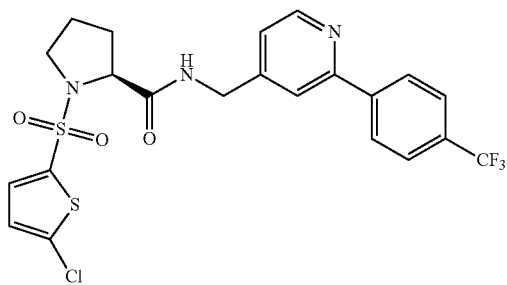 [SMILES: O=C(NCc1ccnc(-c2ccc(C(F)(F)F)cc2)c1)[C@@H]1CCCN1S(=O)(=O)c1ccc(Cl)s1]

MS (ESI): mass calcd. for $C_{22}H_{19}ClF_3N_3O_3S_2$, 529.99; m/z found 530.1 [M$^+$]. $^1$H NMR (400 MHz, DMSO) δ 8.86 (t, J=6.1, 1H), 8.68 (d, J=5.1, 1H), 8.29 (d, J=8.3, 2H), 8.00 (s, 1H), 7.87 (d, J=8.5, 2H), 7.73 (d, J=4.1, 1H), 7.44-7.36 (m, 2H), 4.52 (dd, J=16.6, 6.2, 1H), 4.43 (dd, J=16.6, 5.8, 1H), 4.18-4.09 (m, 1H), 3.62-3.51 (m, 1H), 3.33-3.21 (m, 1H), 2.00-1.82 (m, 3H), 1.73-1.58 (m, 1H).

Example 125

4,4-Difluoro-1-(4-fluorobenzenesulfonyl)-pyrrolidine-2S-carboxylic acid [2-(4-trifluoromethylphenyl)-pyridin-4-ylmethyl]-amide

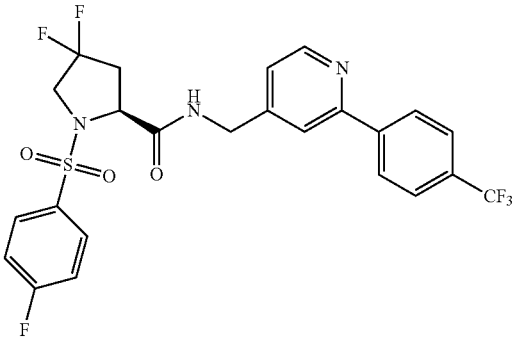 [SMILES: O=C(NCc1ccnc(-c2ccc(C(F)(F)F)cc2)c1)[C@@H]1CC(F)(F)CN1S(=O)(=O)c1ccc(F)cc1]

MS (ESI): mass calcd. for $C_{24}H_{19}F_6N_3O_3S$, 543.49; m/z found 544.1 [M+H]$^+$. $^1$H NMR (500 MHz, DMSO) δ 9.03 (s, 1H), 8.68 (s, 1H), 8.30 (d, J=8.2, 2H), 8.11-8.00 (m, 3H), 7.84 (d, J=8.5, 2H), 7.56-7.47 (m, 2H), 7.43-7.36 (m, 1H), 4.55-4.44 (m, 2H), 4.44-4.36 (m, 1H), 3.96-3.85 (m, 1H), 2.72-2.57 (m, 1H), 2.48-2.34 (m, 2H).

Example 126

1-(5-Chlorothiophene-2-sulfonyl)-4,4-difluoropyrrolidine-2S-carboxylic acid [2-(4-trifluoromethylphenyl)-pyridin-4-ylmethyl]-amide

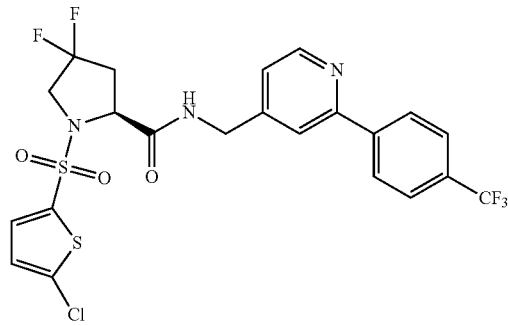 [SMILES: O=C(NCc1ccnc(-c2ccc(C(F)(F)F)cc2)c1)[C@@H]1CC(F)(F)CN1S(=O)(=O)c1ccc(Cl)s1]

MS (ESI): mass calcd. for $C_{22}H_{17}ClF_5N_3O_3S_2$, 565.97; m/z found 566.0 [M$^+$]. $^1$H NMR (500 MHz, DMSO) δ 9.04 (s, 1H), 8.67 (d, J=5.0, 1H), 8.29 (d, J=7.9, 2H), 7.99 (s, 1H), 7.86 (d, J=8.1, 2H), 7.83 (d, J=4.1, 1H), 7.43 (d, J=4.1, 1H), 7.36 (s, 1H), 4.48 (d, J=5.8, 2H), 4.44-4.35 (m, 1H), 4.06-3.94 (m, 2H), 2.80-2.69 (m, 1H), 2.57-2.43 (m, 1H).

Example 127

1-(4-Fluorobenzenesulfonyl)-2,5-dihydro-1H-pyrrole-2S-carboxylic acid [2-(4-trifluoromethylphenyl)-pyridin-4-ylmethyl]-amide

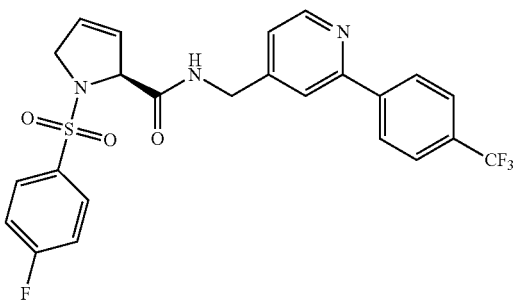 [SMILES: O=C(NCc1ccnc(-c2ccc(C(F)(F)F)cc2)c1)[C@@H]1C=CCN1S(=O)(=O)c1ccc(F)cc1]

MS (ESI): mass calcd. for $C_{24}H_{19}ClF_4N_3O_3S$, 505.49; m/z found 506.1, [M+H]$^+$. $^1$H NMR (600 MHz, DMSO) δ 8.91 (t, J=6.1, 1H), 8.67 (d, J=5.0, 1H), 8.30 (d, J=8.1, 2H), 8.02-7.97 (m, 3H), 7.85 (d, J=8.3, 2H), 7.49 (t, J=8.8, 2H), 7.38 (d, J=5.1, 1H), 5.96-5.88 (m, 1H), 5.76-5.71 (m, 1H), 4.91 (dd, J=5.8, 2.3, 1H), 4.52 (dd, J=16.6, 6.3, 1H), 4.42 (dd, J=16.6, 5.9, 1H), 4.33-4.25 (m, 1H), 4.19-4.11 (m, 1H).

Example 128

1-(5-Chlorothiophene-2-sulfonyl)-2,5-dihydro-1H-pyrrole-2S-carboxylic acid [2-(4-trifluoromethylphenyl)-pyridin-4-ylmethyl]-amide

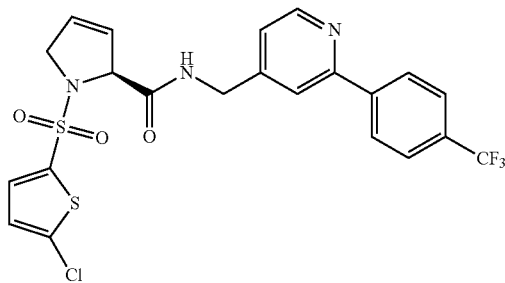 [SMILES: O=C(NCc1ccnc(-c2ccc(C(F)(F)F)cc2)c1)[C@@H]1C=CCN1S(=O)(=O)c1ccc(Cl)s1]

MS (ESI): mass calcd. for $C_{22}H_{17}ClF_3N_3O_3S_2$, 527.98; m/z found 528.1 [M$^+$]. $^1$H NMR (600 MHz, DMSO) δ 8.94 (t, J=6.1, 1H), 8.67 (d, J=5.1, 1H), 8.29 (d, J=8.1, 2H), 7.97 (s, 1H), 7.87 (d, J=8.3, 2H), 7.75 (d, J=4.1, 1H), 7.39 (d, J=4.1, 1H), 7.37 (d, J=5.1, 1H), 5.99-5.96 (m, 1H), 5.81-5.78 (m, 1H), 4.92 (dd, J=5.6, 2.3, 1H), 4.53 (dd, J=16.5, 6.3, 1H), 4.41 (dd, J=16.5, 5.9, 1H), 4.38-4.32 (m, 1H), 4.22-4.17 (m, 1H).

Example 129

1-(4-Fluoro-benzenesulfonyl)-pyrrolidine-2S-carboxylic acid [2-(4-trifluoromethoxy-phenyl)-pyridin-4-ylmethyl]-amide

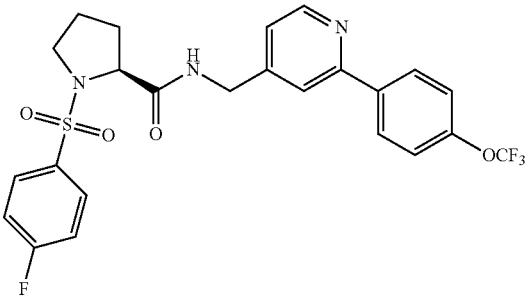

MS (ESI): mass calcd. for $C_{24}H_{21}F_4N_3O_4S$, 523.50; m/z found 524.2, [M+H]$^+$. $^1$H NMR (400 MHz, DMSO) δ 8.82 (t, J=6.1, 1H), 8.64 (d, J=5.3, 1H), 8.25-8.17 (m, 2H), 8.04-7.96 (m, 2H), 7.95 (s, 1H), 7.54-7.45 (m, 4H), 7.36 (d, J=4.1, 1H), 4.49 (dd, J=16.6, 6.2, 1H), 4.42 (dd, J=16.6, 6.0, 1H), 4.10 (t, J=6.1, 1H), 3.51-3.36 (m, 1H), 3.27-3.13 (m, 1H), 1.92-1.73 (m, 3H), 1.62-1.47 (m, 1H).

Example 130

1-(5-Chloro-thiophene-2-sulfonyl)-pyrrolidine-2S-carboxylic acid [2-(4-trifluoromethoxy-phenyl)-pyridin-4-ylmethyl]-amide

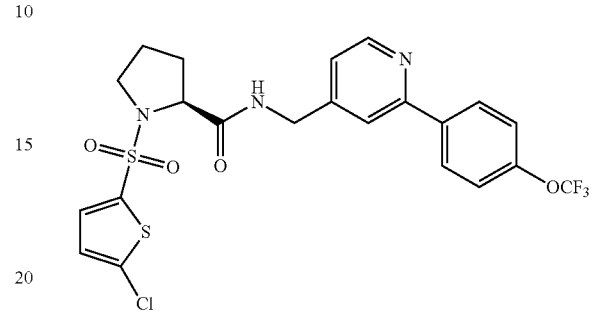

MS (ESI): mass calcd. for $C_{22}H_{19}ClF_3N_3O_4S_2$, 523.50; m/z found 524.2, [M+H]$^+$. $^1$H NMR (400 MHz, DMSO) δ 8.84 (t, J=6.1, 1H), 8.63 (d, J=5.1, 1H), 8.23-8.13 (m, 2H), 7.91 (s, 1H), 7.72 (d, J=4.1, 1H), 7.49 (d, J=8.0, 2H), 7.39 (d, J=4.1, 1H), 7.32 (d, J=3.8, 1H), 4.49 (dd, J=16.5, 6.3, 1H), 4.40 (dd, J=16.5, 5.9, 1H), 4.16-4.09 (m, 1H), 3.61-3.51 (m, 1H), 3.32-3.22 (m, 1H), 1.99-1.81 (m, 3H), 1.72-1.58 (m, 1H).

Example 131

4,4-Difluoro-1-(4-fluoro-benzenesulfonyl)-pyrrolidine-2S-carboxylic acid [2-(4-trifluoromethoxy-phenyl)-pyridin-4-ylmethyl]-amide

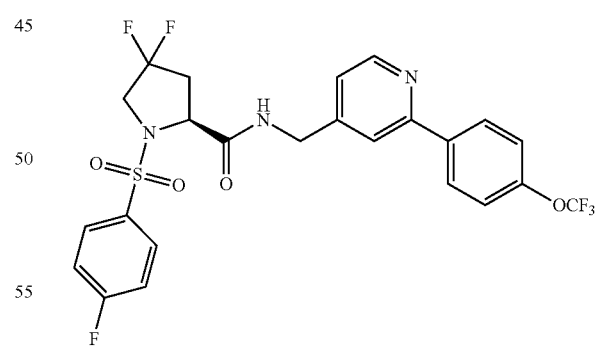

MS (ESI): mass calcd. for $C_{24}H_{19}F_6N_3O_4S$, 559.48; m/z found 560.1, [M+H]$^+$. $^1$H NMR (400 MHz, DMSO) δ 9.04 (t, J=6.0, 1H), 8.65 (d, J=5.2, 1H), 8.25-8.15 (m, 2H), 8.11-8.01 (m, 2H), 7.97 (s, 1H), 7.57-7.43 (m, 4H), 7.41-7.34 (m, 1H), 4.54-4.42 (m, 2H), 4.38 (dd, J=8.5, 7.1, 1H), 3.94-3.81 (m, 1H), 3.75-3.61 (m, 1H), 2.73-2.53 (m, 1H), 2.50-2.34 (m, 1H).

Example 132

1-(5-Chloro-thiophene-2-sulfonyl)-4,4-difluoro-pyrrolidine-2S-carboxylic acid [2-(4-trifluoromethoxyphenyl)-pyridin-4-ylmethyl]-amide

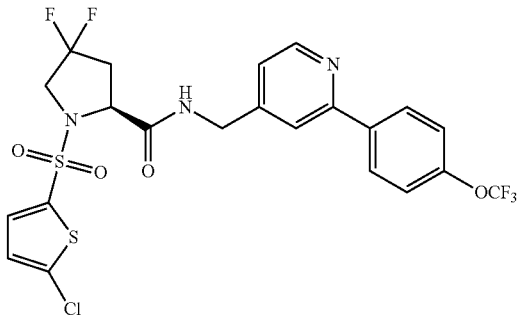 [SMILES: O=C(NCc1ccnc(-c2ccc(OC(F)(F)F)cc2)c1)[C@@H]1CC(F)(F)CN1S(=O)(=O)c1ccc(Cl)s1]

MS (ESI): mass calcd. for $C_{22}H_{17}ClF_5N_3O_4S_2$, 581.96; m/z found 582.2, [M+H]$^+$. $^1$H NMR (400 MHz, DMSO) δ 9.03 (t, J=6.0, 1H), 8.63 (d, J=5.6, 1H), 8.25-8.12 (m, 2H), 7.92 (s, 1H), 7.83 (d, J=4.1, 1H), 7.54-7.46 (m, 2H), 7.43 (d, J=4.2, 1H), 7.37-7.30 (m, 1H), 4.51-4.43 (m, 2H), 4.40 (dd, J=8.6, 7.0, 1H), 4.05-3.80 (m, 2H), 2.86-2.64 (m, 1H), 2.59-2.39 (m, 1H).

Example 133

1-(4-Fluoro-benzenesulfonyl)-2,5-dihydro-1H-pyrrole-2S-carboxylic acid [2-(4-trifluoromethoxy-phenyl)-pyridin-4-ylmethyl]-amide

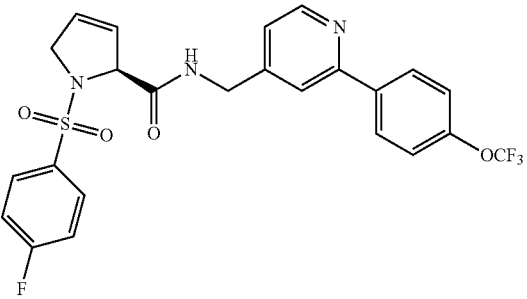 [SMILES: O=C(NCc1ccnc(-c2ccc(OC(F)(F)F)cc2)c1)[C@@H]1C=CCN1S(=O)(=O)c1ccc(F)cc1]

MS (ESI): mass calcd. for $C_{24}H_{19}F_4N_3O_4S$, 521.49; m/z found 522.1, [M+H]$^+$. $^1$H NMR (400 MHz, DMSO) δ 8.92 (t, J=6.1, 1H), 8.64 (d, J=5.1, 1H), 8.25-8.16 (m, 2H), 8.04-7.96 (m, 2H), 7.94 (s, 1H), 7.54-7.44 (m, 4H), 7.36 (d, J=5.1, 1H), 5.95-5.90 (m, 1H), 5.78-5.70 (m, 1H), 4.90 (dd, J=5.7, 2.3, 1H), 4.51 (dd, J=16.7, 6.3, 1H), 4.41 (dd, J=16.6, 5.9, 1H), 4.35-4.24 (m, 1H), 4.20-4.08 (m, 1H).

Example 134

1-(5-Chloro-thiophene-2-sulfonyl)-2,5-dihydro-1H-pyrrole-2S-carboxylic acid [2-(4-trifluoromethoxyphenyl)-pyridin-4-ylmethyl]-amide

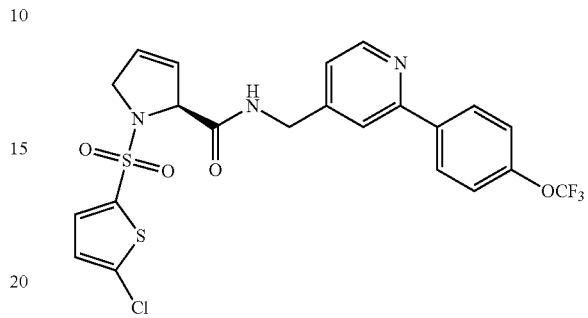

MS (ESI): mass calcd. for $C_{22}H_{17}ClF_3N_3O_4S_2$, 543.97; m/z found 544.1, [M+H]$^+$. $^1$H NMR (400 MHz, DMSO) δ 8.95 (t, J=6.1, 1H), 8.64 (d, J=5.1, 1H), 8.23-8.15 (m, 2H), 7.91 (s, 1H), 7.75 (d, J=4.1, 1H), 7.56-7.47 (m, 2H), 7.39 (d, J=4.1, 1H), 7.36-7.31 (m, 1H), 6.02-5.93 (m, 1H), 5.85-5.75 (m, 1H), 4.91 (dd, J=5.6, 2.3, 1H), 4.52 (dd, J=16.6, 6.3, 1H), 4.39 (dd, J=17.4, 5.8, 1H), 4.37-4.30 (m, 1H), 4.23-4.14 (m, 1H).

Example 135

1-(4-Fluoro-benzenesulfonyl)-pyrrolidine-2S-carboxylic acid [4-(4-trifluoromethyl-phenyl)-pyridin-2-ylmethyl]-amide MS (ESI): mass calcd. for $C_{24}H_{21}F_4N_3O_3S$, 507.50; m/z found 508.2, [M+H]$^+$. $^1$H NMR (600 MHz, DMSO) δ 8.88-8.80 (m, 1H), 8.70 (d, J=5.2, 1H), 8.05 (d, J=8.1, 2H), 8.01-7.96 (m, 2H), 7.87 (d, J=8.3, 2H), 7.84 (s, 1H), 7.80 (d, J=5.3, 1H), 7.52-7.45 (m, 2H), 4.61-4.55 (m, 1H), 4.54-4.47 (m, 1H), 4.17-4.11 (m, 1H), 3.52-3.44 (m, 1H), 3.24-3.15 (m, 1H), 1.90-1.78 (m, 3H), 1.60-1.49 (m, 1H).

Example 136

1-(5-Chloro-thiophene-2-sulfonyl)-pyrrolidine-2S-carboxylic acid [4-(4-trifluoromethyl-phenyl)-pyridin-2-ylmethyl]-amide

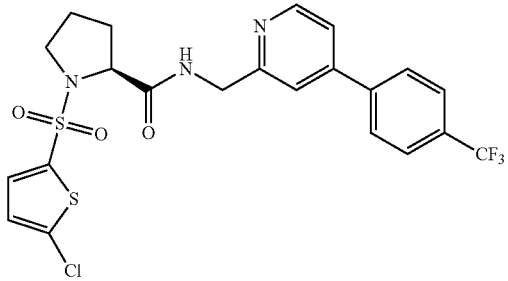

MS (ESI): mass calcd. for $C_{22}H_{19}ClF_3N_3O_3S_2$, 529.99; m/z found 530.1 [M+]. $^1$H NMR (600 MHz, DMSO) δ 8.90-8.81 (m, 1H), 8.70 (d, J=6.0, 1H), 8.04 (d, J=8.2, 2H), 7.88 (d, J=8.2, 2H), 7.82-7.78 (m, 2H), 7.72 (d, J=4.1, 1H), 7.38 (d, J=4.1, 1H), 4.58 (dd, J=16.4, 6.2, 1H), 4.49 (dd, J=16.4, 5.8, 1H), 4.19-4.11 (m, 1H), 3.59-3.50 (m, 2H), 3.32-3.20 (m, 1H), 1.99-1.83 (m, 3H), 1.74-1.55 (m, 1H).

Example 137

1-(4-Fluoro-benzenesulfonyl)-pyrrolidine-2S-carboxylic acid [4-(4-trifluoromethoxy-phenyl)-pyridin-2-ylmethyl]-amide

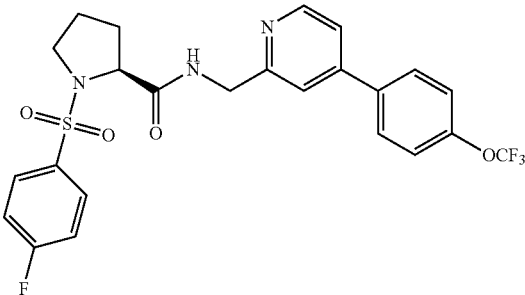

MS (ESI): mass calcd. for $C_{24}H_{21}F_4N_3O_4S$, 523.51; m/z found 524.1 [M+H]+. $^1$H NMR (600 MHz, DMSO) δ 8.85 (t, J=6.0, 1H), 8.70 (d, J=5.4, 1H), 8.02-7.95 (m, 4H), 7.85 (s, 1H), 7.84-7.79 (m, 1H), 7.54-7.44 (m, 4H), 4.58 (dd, J=16.4, 6.1, 1H), 4.51 (dd, J=16.4, 5.8, 1H), 4.16-4.11 (m, 1H), 3.56-3.41 (m, 1H), 3.26-3.15 (m, 1H), 1.92-1.77 (m, 3H), 1.61-1.49 (m, 1H).

Example 138

1-(5-Chloro-thiophene-2-sulfonyl)-pyrrolidine-2S-carboxylic acid [4-(4-trifluoromethoxy-phenyl)-pyridin-2-ylmethyl]-amide

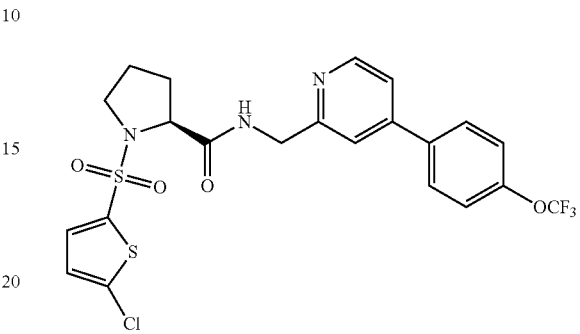

MS (ESI): mass calcd. for $C_{22}H_{19}ClF_3N_3O_4S_2$, 545.99; m/z found 546.1 [M+H]+. $^1$H NMR (600 MHz, DMSO) δ 8.86 (t, J=6.0, 1H), 8.69 (d, J=5.4, 1H), 7.97 (d, J=8.9, 2H), 7.83-7.76 (m, 2H), 7.71 (d, J=4.1, 1H), 7.52 (d, J=8.0, 2H), 7.38 (d, J=4.1, 1H), 4.58 (dd, J=16.4, 6.2, 1H), 4.49 (dd, J=16.4, 5.8, 1H), 4.19-4.12 (m, 1H), 3.59-3.46 (m, 1H), 3.31-3.19 (m, 1H), 1.98-1.80 (m, 3H), 1.71-1.58 (m, 1H).

Example 139

4,4-Difluoro-1-(4-fluoro-benzenesulfonyl)-pyrrolidine-2S-carboxylic acid [4-(4-trifluoromethyl-phenyl)-pyridin-2-ylmethyl]-amide

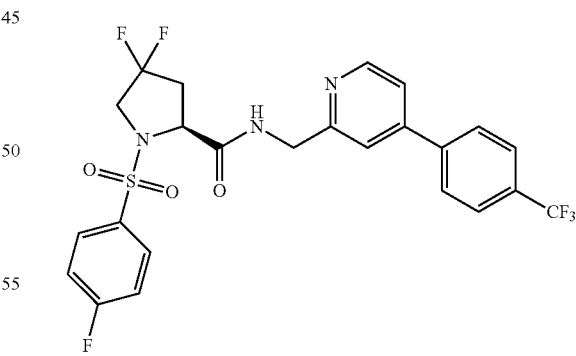

MS (ESI): mass calcd. for $C_{24}H_{19}F_6N_3O_3S$, 543.49; m/z found 544.1 [M+H]+. $^1$H NMR (600 MHz, DMSO) δ 9.03 (t, J=5.9, 1H), 8.68 (d, J=5.3, 1H), 8.07-8.00 (m, 4H), 7.85 (d, J=8.2, 2H), 7.81 (s, 1H), 7.76 (d, J=5.3, 1H), 7.53-7.45 (m, 2H), 4.60-4.48 (m, 2H), 4.43 (dd, J=8.6, 7.0, 1H), 3.93-3.80 (m, 2H), 2.68-2.54 (m, 1H), 2.50-2.35 (m, 1H).

Example 140

1-(5-Chloro-thiophene-2-sulfonyl)-4,4-difluoro-pyrrolidine-2S-carboxylic acid [4-(4-trifluoromethyl-phenyl)-pyridin-2-ylmethyl]-amide

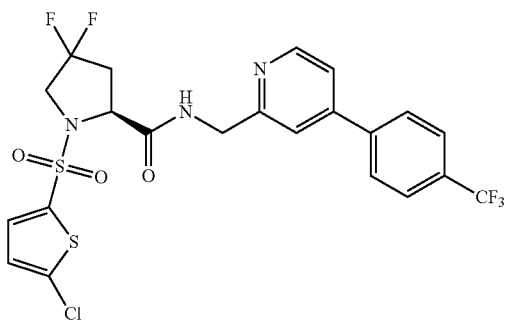 [SMILES: O=C(NCc1cc(-c2ccc(C(F)(F)F)cc2)ccn1)[C@@H]1CC(F)(F)CN1S(=O)(=O)c1ccc(Cl)s1]

MS (ESI): mass calcd. for $C_{22}H_{17}ClF_5N_3O_3S_2$, 565.97; m/z found 566.1 [M+H]$^+$. $^1$H NMR (600 MHz, DMSO) δ 9.06 (t, J=5.9, 1H), 8.70 (d, J=6.2, 1H), 8.03 (d, J=8.2, 2H), 7.88 (d, J=8.2, 2H), 7.84-7.75 (m, 3H), 7.41 (d, J=4.1, 1H), 4.58-4.53 (m, J=5.9, 2H), 4.44 (dd, J=8.7, 7.0, 1H), 3.98-3.84 (m, 2H), 2.81-2.70 (m, 1H), 2.56-2.44 (m, 1H).

Example 141

4,4-Difluoro-1-(4-fluoro-benzenesulfonyl)-pyrrolidine-2S-carboxylic acid [4-(4-trifluoromethoxy-phenyl)-pyridin-2-ylmethyl]-amide

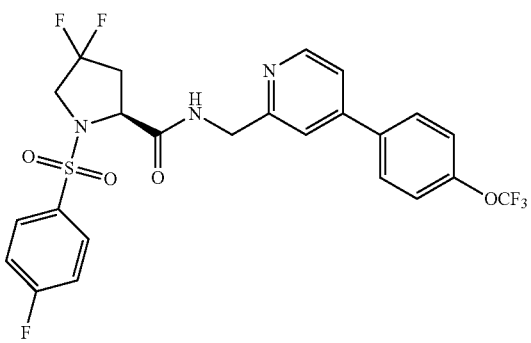 [SMILES: O=C(NCc1cc(-c2ccc(OC(F)(F)F)cc2)ccn1)[C@@H]1CC(F)(F)CN1S(=O)(=O)c1ccc(F)cc1]

MS (ESI): mass calcd. for $C_{24}H_{19}F_6N_3O_4S$, 559.49; m/z found 560.1 [M+H]$^+$. $^1$H NMR (600 MHz, DMSO) δ 9.04 (t, J=5.9, 1H), 8.68 (d, J=5.4, 1H), 8.06-8.01 (m, 2H), 7.98-7.94 (m, 2H), 7.81 (s, 1H), 7.79-7.75 (m, 1H), 7.53-7.45 (m, 4H), 4.59-4.49 (m, 2H), 4.46-4.39 (m, 1H), 3.97-3.78 (m, 2H), 2.75-2.55 (m, 1H), 2.52-2.38 (m, 1H).

Example 142

1-(5-Chloro-thiophene-2-sulfonyl)-4,4-difluoro-pyrrolidine-2S-carboxylic acid [4-(4-trifluoromethoxy-phenyl)-pyridin-2-ylmethyl]-amide

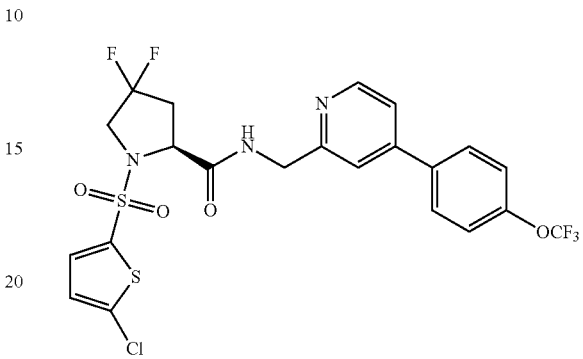

MS (ESI): mass calcd. for $C_{22}H_{17}ClF_5N_3O_4S_2$, 581.97; m/z found 582.1 [M+H]$^+$. $^1$H NMR (600 MHz, DMSO) δ 9.03 (t, J=5.9, 1H), 8.66 (d, J=6.1, 1H), 7.98-7.91 (m, 2H), 7.81 (d, J=4.1, 1H), 7.78-7.73 (m, 2H), 7.52 (d, J=8.1, 2H), 7.41 (d, J=4.1, 1H), 4.59-4.49 (m, J=5.9, 2H), 4.48-4.39 (m, 1H), 4.02-3.83 (m, 2H), 2.82-2.67 (m, 1H), 2.55-2.44 (m, 1H).

Example 143

1-(4-Fluoro-benzenesulfonyl)-2,5-dihydro-1H-pyrrole-2S-carboxylic acid [4-(4-trifluoromethyl-phenyl)-pyridin-2-ylmethyl]-amide

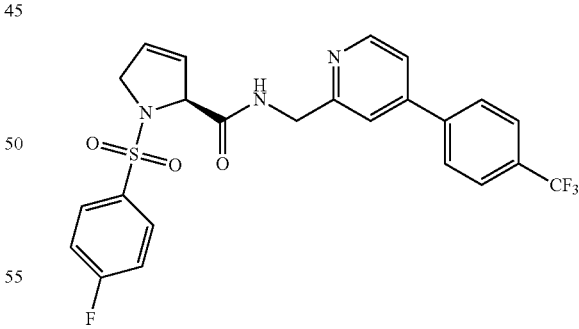

MS (ESI): mass calcd. for $C_{24}H_{19}F_4N_3O_3S$, 505.49; m/z found 506.1 [M+H]$^+$. $^1$H NMR (600 MHz, DMSO) δ 8.95 (t, J=6.0, 1H), 8.70 (d, J=5.9, 1H), 8.05 (d, J=8.2, 2H), 8.02-7.97 (m, 2H), 7.88 (d, J=8.2, 2H), 7.83-7.77 (m, 2H), 7.51-7.44 (m, 2H), 5.95-5.91 (m, 1H), 5.76-5.72 (m, 1H), 4.97-4.92 (m, 1H), 4.59 (dd, J=16.4, 6.3, 1H), 4.48 (dd, J=16.4, 5.8, 1H), 4.34-4.24 (m, 1H), 4.18-4.10 (m, 1H).

Example 144

1-(5-Chloro-thiophene-2-sulfonyl)-2,5-dihydro-1H-pyrrole-2S-carboxylic acid [4-(4-trifluoromethyl-phenyl)-pyridin-2-ylmethyl]-amide

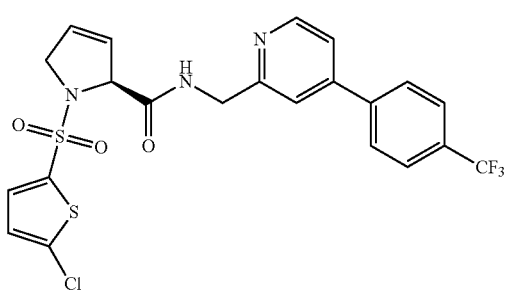 [SMILES: O=C(NCc1cc(-c2ccc(C(F)(F)F)cc2)ccn1)[C@@H]1C=CCN1S(=O)(=O)c1ccc(Cl)s1]

MS (ESI): mass calcd. for $C_{22}H_{17}ClF_3N_3O_3S_2$, 527.98; m/z found 528.1 [M+H]$^+$. $^1$H NMR (600 MHz, DMSO) δ 8.98 (t, J=6.0, 1H), 8.70 (d, J=5.4, 1H), 8.03 (d, J=8.2, 2H), 7.89 (d, J=8.2, 2H), 7.80 (d, J=5.3, 1H), 7.76 (s, 1H), 7.75 (d, J=4.1, 1H), 7.38 (d, J=4.1, 1H), 6.00-5.94 (m, 1H), 5.81-5.76 (m, 1H), 4.97-4.94 (m, 1H), 4.59 (dd, J=16.4, 6.3, 1H), 4.47 (dd, J=16.4, 5.7, 1H), 4.39-4.29 (m, 1H), 4.23-4.16 (m, 2H).

Example 145

1-(4-Fluoro-benzenesulfonyl)-2,5-dihydro-1H-pyrrole-2S-carboxylic acid [4-(4-trifluoromethoxy-phenyl)-pyridin-2-ylmethyl]-amide

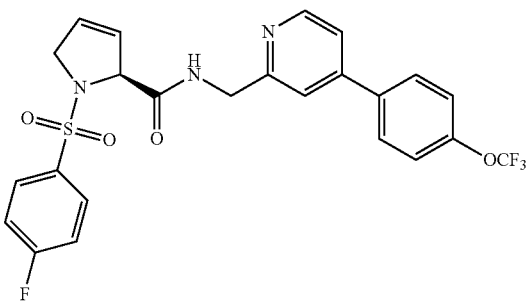 [SMILES: O=C(NCc1cc(-c2ccc(OC(F)(F)F)cc2)ccn1)[C@@H]1C=CCN1S(=O)(=O)c1ccc(F)cc1]

MS (ESI): mass calcd. for $C_{24}H_{19}F_4N_3O_4S$, 521.49; m/z found 522.1 [M+H]$^+$. $^1$H NMR (600 MHz, DMSO) δ 8.94 (t, J=6.0, 1H), 8.72-8.65 (m, 1H), 8.02-7.95 (m, 4H), 7.83-7.76 (m, 2H), 7.56-7.44 (m, 4H), 5.95-5.90 (m, 1H), 5.77-5.68 (m, 1H), 4.97-4.87 (m, 1H), 4.59 (dd, J=16.4, 6.2, 1H), 4.48 (dd, J=16.4, 5.8, 1H), 4.32-4.25 (m, 1H), 4.19-4.11 (m, 1H).

Example 146

1-(5-Chloro-thiophene-2-sulfonyl)-2,5-dihydro-1H-pyrrole-2S-carboxylic acid [4-(4-trifluoromethoxy-phenyl)-pyridin-2-ylmethyl]-amide

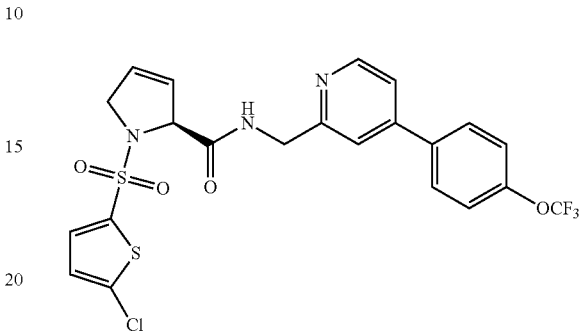

MS (ESI): mass calcd. for $C_{22}H_{17}ClF_3N_3O_4S_2$, 543.97; m/z found 544.1 [M+H]$^+$. $^1$H NMR (600 MHz, DMSO) δ 8.97 (t, J=6.0, 1H), 8.68 (d, J=5.4, 1H), 8.00-7.92 (m, 2H), 7.78 (d, J=5.3, 1H), 7.74 (d, J=4.1, 2H), 7.53 (d, J=8.0, 2H), 7.38 (d, J=4.1, 1H), 6.01-5.93 (m, 1H), 5.84-5.71 (m, 1H), 4.96-4.85 (m, 1H), 4.59 (dd, J=16.4, 6.3, 1H), 4.47 (dd, J=16.4, 5.7, 1H), 4.37-4.28 (m, 1H), 4.24-4.13 (m, 2H).

Example 147

1-(4-Bromobenzenesulfonyl)-pyrrolidine-2S-carboxylic acid [6-(4-trifluoromethylphenyl)-pyrimidin-4-ylmethyl]-amide

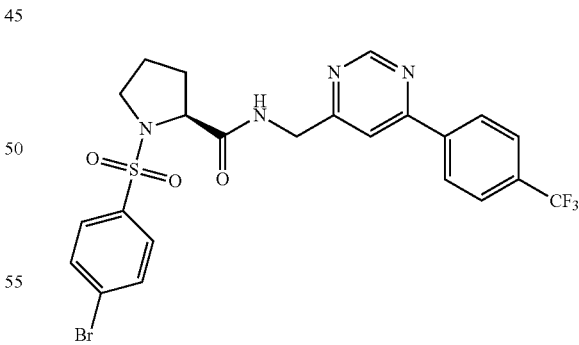

MS (ESI): Mass calcd. for $C_{23}H_{20}BrF_3N_4O_3S$, 569.40; m/z found 569.4 [M$^+$]. $^1$H NMR (400 MHz, CDCl3) δ 9.29 (s, 1H), 8.36 (d, J=8.2, 2H), 8.19 (s, 1H), 7.97 (bs, 1H), 7.85-7.66 (m, 6H), 5.11-4.88 (m, 1H), 4.83-4.52 (m, 1H), 4.26-4.06 (m, 1H), 3.79-3.59 (m, 1H), 3.32-2.96 (m, 1H), 2.24-2.03 (m, 1H), 2.01-1.79 (m, 2H), 1.76-1.58 (m, 1H).

Example 148

1-(3,4-Difluorobenzenesulfonyl)-pyrrolidine-2S-carboxylic acid [6-(4-trifluoromethylphenyl)-pyrimidin-4-ylmethyl]-amide

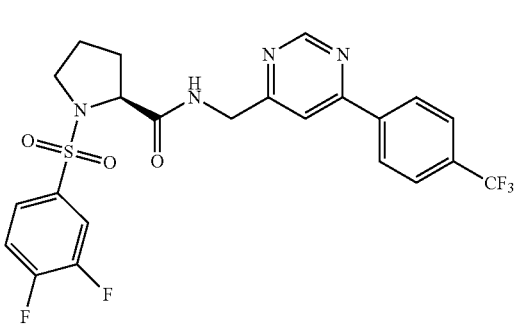 [SMILES: O=C(NCc1cc(-c2ccc(C(F)(F)F)cc2)ncn1)[C@@H]1CCCN1S(=O)(=O)c1ccc(F)c(F)c1]

MS (ESI): Mass calcd. for $C_{23}H_{19}F_5N_4O_3S$, 526.48; m/z found 527.5 [M+H]$^+$. $^1$H NMR (400 MHz, CDCl3) δ 9.31 (s, 1H), 8.37 (d, J=8.2, 2H), 8.24 (s, 1H), 8.13 (s, 1H), 7.81-7.68 (m, 4H), 7.45-7.31 (m, 1H), 5.12-4.94 (m, 1H), 4.88-4.68 (m, 1H), 4.25-4.12 (m, 1H), 3.74-3.63 (m, 1H), 3.25-3.08 (m, 1H), 2.23-2.10 (m, 1H), 2.05-1.83 (m, 2H), 1.78-1.62 (m, 1H).

Example 149

1-(4-Trifluoromethoxybenzenesulfonyl)-pyrrolidine-2S-carboxylic acid [6-(4-trifluoromethylphenyl)-pyrimidin-4-ylmethyl]-amide

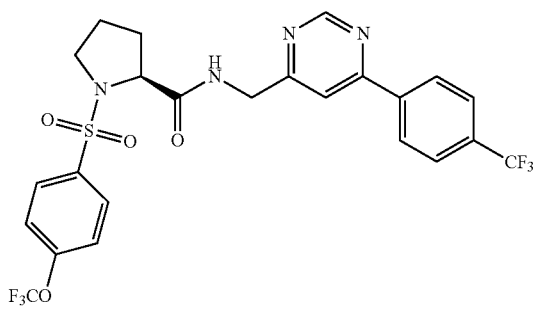 [SMILES: O=C(NCc1cc(-c2ccc(C(F)(F)F)cc2)ncn1)[C@@H]1CCCN1S(=O)(=O)c1ccc(OC(F)(F)F)cc1]

MS (ESI): Mass calcd. for $C_{24}H_{20}F_6N_4O_4S$, 574.5; m/z found 575.5 [M+H]$^+$. $^1$H NMR (400 MHz, CDCl3) δ 9.30 (s, 1H), 8.36 (d, J=8.2, 2H), 8.16 (s, 1H), 7.97 (d, J=8.8, 2H), 7.89 (bs, 1H), 7.77 (d, J=8.2, 2H), 7.41 (d, J=8.1, 2H), 5.10-4.91 (m, 1H), 4.82-4.53 (m, 1H), 4.28-4.09 (m, 1H), 3.81-3.59 (m, 1H), 3.30-3.10 (m, 1H), 2.23-2.06 (m, 1H), 2.00-1.80 (m, 2H), 1.79-1.63 (m, 1H).

Example 150

1-(4-Methoxybenzenesulfonyl)-pyrrolidine-2S-carboxylic acid [6-(4-trifluoromethylphenyl)-pyrimidin-4-ylmethyl]-amide

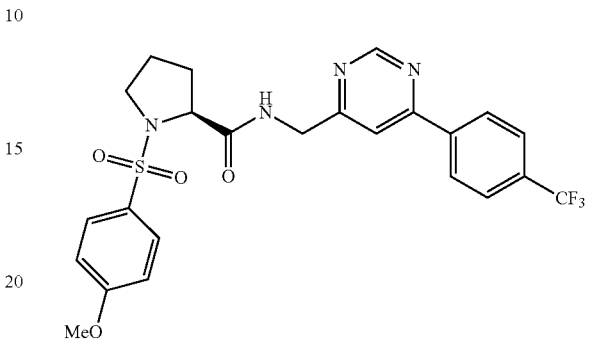

MS (ESI): Mass calcd. for $C_{24}H_{23}F_3N_4O_4S$, 520.53; m/z found 521.5 [M+H]$^+$. $^1$H NMR (400 MHz, CDCl3) δ 9.22 (d, J=1.3, 1H), 8.33 (d, J=8.1, 2H), 8.01 (s, 1H), 7.89-7.79 (m, 2H), 7.74 (d, J=8.2, 2H), 7.72-7.66 (m, 1H), 7.09-7.00 (m, 2H), 4.94 (dd, J=17.6, 7.5, 1H), 4.50 (dd, J=17.6, 5.0, 1H), 4.18 (dd, J=8.7, 3.4, 1H), 3.90 (s, 3H), 3.69-3.57 (m, 1H), 3.27-3.15 (m, 1H), 2.22-2.12 (m, 1H), 1.92-1.72 (m, 2H), 1.71-1.60 (m, 1H).

Example 151

1-(1,2-Dimethyl-1H-imidazole-4-sulfonyl)-pyrrolidine-2S-carboxylic acid [6-(4-trifluoromethylphenyl)-pyrimidin-4-ylmethyl]-amide

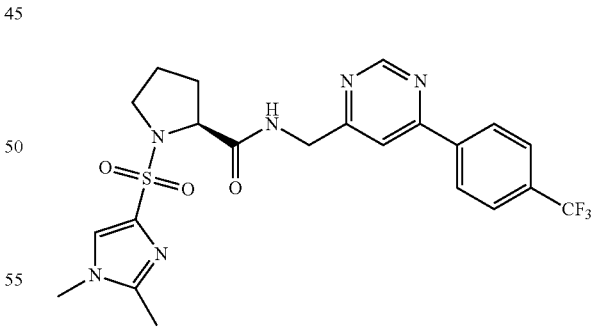

MS (ESI): Mass calcd. for $C_{22}H_{23}F_3N_6O_3S$, 508.52; m/z found 509.5 [M+H]$^+$. $^1$H NMR (400 MHz, CDCl3) δ 9.19 (d, J=1.3, 1H), 8.30 (d, J=8.1, 2H), 8.26 (s, 1H), 8.00 (s, 1H), 7.72 (d, J=8.2, 2H), 7.44 (s, 1H), 4.98 (dd, J=17.6, 7.8, 1H), 4.62 (dd, J=9.0, 3.3, 1H), 4.45 (dd, J=17.6, 4.8, 1H), 3.62 (s, 3H), 3.56-3.42 (m, 2H), 2.32 (s, 3H), 2.32-2.19 (m, 1H), 2.14-1.98 (m, 2H), 1.94-1.82 (m, 1H).

Example 152

1-(4-Chlorobenzenesulfonyl)-pyrrolidine-2S-carboxylic acid [6-(4-trifluoromethyl-Phenyl)-pyrimidin-4-ylmethyl]-amide

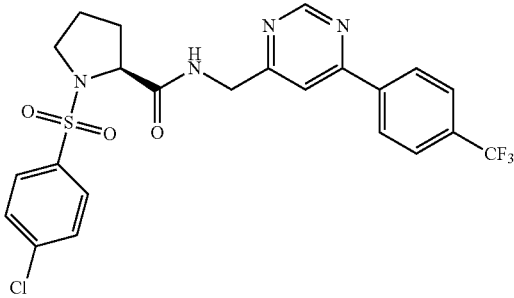 [SMILES: O=C(NCc1cc(-c2ccc(C(F)(F)F)cc2)ncn1)[C@@H]1CCCN1S(=O)(=O)c1ccc(Cl)cc1]

MS (ESI): Mass calcd. for $C_{23}H_{20}ClF_3N_4O_3S$, 524.94; m/z found 525.2 [M+H]$^+$. $^1$H NMR (400 MHz, CDCl3) δ 9.23 (s, 1H), 8.31 (d, J=8.2, 2H), 7.96 (s, 1H), 7.84 (d, J=8.5, 2H), 7.74 (d, J=8.2, 2H), 7.67-7.52 (m, 3H), 4.99-4.82 (m, 1H), 4.62-4.45 (m, 1H), 4.24-4.16 (m, 1H), 3.74-3.60 (m, 1H), 3.35-3.07 (m, 1H), 2.28-2.17 (m, 1H), 1.97-1.65 (m, 3H).

Example 153

1-(2-Fluorobenzenesulfonyl)-pyrrolidine-2S-carboxylic acid [6-(4-trifluoromethylphenyl)-pyrimidin-4-ylmethyl]-amide

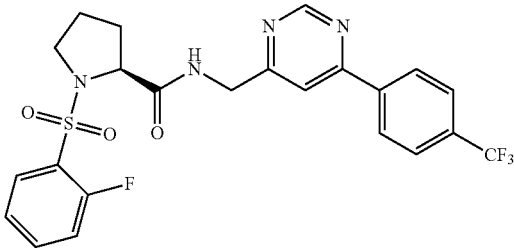 [SMILES: O=C(NCc1cc(-c2ccc(C(F)(F)F)cc2)ncn1)[C@@H]1CCCN1S(=O)(=O)c1ccccc1F]

MS (ESI): Mass calcd. for $C_{23}H_{20}F_4N_4O_3S$, 508.49; m/z found 509.5 [M+H]$^+$. $^1$H NMR (400 MHz, CDCl3) δ 9.22 (s, 1H), 8.31 (d, J=8.1, 2H), 8.03-7.89 (m, 2H), 7.74 (d, J=8.3, 2H), 7.71-7.54 (m, 2H), 7.41-7.25 (m, 2H), 4.89 (dd, J=17.5, 7.1, 1H), 4.60-4.44 (m, 2H), 3.69-3.55 (m, 1H), 3.42-3.31 (m, 1H), 2.38-2.24 (m, 1H), 2.02-1.90 (m, 2H), 1.87-1.75 (m, 1H).

Example 154

1-(3-Fluorobenzenesulfonyl)-pyrrolidine-2S-carboxylic acid [6-(4-trifluoromethylphenyl)-pyrimidin-4-ylmethyl]-amide

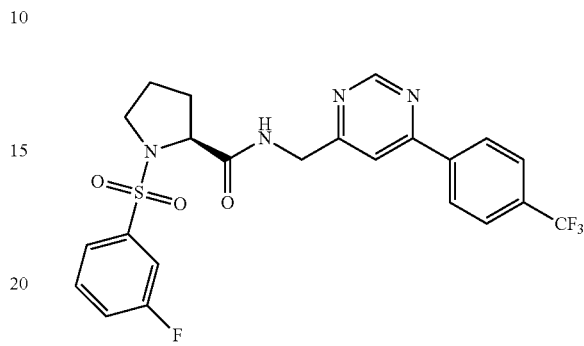

MS (ESI): Mass calcd. for $C_{23}H_{20}F_4N_4O_3S$, 508.49; m/z found 509.5 [M+H]$^+$. $^1$H NMR (400 MHz, CDCl3) δ 9.24 (d, J=1.3, 1H), 8.31 (d, J=8.1, 2H), 7.95 (d, J=1.2, 1H), 7.75 (d, J=8.2, 2H), 7.72-7.69 (m, 1H), 7.65-7.56 (m, 3H), 7.43-7.36 (m, 1H), 4.91 (dd, J=17.5, 7.1, 1H), 4.53 (dd, J=17.5, 4.9, 1H), 4.22 (dd, J=8.7, 3.0, 1H), 3.68 (ddd, J=10.5, 6.9, 3.6, 1H), 3.30-3.17 (m, 1H), 2.27-2.17 (m, 1H), 1.96-1.65 (m, 3H).

Example 155

1-(Toluene-2-sulfonyl)-pyrrolidine-2S-carboxylic acid [6-(4-trifluoromethylphenyl)-pyrimidin-4-ylmethyl]-amide

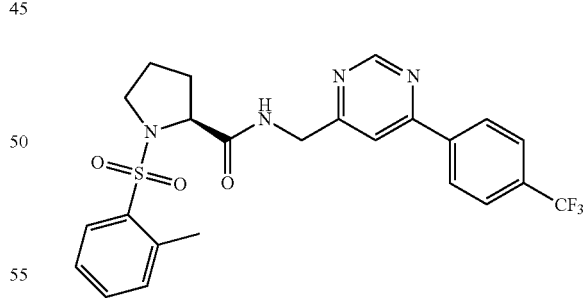

MS (ESI): Mass calcd. for $C_{24}H_{23}F_3N_4O_3S$, 504.53; m/z found 505.5 [M+H]$^+$. $^1$H NMR (400 MHz, CDCl3) δ 9.22 (d, J=1.2, 1H), 8.30 (d, J=8.3, 3H), 7.94 (d, J=6.5, 1H), 7.74 (d, J=8.3, 3H), 7.38-7.33 (m, 3H), 4.84 (dd, J=17.5, 7.0, 1H), 4.50 (dd, J=17.4, 5.0, 1H), 4.38 (dd, J=8.5, 3.0, 1H), 3.60 (ddd, J=10.2, 6.6, 3.7, 1H), 3.35-3.21 (m, 1H), 2.94 (s, 3H) 2.32-2.23 (m, 1H), 2.03-1.89 (m, 2H), 1.88-1.78 (m, 1H).

Example 156

1-(Toluene-3-sulfonyl)-pyrrolidine-2S-carboxylic acid [6-(4-trifluoromethylphenyl)-pyrimidin-4-ylmethyl]-amide

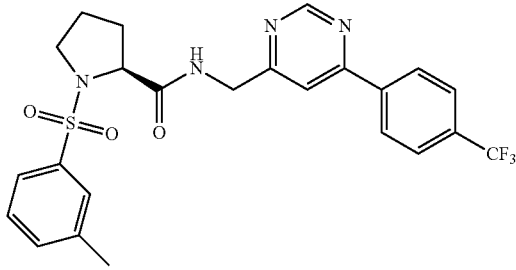 [SMILES: Cc1cccc(S(=O)(=O)N2CCC[C@H]2C(=O)NCc2cc(-c3ccc(C(F)(F)F)cc3)ncn2)c1]

MS (ESI): Mass calcd. for $C_{24}H_{23}F_3N_4O_3S$, 504.53; m/z found 505.5 [M+H]$^+$. $^1$H NMR (400 MHz, CDCl3) δ 9.23 (s, 1H), 8.33 (d, J=7.7, 2H), 8.01 (s, 1H), 7.78-7.71 (m, 2H), 7.70 (s, 3H), 7.50-7.46 (m, 2H), 5.02-4.85 (m, 1H), 4.58-4.43 (m, 1H), 4.27-4.15 (m, 1H), 3.73-3.59 (m, 1H), 3.29-3.17 (m, 1H), 2.47 (s, 3H), 2.26-2.11 (m, 1H), 1.93-1.61 (m, 3H).

Example 157

1-(3-Trifluoromethylbenzenesulfonyl)-pyrrolidine-2S-carboxylic acid [6-(4-trifluoromethylphenyl)-pyrimidin-4-ylmethyl]-amide

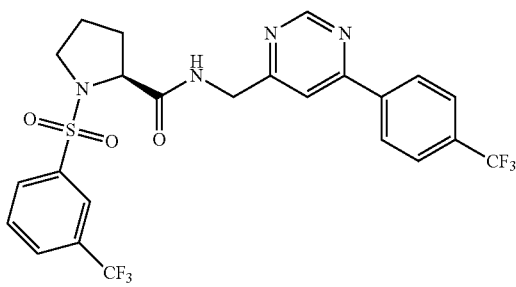 [SMILES: O=C(NCc1cc(-c2ccc(C(F)(F)F)cc2)ncn1)[C@@H]1CCCN1S(=O)(=O)c1cccc(C(F)(F)F)c1]

MS (ESI): Mass calcd. for $C_{24}H_{20}F_6N_4O_3S$, 558.50; m/z found 559.1 [M+H]$^+$. $^1$H NMR (400 MHz, CDCl3) δ 9.24 (s, 1H), 8.30 (d, J=8.3, 2H), 8.16 (s, 1H), 8.10 (d, J=7.9, 1H), 8.00-7.91 (m, 2H), 7.83-7.71 (m, 3H), 7.66-7.55 (m, 1H), 4.89 (dd, J=17.5, 7.0, 1H), 4.55 (dd, J=17.4, 5.1, 1H), 4.30-4.18 (m, 1H), 3.76-3.64 (m, 1H), 3.29-3.15 (m, 1H), 2.32-2.19 (m, 1H), 2.02-1.87 (m, 1H), 1.87-1.67 (m, 2H).

Example 158

1-(4-Trifluoromethylbenzenesulfonyl)-pyrrolidine-2S-carboxylic acid [6-(4-trifluoromethylphenyl)-pyrimidin-4-ylmethyl]-amide

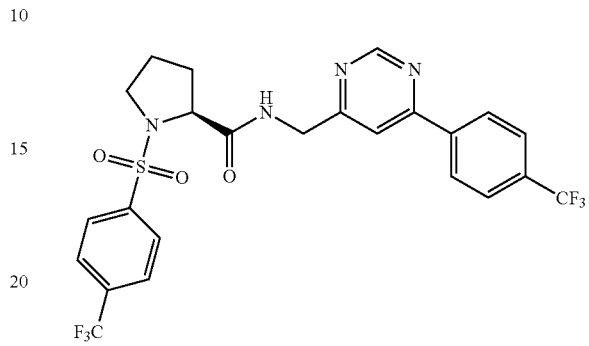

MS (ESI): Mass calcd. for $C_{24}H_{20}F_6N_4O_3S$, 558.50; m/z found 559.1 [M+H]$^+$. $^1$H NMR (400 MHz, CDCl3) δ 9.24 (s, 1H), 8.30 (d, J=8.2, 2H), 8.04 (d, J=8.3, 2H), 7.94 (s, 1H), 7.87 (d, J=8.5, 2H), 7.75 (d, J=8.4, 2H), 7.64-7.55 (m, 1H), 4.89 (dd, J=17.4, 7.0, 1H), 4.62-4.49 (m, 1H), 4.29-4.18 (m, 1H), 3.76-3.65 (m, 1H), 3.31-3.14 (m, 1H), 2.31-2.17 (m, 1H), 2.01-1.86 (m, 1H), 1.86-1.67 (m, 2H).

Example 159

1-(4-Cyanobenzenesulfonyl)-pyrrolidine-2S-carboxylic acid [6-(4-trifluoromethylphenyl)-pyrimidin-4-ylmethyl]-amide

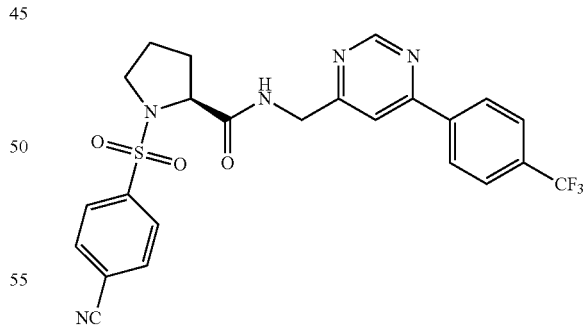

MS (ESI): Mass calcd. for $C_{24}H_{20}F_3N_5O_3S$, 515.51; m/z found 516.1 [M+H]$^+$. $^1$H NMR (400 MHz, CDCl3) δ 9.24 (d, J=1.2, 1H), 8.28 (d, J=8.1, 2H), 8.06-7.98 (m, 2H), 7.93-7.86 (m, 3H), 7.75 (d, J=8.3, 2H), 7.55 (m, 1H), 4.86 (dd, J=17.5, 6.8, 1H), 4.56 (dd, J=17.5, 5.1, 1H), 4.22 (dd, J=8.7, 3.0, 1H), 3.75-3.64 (m, 1H), 3.26-3.16 (m, 1H), 2.30-2.19 (m, 1H), 2.02-1.87 (m, 1H), 1.87-1.68 (m, 2H).

Example 160

1-Benzenesulfonylpyrrolidine-2S-carboxylic acid [6-(4-trifluoromethylphenyl)-pyrimidin-4-ylmethyl]-amide

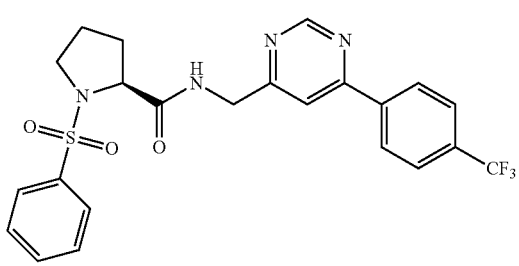 [SMILES: O=C(NCc1cc(-c2ccc(C(F)(F)F)cc2)ncn1)[C@@H]1CCCN1S(=O)(=O)c1ccccc1]

MS (ESI): Mass calcd. for $C_{23}H_{21}F_3N_4O_3S$, 490.50; m/z found 491.5 [M+H]$^+$. $^1$H NMR (400 MHz, CDCl3) δ 9.23 (d, J=1.3, 1H), 8.33 (d, J=8.1, 2H), 8.00 (s, 1H), 7.94-7.88 (m, 2H), 7.74 (d, J=8.2, 2H), 7.72-7.64 (m, 2H), 7.64-7.56 (m, 2H), 4.93 (dd, J=17.6, 7.4, 1H), 4.51 (dd, J=17.7, 5.0, 1H), 4.22 (dd, J=8.8, 3.2, 1H), 3.67 (ddd, J=10.4, 6.7, 3.7, 1H), 3.29-3.17 (m, 1H), 2.24-2.14 (m, 1H), 1.93-1.80 (m, 1H), 1.80-1.60 (m, 2H).

Example 161

1-(Toluene-4-sulfonyl)-pyrrolidine-2S-carboxylic acid [6-(4-trifluoromethylphenyl)-pyrimidin-4-ylmethyl]-amide

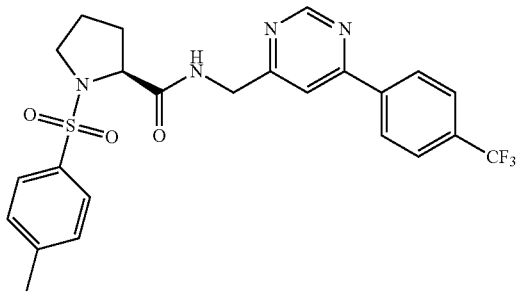 [SMILES: Cc1ccc(S(=O)(=O)N2CCC[C@H]2C(=O)NCc2cc(-c3ccc(C(F)(F)F)cc3)ncn2)cc1]

MS (ESI): Mass calcd. for $C_{24}H_{23}F_3N_4O_3S$, 504.53; m/z found 505.5 [M+H]$^+$. $^1$H NMR (400 MHz, CDCl3) δ 9.23 (d, J=1.3, 1H), 8.33 (d, J=8.1, 2H), 8.01 (s, 1H), 7.78 (d, J=8.3, 2H), 7.75 (s, 2H), 7.72-7.63 (m, 1H), 7.39 (d, J=7.9, 2H), 4.94 (dd, J=17.6, 7.4, 1H), 4.50 (dd, J=17.6, 4.9, 1H), 4.20 (dd, J=8.7, 3.3, 1H), 3.73-3.56 (m, 1H), 3.30-3.12 (m, 1H), 2.39 (s, 3H), 2.25-2.10 (m, 1H), 1.92-1.61 (m, 3H).

Example 162

1-(4-Acetylbenzenesulfonyl)-pyrrolidine-2S-carboxylic acid [6-(4-trifluoromethylphenyl)-pyrimidin-4-ylmethyl]-amide

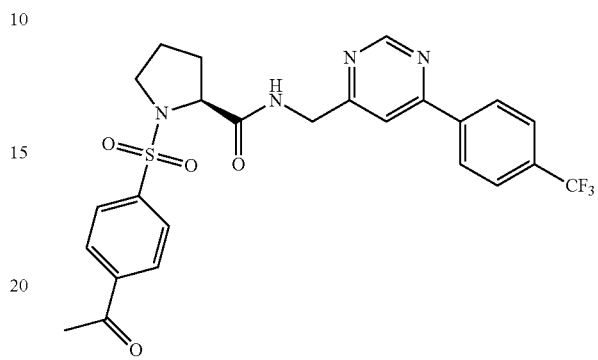

MS (ESI): Mass calcd. for $C_{25}H_{23}F_3N_4O_4S$, 532.54; m/z found 533.5 [M+H]$^+$. $^1$H NMR (400 MHz, CDCl3) δ 9.24 (d, J=1.3, 1H), 8.31 (d, J=8.1, 2H), 8.17-8.11 (m, 2H), 8.04-7.98 (m, 2H), 7.96 (s, 1H), 7.75 (d, J=8.2, 2H), 7.67-7.57 (m, 1H), 4.90 (dd, J=17.5, 7.1, 1H), 4.54 (dd, J=17.5, 5.0, 1H), 4.23 (dd, J=8.8, 3.0, 1H), 3.69 (ddd, J=10.5, 7.0, 3.6, 1H), 3.29-3.17 (m, 1H), 2.68 (s, 3H), 2.26-2.17 (m, 1H), 1.97-1.83 (m, 1H), 1.82-1.64 (m, 2H).

Example 163

1-(4-Nitrobenzenesulfonyl)-pyrrolidine-2S-carboxylic acid [6-(4-trifluoromethylphenyl)-pyrimidin-4-ylmethyl]-amide

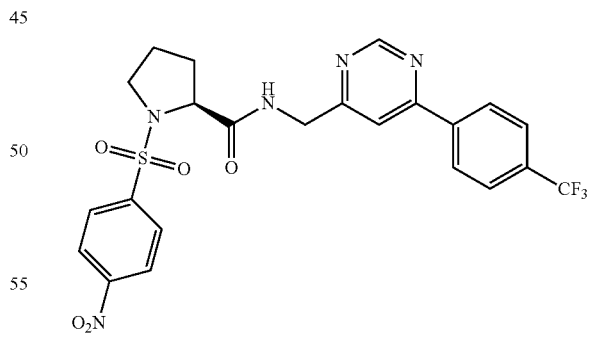

MS (ESI): Mass calcd. for $C_{23}H_{20}F_3N_5O_5S$, 535.50; m/z found 536.5 [M+H]$^+$. $^1$H NMR (400 MHz, CDCl3) δ 9.24 (d, J=1.2, 1H), 8.43 (d, J=8.9, 2H), 8.28 (d, J=8.1, 2H), 8.10 (d, J=9.0, 2H), 7.91 (s, 1H), 7.75 (d, J=8.3, 2H), 7.59-7.48 (m, 1H), 4.86 (dd, J=17.5, 6.7, 1H), 4.57 (dd, J=17.5, 5.1, 1H), 4.31-4.21 (m, 1H), 3.78-3.64 (m, 1H), 3.32-3.14 (m, 1H), 2.30-2.20 (m, 1H), 2.02-1.88 (m, 1H), 1.88-1.70 (m, 2H).

Example 164

1-(1-Methyl-1H-imidazole-4-sulfonyl)-pyrrolidine-2S-carboxylic acid [6-(4-trifluoromethylphenyl)-pyrimidin-4-ylmethyl]-amide

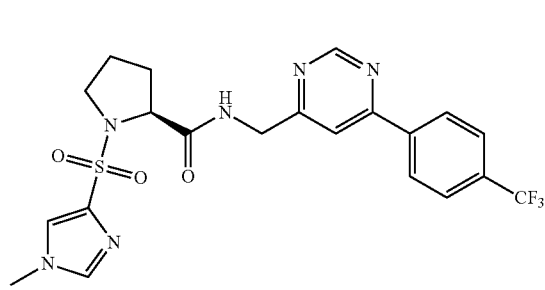 [SMILES: Cn1cnc(S(=O)(=O)N2CCC[C@H]2C(=O)NCc2cc(-c3ccc(C(F)(F)F)cc3)ncn2)c1]

MS (ESI): Mass calcd. for $C_{21}H_{21}F_3N_6O_3S$, 494.49; m/z found 495.5 [M+H]$^+$. $^1$H NMR (400 MHz, CDCl3) δ 9.20 (d, J=1.3, 1H), 8.30 (d, J=8.1, 2H), 8.14-8.03 (m, 1H), 7.99 (s, 1H), 7.73 (d, J=8.3, 2H), 7.54 (d, J=1.3, 1H), 7.48 (s, 1H), 4.97 (dd, J=17.6, 7.7, 1H), 4.60 (dd, J=8.9, 3.4, 1H), 4.47 (dd, J=17.6, 4.8, 1H), 3.78 (s, 3H), 3.58-3.48 (m, 2H), 2.32-2.24 (m, 1H), 2.13-2.01 (m, 1H), 1.98-1.79 (m, 2H).

Example 165

1-(4,5-Dichlorothiophene-2-sulfonyl)-pyrrolidine-2S-carboxylic acid [6-(4-trifluoromethylphenyl)-pyrimidin-4-ylmethyl]-amide

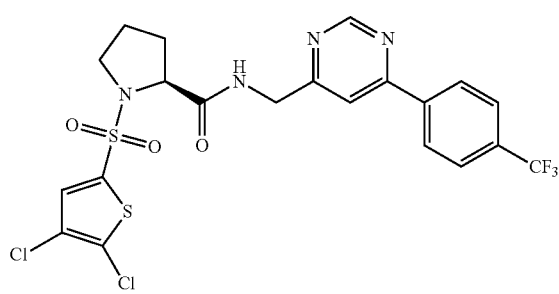 [SMILES: O=C(NCc1cc(-c2ccc(C(F)(F)F)cc2)ncn1)[C@@H]1CCCN1S(=O)(=O)c1cc(Cl)c(Cl)s1]

MS (ESI): Mass calcd. for $C_{21}H_{17}Cl_2F_3N_4O_3S_2$, 565.42; m/z found 565.4 [M$^+$]. $^1$H NMR (400 MHz, CDCl3) δ 9.23 (d, J=1.3, 1H), 8.27 (d, J=8.1, 2H), 7.86 (s, 1H), 7.76 (d, J=8.2, 2H), 7.57-7.50 (m, 1H), 7.48 (s, 1H), 4.87 (dd, J=17.5, 7.0, 1H), 4.54 (dd, J=17.6, 5.1, 1H), 4.22 (dd, J=8.2, 3.0, 1H), 3.75-3.65 (m, 1H), 3.33-3.23 (m, 1H), 2.35-2.24 (m, 1H), 2.03-1.92 (m, 2H), 1.92-1.79 (m, 1H).

Example 166

1-(5-Chlorothiophene-2-sulfonyl)-pyrrolidine-2S-carboxylic acid [6-(4-trifluoromethylphenyl)-pyrimidin-4-ylmethyl]-amide

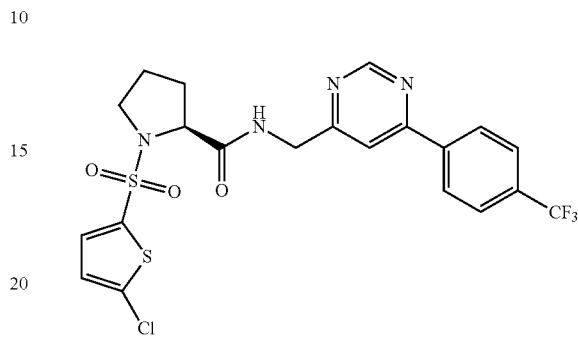

MS (ESI): Mass calcd. for $C_{21}H_{18}ClF_3N_4O_3S_2$, 530.97; m/z found 531.4 [M+H]$^+$. $^1$H NMR (400 MHz, CDCl3) δ 9.23 (d, J=1.3, 1H), 8.29 (d, J=8.1, 2H), 7.90 (s, 1H), 7.75 (d, J=8.2, 2H), 7.62-7.54 (m, 1H), 7.49 (d, J=4.0, 1H), 7.05 (d, J=4.0, 1H), 4.90 (dd, J=17.5, 7.2, 1H), 4.52 (dd, J=17.6, 5.1, 1H), 4.22 (dd, J=8.3, 3.1, 1H), 3.76-3.63 (m, 1H), 3.36-3.23 (m, 1H), 2.33-2.22 (m, 1H), 2.01-1.75 (m, 3H).

Example 167

1-(Furan-2-sulfonyl)-pyrrolidine-2S-carboxylic acid [6-(4-trifluoromethylphenyl)-pyrimidin-4-ylmethyl]-amide

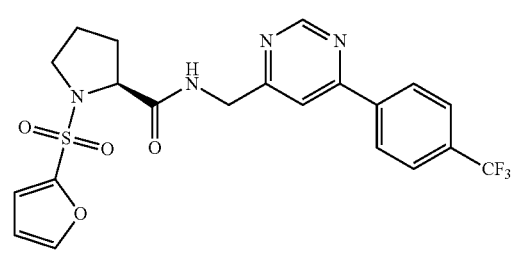 [SMILES: O=C(NCc1cc(-c2ccc(C(F)(F)F)cc2)ncn1)[C@@H]1CCCN1S(=O)(=O)c1ccco1]

MS (ESI): Mass calcd. for $C_{21}H_{19}F_3N_4O_4S$, 480.46; m/z found 481.5 [M+H]$^+$. $^1$H NMR (400 MHz, CDCl3) δ 9.23 (d, J=1.2, 1H), 8.29 (d, J=8.1, 2H), 7.91 (s, 1H), 7.75 (d, J=8.3, 2H), 7.64 (d, J=0.9, 1H), 7.60 (s, 1H), 7.20-7.15 (m, 1H), 6.60 (dd, J=3.5, 1.8, 1H), 4.90 (dd, J=17.5, 7.2, 1H), 4.52 (dd, J=17.5, 5.1, 1H), 4.43 (dd, J=8.2, 3.4, 1H), 3.71-3.59 (m, 1H), 3.45-3.37 (m, 1H), 2.35-2.24 (m, 1H), 2.00-1.85 (m, 2H), 1.82-1.70 (m, 1H).

Example 168

1-(2-Trifluoromethylbenzenesulfonyl)-pyrrolidine-2S-carboxylic acid [6-(4-trifluoromethylphenyl)-pyrimidin-4-ylmethyl]-amide

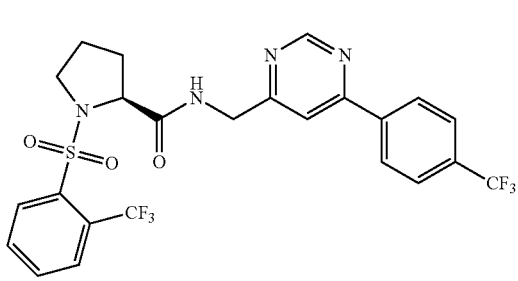 [SMILES: O=C(NCc1cc(-c2ccc(C(F)(F)F)cc2)ncn1)[C@@H]1CCCN1S(=O)(=O)c1ccccc1C(F)(F)F]

MS (ESI): Mass calcd. for $C_{24}H_{20}F_6N_4O_3S$, 558.50; m/z found 559.5 [M+H]$^+$. $^1$H NMR (400 MHz, CDCl3) δ 9.20 (d, J=1.2, 1H), 8.28 (d, J=8.2, 2H), 8.21-8.13 (m, 1H), 7.97-7.90 (m, 1H), 7.88 (s, 1H), 7.80-7.67 (m, 4H), 7.39-7.30 (m, 1H), 4.77 (dd, J=17.5, 6.7, 1H), 4.57-4.46 (m, 2H), 3.70-3.59 (m, 1H), 3.47-3.35 (m, 1H), 2.38-2.23 (m, 1H), 2.15-1.86 (m, 3H).

Example 169

1-(3,5-Difluorobenzenesulfonyl)-pyrrolidine-2S-carboxylic acid [6-(4-trifluoromethylphenyl)-pyrimidin-4-ylmethyl]-amide

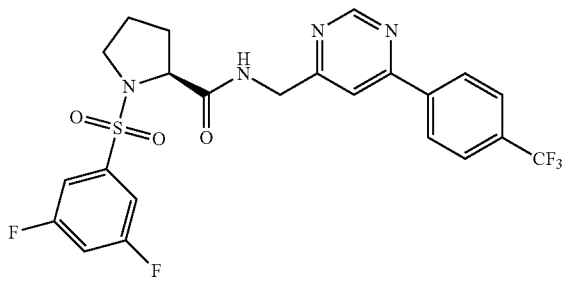 [SMILES: O=C(NCc1cc(-c2ccc(C(F)(F)F)cc2)ncn1)[C@@H]1CCCN1S(=O)(=O)c1cc(F)cc(F)c1]

MS (ESI): Mass calcd. for $C_{23}H_{19}F_5N_4O_3S$, 526.48; m/z found 527.1 [M+H]$^+$. $^1$H NMR (400 MHz, CDCl3) δ 9.27 (d, J=1.2, 1H), 8.30 (d, J=8.1, 2H), 8.01 (s, 1H), 7.77 (d, J=8.3, 2H), 7.76-7.69 (m, 1H), 7.51-7.41 (m, 2H), 7.18-7.07 (m, 1H), 4.94 (dd, J=17.4, 7.1, 1H), 4.59 (dd, J=17.4, 5.1, 1H), 4.28-4.18 (m, 1H), 3.75-3.65 (m, 1H), 3.28-3.18 (m, 1H), 2.27-2.16 (m, 1H), 2.01-1.84 (m, 2H), 1.84-1.69 (m, 1H).

Example 170

1-(Thiophene-2-sulfonyl)-pyrrolidine-2S-carboxylic acid [6-(4-trifluoromethylphenyl)-pyrimidin-4-ylmethyl]-amide

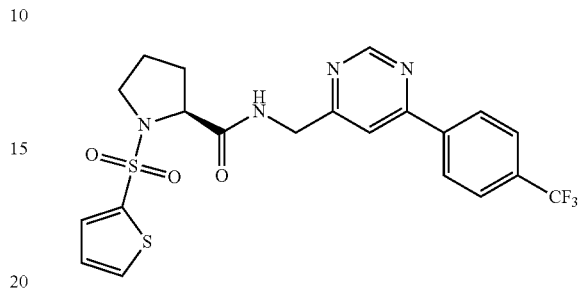

MS (ESI): Mass calcd. for $C_{21}H_{19}F_3N_4O_3S_2$, 496.53; m/z found 497.1 [M+H]$^+$. $^1$H NMR (400 MHz, CDCl3) δ 9.25 (d, J=1.2, 1H), 8.32 (d, J=8.1, 2H), 8.01 (s, 1H), 7.79-7.66 (m, 5H), 7.23 (dd, J=5.0, 3.8, 1H), 4.98 (dd, J=17.5, 7.4, 1H), 4.55 (dd, J=17.5, 4.9, 1H), 4.26 (dd, J=8.5, 3.5, 1H), 3.76-3.65 (m, 1H), 3.37-3.26 (m, 1H), 2.26-2.16 (m, J=10.5, 1H), 1.96-1.79 (m, 2H), 1.77-1.64 (m, 1H).

Example 171 was prepared using methods analogous to those described for Example 103.

Example 171

1-(4-Fluorobenzenesulfonyl)-pyrrolidine-2S-carboxylic acid (4'-chlorobiphenyl-3-ylmethyl)-amide

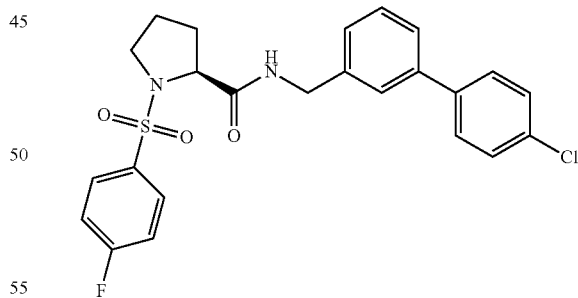

MS (ESI): Mass calcd. for $C_{24}H_{22}ClFN_2O_3S$, 472.96; m/z found 473.1 [M+H]$^+$. $^1$H NMR (400 MHz, CDCl3) δ 7.92-7.83 (m, 2H), 7.58-7.20 (m, 9H), 4.65 (dd, J=15.1, 6.2, 1H), 4.53 (dd, J=15.2, 5.7, 1H), 4.19 (dd, J=8.6, 3.0, 1H), 3.63-3.52 (m, 1H), 3.23-3.10 (m, 1H), 2.28-2.17 (m, 1H), 1.87-1.59 (m, 3H).

Examples 172 to 180 were prepared using methods analogous to those described for Example 65.

Example 172

1-(Thiophene-3-sulfonyl)-pyrrolidine-2S-carboxylic acid [6-(4-trifluoromethyl-phenyl)-pyrimidin-4-ylmethyl]-amide

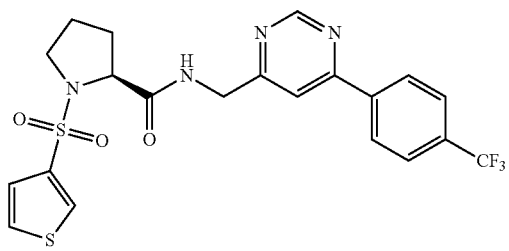 [SMILES: O=C(NCc1cc(-c2ccc(C(F)(F)F)cc2)ncn1)[C@@H]1CCCN1S(=O)(=O)c1ccsc1]

MS (ESI): Mass calcd. for $C_{21}H_{19}F_3N_4O_3S_2$, 496.53; m/z found 497.1 [M+H]$^+$. $^1$H NMR (600 MHz, CDCl3) δ 9.24 (d, J=1.2, 1H), 8.32 (d, J=8.1, 2H), 8.08 (dd, J=3.1, 1.3, 1H), 8.01 (s, 1H), 7.75 (d, J=8.3, 2H), 7.74-7.67 (m, 1H), 7.54 (dd, J=5.1, 3.1, 1H), 7.42 (dd, J=5.1, 1.3, 1H), 4.96 (dd, J=17.5, 7.4, 1H), 4.52 (dd, J=17.5, 4.9, 1H), 4.23 (dd, J=8.7, 3.5, 1H), 3.73-3.62 (m, 1H), 3.26 (ddd, J=8.8, 6.6, 6.6, 1H), 2.25-2.16 (m, 1H), 1.94-1.79 (m, 2H), 1.75-1.65 (m, 1H).

Example 173

1-(2,5-Dichlorothiophene-3-sulfonyl)-pyrrolidine-2S-carboxylic acid [6-(4-trifluoromethylphenyl)-pyrimidin-4-ylmethyl]-amide

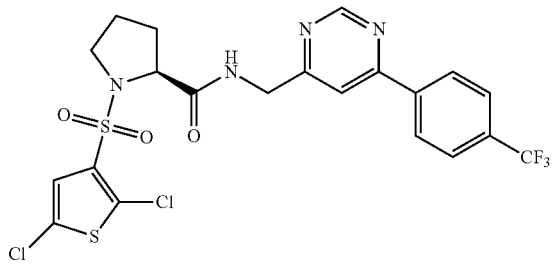 [SMILES: O=C(NCc1cc(-c2ccc(C(F)(F)F)cc2)ncn1)[C@@H]1CCCN1S(=O)(=O)c1cc(Cl)sc1Cl]

MS (ESI): Mass calcd. for $C_{21}H_{17}Cl_2F_3N_4O_3S_2$, 565.42; m/z found 565.0 [M$^+$]. $^1$H NMR (600 MHz, CDCl3) δ 9.23 (d, J=1.2, 1H), 8.29 (d, J=8.1, 2H), 7.93 (s, 1H), 7.75 (d, J=8.3, 2H), 7.60-7.52 (m, 1H), 7.14 (d, J=19.8, 1H), 4.90 (dd, J=17.5, 7.1, 1H), 4.53 (dd, J=17.5, 5.0, 1H), 4.45 (dd, J=9.0, 3.2, 1H), 3.69 (ddd, J=10.5, 7.0, 3.9, 1H), 3.46-3.34 (m, 1H), 2.34-2.27 (m, 1H), 2.13-2.01 (m, 1H), 2.01-1.91 (m, 1H), 1.91-1.83 (m, 1H).

Example 174

1-(6-Chloropyridine-3-sulfonyl)-pyrrolidine-2S-carboxylic acid [6-(4-trifluoromethylphenyl)-pyrimidin-4-ylmethyl]-amide

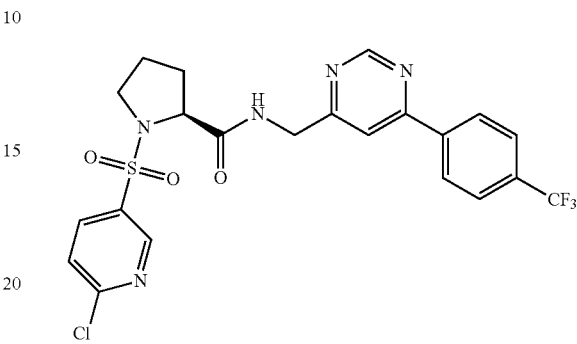

$^1$H NMR (500 MHz, CD2Cl2) δ 9.26 (d, J=1.2, 1H), 8.92 (d, J=2.1, 1H), 8.36 (d, J=8.1, 2H), 8.17 (dd, J=8.4, 2.5, 1H), 7.99 (s, 1H), 7.80 (d, J=8.3, 2H), 7.66-7.53 (m, 2H), 4.86 (dd, J=17.4, 6.8, 1H), 4.58 (dd, J=17.4, 5.2, 1H), 4.23 (dd, J=8.7, 3.2, 1H), 3.78-3.66 (m, 1H), 3.34-3.19 (m, 1H), 2.28-2.14 (m, 1H), 2.06-1.85 (m, 2H), 1.84-1.72 (m, 1H).

Example 175

4-(2S-{[6-(4-Trifluoromethylphenyl)-pyrimidin-4-ylmethyl]-carbamoyl}-pyrrolidine-1-sulfonyl)-benzoic acid

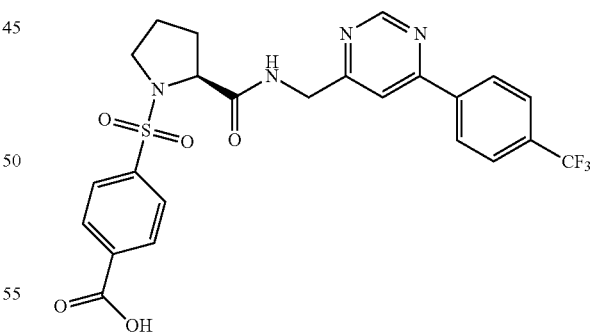

MS (ESI): Mass calcd. for $C_{24}H_{21}F_3N_4O_5S$, 534.51; m/z found 535.2 [M+H]$^+$. $^1$H NMR (500 MHz, MeOD) δ 8.96 (s, 1H), 8.91-8.83 (m, 1H), 8.23 (d, J=8.4, 2H), 8.04 (d, J=8.5, 2H), 8.01 (s, 1H), 7.85 (d, J=8.4, 2H), 7.57 (d, J=8.5, 2H), 4.57-4.44 (m, 1H), 4.37-4.25 (m, 1H), 4.06-3.91 (m, 1H), 3.54-3.42 (m, 1H), 3.17-3.03 (m, J=3.3, 1.6, 1H), 1.83-1.68 (m, 3H), 1.50-1.31 (m, 1H).

Example 176

1-(Furan-3-sulfonyl)-pyrrolidine-2S-carboxylic acid [6-(4-trifluoromethylphenyl)-pyrimidin-4-ylmethyl]-amide

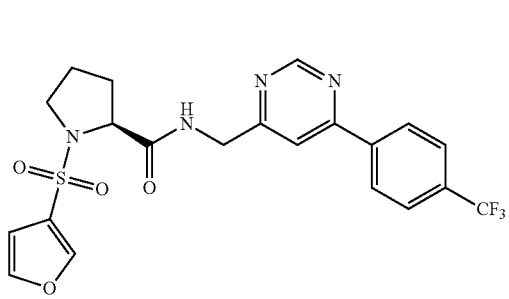

MS (ESI): Mass calcd. for $C_{21}H_{19}F_3N_4O_4S$, 480.46; m/z found 481.1 [M+H]⁺. ¹H NMR (500 MHz, CDCl3) δ 9.26 (s, 1H), 8.31 (d, J=8.3, 2H), 8.04 (s, 1H), 8.01 (s, 1H), 7.76 (d, J=8.6, 2H), 7.76-7.70 (m, 1H), 7.65-7.60 (m, 1H), 6.72 (s, 1H), 4.98 (dd, J=17.6, 7.5, 1H), 4.54 (dd, J=17.5, 4.9, 1H), 4.26-4.18 (m, 1H), 3.73-3.65 (m, 1H), 3.29-3.19 (m, 1H), 2.29-2.21 (m, 1H), 2.04-1.89 (m, 2H), 1.86-1.75 (m, 1H).

Example 177

1-(4-Fluorobenzenesulfonyl)-pyrrolidine-2S-carboxylic acid [6-(4-trifluoromethoxyphenyl)-pyrimidin-4-ylmethyl]-amide

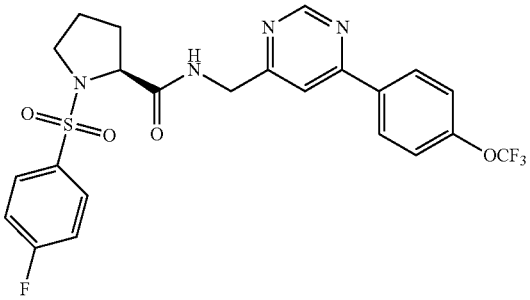 [SMILES: O=C(NCc1cc(-c2ccc(OC(F)(F)F)cc2)ncn1)[C@@H]1CCCN1S(=O)(=O)c1ccc(F)cc1]

MS (ESI): Mass calcd. for $C_{23}H_{20}F_4N_4O_4S$, 524.49; m/z found 525.1 [M+H]⁺. ¹H NMR (500 MHz, CDCl3) δ 9.19 (s, 1H), 8.25 (d, J=8.5, 2H), 7.99-7.89 (m, 3H), 7.67 (s, 1H), 7.34-7.26 (m, 4H), 4.99-4.81 (m, 1H), 4.62-4.40 (m, 1H), 4.22-4.13 (m, 1H), 3.75-3.55 (m, 1H), 3.26-3.09 (m, 1H), 2.25-2.13 (m, 1H), 1.96-1.85 (m, 1H), 1.83-1.73 (m, 1H), 1.73-1.64 (m, 1H).

Example 178

1-(4-Fluoro-benzenesulfonyl)-pyrrolidine-2S-carboxylic acid [6-(6-trifluoromethyl-pyridin-3-yl)-pyrimidin-4-ylmethyl]-amide

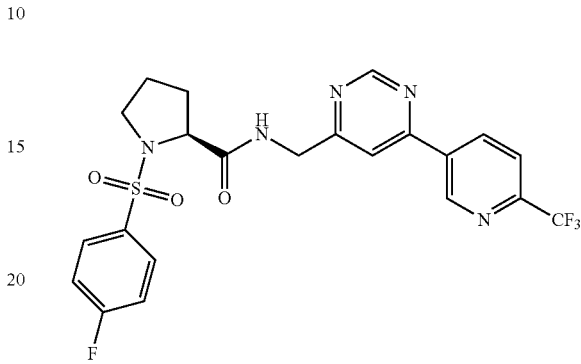

MS (ESI): Mass calcd. for $C_{22}H_{19}F_4N_5O_3S$, 509.48; m/z found 510.1 [M+H]⁺. ¹H NMR (500 MHz, CDCl3) δ 9.50 (s, 1H), 9.26 (d, J=1.1, 1H), 8.70 (d, J=8.2, 1H), 8.07 (s, 1H), 7.93 (dd, J=8.8, 5.0, 2H), 7.81 (d, J=8.2, 1H), 7.68-7.60 (m, 1H), 7.32 (dd, J=8.5, 2H), 5.00 (dd, J=17.7, 7.7, 1H), 4.49 (dd, J=17.6, 4.8, 1H), 4.17 (dd, J=8.8, 3.3, 1H), 3.76-3.59 (m, 1H), 3.24-3.09 (m, 1H), 2.23-2.16 (m, 1H), 1.96-1.76 (m, 2H), 1.76-1.67 (m, 1H).

Example 179

(2S)-4,4-Difluoro-1-(4-fluoro-benzenesulfonyl)-pyrrolidine-2-carboxylic acid [6-(4-trifluoromethyl-phenyl)-pyrimidin-4-ylmethyl]-amide

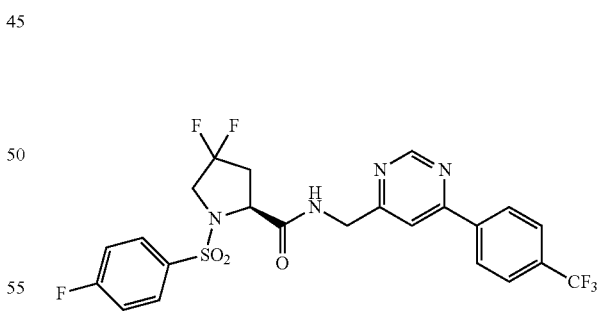

MS (ESI): mass calcd. for $C_{23}H_{18}F_6N_4O_3S$, 544.1; m/z found, 545.1 [M+H]⁺. ¹H NMR (500 MHz, CDCl₃) δ 9.27 (s, 1H), 8.28 (d, J=8.2, 2H), 7.93 (dd, J=8.8, 4.9, 3H), 7.76 (d, J=8.3, 3H), 7.32 (t, J=8.4, 2H), 4.85 (dd, J=17.4, 6.7, 1H), 4.65 (dd, J=17.3, 5.3, 1H), 4.39 (dd, J=9.8, 4.9, 1H), 3.97-3.83 (m, 1H), 3.72-3.58 (m, 1H), 2.76-2.68 (m, 1H), 2.49-2.33 (m, 1H).

Example 180

(2S)-1-(5-Chloro-thiophene-2-sulfonyl)-4,4-difluoro-pyrrolidine-2-carboxylic acid [6-(4-trifluoromethyl-phenyl)-pyrimidin-4-ylmethyl]-amide

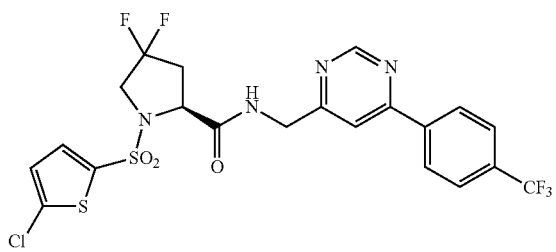 [SMILES: O=C(NCc1cc(-c2ccc(C(F)(F)F)cc2)ncn1)[C@@H]1CC(F)(F)CN1S(=O)(=O)c1ccc(Cl)s1]

MS (ESI): mass calcd. for $C_{21}H_{16}ClF_5N_4O_3S_2$, 566.0; m/z found, 567.1 [M+H]+. $^1$H NMR (500 MHz, CDCl$_3$) δ 9.27 (s, 1H), 8.27 (d, J=8.2, 2H), 7.92 (s, 1H), 7.77 (d, J=8.3, 3H), 7.53 (d, J=4.1, 1H), 7.09 (d, J=4.1, 1H), 4.86 (dd, J=17.3, 6.7, 1H), 4.65 (dd, J=17.3, 5.4, 1H), 4.43 (dd, J=9.9, 4.6, 1H), 4.02-3.85 (m, 1H), 3.77-3.63 (m, 1H), 2.80-2.72 (m, 1H), 2.57-2.43 (m, 1H).

Examples 181 to 182 were prepared using methods analogous to those described for example 113.

Example 181

(1S*,2S)-1-(4-Fluoro-benzenesulfonyl)-pyrrolidine-2-carboxylic acid {1-[6-(4-trifluoromethyl-phenyl)-pyrimidin-4-yl]-ethyl}-amide

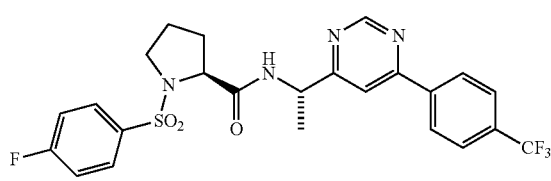

The title compound was generated as an 8:1 mixture of (S) to (R) enantiomers. MS (ESI): mass calcd. for $C_{24}H_{22}F_4N_2O_3S$, 522.1; m/z found, 523.5 [M+H]+. $^1$H NMR for major only (500 MHz, CDCl$_3$) δ 9.32-9.25 (m, 1H), 8.36 (d, J=8.2, 2H), 8.07 (app s, 1H), 7.98-7.88 (m, 2H), 7.81-7.68 (m, 2H), 7.52 (d, J=7.9, 1H), 7.34-7.22 (m, 2H), 5.23 (dd, J=14.7, 7.3, 1H), 4.12 (dd, J=8.8, 3.4, 1H), 3.73 (ddd, J=10.2, 6.7, 3.9, 1H), 3.29-3.19 (m, 1H), 2.26-2.12 (m, 1H), 1.96-1.75 (m, 2H), 1.77-1.58 (m, 4H).

Example 182

(1R*,2S)-1-(4-Fluoro-benzenesulfonyl)-pyrrolidine-2-carboxylic acid {1-[6-(4-trifluoromethyl-phenyl)-pyrimidin-4-yl]-ethyl}-amide

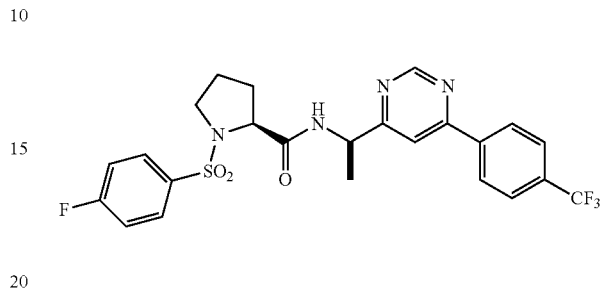

The title compound was generated as an 8:1 mixture of (S) to (R) enantiomers. MS (ESI): mass calcd. for $C_{24}H_{22}F_4N_2O_3S$, 522.1; m/z found, 523.5 [M+H]+. $^1$H NMR for major only (500 MHz, CDCl$_3$) δ 9.27 (s, 1H), 8.23 (d, J=8.1, 2H), 7.98-7.91 (m, 2H), 7.77 (dd, J=12.2, 4.7, 3H), 7.68 (d, J=7.7, 1H), 7.33-7.23 (m, 2H), 5.28-5.12 (m, 1H), 4.17 (dd, J=8.7, 3.1, 1H), 3.63 (dd, J=13.7, 6.8, 1H), 3.23 (dt, J=16.2, 8.2, 1H), 2.22-2.12 (m, 1H), 1.87-1.76 (m, 1H), 1.75-1.58 (m, 5H).

Examples 183 to 184 were prepared using methods analogous to those described for example 65.

Example 183

1-(4-Fluoro-benzenesulfonyl)-pyrrolidine-2S-carboxylic acid [2-methyl-6-(4-trifluoromethyl-phenyl)-pyrimidin-4-ylmethyl]-amide

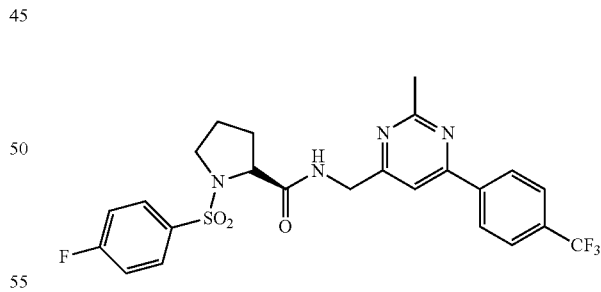

MS (ESI): mass calcd. for $C_{24}H_{22}F_4N_4O_3S$, 522.1; m/z found, 523.5 [M+H]+. $^1$H NMR (500 MHz, CDCl$_3$) δ 8.32 (d, J=8.12 Hz, 2H), 7.97-7.91 (m, 2H), 7.85-7.83 (m, 2H), 7.75 (d, J=8.23 Hz, 2H), 7.33-7.27 (m, 1H), 4.91 (dd, J=17.40, 7.26 Hz, 1H), 4.53 (dd, J=17.41, 4.99 Hz, 1H), 4.19 (dd, J=8.94, 3.26 Hz, 1H), 3.73-3.66 (m, 1H), 3.24-3.15 (m, 1H), 2.85 (s, 3H), 2.26-2.15 (m, 1H), 1.98-1.87 (m, 1H), 1.86-1.76 (m, 1H), 1.75-1.67 (m, 1H).

Example 184

1-(4-Fluoro-benzenesulfonyl)-pyrrolidine-2S-carboxylic acid [2-trifluoromethyl-6-(4-trifluoromethyl-phenyl)-pyrimidin-4-ylmethyl]-amide

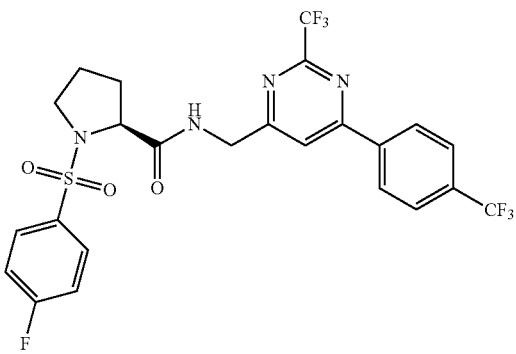 [SMILES: O=C(NCc1cc(-c2ccc(C(F)(F)F)cc2)nc(C(F)(F)F)n1)[C@@H]1CCCN1S(=O)(=O)c1ccc(F)cc1]

$^1$H NMR (360 MHz, DMSO-$d_6$) δ 1.50-1.63 (m, 1H), 1.80-1.94 (m, 3H), 3.16-3.25 (m, 1H), 3.47-3.56 (m, 1H), 4.56 (dd, J=17.6, 5.8 Hz, 1H), 4.65 (dd, J=17.6, 6.0 Hz, 1H), 7.50 (t, J=8.8 Hz, 2H), 7.95 (d, J=8.2 Hz, 2H), 8.02 (dd, J=8.7, 5.2 Hz, 1H), 8.36 (s, 1H), 8.44 (d, J=8.1 Hz, 2H), 9.03 (t, J=6.0 Hz, 1H).

Example 185

(2S)-1-(4-Fluoro-benzenesulfonyl)-pyrrolidine-2-carboxylic acid [4-(4-trifluoromethyl-phenyl)-pyrimidin-2-ylmethyl]-amide

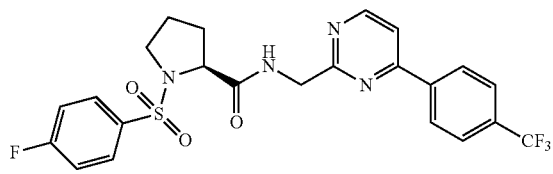 [SMILES: O=C(NCc1nccc(-c2ccc(C(F)(F)F)cc2)n1)[C@@H]1CCCN1S(=O)(=O)c1ccc(F)cc1]

A mixture of C-[4-(4-trifluoromethyl-phenyl)-pyrimidin-2-yl]-methylamine (92 mg, 0.4 mmol), (S)-1-(4-fluoro-benzenesulfonyl)-pyrrolidine-2-carboxylic acid (99 mg, 0.4 mmol), N-(3-dimethylamniopropyl)-N'-ethylcarbodiimide hydrochloride (139 mg, 0.72 mmol), 1-hydroxybenzotriazole (98 mg, 0.73 mmol), Et$_3$N (0.15 mL, 1.10 mmol), and DMF (2 mL) was stirred at rt for 12 hours. After 12 h, MeOH (0.5 mL) was added to the reaction mixture and resulting solution was purified by preparative reverse-phase HPLC to afford (35 mg, 19%) of a white solid. MS (ESI): mass calcd. for C$_{23}$H$_{20}$F$_4$N$_4$O$_3$S, 508.1; m/z found, 509.5 [M+H]$^+$. $^1$H NMR (500 MHz, CDCl$_3$) δ 8.86 (d, J=5.3, 1H), 8.38 (d, J=8.1, 2H), 8.37-8.33 (m, 1H), 7.99-7.92 (m, 2H), 7.82 (d, J=8.2, 2H), 7.70 (d, J=5.3, 1H), 7.30-7.25 (m, 1H), 4.93-4.76 (m, 2H), 4.31-4.22 (m, 1H), 3.69 (td, J=7.3, 3.7, 1H), 3.25 (td, J=9.8, 6.7, 1H), 2.36-2.29 (m, 1H), 1.97-1.59 (m, 3H).

Examples 186 to 188 were prepared using methods analogous to those described for Example 185.

Example 186

(2S)-1-(4-Fluoro-benzenesulfonyl)-pyrrolidine-2-carboxylic acid [4-(4-trifluoromethyl-phenyl)-pyrimidin-2-ylmethyl]-amide

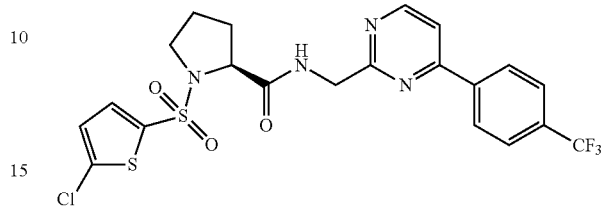

MS (ESI): mass calcd. for C$_{21}$H$_{18}$ClF$_3$N$_4$O$_3$S$_2$, 530.0; m/z found, 531.4 [M+H]$^+$. $^1$H NMR (500 MHz, CDCl$_3$) δ 8.85 (d, J=5.3, 1H), 8.36 (d, J=8.1, 2H), 8.34-8.30 (m, 1H), 7.82 (d, J=8.2, 2H), 7.70 (d, J=5.3, 1H), 7.50 (d, J=4.0, 1H), 7.06 (d, J=4.0, 1H), 4.93-4.76 (m, 2H), 4.34-4.24 (m, 1H), 3.71 (ddd, J=10.3, 7.2, 2.7, 1H), 3.32 (td, J=9.8, 6.7, 1H), 2.45-2.34 (m, 1H), 2.00-1.68 (m, 3H).

Example 187

(2S)-1-(4-Fluoro-benzenesulfonyl)-pyrrolidine-2-carboxylic acid [2-(4-trifluoromethyl-phenyl)-pyrimidin-4-ylmethyl]-amide

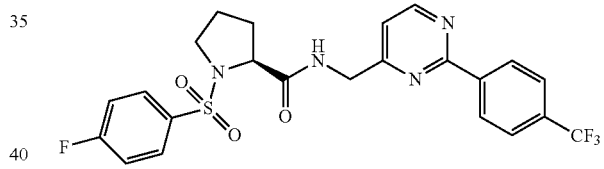

MS (ESI): mass calcd. for C$_{23}$H$_{20}$F$_4$N$_4$O$_3$S, 508.1; m/z found, 509.1 [M+H]$^+$. $^1$H NMR (400 MHz, CDCl3) δ 8.81 (d, J=5.1, 1H), 8.68 (d, J=8.1, 2H), 8.23 (app br s, 1H), 7.99-7.89 (m, 2H), 7.77 (d, J=8.3, 2H), 7.33-7.21 (m, 2H), 4.79 (dd, J=17.9, 5.5, 1H), 4.63 (dd, J=17.9, 5.0, 1H), 4.23 (dd, J=8.7, 2.6, 1H), 3.68 (ddd, J=10.2, 7.2, 3.0, 1H), 3.21 (td, J=9.8, 6.4, 1H), 3.06 (s, 1H), 2.34-2.19 (m, 1H), 1.93-1.55 (m, 3H).

Example 188

(2S)-1-(5-Chloro-thiophene-2-sulfonyl)-pyrrolidine-2-carboxylic acid [4-(4-trifluoromethyl-phenyl)-pyrimidin-2-ylmethyl]-amide

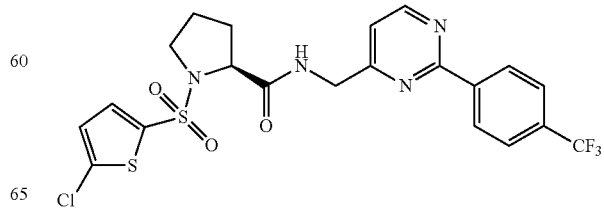

MS (ESI): mass calcd. for $C_{21}H_{18}ClF_3N_4O_3S_2$, 530.0; m/z found, 531.1 [M+H]$^+$. $^1$H NMR (400 MHz, CDCl$_3$) δ 8.81 (d, J=5.1, 1H), 8.66 (d, J=8.1, 2H), 8.23-8.20 (m, 1H), 7.77 (d, J=8.3, 2H), 7.50 (d, J=4.0, 1H), 7.30-7.23 (m, 1H), 7.05 (d, J=4.0, 1H), 4.79 (dd, J=17.9, 5.4, 1H), 4.62 (dd, J=18.0, 5.0, 1H), 4.31-4.22 (m, 1H), 3.69 (dd, J=11.7, 4.9, 1H), 3.30 (dd, J=12.9, 6.6, 1H), 2.40-2.27 (m, 1H), 1.95-1.74 (m, 3H).

The compounds of the following Examples 189 to 225 and 286 to 316 were obtained by our employer from a third party as library compounds and therefore were known to us as compounds per se. We discovered that these compounds have TRPA1-modulating activity, and that they therefore have utility in the therapeutic compositions and methods according to the invention, as reflected by the assay results for these compounds shown in Table 1.

Examples 189 to 282 were prepared using methods analogous to those described for Example 1 substituting the appropriate amine to provide the desired product.

Example 189

1-(4-Fluoro-benzenesulfonyl)-pyrrolidine-2S-carboxylic acid [2-(4-benzyl-piperidin-1-yl)-6-(4-trifluoromethyl-phenyl)-pyrimidin-4-ylmethyl]-amide

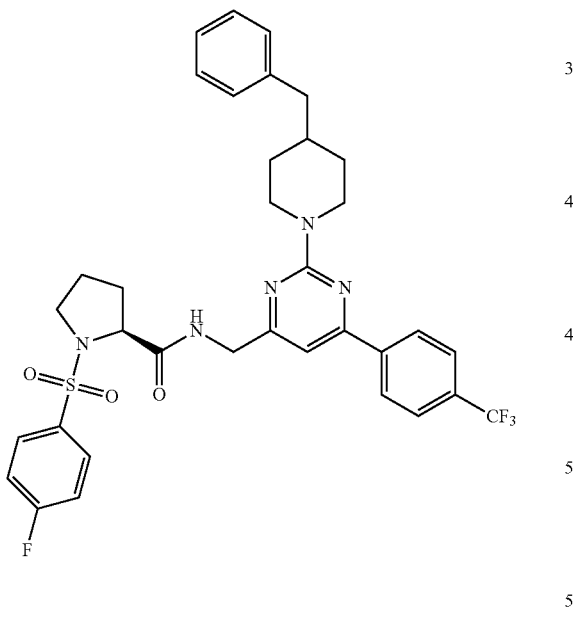

$^1$H NMR (360 MHz, DMSO-d$_6$) δ 1.16 (qd, J=12.3, 3.9 Hz, 2H), 1.50-1.61 (m, 1H), 1.68 (d, J=12.7 Hz, 2H), 1.73-1.90 (m, 4H), 2.54 (d, J=7.1 Hz, 2H), 2.89 (t, J=12.5 Hz, 2H), 3.15-3.24 (m, 1H), 3.45-3.53 (m, 1H), 4.11-4.18 (m, 1H), 4.25 (dd, J=17.1, 5.8 Hz, 1H), 4.33 (dd, J=17.0, 6.1 Hz, 1H), 4.83 (d, J=12.4 Hz, 2H), 7.16-7.22 (m, 3H), 7.23 (s, 1H), 7.29 (t, J=8.1, 7.0 Hz, 2H), 7.49 (t, J=8.7 Hz, 2H), 7.83 (d, J=8.2 Hz, 2H), 8.00 (dd, J=8.7, 5.2 Hz, 2H), 8.30 (d, J=8.1 Hz, 2H), 8.73 (t, J=5.9 Hz, 1H).

Example 190

1-(4-Fluoro-benzenesulfonyl)-pyrrolidine-2S-carboxylic acid [2-(2S-hydroxymethyl-pyrrolidin-1-yl)-6-(4-trifluoromethyl-phenyl)-pyrimidin-4-ylmethyl]-amide

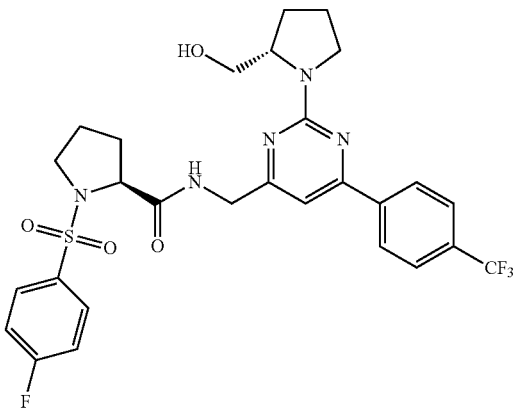 [SMILES: O=C(NCc1cc(-c2ccc(C(F)(F)F)cc2)nc(N2CCC[C@H]2CO)n1)[C@@H]1CCCN1S(=O)(=O)c1ccc(F)cc1]

MS (ESI): mass calcd. for $C_{28}H_{29}F_4N_6O_4S$, 607; m/z found 608 [M+H]$^+$. $R_t$ (min) 1.52.

Example 191

1-(4-Fluoro-benzenesulfonyl)-pyrrolidine-2S-carboxylic acid [2-(1S-hydroxymethyl-2-phenyl-ethylamino)-6-(4-trifluoromethyl-phenyl)-pyrimidin-4-ylmethyl]-amide

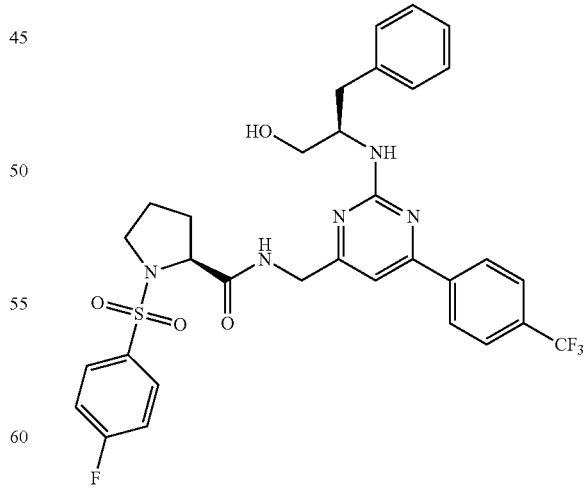

MS (ESI): mass calcd. for $C_{32}H_{31}F_4N_5O_4S$, 657; m/z found 658 [M+H]$^+$. $R_t$ (min) 1.54.

Example 192

1-(4-Fluoro-benzenesulfonyl)-pyrrolidine-2S-carboxylic acid [2-cyclopropylamino-6-(4-trifluoromethyl-phenyl)-pyrimidin-4-ylmethyl]-amide

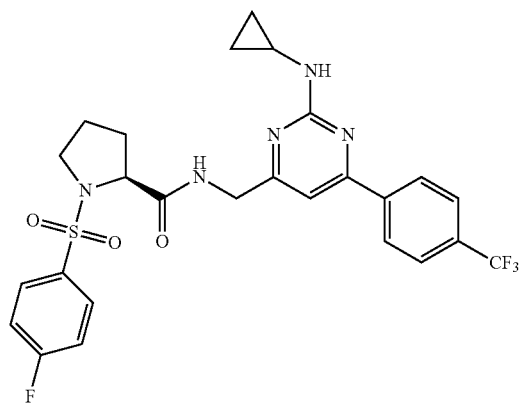 [SMILES: O=C(NCc1cc(-c2ccc(C(F)(F)F)cc2)nc(NC2CC2)n1)[C@@H]1CCCN1S(=O)(=O)c1ccc(F)cc1]

MS (ESI): mass calcd. for $C_{26}H_{25}F_4N_5O_3S$, 563; m/z found 564 [M+H]$^+$. $R_t$ (min) 1.52.

Example 193

1-(4-Fluoro-benzenesulfonyl)-pyrrolidine-2S-carboxylic acid [2-cyclopentylamino-6-(4-trifluoromethyl-phenyl)-pyrimidin-4-ylmethyl]-amide

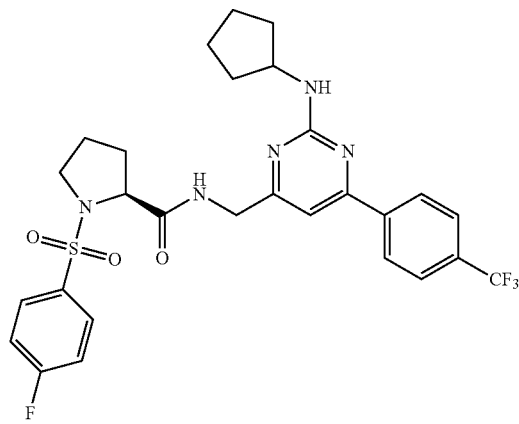 [SMILES: O=C(NCc1cc(-c2ccc(C(F)(F)F)cc2)nc(NC2CCCC2)n1)[C@@H]1CCCN1S(=O)(=O)c1ccc(F)cc1]

MS (ESI): mass calcd. for $C_{28}H_{29}F_4N_5O_3S$, 591; m/z found 592 [M+H]$^+$. $R_t$ (min) 1.62.

Example 194

1-[4-({[1-(4-Fluoro-benzenesulfonyl)-pyrrolidine-2S-carbonyl]-amino}-methyl)-6-(4-trifluoromethyl-phenyl)-pyrimidin-2-yl]-piperidine-4(R,S)-carboxylic acid ethyl ester

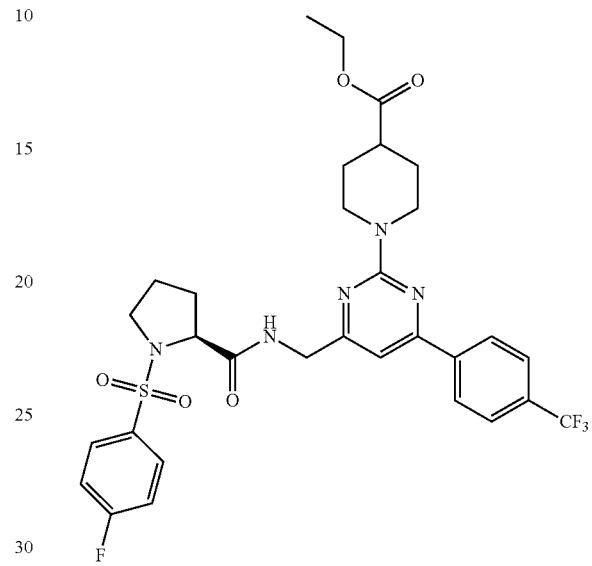

MS (ESI): mass calcd. for $C_{31}H_{33}F_4N_5O_5S$, 663; m/z found 664 [M+H]$^+$. $R_t$ (min) 1.62.

Example 195

1-(4-Fluoro-benzenesulfonyl)-pyrrolidine-2S-carboxylic acid [2-[2-(2,4-dichloro-phenyl)-ethylamino]-6-(4-trifluoromethyl-phenyl)-pyrimidin-4-ylmethyl]-amide

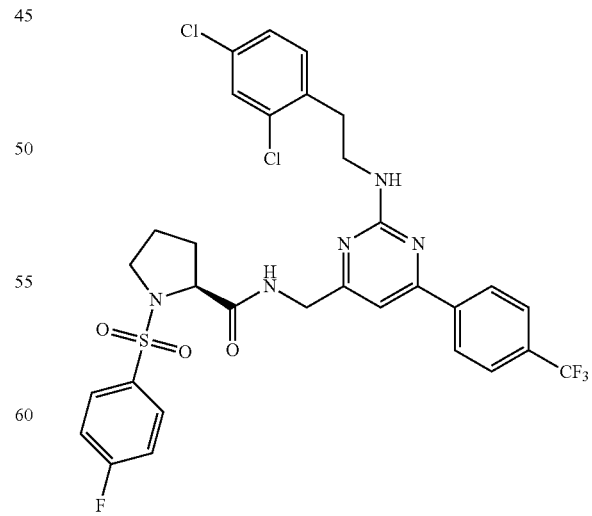

MS (ESI): mass calcd. for $C_{31}H_{27}Cl_2F_4N_5O_3S$, 695; m/z found 696 [M+H]$^+$. $R_t$ (min) 1.69.

Example 196

1-(4-Fluoro-benzenesulfonyl)-pyrrolidine-2S-carboxylic acid [2-[2-(1-methyl-pyrrolidin-2(R,S)-yl)-ethylamino]-6-(4-trifluoromethyl-phenyl)-pyrimidin-4-ylmethyl]-amide

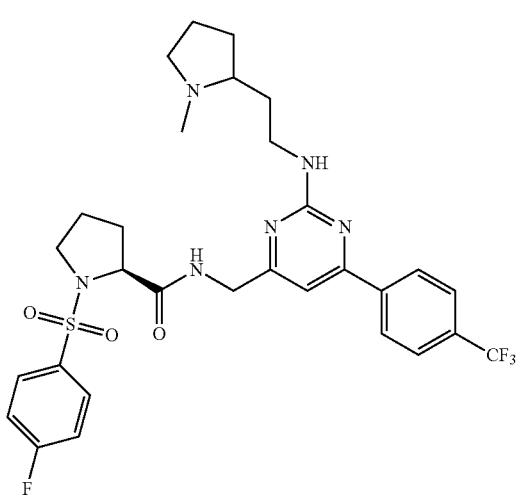 [SMILES: CN1CCCC1CCNc1nc(CNC(=O)[C@@H]2CCCN2S(=O)(=O)c2ccc(F)cc2)cc(-c2ccc(C(F)(F)F)cc2)n1]

MS (ESI): mass calcd. for $C_{30}H_{34}F_4N_6O_3S$, 634; m/z found 635 [M+H]. $R_t$ (min) 1.24.

Example 197

1-(4-Fluoro-benzenesulfonyl)-pyrrolidine-2S-carboxylic acid [2-[2-(3,4-dimethoxy-phenyl)-ethylamino]-6-(4-trifluoromethyl-phenyl)-pyrimidin-4-ylmethyl]-amide

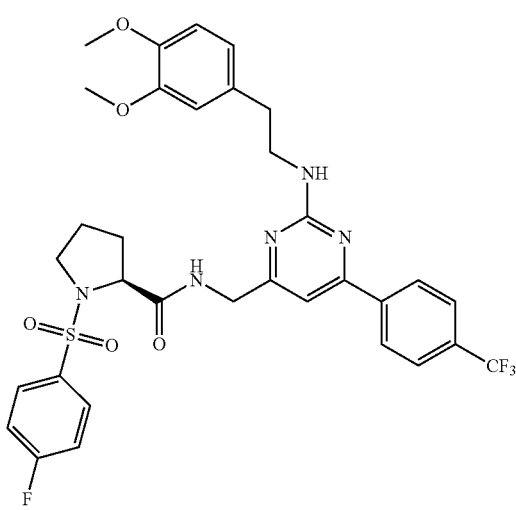 [SMILES: COc1ccc(CCNc2nc(CNC(=O)[C@@H]3CCCN3S(=O)(=O)c3ccc(F)cc3)cc(-c3ccc(C(F)(F)F)cc3)n2)cc1OC]

MS (ESI): mass calcd. for $C_{33}H_{33}F_4N_5O_5S$, 687; m/z found 688 [M+H]$^+$. $R_t$ (min) 1.55.

Example 198

1-(4-Fluoro-benzenesulfonyl)-pyrrolidine-2S-carboxylic acid [2-(4-methyl-[1,4]diazepan-1-yl)-6-(4-trifluoromethyl-phenyl)-pyrimidin-4-ylmethyl]-amide

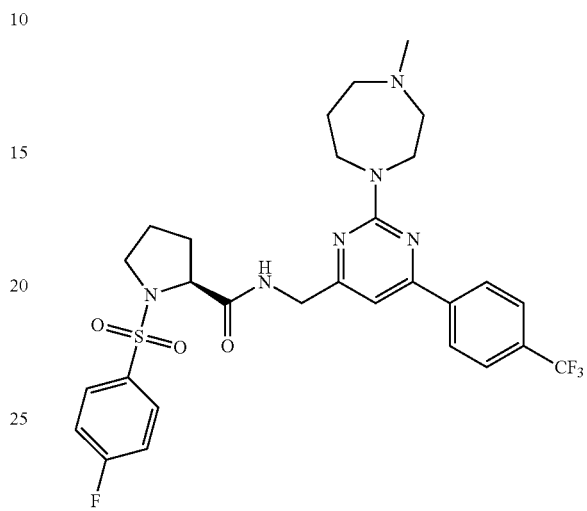

MS (ESI): mass calcd. for $C_{29}H_{32}F_4N_6O_3S$, 620; m/z found 621 [M+H]$^+$. $R_t$ (min) 1.23.

Example 199

1-(4-Fluoro-benzenesulfonyl)-pyrrolidine-2S-carboxylic acid [2-[2-(4-sulfamoyl-phenyl)-ethylamino]-6-(4-trifluoromethyl-phenyl)-pyrimidin-4-ylmethyl]-amide

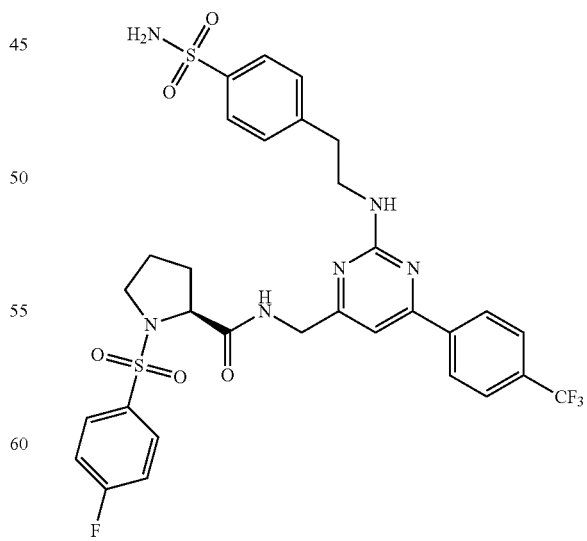

MS (ESI): mass calcd. for $C_{31}H_{30}F_4N_6O_5S_2$, 706; m/z found 707 [M+H]$^+$. $R_t$ (min) 1.43.

Example 200

1-(4-Fluoro-benzenesulfonyl)-pyrrolidine-2S-carboxylic acid (6-benzo[1,3]dioxol-5-yl-2-prop-2-ynylamino-pyrimidin-4-ylmethyl)-amide

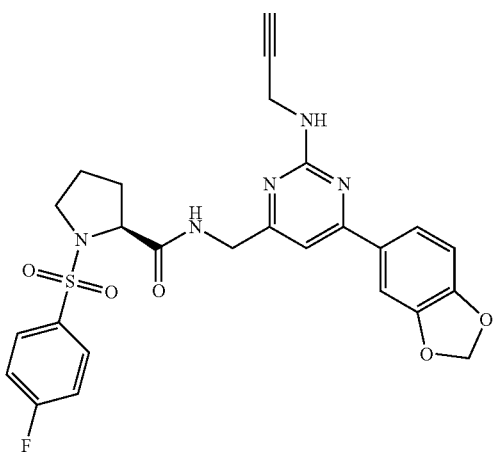 [SMILES: C#CCNc1nc(CNC(=O)[C@@H]2CCCN2S(=O)(=O)c2ccc(F)cc2)cc(-c2ccc3c(c2)OCO3)n1]

MS (ESI): mass calcd. for $C_{26}H_{24}FN_5O_5S$, 537; m/z found 538 [M+H]$^+$. $R_t$ (min) 1.22.

Example 201

1-(4-Fluoro-benzenesulfonyl)-pyrrolidine-2S-carboxylic acid {6-benzo[1,3]dioxol-5-yl-2-[(pyridin-3-ylmethyl)-amino]-pyrimidin-4-ylmethyl}-amide

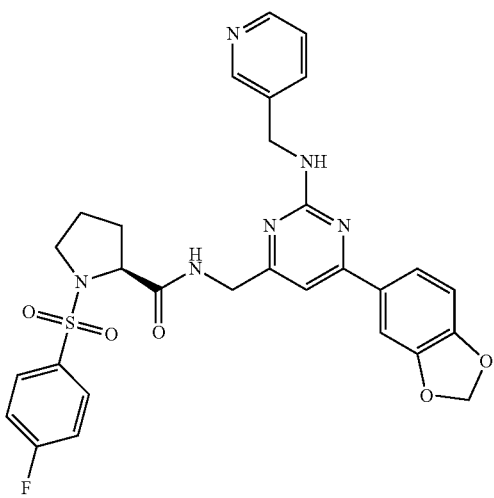 [SMILES: O=C(NCc1cc(-c2ccc3c(c2)OCO3)nc(NCc2cccnc2)n1)[C@@H]1CCCN1S(=O)(=O)c1ccc(F)cc1]

MS (ESI): mass calcd. for $C_{29}H_{27}FN_6O_5S$, 590; m/z found 591 [M+H]$^+$. $R_t$ (min) 1.19.

Example 202

1-(4-Fluoro-benzenesulfonyl)-pyrrolidine-2S-carboxylic acid (6-benzo[1,3]dioxol-5-yl-2-butylamino-pyrimidin-4-ylmethyl)-amide

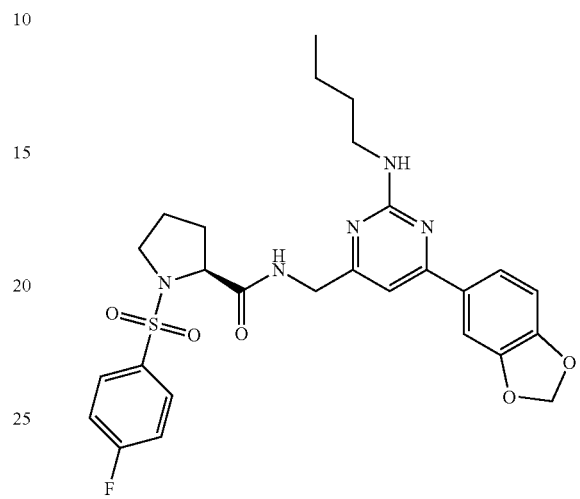

MS (ESI): mass calcd. for $C_{27}H_{30}FN_5O_5S$, 555; m/z found 556 [M+H]$^+$. $R_t$ (min) 1.47.

Example 203

1-(4-Fluoro-benzenesulfonyl)-pyrrolidine-2S-carboxylic acid [6-benzo[1,3]dioxol-5-yl-2-(2-pyridin-2-yl-ethylamino)-pyrimidin-4-ylmethyl]-amide

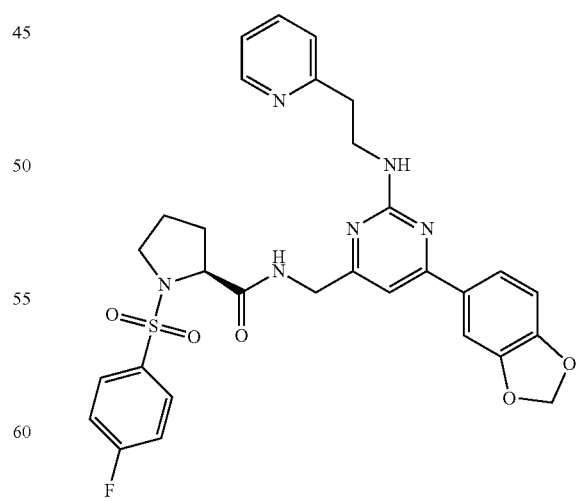

MS (ESI): mass calcd. for $C_{30}H_{29}FN_5O_5S$, 604; m/z found 605 [M+H]$^+$. $R_t$ (min) 1.18.

Example 204

1-(4-Fluoro-benzenesulfonyl)-pyrrolidine-2S-carboxylic acid (6-benzo[1,3]dioxol-5-yl-2-cyclopentylamino-pyrimidin-4-ylmethyl)-amide

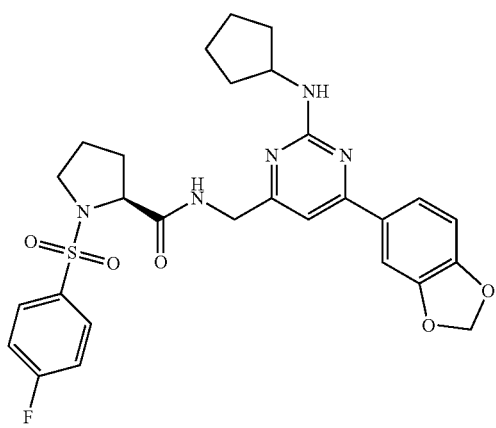 [SMILES: O=C(NCc1cc(-c2ccc3c(c2)OCO3)nc(NC2CCCC2)n1)[C@@H]1CCCN1S(=O)(=O)c1ccc(F)cc1]

MS (ESI): mass calcd. for $C_{28}H_{30}FN_5O_5S$, 567; m/z found 568 [M+H]$^+$. $R_t$ (min) 1.49.

Example 205

1-[4-Benzo[1,3]dioxol-5-yl-6-({[1-(4-fluoro-benzenesulfonyl)-pyrrolidine-2S-carbonyl]-amino}-methyl)-pyrimidin-2-yl]-piperidine-4-carboxylic acid ethyl ester

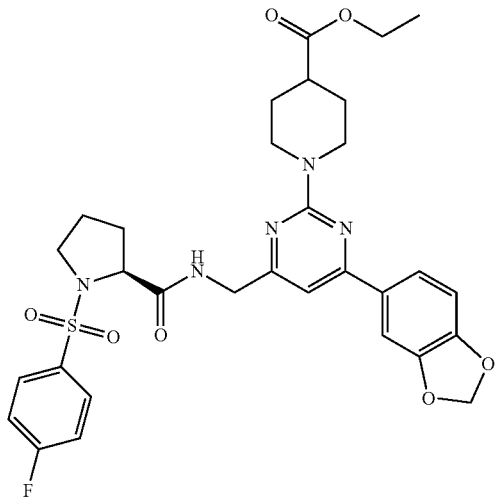 [SMILES: CCOC(=O)C1CCN(c2nc(CNC(=O)[C@@H]3CCCN3S(=O)(=O)c3ccc(F)cc3)cc(-c3ccc4c(c3)OCO4)n2)CC1]

MS (ESI): mass calcd. for $C_{31}H_{34}FN_5O_7S$, 639; m/z found 640 [M+H]$^+$. $R_t$ (min) 1.53.

Example 206

1-(4-Fluoro-benzenesulfonyl)-pyrrolidine-2S-carboxylic acid [6-benzo[1,3]dioxol-5-yl-2-(4-pyridin-2-yl-piperazin-1-yl)-pyrimidin-4-ylmethyl]-amide

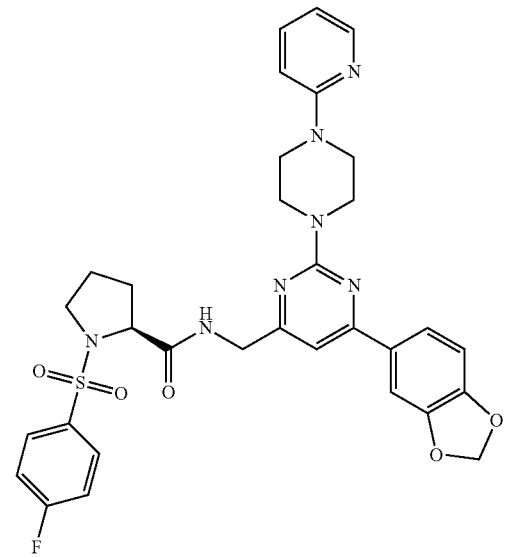 [SMILES: O=C(NCc1cc(-c2ccc3c(c2)OCO3)nc(N2CCN(c3ccccn3)CC2)n1)[C@@H]1CCCN1S(=O)(=O)c1ccc(F)cc1]

MS (ESI): mass calcd. for $C_{32}H_{32}FN_7O_5S$, 645; m/z found 646 [M+1-1]. $R_t$ (min) 1.18.

Example 207

1-(4-Fluoro-benzenesulfonyl)-pyrrolidine-2S-carboxylic acid (6-benzo[1,3]dioxol-5-yl-2-morpholin-4-yl-pyrimidin-4-ylmethyl)-amide

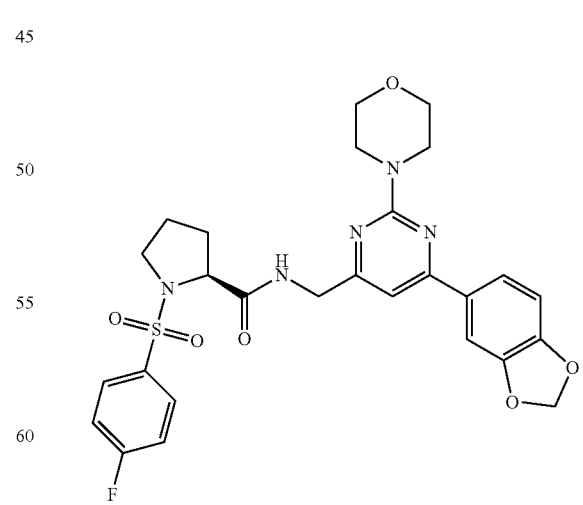

MS (ESI): mass calcd. for $C_{27}H_{28}FN_5O_6S$, 569; m/z found 570 [M+H]$^+$. $R_t$ (min) 1.44.

Example 208

1-(4-Fluoro-benzenesulfonyl)-pyrrolidine-2S-carboxylic acid [6-benzo[1,3]dioxol-5-yl-2-(3,4-dihydro-1H-isoquinolin-2-yl)-pyrimidin-4-ylmethyl]-amide

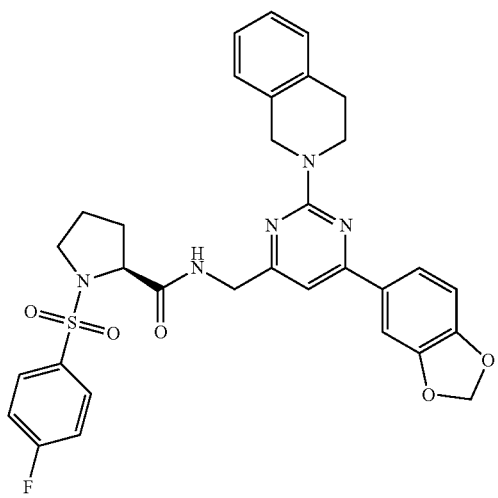 [SMILES: O=C(NCc1cc(-c2ccc3c(c2)OCO3)nc(N2CCc3ccccc3C2)n1)[C@@H]1CCCN1S(=O)(=O)c1ccc(F)cc1]

MS (ESI): mass calcd. for $C_{32}H_{30}FN_5O_5S$, 615; m/z found 616 [M+H]$^+$. $R_t$ (min) 1.50.

Example 209

1-(4-Fluoro-benzenesulfonyl)-pyrrolidine-2S-carboxylic acid [6-(4-bromo-phenyl)-2-prop-2-ynylamino-pyrimidin-4-ylmethyl]-amide

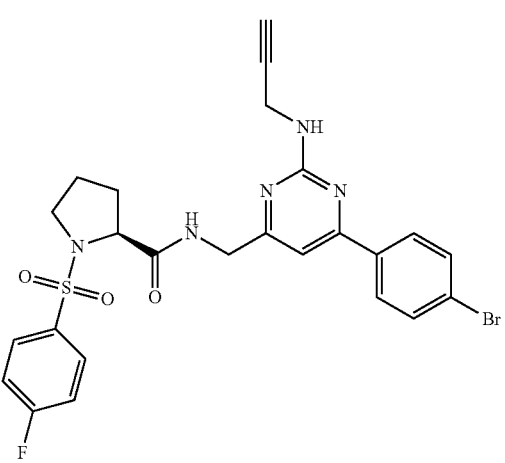 [SMILES: C#CCNc1nc(CNC(=O)[C@@H]2CCCN2S(=O)(=O)c2ccc(F)cc2)cc(-c2ccc(Br)cc2)n1]

MS (ESI): mass calcd. for $C_{25}H_{23}BrFN_5O_3S$, 571; m/z found 572 [M+H]$^+$. $R_t$ (min) 1.49.

Example 210

1-(4-Fluoro-benzenesulfonyl)-pyrrolidine-2S-carboxylic acid [6-(4-bromo-phenyl)-2-(1S-hydroxymethyl-2-phenyl-ethylamino)-pyrimidin-4-ylmethyl]-amide

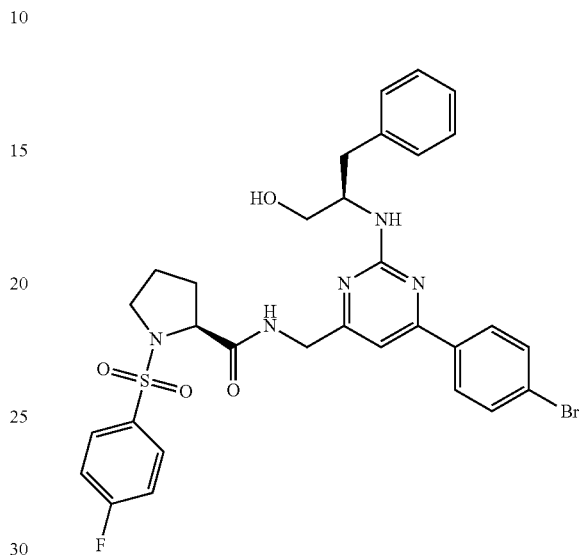

MS (ESI): mass calcd. for $C_{31}H_{31}BrFN_5O_4S$, 667; m/z found 668 [M+H]$^+$. $R_t$ (min) 1.55.

Example 211

1-(4-Fluoro-benzenesulfonyl)-pyrrolidine-2S-carboxylic acid [6-(4-bromo-phenyl)-2-cyclopentylamino-pyrimidin-4-ylmethyl]-amide

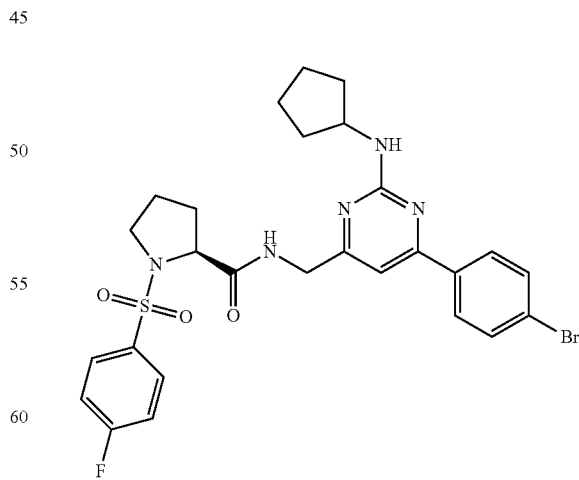

MS (ESI): mass calcd. for $C_{27}H_{29}BrFN_5O_3S$, 601; m/z found 602 [M+H]$^+$. $R_t$ (min) 1.51.

Example 212

1-(4-Fluoro-benzenesulfonyl)-pyrrolidine-2S-carboxylic acid [6-(4-bromo-phenyl)-2-(1(R,S)-phenyl-ethylamino)-pyrimidin-4-ylmethyl]-amide

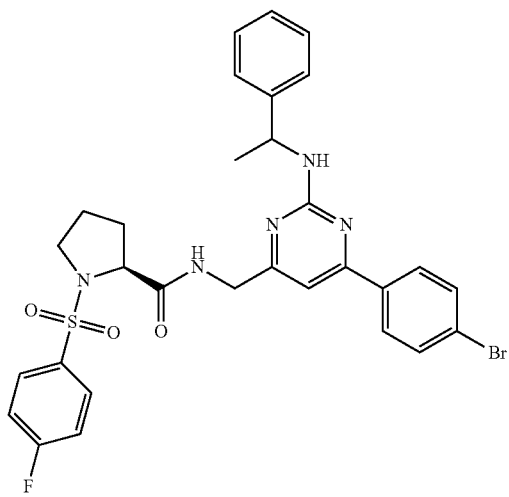 [SMILES: CC(Nc1nc(CNC(=O)[C@@H]2CCCN2S(=O)(=O)c2ccc(F)cc2)cc(-c2ccc(Br)cc2)n1)c1ccccc1]

MS (ESI): mass calcd. for $C_{30}H_{29}BrFN_5O_3S$, 637; m/z found 638 [M+H]$^+$. $R_t$ (min) 1.50.

Example 213

1-(4-Fluoro-benzenesulfonyl)-pyrrolidine-2S-carboxylic acid [2-(4-benzyl-piperidin-1-yl)-6-(4-bromo-phenyl)-pyrimidin-4-ylmethyl]-amide

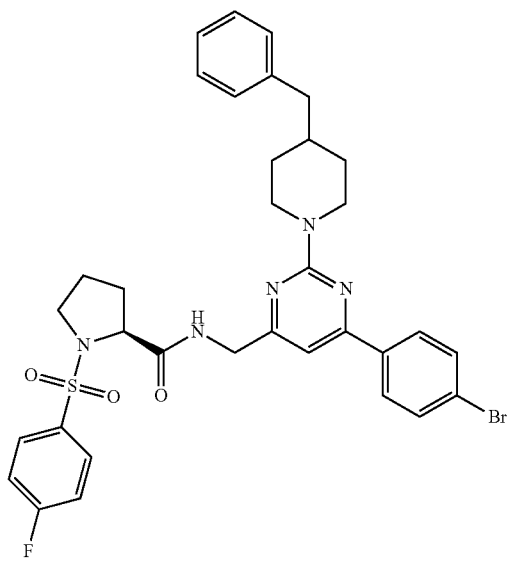 [SMILES: O=C(NCc1cc(-c2ccc(Br)cc2)nc(N2CCC(Cc3ccccc3)CC2)n1)[C@@H]1CCCN1S(=O)(=O)c1ccc(F)cc1]

MS (ESI): mass calcd. for $C_{34}H_{35}BrFN_5O_3S$, 691; m/z found 692 [M+H]$^+$. $R_t$ (min) 1.78.

Example 214

1-[4-(4-Bromo-phenyl)-6-({[1-(4-fluoro-benzenesulfonyl)-pyrrolidine-2S-carbonyl]-amino}-methyl)-pyrimidin-2-yl]-piperidine-4-carboxylic acid ethyl ester

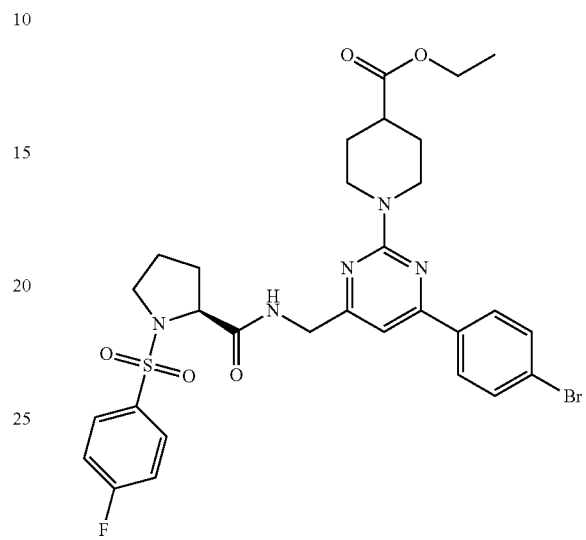

MS (ESI): mass calcd. for $C_{30}H_{33}BrFN_5O_5S$, 673; m/z found 674 [M+H]$^+$. $R_t$ (min) 1.64.

Example 215

1-(4-Fluoro-benzenesulfonyl)-pyrrolidine-2S-carboxylic acid [6-(4-bromo-phenyl)-2-butylamino-pyrimidin-4-ylmethyl]-amide

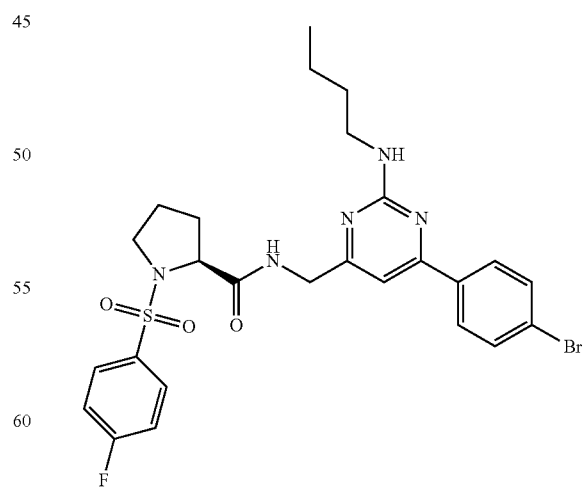

MS (ESI): mass calcd. for $C_{26}H_{29}BrFN_5O_3S$, 589; m/z found 590 [M+H]$^+$. $R_t$ (min) 1.62.

Example 216

1-(4-Fluoro-benzenesulfonyl)-pyrrolidine-2S-carboxylic acid [6-(4-bromo-phenyl)-2-(4-pyridin-2-yl-piperazin-1-yl)-pyrimidin-4-ylmethyl]-amide

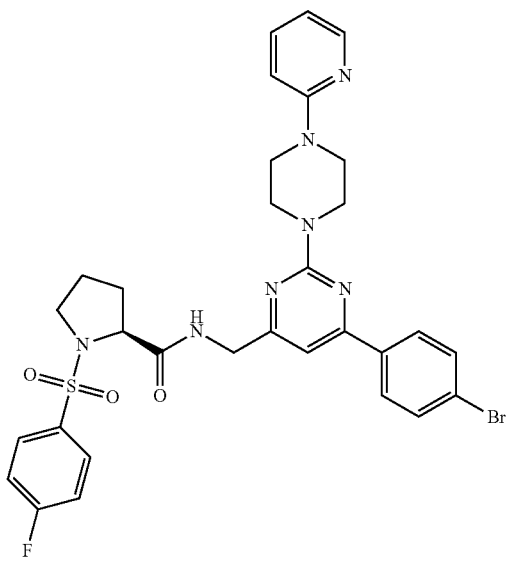 [SMILES: O=C(NCc1cc(-c2ccc(Br)cc2)nc(N2CCN(c3ccccn3)CC2)n1)[C@@H]1CCCN1S(=O)(=O)c1ccc(F)cc1]

MS (ESI): mass calcd. for $C_{31}H_{31}BrFN_7O_3S$, 680; m/z found 680 [M$^+$]. R$_t$ (min) 1.46.

Example 217

1-(4-Fluoro-benzenesulfonyl)-pyrrolidine-2S-carboxylic acid [6-(4-bromo-phenyl)-2-morpholin-4-yl-pyrimidin-4-ylmethyl]-amide

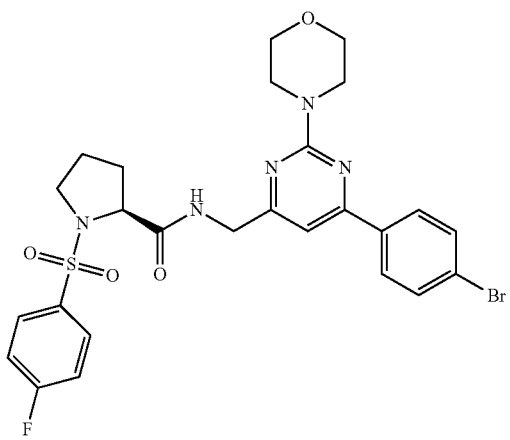 [SMILES: O=C(NCc1cc(-c2ccc(Br)cc2)nc(N2CCOCC2)n1)[C@@H]1CCCN1S(=O)(=O)c1ccc(F)cc1]

MS (ESI): mass calcd. for $C_{26}H_{27}BrFN_5O_4S$, 604; m/z found 604 [M$^+$]. R$_t$ (min) 1.46.

Example 218

1-(4-Fluoro-benzenesulfonyl)-pyrrolidine-2S-carboxylic acid [6-(4-bromo-phenyl)-2-(4-methyl-[1,4]diazepan-1-yl)-pyrimidin-4-ylmethyl]-amide

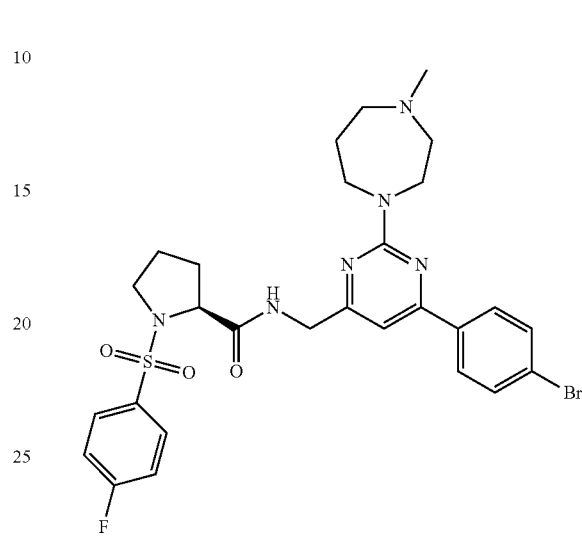

MS (ESI): mass calcd. for $C_{28}H_{32}BrFN_6O_3S$, 631; m/z found 631 [M$^+$]. R$_t$ (min) 1.25.

Example 219

1-(4-Fluoro-benzenesulfonyl)-pyrrolidine-2S-carboxylic acid {6-(4-bromo-phenyl)-2-[(pyridin-3-ylmethyl)-amino]-pyrimidin-4-ylmethyl}-amide

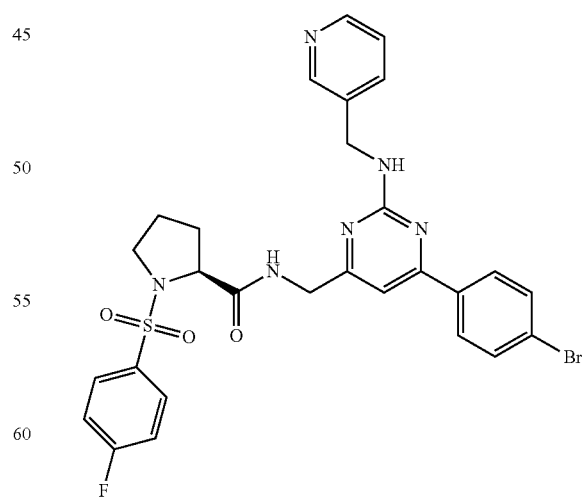

MS (ESI): mass calcd. for $C_{28}H_{26}BrFN_6O_3S$, 625; m/z found 625 [M$^+$]. R$_t$ (min) 1.27.

Example 220

1-(4-Fluoro-benzenesulfonyl)-pyrrolidine-2S-carboxylic acid [6-(4-bromo-phenyl)-2-(4-methyl-piperazin-1-yl)-pyrimidin-4-ylmethyl]-amide

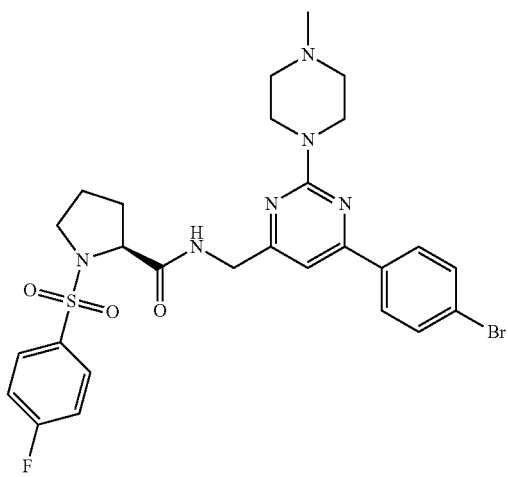

MS (ESI): mass calcd. for $C_{27}H_{30}BrFN_6O_3S$, 617; m/z found 617 [M$^+$]. $R_t$ (min) 1.23.

Example 221

1-(4-Fluoro-benzenesulfonyl)-pyrrolidine-2S-carboxylic acid {6-(4-bromo-phenyl)-2-[2-(2,4-dichloro-phenyl)-ethylamino]-pyrimidin-4-ylmethyl}-amide

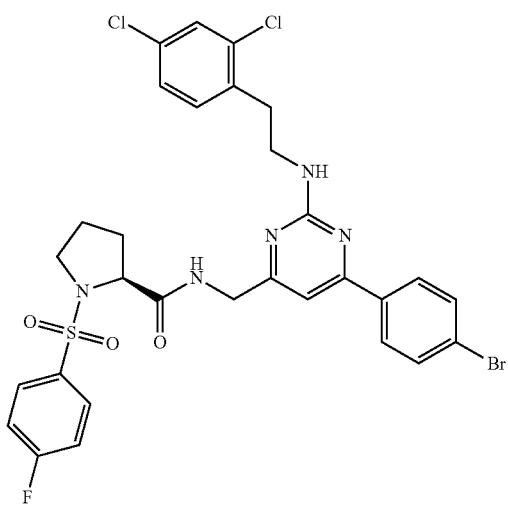 [SMILES: O=C(NCc1cc(-c2ccc(Br)cc2)nc(NCCc2ccc(Cl)cc2Cl)n1)[C@@H]1CCCN1S(=O)(=O)c1ccc(F)cc1]

MS (ESI): mass calcd. for $C_{30}H_{27}BrCl_2FN_5O_3S$, 707; m/z found 708 [M+H]$^+$. $R_t$ (min) 1.72.

Example 222

1-(4-Fluoro-benzenesulfonyl)-pyrrolidine-2S-carboxylic acid [6-(4-bromo-phenyl)-2-(3,4-dihydro-1H-isoquinolin-2-yl)-pyrimidin-4-ylmethyl]-amide

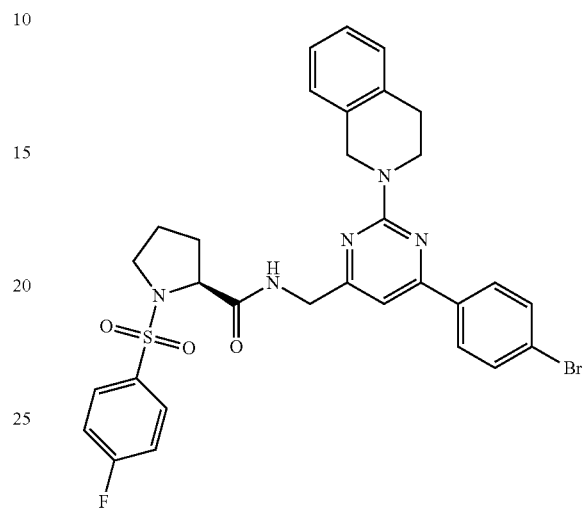

MS (ESI): mass calcd. for $C_{31}H_{29}BrFN_5O_3S$, 650; m/z found 651 [M+H]$^+$. $R_t$ (min) 1.56.

Example 223

1-(4-Fluoro-benzenesulfonyl)-pyrrolidine-2S-carboxylic acid [6-benzo[1,3]dioxol-5-yl-2-(3-chlorophenylamino)-pyrimidin-4-ylmethyl]-amide

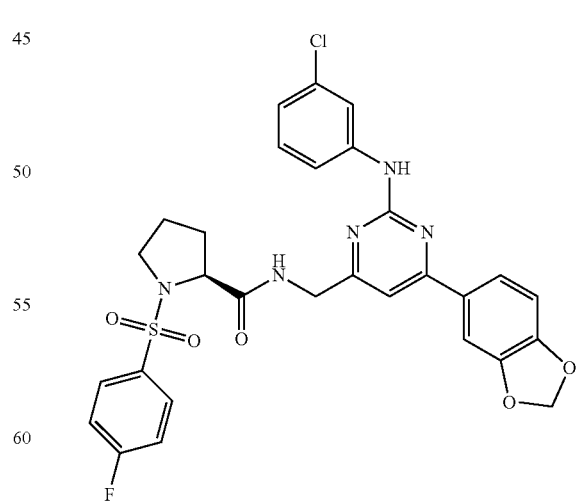

MS (ESI): mass calcd. for $C_{29}H_{25}ClFN_5O_5S$, 610; m/z found 610 [M$^+$]. $R_t$ (min) 1.54.

Example 224

1-(4-Fluoro-benzenesulfonyl)-pyrrolidine-2S-carboxylic acid [6-benzo[1,3]dioxol-5-yl-2-(4-chlorophenylamino)-pyrimidin-4-ylmethyl]-amide

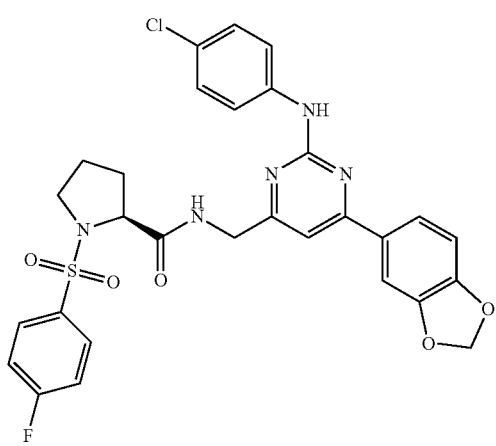

MS (ESI): mass calcd. for $C_{29}H_{25}ClFN_5O_5S$, 610; m/z found 610 [M⁺]. $R_t$ (min) 1.54.

Example 225

1-(4-Fluoro-benzenesulfonyl)-pyrrolidine-2S-carboxylic acid [6-benzo[1,3]dioxol-5-yl-2-(4-fluorophenylamino)-pyrimidin-4-ylmethyl]-amide

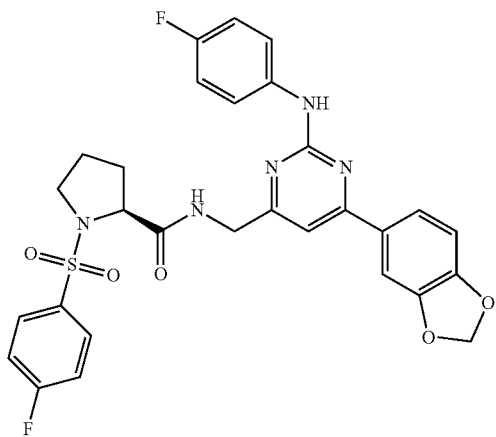 [SMILES: O=C(NCc1cc(-c2ccc3c(c2)OCO3)nc(Nc2ccc(Cl)cc2)n1)[C@@H]1CCCN1S(=O)(=O)c1ccc(F)cc1]

MS (ESI): mass calcd. for $C_{29}H_{25}F_2N_5O_5S$, 593; m/z found 594 [M+H]⁺. $R_t$ (min) 1.48.

Example 226

1-(4-Fluoro-benzenesulfonyl)-pyrrolidine-2S-carboxylic acid [2-[4-(2-fluoro-phenyl)-piperazin-1-yl]-6-(4-trifluoromethoxy-phenyl)-pyrimidin-4-ylmethyl]-amide

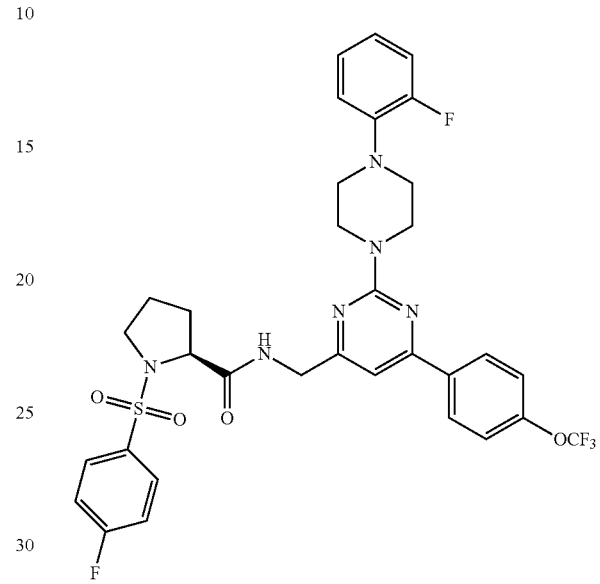

Example 227

1-(4-Fluoro-benzenesulfonyl)-pyrrolidine-2S-carboxylic acid {6-(4-fluoro-phenyl)-2-[4-(2-fluoro-phenyl)-piperazin-1-yl]-pyrimidin-4-ylmethyl}-amide

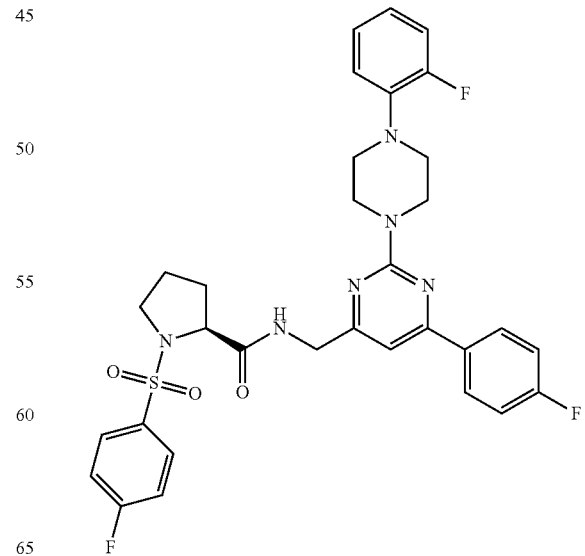

Example 228

1-(4-Fluoro-benzenesulfonyl)-pyrrolidine-2S-carboxylic acid {6-(2,6-dimethoxy-phenyl)-2-[4-(2-fluoro-phenyl)-piperazin-1-yl]-pyrimidin-4-ylmethyl}-amide

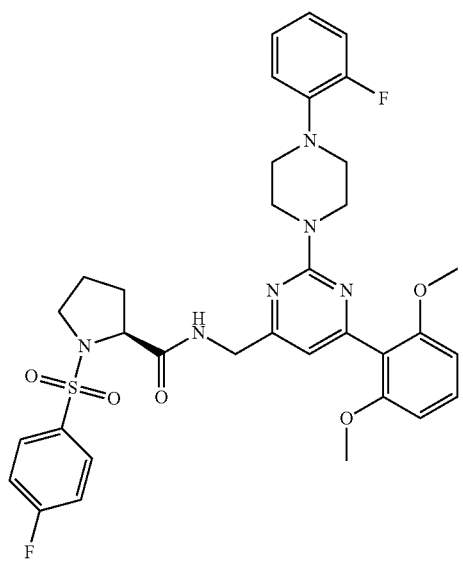 [SMILES: COc1cccc(OC)c1-c1cc(CNC(=O)[C@@H]2CCCN2S(=O)(=O)c2ccc(F)cc2)nc(N2CCN(c3ccccc3F)CC2)n1]

Example 229

1-(4-Fluoro-benzenesulfonyl)-pyrrolidine-2-carboxylic acid {6-(4-cyano-phenyl)-2-[4-(2-fluoro-phenyl)-piperazin-1-yl]-pyrimidin-4-ylmethyl}-amide

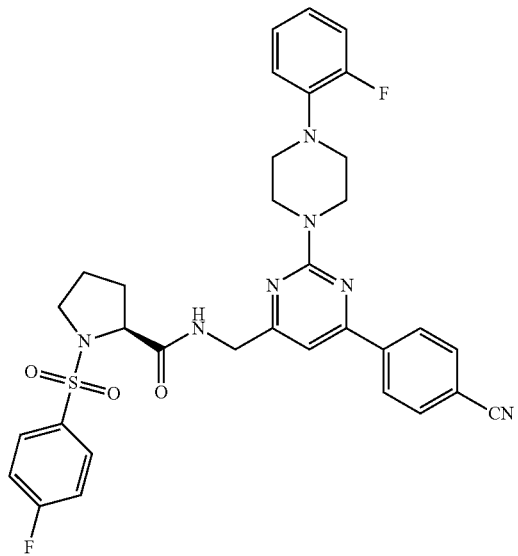 [SMILES: N#Cc1ccc(-c2cc(CNC(=O)[C@@H]3CCCN3S(=O)(=O)c3ccc(F)cc3)nc(N3CCN(c4ccccc4F)CC3)n2)cc1]

Example 230

1-(4-Fluoro-benzenesulfonyl)-pyrrolidine-2S-carboxylic acid {6-(5-fluoro-2-methoxy-phenyl)-2-[4-(2-fluoro-phenyl)-piperazin-1-yl]-pyrimidin-4-ylmethyl}-amide

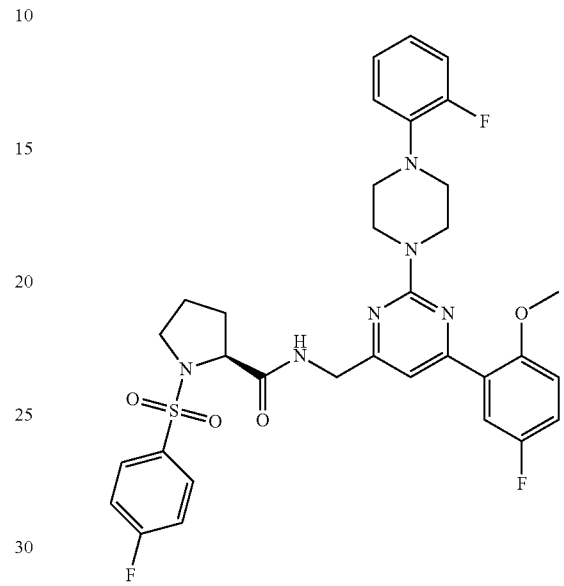

Example 231

1-(4-Fluoro-benzenesulfonyl)-pyrrolidine-2-carboxylic acid {6-(5-fluoro-2-methoxy-phenyl)-2-[4-(2-fluoro-phenyl)-piperazin-1-yl]-pyrimidin-4-ylmethyl}-amide

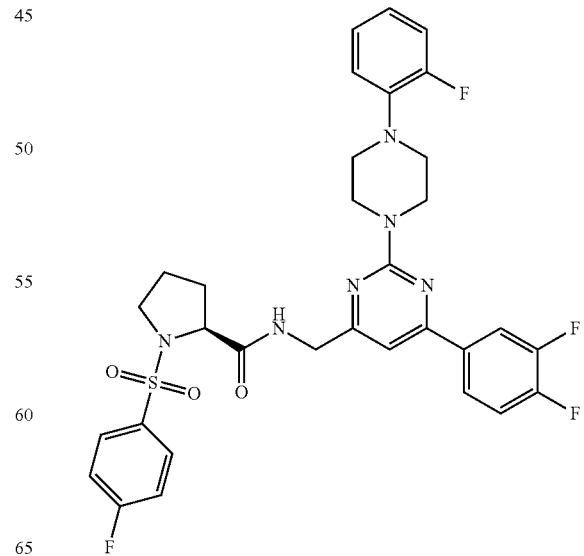

Example 232

1-(4-Fluoro-benzenesulfonyl)-pyrrolidine-2S-carboxylic acid {6-(2,5-dimethyl-phenyl)-2-[4-(2-fluoro-phenyl)-piperazin-1-yl]-pyrimidin-4-ylmethyl}-amide

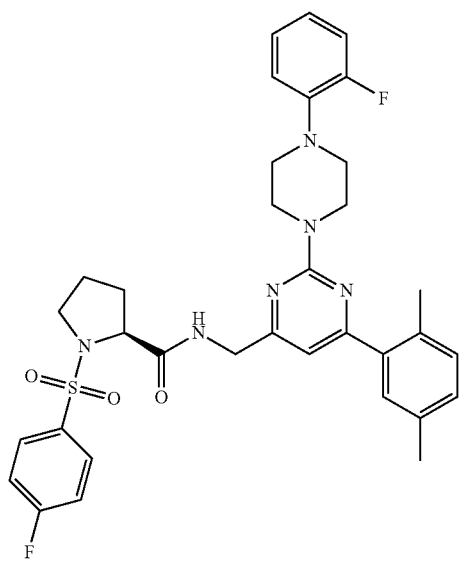 [SMILES: Cc1ccc(C)c(-c2cc(CNC(=O)[C@@H]3CCCN3S(=O)(=O)c3ccc(F)cc3)nc(N3CCN(c4ccccc4F)CC3)n2)c1]

Example 233

1-(4-Fluoro-benzenesulfonyl)-pyrrolidine-2S-carboxylic acid {6-(2,4-difluoro-phenyl)-2-[4-(2-fluoro-phenyl)-piperazin-1-yl]-pyrimidin-4-ylmethyl}-amide

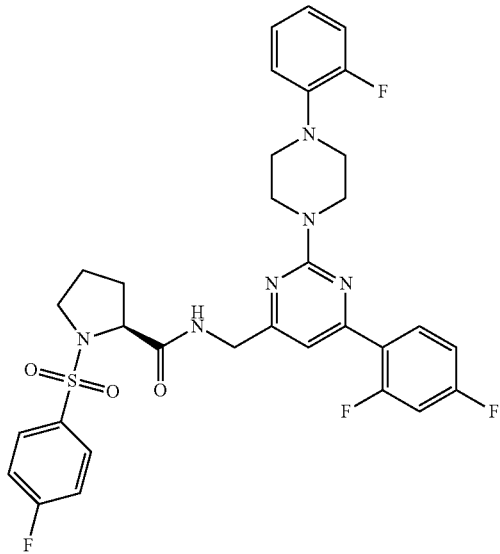 [SMILES: O=C(NCc1cc(-c2ccc(F)cc2F)nc(N2CCN(c3ccccc3F)CC2)n1)[C@@H]1CCCN1S(=O)(=O)c1ccc(F)cc1]

Example 234

1-(4-Fluoro-benzenesulfonyl)-pyrrolidine-2S-carboxylic acid [2-[4-(2-fluoro-phenyl)-piperazin-1-yl]-6-(3-trifluoromethoxy-phenyl)-pyrimidin-4-ylmethyl]-amide

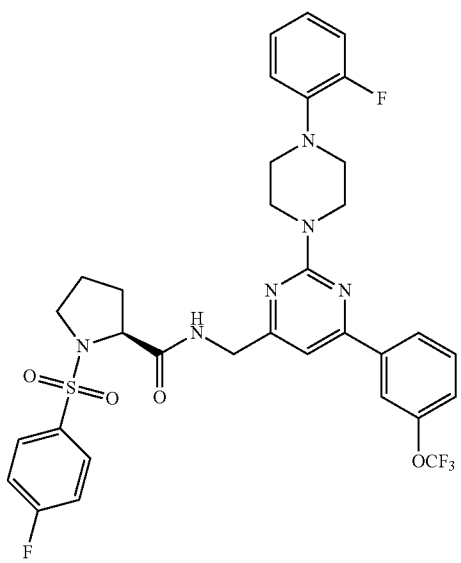 [SMILES: O=C(NCc1cc(-c2cccc(OC(F)(F)F)c2)nc(N2CCN(c3ccccc3F)CC2)n1)[C@@H]1CCCN1S(=O)(=O)c1ccc(F)cc1]

Example 235

1-(4-Fluoro-benzenesulfonyl)-pyrrolidine-2S-carboxylic acid {6-(3-cyano-phenyl)-2-[4-(2-fluoro-phenyl)-piperazin-1-yl]-pyrimidin-4-ylmethyl}-amide

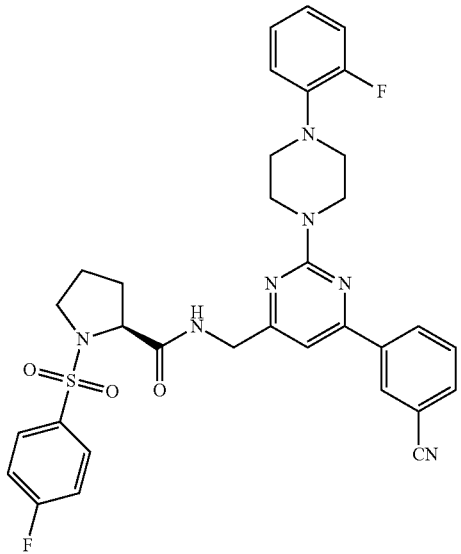 [SMILES: N#Cc1cccc(-c2cc(CNC(=O)[C@@H]3CCCN3S(=O)(=O)c3ccc(F)cc3)nc(N3CCN(c4ccccc4F)CC3)n2)c1]

171

Example 236

1-(4-Fluoro-benzenesulfonyl)-pyrrolidine-2S-carboxylic acid {6-(3,5-dimethyl-phenyl)-2-[4-(2-fluoro-phenyl)-piperazin-1-yl]-pyrimidin-4-ylmethyl}-amide

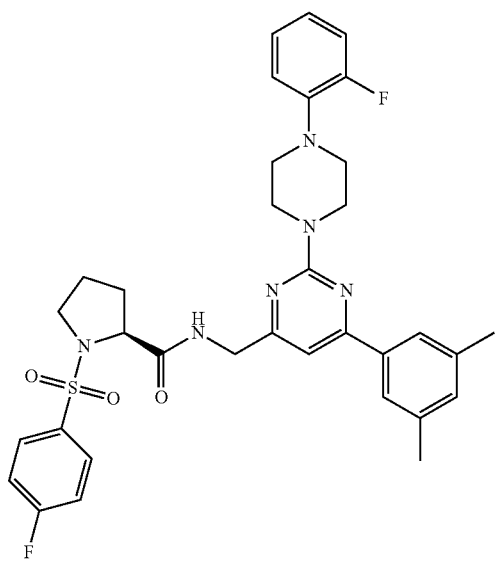 [SMILES: Cc1cc(C)cc(-c2cc(CNC(=O)[C@@H]3CCCN3S(=O)(=O)c3ccc(F)cc3)nc(N3CCN(c4ccccc4F)CC3)n2)c1]

Example 237

1-(4-Fluoro-benzenesulfonyl)-pyrrolidine-2S-carboxylic acid {6-(3-dimethylamino-phenyl)-2-[4-(2-fluoro-phenyl)-piperazin-1-yl]-pyrimidin-4-ylmethyl}-amide

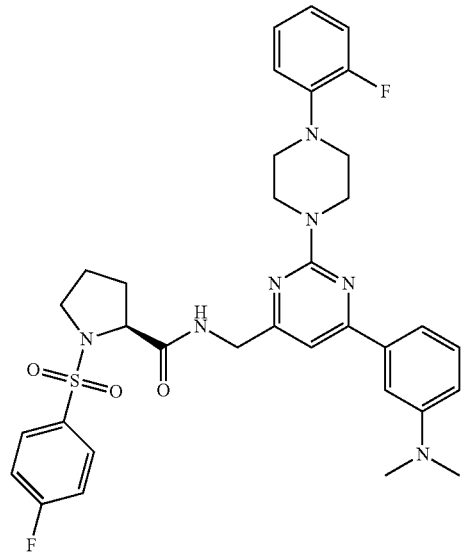 [SMILES: CN(C)c1cccc(-c2cc(CNC(=O)[C@@H]3CCCN3S(=O)(=O)c3ccc(F)cc3)nc(N3CCN(c4ccccc4F)CC3)n2)c1]

172

Example 238

1-(4-Fluoro-benzenesulfonyl)-pyrrolidine-2S-carboxylic acid {6-benzo[1,3]dioxol-5-yl-2-[4-(2-fluoro-phenyl)-piperazin-1-yl]-pyrimidin-4-ylmethyl}-amide

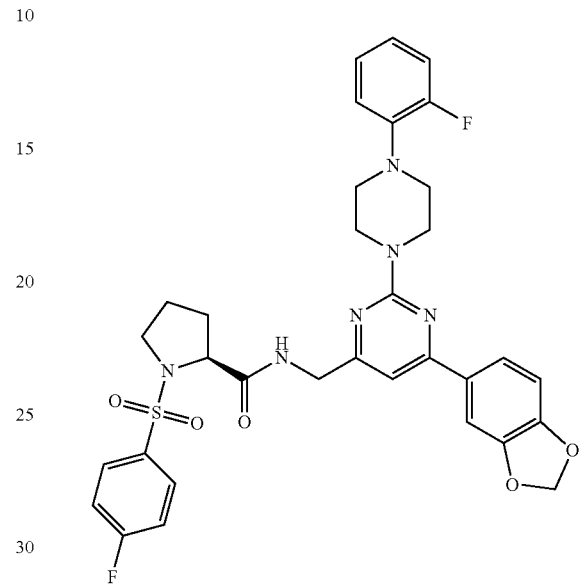

Example 239

1-(4-Fluoro-benzenesulfonyl)-pyrrolidine-2S-carboxylic acid {6-(3-chloro-phenyl)-2-[4-(2-fluoro-phenyl)-piperazin-1-yl]-pyrimidin-4-ylmethyl}-amide

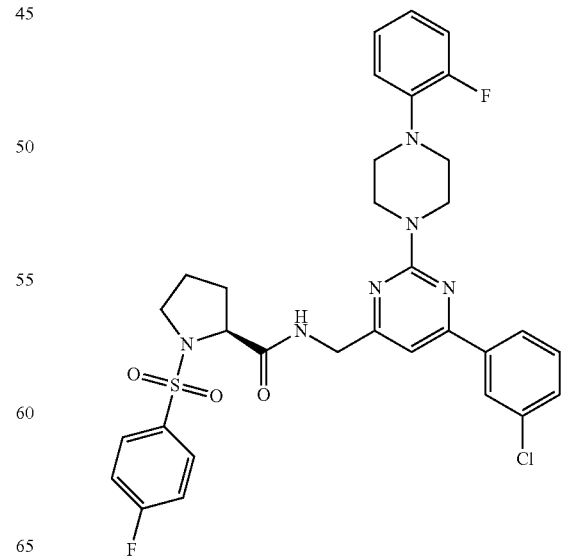

Example 240

1-(4-Fluoro-benzenesulfonyl)-pyrrolidine-2S-carboxylic acid {6-(2,6-dimethyl-phenyl)-2-[4-(2-fluoro-phenyl)-piperazin-1-yl]-pyrimidin-4-ylmethyl}-amide

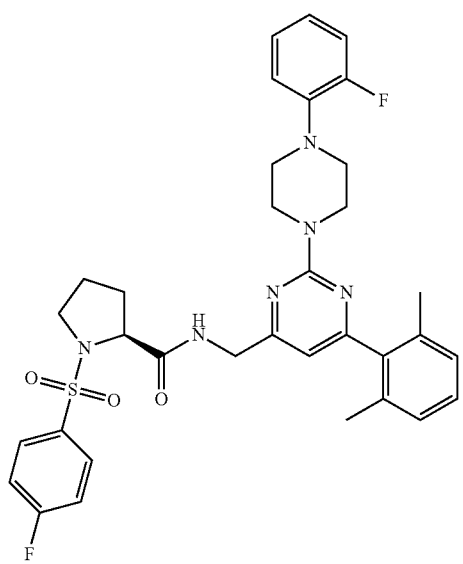 [SMILES: Cc1cccc(C)c1-c1cc(CNC(=O)[C@@H]2CCCN2S(=O)(=O)c2ccc(F)cc2)nc(N2CCN(c3ccccc3F)CC2)n1]

Example 241

1-(4-Fluoro-benzenesulfonyl)-pyrrolidine-2-carboxylic acid {6-(4-chloro-phenyl)-2-[4-(2-fluoro-phenyl)-piperazin-1-yl]-pyrimidin-4-ylmethyl}-amide

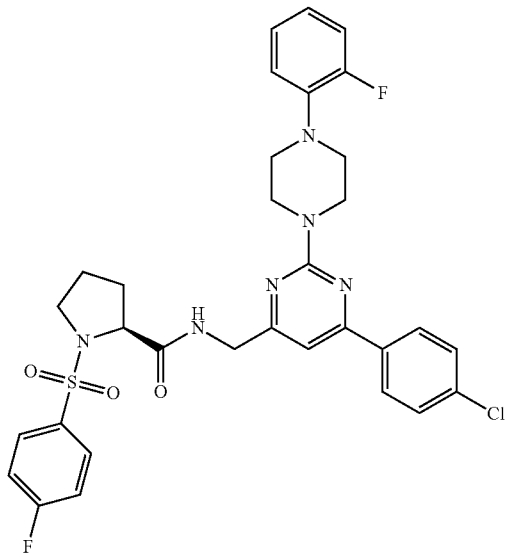 [SMILES: O=C(NCc1cc(-c2ccc(Cl)cc2)nc(N2CCN(c3ccccc3F)CC2)n1)[C@@H]1CCCN1S(=O)(=O)c1ccc(F)cc1]

Example 242

1-(4-Fluoro-benzenesulfonyl)-pyrrolidine-2-carboxylic acid {6-(2-chloro-phenyl)-2-[4-(2-fluoro-phenyl)-piperazin-1-yl]-pyrimidin-4-ylmethyl}-amide

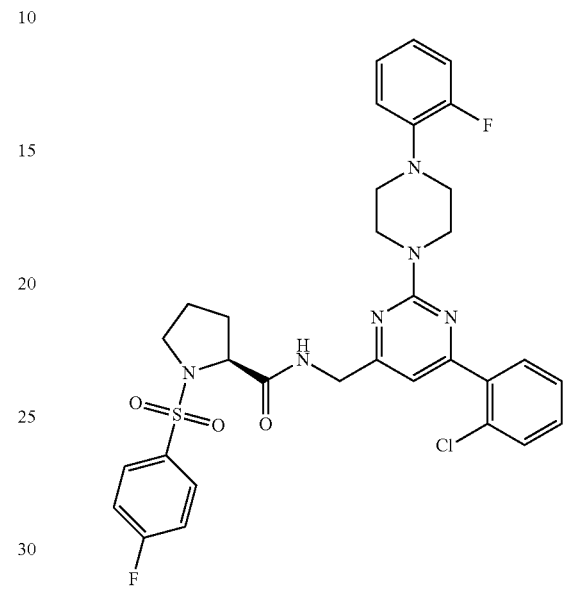

Example 243

1-(4-Fluoro-benzenesulfonyl)-pyrrolidine-2S-carboxylic acid [2-[4-(2-fluoro-phenyl)-piperazin-1-yl]-6-(3-trifluoromethyl-phenyl)-pyrimidin-4-ylmethyl]-amide

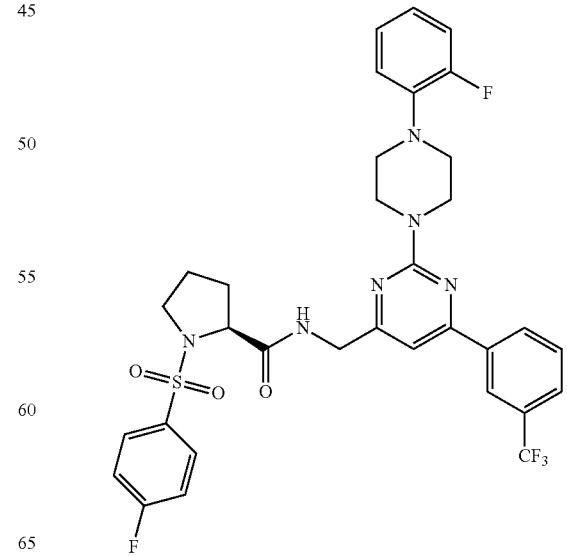

Example 244

1-(4-Fluoro-benzenesulfonyl)-pyrrolidine-2-carboxylic acid {6-(3-chloro-4-fluoro-phenyl)-2-[4-(2-fluoro-phenyl)-piperazin-1-yl]-pyrimidin-4-ylmethyl}-amide

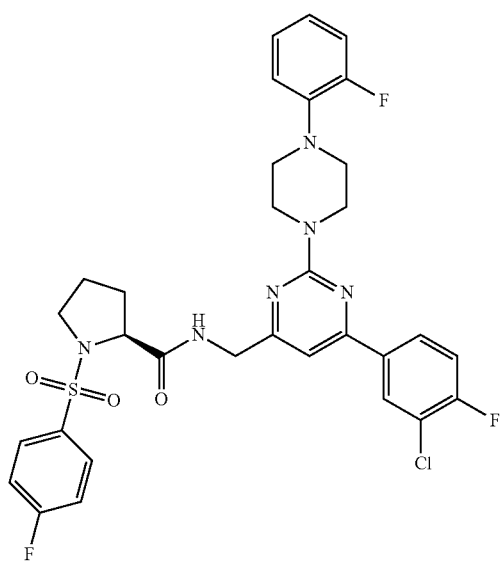

Example 245

1-(4-Fluoro-benzenesulfonyl)-pyrrolidine-2S-carboxylic acid {6-(2-fluoro-phenyl)-2-[4-(2-fluoro-phenyl)-piperazin-1-yl]-pyrimidin-4-ylmethyl}-amide

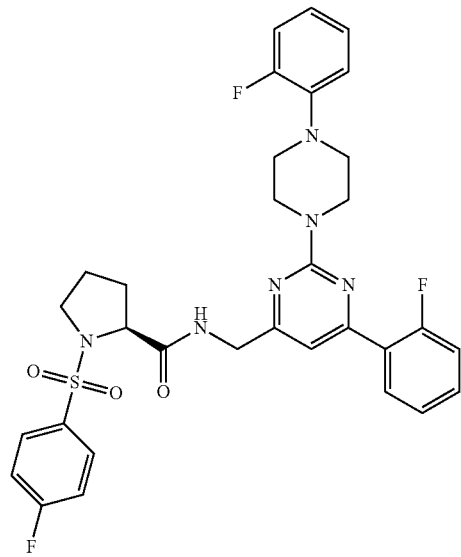 [SMILES: O=C(NCc1cc(-c2ccccc2F)nc(N2CCN(c3ccccc3F)CC2)n1)[C@@H]1CCCN1S(=O)(=O)c1ccc(F)cc1]

Example 246

1-(4-Fluoro-benzenesulfonyl)-pyrrolidine-2S-carboxylic acid {6-(3-fluoro-phenyl)-2-[4-(2-fluoro-phenyl)-piperazin-1-yl]-pyrimidin-4-ylmethyl}-amide

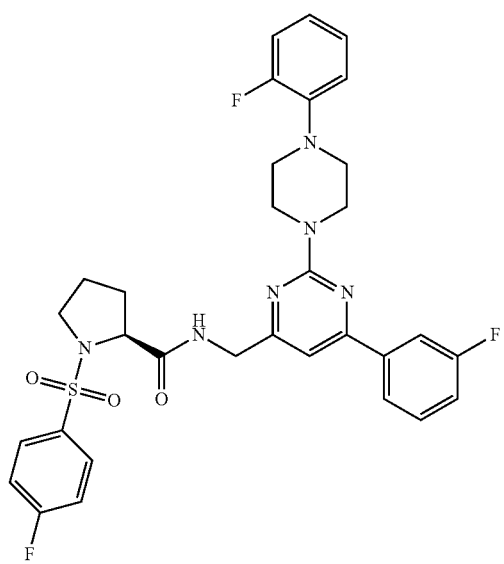 [SMILES: O=C(NCc1cc(-c2cccc(F)c2)nc(N2CCN(c3ccccc3F)CC2)n1)[C@@H]1CCCN1S(=O)(=O)c1ccc(F)cc1]

Example 247

1-(4-Fluoro-benzenesulfonyl)-pyrrolidine-2S-carboxylic acid {2-[4-(2-fluoro-phenyl)-piperazin-1-yl]-6-o-tolyl-pyrimidin-4-ylmethyl}-amide

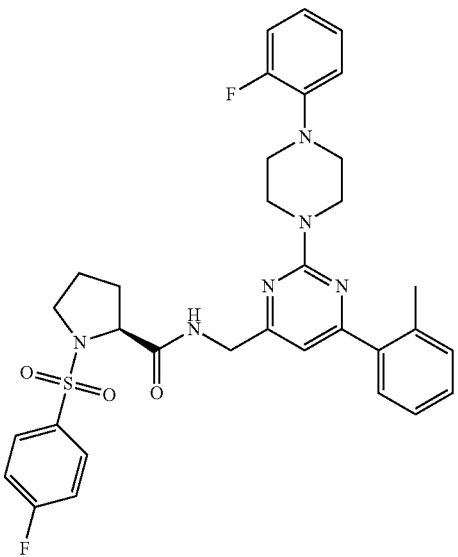 [SMILES: Cc1ccccc1-c1cc(CNC(=O)[C@@H]2CCCN2S(=O)(=O)c2ccc(F)cc2)nc(N2CCN(c3ccccc3F)CC2)n1]

177

Example 248

1-(4-Fluoro-benzenesulfonyl)-pyrrolidine-2S-carboxylic acid {6-(3,4-dichloro-phenyl)-2-[4-(2-fluoro-phenyl)-piperazin-1-yl]-pyrimidin-4-ylmethyl}-amide

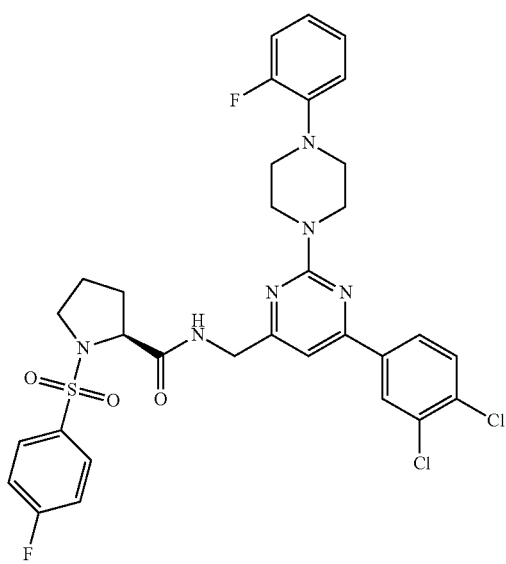 [SMILES: O=C(NCc1cc(-c2ccc(Cl)c(Cl)c2)nc(N2CCN(c3ccccc3F)CC2)n1)[C@@H]1CCCN1S(=O)(=O)c1ccc(F)cc1]

Example 249

1-(4-Fluoro-benzenesulfonyl)-pyrrolidine-2S-carboxylic acid {6-(3,5-difluoro-phenyl)-2-[4-(2-fluoro-phenyl)-piperazin-1-yl]-pyrimidin-4-ylmethyl}-amide

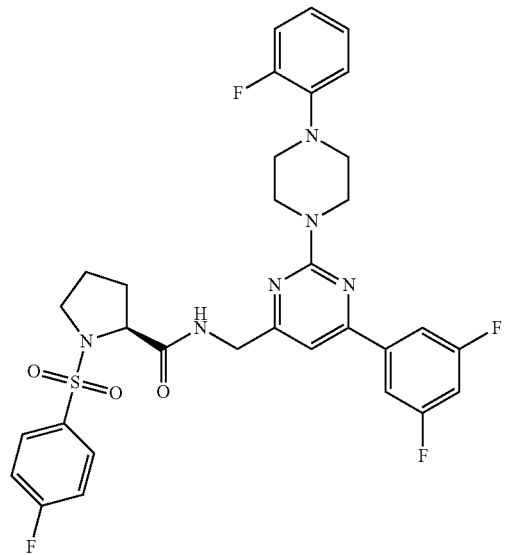 [SMILES: O=C(NCc1cc(-c2cc(F)cc(F)c2)nc(N2CCN(c3ccccc3F)CC2)n1)[C@@H]1CCCN1S(=O)(=O)c1ccc(F)cc1]

178

Example 250

1-(4-Fluoro-benzenesulfonyl)-pyrrolidine-2S-carboxylic acid {6-(2,4-dichloro-phenyl)-2-[4-(2-fluoro-phenyl)-piperazin-1-yl]-pyrimidin-4-ylmethyl}-amide

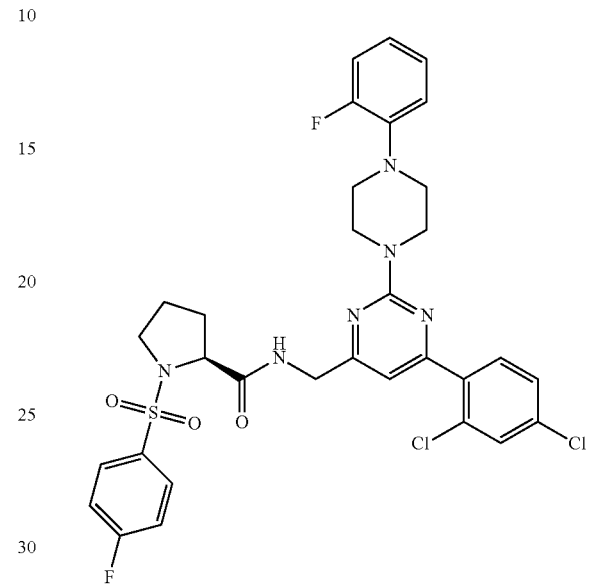

Example 251

1-(4-Fluoro-benzenesulfonyl)-pyrrolidine-2S-carboxylic acid {2-[4-(2-fluoro-phenyl)-piperazin-1-yl]-6-phenyl-pyrimidin-4-ylmethyl}-amide

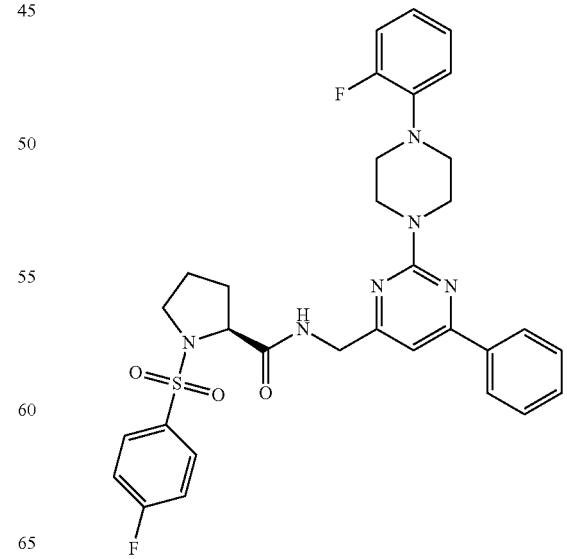

Example 252

1-(2-Chloro-4-fluoro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide

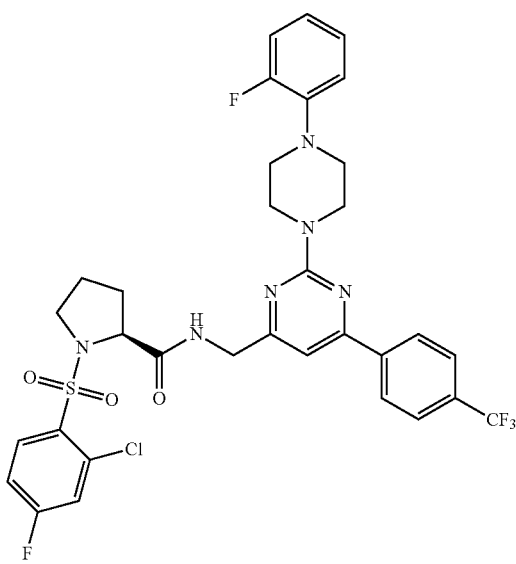 [SMILES: O=C(NCc1cc(-c2ccc(C(F)(F)F)cc2)nc(N2CCN(c3ccccc3F)CC2)n1)[C@@H]1CCCN1S(=O)(=O)c1ccc(F)cc1Cl]

Example 253

1-(3-Methoxy-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide

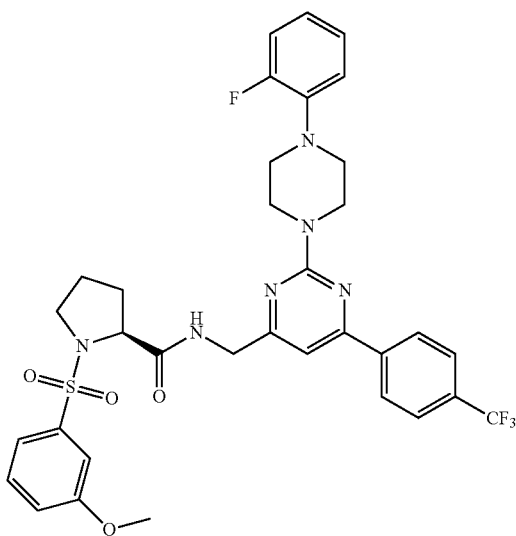 [SMILES: COc1cccc(S(=O)(=O)N2CCC[C@H]2C(=O)NCc2cc(-c3ccc(C(F)(F)F)cc3)nc(N3CCN(c4ccccc4F)CC3)n2)c1]

Example 254

1-(3-Chloro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide

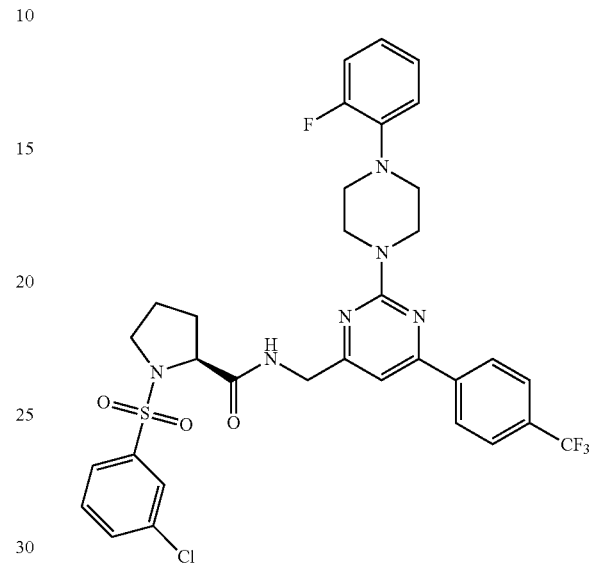

Example 255

1-(4-Methoxy-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide

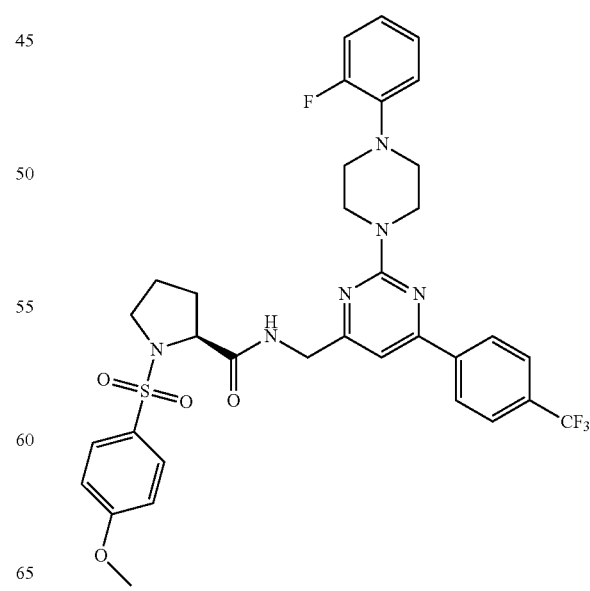

Example 256

1-(5-Fluoro-2-methyl-benzenesulfonyl)-pyrrolidine-2-carboxylic acid [2-[4-(2-fluoro-phenyl)-piperazin-1-yl]-6-(4-trifluoromethyl-phenyl)-pyrimidin-4-ylmethyl]-amide

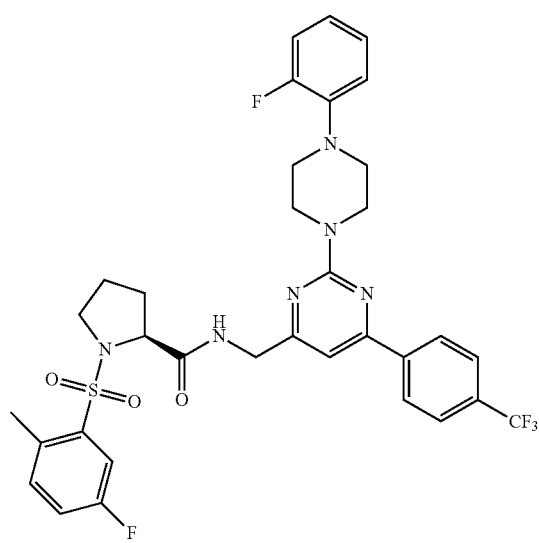 [SMILES: Cc1ccc(F)cc1S(=O)(=O)N1CCC[C@H]1C(=O)NCc1cc(-c2ccc(C(F)(F)F)cc2)nc(N2CCN(c3ccccc3F)CC2)n1]

Example 257

1-(5-Chloro-2-fluoro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide

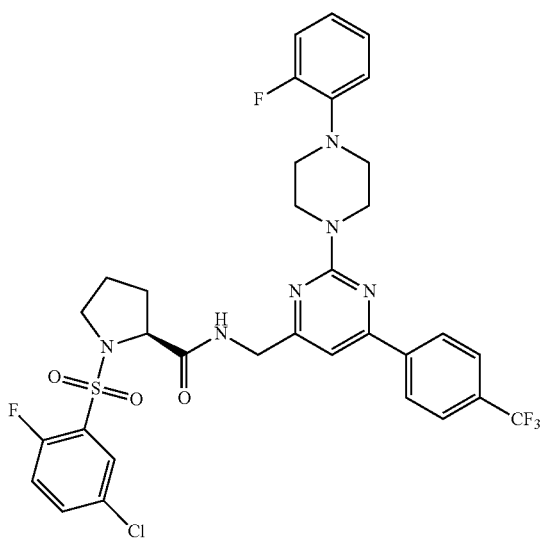 [SMILES: O=C(NCc1cc(-c2ccc(C(F)(F)F)cc2)nc(N2CCN(c3ccccc3F)CC2)n1)[C@@H]1CCCN1S(=O)(=O)c1cc(Cl)ccc1F]

Example 258

1-(3,4-Difluoro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide

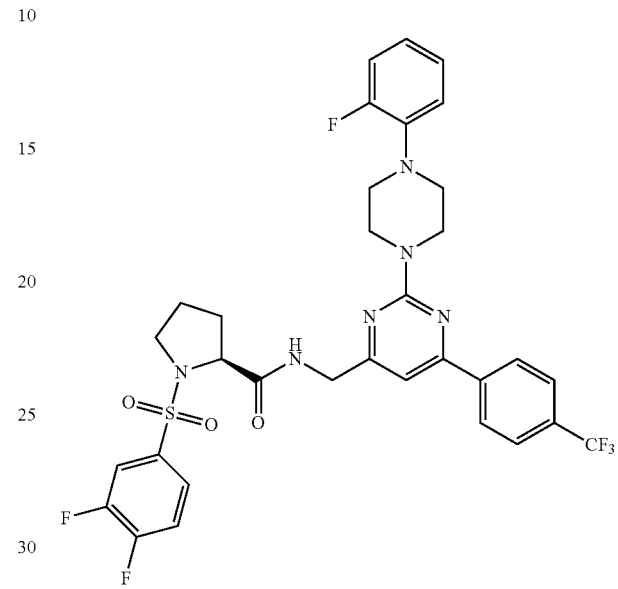

Example 259

1-(3-Chloro-4-fluoro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide

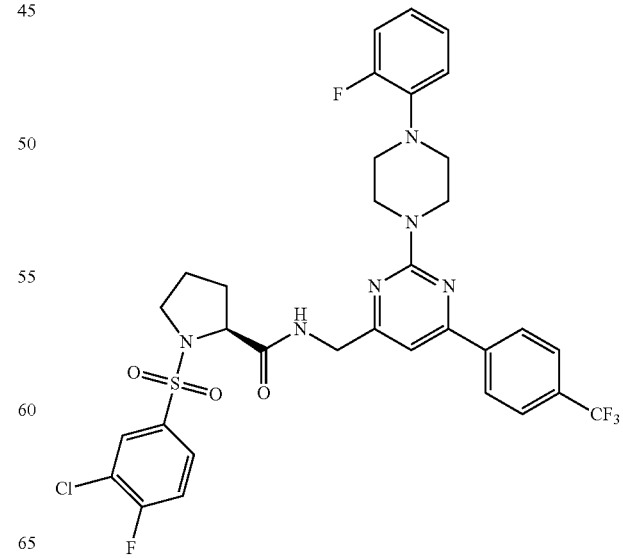

183

Example 260

1-(4-Isopropyl-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide

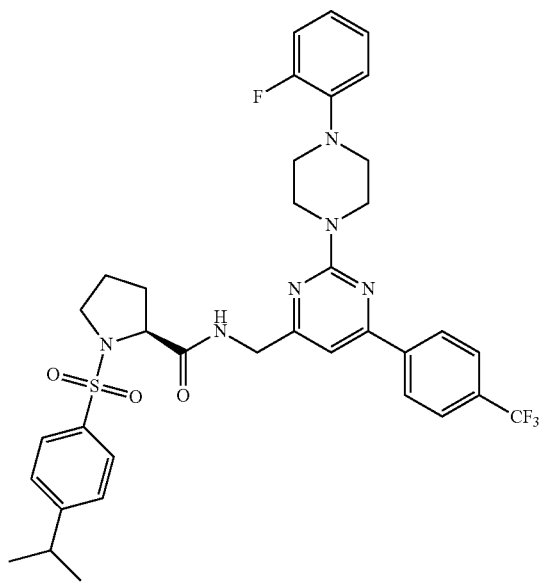 [SMILES: CC(C)c1ccc(S(=O)(=O)N2CCC[C@H]2C(=O)NCc2cc(-c3ccc(C(F)(F)F)cc3)nc(N3CCN(c4ccccc4F)CC3)n2)cc1]

Example 261

1-(2,3,4-Trifluoro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide

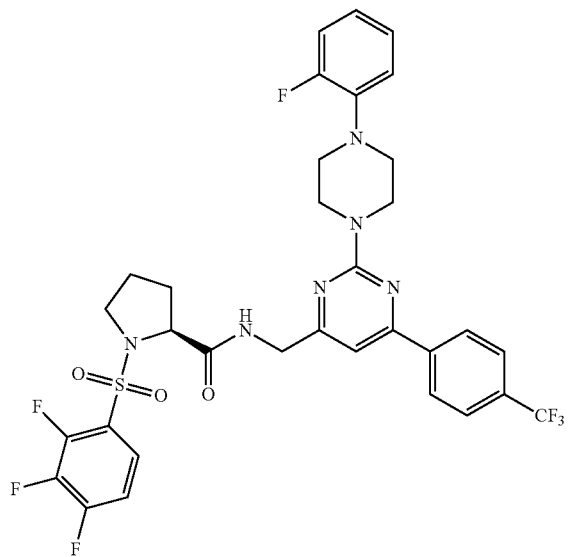 [SMILES: O=C(NCc1cc(-c2ccc(C(F)(F)F)cc2)nc(N2CCN(c3ccccc3F)CC2)n1)[C@@H]1CCCN1S(=O)(=O)c1ccc(F)c(F)c1F]

184

Example 262

1-(3-Chloro-2-methyl-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide

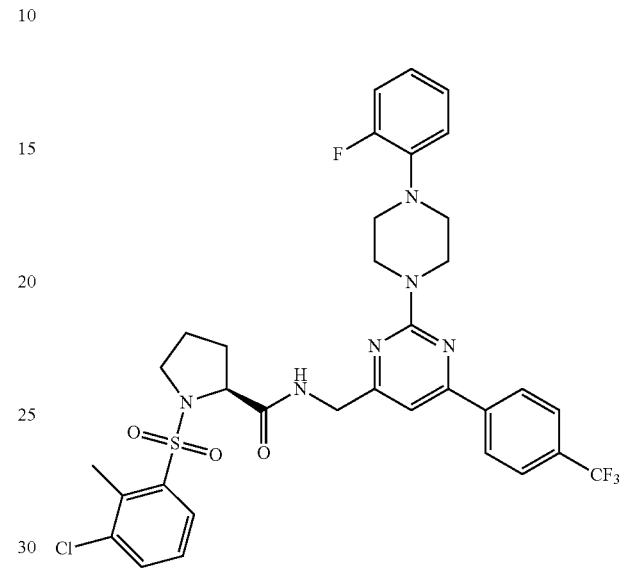

Example 263

1-(5-Chloro-thiophene-2-sulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide

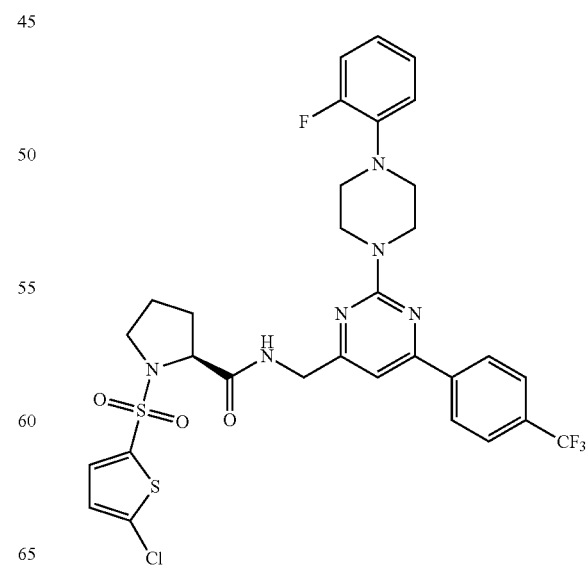

Example 264

1-(Thiophene-2-sulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide Example 266

1-(2,5-Dimethyl-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide

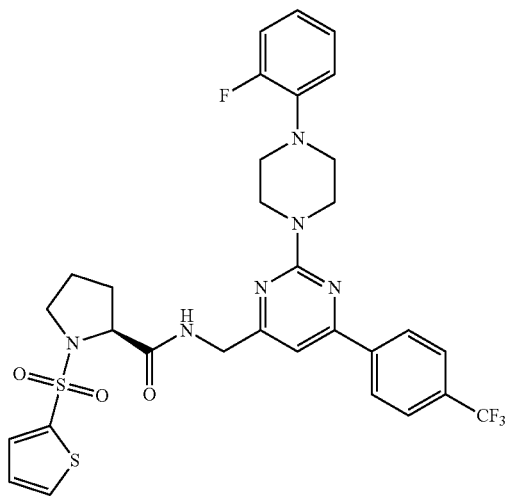 [SMILES: O=C(NCc1cc(-c2ccc(C(F)(F)F)cc2)nc(N2CCN(c3ccccc3F)CC2)n1)[C@@H]1CCCN1S(=O)(=O)c1cccs1]

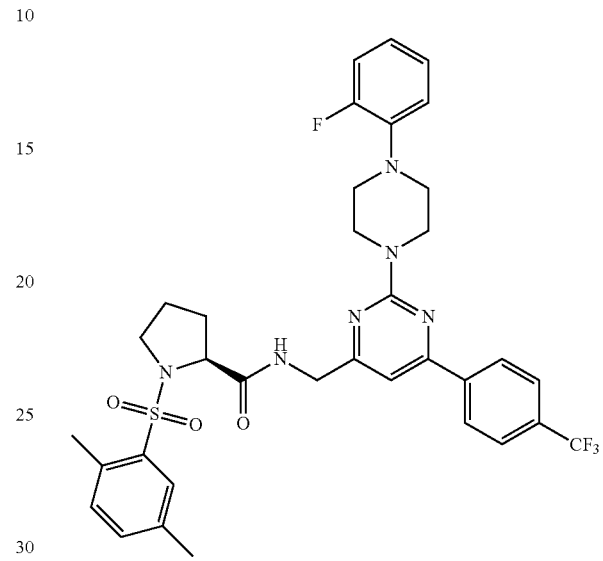

Example 265

1-(4-Propyl-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide Example 267

1-(2,4-Difluoro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide

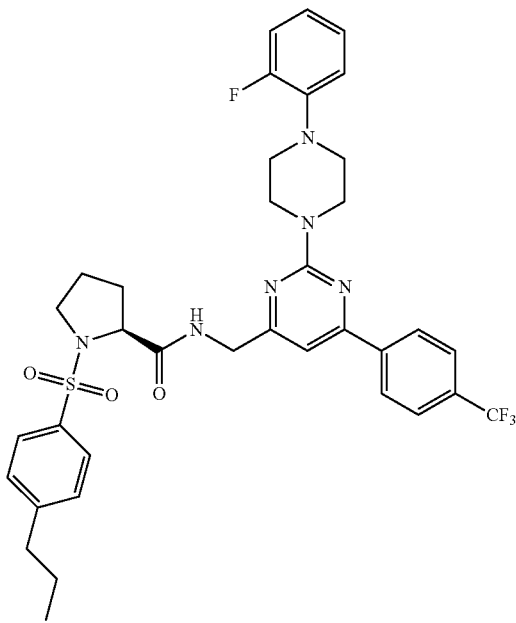 [SMILES: CCCc1ccc(S(=O)(=O)N2CCC[C@H]2C(=O)NCc2cc(-c3ccc(C(F)(F)F)cc3)nc(N3CCN(c4ccccc4F)CC3)n2)cc1]

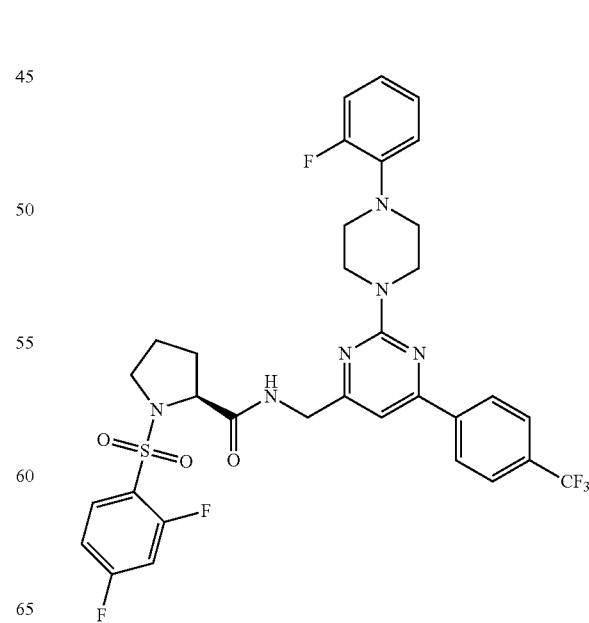

Example 268

1-(2-Chloro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide

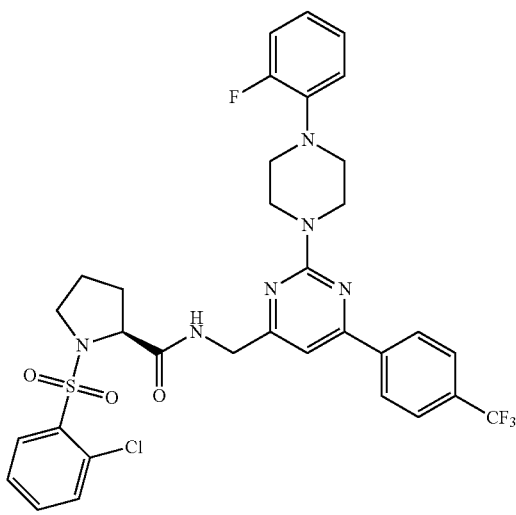

Example 269

1-(4-Chloro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide

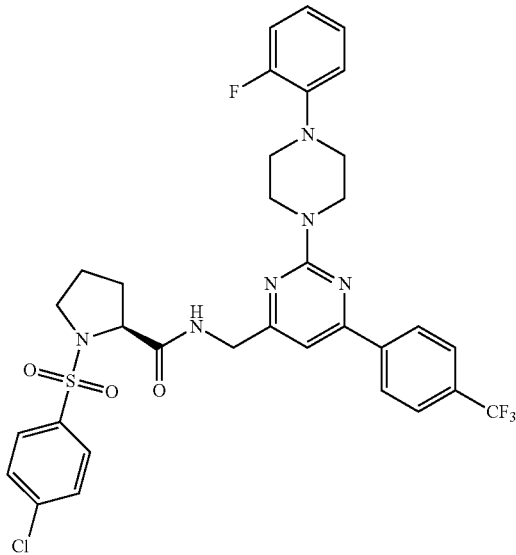

Example 270

1-(3-Fluoro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide

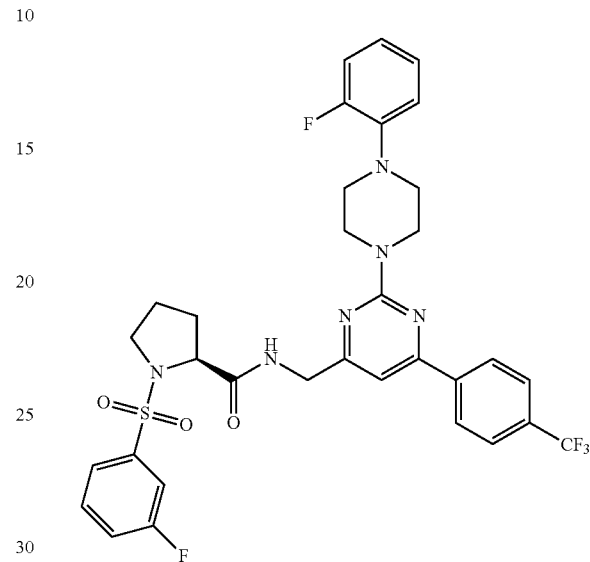

Example 271

1-(Toluene-3-sulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide

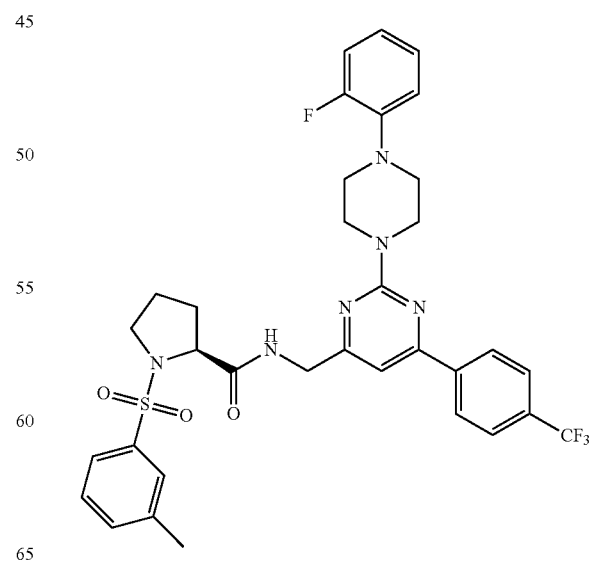

Example 272

1-Benzenesulfonyl-pyrrolidine-2S-carboxylic acid [2-[4-(2-fluoro-phenyl)-piperazin-1-yl]-6-(4-trifluoromethyl-phenyl)-pyrimidin-4-ylmethyl]-amide

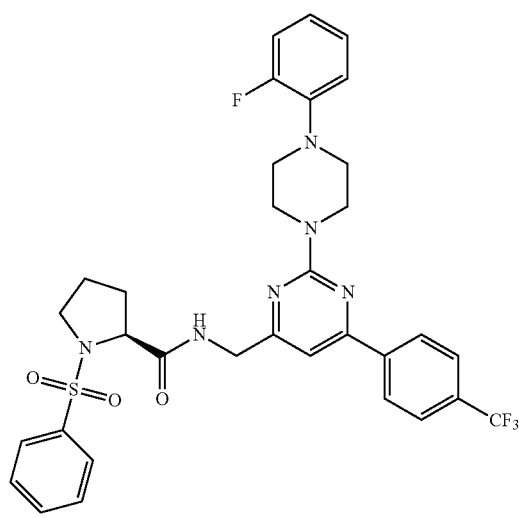 [SMILES: O=C(NCc1cc(-c2ccc(C(F)(F)F)cc2)nc(N2CCN(c3ccccc3F)CC2)n1)[C@@H]1CCCN1S(=O)(=O)c1ccccc1]

Example 273

1-(3-Chloro-2-fluoro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide

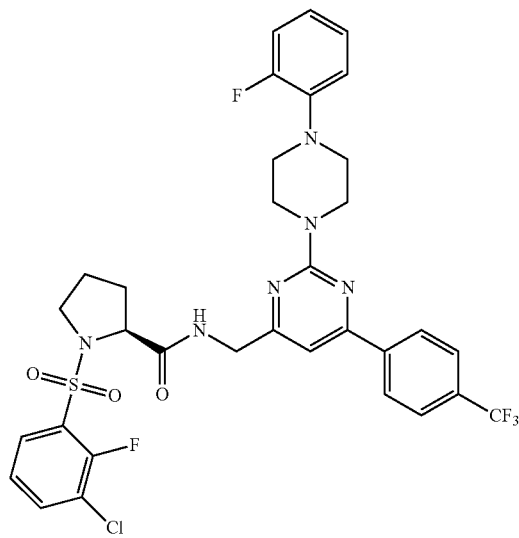 [SMILES: O=C(NCc1cc(-c2ccc(C(F)(F)F)cc2)nc(N2CCN(c3ccccc3F)CC2)n1)[C@@H]1CCCN1S(=O)(=O)c1cccc(Cl)c1F]

Example 274

1-(4-Acetyl-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide

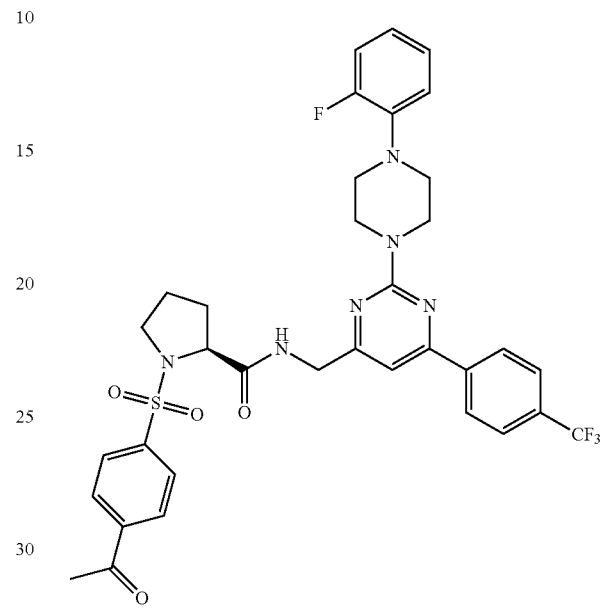

Example 275

1-(2,4,6-Trimethyl-benzenesulfonyl)-pyrrolidine-2-carboxylic acid [2-[4-(2-fluoro-phenyl)-piperazin-1-yl]-6-(4-trifluoromethyl-phenyl)-pyrimidin-4-ylmethyl]-amide

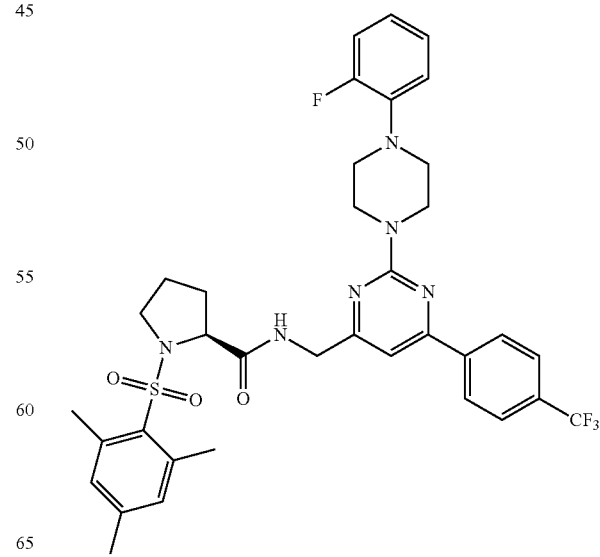

191

Example 276

1-(2-Fluoro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide

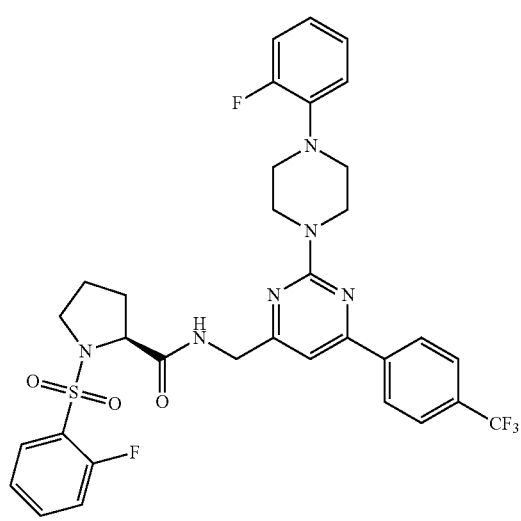

Example 277

1-(2-Chloro-6-methyl-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide

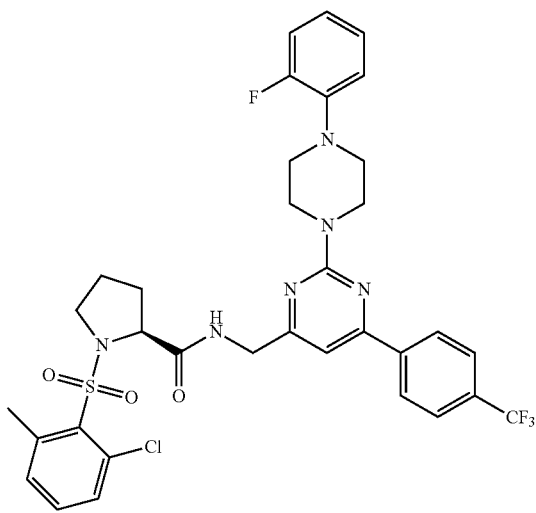 [SMILES: Cc1cccc(Cl)c1S(=O)(=O)N1CCC[C@H]1C(=O)NCc1cc(-c2ccc(C(F)(F)F)cc2)nc(N2CCN(c3ccccc3F)CC2)n1]

192

Example 278

1-(4-Chloro-2-fluoro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide

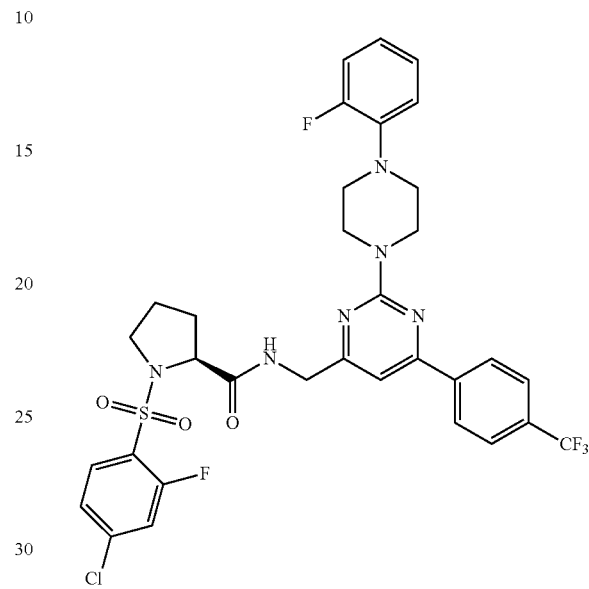

Example 279

1-(Toluene-2-sulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide

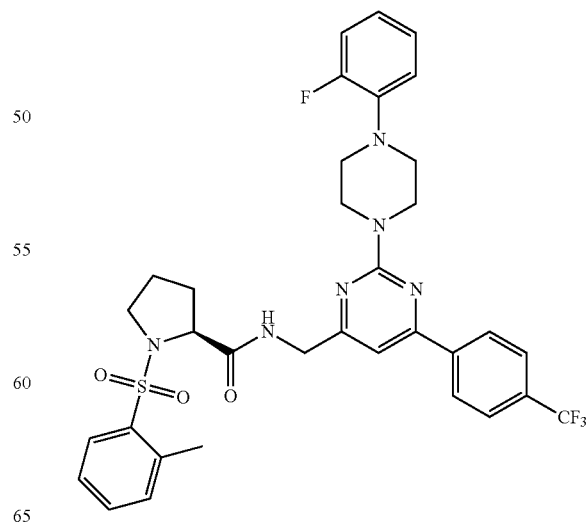

Example 280

1-(3-Chloro-4-methyl-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide

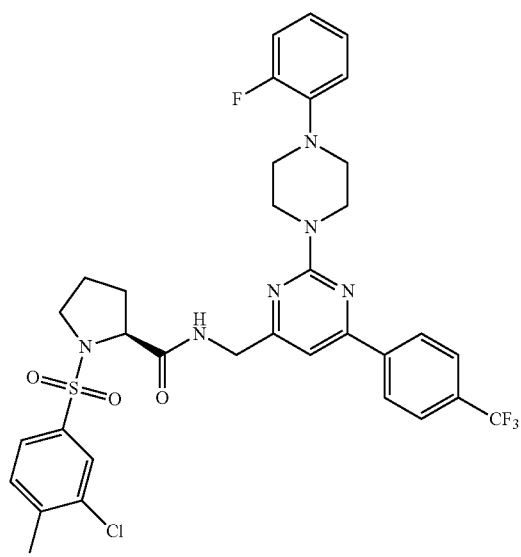 [SMILES: Cc1ccc(S(=O)(=O)N2CCC[C@H]2C(=O)NCc2cc(-c3ccc(C(F)(F)F)cc3)nc(N3CCN(c4ccccc4F)CC3)n2)cc1Cl]

Example 281

1-(3,5-Difluoro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide

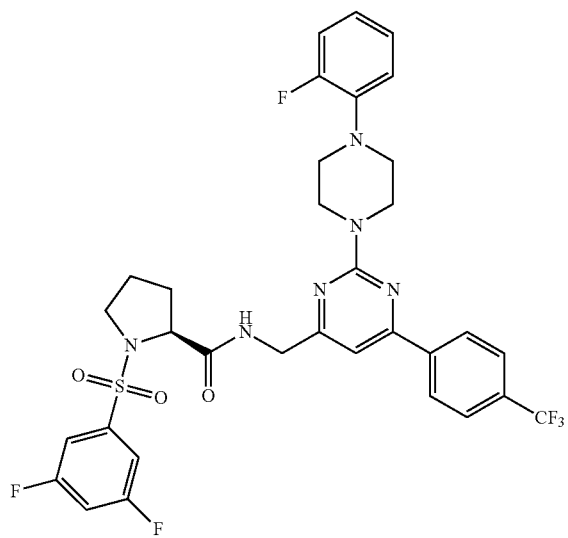 [SMILES: O=C(NCc1cc(-c2ccc(C(F)(F)F)cc2)nc(N2CCN(c3ccccc3F)CC2)n1)[C@@H]1CCCN1S(=O)(=O)c1cc(F)cc(F)c1]

Example 282

1-(4-tert-Butyl-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide

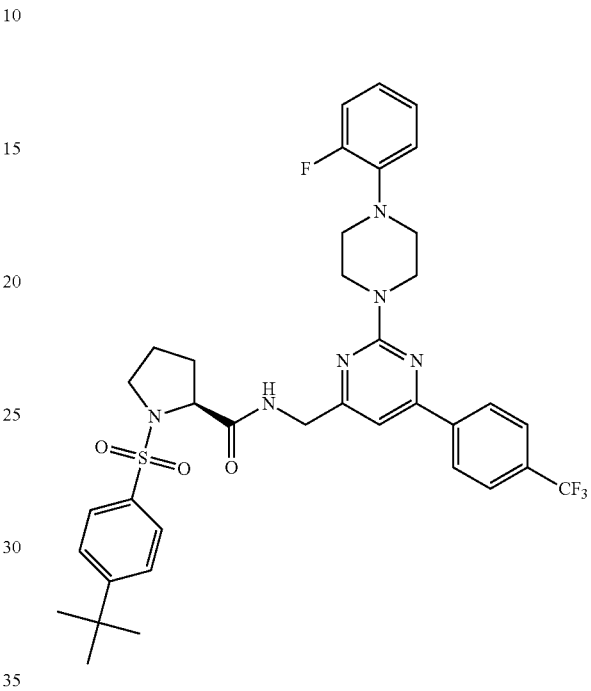

Examples 283 to 284 were prepared using methods analogous to those described for Example 102.

Example 283

1-(4-Fluoro-benzenesulfonyl)-pyrrolidine-2S-carboxylic acid [6-(4-trifluoromethyl-phenyl)-pyridin-2-ylmethyl]-amide

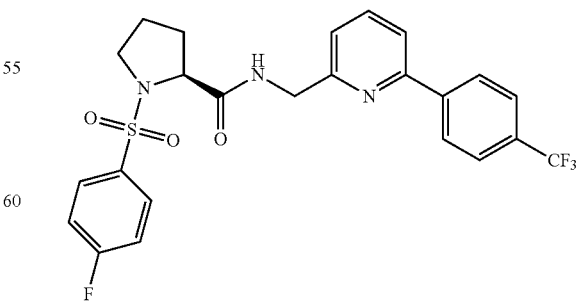

Example 284

1-(5-Chloro-thiophene-2-sulfonyl)-pyrrolidine-2S-carboxylic acid [6-(4-trifluoromethyl-phenyl)-pyridin-2-ylmethyl]-amide

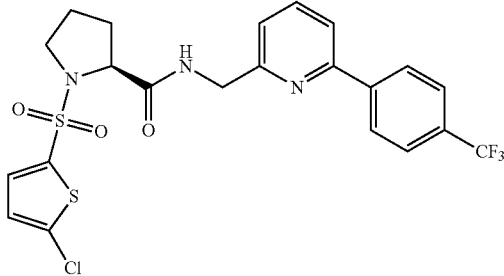 [SMILES: O=C(NCc1cccc(-c2ccc(C(F)(F)F)cc2)n1)[C@@H]1CCCN1S(=O)(=O)c1ccc(Cl)s1]

Example 285 was prepared using methods analogous to those described for Example 3.

Example 285

1-(4-Fluoro-benzenesulfonyl)-pyrrolidine-2S-carboxylic acid [2,6-bis-(4-trifluoromethyl-phenyl)-pyrimidin-4-ylmethyl]-amide

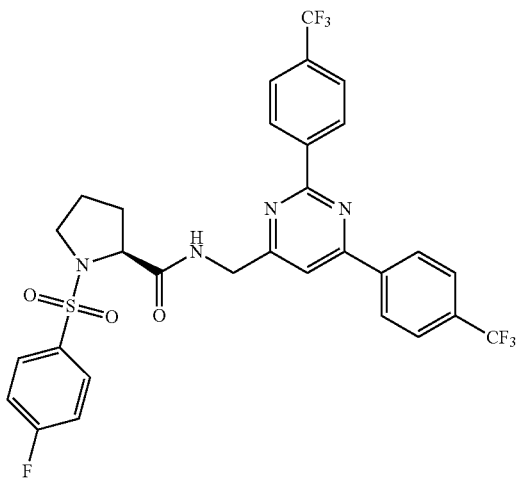 [SMILES: O=C(NCc1cc(-c2ccc(C(F)(F)F)cc2)nc(-c2ccc(C(F)(F)F)cc2)n1)[C@@H]1CCCN1S(=O)(=O)c1ccc(F)cc1]

Examples 286 to 316 were prepared using methods analogous to those described for Example 1.

Example 286

1-(4-Fluoro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide

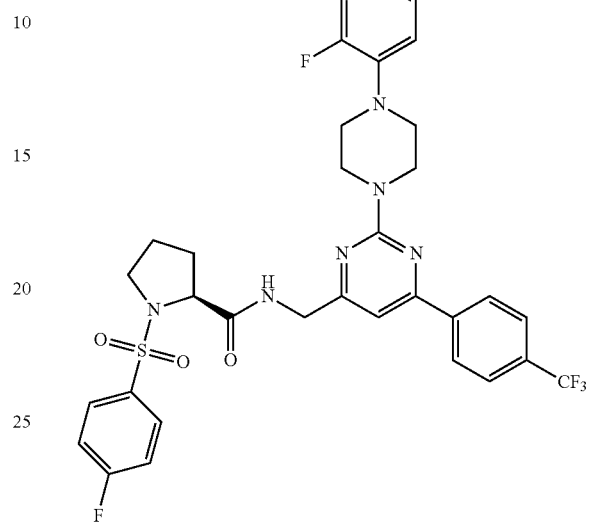

MS (ESI): Mass calcd. for $C_{33}H_{31}F_5N_6O_3S$, 686.21; m/z found 687.7 [M+H]$^+$. $^1$H NMR (400 MHz, CDCl$_3$) δ 8.19 (d, J=8.1, 3H), 7.95-7.85 (m, 2H), 7.72 (d, J=8.2, 2H), 7.31-7.21 (m, 1H), 7.20-7.13 (m, 1H), 7.12-6.93 (m, 5H), 4.65 (dd, J=17.6, 5.4, 1H), 4.45 (dd, J=17.6, 4.7, 1H), 4.30-4.12 (m, 5H), 3.64 (ddd, J=10.1, 7.2, 2.9, 1H), 3.28-3.23 (m, 4H), 3.23-3.14 (m, 1H), 2.32-2.20 (m, 1H), 1.83 (m, 1H), 1.74-1.58 (m, 2H).

Example 287

1-(4-Fluoro-benzenesulfonyl)-pyrrolidine-2S-carboxylic acid [6-benzo[1,3]dioxol-5-yl-2-(4-methoxy-phenylamino)-pyrimidin-4-ylmethyl]-amide

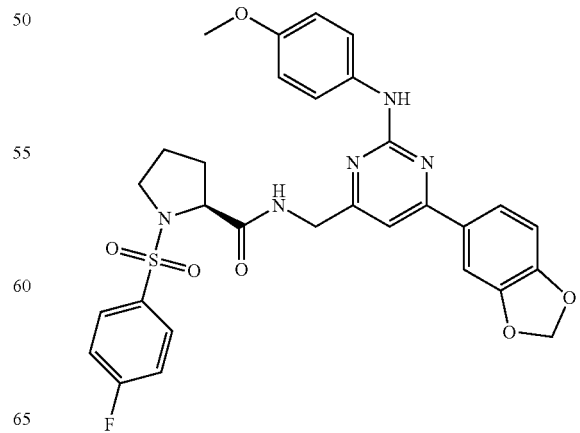

Example 288

1-(4-Fluoro-benzenesulfonyl)-pyrrolidine-2S-carboxylic acid {6-benzo[1,3]dioxol-5-yl-2-[4-(4-methyl-piperazine-1-carbonyl)-phenylamino]-pyrimidin-4-ylmethyl}-amide

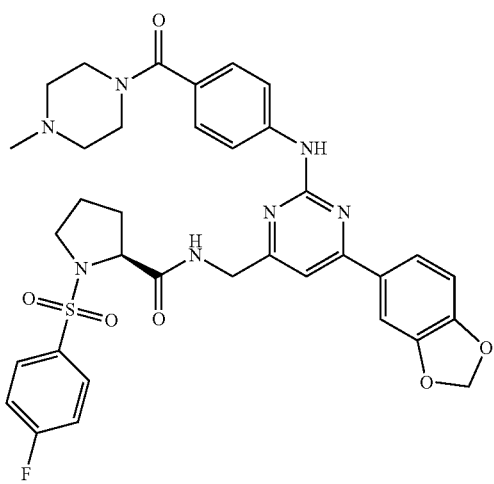 [SMILES: CN1CCN(C(=O)c2ccc(Nc3nc(CNC(=O)[C@@H]4CCCN4S(=O)(=O)c4ccc(F)cc4)cc(-c4ccc5c(c4)OCO5)n3)cc2)CC1]

Example 289

1-(4-Fluoro-benzenesulfonyl)-pyrrolidine-2S-carboxylic acid {6-(4-bromo-phenyl)-2-[(2-hydroxy-ethyl)-isobutyl-amino]-pyrimidin-4-ylmethyl}-amide

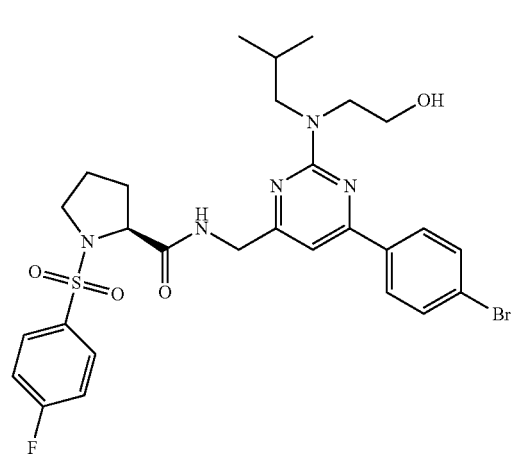 [SMILES: CC(C)CN(CCO)c1nc(CNC(=O)[C@@H]2CCCN2S(=O)(=O)c2ccc(F)cc2)cc(-c2ccc(Br)cc2)n1]

Example 290

1-(4-Fluoro-benzenesulfonyl)-pyrrolidine-2S-carboxylic acid [6-(4-bromo-phenyl)-2-cyclopropylamino-pyrimidin-4-ylmethyl]-amide

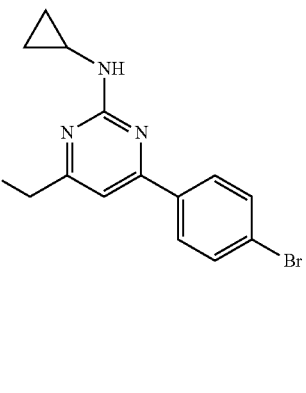

Example 291

1-(4-Fluoro-benzenesulfonyl)-pyrrolidine-2S-carboxylic acid [6-(4-bromo-phenyl)-2-prop-2-ynylamino-pyrimidin-4-ylmethyl]-amide

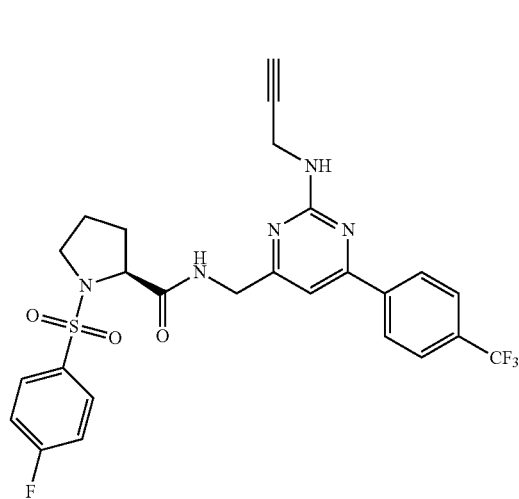 [SMILES: C#CCNc1nc(CNC(=O)[C@@H]2CCCN2S(=O)(=O)c2ccc(F)cc2)cc(-c2ccc(C(F)(F)F)cc2)n1]

Example 292

1-(4-Fluoro-benzenesulfonyl)-pyrrolidine-2S-carboxylic acid {6-benzo[1,3]dioxol-5-yl-2-[2-(2,4-dichloro-phenyl)-ethylamino]-pyrimidin-4-ylmethyl}-amide

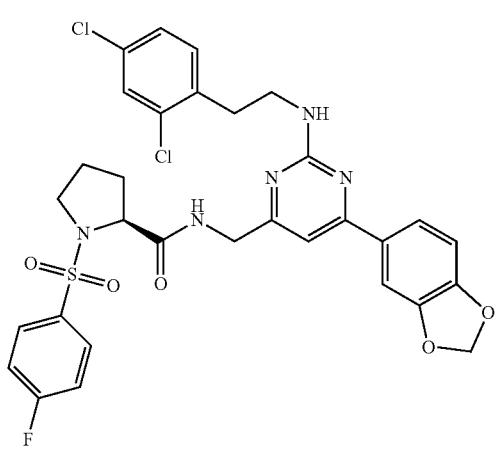 [SMILES: O=C(NCc1cc(-c2ccc3c(c2)OCO3)nc(NCCc2ccc(Cl)cc2Cl)n1)[C@@H]1CCCN1S(=O)(=O)c1ccc(F)cc1]

Example 293

1-(4-Fluoro-benzenesulfonyl)-pyrrolidine-2S-carboxylic acid [6-(4-bromo-phenyl)-2-(2-hydroxy-ethylamino)-pyrimidin-4-ylmethyl]-amide

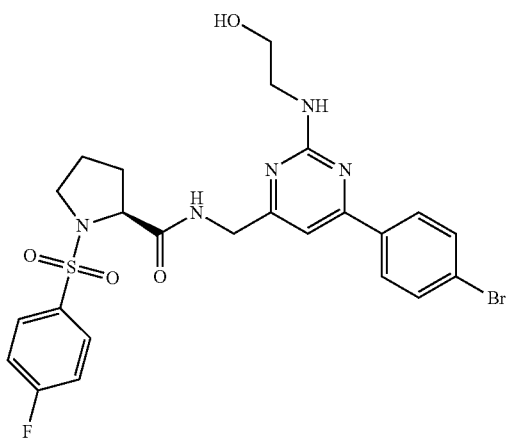 [SMILES: O=C(NCc1cc(-c2ccc(Br)cc2)nc(NCCO)n1)[C@@H]1CCCN1S(=O)(=O)c1ccc(F)cc1]

Example 294

1-(4-Fluoro-benzenesulfonyl)-pyrrolidine-2S-carboxylic acid [2-[(pyridin-3-ylmethyl)-amino]-6-(4-trifluoromethyl-phenyl)-pyrimidin-4-ylmethyl]-amide

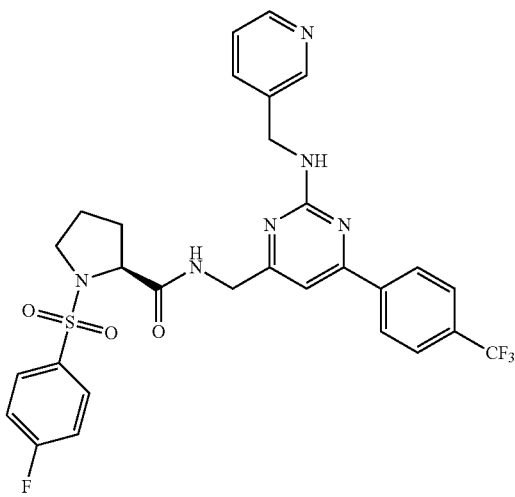 [SMILES: O=C(NCc1cc(-c2ccc(C(F)(F)F)cc2)nc(NCc2cccnc2)n1)[C@@H]1CCCN1S(=O)(=O)c1ccc(F)cc1]

Example 295

1-(4-Fluoro-benzenesulfonyl)-pyrrolidine-2S-carboxylic acid [6-(4-bromo-phenyl)-2-(2-pyridin-2-yl-ethylamino)-pyrimidin-4-ylmethyl]-amide

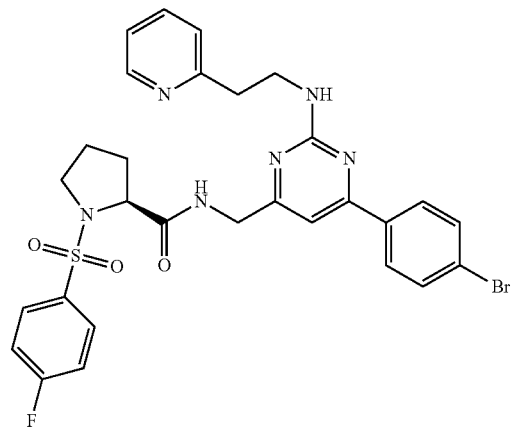 [SMILES: O=C(NCc1cc(-c2ccc(Br)cc2)nc(NCCc2ccccn2)n1)[C@@H]1CCCN1S(=O)(=O)c1ccc(F)cc1]

Example 296

1-(4-Fluoro-benzenesulfonyl)-pyrrolidine-2S-carboxylic acid [6-(4-bromo-phenyl)-2-(4-methyl-piperidin-1-yl)-pyrimidin-4-ylmethyl]-amide

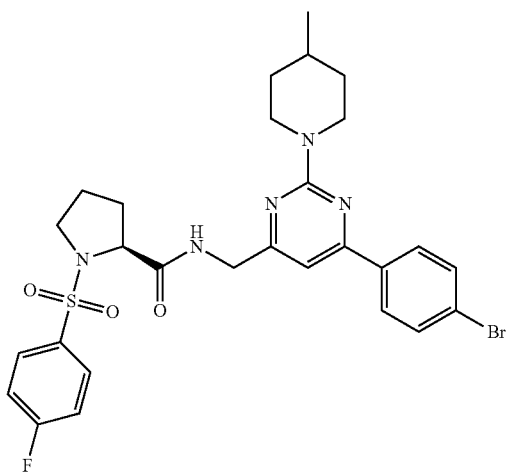 [SMILES: CC1CCN(c2nc(CNC(=O)[C@@H]3CCCN3S(=O)(=O)c3ccc(F)cc3)cc(-c3ccc(Br)cc3)n2)CC1]

Example 297

1-(4-Fluoro-benzenesulfonyl)-pyrrolidine-2S-carboxylic acid [2-(4-benzo[1,3]dioxol-5-ylmethyl-piperazin-1-yl)-6-(4-trifluoromethyl-phenyl)-pyrimidin-4-ylmethyl]-amide

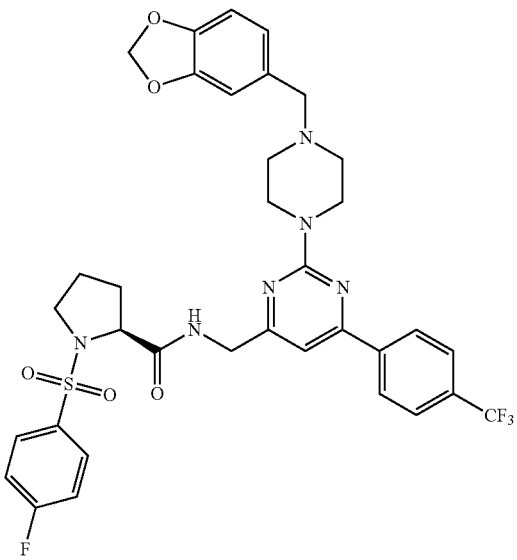 [SMILES: O=C(NCc1cc(-c2ccc(C(F)(F)F)cc2)nc(N2CCN(Cc3ccc4c(c3)OCO4)CC2)n1)[C@@H]1CCCN1S(=O)(=O)c1ccc(F)cc1]

Example 298

1-[4-({[1-(4-Fluoro-benzenesulfonyl)-pyrrolidine-2S-carbonyl]-amino}-methyl)-6-(4-trifluoromethyl-phenyl)-pyrimidin-2-yl]-piperidine-3-carboxylic acid amide

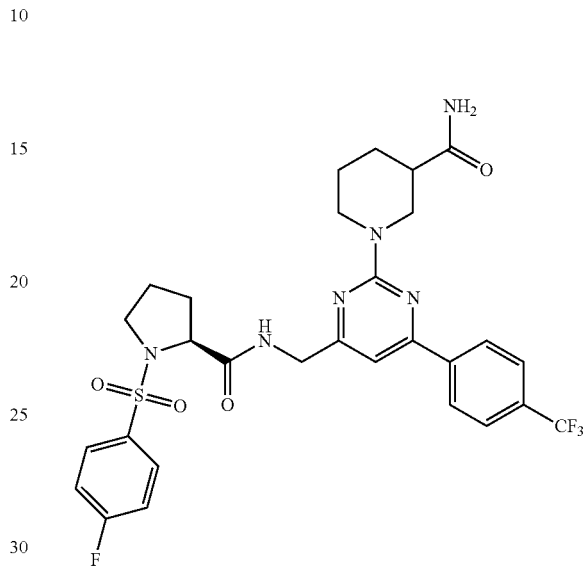

Example 299

1-(4-Fluoro-benzenesulfonyl)-pyrrolidine-2S-carboxylic acid [2-[2-(3H-indol-3-yl)-ethylamino]-6-(4-trifluoromethyl-phenyl)-pyrimidin-4-ylmethyl]-amide

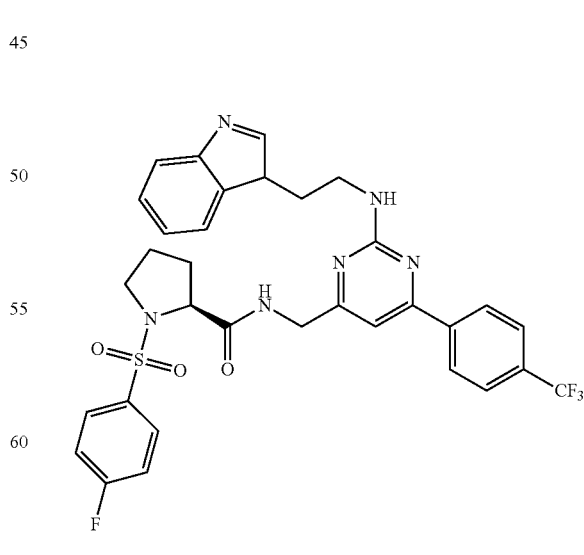

Example 300

1-(4-Fluoro-benzenesulfonyl)-pyrrolidine-2S-carboxylic acid {6-(4-bromo-phenyl)-2-[4-(4-fluoro-phenyl)-piperazin-1-yl]-pyrimidin-4-ylmethyl}-amide

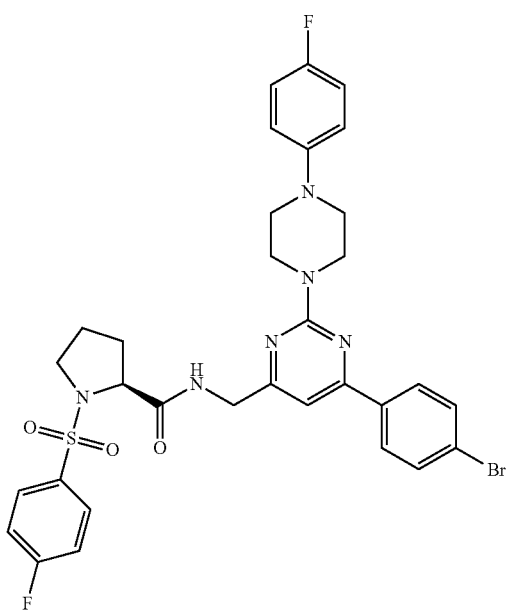 [SMILES: O=C(NCc1cc(-c2ccc(Br)cc2)nc(N2CCN(c3ccc(F)cc3)CC2)n1)[C@@H]1CCCN1S(=O)(=O)c1ccc(F)cc1]

Example 301

1-(4-Fluoro-benzenesulfonyl)-pyrrolidine-2S-carboxylic acid {6-(4-bromo-phenyl)-2-[2-(4-sulfamoyl-phenyl)-ethylamino]-pyrimidin-4-ylmethyl}-amide

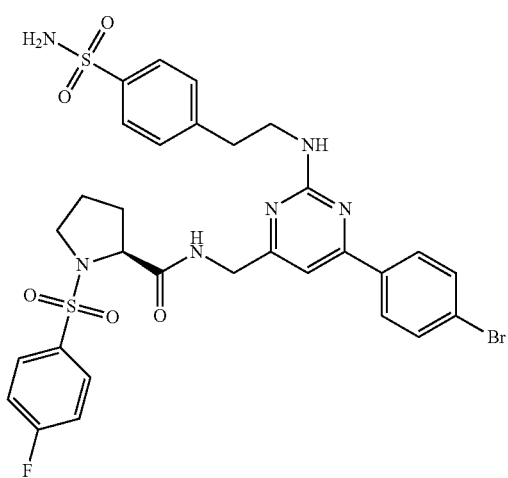 [SMILES: NS(=O)(=O)c1ccc(CCNc2nc(CNC(=O)[C@@H]3CCCN3S(=O)(=O)c3ccc(F)cc3)cc(-c3ccc(Br)cc3)n2)cc1]

Example 302

1-(4-Fluoro-benzenesulfonyl)-pyrrolidine-2S-carboxylic acid [6-(4-bromo-phenyl)-2-(2S-hydroxymethyl-pyrrolidin-1-yl)-pyrimidin-4-ylmethyl]-amide

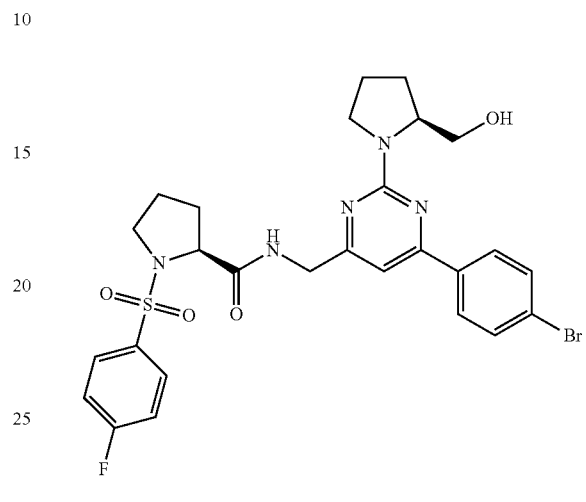

Example 303

1-(4-Fluoro-benzenesulfonyl)-pyrrolidine-2S-carboxylic acid [2-(3,4-dihydro-1H-isoquinolin-2-yl)-6-(4-trifluoromethyl-phenyl)-pyrimidin-4-ylmethyl]-amide

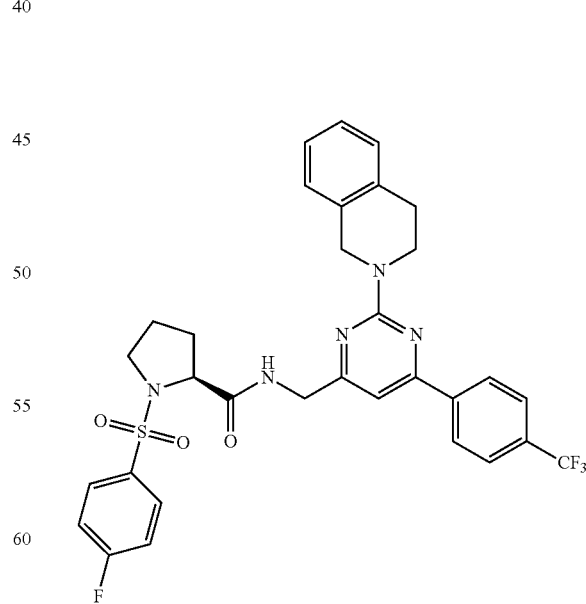

Example 304

1-(4-Fluoro-benzenesulfonyl)-pyrrolidine-2S-carboxylic acid [2-[4-(4-fluoro-phenyl)-piperazin-1-yl]-6-(4-trifluoromethyl-phenyl)-pyrimidin-4-ylmethyl]-amide

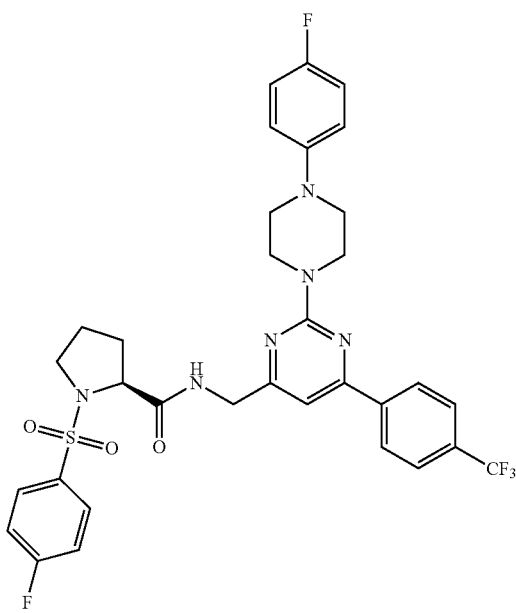 [SMILES: O=C(NCc1cc(-c2ccc(C(F)(F)F)cc2)nc(N2CCN(c3ccc(F)cc3)CC2)n1)[C@@H]1CCCN1S(=O)(=O)c1ccc(F)cc1]

Example 305

1-(4-Fluoro-benzenesulfonyl)-pyrrolidine-2S-carboxylic acid [6-benzo[1,3]dioxol-5-yl-2-(4-benzo[1,3]dioxol-5-ylmethyl-piperazin-1-yl)-pyrimidin-4-ylmethyl]-amide

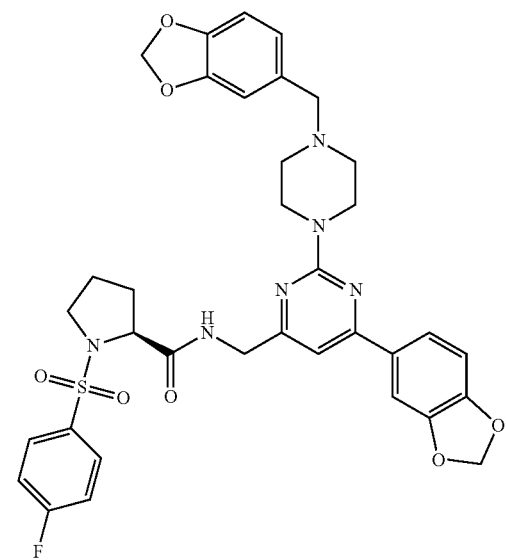 [SMILES: O=C(NCc1cc(-c2ccc3c(c2)OCO3)nc(N2CCN(Cc3ccc4c(c3)OCO4)CC2)n1)[C@@H]1CCCN1S(=O)(=O)c1ccc(F)cc1]

Example 306

1-(4-Fluoro-benzenesulfonyl)-pyrrolidine-2S-carboxylic acid [6-benzo[1,3]dioxol-5-yl-2-(4-methyl-piperidin-1-yl)-pyrimidin-4-ylmethyl]-amide

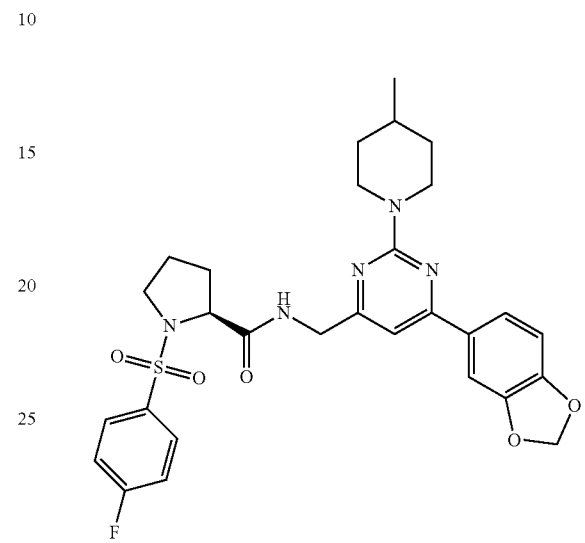

Example 307

1-(4-Fluoro-benzenesulfonyl)-pyrrolidine-2S-carboxylic acid [2-(indan-1-ylamino)-6-(4-trifluoromethyl-phenyl)-pyrimidin-4-ylmethyl]-amide

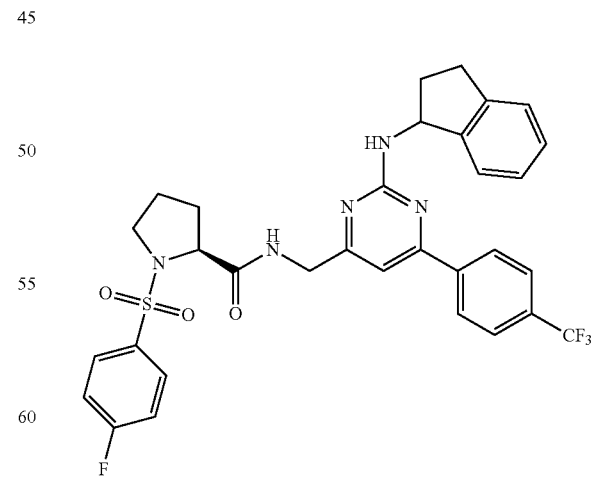

Example 308

1-(4-Fluoro-benzenesulfonyl)-pyrrolidine-2S-carboxylic acid [2-(1-hydroxymethyl-2-methyl-propylamino)-6-(4-trifluoromethyl-phenyl)-pyrimidin-4-ylmethyl]-amide

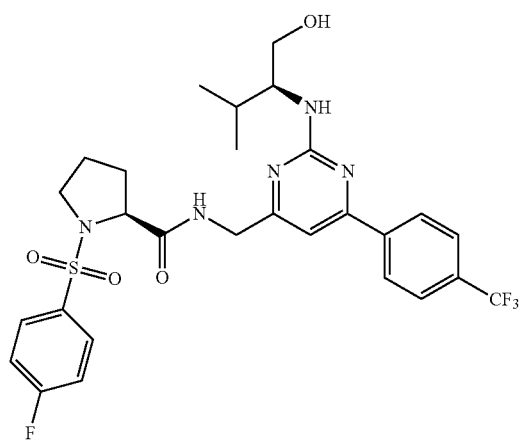 [SMILES: CC(C)[C@@H](CO)Nc1nc(CNC(=O)[C@@H]2CCCN2S(=O)(=O)c2ccc(F)cc2)cc(-c2ccc(C(F)(F)F)cc2)n1]

Example 309

1-(4-Fluoro-benzenesulfonyl)-pyrrolidine-2S-carboxylic acid [2-[4-(4-acetyl-phenyl)-piperazin-1-yl]-6-(4-trifluoromethyl-phenyl)-pyrimidin-4-ylmethyl]-amide

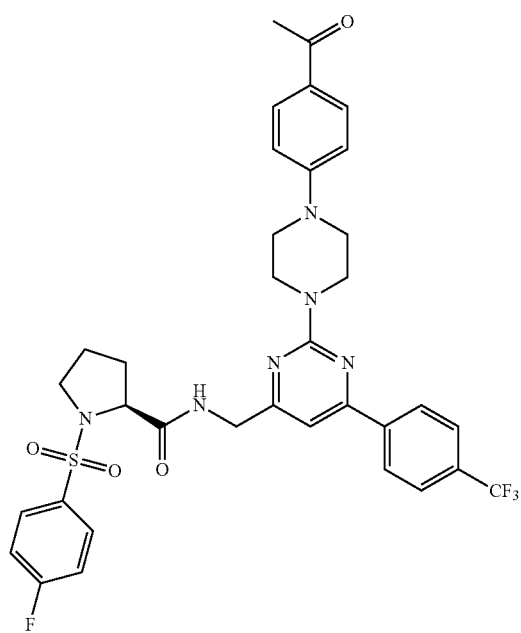 [SMILES: CC(=O)c1ccc(N2CCN(c3nc(CNC(=O)[C@@H]4CCCN4S(=O)(=O)c4ccc(F)cc4)cc(-c4ccc(C(F)(F)F)cc4)n3)CC2)cc1]

Example 310

1-(4-Fluoro-benzenesulfonyl)-pyrrolidine-2S-carboxylic acid [2-butylamino-6-(4-trifluoromethyl-phenyl)-pyrimidin-4-ylmethyl]-amide

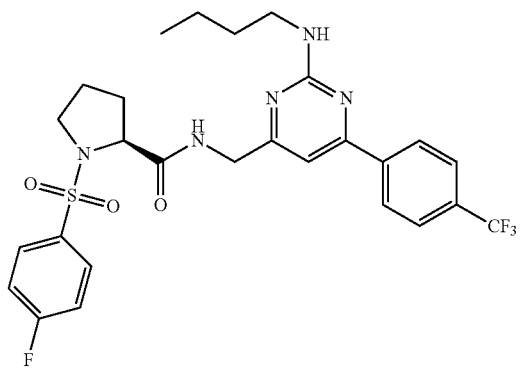 [SMILES: CCCCNc1nc(CNC(=O)[C@@H]2CCCN2S(=O)(=O)c2ccc(F)cc2)cc(-c2ccc(C(F)(F)F)cc2)n1]

Example 311

1-(4-Fluoro-benzenesulfonyl)-pyrrolidine-2S-carboxylic acid [6-benzo[1,3]dioxol-5-yl-2-(1-phenyl-ethylamino)-pyrimidin-4-ylmethyl]-amide

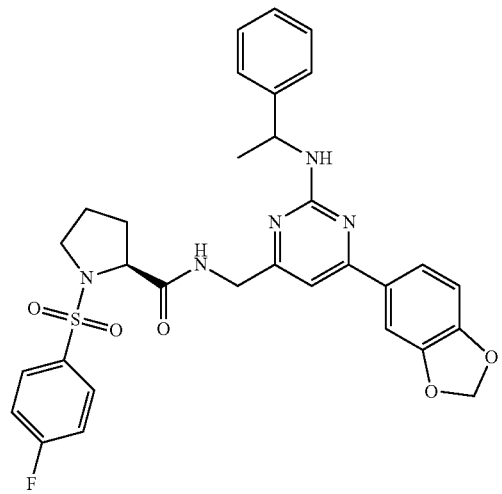 [SMILES: CC(Nc1nc(CNC(=O)[C@@H]2CCCN2S(=O)(=O)c2ccc(F)cc2)cc(-c2ccc3c(c2)OCO3)n1)c1ccccc1]

Example 312

1-(4-Fluoro-benzenesulfonyl)-pyrrolidine-2S-carboxylic acid [2-(2-pyridin-3-yl-ethylamino)-6-(4-trifluoromethyl-phenyl)-pyrimidin-4-ylmethyl]-amide

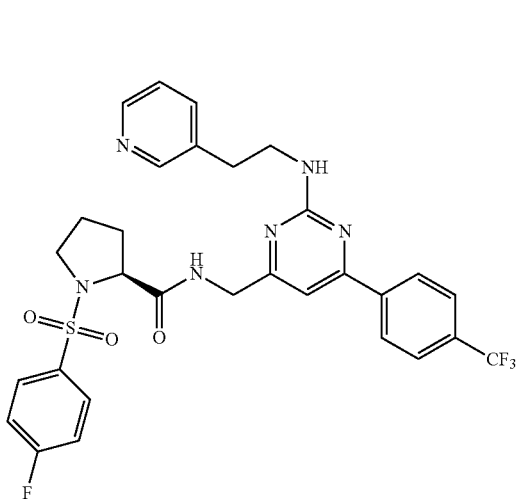 [SMILES: O=C(NCc1cc(-c2ccc(C(F)(F)F)cc2)nc(NCCc2cccnc2)n1)[C@@H]1CCCN1S(=O)(=O)c1ccc(F)cc1]

Example 314

1-(4-Fluoro-benzenesulfonyl)-pyrrolidine-2-carboxylic acid [2-(4-methyl-piperazin-1-yl)-6-(4-trifluoromethyl-phenyl)-pyrimidin-4-ylmethyl]-amide

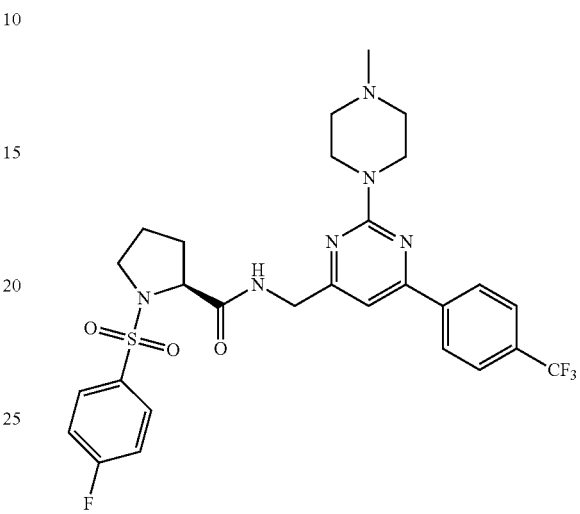

Example 313

1-(4-Fluoro-benzenesulfonyl)-pyrrolidine-2S-carboxylic acid [2-(1-phenyl-ethylamino)-6-(4-trifluoromethyl-phenyl)-pyrimidin-4-ylmethyl]-amide

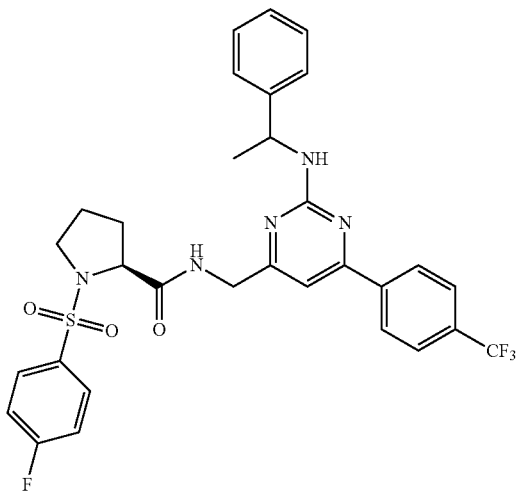 [SMILES: CC(Nc1nc(CNC(=O)[C@@H]2CCCN2S(=O)(=O)c2ccc(F)cc2)cc(-c2ccc(C(F)(F)F)cc2)n1)c1ccccc1]

Example 315

1-(4-Fluoro-benzenesulfonyl)-pyrrolidine-2S-carboxylic acid [2-(2-morpholin-4-yl-ethylamino)-6-(4-trifluoromethyl-phenyl)-pyrimidin-4-ylmethyl]-amide

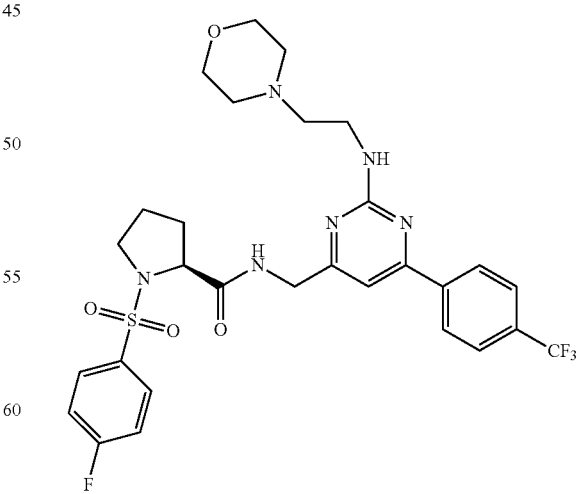

Example 316

1-(4-Fluoro-benzenesulfonyl)-pyrrolidine-2S-carboxylic acid [6-(4-bromo-phenyl)-2-(2-morpholin-4-yl-ethylamino)-pyrimidin-4-ylmethyl]-amide

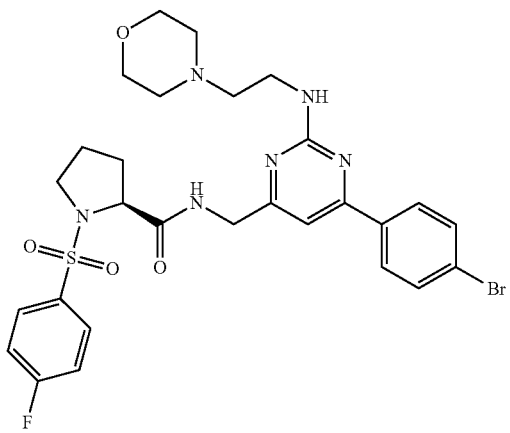 [SMILES: O=C(NCc1cc(-c2ccc(Br)cc2)nc(NCCN2CCOCC2)n1)[C@@H]1CCCN1S(=O)(=O)c1ccc(F)cc1]

Examples 317 to 417 were prepared using methods analogous to that described for intermediate 6 wherein the appropriate amine, generated by procedures analogous to the formation of intermediate 57, and the appropriate acid, either intermediate 4 or intermediate 5, were employed to provide the desired product.

Example 317

1-(4-Fluoro-benzenesulfonyl)-pyrrolidine-S2-carboxylic acid [2-pyrrolidin-1-yl-6-(4-trifluoromethyl-phenyl)-pyridin-4-ylmethyl]-amide

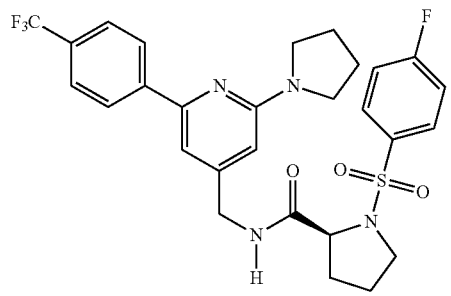 [SMILES: O=C(NCc1cc(-c2ccc(C(F)(F)F)cc2)nc(N2CCCC2)c1)[C@@H]1CCCN1S(=O)(=O)c1ccc(F)cc1]

$^1$H NMR (600 MHz, DMSO) δ 8.71 (t, J=6.1 Hz, 1H), 8.27 (d, J=8.1 Hz, 2H), 8.03-7.94 (m, 2H), 7.79 (d, J=8.2 Hz, 2H), 7.53-7.45 (m, 2H), 7.18 (s, 1H), 6.45 (s, 1H), 4.38 (dd, J=16.2, 6.3 Hz, 1H), 4.30 (dd, J=16.2, 5.9 Hz, 1H), 4.11 (dd, J=8.1, 4.1 Hz, 1H), 3.53-3.42 (m, 5H), 3.23-3.13 (m, J=10.0, 7.0 Hz, 1H), 1.99-1.92 (m, 4H), 1.89-1.74 (m, 3H), 1.60-1.49 (m, 1H).

Example 318

1-(4-Fluoro-benzenesulfonyl)-pyrrolidine-S2-carboxylic acid [6'-(4-trifluoromethyl-phenyl)-3,4,5,6-tetrahydro-2H-[1,2']bipyridinyl-4'-ylmethyl]-amide

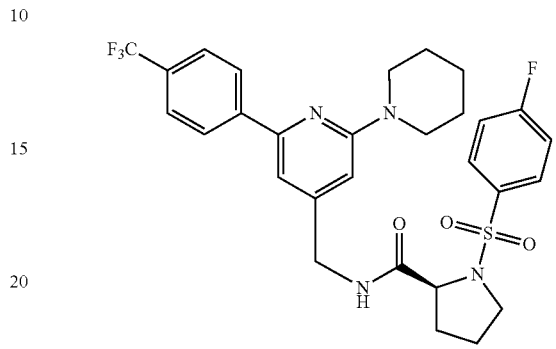

MS calcd. for $C_{29}H_{30}F_4N_4O_3S$, 590.64, m/z found 590.2 [M+H]$^+$. $^1$H NMR (400 MHz, DMSO) δ 8.66 (s, 1H), 8.23 (d, J=8.1 Hz, 2H), 7.98 (dd, 2H), 7.78 (d, J=8.3 Hz, 2H), 7.21 (s, 1H), 6.79 (s, 1H), 4.42-4.27 (m, 2H), 4.14-4.07 (m, 1H), 3.64 (d, J=6.6 Hz, 5H), 3.48 (s, 1H), 3.26-3.10 (m, 3H), 1.89-1.73 (m, 3H), 1.68-1.43 (m, J=22.0 Hz, 5H).

Example 319

1-(5-Chloro-thiophene-2-sulfonyl)-pyrrolidine-S2-carboxylic acid [6'-(4-trifluoromethyl-phenyl)-3,4,5,6-tetrahydro-2H-[1,2']bipyridinyl-4'-ylmethyl]-amide

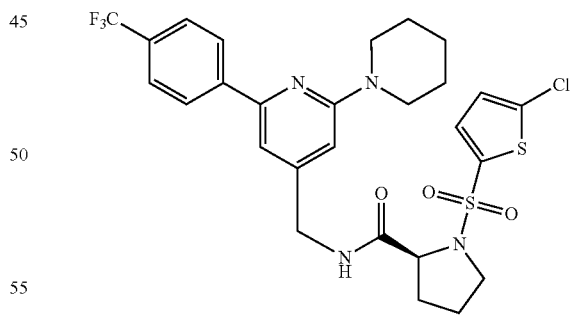

MS calcd. for $C_{27}H_{28}ClF_3N_4O_3S_2$, 612.12, m/z found 613.2 [M+H]$^+$. $^1$H NMR (400 MHz, DMSO) δ 8.69 (t, J=6.1 Hz, 1H), 8.22 (d, J=8.1 Hz, 2H), 7.79 (d, J=8.3 Hz, 2H), 7.69 (t, J=6.2 Hz, 1H), 7.38 (d, J=4.1 Hz, 1H), 7.18 (s, 1H), 6.76 (s, 1H), 4.38 (dd, J=16.3, 6.2 Hz, 1H), 4.29 (dd, J=16.2, 5.9 Hz, 1H), 4.12 (dd, J=7.8, 4.0 Hz, 1H), 3.67-3.60 (m, 4H), 3.59-3.51 (m, 1H), 3.28-3.21 (m, 1H), 1.97-1.80 (m, 3H), 1.71-1.60 (m, 3H), 1.59-1.49 (m, 4H).

Example 320

(2S)—N-({2-(Benzylamino)-6-[4-(trifluoromethyl)phenyl]pyridin-4-yl}methyl)-1-[(5-chlorothiophen-2-yl)sulfonyl]-2,5-dihydro-1H-pyrrole-2-carboxamide

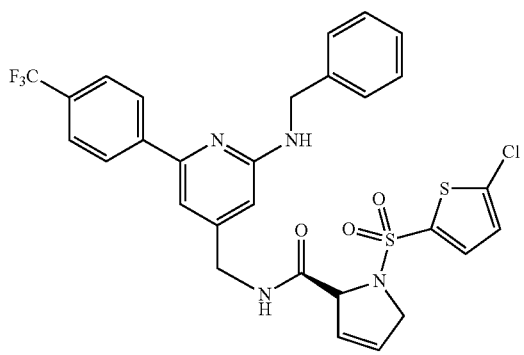

MS (ESI): mass calcd. for $C_{29}H_{24}ClF_3N_4O_3S_2$, 633.123 m/z found, 633.1 (100%), 635.1 (50%) [M+H]$^+$. DMSO-d6: 8.78 (t, J=5.7 Hz, 1H), 8.15 (d, J=8.1 Hz, 2H), 7.75 (d, J=8.4 Hz, 2H), 7.72 (d, J=4.2 Hz, 1H), 7.37-7.19 (m, 7H), 7.07 (s, 1H), 6.40 (s, 1H), 5.95-5.92 (m, 1H), 5.75-5.70 (m, 1H), 4.86 (br s, 1H), 4.56 (d, J=5.7 Hz, 2H), 4.33-4.28 (m, 2H), 4.21-4.12 (m, 2H).

Example 321

(2S)—N-({2-(Benzylamino)-6-[4-(trifluoromethyl)phenyl]pyridin-4-yl}methyl)-1-[(4-fluorophenyl)sulfonyl]-2,5-dihydro-1H-pyrrole-2-carboxamide

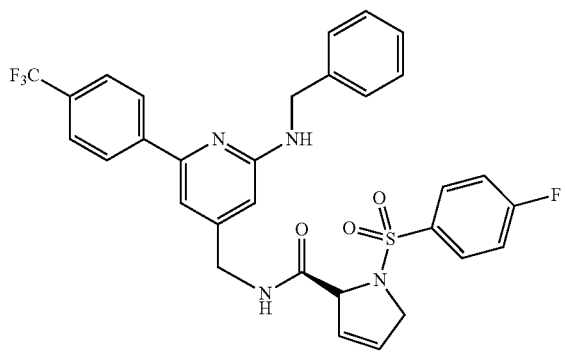

MS (ESI): mass calcd. for $C_{31}H_{26}F_4N_4O_3S$, 610.64 m/z found, 611.1 [M+H]$^+$. DMSO-d6: 8.73 (t, J=6 Hz, 1H), 8.18 (d, J=8.1 Hz, 1H), 7.99-7.94 (m, 2H), 7.75 (d, J=8.4 Hz, 2H), 7.47 (t, J=8.4 Hz, 2H), 7.39-7.18 (m, 6H), 7.12 (s, 1H), 6.43 (s, 1H), 5.89 (d, J=5.7 Hz, 1H), 5.71 (d, J=4.5 Hz, 1H), 4.88 (br s, 1H), 4.58 (d, J=5.7 Hz, 2H), 4.29-4.10 (m, 4H).

Example 322

N-({2-(Benzylamino)-6-[4-(trifluoromethyl)phenyl]pyridin-4-yl}methyl)-1-[(4-fluorophenyl)sulfonyl]-L-prolinamide

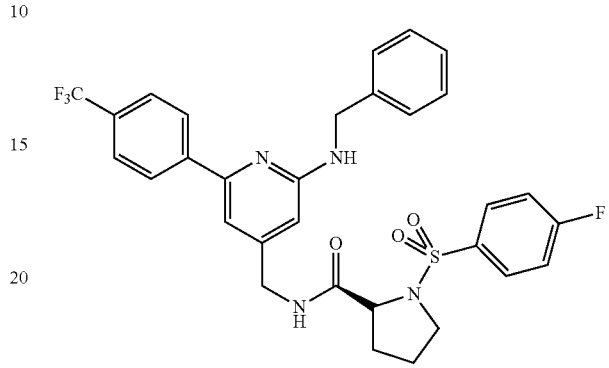

MS (ESI): mass calcd. for $C_{31}H_{28}F_4N_4O_3S$, 612.65 m/z found, 613.1 [M+H]$^+$. CDCl$_3$: 8.11 (d, J=8.1 Hz, 2H), 7.89-7.85 (m, 2H), 7.66 (d, J=8.1 Hz, 2H), 7.41-7.23 (m, 7H), 7.07 (s, 1H), 6.44 (s, 1H), 4.68-4.60 (m, 3H), 4.34 (dd, J=16.5 Hz, 5.4 Hz, 1H), 4.13-4.10 (m, 1H), 3.61-3.56 (m, 1H), 3.17-3.13 (m, 1H), 2.02-2.19 (m, 1H), 1.74-1.63 (m, 3H).

Example 323

N-({2-(Benzylamino)-6-[4-(trifluoromethyl)phenyl]pyridin-4-yl}methyl)-1-[(5-chlorothiophen-2-yl)sulfonyl]-L-prolinamide

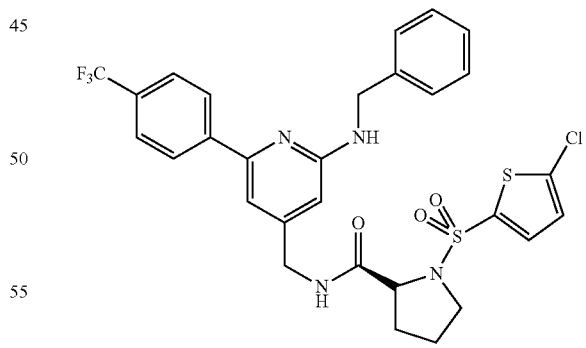

MS (ESI): mass calcd. for $C_{29}H_{26}ClF_3N_4O_3S_2$, 635.13 m/z found, 635.1 (100%), 637.1 (50%) [M+H]$^+$. CDCl$_3$: 8.10 (d, J=8.1 Hz, 2H), 7.67 (d, J=8.4 Hz, 2H), 7.45-7.30 (m, 6H), 7.05-7.02 (m, 2H), 6.39 (s, 1H), 4.66-4.58 (m, 3H), 4.34 (dd, J=15.9 Hz, 5.4 Hz, 1H), 4.16 (d, J=8.7 Hz, 1H), 3.63-3.59 (m, 1H), 3.28-3.22 (m, 1H), 2.28-2.27 (m, 1H), 1.87-1.78 (m, 3H).

Example 324

1-[(5-Chlorothiophen-2-yl)sulfonyl]-N-({2-[4-(2-fluorophenyl)piperazin-1-yl]-6-[4-(trifluoromethyl)phenyl]pyridin-4-yl}methyl)-L-prolinamide

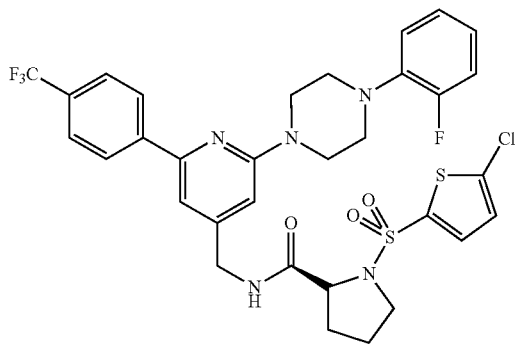

MS (ESI): mass calcd. for $C_{32}H_{30}ClF_4N_5O_3S_2$, 708.2 m/z found, 708.1 (100), 709.1 (40), 710.1 (50), [M+H]$^+$. DMSO-d6: 8.77 (t, J=5.7 Hz, 1H), 8.27 (d, J=8.4 Hz, 2H), 8.21 (d, J=7.8 Hz, 2H), 7.73 (d, J=3.9 Hz, 1H), 7.39 (d, J=3.9 Hz, 1H), 7.30 (s, 1H), 7.20-7.00 (m, 4H), 6.86 (s, 1H), 4.43-4.33 (m, 2H), 4.13-4.10 (m, 1H), 3.78 (br s, 4H), 3.56-3.54 (m, 1H), 3.33-3.27 (m, 1H), 3.14 (br s, 4H), 1.90-1.88 (m, 3H), 1.67-1.65 (m, 1H).

Example 325

N-({2-[4-(2-Fluorophenyl)piperazin-1-yl]-6-[4-(trifluoromethyl)phenyl]pyridin-4-yl}methyl)-1-[(4-fluorophenyl)sulfonyl]-L-prolinamide

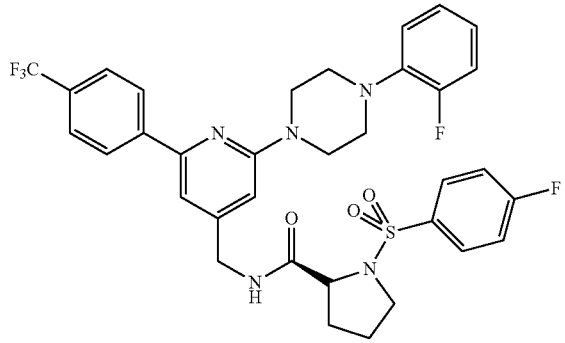

MS (ESI): mass calcd. for $C_{34}H_{32}F_5N_5O_3S$, 685.72 m/z found, 686.2 [M+H]$^+$. DMSO-d6: 8.77 (d, J=6.0 Hz, 1H), 8.30 (d, J=8.1 Hz, 2H), 7.99 (dd, J=8.4 Hz, 3.3 Hz, 2H), 7.82 (d, J=8.1 Hz, 2H), 7.51 (t, J=8.4 Hz, 2H), 7.34 (s, 1H), 7.21-7.00 (m, 4H), 6.91 (s, 1H), 4.42-4.36 (m, 2H), 4.14-4.10 (m, 1H), 3.80 (br s, 4H), 3.53-3.48 (m, 1H), 3.21-3.14 (m, 5H), 1.842-1.84 (m, 3H), 1.57-1.55 (m, 1H).

Example 326

(2S)—N-({2-[4-(2-Fluorophenyl)piperazin-1-yl]-6-[4-(trifluoromethyl)phenyl]pyridin-4-yl}methyl)-1-[(4-fluorophenyl)sulfonyl]-2,5-dihydro-1H-pyrrole-2-carboxamide

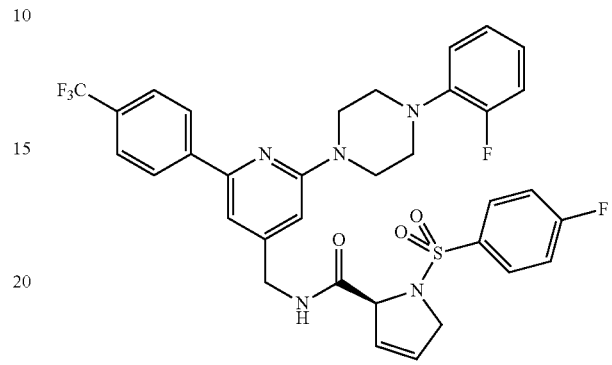

MS (ESI): mass calcd. for $C_{34}H_{30}F_5N_5O_3S$, 683.71 m/z found, 684.2 [M+H]$^+$. DMSO-d6: 8.84 (s, 1H), 8.28 (d, J=8.4 Hz, 2H), 8.02-7.98 (m, 2H), 7.81 (d, J=7.8 Hz, 2H), 7.49 (t, J=8.4 Hz, 2H), 7.32 (s, 1H), 7.19-7.01 (m, 4H), 6.88 (s, 1H), 5.94-5.92 (m, 1H), 5.74-5.73 (m, 1H), 4.91 ((m, 1H), 4.42-4.16 (m, 4H), 3.78 (br s, 4H), 3.33 (br s, 4H).

Example 327

1-[(5-Chlorothiophen-2-yl)sulfonyl]-N-({2-[4-(pyridin-4-ylmethyl)piperazin-1-yl]-6-[4-(trifluoromethyl)phenyl]pyridin-4-yl}methyl)-L-prolinamide

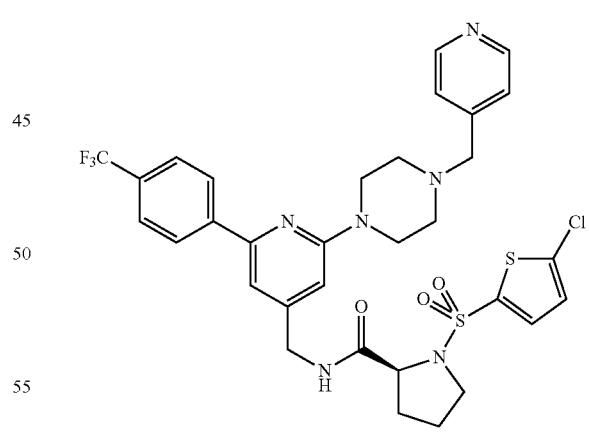

MS (ESI): mass calcd. for $C_{32}H_{32}ClF_3N_6O_3S_2$, 705.23 m/z found, 705.2 (70), 7.0-7.2 (30) [M+H]$^+$. CDCl$_3$: 8.56 (d, J=5.7 Hz, 2H), 8.12 (d, J=7.8 Hz, 2H), 7.66 (d, J=8.4 Hz, 2H), 7.45 (d, J=4.2 Hz, 1H), 7.34-7.32 (m, 2H), 7.07 (s, 1H), 7.03 (d, J=3.9 Hz, 1H), 6.64 (s, 1H), 4.72 (dd, J=16.2 Hz, 7.5 Hz, 1H), 4.31 (dd, J=16.2 Hz, 4.8 Hz, 1H), 4.17 (d, J=5.4 Hz, 1H), 3.71-3.69 (m, 4H), 3.65-3.62 (m, 1H), 3.58 (s, 2H), 3.21-3.19 (m, 1H, including trance of ether), 2.65-2.57 (m, 4H), 2.28-2.27 (m, 1H), 1.84-1.81 (m, 3H), 1.39 (t, 1H, peak of ether).

Example 328

1-[(4-Fluorophenyl)sulfonyl]-N-({2-[4-(pyridin-3-ylmethyl)piperazin-1-yl]-6-[4-(trifluoromethyl)phenyl]pyridin-4-yl}methyl)-L-prolinamide

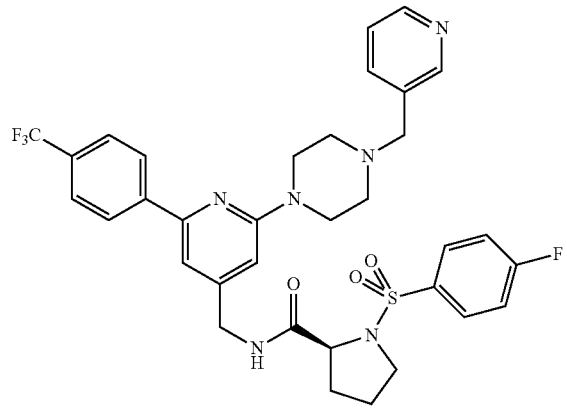 [SMILES: O=C(NCc1cc(-c2ccc(C(F)(F)F)cc2)nc(N2CCN(Cc3cccnc3)CC2)c1)[C@@H]1CCCN1S(=O)(=O)c1ccc(F)cc1]

MS (ESI): mass calcd. for $C_{34}H_{34}F_4N_6O_3S$, 682.75 m/z found, 683.2 [M+H]$^+$. CDCl$_3$: 8.57 (s, 1H), 8.53 (d, J=3.3 Hz, 1H), 8.12 (d, J=8.1 Hz, 2H), 7.89-7.85 (m, 2H), 7.71-7.64 (m, 3H), 7.33-7.22 (m, 3H), 7.08 (s, 1H), 6.67 (s, 1H), 4.71 (dd, J=16.2 Hz, 7.2 Hz, 1H), 4.33 (dd, J=16.2 Hz, 5.1 Hz, 1H), 4.14-4.12 (m, 1H), 3.70 (br s, 4H), 3.62-3.58 (m, 3H), 3.18-3.13 (m, 1H), 2.63 (br s, 4H), 2.24-2.20 (m, 1H), 1.79-1.67 (m, 3H).

Example 329

(2S)-1-[(4-Fluorophenyl)sulfonyl]-N-({2-[4-(pyridin-4-ylmethyl)piperazin-1-yl]-6-[4-(trifluoromethyl)phenyl]pyridin-4-yl}methyl)-2,5-dihydro-1H-pyrrole-2-carboxamide

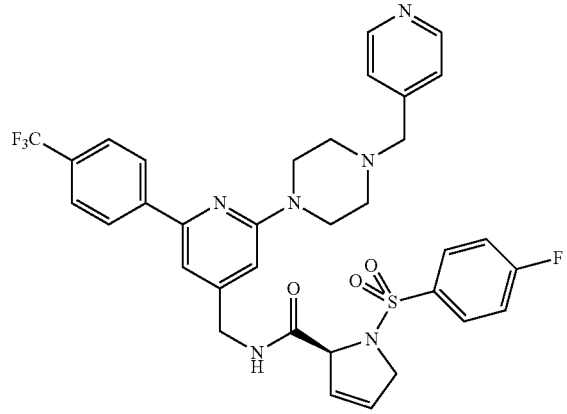 [SMILES: O=C(NCc1cc(-c2ccc(C(F)(F)F)cc2)nc(N2CCN(Cc3ccncc3)CC2)c1)[C@@H]1C=CCN1S(=O)(=O)c1ccc(F)cc1]

MS (ESI): mass calcd. for $C_{34}H_{32}F_4N_6O_3S$, 680.73 m/z found, 681.2 [M+H]$^+$. CDCl$_3$: 8.57 (d, J=5.7 Hz, 2H), 8.14 (d, J=8.1 Hz, 2H), 7.89-7.84 (m, 2H), 7.66 (d, J=8.4 Hz, 2H), 7.33 (d, J=5.4 Hz, 2H), 7.28-7.22 (m, 2H), 7.10 (s, 1H), 6.69 (s, 1H), 5.81-5.74 (m, 2H), 4.90-4.89 (m, 1H), 4.77 (dd, J=16.2 Hz, 7.5 Hz, 1H), 4.31-4.18 (m, 3H), 3.72 (br s, 4H), 3.57 (s, 2H), 2.58 (br s, 4H).

Example 330

(2S)-1-[(5-Chlorothiophen-2-yl)sulfonyl]-N-({2-[(pyridin-2-ylmethyl)amino]-6-[4-(trifluoromethyl)phenyl]pyridin-4-yl}methyl)-2,5-dihydro-1H-pyrrole-2-carboxamide

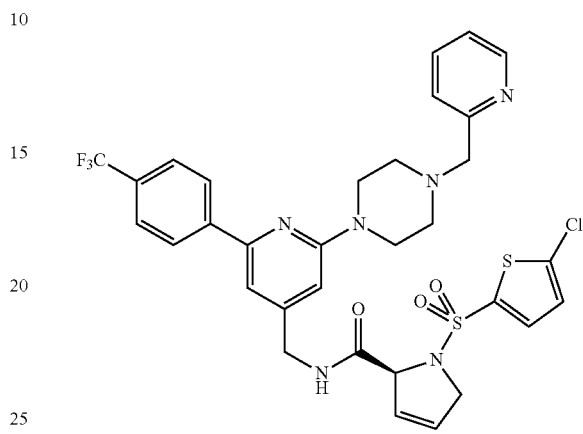

MS (ESI): mass calcd. for $C_{28}H_{23}ClF_3N_5O_3S_2$, 634.1 m/z found, 634.1 (90), 636.1 (40), [M+H]$^+$. CDCl$_3$: 8.56 (d, J=3.9 Hz, 1H), 8.08 (d, J=7.8 Hz, 2H), 7.65-7.62 (m, 3H), 7.43-7.35 (m, 3H), 7.17 (t, J=6.9 Hz, 1H), 7.05 (s, 1H), 6.97 (t, J=3.6 Hz, 2H), 6.44 (s, 1H), 5.87-5.70 (m, 3H), 4.90-4.89 (m, 1H), 4.74 (s, 2H), 4.68-4.59 (m, 1H), 4.34-4.13 (m, 3H).

Example 331

N-({2-(Dimethylamino)-6-[4-(trifluoromethyl)phenyl]pyridin-4-yl}methyl)-1-[(4-fluorophenyl)sulfonyl]-L-prolinamide

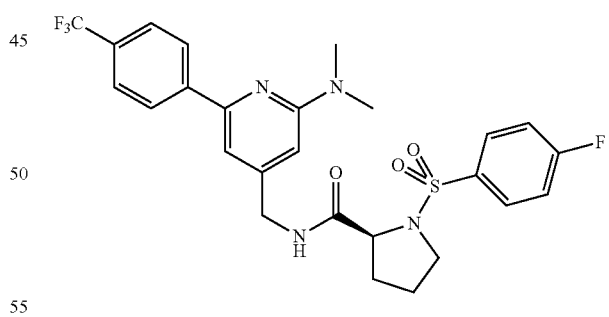

MS (ESI): mass calcd. for $C_{26}H_{26}F_4N_4O_3S$, 550.58 m/z found, 551.2 [M+H]$^+$. CDCl$_3$: 8.14 (d, J=7.5 Hz, 2H), 7.92-7.88 (m, 2H), 7.68 (d, J=8.1 Hz, 2H), 7.29 (br, 1H), 7.26 (1H, overlapped with CDCl$_3$ peak), 7.03 (s, 1H), 6.60 (s, 1H), 4.68 (dd, J=15.6 Hz, 6.6 Hz, 1H), 4.40 (dd, J=16.2 Hz, 4.5 Hz, 1H), 4.15 (d, J=5.7 Hz, 1H), 3.63-3.62 (m, 1H), 3.21-3.14 (m, 7H), 2.24-2.22 (m, 1H), 1.82-1.69 (m, 3H) DMSO-d6: 8.72 (br s, 1H), 8.26 (d, J=7.2 Hz, 2H), 7.98-7.95 (m, 2H), 7.78 (d, J=7.5 Hz, 2H), 7.51-7.46 (m, 2H), 7.21 (s, 1H), 6.64 (s, 1H), 4.40-4.34 (m, 2H), 4.12-4.10 (m, 1H), 3.51-3.49 (m, 1H), 3.20-3.10 (m, 7H), 1.82-1.79 (m, 3H), 1.54-1.52 (m, 1H).

Example 332

1-[(5-Chlorothiophen-2-yl)sulfonyl]-N-({2-(dimethylamino)-6-[4-(trifluoromethyl)phenyl]pyridin-4-yl}methyl)-L-prolinamide

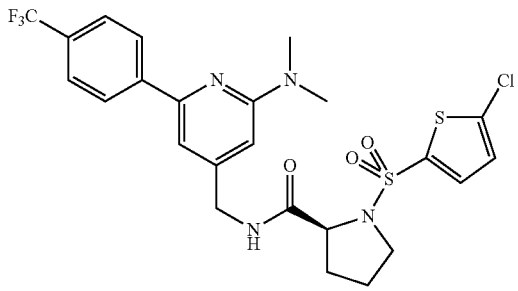 [SMILES: CN(C)c1cc(CNC(=O)[C@@H]2CCCN2S(=O)(=O)c2ccc(Cl)s2)cc(-c2ccc(C(F)(F)F)cc2)n1]

MS (ESI): mass calcd. for $C_{24}H_{24}ClF_3N_4O_3S_2$, 573.06 m/z found, 573.1 (100), 575.0 (50), [M+H]$^+$. CDCl$_3$: 8.15 (d, J=8.1 Hz, 2H), 7.67 (d, J=8.1 Hz, 2H), 7.46 (d, J=5.6 Hz, 1H), 7.04 (d, J=3.9 Hz, 1H), 6.99 (s, 1H), 6.51 (s, 1H), 4.68 (dd, J=15.3 Hz, 6.6 Hz, 1H), 4.37 (dd, J=16.2 Hz, 4.8 Hz, 1H), 4.19-4.17 (m, 1H), 3.66-3.60 (m, 1H), 3.26-3.22 (m, 1H), 3.18 (s, 6H), 2.30-2.29 (m, 1H), 1.86-1.76 (m, 3H).

Example 333

1-[(5-Chlorothiophen-2-yl)sulfonyl]-N-({2-(2-methylpyrrolidin-1-yl)-6-[4-(trifluoromethyl)phenyl]pyridin-4-yl}methyl)-L-prolinamide

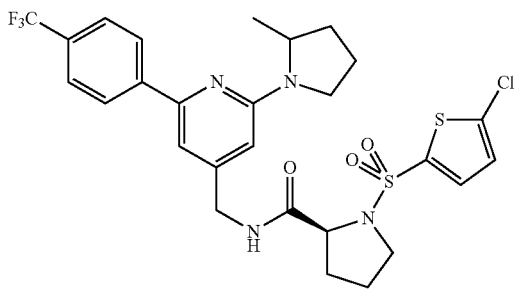 [SMILES: CC1CCCN1c1cc(CNC(=O)[C@@H]2CCCN2S(=O)(=O)c2ccc(Cl)s2)cc(-c2ccc(C(F)(F)F)cc2)n1]

MS (ESI): mass calcd. for $C_{27}H_{28}ClF_3N_4O_3S_2$, 613.13 m/z found, 613.1 (100), 615.1 (50), [M+H]$^+$. CDCl$_3$: 8.13 (d, J=8.1 Hz, 2H), 7.67 (d, J=8.1 Hz, 2H), 7.47 (d, J=3.9 Hz, 1H), 7.04 (d, J=3.9 Hz, 1H), 6.91 (s, 1H), 6.37 (s, 1H), 4.64 (dd, J=15.6 Hz, 6.6 Hz, 1H), 4.38 (dd, J=15.6 Hz, 5.1 Hz, 2H), 4.18 (d, J=6.0 Hz, 1H), 3.65-3.63 (m, 2H), 3.47-3.45 (m, 1H), 3.29-3.20 (m, 1H), 2.31-2.33 (m, 1H), 2.16-2.00 (m, 3H), 1.81-1.76 (m, 4H), 1.29 (d, J=6.3 Hz, 3H).

Example 334

(2S)-1-[(5-Chlorothiophen-2-yl)sulfonyl]-N-({2-(dimethylamino)-6-[4-(trifluoromethyl)phenyl]pyridin-4-yl}methyl)-2,5-dihydro-1H-pyrrole-2-carboxamide

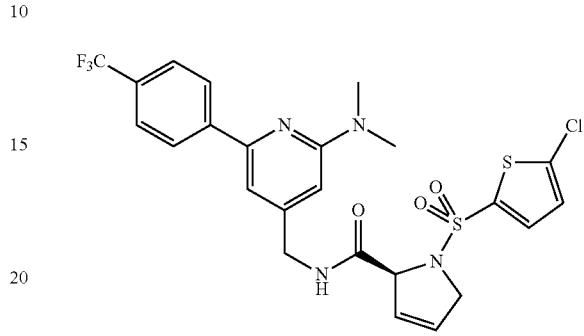

MS (ESI): mass calcd. for $C_{24}H_{22}ClF_3N_4O_3S_2$, 571.04 m/z found, 571.0 (100), 573.0 (50), [M+H]$^+$. CDCl$_3$: 8.15 (d, J=7.8 Hz, 2H), 7.67 (d, J=8.4 Hz, 2H), 7.47 (d, J=3.9 Hz, 1H), 7.19 (br s, 1H), 7.03 (d, J=3.9 Hz, 1H), 7.00 (s, 1H), 6.52 (s, 1H), 5.89-5.88 (m, 1H), 5.79-5.76 (m, 1H), 4.94-4.93 (m, 1H), 4.72 (dd, J=15.9 Hz, 7.2 Hz, 1H), 4.39-4.20 (m, 3H), 3.18 (s, 6H).

Example 335

1-[(5-Chlorothiophen-2-yl)sulfonyl]-N-({2-(methylamino)-6-[4-(trifluoromethyl)phenyl]pyridin-4-yl}methyl)-L-prolinamide

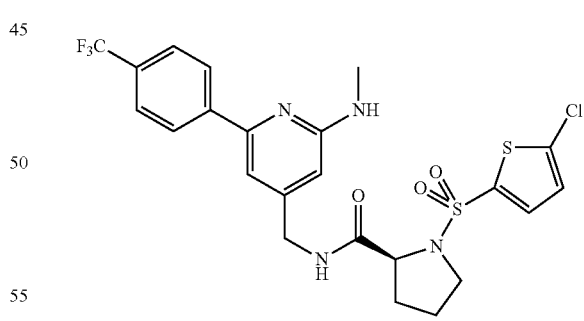

MS (ESI): mass calcd. for $C_{23}H_{22}ClF_3N_4O_3S_2$, 559.03 m/z found, 559.0 (100), 561.0 (50), [M+H]$^+$. CDCl$_3$: 8.11 (d, J=8.1 Hz, 2H), 7.68 (d, J=8.1 Hz, 2H), 7.47 (d, J=3.9 Hz, 1H), 7.05 (d, J=3.9 Hz, 1H), 7.02 (s, 1H), 6.41 (s, 1H), 4.92 (br s, 1H), 4.69 (dd, J=15.9 Hz, 7.2 Hz, 1H), 4.34 (dd, J=15.9 Hz, 5.1 Hz, 1H), 4.20-4.18 (m, 1H), 3.67-3.61 (m, 1H), 3.27-3.24 (m, 1H), 3.01 (s, 3H), 2.31-2.30 (m, 1H), 1.87-1.78 (m, 3H).

Example 336

1-[(4-Fluorophenyl)sulfonyl]-N-({2-(2-methylpyrrolidin-1-yl)-6-[4-(trifluoromethyl)phenyl]pyridin-4-yl}methyl)-L-prolinamide

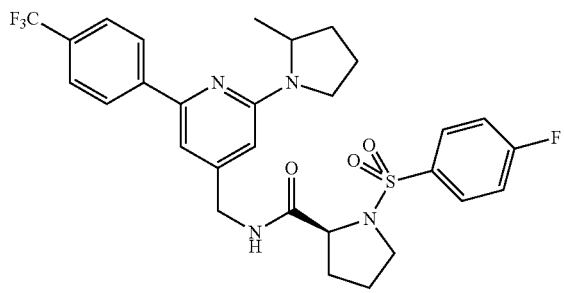 [SMILES: CC1CCCN1c1cc(CNC(=O)[C@@H]2CCCN2S(=O)(=O)c2ccc(F)cc2)cc(-c2ccc(C(F)(F)F)cc2)n1]

MS (ESI): mass calcd. for $C_{29}H_{30}F_4N_4O_3S$, 590.65 m/z found, 591.2 [M+H]$^+$. CDCl$_3$: 8.17 (d, J=8.1 Hz, 2H), 7.92-7.87 (m, 2H), 7.68 (d, J=8.1 Hz, 2H), 7.33-7.20 (m, 2H), 7.00 (s, 1H), 6.36 (s, 1H), 4.64 (dd, J=15.0 Hz, 6 Hz, 1H), 4.42-4.33 (m, 2H), 4.17-4.14 (m, 1H), 3.64-3.58 (m, 2H), 3.45-3.42 (m, 1H), 3.18-3.15 (m, 1H), 2.26-2.22 (m, 1H), 2.09-1.99 (m, 3H), 1.79-1.66 (m, 4H), 1.30 (d, J=6.3 Hz, 3H).

Example 337

1-[(4-Fluorophenyl)sulfonyl]-N-({2-(methylamino)-6-[4-(trifluoromethyl)phenyl]pyridin-4-yl}methyl)-L-prolinamide

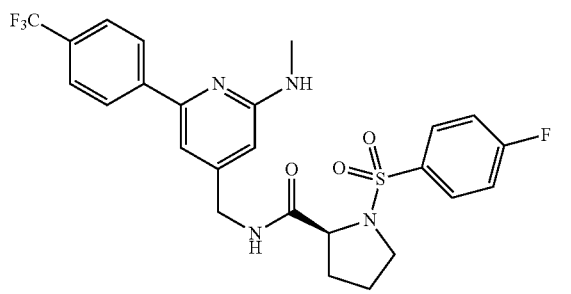

MS (ESI): mass calcd. for $C_{25}H_{24}F_4N_4O_3S$, 536.55 m/z found, 537.1 [M+H]$^+$. CDCl$_3$: 8.13 (d, J=7.8 Hz, 2H), 7.93-7.88 (m, 2H), 7.69 (d, J=8.1 Hz, 2H), 7.39-7.37 (m, 1H), 7.30-7.25 (m, 2H), 7.03 (s, 1H), 6.48 (s, 1H), 4.72 (dd, J=16.2 Hz, 7.2 Hz, 1H), 4.36 (dd, J=16.2 Hz, 5.4 Hz, 1H), 4.17-4.14 (m, 1H), 3.67-3.61 (m, 1H), 3.21-3.13 (m, 1H), 3.02 (d, J=5.1 Hz, 3H), 2.26-2.22 (m, 1H), 1.85-1.69 (m, 3H).

Example 338

(2S)—N-({2-(Dimethylamino)-6-[4-(trifluoromethyl)phenyl]pyridin-4-yl}methyl)-1-[(4-fluorophenyl)sulfonyl]-2,5-dihydro-1H-pyrrole-2-carboxamide

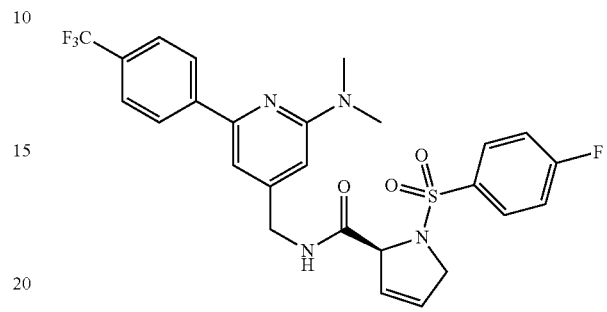

MS (ESI): mass calcd. for $C_{26}H_{24}F_4N_4O_3S$, 548.56 m/z found, 549.1 [M+H]$^+$. CDCl$_3$: 8.16 (d, J=8.1 Hz, 2H), 7.90-7.86 (m, 2H), 7.68-7.65 (d, J=8.1 Hz, 2H), 7.28-7.20 (m, 2H), 7.04 (s, 1H), 6.56 (s, 1H), 5.84-5.81 (m, 1H), 5.75-5.72 (m, 1H), 4.92-4.89 (m, 1H), 4.73 (dd, J=16.2 Hz, 7.2 Hz, 1H), 4.38-4.29 (m, 2H), 4.18-4.11 (m, 1H), 3.19 (s, 6H).

Example 339

1-[(5-Chlorothiophen-2-yl)sulfonyl]-N-({2-[4-(pyridin-2-ylmethyl)piperazin-1-yl]-6-[4-(trifluoromethyl)phenyl]pyridin-4-yl}methyl)-L-prolinamide

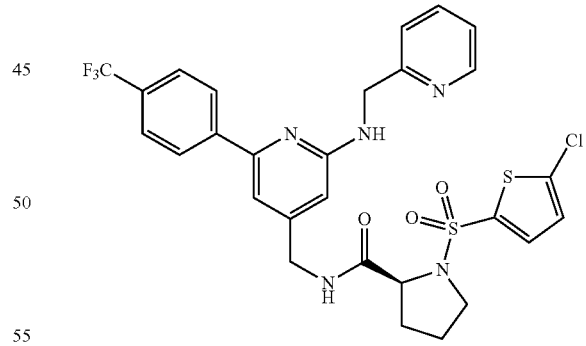

MS (ESI): mass calcd. for $C_{32}H_{32}ClF_3N_6O_3S_2$, 705.23 m/z found, 705.2 (25), 706.2 (15), [M+H]$^+$. CDCl$_3$: 8.60 (d, J=4.2 Hz, 1H), 8.12 (d, J=8.4 Hz, 2H), 7.72-7.65 (m, 3H), 7.51-7.45 (m, 2H), 7.22-7.18 (m, 1H), 7.07 (s, 1H), 7.04 (d, J=3.9 Hz, 1H), 6.64 (s, 1H), 4.71 (dd, J=15.2 Hz, 7.5 Hz, 1H), 4.33 (dd, J=15.2 Hz, 5.1 Hz, 1H), 4.19-4.16 (m, 1H), 3.77-3.75 (m, 6H), 3.67-3.60 (m, 1H), 3.28-3.19 (m, 1H), 3.19-2.29 (m, 4H), 2.30-2.28 (m, 1H), 1.90-1.76 (m, 3H).

Example 340

(2S)-1-[(5-Chlorothiophen-2-yl)sulfonyl]-N-({2-[4-(pyridin-4-ylmethyl)piperazin-1-yl]-6-[4-(trifluoromethyl)phenyl]pyridin-4-yl}methyl)-2,5-dihydro-1H-pyrrole-2-carboxamide

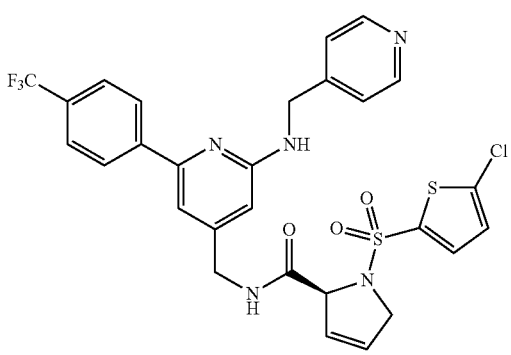 [SMILES: O=C(NCc1cc(NCc2ccncc2)nc(-c2ccc(C(F)(F)F)cc2)c1)[C@@H]1C=CCN1S(=O)(=O)c1ccc(Cl)s1]

MS (ESI): mass calcd. for $C_{32}H_{30}ClF_3N_6O_3S_2$, 703.21 m/z found, 703.2 (10), 705.1 (5), [M+H]$^+$. CDCl$_3$: 8.58 (d, J=5.4 Hz, 2H), 8.12 (d, J=8.1 Hz, 2H), 7.67 (d, J=8.1 Hz, 2H), 7.47 (d, J=3.9 Hz, 1H), 7.35 (d, J=4.8 Hz, 2H), 7.20-7.16 (m, 1H), 7.08 (s, 1H), 7.04 (d, J=3.9 Hz, 1H), 6.66 (s, 1H), 5.89-5.87 (m, 1H), 5.80-5.78 (m, 1H), 4.94-4.93 (m, 1H), 4.79 (dd, J=15.9 Hz, 7.2 Hz, 1H), 4.40-4.20 (m, 3H), 3.74 (br s, 4H), 3.59 (s, 2H), 2.61 (br s, 4H).

Example 341

1-[(5-Chlorothiophen-2-yl)sulfonyl]-N-({2-[4-(pyridin-3-ylmethyl)piperazin-1-yl]-6-[4-(trifluoromethyl)phenyl]pyridin-4-yl}methyl)-L-prolinamide

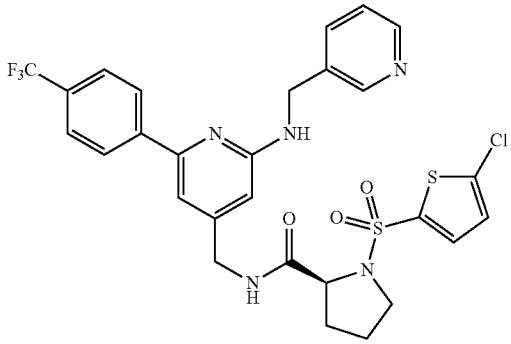 [SMILES: O=C(NCc1cc(NCc2cccnc2)nc(-c2ccc(C(F)(F)F)cc2)c1)[C@@H]1CCCN1S(=O)(=O)c1ccc(Cl)s1]

MS (ESI): mass calcd. for $C_{32}H_{32}ClF_3N_6O_3S_2$, 705.23 m/z found, 705.2 (15), 706.2 (5), [M+H]$^+$. CDCl$_3$: 8.58 (s, 1H), 8.55-8.53 (m, 1H), 8.11 (d, J=8.1 Hz, 2H), 7.79 (br s, 1H), 7.66 (d, J=8.4 Hz, 2H), 7.45 (d, J=4.2 Hz, 1H), 7.31-7.29 (m, 2H), 7.07 (s, 1H), 7.04 (d, J=4.2 Hz, 1H), 6.64 (s, 1H), 4.73 (dd, J=16.2 Hz, 7.5 Hz, 1H), 4.32 (dd, J=16.2 Hz, 4.8 Hz, 1H), 3.72 (br s, 4H), 3.67-3.61 (m, 3H), 3.25-3.22 (m, 1H), 2.63 (br s, 4H), 2.29-2.27 (m, 1H), 1.86-1.76 (m, 3H).

Example 342

1-[(4-Fluorophenyl)sulfonyl]-N-({2-[4-(pyridin-4-ylmethyl)piperazin-1-yl]-6-[4-(trifluoromethyl)phenyl]pyridin-4-yl}methyl)-L-prolinamide

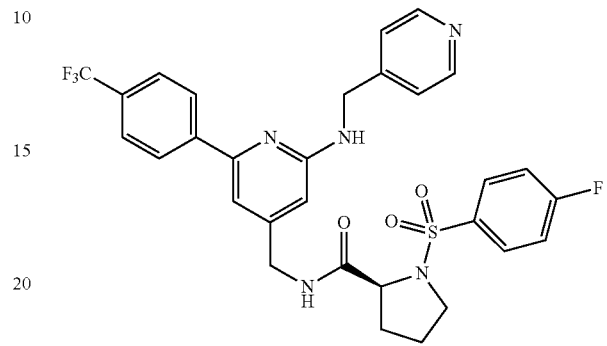

MS (ESI): mass calcd. for $C_{34}H_{34}F_4N_6O_3S$, 682.75 m/z found, 683.2 (15), 684.2 (5), [M+H]$^+$. CDCl$_3$: 8.57 (d, J=5.7 Hz, 2H), 8.13 (d, J=8.1 Hz, 2H), 7.90-7.85 (m, 2H), 7.66 (d, J=8.1 Hz, 2H), 7.35-7.23 (m, 4H), 7.10 (s, 1H), 6.69 (s, 1H), 4.72 (dd, J=16.2 Hz, 7.2 Hz, 1H), 4.33 (dd, J=16.2 Hz, 4.8 Hz, 1H), 4.14-4.12 (m, 1H), 3.75 (br s, 4H), 3.62-3.60 (m, 3H), 3.15-3.13 (m, 1H), 2.63 (br s, 4H), 2.22-2.21 (m, 1H), 1.71-1.67 (m, 3H).

Example 343

4,4-Difluoro-1-[(4-fluorophenyl)sulfonyl]-N-({2-[(pyridin-4-ylmethyl)amino]-6-[4-(trifluoromethyl)phenyl]pyridin-4-yl}methyl)-L-prolinamide

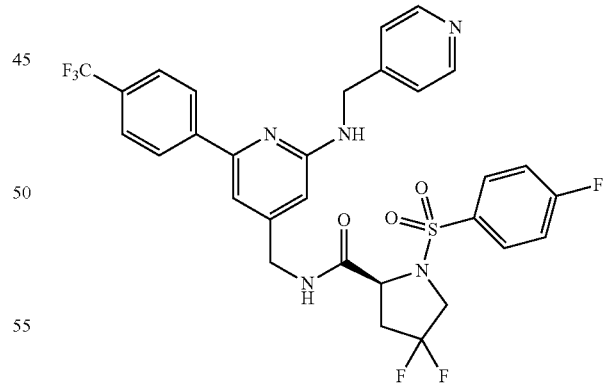

MS (ESI): mass calcd. for $C_{30}H_{25}F_6N_5O_3S$, 649.62 m/z found, 650.1 [M+H]$^+$. CDCl$_3$: 8.52 (d, J=5.1 Hz, 2H), 7.97 (d, J=8.1 Hz, 2H), 7.87-7.83 (m, 2H), 7.61 (d, J=8.4 Hz, 2H), 7.46 (t, J=6.0 Hz, 1H), 7.31-7.24 (m, 3H), 7.05 (s, 1H), 6.39 (s, 1H), 5.23 (t, J=6.0 Hz, 1H), 4.64 (d, J=5.7 Hz, 2H), 4.54 (dd, J=16.2 Hz, 6.6 Hz, 1H), 4.39 (dd, J=16.2 Hz, 5.7 Hz, 1H), 4.31 (dd, J=13.2 Hz, 4.5 Hz, 1H), 385-3.71 (m, 1H), 3.64-3.52 (m, 1H), 2.73-2.59 (m, 1H), 2.37-2.20 (m, 1H).

Example 344

(2S)-1-[(4-Fluorophenyl)sulfonyl]-N-({2-[(pyridin-4-ylmethyl)amino]-6-[4-(trifluoromethyl)phenyl]pyridin-4-yl}methyl)-2,5-dihydro-1H-pyrrole-2-carboxamide

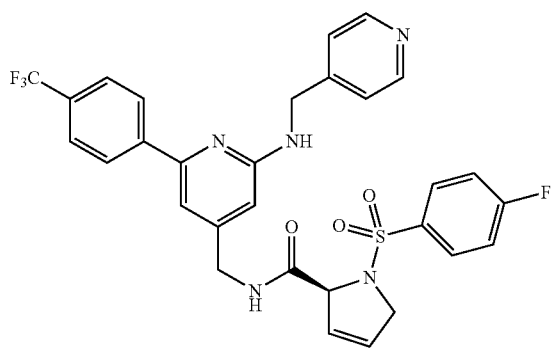 [SMILES: O=C(NCc1cc(NCc2ccncc2)nc(-c2ccc(C(F)(F)F)cc2)c1)[C@@H]1C=CCN1S(=O)(=O)c1ccc(F)cc1]

MS (ESI): mass calcd. for $C_{30}H_{25}F_4N_5O_3S$, 611.62 m/z found, 612.2 [M+H]$^+$. CDCl$_3$: 8.53 (d, J=5.4 Hz, 2H), 8.00 (d, J=8.1 Hz, 2H), 7.87-7.83 (m, 2H), 7.62 (d, J=8.4 Hz, 2H), 7.32-7.22 (m, 4H), 7.09 (s, 1H), 6.46 (s, 1H), 5.78-5.76 (m, 1H), 5.71-5.70 (m, 1H), 5.18 (t, J=6.0 Hz, 1H), 4.87 (br s, 1H), 4.74-4.65 (m, 3H), 4.35-4.11 (m, 3H).

Example 345

(2S)-1-[(5-Chlorothiophen-2-yl)sulfonyl]-N-({2-[(pyridin-3-ylmethyl)amino]-6-[4-(trifluoromethyl)phenyl]pyridin-4-yl}methyl)-2,5-dihydro-1H-pyrrole-2-carboxamide

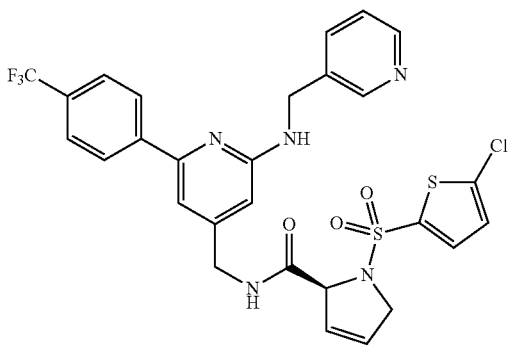 [SMILES: O=C(NCc1cc(NCc2cccnc2)nc(-c2ccc(C(F)(F)F)cc2)c1)[C@@H]1C=CCN1S(=O)(=O)c1ccc(Cl)s1]

MS (ESI): mass calcd. for $C_{28}H_{23}ClF_3N_5O_3S_2$, 634.1 m/z found, 634.0 (10) [M+H]$^+$. CD$_3$OD: 8.89 (s, 1H), 8.75 (d, J=5.4 Hz, 2H), 8.63 (d, J=8.1 Hz, 2H), 8.08-8.00 (m, 3H), 7.78 (d, J=8.4 Hz, 2H), 7.62 9 d, J=3.9 Hz, 1H), 7.28 (s, 1H), 7.21 (d, J=3.9 Hz, 1H), 6.85 (s, 1H), 5.97-5.94 (m, 1H), 5.76-5.73 (m, 1H), 4.93-4.90 (m, 3H), 4.64 (d, J=16.2 Hz, 1H), 4.44-4.19 (m, 3H).

Example 346

(2S)-1-[(4-Fluorophenyl)sulfonyl]-N-({2-[(pyridin-3-ylmethyl)amino]-6-[4-(trifluoromethyl)phenyl]pyridin-4-yl}methyl)-2,5-dihydro-1H-pyrrole-2-carboxamide

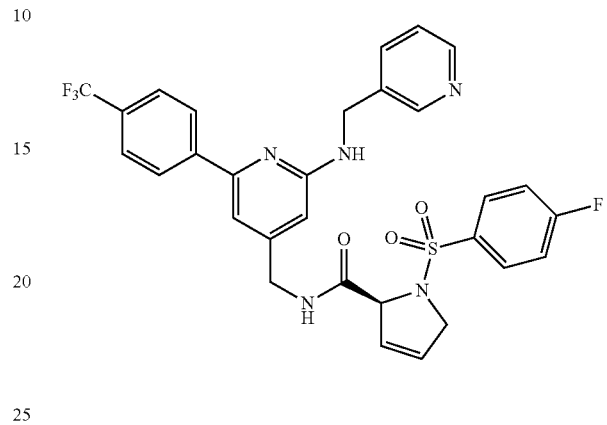

MS (ESI): mass calcd. for $C_{30}H_{25}F_4N_5O_3S$, 611.62 m/z found, 612.2 [M+H]$^+$. CDCl$_3$: 8.63 (s, 1H), 8.49 (d, J=4.2 Hz, 1H), 8.04 (d, J=8.1 Hz, 2H), 7.89-7.85 (m, 2H), 7.80 (d, J=7.8 Hz, 1H), 7.64 (d, J=8.4 Hz, 2H), 7.31-7.20 (m, 3H), 7.08 (s, 1H), 6.47 (s, 1H), 5.81-5.72 (m, 2H), 5.16 (br s, 1H), 4.91-4.88 (m, 1H), 4.71-4.63 (m, 3H), 4.37-4.13 (m, 3H).

Example 347

1-[(5-Chlorothiophen-2-yl)sulfonyl]-N-({2-[(pyridin-2-ylmethyl)amino]-6-[4-(trifluoromethyl)phenyl]pyridin-4-yl}methyl)-L-prolinamide

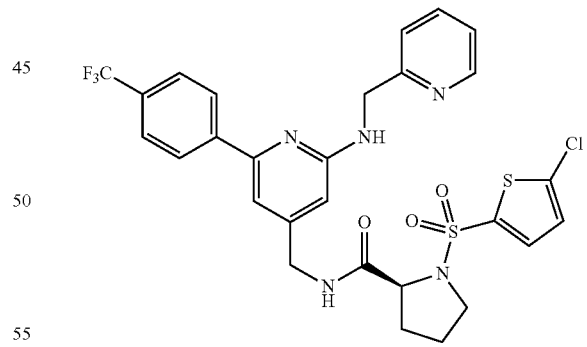

MS (ESI): mass calcd. for $C_{28}H_{25}ClF_3N_5O_3S_2$, 636.12 m/z found, 636.1 (55), 637.1 (20), [M+H]$^+$. CDCl$_3$: 8.56 (d, J=4.2 Hz, 1H), 8.07 (d, J=8.1 Hz, 2H), 7.65-7.62 (m, 3H), 7.45 (d, J=4.2 Hz, 1H), 7.37-7.30 (m, 3H), 7.19-7.15 (m, 1H), 7.04 (s, 1H), 7.01 (d, J=4.2 Hz, 1H), 6.42 (s, 1H), 5.76 (br s, 1H), 4.74 (s, 2H), 4.58 (dd, J=16.2 Hz, 7.2 Hz, 1H), 4.31 (dd, J=16.2 Hz, 5.4 Hz, 1H), 4.16 (d, J=5.7 Hz, 1H), 3.69-3.60 (m, 1H), 3.26-3.18 (m, 1H), 2.25-2.21 (m, 1H), 1.83-1.74 (m, 3H), (3.70 and 1.22 trace of ethanol).

Example 348

1-[(4-Fluorophenyl)sulfonyl]-N-({2-[4-(pyridin-2-ylmethyl)piperazin-1-yl]-6-[4-(trifluoromethyl)phenyl]pyridin-4-yl}methyl)-L-prolinamide

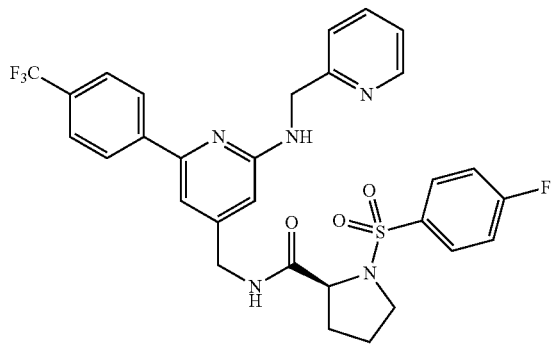 [SMILES: O=C(NCc1cc(NCc2ccccn2)nc(-c2ccc(C(F)(F)F)cc2)c1)[C@@H]1CCCN1S(=O)(=O)c1ccc(F)cc1]

MS (ESI): mass calcd. for $C_{34}H_{34}F_4N_6O_3S$, 682.75 m/z found, 683.2 [M+H]$^+$. CDCl$_3$: 8.59 (d, J=4.5 Hz, 1H), 8.13 (d, J=8.4 Hz, 2H), 7.90-7.85 (m, 2H), 7.70-7.64 (m, 3H), 7.47-7.45 (m, 1H), 7.36-7.34 (m, 1H), 7.32-7.16 (m, 2H), 7.09 (s, 1H), 6.66 (s, 1H), 4.69 (dd, J=15.9 Hz, 7.2 Hz, 1H), 4.34 (dd, J=15.9 Hz, 5.1 Hz, 1H), 4.14-4.12 (m, 1H), 3.73 (br s, 6H), 3.63-3.57 (m, 1H), 3.18-3.10 (m, 1H), 2.66 (br s, 4H), 2.25-2.21 (m, 1H), 1.84-1.64 (m, 3H).

Example 349

1-[(4-Fluorophenyl)sulfonyl]-N-({2-[(1-pyridin-3-ylethyl)amino]-6-[4-(trifluoromethyl)phenyl]pyridin-4-yl}methyl)-L-prolinamide

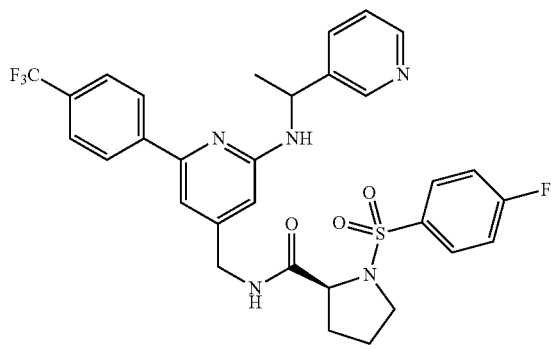 [SMILES: CC(Nc1cc(CNC(=O)[C@@H]2CCCN2S(=O)(=O)c2ccc(F)cc2)cc(-c2ccc(C(F)(F)F)cc2)n1)c1cccnc1]

MS (ESI): mass calcd. for $C_{31}H_{29}F_4N_5O_3S$, 627.67 m/z found, 628.2 [M+H]$^+$. DMSO-d6: 8.70 (br s, 2H), 8.42 (d, J=4.5 Hz, 1H), 8.14 (d, J=7.8 Hz, 2H), 8.03-7.98 (m, 2H), 7.85 (d, J=7.8 Hz, 1H), 7.77 (d, J=7.8 Hz, 2H), 7.51 (t, J=8.1 Hz, 2H), 7.38-7.34 (m, 2H), 7.16 (s, 1H), 6.49 (s, 1H), 5.23 (t, J=6.6 Hz, 1H), 4.30-4.22 (m, 2H), 4.15-4.12 (m, 1H), 3.53-3.50 (m, 1H), 3.24-3.22 (m, 1H), 1.845-1.83 (m, 3H), 1.56-1.54 (m, 4H).

Example 350

(2S)-1-[(4-Fluorophenyl)sulfonyl]-N-({2-[(1-pyridin-3-ylethyl)amino]-6-[4-(trifluoromethyl)phenyl]pyridin-4-yl}methyl)-2,5-dihydro-1H-pyrrole-2-carboxamide

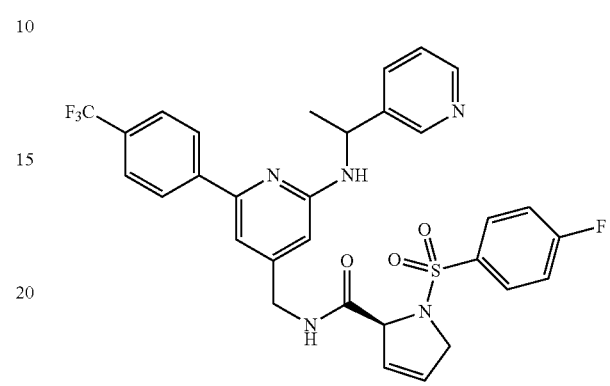

MS (ESI): mass calcd. for $C_{31}H_{27}F_4N_5O_3S$, 625.65 m/z found, 626.2 [M+H]$^+$. DMSO-d6: 8.72 (t, J=5.7 Hz, 1H), 8.66 (s, 1H), 8.38 (d, J=4.5 Hz, 1H), 8.09 (d, J=8.4 Hz, 2H), 7.99-7.95 (m, 2H), 7.81 (d, J=7.8 Hz, 1H), 7.73 (d, J=8.1 Hz, 2H), 7.47 (t, J=8.7 Hz, 2H), 7.34-7.27 (m, 2H), 7.10 (s, 1H), 6.45 (s, 1H), 5.90 (d, J=4.5 Hz, 1H), 5.72 (d, J=4.5 Hz, 1H), 5.20-5.16 (m, 1H), 4.89-4.88 (m, 1H), 4.31-4.10 (m, 4H), 1.51 (d, J=7.2 Hz, 3H).

Example 351

(2S)-1-[(5-Chlorothiophen-2-yl)sulfonyl]-N-({2-[(1-pyridin-3-ylethyl)amino]-6-[4-(trifluoromethyl)phenyl]pyridin-4-yl}methyl)-2,5-dihydro-1H-pyrrole-2-carboxamide

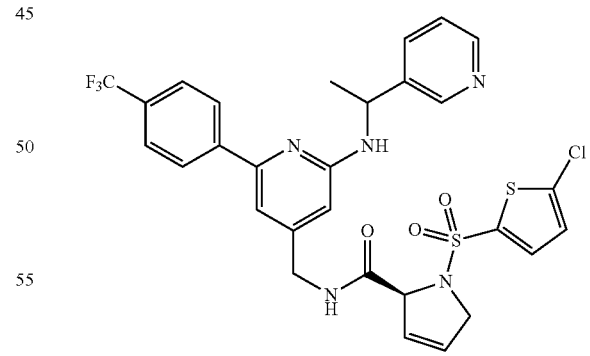

MS (ESI): mass calcd. for $C_{29}H_{25}ClF_3N_5O_3S_2$, 648.13 m/z found, 648.1 (45), 649.1 (15), 650.1 (25), [M+H]$^+$. DMSO-d6: 8.75 (t, J=5.7 Hz, 1H), 8.66 (s, 1H), 8.38 (d, J=4.5 Hz, 1H), 8.08 (d, J=8.1 Hz, 2H), 7.82-7.71 (m, 4H), 7.38-7.27 (m, 3H), 7.07 (s, 1H), 6.44 (s, 1H), 5.95 (d, J=4.5 Hz, 1H), 5.76 (d, J=5.7 Hz, 1H), 5.20-5.16 (m, 1H), 4.89-4.88 (m, 1H), 4.33-4.14 (m, 4H), 1.51 (d, J=6.9 Hz, 3H).

Example 352

N-({2-(Benzylamino)-6-[4-(trifluoromethyl)phenyl]pyridin-4-yl}methyl)-1-[(5-chlorothiophen-2-yl)sulfonyl]-4,4-difluoro-L-prolinamide

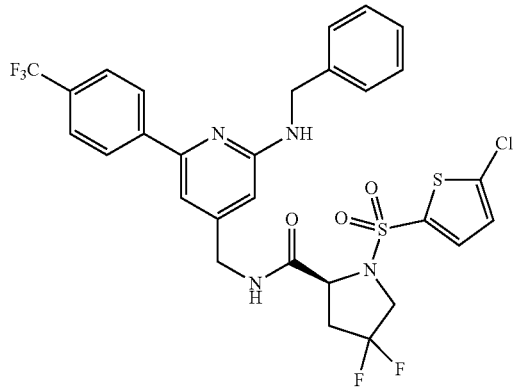 [SMILES: O=C(NCc1cc(NCc2ccccc2)nc(-c2ccc(C(F)(F)F)cc2)c1)[C@@H]1CC(F)(F)CN1S(=O)(=O)c1ccc(Cl)s1]

MS (ESI): mass calcd. for $C_{29}H_{24}ClF_5N_4O_3S_2$, 671.11 m/z found, 671.0 (100), 673.1 (50), [M+H]$^+$. CDCl$_3$: 8.08 (d, J=7.8 Hz, 2H), 7.66 (d, J=8.1 Hz, 2H), 7.48 (dd, J=4.2 Hz, 1.2 Hz, 1H), 7.41-7.26 (m, 5H), 7.22-7.20 (m, 1H), 7.06 (dd, J=3.9 Hz, 1.2 Hz, 1H), 7.03 (s, 1H), 6.35 (s, 1H), 5.05 (br s, 1H), 4.61 (d, J=5.4 Hz, 2H), 4.58-4.35 (m, 3H), 3.84-3.77 (m, 1H), 3.71-3.62 (m, 1H), 2.81-2.76 (m, 1H), 2.46-2.39 (m, 1H).

Example 353

(2S)-1-[(4-Fluorophenyl)sulfonyl]-N-({2-[4-(pyridin-2-ylmethyl)piperazin-1-yl]-6-[4-(trifluoromethyl)phenyl]pyridin-4-yl}methyl)-2,5-dihydro-1H-pyrrole-2-carboxamide

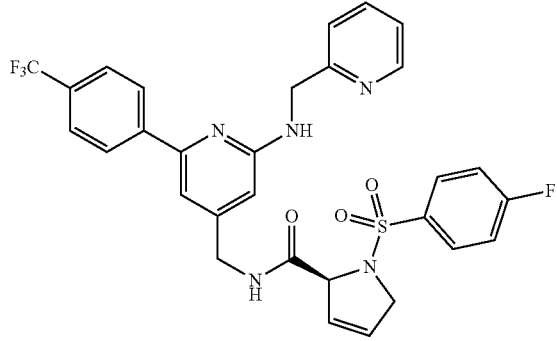 [SMILES: O=C(NCc1cc(NCc2ccccn2)nc(-c2ccc(C(F)(F)F)cc2)c1)[C@@H]1C=CCN1S(=O)(=O)c1ccc(F)cc1]

MS (ESI): mass calcd. for $C_{34}H_{32}F_4N_6O_3S$, 680.73 m/z found, 681.2 [M+H]$^+$. CDCl$_3$: 8.58 (d, J=4.5 Hz, 1H), 8.13 (d, J=8.4 Hz, 2H), 7.88-7.84 (m, 2H), 7.70-7.64 (m, 3H), 7.48-7.45 (m, 1H), 7.27-7.16 (m, 3H), 7.10 (s, 1H), 6.68 (s, 1H), 5.82-5.80 (m, 1H), 5.74-5.71 (m, 1H), 4.90-4.88 (m, 1H), 4.75 (dd, J=16.2 Hz, 7.5 Hz, 1H), 4.36-4.25 (m, 3H), 3.73 (br s, 6H), 2.66 (br s, 4H).

Example 354

(2S)-1-[(5-Chlorothiophen-2-yl)sulfonyl]-N-({2-[4-(pyridin-2-ylmethyl)piperazin-1-yl]-6-[4-(trifluoromethyl)phenyl]pyridin-4-yl}methyl)-2,5-dihydro-1H-pyrrole-2-carboxamide

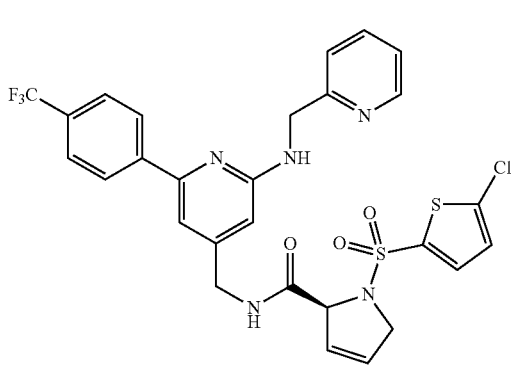 [SMILES: O=C(NCc1cc(NCc2cccnc2)nc(-c2ccc(C(F)(F)F)cc2)c1)[C@@H]1C=CCN1S(=O)(=O)c1ccc(Cl)s1]

MS (ESI): mass calcd. for $C_{32}H_{30}ClF_3N_6O_3S_2$, 703.21 m/z found, 703.2 (50), 705.2 (25), [M+H]$^+$. CDCl$_3$: 8.59 (d, J=4.8 Hz, 1H), 8.12 (d, J=8.1 Hz, 2H), 7.70-7.64 (m, 3H), 7.49-7.44 (m, 2H), 7.21-7.17 (m, 2H), 7.07 (s, 1H), 7.02 (d, J=3.9 Hz, 1H), 6.64 (s, 1H), 5.88-5.85 (m, 1H), 5.77-5.76 (m, 1H), 4.93-4.90 (m, 1H), 4.75 (dd, J=16.2 Hz, 7.5 Hz, 1H), 4.38-4.17 (m, 3H), 3.74 (br s, 6H), 2.66 (br s, 4H).

Example 355

(2S)-1-[(5-Chlorothiophen-2-yl)sulfonyl]-N-({2-[4-(pyridin-3-ylmethyl)piperazin-1-yl]-6-[4-(trifluoromethyl)phenyl]pyridin-4-yl}methyl)-2,5-dihydro-1H-pyrrole-2-carboxamide

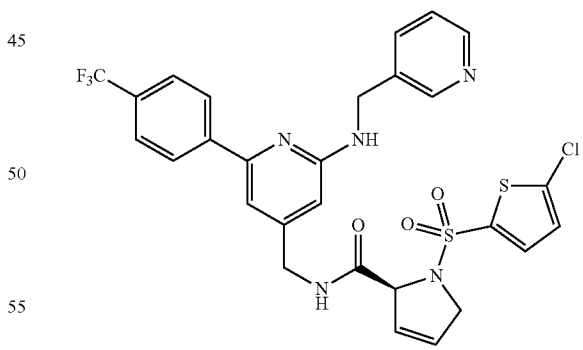

MS (ESI): mass calcd. for $C_{32}H_{30}ClF_3N_6O_3S_2$, 703.21 m/z found, 703.1 (40), 705.1 (20), [M+H]$^+$. CDCl$_3$: 8.58 (d, J=1.2 Hz, 1H), 8.53 (d, J=3.6 Hz, 1H), 8.11 (d, J=8.1 Hz, 2H), 7.75-7.73 (m, 1H), 7.66 (d, J=8.4 Hz, 2H), 7.45 (d, J=4.2 Hz, 1H), 7.30-7.26 (m, 1H), 7.21-7.18 (m, 1H), 7.07 (s, 1H), 7.02 (d, J=3.9 Hz, 1H), 6.65 (s, 1H), 5.88-5.85 (m, 1H), 5.79-5.76 (m, 1H), 4.93-4.91 (m, 1H), 4.76 (dd, J=16.2 Hz, 7.8 Hz, 1H), 4.38-4.17 (m, 3H), 3.70 (br s, 4H), 3.59 (s, 2H), 2.59 (br s, 4H).

Example 356

4,4-Difluoro-1-[(4-fluorophenyl)sulfonyl]-N-({2-[4-(pyridin-4-ylmethyl)piperazin-1-yl]-6-[4-(trifluoromethyl)phenyl]pyridin-4-yl}methyl)-L-prolinamide

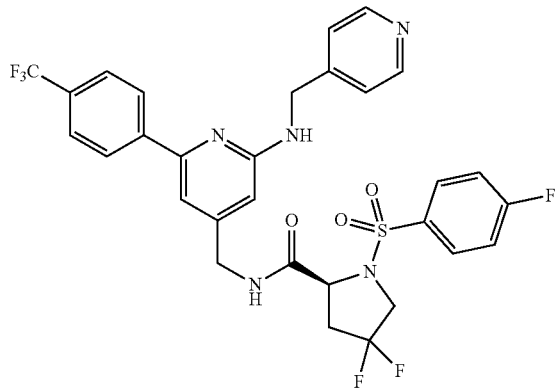 [SMILES: O=C(NCc1cc(NCc2ccncc2)nc(-c2ccc(C(F)(F)F)cc2)c1)[C@@H]1CC(F)(F)CN1S(=O)(=O)c1ccc(F)cc1]

MS (ESI): mass calcd. for $C_{34}H_{32}F_6N_6O_3S$, 718.73 m/z found, 719.2 (50), 720.2 (20), [M+H]$^+$. CDCl$_3$: 8.61 (d, J=6.0 Hz, 2H), 8.12 (d, J=8.4 Hz, 2H), 7.90-7.86 (m, 2H), 7.66 (d, J=8.1 Hz, 2H), 7.40 (d, J=5.7 Hz, 1H), 7.32-7.26 (m, 2H), 7.08 (s, 1H), 6.64 (s, 1H), 4.64 (dd, J=16.2 Hz, 6.9 Hz, 1H), 4.45 (dd, J=16.2 Hz, 5.4 Hz, 1H), 4.36-4.31 (m, 1H), 3.84-3.66 (m, 6H), 3.54 (s, 2H), 2.73-2.60 (m, 5H), 2.36-2.26 (m, 1H).

Example 357

4,4-Difluoro-N-({2-[4-(2-fluorophenyl)piperazin-1-yl]-6-[4-(trifluoromethyl)phenyl]pyridin-4-yl}methyl)-1-[(4-fluorophenyl)sulfonyl]-L-prolinamide

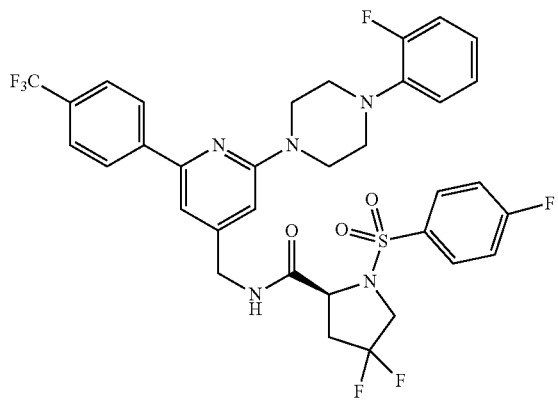 [SMILES: O=C(NCc1cc(-c2ccc(C(F)(F)F)cc2)nc(N2CCN(c3ccccc3F)CC2)c1)[C@@H]1CC(F)(F)CN1S(=O)(=O)c1ccc(F)cc1]

MS (ESI): mass calcd. for $C_{34}H_{30}F_7N_5O_3S$, 721.7 m/z found, 722.1 [M+H]$^+$. CDCl$_3$: 8.14 (d, J=8.1 Hz, 2H), 7.97-7.87 (m, 2H), 7.68 (d, J=8.1 Hz, 2H), 7.34-7.20 (m, 3H), 7.11 (s, 1H), 7.08-6.93 (m, 4H), 6.70 (s, 1H), 4.65 (dd, J=15.9 Hz, 6.9 Hz, 1H), 4.47 (dd, J=15.9 Hz, 5.7 Hz, 1H), 4.37-4.33 (m, 1H), 3.88-3.78 (m, 6H), 3.23-3.20 (m, 4H), 2.75-2.70 (m, 1H), 2.37-2.26 (m, 1H).

Example 358

1-[(5-Chlorothiophen-2-yl)sulfonyl]-4,4-difluoro-N-({2-[4-(2-fluorophenyl)piperazin-1-yl]-6-[4-(trifluoromethyl)phenyl]pyridin-4-yl}methyl)-L-prolinamide

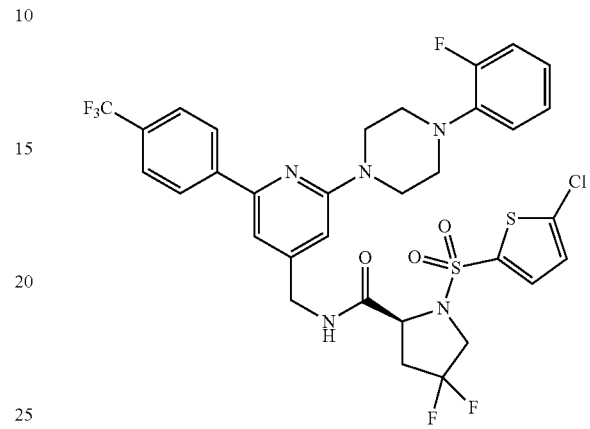

MS (ESI): mass calcd. for $C_{32}H_{28}ClF_6N_5O_3S_2$, 744.18 m/z found, 744.1 (100), 746.1 (55), [M+H]$^+$. CDCl$_3$: 8.14 (d, J=8.1 Hz, 2H), 7.68 (d, J=8.1 Hz, 2H), 7.52-7.49 (m, 1H), 7.10-6.93 (m, 6H), 6.67 (s, 1H), 4.64 (dd, J=15.9 Hz, 6.6 Hz, 1H), 4.50-4.38 (m, 2H), 3.93-3.82 (m, 5H), 3.72-3.60 (m, 1H), 3.25-3.20 (m, 4H), 2.83-2.79 (m, 1H), 2.49-2.38 (m, 1H).

Example 359

(2S)-1-[(5-Chlorothiophen-2-yl)sulfonyl]-N-({2-[4-(2-fluorophenyl)piperazin-1-yl]-6-[4-(trifluoromethyl)phenyl]pyridin-4-yl}methyl)-2,5-dihydro-1H-pyrrole-2-carboxamide

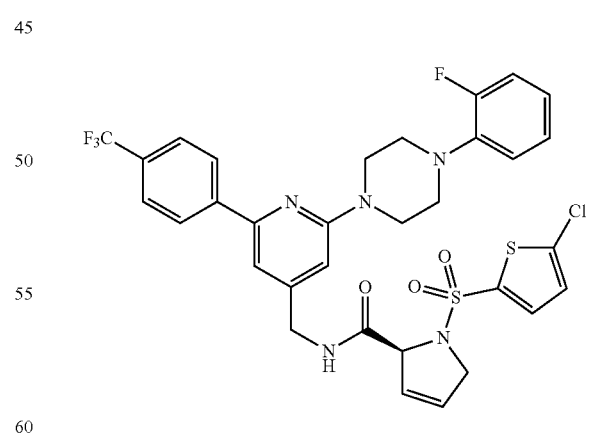

MS (ESI): mass calcd. for $C_{32}H_{28}ClF_4N_5O_3S_2$, 706.19 m/z found, 706.1 (100), 708.1 (50), [M+H]$^+$. DMSO-d6: 8.93 (br s, 1H), 8.32 (d, J=8.1 Hz, 2H), 7.87-7.80 (m, 3H), 7.44 (d, J=3.6 Hz, 1H), 7.34 (s, 1H), 7.22-7.04 (m, 4H), 6.89 (s, 1H), 6.02-6.01 (m, 1H), 5.84-5.81 (m, 1H), 4.97 (br s, 1H), 4.48-4.25 (m, 4H), 3.82 (br s, 4H), 3.81 (br s, 4H).

Example 360

4,4-Difluoro-1-[(4-fluorophenyl)sulfonyl]-N-({2-(methylamino)-6-[4-(trifluoromethyl)phenyl]pyridin-4-yl}methyl)-L-prolinamide

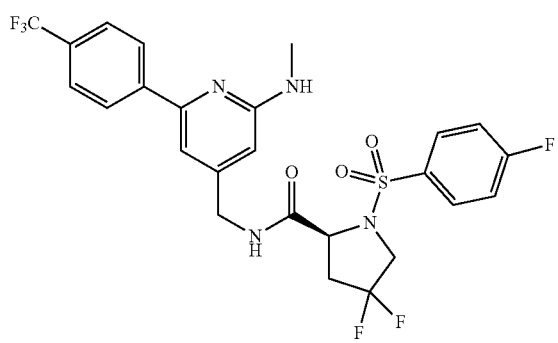 [SMILES: CNc1cc(CNC(=O)[C@@H]2CC(F)(F)CN2S(=O)(=O)c2ccc(F)cc2)cc(-c2ccc(C(F)(F)F)cc2)n1]

MS (ESI): mass calcd. for C$_{25}$H$_{22}$F$_6$N$_4$O$_3$S, 572.53 m/z found, 573.2 [M+H]$^+$. CDCl$_3$: 8.10 (d, J=8.1 Hz, 2H), 7.93-7.88 (m, 2H), 7.69 (d, J=8.1 Hz, 2H), 7.56 (br s, 1H), 7.33-7.26 (m, 2H), 6.97 (s, 1H), 6.50 (s, 1H), 4.64 (dd, J=16.2 Hz, 6.9 Hz, 1H), 4.45 (dd, J=16.2 Hz, 5.4 Hz, 1H), 4.35 (dd, J=9.9 Hz, 4.5 Hz, 1H), 3.90-3.87 (m, 1H), 3.64-3.60 (m, 1H), 2.99 (s, 3H), 2.78-2.66 (m, 1H), 2.43-2.31 (m, 1H).

Example 361

(2S)—N-({2-(4-Benzylpiperazin-1-yl)-6-[4-(trifluoromethyl)phenyl]pyridin-4-yl}methyl)-1-[(4-fluorophenyl)sulfonyl]-2,5-dihydro-1H-pyrrole-2-carboxamide

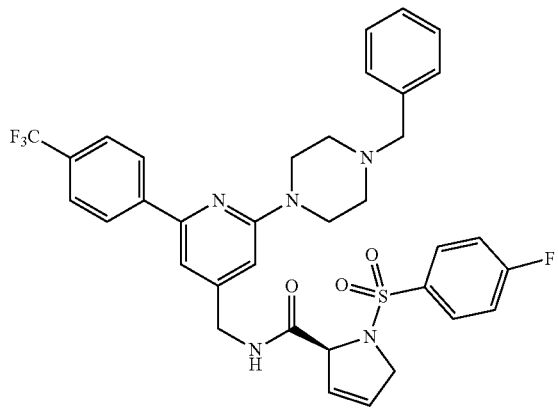 [SMILES: O=C(NCc1cc(-c2ccc(C(F)(F)F)cc2)nc(N2CCN(Cc3ccccc3)CC2)c1)[C@@H]1C=CCN1S(=O)(=O)c1ccc(F)cc1]

MS (ESI): mass calcd. for C$_{35}$H$_{33}$F$_4$N$_5$O$_3$S, 679.74 m/z found, 680.2 (100), 681.2 (40), [M+H]$^+$. CDCl$_3$: 8.14 (d, J=7.8 Hz, 2H), 7.85-7.81 (m, 2H), 7.66 (d, J=8.1 Hz, 2H), 7.36-7.19 (m, 7H), 7.11 (s, 1H), 6.67 (s, 1H), 5.79-5.77 (m, 1H), 5.69-5.67 (m, 1H), 4.88 (br s, 1H), 4.75-4.73 (m, 1H), 4.31-4.25 (m, 2H), 4.13-4.11 (m, 2H), 3.70 (br s, 4H), 3.57 (s, 2H), 2.58 (br s, 4H).

Example 362

4,4-Difluoro-1-[(4-fluorophenyl)sulfonyl]-N-({2-[(pyridin-3-ylmethyl)amino]-6-[4-(trifluoromethyl)phenyl]pyridin-4-yl}methyl)-L-prolinamide

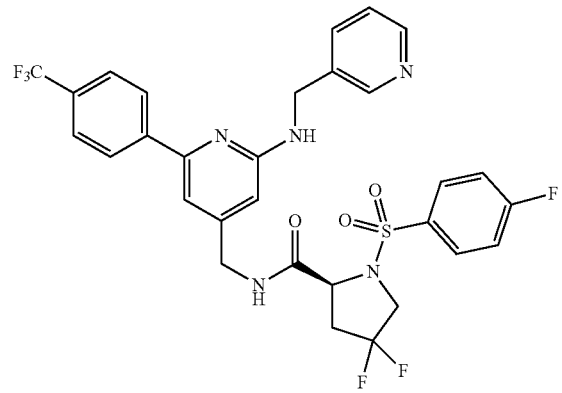 [SMILES: O=C(NCc1cc(NCc2cccnc2)nc(-c2ccc(C(F)(F)F)cc2)c1)[C@@H]1CC(F)(F)CN1S(=O)(=O)c1ccc(F)cc1]

MS (ESI): mass calcd. for C$_{30}$H$_{25}$F$_6$N$_5$O$_3$S, 649.62 m/z found, 650.0 [M+H]$^+$. CD$_3$OD: 8.78 (s, 1H), 8.63 (d, J=5.4 Hz, 1H), 8.53 (d, J=8.4 Hz, 1H), 7.98-7.88 (m, 5H), 7.67 (d, J=8.1 Hz, 2H), 7.29 (t, J=8.4 Hz, 2H), 7.21 (s, 1H), 6.80 (s, 1H), 4.42 (s, 2H), 4.26 (t, J=7.2 Hz, 1H), 3.82-3.66 (m, 2H), 2.48-2.38 (m, 2H).

Example 363

4,4-Difluoro-1-[(4-fluorophenyl)sulfonyl]-N-({2-[4-(pyridin-3-ylmethyl)piperazin-1-yl]-6-[4-(trifluoromethyl)phenyl]pyridin-4-yl}methyl)-L-prolinamide

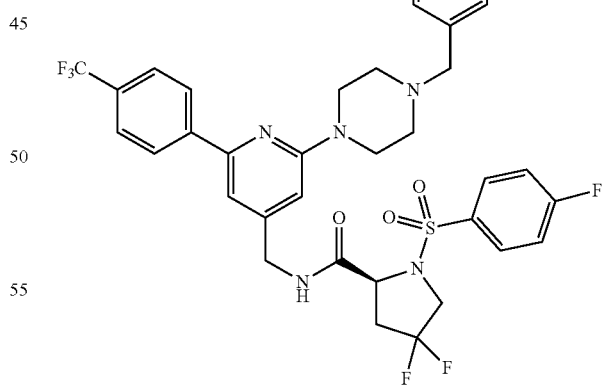

MS (ESI): mass calcd. for C$_{34}$H$_{32}$F$_6$N$_6$O$_3$S, 718.73 m/z found, 719.2 (70), 702.2 (25), [M+H]$^+$. CDCl$_3$: 8.58 (s, 1H), 8.55 (d, J=4.2 Hz, 1H), 8.11 (d, J=8.1 Hz, 2H), 7.90-7.86 (m, 2H), 7.66 (d, J=8.1 Hz, 2H), 7.32-7.26 (m, 4H), 7.08 (s, 1H), 6.64 (s, 1H), 4.64 (dd, J=16.2 Hz, 6.6 Hz, 1H), 4.64 (dd, J=16.2 Hz, 5.4 Hz, 1H), 4.33 (dd, J=10.2 Hz, 4.5 Hz, 1H), 3.88-3.54 (m, 8H), 2.78-2.61 (m, 5H), 2.40-2.27 (m, 1H).

Example 364

1-[(5-Chlorothiophen-2-yl)sulfonyl]-N-({2-[(pyridin-4-ylmethyl)amino]-6-[4-(trifluoromethyl)phenyl]pyridin-4-yl}methyl)-L-prolinamide

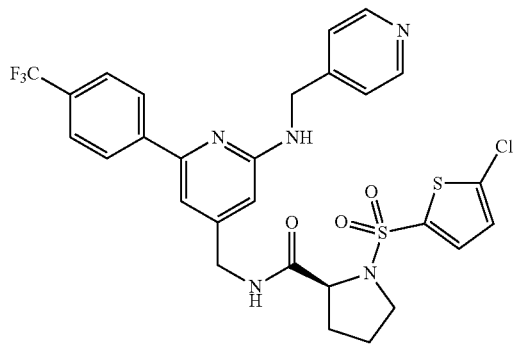 [SMILES: O=C(NCc1cc(NCc2ccncc2)nc(-c2ccc(C(F)(F)F)cc2)c1)[C@@H]1CCCN1S(=O)(=O)c1ccc(Cl)s1]

MS (ESI): mass calcd. for $C_{28}H_{25}ClF_3N_5O_3S_2$, 636.12 m/z found, 636.1 (5), [M+H]$^+$. CDCl$_3$: 8.53 (d, J=5.1 Hz, 2H), 7.99 (d, J=8.1 Hz, 2H), 7.63 (d, J=8.1 Hz, 2H), 7.45 (d, J=3.9 Hz, 1H), 7.37 (d, J=5.1 Hz, 2H), 7.31-7.29 (m, 1H), 7.06-7.03 (m, 2H), 6.42 (s, 1H), 5.24 (br s, 1H), 4.70-4.62 (m, 3H), 4.28 (dd, J=16.2 Hz, 5.1 Hz, 1H), 4.16-4.14 (m, 1H), 3.64-3.61 (m, 1H), 3.21-3.18 (m, 1H), 2.24-2.23 (m, 1H), 1.84-1.75 (m, 3H), (3.18 and 1.35 trace of ethanol).

Example 365

(2S)-1-[(4-Fluorophenyl)sulfonyl]-N-({2-[4-(pyridin-3-ylmethyl)piperazin-1-yl]-6-[4-(trifluoromethyl)phenyl]pyridin-4-yl}methyl)-2,5-dihydro-1H-pyrrole-2-carboxamide

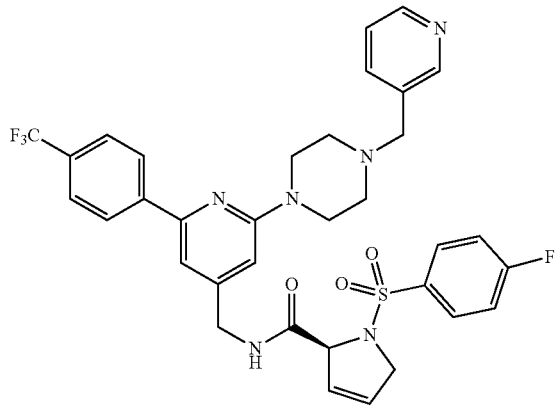 [SMILES: O=C(NCc1cc(-c2ccc(C(F)(F)F)cc2)nc(N2CCN(Cc3cccnc3)CC2)c1)[C@@H]1C=CCN1S(=O)(=O)c1ccc(F)cc1]

MS (ESI): mass calcd. for $C_{34}H_{32}F_4N_6O_3S$, 680.73 m/z found, 681.2 [M+H]$^+$. CDCl$_3$: 8.58 (s, 1H), 8.55 (s, 1H), 8.13 (d, J=8.1 Hz, 2H), 7.89-7.85 (m, 2H), 7.66 (d, J=8.1 Hz, 2H), 7.29-7.23 (m, 2H), 7.10 (s, 1H), 6.70 (s, 1H), 5.83-5.81 (m, 1H), 5.75-5.73 (m, 1H), 4.90 (br s, 1H), 4.78 (dd, J=16.2 Hz, 7.8 Hz, 1H), 4.37-4.13 (m, 3H), 3.73-3.61 (m, 6H), 2.61 (br s, 4H).

Example 366

1-[(5-Chlorothiophen-2-yl)sulfonyl]-4,4-difluoro-N-({2-[4-(pyridin-3-ylmethyl)piperazin-1-yl]-6-[4-(trifluoromethyl)phenyl]pyridin-4-yl}methyl-L-prolinamide

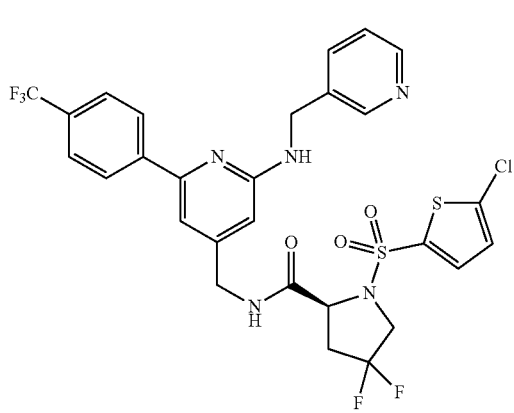 [SMILES: O=C(NCc1cc(NCc2cccnc2)nc(-c2ccc(C(F)(F)F)cc2)c1)[C@@H]1CC(F)(F)CN1S(=O)(=O)c1ccc(Cl)s1]

MS (ESI): mass calcd. for $C_{32}H_{30}ClF_5N_6O_3S_2$, 741.21 m/z found, 741.1 (15), 742.1 (5), [M+H]$^+$. CDCl$_3$: 8.58 (s, 1H), 8.54 (d, J=4.5 Hz, 1H), 8.11 (d, J=8.1 Hz, 2H), 7.73 (br s, 1H), 7.66 (d, J=7.8 Hz, 2H), 7.49 (d, J=3.9 Hz, 1H), 7.30-7.26 (m, 2H), 7.08-7.05 (m, 2H), 6.60 (s, 1H), 4.63 (dd, J=15.9 Hz, 6.6 Hz, 1H), 4.48-4.36 (m, 2H), 3.92-3.81 (m, 1H), 3.69-3.59 (m, 7H), 2.82-2.77 (m, 1H), 2.59 (br s, 4H), 2.52-2.37 (m, 1H).

Example 367

N-({2-(4-Benzylpiperazin-1-yl)-6-[4-(trifluoromethyl)phenyl]pyridin-4-yl}methyl)-1-[(5-chlorothiophen-2-yl)sulfonyl]-L-prolinamide

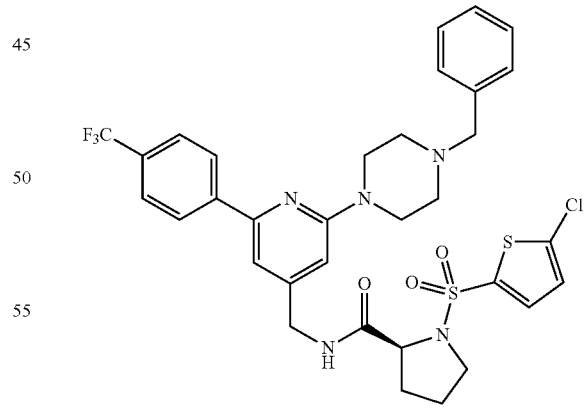

MS (ESI): mass calcd. for $C_{33}H_{33}ClF_3N_5O_3S_2$, 704.24 m/z found, 704.1 (100), 706.1 (50), [M+H]$^+$. CDCl$_3$: 8.12 (d, J=8.1 Hz, 2H), 7.66 (d, J=8.1 Hz, 2H), 7.45 (d, J=4.2 hz, 1H), 7.36-7.26 (m, 5H), 7.06-7.03 (m, 2H), 6.62 (s, 1H), 4.69 (dd, J=15.9 Hz, 7.2 Hz, 1H), 4.32 (dd, J=16.2 Hz, 5.1 Hz, 1H), 4.29-4.16 (m, 1H), 3.69-3.57 (m, 7H), 3.28-3.22 (m, 1H), 2.58 (br s, 4H), 2.29-2.28 (m, 1H), 1.85-1.76 (m, 3H).

Example 368

(2S)—N-({2-(4-Benzylpiperazin-1-yl)-6-[4-(trifluoromethyl)phenyl]pyridin-4-yl}methyl)-1-[(5-chlorothiophen-2-yl)sulfonyl]-2,5-dihydro-1H-pyrrole-2-carboxamide

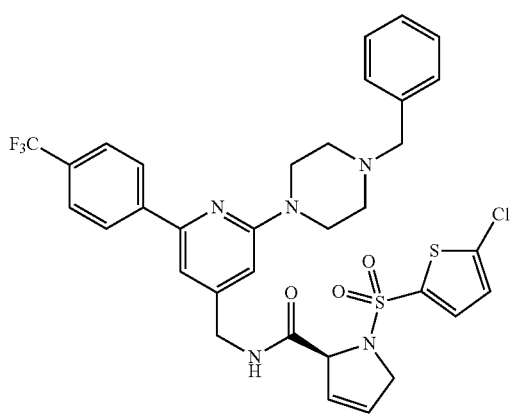 [SMILES: O=C(NCc1cc(-c2ccc(C(F)(F)F)cc2)nc(N2CCN(Cc3ccccc3)CC2)c1)[C@@H]1C=CCN1S(=O)(=O)c1ccc(Cl)s1]

MS (ESI): mass calcd. for $C_{33}H_{31}ClF_3N_5O_3S_2$, 702.22 m/z found, 702.1 (100), 704.1 (50), [M+H]⁺. CDCl₃: 8.12 (d, J=8.1 Hz, 2H), 7.66 (d, J=8.1 Hz, 2H), 7.46 (d, J=3.9 Hz, 1H), 7.38-7.26 (m, 4H), 7.20-7.18 (m, 1H), 7.06 (s, 1H), 7.03-7.01 (m, 1H), 6.63 (s, 1H), 5.88-5.86 (m, 1H), 5.79-5.77 (m, 1H), 4.92 (br s, 1H), 4.81-4.76 (m, 1H), 4.32-4.23 (m, 3H), 3.69 (br s, 4H), 3.57 (s, 2H), 2.58 (br s, 4H).

Example 369

1-[(5-Chlorothiophen-2-yl)sulfonyl]-N-({2-[4-(2-methylpropyl)piperazin-1-yl]-6-[4-(trifluoromethyl)phenyl]pyridin-4-yl}methyl)-L-prolinamide

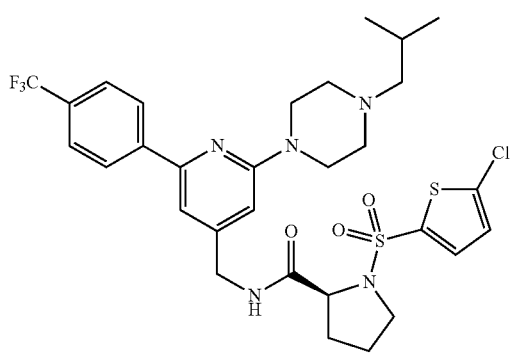 [SMILES: CC(C)CN1CCN(c2cc(CNC(=O)[C@@H]3CCCN3S(=O)(=O)c3ccc(Cl)s3)cc(-c3ccc(C(F)(F)F)cc3)n2)CC1]

MS (ESI): mass calcd. for $C_{30}H_{35}ClF_3N_5O_3S_2$, 670.22 m/z found, 670.1 (100), 672.1 (45), [M+H]⁺. CDCl₃: 8.13 (d, J=8.1 Hz, 2H), 7.66 (d, J=8.1 Hz, 2H), 7.46 (d, J=3.9 Hz, 1H), 7.05-7.03 (m, 2H), 6.62 (s, 1H), 4.72-4.64 (m, 1H), 4.37-4.30 (m, 1H), 4.19-4.16 (m, 1H), 3.68-3.60 (m, 5H), 3.26-3.23 (m, 1H), 2.52 (br s, 4H), 2.30-2.29 (m, 1H), 2.15-2.11 (m, 2H), 1.88-1.76 (m, 4H), 0.93 (d, J=6.6 Hz, 6H).

Example 370

1-[(4-Fluorophenyl)sulfonyl]-N-({2-[4-(2-methylpropyl)piperazin-1-yl]-6-[4-(trifluoromethyl)phenyl]pyridin-4-yl}methyl)-L-prolinamide

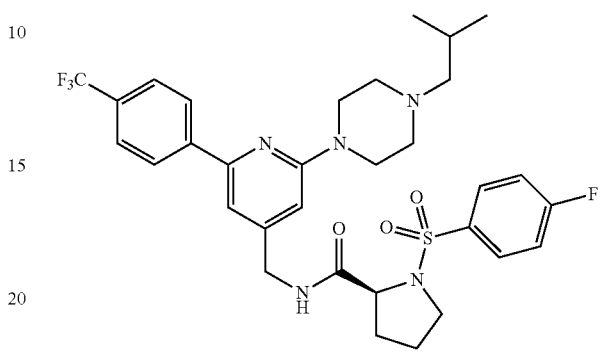

MS (ESI): mass calcd. for $C_{32}H_{37}F_4N_5O_3S$, 647.74 m/z found, 648.2 (100), 649.2 (40), [M+H]⁺. CDCl₃: 8.13 (d, J=8.1 Hz, 2H), 7.93-7.86 (m, 2H), 7.66 (d, J=8.1 Hz, 2H), 7.35-7.23 (m, 2H), 7.08 (s, 1H), 6.67 (s, 1H), 4.70 (dd, J=16.2 Hz, 7.2 Hz, 1H), 4.35 (dd, J=16.2 Hz, 5.1 Hz, 1H), 4.15-4.13 (m, 1H), 3.73 (br s, 4H), 3.64-3.58 (m, 1H), 3.19-3.12 (m, 1H), 2.59 (br s, 4H), 2.25-2.08 (m, 3H), 1.89-1.63 (m, 4H), 0.95 (d, J=6.6 Hz, 6H).

Example 371

1-[(5-Chlorothiophen-2-yl)sulfonyl]-N-({2-[(pyridin-3-ylmethyl)amino]-6-[4-(trifluoromethyl)phenyl]pyridin-4-yl}methyl)-L-prolinamide

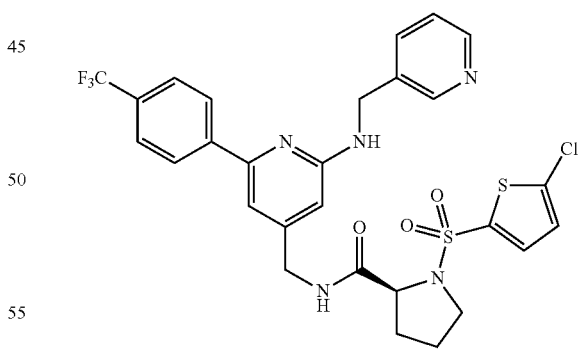

MS (ESI): mass calcd. for $C_{28}H_{25}ClF_3N_5O_3S_2$, 636.12 m/z found, 636.1 (20), 637.1 (5), [M+H]⁺. CDCl₃: 8.63 (s, 1H), 8.50 (d, J=4.5 Hz, 1H), 8.01 (d, J=8.1 Hz, 2H), 7.84 (d, J=7.8 Hz, 1H), 7.63 (d, J=8.1 Hz, 2H), 7.47 (d, J=3.9 Hz, 1H), 7.34-7.30 (m, 2H), 7.05-7.02 (m, 2H), 6.44 (s, 1H), 4.68-4.60 (m, 3H), 4.28 (dd, J=16.2 Hz, 4.8 Hz, 1H), 4.17-4.14 (m, 1H), 3.65-3.63 (m, 1H), 3.25-3.19 (m, 2H), 2.25-2.24 (m, 1H), 1.84-1.75 (m, 3H). (3.22 and 1.38, trace of ethanol).

Example 372

(2S)-1-[(4-Fluorophenyl)sulfonyl]-N-({2-(methylamino)-6-[4-(trifluoromethyl)phenyl]pyridin-4-yl}methyl)-2,5-dihydro-1H-pyrrole-2-carboxamide

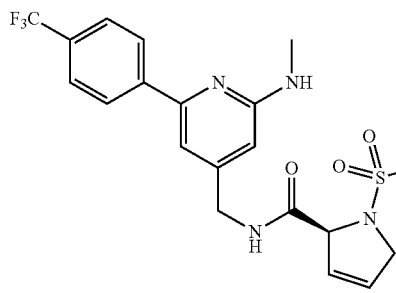

MS (ESI): mass calcd. for $C_{25}H_{22}F_4N_4O_3S$, 534.54 m/z found, 535.1 [M+H]$^+$. CDCl$_3$: 8.12 (d, J=7.8 Hz, 2H), 7.90-7.86 (m, 2H), 7.67 (d, J=7.8 Hz, 2H), 7.35-7.23 (m, 3H), 7.03 (s, 1H), 6.49 (s, 1H), 5.82-5.80 (m, 1H), 5.75-5.73 (m, 1H), 5.36 (br s, 1H), 4.91 (br s, 1H), 4.75 (dd, J=16.2 Hz, 7.5 Hz, 1H), 4.35-4.13 (m, 3H), 3.00 (d, J=3 Hz, 3H).

Example 373

N-({2-(4-Benzylpiperazin-1-yl)-6-[4-(trifluoromethyl)phenyl]pyridin-4-yl}methyl)-1-[(4-fluorophenyl)sulfonyl]-L-prolinamide

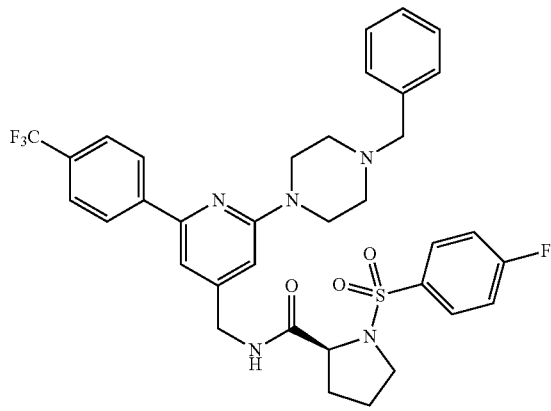 [SMILES: O=C(NCc1cc(-c2ccc(C(F)(F)F)cc2)nc(N2CCN(Cc3ccccc3)CC2)c1)[C@@H]1CCCN1S(=O)(=O)c1ccc(F)cc1]

MS (ESI): mass calcd. for $C_{35}H_{35}F_4N_5O_3S$, 681.76 m/z found, 682.2 (100), 683.2 (40), [M+H]$^+$. CDCl$_3$: 8.12 (d, J=7.5 Hz, 2H), 7.90-7.85 (m, 2H), 7.66 (d, J=8.1 Hz, 2H), 7.34-7.23 (m, 7H), 7.09 (s, 1H), 6.67 (s, 1H), 4.78-4.72 (m, 1H), 4.34-4.30 (m, 1H), 4.14-4.11 (m, 1H), 3.70-3.58 (m, 7H), 3.18-3.13 (m, 1H), 2.59 (br s, 4H), 2.24-2.21 (m, 1H), 1.80-1.75 (m, 3H).

Example 374

4,4-Difluoro-1-[(4-fluorophenyl)sulfonyl]-N-({2-[(pyridin-2-ylmethyl)amino]-6-[4-(trifluoromethyl)phenyl]pyridin-4-yl}methyl)-L-prolinamide

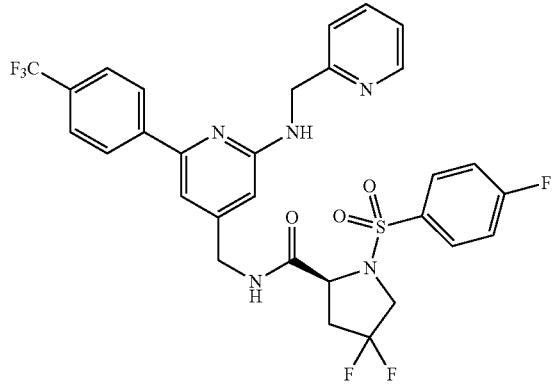 [SMILES: O=C(NCc1cc(NCc2ccccn2)nc(-c2ccc(C(F)(F)F)cc2)c1)[C@@H]1CC(F)(F)CN1S(=O)(=O)c1ccc(F)cc1]

MS (ESI): mass calcd. for $C_{30}H_{25}F_6N_5O_3S$, 649.62 m/z found, 650.2 (20), 651.2 (5), [M+H]$^+$. CD$_3$OD: 8.56 (d, J=5.7 Hz, 1H), 8.33 (t, J=8.1 Hz, 1H), 7.94-7.84 (m, 5H), 7.72 (t, J=6.6 Hz, 1H), 7.61 (d, J=8.1 Hz, 2H), 7.30-7.24 (m, 3H), 6.84 (s, 1H), 4.91 (s, 2H), 4.43 (s, 2H), 4.27 (t, J=7.5 Hz, 1H), 3.87-3.65 (m, 2H), 2.48-2.41 (m, 2H).

Example 375

1-[(5-Chlorothiophen-2-yl)sulfonyl]-4,4-difluoro-N-({2-[4-(pyridin-2-ylmethyl)piperazin-1-yl]-6-[4-(trifluoromethyl)phenyl]pyridin-4-yl}methyl)-L-prolinamide

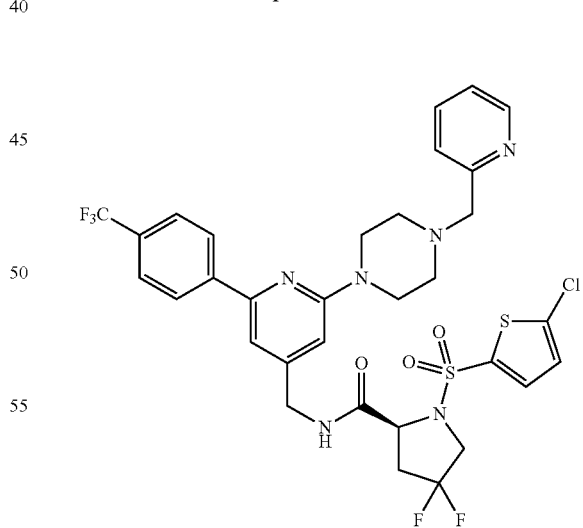

MS (ESI): mass calcd. for $C_{32}H_{30}ClF_5N_6O_3S_2$, 741.21 m/z found, 741.1 (70), 743.0 (30), [M+H]$^+$. CDCl$_3$: 8.60 (d, J=4.2 Hz, 1H), 8.10 (d, J=7.8 Hz, 2H), 7.67-7.65 (m, 3H), 7.50-7.45 (m, 2H), 7.26-7.22 (m, 2H), 7.08-7.06 (m, 2H), 6.61 (s, 1H), 465-4.60 (m, 1H), 4.48-4.36 (m, 2H), 3.92-3.59 (m, 8H), 2.82-2.66 (m, 5H), 2.52-2.42 (m, 1H).

Example 376

1-[(5-Chlorothiophen-2-yl)sulfonyl]-N-({2-(dimethylamino)-6-[4-(trifluoromethyl)phenyl]pyridin-4-yl}methyl)-4,4-difluoro-L-prolinamide

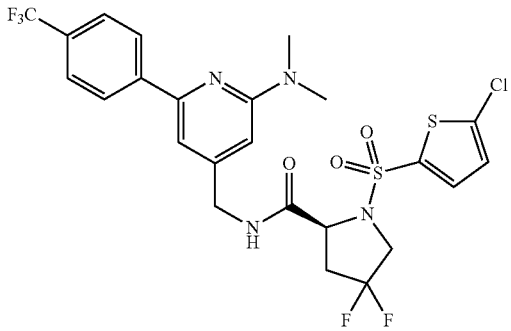 [SMILES: CN(C)c1cc(CNC(=O)[C@@H]2CC(F)(F)CN2S(=O)(=O)c2ccc(Cl)s2)cc(-c2ccc(C(F)(F)F)cc2)n1]

MS (ESI): mass calcd. for $C_{24}H_{22}ClF_5N_4O_3S_2$, 609.04 m/z found, 609.0 (100), 611.0 (50), [M+H]$^+$. CDCl$_3$: 8.12 (d, J=8.1 Hz, 2H), 7.68 (d, J=8.4 Hz, 2H), 7.53 (d, J=3.9 Hz, 1H), 7.08 (d, J=3.9 Hz, 1H), 6.99 (s, 1H), 6.53 (s, 1H), 4.63-4.39 (m, 3H), 3.88 (q, J=11.1 Hz, 1H), 3.70 (q, J=12.6 Hz, 1H), 3.19 (s, 6H), 2.82-2.75 (m, 1H), 2.49-2.40 (m, 1H).

Example 377

N-({2-(4-Benzylpiperazin-1-yl)-6-[4-(trifluoromethyl)phenyl]pyridin-4-yl}methyl)-1-[(5-chlorothiophen-2-yl)sulfonyl]-4,4-difluoro-L-prolinamide

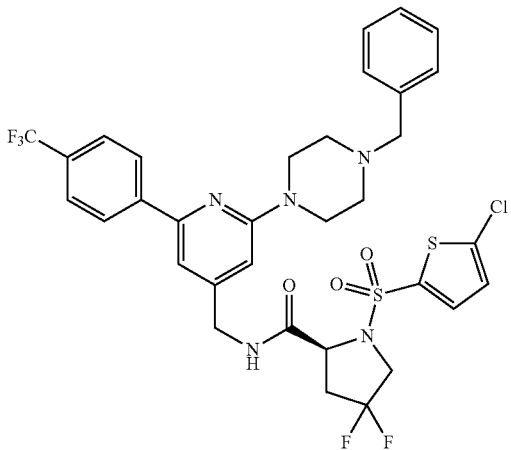 [SMILES: O=C(NCc1cc(-c2ccc(C(F)(F)F)cc2)nc(N2CCN(Cc3ccccc3)CC2)c1)[C@@H]1CC(F)(F)CN1S(=O)(=O)c1ccc(Cl)s1]

MS (ESI): mass calcd. for $C_{33}H_{31}ClF_5N_5O_3S_2$, 740.22 m/z found, 740.1 (100), 742.1 (50), [M+H]$^+$. CDCl$_3$: 8.11 (d, J=8.1 Hz, 2H), 7.66 (d, J=8.1 Hz, 2H), 7.49 (d, J=4.2 Hz, 1H), 7.38-7.22 (m, 5H), 7.07-7.04 (m, 2H), 6.58 (s, 1H), 4.59 (dd, J=15.6 Hz, 5.7 Hz, 1H), 4.48-4.36 (m, 2H), 3.88-3.79 (m, 1H), 3.68-3.62 (m, 5H), 3.57 (s, 2H), 2.82-2.77 (m, 1H), 2.58 (br s, 4H), 2.48-2.38 (m, 1H).

Example 378

1-[(5-Chlorothiophen-2-yl)sulfonyl]-4,4-difluoro-N-({2-[(pyridin-4-ylmethyl)amino]-6-[4-(trifluoromethyl)phenyl]pyridin-4-yl}methyl)-L-prolinamide

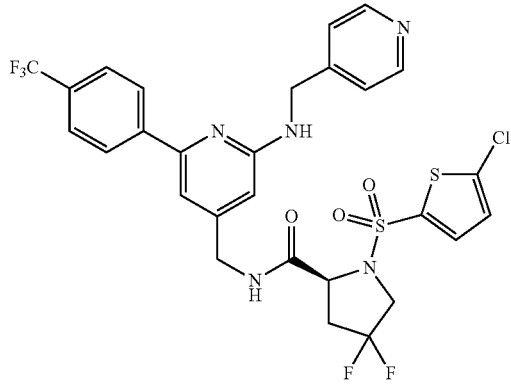 [SMILES: O=C(NCc1cc(NCc2ccncc2)nc(-c2ccc(C(F)(F)F)cc2)c1)[C@@H]1CC(F)(F)CN1S(=O)(=O)c1ccc(Cl)s1]

MS (ESI): mass calcd. for $C_{28}H_{23}ClF_5N_5O_3S_2$, 672.1 m/z found, 672.1 (10), 673.1 (5), [M+H]$^+$. CDCl$_3$: 8.57 (s, 2H), 7.98 (d, J=8.1 Hz, 2H), 7.65 (d, J=8.1 Hz, 2H), 7.50 (d, J=3.9 Hz, 1H), 7.41-7.33 (m, 3H), 7.08-7.05 (m, 2H), 6.46 (s, 1H), 4.70-4.56 (m, 3H), 4.45-4.35 (m, 2H), 3.88-3.81 (m, 1H), 3.70-3.57 (m, 1H), 2.76-2.73 (m, 1H), 2.50-2.40 (m, 1H).

Example 379

(2S)-1-[(5-Chlorothiophen-2-yl)sulfonyl]-N-({2-(methylamino)-6-[4-(trifluoromethyl)phenyl]pyridin-4-yl}methyl)-2,5-dihydro-1H-pyrrole-2-carboxamide

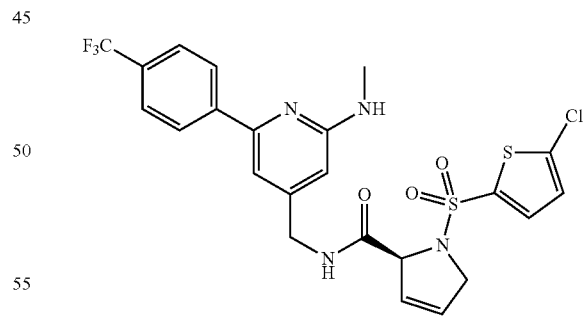

MS (ESI): mass calcd. for $C_{23}H_{20}ClF_3N_4O_3S_2$, 557.02 m/z found, 557.0 (100), 559.0 (50), [M+H]$^+$. CDCl$_3$: 8.10 (d, J=8.1 Hz, 2H), 7.65 (d, J=8.1 Hz, 2H), 7.44 (d, J=3.9 Hz, 1H), 7.30-7.26 (m, 1H), 7.02-6.99 (m, 2H), 6.37 (s, 1H), 5.86-5.84 (m, 1H), 5.75-5.73 (m, 1H), 4.93-4.86 (m, 2H), 4.72 (d d, J=16.2 Hz, 7.5 Hz, 1H), 4.38-4.15 (m, 2H), 2.98 (d, J=4.8 Hz, 3H).

Example 380

(2S)-1-[(4-Fluorophenyl)sulfonyl]-N-({2-[(pyridin-2-ylmethyl)amino]-6-[4-(trifluoromethyl)phenyl]pyridin-4-yl}methyl)-2,5-dihydro-1H-pyrrole-2-carboxamide

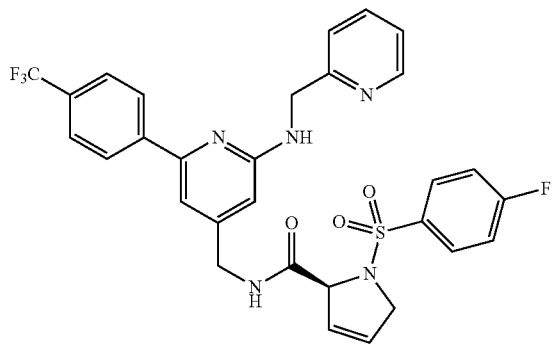 [SMILES: O=C(NCc1cc(NCc2ccccn2)nc(-c2ccc(C(F)(F)F)cc2)c1)[C@@H]1C=CCN1S(=O)(=O)c1ccc(F)cc1]

MS (ESI): mass calcd. for $C_{30}H_{25}F_4N_5O_3S$, 611.62 m/z found, 612.2 (50), 613.2 (15), [M+H]$^+$. CDCl$_3$: 8.58 (d, J=4.2 Hz, 1H), 8.10 (d, J=8.1 Hz, 2H), 7.88-7.83 (m, 2H), 7.67-7.62 (m, 3H), 7.39-7.33 (m, 2H), 7.26-7.16 (m, 2H), 7.09 (s, 1H), 6.48 (s, 1H), 5.82-5.77 (m, 2H), 5.70 (br s, 1H), 4.88 (d, J=2.4 Hz, 1H), 4.77 (d, J=2.7 Hz, 2H), 4.65 (dd, J=15.9 Hz, 7.2 Hz, 1H), 4.35-4.25 (m, 2H), 4.15-4.10 (m, 1H). (3.75 and 1.23, trace of ethanol).

Example 381

1-[(5-Chlorothiophen-2-yl)sulfonyl]-4,4-difluoro-N-({2-[4-(pyridin-4-ylmethyl)piperazin-1-yl]-6-[4-(trifluoromethyl)phenyl]pyridin-4-yl}methyl)-L-prolinamide

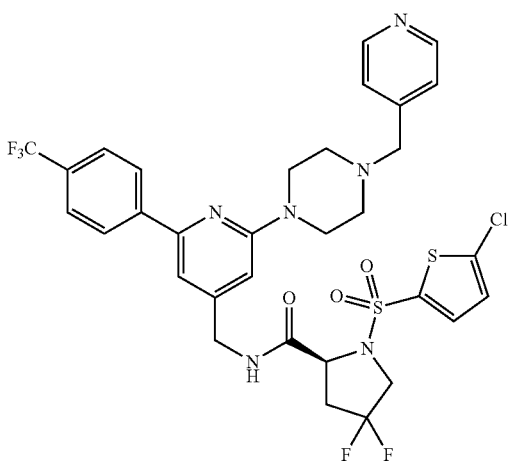 [SMILES: O=C(NCc1cc(-c2ccc(C(F)(F)F)cc2)nc(N2CCN(Cc3ccncc3)CC2)c1)[C@@H]1CC(F)(F)CN1S(=O)(=O)c1ccc(Cl)s1]

MS (ESI): mass calcd. for $C_{32}H_{30}ClF_5N_6O_3S_2$, 741.21 m/z found, 741.2 (15), 743.2 (5), [M+H]$^+$. CDCl$_3$: 8.57 (d, J=5.4 Hz, 2H), 8.10 (d, J=8.1 Hz, 2H), 7.66 (d, J=8.4 Hz, 2H), 7.49 (d, J=3.9 Hz, 1H), 7.34 (d, J=4.8 Hz, 1H), 7.08-7.06 (m, 2H), 6.61 (s, 1H), 4.63 (dd, J=15.9 Hz, 6.6 Hz, 1H), 4.48-4.36 (m, 2H), 3.88-3.81 (m, 1H), 3.71-3.62 (m, 5H), 3.58 (s, 2H), 2.81-2.77 (m, 1H), 2.60 (br s, 4H), 2.49-2.42 (m, 1H).

Example 382

1-[(5-Chlorothiophen-2-yl)sulfonyl]-4,4-difluoro-N-({2-[(pyridin-2-ylmethyl)amino]-6-[4-(trifluoromethyl)phenyl]pyridin-4-yl}methyl)-L-prolinamide

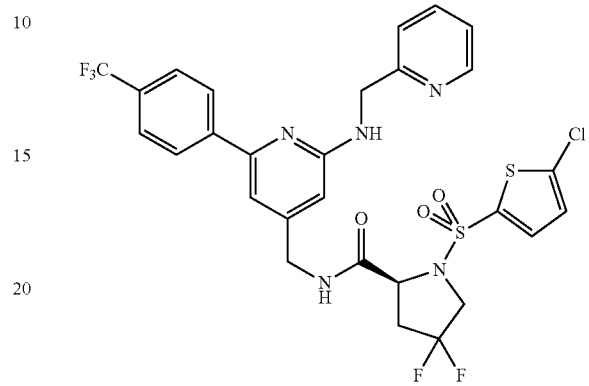

MS (ESI): mass calcd. for $C_{28}H_{23}ClF_5N_5O_3S_2$, 672.1 m/z found, 672.1 (25), 674.1 (15), [M+H]$^+$. CD$_3$OD: 8.57 (d, J=5.1 Hz, 1H), 8.34 (t, J=7.5 Hz, 1H), 7.93 (d, J=8.4 Hz, 1H), 7.84 (d, J=8.1 Hz, 2H), 7.72 (t, J=6.6 Hz, 1H), 7.60-7.55 (m, 3H), 7.20 (s, 1H), 7.12 (d, J=4.5 Hz, 1H), 6.76 (s, 1H), 4.88 (s, 2H), 4.40 (s, 2H), 4.30 (t, J=7.8 Hz, 1H), 3.90-3.66 (m, 2H), 2.61-2.40 (m, 2H).

Example 383

1-[(5-Chlorothiophen-2-yl)sulfonyl]-4,4-difluoro-N-({2-[4-(2-methylpropyl)piperazin-1-yl]-6-[4-(trifluoromethyl)phenyl]pyridin-4-yl}methyl)-L-prolinamide

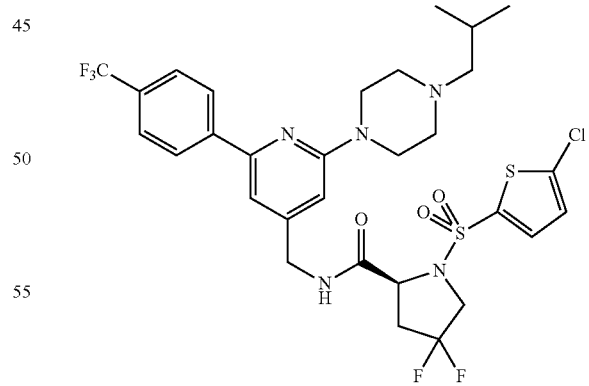

MS (ESI): mass calcd. for $C_{30}H_{33}ClF_5N_5O_3S_2$, 706.2 m/z found, 706.1 (100), 708.1 (50), [M+H]$^+$. CDCl$_3$: 8.12-8.09 (m, 2H), 7.66 (d, J=8.1 Hz, 2H), 7.50 (d, J=3.9 Hz, 1H), 7.21 (br s, 1H), 7.08-7.04 (m, 2H), 6.59 (s, 1H), 4.62-4.59 (m, 1H), 4.49-4.37 (m, 3H), 3.89-3.85 (m, 1H), 3.72-3.59 (m, 5H), 2.80-2.78 (m, 1H), 2.51-2.35 (m, 5H), 2.15-2.12 (m, 2H), 1.85-1.82 (m, 1H), 0.94 (d, J=5.1 Hz, 6H).

Example 384

1-[(5-Chlorothiophen-2-yl)sulfonyl]-4,4-difluoro-N-({2-(methylamino)-6-[4-(trifluoromethyl)phenyl]pyridin-4-yl}methyl)-L-prolinamide

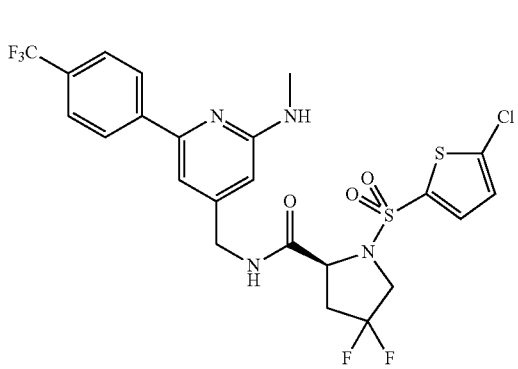 [SMILES: CNc1cc(CNC(=O)[C@@H]2CC(F)(F)CN2S(=O)(=O)c2ccc(Cl)s2)cc(-c2ccc(C(F)(F)F)cc2)n1]

MS (ESI): mass calcd. for $C_{23}H_{20}ClF_5N_4O_3S_2$, 595.01 m/z found, 595.0 (100), 597.1 (50), [M+H]$^+$. CDCl$_3$: 8.08 (d, J=7.5 Hz, 2H), 7.66 (d, J=7.8 Hz, 2H), 7.48 (d, J=3.9 Hz, 1H), 7.35-7.33 (m, 1H), 7.05 (d, J=3.9 Hz, 1H), 6.98 (s, 1H), 6.34 (s, 1H), 4.90 (br s, 1H), 4.55-4.37 (m, 3H), 4.08-3.81 (m, 1H), 3.71-3.58 (m, 1H), 2.97 (s, 3H), 2.81-2.77 (m, 1H), 2.50-2.37 (m, 1H).

Example 385

1-[(4-Fluorophenyl)sulfonyl]-N-({2-[(pyridin-4-ylmethyl)amino]-6-[4-(trifluoromethyl)phenyl]pyridin-4-yl}methyl)-L-prolinamide

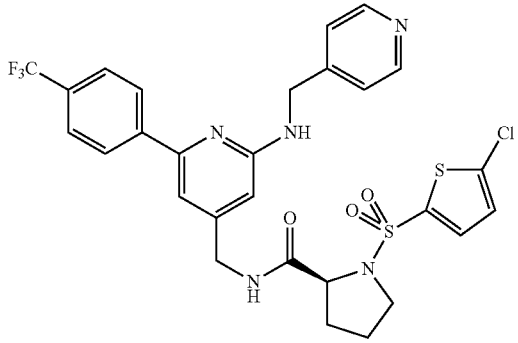 [SMILES: O=C(NCc1cc(NCc2ccncc2)nc(-c2ccc(C(F)(F)F)cc2)c1)[C@@H]1CCCN1S(=O)(=O)c1ccc(Cl)s1]

MS (ESI): mass calcd. for $C_{30}H_{27}F_4N_5O_3S$, 613.64 m/z found, 614.2 [M+H]$^+$. CDCl$_3$: 8.53 (d, J=5.4 Hz, 2H), 8.00 (d, J=8.1 Hz, 2H), 7.89-7.83 (m, 2H), 7.62 (d, J=8.4 Hz, 2H), 7.41-7.37 (m, 1H), 7.31-7.22 (m, 5H), 7.07 (s, 1H), 6.44 (s, 1H), 5.24 (t, J=6.0 Hz, 1H), 4.69-4.62 (m, 3H), 4.28 (dd, J=16.2 Hz, 4.8 Hz, 1H), 4.11-4.09 (m, 1H), 3.60-3.55 (m, 1H), 3.14-3.10 (m, 1H), 2.19-2.15 (m, 1H), 1.76-1.61 (m, 3H).

Example 386

4,4-Difluoro-1-[(4-fluorophenyl)sulfonyl]-N-({2-[4-(2-methylpropyl)piperazin-1-yl]-6-[4-(trifluoromethyl)phenyl]pyridin-4-yl}methyl)-L-prolinamide

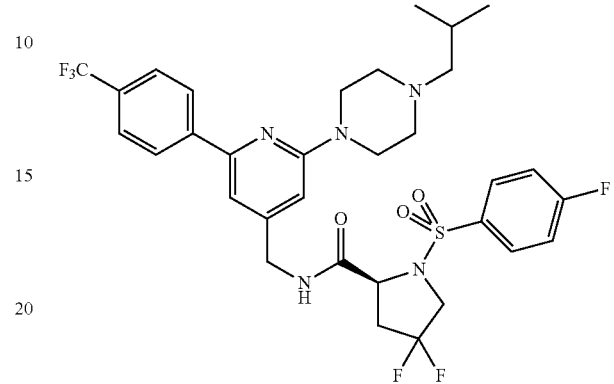

MS (ESI): mass calcd. for $C_{32}H_{35}F_6N_5O_3S$, 683.72 m/z found, 684.2 (100), 685.2 (40), [M+H]$^+$. CDCl$_3$: 8.12 (d, J=7.8 Hz, 2H), 7.91-7.87 (m, 2H), 7.67-7.65 (d, J=8.4 Hz, 2H), 7.32-7.26 (m, 3H), 7.07 (s, 1H), 6.62 (s, 1H), 4.62-4.57 (m, 1H), 4.46 (dd, J=15.9 Hz, 5.4 Hz, 1H), 4.36-4.32 (m, 1H), 3.84-3.77 (m, 1H), 3.67-3.56 (m, 5H), 2.75-2.71 (m, 1H), 2.51 (br s, 4H), 2.35-2.27 (m, 1H), 2.13 (br s, 2H), 1.83 b(br s, 1H), 0.94 (d, J=5.1 Hz, 6H).

Example 387

4,4-Difluoro-1-[(4-fluorophenyl)sulfonyl]-N-({2-[4-(pyridin-2-ylmethyl)piperazin-1-yl]-6-[4-(trifluoromethyl)phenyl]pyridin-4-yl}methyl)-L-prolinamide

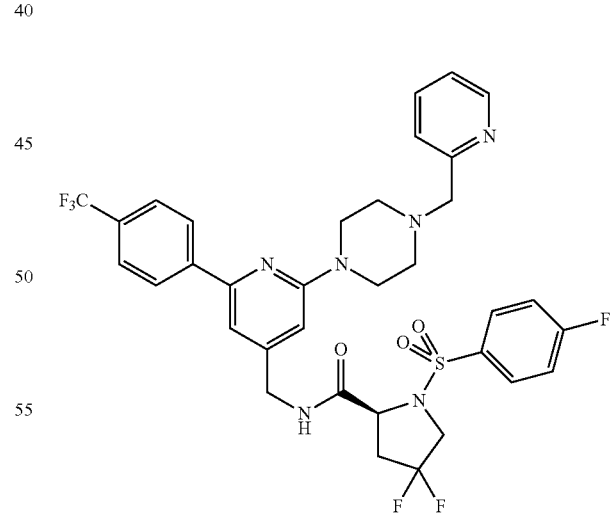

MS (ESI): mass calcd. for $C_{34}H_{32}F_6N_6O_3S$, 718.73 m/z found, 719.1 [M+H]$^+$. CDCl$_3$: 8.59 (d, J=4.5 Hz, 1H), 8.12 (d, J=8.1 Hz, 2H), 7.90-7.85 (m, 2H), 7.71-7.64 (m, 3H), 7.48 (br s, 1H), 7.34-7.26 (m, 2H), 7.21-7.17 (m, 1H), 7.08 (s, 1H), 6.63 (s, 1H), 4.63 (dd, J=15.9 Hz, 6.6 Hz, 1H), 4.45 (dd, J=15.9 Hz, 5.4 Hz, 1H), 4.33 (dd, J=9.9 Hz, 4.5 Hz, 1H), 3.87-3.55 (m, 8H), 2.79-2.66 (m, 5H), 2.39-2.26 (m, 1H).

Example 388

N-({2-(4-Benzylpiperazin-1-yl)-6-[4-(trifluoromethyl)phenyl]pyridin-4-yl}methyl)-4,4-difluoro-1-[(4-fluorophenyl)sulfonyl]-L-prolinamide

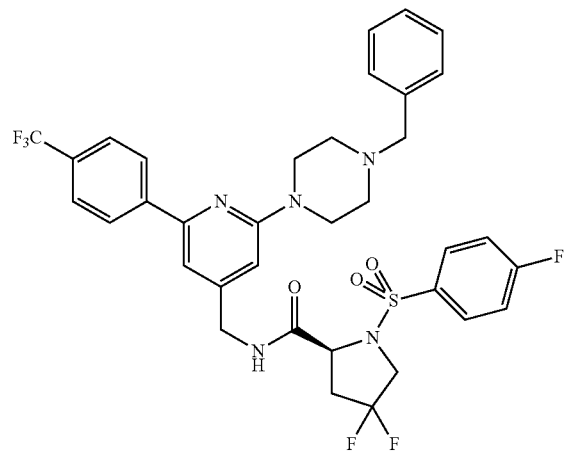 [SMILES: O=C(NCc1cc(-c2ccc(C(F)(F)F)cc2)nc(N2CCN(Cc3ccccc3)CC2)c1)[C@@H]1CC(F)(F)CN1S(=O)(=O)c1ccc(F)cc1]

MS (ESI): mass calcd. for $C_{35}H_{33}F_6N_5O_3S$, 717.74 m/z found, 718.2 (100), 719.2 (40), [M+H]$^+$. CDCl$_3$: 8.12 (d, J=8.1 Hz, 2H), 7.90-7.85 (m, 2H), 7.66 (d, J=8.1 Hz, 2H), 7.36-7.26 (m, 9H), 7.07 (s, 1H), 6.61 (s, 1H), 4.60 (dd, J=15.9 Hz, 6.9 Hz, 1H), 4.46 (dd, J=15.9 Hz, 5.7 Hz, 1H), 4.35-4.31 (m, 1H), 3.88-3.76 (m, 1H), 3.69-3.63 (m, 5H), 3.57 (s, 2H), 2.74-2.65 (m, 1H), 2.58 (br s, 4H), 2.35-2.26 (m, 1H).

Example 389

(2S)-1-[(5-Chlorothiophen-2-yl)sulfonyl]-N-({2-[4-(2-methylpropyl)piperazin-1-yl]-6-[4-(trifluoromethyl)phenyl]pyridin-4-yl}methyl)-2,5-dihydro-1H-pyrrole-2-carboxamide

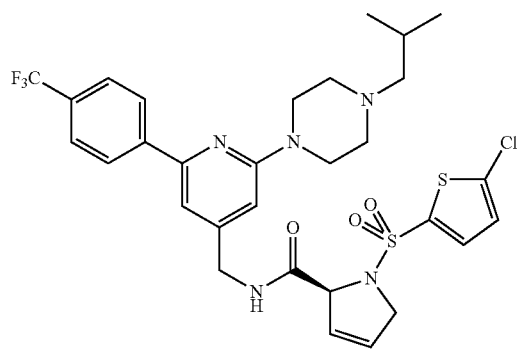 [SMILES: CC(C)CN1CCN(c2cc(CNC(=O)[C@@H]3C=CCN3S(=O)(=O)c3ccc(Cl)s3)cc(-c3ccc(C(F)(F)F)cc3)n2)CC1]

MS (ESI): mass calcd. for $C_{30}H_{33}ClF_3N_5O_3S_2$, 668.21 m/z found, 668.1 (100), 670.1 (45), [M+H]$^+$. CDCl$_3$: 8.13 (d, J=7.8 Hz, 2H), 7.66 (d, J=8.1 Hz, 2H), 7.46 (dd, J=3.9 Hz, 3.4 Hz, 1H), 7.16 (br s, 1H), 7.05-7.01 (m, 2H), 6.63 (s, 1H), 5.89-5.85 (m, 1H), 5.79-5.76 (m, 1H), 4.94-4.91 (m, 1H), 4.77-4.69 (m, 1H), 4.39-4.18 (m, 3H), 3.67 (br s, 4H), 2.51 (br s, 4H), 2.14-2.12 (m, 2H), 1.84-1.82 (m, 1H), 0.94 (d, J=6.3 Hz, 6H).

Example 390

(2S)-1-[(4-Fluorophenyl)sulfonyl]-N-({2-[4-(2-methylpropyl)piperazin-1-yl]-6-[4-(trifluoromethyl)phenyl]pyridin-4-yl}methyl)-2,5-dihydro-1H-pyrrole-2-carboxamide

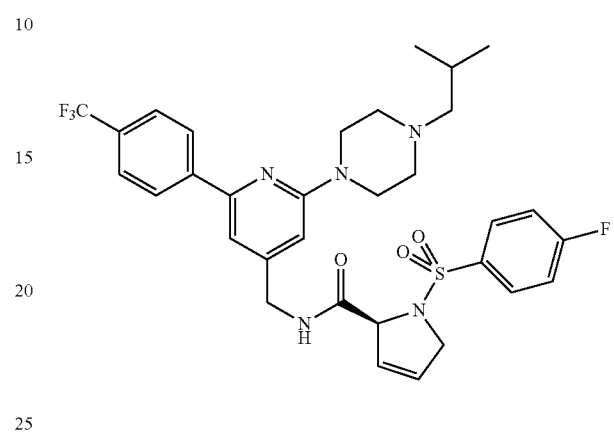

MS (ESI): mass calcd. for $C_{32}H_{35}F_4N_5O_3S$, 645.73 m/z found, 646.2 (100), 647.2 (40), [M+H]$^+$. CDCl$_3$: 8.14 (d, J=7.8 Hz, 2H), 7.89-7.84 (m, 2H), 7.66 (d, J=8.1 Hz, 2H), 7.27-7.22 (m, 4H), 7.09 (s, H), 6.67 (s, 1H), 5.82-5.80 (m, 1H), 5.73-5.72 (m, 1H), 4.90 (br s, 1H), 4.75-4.70 (m, 1H), 4.36-4.25 (m, 2H), 4.17-4.12 (m, 1H), 3.68 (br s, 4H), 2.51 (br s, 4H), 2.13 (br s, 2H), 1.83 (br s, 1H), 0.93 (d, J=6.3 Hz, 6H).

Example 391

(2S)-1-[(5-Chlorothiophen-2-yl)sulfonyl]-N-({2-[(pyridin-4-ylmethyl)amino]-6-[4-(trifluoromethyl)phenyl]pyridin-4-yl}methyl)-2,5-dihydro-1H-pyrrole-2-carboxamide

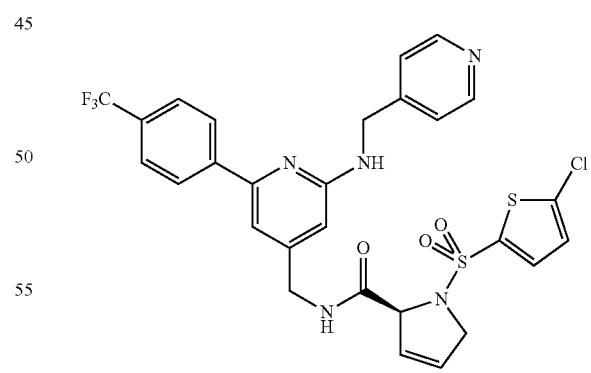

MS (ESI): mass calcd. for $C_{28}H_{23}ClF_3N_5O_3S_2$, 634.1 m/z found, 634.2 [M+H]$^+$. CD$_3$OD: 8.85 (d, J=4.2 Hz, 2H), 8.15 (br s, 4H), 7.95 (d, J=7.8 Hz, 2H), 7.62 (d, J=3.6 Hz, 1H), 7.42 (s, 1H), 7.25 (d, J=3.6 Hz, 1H), 7.06 (s, 1H), 5.95-5.94 (m, 1H), 5.72-5.70 (m, 1H), 5.16 (s, 2H), 4.77-4.71 (m, 2H), 4.46-4.37 (m, 1H), 4.20-4.15 (m, 1H).

Example 392

1-[(4-Fluorophenyl)sulfonyl]-N-({2-[(pyridin-2-ylmethyl)amino]-6-[4-(trifluoromethyl)phenyl]pyridin-4-yl}methyl)-L-prolinamide

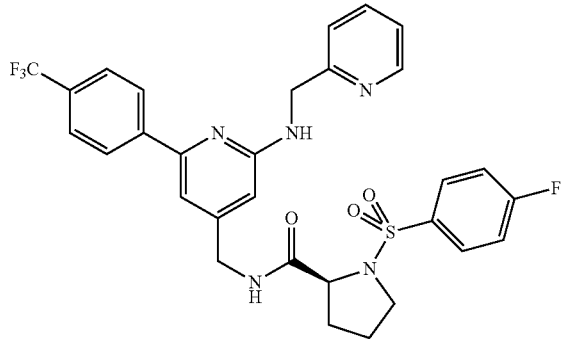 [SMILES: O=C(NCc1cc(NCc2ccccn2)nc(-c2ccc(C(F)(F)F)cc2)c1)[C@@H]1CCCN1S(=O)(=O)c1ccc(F)cc1]

MS (ESI): mass calcd. for $C_{30}H_{27}F_4N_5O_3S$, 613.64 m/z found, m/z=614.2 (100), 615.2 (35), [M+H]$^+$. CDCl$_3$: 8.57 (d, J=4.5 Hz, 1H), 8.10 (d, J=8.1 Hz, 2H), 7.91-7.87 (m, 2H), 7.67-7.63 (m, 3H), 7.39-7.36 (m, 2H), 7.28-7.16 (m, 2H), 7.08 (s, 1H), 6.48 (s, 1H), 5.72 (br s, 1H), 4.76 (s, 2H), 4.61 (dd, J=16.2 Hz, 6.9 Hz, 1H), 4.35 (dd, J=16.2 Hz, 5.4 Hz, 1H), 4.15-4.12 (m, 1H), 3.60-3.57 (m, 1H), 3.17-3.14 (m, 1H), 2.21-2.20 (m, 1H), 1.79-1.63 (m, 3H).

Example 393

N-({2-(Dimethylamino)-6-[4-(trifluoromethyl)phenyl]pyridin-4-yl}methyl)-4,4-difluoro-1-[(4-fluorophenyl)sulfonyl]-L-prolinamide

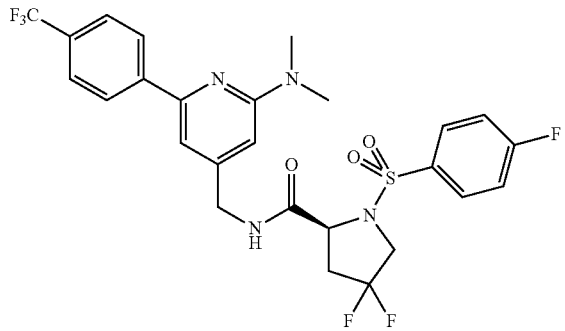 [SMILES: CN(C)c1cc(CNC(=O)[C@@H]2CC(F)(F)CN2S(=O)(=O)c2ccc(F)cc2)cc(-c2ccc(C(F)(F)F)cc2)n1]

MS (ESI): mass calcd. for $C_{26}H_{24}F_6N_4O_3S$, 586.56 m/z found, 587.1 [M+H]$^+$. CDCl$_3$: 8.14 (d, J=8.1 Hz, 2H), 7.93-7.88 (m, 2H), 7.67 (d, J=8.1 Hz, 2H), 7.40-7.19 (m, 2H), 7.02 (s, 1H), 6.55 (s, 1H), 4.61 (dd, J=15.9 Hz, 6.6 Hz, 1H), 4.58 (dd, J=15.9 Hz, 5.4 Hz, 1H), 4.36 (dd, J=9.9 Hz, 4.5 Hz, 1H), 3.84 (m, 1H), 3.63 (m, 1H), 3.19 (s, 6H), 2.79-2.66 (m, 1H), 2.41-2.28 (m, 1H).

Example 394

N-({2-(Benzylamino)-6-[4-(trifluoromethyl)phenyl]pyridin-4-yl}methyl)-4,4-difluoro-1-[(4-fluorophenyl)sulfonyl]-L-prolinamide

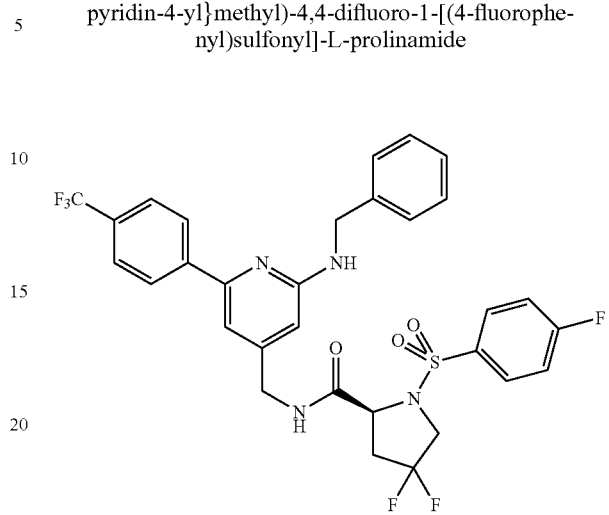

MS (ESI): mass calcd. for $C_{31}H_{26}F_6N_4O_3S$, 648.63 m/z found, 649.2 (100), 650.2 (40), [M+H]$^+$. CDCl$_3$: 8.10 (d, J=8.1 Hz, 2H), 7.90-7.85 (m, 2H), 7.67 (d, J=8.4 Hz, 2H), 7.41-7.26 (m, 7H), 7.05 (s, 1H), 4.62 (d, J=5.7 Hz, 2H), 4.58-4.40 (m, 2H), 4.32 (dd, J=9.9 Hz, 4.5 Hz, 1H), 3.85-3.74 (m, 1H), 3.67-3.55 (m, 1H), 3.72-3.63 (m, 1H), 2.34-2.24 (m, 1H).

Example 395

1-[(4-Fluorophenyl)sulfonyl]-N-({2-[(pyridin-3-ylmethyl)amino]-6-[4-(trifluoromethyl)phenyl]pyridin-4-yl}methyl)-L-prolinamide

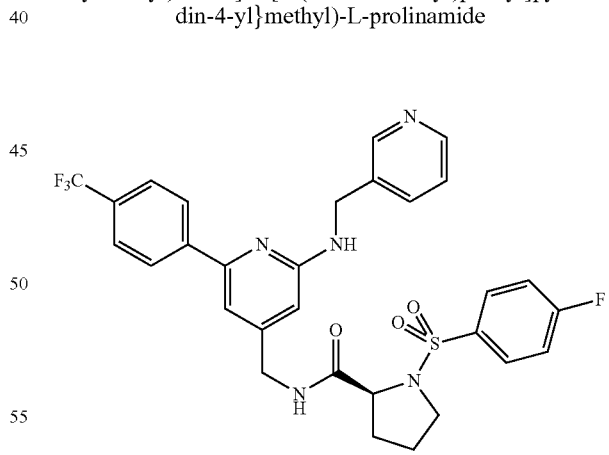

MS (ESI): mass calcd. for $C_{30}H_{27}F_4N_5O_3S$, 613.64 m/z found, 614.2 (20), 615.1 (10), [M+H]$^+$. CDCl$_3$: 8.64 (s, 1H), 8.49 (d, J=3.9 Hz, 1H), 8.04 (d, J=8.1 Hz, 2H), 7.91-7.86 (m, 2H), 7.80 (d, J=7.8 Hz, 1H), 7.64 (d, J=8.1 Hz, 2H), 7.39-7.23 (m, 3H), 7.23 (m, 1H), 6.46 (s, 1H), 5.19 (br s, 1H), 4.67-4.60 (m, 3H), 4.30 (dd, J=16.2 Hz, 5.1 Hz, 1H), 4.13 (d, J=6.0 Hz, 1H), 3.63-3.58 (m, 1H), 3.23-3.09 (m, 1H), 2.21-2.17 (m, 1H), 1.82-1.65 (m, 3H). (3.21 and 1.35 trace of ethanol).

Example 396

4,4-Difluoro-1-[(4-fluorophenyl)sulfonyl]-N-({2-(2-methylpyrrolidin-1-yl)-6-[4-(trifluoromethyl)phenyl]pyridin-4-yl}methyl)-L-prolinamide

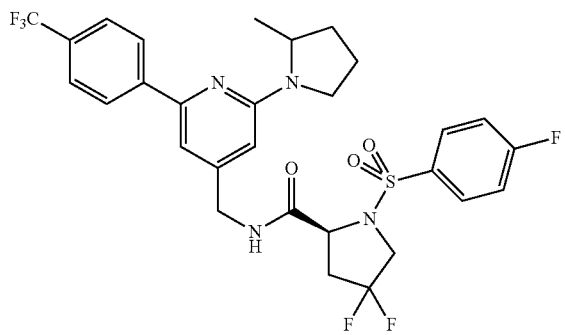 [SMILES: CC1CCCN1c1cc(CNC(=O)[C@@H]2CC(F)(F)CN2S(=O)(=O)c2ccc(F)cc2)cc(-c2ccc(C(F)(F)F)cc2)n1]

MS (ESI): mass calcd. for $C_{29}H_{28}F_6N_4O_3S$, 626.63 m/z found, 627.3 [M+H]$^+$. CDCl$_3$: 8.15 (d, J=8.1 Hz, 2H), 7.90-7.86 (m, 2H), 7.68 (d, J=8.4 Hz, 2H), 7.35-7.24 (m, 3H), 6.98 (s, 1H), 6.33 (s, 1H), 4.56-4.45 (m, 2H), 4.37-4.33 (m, 2H), 3.84-3.76 (m, 1H), 3.68-3.56 (m, 2H), 3.43-3.40 (m, 1H), 2.75-2.71 (m, 1H), 2.34-2.26 (m, 1H), 2.15-1.98 (m, 3H), 1.80-1.73 (m, 1H), 1.28 (d, J=6.3 Hz, 3H).

Example 397

1-[(5-Chlorothiophen-2-yl)sulfonyl]-4,4-difluoro-N-({2-(2-methylpyrrolidin-1-yl)-6-[4-(trifluoromethyl)phenyl]pyridin-4-yl}methyl)-L-prolinamide

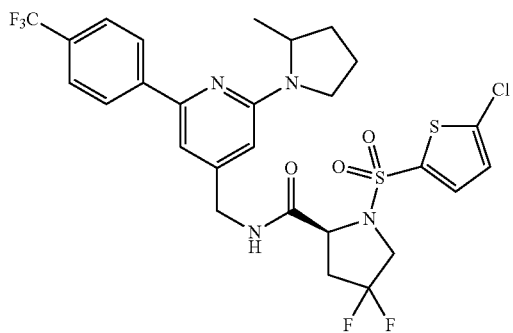 [SMILES: CC1CCCN1c1cc(CNC(=O)[C@@H]2CC(F)(F)CN2S(=O)(=O)c2ccc(Cl)s2)cc(-c2ccc(C(F)(F)F)cc2)n1]

MS (ESI): mass calcd. for $C_{27}H_{26}ClF_5N_4O_3S_2$, 649.11 m/z found, 649.1 (100), 651.0 (50), [M+H]$^+$. CDCl$_3$: 8.14 (d, J=8.1 Hz, 2H), 7.67 (d, J=8.1 Hz, 2H), 7.48 (d, J=3.9 Hz, 1H), 7.29 (br s, 1H), 7.05 (d, J=4.2 Hz, 1H), 6.95 (s, 1H), 6.31 (s, 1H), 4.53-4.37 (m, 3H), 4.30 (br s, 1H), 3.88-3.80 (m, 1H), 3.71-3.59 (m, 2H), 3.45-3.40 (m, 1H), 2.82-2.78 (m, 1H), 2.47-2.36 (m, 1H), 2.15-1.98 (m, 3H), 1.75-1.73 (m, 1H), 1.28 (d, J=6.3 Hz, 3H).

Example 398

4,4-Difluoro-1-[(4-fluorophenyl)sulfonyl]-N-({2-[(1-pyridin-3-ylethyl)amino]-6-[4-(trifluoromethyl)phenyl]pyridin-4-yl}methyl)-L-prolinamide

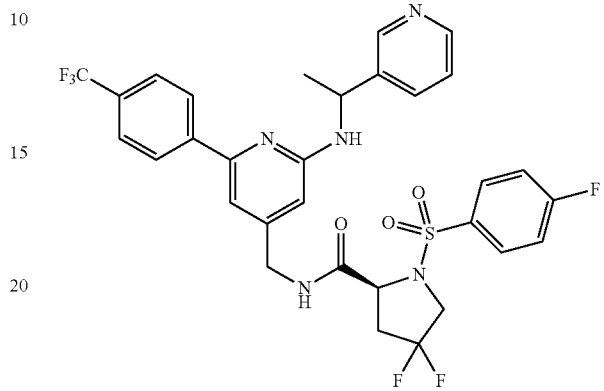

MS (ESI): mass calcd. for $C_{31}H_{27}F_6N_5O_3S$, 663.65 m/z found, 664.2 [M+H]$^+$. CDCl$_3$: 8.76 (s, 1H), 8.54 (d, J=4.2 Hz, 1H), 8.03-7.92 (m, 4H), 7.80 (d, J=6.3 Hz, 1H), 7.69 (d, J=8.1 Hz, 2H), 7.37-7.24 (m, 3H), 7.07 (s, 1H), 6.33 (d, J=6.6 Hz, 1H), 5.11-5.05 (m, 2H), 4.59-4.51 (m, 1H), 4.46-4.35 (m, 2H), 3.88-3.81 (m, 1H), 3.69-3.65 (m, 1H), 2.81-2.70 (m, 1H), 2.38-2.22 (m, 1H), 1.65 (d, J=6.6 Hz, 3H).

Example 399

1-[(5-Chlorothiophen-2-yl)sulfonyl]-4,4-difluoro-N-({2-[(1-pyridin-3-ylethyl)amino]-6-[4-(trifluoromethyl)phenyl]pyridin-4-yl}methyl)-L-prolinamide

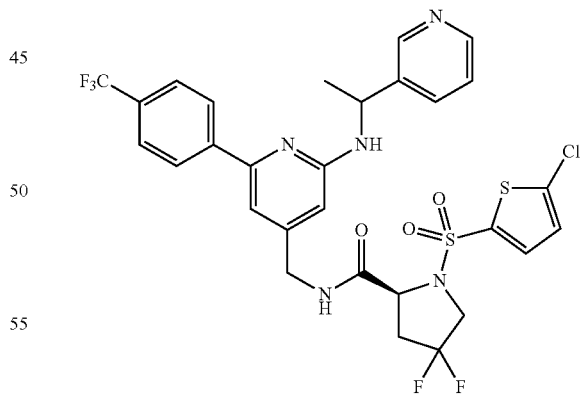

MS (ESI): mass calcd. for $C_{29}H_{25}ClF_5N_5O_3S_2$, 686.13 m/z found, 686.1 (100), 688.1 (45), [M+H]$^+$. CDCl$_3$: 8.75 (s, 1H), 8.54 (d, J=3.6 Hz, 1H), 8.01 (d, J=8.1 Hz, 2H), 7.78 (d, J=6.6 Hz, 1H), 7.68 (d, J=8.1 Hz, 2H), 7.57 (dd, J=13.2 Hz, 4.2 Hz, 1H), 7.32-7.23 (m, 2H), 7.13-7.11 (m, 1H), 7.04 (s, 1H), 6.29 (d, J=6.6 Hz, 1H), 5.11-5.03 (m, 2H), 5.11-4.50 (m, 1H), 4.45-3.68 (m, 2H), 3.92-3.68 (m, 2H), 2.84-2.81 (m, 1H), 2.51-2.40 (m, 1H), 1.65 (d, J=6.3 Hz, 3H).

Example 400

1-[(5-Chlorothiophen-2-yl)sulfonyl]-4,4-difluoro-N-({2-[(1-pyridin-4-ylethyl)amino]-6-[4-(trifluoromethyl)phenyl]pyridin-4-yl}methyl)-L-prolinamide

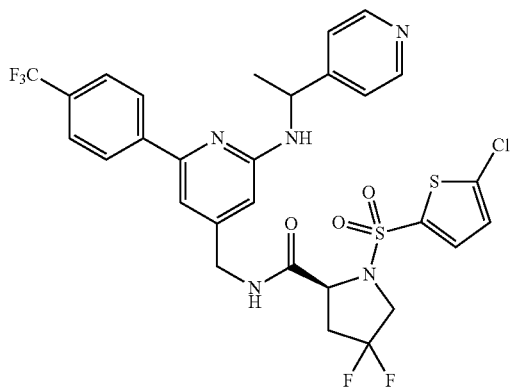 [SMILES: CC(Nc1cc(CNC(=O)[C@@H]2CC(F)(F)CN2S(=O)(=O)c2ccc(Cl)s2)cc(-c2ccc(C(F)(F)F)cc2)n1)c1ccncc1]

MS (ESI): mass calcd. for $C_{29}H_{25}ClF_5N_5O_3S_2$, 686.13 m/z found, 686.1 (100), 688.1 (45), [M+H]$^+$. CDCl$_3$: 8.61 (d, J=5.1 Hz, 2H), 7.98 (d, J=8.1 Hz, 2H), 7.68 (d, J=8.1 Hz, 2H), 7.55 (t, J=4.5 Hz, 1H), 7.40 (d, J=5.1 Hz, 2H), 7.25-7.20 (m, 1H), 7.13 (d, J=3.9 Hz, 1H), 7.06 (s, 1H), 6.31 (d, J=3.0 Hz, 1H), 5.19 (br s, 1H), 5.01-5.00 (m, 1H), 4.62-4.53 (m, 1H), 4.45-4.38 (m, 2H), 3.91-3.81 (m, 1H), 3.75-3.67 (m, 1H), 2.83-2.80 (m, 1H), 2.51-2.40 (m, 1H), 1.63 (d, J=6.9 Hz, 3H).

Example 401

4,4-Difluoro-1-[(4-fluorophenyl)sulfonyl]-N-({2-[(1-pyridin-4-ylethyl)amino]-6-[4-(trifluoromethyl)phenyl]pyridin-4-yl}methyl)-L-prolinamide

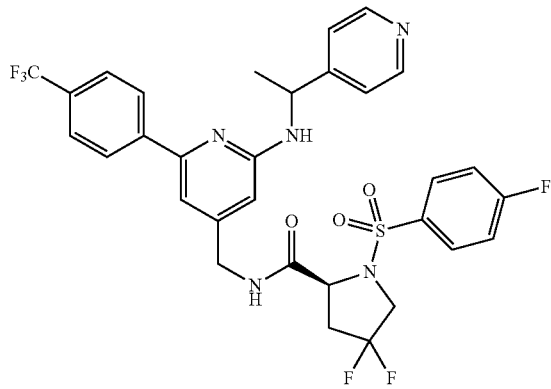 [SMILES: CC(Nc1cc(CNC(=O)[C@@H]2CC(F)(F)CN2S(=O)(=O)c2ccc(F)cc2)cc(-c2ccc(C(F)(F)F)cc2)n1)c1ccncc1]

MS (ESI): mass calcd. for $C_{31}H_{27}F_6N_5O_3S$, 663.65 m/z found, 664.2 [M+H]$^+$. CDCl$_3$: 8.61 (d, J=5.4 Hz, 2H), 8.00-7.91 (m, 4H), 7.68 (d, J=8.4 Hz, 2H), 7.40-7.26 (m, 3H), 7.08 (d, J=2.4 Hz, 1H), 6.32 (s, 1H), 5.03 (br s, 2H), 4.61-4.33 (m, 3H), 3.87-3.60 (m, 2H), 2.77-2.72 (m, 1H), 2.38-2.33 (m, 1H), 1.62 (d, J=6.6 Hz, 3H).

Example 402

1-[(4-Fluorophenyl)sulfonyl]-N-({2-[(1-pyridin-4-ylethyl)amino]-6-[4-(trifluoromethyl)phenyl]pyridin-4-yl}methyl)-L-prolinamide

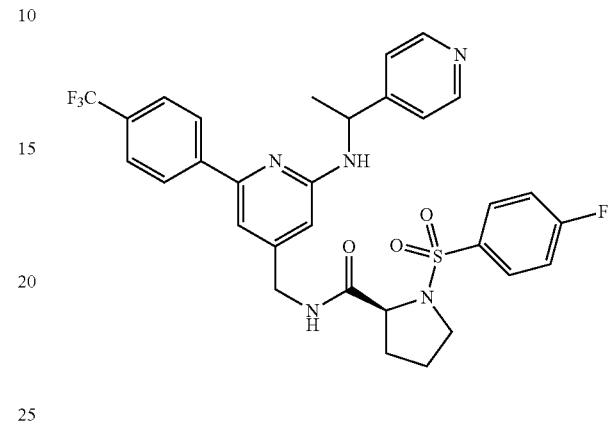

MS (ESI): mass calcd. for $C_{31}H_{29}F_4N_5O_3S$, 627.67 m/z found, 628.2 [M+H]$^+$. CD$_3$OD: 8.38 (d, J=5.7 Hz, 2H), 7.93-7.89 (m, 4H), 7.55 (d, J=8.4 Hz, 2H), 7.45 (d, J=4.5 Hz, 2H), 7.30 (t, J=8.4 Hz, 2H), 7.10 (s, 1H), 6.47 (s, 1H), 5.08 (q, J=6.9 Hz, 1H), 4.43-4.24 (m, 2H), 4.09-4.07 (m, 1H), 3.60-3.53 (m, 1H), 3.26-3.25 (m, 1H), 1.93-1.85 (m, 3H), 1.61-1.58 (m, 1H), 1.50 (d, J=6.9 Hz, 3H).

Example 403

1-[(5-Chlorothiophen-2-yl)sulfonyl]-N-({2-[(1-pyridin-4-ylethyl)amino]-6-[4-(trifluoromethyl)phenyl]pyridin-4-yl}methyl)-L-prolinamide

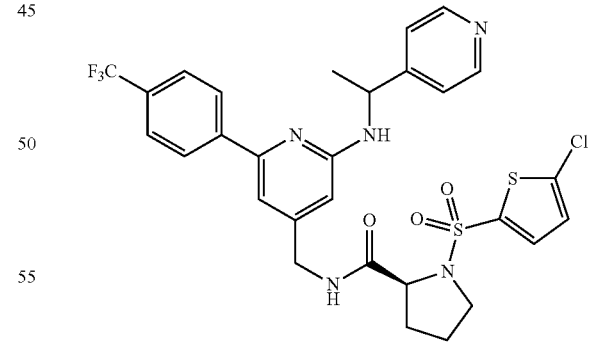

MS (ESI): mass calcd. for $C_{29}H_{27}ClF_3N_5O_3S_2$, 650.15 m/z found, 650.1 (15), 652.1 (5), [M+H]$^+$. CD$_3$OD: 8.37 (d, J=5.7 Hz, 2H), 7.92 (d, J=7.8 Hz, 2H), 7.56-7.51 (m, 3H), 7.44 (d, J=5.1 Hz, 2H), 7.13 (d, J=3.9 Hz, 1H), 7.06 (s, 1H), 6.44 (s, 1H), 5.07-5.03 (m, 1H), 4.42-4.23 (m, 2H), 4.11-4.07 (m, 1H), 3.61-3.58 (m, 1H), 3.32-3.29 (m, 1H), 1.98-1.87 (m, 3H), 1.69-1.66 (m, 1H), 1.50 (d, J=6.9 Hz, 3H).

Example 404

(2S)-1-[(5-Chlorothiophen-2-yl)sulfonyl]-N-({2-[(1-pyridin-4-ylethyl)amino]-6-[4-(trifluoromethyl)phenyl]pyridin-4-yl}methyl)-2,5-dihydro-1H-pyrrole-2-carboxamide

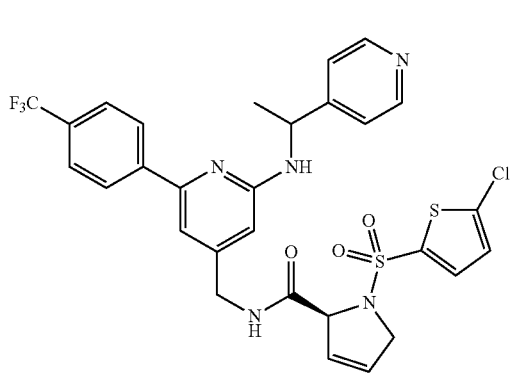

MS (ESI): mass calcd. for $C_{29}H_{25}ClF_3N_5O_3S_2$, 648.13 m/z found, 648.1 (20), 649.1 (5), [M+H]+. CD3OD: 8.37 (d, J=5.7 Hz, 2H), 7.90 (d, J=7.2 Hz, 2H), 7.56-7.52 (m, 3H), 7.44 (d, J=5.1 Hz, 2H), 7.11 (d, J=4.2 Hz, 1H), 7.05 (s, 1H), 6.43 (s, 1H), 5.89-5.86 (m, 1H), 5.70-5.67 (m, 1H), 5.06-5.04 (m, 1H), 4.88-4.87 (m, 1H), 4.43-4.16 (m, 4H), 1.49 (d, J=6.9 Hz, 3H).

Example 405

1-[(5-Chlorothiophen-2-yl)sulfonyl]-N-({2-[(1-pyridin-3-ylethyl)amino]-6-[4-(trifluoromethyl)phenyl]pyridin-4-yl}methyl)-L-prolinamide

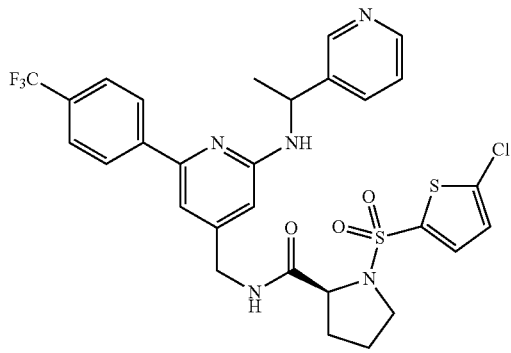 [SMILES: CC(Nc1cc(CNC(=O)[C@@H]2CCCN2S(=O)(=O)c2ccc(Cl)s2)cc(-c2ccc(C(F)(F)F)cc2)n1)c1cccnc1]

MS (ESI): mass calcd. for $C_{29}H_{27}ClF_3N_5O_3S_2$, 650.15 m/z found, 650.1 (50), 652.1 (25), [M+H]+. DMSO-d6: 8.70 (br s, 2H), 8.42 (d, J=3.9 Hz, 1H), 8.13 (d, J=8.1 Hz, 2H), 7.86-7.73 (m, 4H), 7.42-7.33 (m, 3H), 7.13 (s, 1H), 6.48 (s, 1H), 5.22 (br s, 1H), 4.30-4.14 (m, 3H), 3.62-3.58 (m, 1H), 3.30-3.25 (m, 1H), 1.91 (br s, 1H), 1.68 (br s, 1H), 1.55 (d, J=6.9 Hz, 3H).

Example 406

(2S)-1-[(4-Fluorophenyl)sulfonyl]-N-({2-[(1-phenyl-ethyl)amino]-6-[4-(trifluoromethyl)phenyl]pyridin-4-yl}methyl)-2,5-dihydro-1H-pyrrole-2-carboxamide

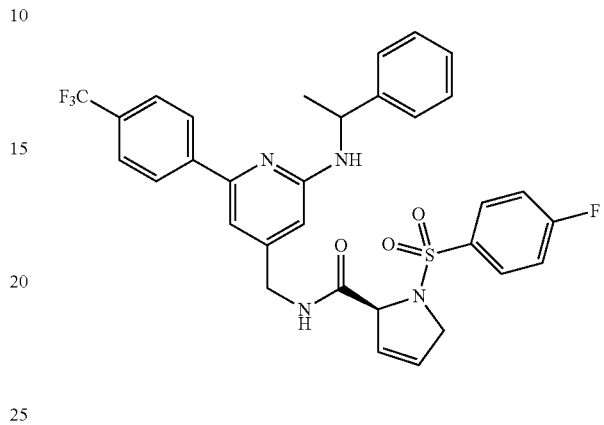

MS (ESI): mass calcd. for $C_{32}H_{28}F_4N_4O_3S$, 624.66 m/z found, 625.2 [M+H]+. DMSO-d6: 8.75 (t, J=5.7 Hz, 1H), 8.16 (d, J=7.8 Hz, 2H), 8.04-7.99 (m, 2H), 7.78 (d, J=8.1 Hz, 2H), 7.54-7.46 (m, 4H), 7.34 (t, J=7.2 Hz, 2H), 7.25-7.19 (m, 2H), 7.12 (s, 1H), 6.46 (s, 1H), 5.96-5.94 (m, 1H), 5.77-5.75 (m, 1H), 5.20-5.18 (m, 1H), 4.92 (br s, 1H), 4.31-4.14 (m, 4H), 1.51 (d, J=6.3 Hz, 3H).

Example 407

(2S)-1-[(5-Chlorothiophen-2-yl)sulfonyl]-N-({2-[(1-phenylethyl)amino]-6-[4-(trifluoromethyl)phenyl]pyridin-4-yl}methyl)-2,5-dihydro-1H-pyrrole-2-carboxamide

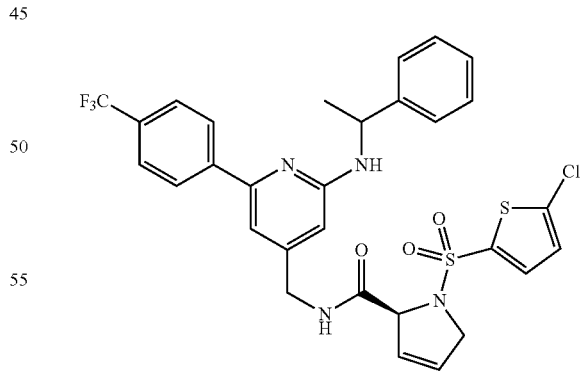

MS (ESI): mass calcd. for $C_{30}H_{26}ClF_3N_4O_3S_2$, 647.14 m/z found, 647.1 (100), 649.1 (50), [M+H]+. DMSO-d6: 8.81 (s, 1H), 8.15 (d, J=7.8 Hz, 2H), 7.81-7.77 (m, 3H), 7.49-7.21 (m, 7H), 7.09 (s, 1H), 6.45 (s, 1H), 6.00-5.99 (m, 1H), 5.82-5.81 (m, 1H), 5.18 (s, 1H), 5.93 (br s, 1H), 4.34-4.18 (m, 4H), 1.51 (d, J=6.6 Hz, 3H).

Example 408

1-[(4-Fluorophenyl)sulfonyl]-N-({2-[(1-pyridin-2-ylethyl)amino]-6-[4-(trifluoromethyl)phenyl]pyridin-4-yl}methyl)-L-prolinamide

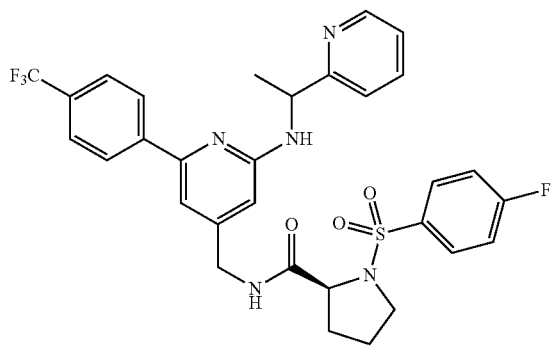 [SMILES: CC(Nc1cc(CNC(=O)[C@@H]2CCCN2S(=O)(=O)c2ccc(F)cc2)cc(-c2ccc(C(F)(F)F)cc2)n1)c1ccccn1]

MS (ESI): mass calcd. for $C_{31}H_{29}F_4N_5O_3S$, 627.67 m/z found, 628.2 (100), 629.2 (40), [M+H]⁺. DMSO-d6: 8.68 (t, J=5.4 Hz, 1H), 8.58 (d, J=5.6 Hz, 1H), 8.12 (d, J=7.5 Hz, 2H), 8.03-7.99 (m, 2H), 7.77-7.72 (m, 3H), 7.55-7.44 (m, 3H), 7.28-7.22 (m, 2H), 7.15 (s, 1H), 6.53 (s, 1H), 5.23 (t, J=7.5 Hz, 1H), 4.31-4.14 (m, 3H), 3.53-3.49 (m, 1H), 3.25-3.23 (m, 1H), 1.87-1.85 (m, 3H), 1.59-1.53 (m, 4H).

Example 409

1-[(5-Chlorothiophen-2-yl)sulfonyl]-N-({2-[(1-pyridin-2-ylethyl)amino]-6-[4-(trifluoromethyl)phenyl]pyridin-4-yl}methyl)-L-prolinamide

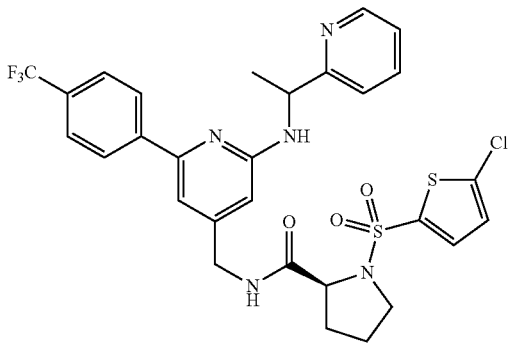

MS (ESI): mass calcd. for $C_{29}H_{27}ClF_3N_5O_3S_2$, 650.15 m/z found, 650.1 (100), 652.1 (45), [M+H]⁺. DMSO-d6: 8.71 (s, 1H), 8.58 (d, J=4.5 Hz, 1H), 8.10 (d, J=7.8 Hz, 2H), 7.78-7.72 (m, 4H), 7.47-7.41 (m, 2H), 7.28-7.22 (m, 2H), 7.13 (s, 1H), 6.52 (s, 1H), 5.23 (t, J=6.6 Hz, 1H), 4.32-4.26 (m, 2H), 4.17-4.13 (m, 1H), 3.59-3.57 (m, 1H), 3.31-3.28 (m, 1H), 1.92-1.91 (m, 3H), 1.70-1.68 (m, 1H), 1.54 (d, J=6.6 Hz, 3H).

Example 410

4,4-Difluoro-1-[(4-fluorophenyl)sulfonyl]-N-({2-[(1-phenylethyl)amino]-6-[4-(trifluoromethyl)phenyl]pyridin-4-yl}methyl)-L-prolinamide

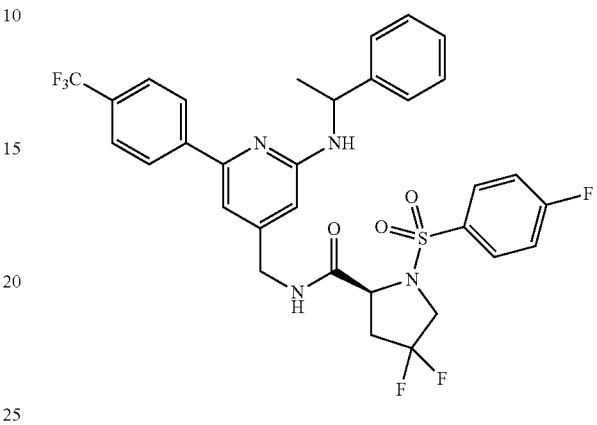

MS (ESI): mass calcd. for $C_{32}H_{28}F_6N_4O_3S$, 662.66 m/z found, 663.1 (100), 664.2 (35), [M+H]⁺. CDCl₃: 8.03 (d, J=8.1 Hz, 2H), 7.89-7.85 (m, 2H), 7.65 (d, J=8.1 Hz, 2H), 7.43-7.20 (m, 8H), 7.00 (s, 1H), 6.22 (s, 1H), 5.12 (br s, 1H), 4.95-4.89 (m, 1H), 4.49-4.28 (m, 3H), 3.80-3.59 (m, 2H), 2.72-2.64 (m, 1H), 2.32-2.23 (m, 1H), 1.59 (d, J=6.6 Hz, 3H).

Example 411

1-[(5-Chlorothiophen-2-yl)sulfonyl]-4,4-difluoro-N-({2-[(1-phenylethyl)amino]-6-[4-(trifluoromethyl)phenyl]pyridin-4-yl}methyl)-L-prolinamide

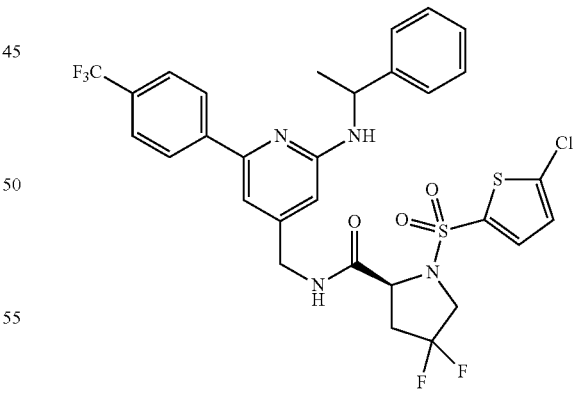

MS (ESI): mass calcd. for $C_{30}H_{26}ClF_5N_4O_3S_2$, 685.14 m/z found, 685.1 (100), 687.1 (45), [M+H]⁺. CDCl₃: 8.20 (d, J=8.1 Hz, 2H), 7.65 (d, J=8.1 Hz, 2H), 7.48 (d, J=3.9 Hz, 1H), 7.42-7.32 (m, 5H), 7.26-7.10 (m, 2H), 7.06 (d, J=4.2 Hz, 1H), 6.98 (s, 1H), 6.19 (s, 1H), 5.08 (br s, 1H), 4.94-4.88 (m, 1H), 4.45-4.33 (m, 3H), 3.84-3.62 (m, 2H), 2.76-2.74 (m, 1H), 2.44-2.38 (m, 1H), 1.59 (d, J=6.6 Hz, 3H).

Example 412

(2S)-1-[(4-Fluorophenyl)sulfonyl]-N-({2-[(1-pyridin-4-ylethyl)amino]-6-[4-(trifluoromethyl)phenyl]pyridin-4-yl}methyl)-2,5-dihydro-1H-pyrrole-2-carboxamide

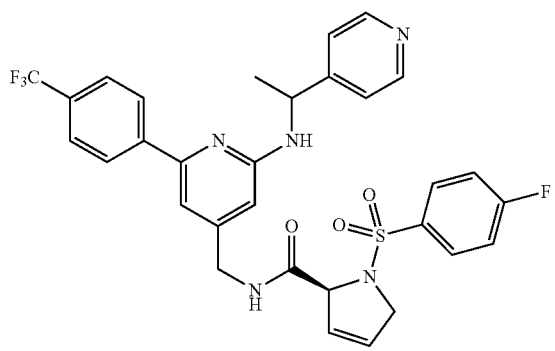

MS (ESI): mass calcd. for $C_{31}H_{27}F_4N_5O_3S$, 625.65 m/z found, 626.2 (15), 627.2 (5), [M+H]$^+$. DMSO-d6: 8.74 (t, J=6.0 Hz, 1H), 8.48 (d, J=6.0 Hz, 1H), 8.05-7.95 (m, 4H), 7.73 (d, J=8.1 Hz, 2H), 7.50-7.40 (m, 4H), 7.31 (d, J=6.9 Hz, 1H), 7.10 (s, 1H), 6.47 (s, 1H), 5.92-5.89 (m, 1H), 5.73-5.71 (m, 1H), 5.13-5.08 (m, 1H), 4.90-4.89 (m, 1H), 4.34-4.10 (m, 4H), 1.47 (d, J=6.6 Hz, 3H).

Example 413

1-[(4-Fluorophenyl)sulfonyl]-N-({2-[(1-phenylethyl)amino]-6-[4-(trifluoromethyl)phenyl]pyridin-4-yl}methyl)-L-prolinamide

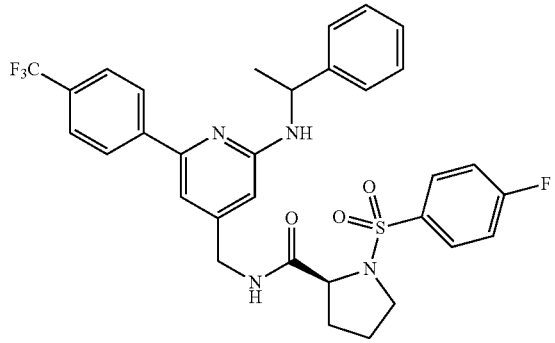

MS (ESI): mass calcd. for $C_{32}H_{30}F_4N_4O_3S$, 626.68 m/z found, 627.2 (100), 628.2 (40), [M+H]$^+$. DMSO-d6: 8.68 (t, J=6.0 Hz, 1H), 8.17 (d, J=8.1 Hz, 2H), 8.03-7.99 (m, 2H), 7.78 (d, J=8.1 Hz, 2H), 7.54-7.47 (m, 4H), 7.37-7.19 (m, 4H), 7.14 (s, 1H), 6.49 (s, 1H), 5.19 (br s, 1H), 4.31-4.14 (m, 3H), 3.54-3.48 (m, 1H), 3.25-3.22 (m, 1H), 1.89-1.83 (m, 3H), 1.60-1.56 (m, 1H), 1.52 (d, J=7.2 Hz, 3H).

Example 414

1-[(5-Chlorothiophen-2-yl)sulfonyl]-N-({2-[(1-phenylethyl)amino]-6-[4-(trifluoromethyl)phenyl]pyridin-4-yl}methyl)-L-prolinamide

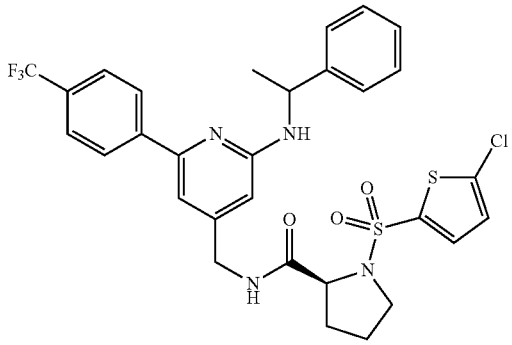

MS (ESI): mass calcd. for $C_{30}H_{28}ClF_3N_4O_3S_2$, 649.16 m/z found, 649.2 (100), 651.2 (45), [M+H]$^+$. DMSO-d6: 8.69 (br s, 1H), 8.15 (d, J=7.8 Hz, 2H), 7.79-7.72 (m, 3H), 7.48-7.18 (m, 7H), 7.10 (s, 1H), 6.46 (s, 1H), 5.18 (br s, 1H), 4.29-4.15 (m, 3H), 3.58-3.30 (m, 3H), 1.83 (br s, 3H), 1.93-1.91 (m, 1H), 1.51 (d, J=6.6 Hz, 3H).

Example 415

1-[(5-Chlorothiophen-2-yl)sulfonyl]-4,4-difluoro-N-({2-[(1-pyridin-2-ylethyl)amino]-6-[4-(trifluoromethyl)phenyl]pyridin-4-yl}methyl)-L-prolinamide

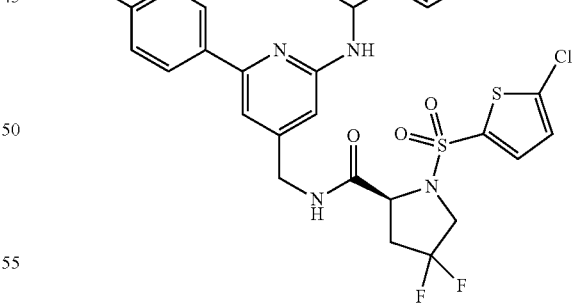

MS (ESI): mass calcd. for $C_{29}H_{25}ClF_5N_5O_3S_2$, 686.13 m/z found, 686.1 (100), 688.1 (50), [M+H]$^+$. CD$_3$OD: 8.40 (d, J=4.8 Hz, 1H), 7.87 (d, J=8.4 Hz, 2H), 7.63 (t, J=7.5 Hz, 1H), 7.55 (d, J=4.2 Hz, 1H), 7.48 (d, J=8.1 Hz, 2H), 7.40 (d, J=8.1 Hz, 1H), 7.14 (t, J=6.0 Hz, 1H), 7.09 (d, J=4.2 Hz, 1H), 7.02 (s, 1H), 6.43 (s, 1H), 5.05 (q, J=6.9 Hz, 1H), 4.34-4.29 (m, 3H), 3.89-3.72 (m, 2H), 2.60-2.47 (m, 2H), 1.47 (d, J=7.2 Hz, 3H).

Example 416

4,4-Difluoro-1-[(4-fluorophenyl)sulfonyl]-N-({2-[(1-pyridin-2-ylethyl)amino]-6-[4-(trifluoromethyl)phenyl]pyridin-4-yl}methyl)-L-prolinamide

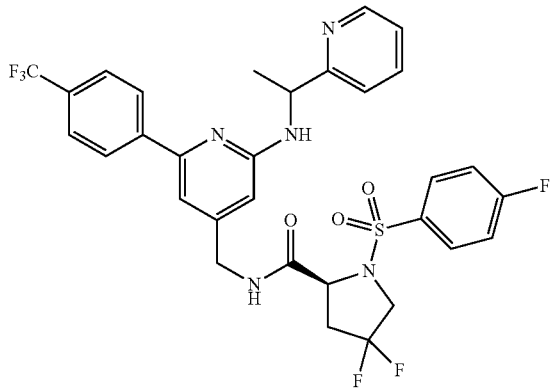 [SMILES: CC(Nc1cc(CNC(=O)[C@@H]2CC(F)(F)CN2S(=O)(=O)c2ccc(F)cc2)cc(-c2ccc(C(F)(F)F)cc2)n1)c1ccccc1]

MS (ESI): mass calcd. for $C_{31}H_{27}F_6N_5O_3S$, 663.65 m/z found, 664.1 (100), 665.1 (35), [M+H]$^+$. CD$_3$OD: 8.40 (d, J=4.2 Hz, 1H), 7.92-7.86 (m, 4H), 7.63 (t, J=7.8 Hz, 1H), 7.47 (d, J=8.1 Hz, 2H), 7.40 (d, J=7.8 Hz, 1H), 7.24 (t, J=8.4 Hz, 2H), 7.14 (t, J=6.6 Hz, 1H), 7.05 (s, 1H), 6.44 (s, 1H), 5.07-5.04 (m, 1H), 4.34-4.29 (m, 3H), 3.82-3.70 (m, 2H), 2.46-2.38 (m, 2H), 1.46 (d, J=6.9 Hz, 3H).

Example 417

(2S)-1-[(5-Chlorothiophen-2-yl)sulfonyl]-N-({2-(2-methylpyrrolidin-1-yl)-6-[4-(trifluoromethyl)phenyl]pyridin-4-yl}methyl)-2,5-dihydro-1H-pyrrole-2-carboxamide

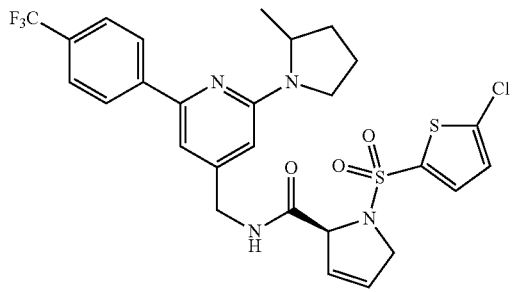 [SMILES: CC1CCCN1c1cc(CNC(=O)[C@@H]2C=CCN2S(=O)(=O)c2ccc(Cl)s2)cc(-c2ccc(C(F)(F)F)cc2)n1]

MS (ESI): mass calcd. for $C_{27}H_{26}ClF_3N_4O_3S_2$, 611.11 m/z found, 611.1 (100), 613.1 (40), [M+H]$^+$. CDCl$_3$: 8.13 (d, J=7.5 Hz, 2H), 7.66 (d, J=8.1 Hz, 2H), 7.47 (d, J=3.9 Hz, 1H), 7.20 (br s, 1H), 7.02 (d, J=3.9 Hz, 1H), 6.96 (s, 1H), 6.36 (s, 1H), 5.88-5.86 (m, 1H), 5.79-5.77 (m, 1H), 4.94-4.93 (m, 1H), 4.67-4.64 (m, 1H), 4.38-4.19 (m, 4H), 3.68-3.62 (m, 1H), 3.45-3.42 (m, 1H), 2.90-1.98 (m, 3H), 1.74-1.72 (m, 1H), 1.28 (d, J=6.0 Hz, 3H).

Biological Methods:

Compounds of the invention were tested in the following assays in their free base, trifluoroacetic salt, or hydrochloride salt forms.

Assay 1: In Vitro Cellular Testing of TRPA1 Modulation

Human TRPA1 (NCBI accession number NM_007332.1) was cloned into pcDNA4/TO. CHO-TREx cells (Invitrogen, Carlsbad, Calif.) were stably transfected with pcDNA4/TO-TRPA1 using lipofection to generate a clonal cell line that expressed human TRPA1 in a tetracycline-inducible manner. Culture medium used was Ham's F-12 supplemented with 10% fetal bovine serum, 2 mM L-glutamine, 5 μg/ml blasticidin and 200 μg/ml zeocin. Cells were seeded in black-walled clear-bottom 96-well plates at a density of 50,000 cells per well and cultured overnight at 37° C. with 5% CO$_2$ in culture medium supplemented with 1 μg/ml tetracycline. On the day of the experiment, cells were washed 3 times with HEPES buffered saline (in mM: NaCl 137, MgCl$_2$ 0.5, KCl 2, dextrose 5, CaCl$_2$ 2 and HEPES 10; pH 7.4). Cells were then loaded with calcium-sensitive fluorescent dye by incubation in the presence of 4 μM Fluo-3 AM (TefLabs, Austin, Tex.) at room temperature in the dark for 60 minutes. After incubation with dye, cells were washed in assay buffer and, if appropriate, antagonists were added at this time. Following a further 30 minute incubation, cells were assayed using a Fluorometric Imaging Plate Reader (FLIPR™) or a Tetra (both manufactured by Molecular Devices, CA) to simultaneously monitor Fluo-3 fluorescence in all wells ($\lambda_{excitation}$=488 nm, $\lambda_{emission}$=540 nm). Changes in fluorescence were monitored for 3 minutes after the addition of 15 μM allyl isothiocyanate (AITC) as an agonist. Concentration-dependence of receptor blocking was determined by exposing each well of cells in duplicate rows of a 96-well plate to a serial dilution of test compound. The concentration series usually started at 10 μM with a three-fold serial decrement in concentration. The magnitude of the response to agonist challenge was determined by measuring the fluorescence before and 3 minutes after the addition of the agonist. The degree of blocking was determined by comparing the response to that of negative (no added antagonist) and positive (10 μM ruthenium red) control wells. Data were analyzed using a non-linear regression program (Origin; OriginLab, MA) to fit the concentration-response data to a Hill function. Antagonist potencies were determined as the concentration required to produce 50% reduction in the response as compared to the negative and positive controls.

In alternative embodiments, the assay was performed using the following procedure for Examples 184, 190 to 192, and 194 to 316:

The human TRPA1 gene was cloned into the pT-Rex-Dest30 inducible vector and stably transfected in T-Rex™-293 cells (Invitrogen, Merelbeke, Belgium). This tetracycline inducible hTRPA1 expression system was used in order to prevent CA$^{2+}$ overload in the cultured cells due to sustained TRPA1 expression. hTRPA1/TREx-HEK293 cells (referred to as jTRPA1 cells in the following text) were maintained under standard sterile cell culture conditions. The culture medium for the jTRPA1-HEK cells was DMEN (Gibco BRL, Invitrogen, Merelbeke, Belgium) supplemented with 5 g/l gengticin (Gibco), 5 mL/l blasticidin (Invitorgen), 14.6 g/l L-Glutamine (200 mMl; Gibco), 5 g/l penicillin/streptomycin (5.10-6 IU/l, Gibco), 5.5 g/l pyruvic acid (Gibco) and 10% foetal calf serum (Hyclone, Logan Utah, USA).

For Ca$^{2+}$ fluorometry experiments, hTRPA1-HEK cells were resuspended in HBSS seeding medium: HBSS (with CaCl2 and MgCl2: Gibco) supplemented with 14.6 g/l L-Glutamine (200 mM; Gibco), 5 g/l penicillin/streptomycin (5.10-6 IU/l. Gibco), 5.5 g/l pyruvic acid (Gibco) and 10% foetal calf serum (heat inactivated for 30 minutes at 56° C.; Hyclone, Logan Utah, USA). The cells were seeded in poly-D-lysine-coated 384-well round bottom polypropylene plates (Costar Corning, Data Packaging, Cambridge Mass., USA) at 12000 cells/well. Fifty ng/ml tetracycline was added to induce the hTRPA1 expression 24 h before the experiment.

The cells were loaded with 5 mg/l Fluo-4-AM (Molecular Probes, Invitorgen, Merelbeke, Belgium) dissolved in HBSS seeding medium supplemented with 0.7 g/l Probenecid (Sigma) and incubated for 1 h at 37° C. and subsequently at 20° C. for 1 to 2 h. The fluorescence was measured in the FDSS 6000 imaging based plate reader (Hamamutsu Photonics K.K., Hamamutsu City, Japan). The excitation wavelength was 488 nm and the emission wavelength 540 nm. After a control period of 12 seconds the inventive compounds were added and the $Ca^{2+}$ signal was measured within 14 minutes after application. Finally, a TRPA1 agonist, 6,11-dihydro-5H-dibenzo[b,e]azepine-10-carboxylic acid methyl ester, was added at a final concentration of 25 nM. The emission ratio was calculated by dividing the emission signal (Em540) by the first EM540 signal of the control period to compensate for the background fluorescence. On every 384 well plate, four series of DMSO control experiments were performed of which 2 contained and 2 did not contain the agonist. For intracellular $Ca^{2+}$ measurements, a compound stock solution (10 to 100 mM) was further diluted in DMSO in order to obtain a final 1% DMSO concentration in the extracellular solution.

Compounds of the invention were tested in the following assays in their free base, hydrochloride, or trifluoroacetic acid salt forms.

The TRPA1 agonist 6,11-dihydro-5H-dibenzo[b,e]azepine-10-carboxylic acid methyl ester was synthesized by use of the following methods:

A: 2-(3-Bromo-phenyl)-1,4-dihydro-2H-benzo[d][1,3]oxazine

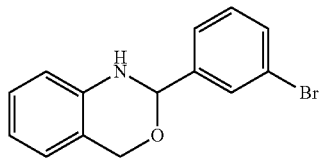 [SMILES: Brc1cccc(C2Nc3ccccc3CO2)c1]

A mixture of 2-amino-benzenemethanol (0.073 mol) and 3-bromo-benzaldehyde (0.073 mol) in 2-propanol (100 mL) was stirred for 3 hours at rt. The solvent was evaporated. Part (3 g) of the residue (20.5 g) was crystallized from hexane. The precipitate was filtered off and dried, yielding 1.37 g of the desired product.

B: [2-(3-Bromo-benzylamino)-phenyl]-methanol

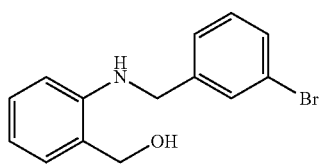 [SMILES: OCc1ccccc1NCc1cccc(Br)c1]

Under a nitrogen atmosphere, sodium borohydride (0.1172 mol) was added slowly to a mixture of 2-(3-bromo-phenyl)-1,4-dihydro-2H-benzo[d][1,3]oxazine (0.0586 mol) in ethanol (200 mL). The reaction mixture was stirred and refluxed for 1 hour. The mixture was cooled on an ice-water bath, quenched with $NH_4Cl$ 20% and extracted with DCM. The organic layer was dried, filtered and the solvent was evaporated, yielding 14.8 g of the desired product.

C: 10-Bromo-6,11-dihydro-5H-dibenzo[b,e]azepine and 8-bromo-6,11-dihydro-5H-dibenzo[b,e]azepine

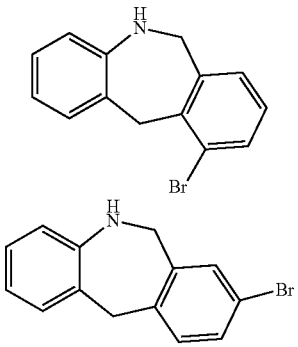

A solution of [2-(3-bromo-benzylamino)-phenyl]-methanol (0.180 mol) in DCM (50 mL) was added over a 5 hr period to a cooled (±−10 to −20° C.) solution of concentrated $H_2SO_4$ (500 mL). The ice-bath was then removed, and the mixture was stirred for one hour at rt. The reaction mixture was added to ice-water, cooled on ice, and alkalized with a 50% aqueous NaOH solution. The resulting mixture (±3 L) was extracted with DCM. The organic layer was separated, dried on $MgSO_4$, filtered and the filtrate was concentrated in vacuo. A part (8 g) of this residue was purified via Supercritical Fluid Chromatography (SFC, column: Diacel AD-H 30×250 mm, mobile phase: 55% MeOH/45% $CO_2$+0.2% isopropylamine, 40° C., 100 bar) to give 2 g of 10-bromo-6,11-dihydro-5H-dibenzo[b,e]azepine and 4.65 g of 8-bromo-6,11-dihydro-5H-dibenzo[b,e]azepine.

D: 6,11-Dihydro-5H-dibenzo[b,e]azepine-10-carboxylic acid methyl ester

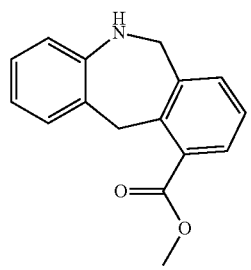 [SMILES: COC(=O)c1cccc2c1Cc1ccccc1NC2]

A mixture of 10-bromo-6,11-dihydro-5H-dibenzo[b,e]azepine (0.008 mol), potassium acetate (4 g), $Pd(OAc)_2$ (0.04 g) and 1,1'-(1,3-propanediyl)bis[1,1-d]phenyl-phosphine (0.16 g) in methanol (100 mL) and THF (100 mL) was placed in a pressure reactor and pressurized with CO gas up to 50 kg/square cm. The reaction mixture was heated at 125° C. for 16 hours, then cooled, filtered over dicalite, and the solvent was evaporated. The residue was partitioned between $CH_2Cl_2$ and water. The organic layer was dried over $MgSO_4$, filtered, and the filtrate concentrated. The residue was purified by column chromatography over silica gel using $CH_2Cl_2$ as an eluent. The desired fractions were collected and the solvent was evaporated, yielding 1.86 g of the desired compound.

TABLE 1

| Example | $IC_{50}$ (μM) |
|---|---|
| 1 | 0.036 |
| 2 | 0.040 |
| 3 | 0.108 |
| 4 | 0.003 |
| 5 | 0.009 |
| 6 | 0.011 |
| 7 | 0.229 |
| 8 | 0.475 |
| 9 | 0.542 |
| 10 | 0.030 |
| 11 | 0.065 |
| 12 | 1.089 |
| 13 | 0.090 |
| 14 | 0.021 |
| 15 | 0.418 |
| 16 | 0.034 |
| 17 | 2.077 |
| 18 | 1.851 |
| 19 | 0.016 |
| 20 | 2.054 |
| 21 | 0.024 |
| 22 | 0.130 |
| 23 | 4.416 |
| 24 | 0.024 |
| 25 | 0.063 |
| 26 | 0.013 |
| 27 | 0.016 |
| 28 | 0.081 |
| 29 | 0.012 |
| 30 | 0.013 |
| 31 | 0.009 |
| 32 | 1.016 |
| 33 | 0.469 |
| 34 | 0.032 |
| 35 | 0.083 |
| 36 | 0.039 |
| 37 | 0.007 |
| 38 | 0.006 |
| 39 | 1.262 |
| 40 | 1.654 |
| 41 | 2.924 |
| 42 | 0.016 |
| 43 | 0.004 |
| 44 | 0.012 |
| 45 | 2.037 |
| 46 | 0.747 |
| 47 | 0.014 |
| 48 | 0.006 |
| 49 | 0.015 |
| 50 | 0.036 |
| 51 | 0.148 |
| 52 | 0.013 |
| 53 | 0.426 |
| 54 | 1.070 |
| 55 | 2.550 |
| 56 | 0.051 |
| 57 | 0.194 |
| 58 | 0.005 |
| 59 | 0.081 |
| 60 | 6.173 |
| 61 | 0.105 |
| 62 | 3.214 |
| 63 | 0.078 |
| 64 | 0.234 |
| 65 | 0.015 |
| 66 | 0.253 |
| 67 | 0.515 |
| 68 | 0.026 |
| 69 | 0.181 |
| 70 | 0.746 |
| 71 | 0.014 |
| 72 | 0.017 |

TABLE 1-continued

| Example | $IC_{50}$ (μM) |
|---|---|
| 73 | 0.004 |
| 74 | 0.017 |
| 75 | 0.771 |
| 76 | 0.024 |
| 77 | 0.059 |
| 78 | 6.046 |
| 79 | 0.137 |
| 80 | 0.410 |
| 81 | 0.093 |
| 82 | 0.050 |
| 83 | 0.073 |
| 84 | 0.340 |
| 85 | 14.125 |
| 86 | 0.085 |
| 87 | 1.793 |
| 88 | 0.017 |
| 89 | 0.844 |
| 90 | 8.299 |
| 91 | 0.175 |
| 92 | 0.017 |
| 93 | 0.086 |
| 94 | 1.633 |
| 95 | 10.000 |
| 96 | 0.432 |
| 97 | 1.708 |
| 98 | 0.381 |
| 99 | 19.953 |
| 100 | 19.953 |
| 101 | 4.046 |
| 102 | 1.704 |
| 103 | 0.252 |
| 104 | 0.460 |
| 105 | 1.028 |
| 106 | 0.594 |
| 107 | 0.518 |
| 108 | 2.529 |
| 109 | 0.319 |
| 110 | 0.092 |
| 111 | 0.014 |
| 112 | 0.011 |
| 113 | 0.062 |
| 114 | 2.928 |
| 115 | 0.015 |
| 116 | 0.386 |
| 117 | 19.953 |
| 118 | 5.768 |
| 119 | 0.047 |
| 120 | 0.030 |
| 121 | 1.526 |
| 122 | 0.267 |
| 123 | 0.032 |
| 124 | 0.011 |
| 125 | 0.063 |
| 126 | 0.046 |
| 127 | 0.042 |
| 128 | 0.049 |
| 129 | 0.019 |
| 130 | 0.006 |
| 131 | 0.087 |
| 132 | 0.117 |
| 133 | 0.026 |
| 134 | 0.021 |
| 135 | 0.022 |
| 136 | 0.035 |
| 137 | 0.037 |
| 138 | 0.017 |
| 139 | 0.073 |
| 140 | 0.079 |
| 141 | 0.073 |
| 142 | 0.078 |
| 143 | 0.010 |
| 144 | 0.022 |
| 145 | 0.028 |
| 146 | 0.052 |
| 147 | 0.092 |
| 148 | 0.028 |
| 149 | 3.648 |
| 150 | 0.383 |

TABLE 1-continued

| Example | IC$_{50}$ (μM) |
|---|---|
| 151 | 19.953 |
| 152 | 0.066 |
| 153 | 0.401 |
| 154 | 0.044 |
| 155 | 1.021 |
| 156 | 0.388 |
| 157 | 4.694 |
| 158 | 0.587 |
| 159 | 1.094 |
| 160 | 0.077 |
| 161 | 0.137 |
| 162 | 1.696 |
| 163 | 0.014 |
| 164 | 19.953 |
| 165 | 0.011 |
| 166 | 0.014 |
| 167 | 0.063 |
| 168 | 19.953 |
| 169 | 0.051 |
| 170 | 0.020 |
| 171 | 0.019 |
| 172 | 0.011 |
| 173 | 1.149 |
| 174 | 0.095 |
| 175 | 19.953 |
| 176 | 0.045 |
| 177 | 0.071 |
| 178 | 0.203 |
| 179 | 0.229 |
| 180 | 0.228 |
| 181 | 0.602 |
| 182 | 0.923 |
| 183 | 0.020 |
| 184 | ~0.033 |
| 185 | 0.433 |
| 186 | 0.227 |
| 187 | 0.806 |
| 188 | 0.647 |
| 189 | 0.002 |
| 190 | ~1.949 |
| 191 | 2.138 |
| 192 | ~0.588 |
| 193 | 0.085 |
| 194 | 0.575 |
| 195 | 0.617 |
| 196 | ~4.786 |
| 197 | ~1.148 |
| 198 | ~3.019 |
| 199 | ~3.311 |
| 200 | 3.311 |
| 201 | 8.128 |
| 202 | ~2.398 |
| 203 | ~6.456 |
| 204 | ~2.691 |
| 205 | ~1.778 |
| 206 | 4.467 |
| 207 | 9.120 |
| 208 | 2.291 |
| 209 | 1.000 |
| 210 | 4.571 |
| 211 | ~1.621 |
| 212 | 0.676 |
| 213 | 2.399 |
| 214 | ~0.977 |
| 215 | 1.023 |
| 216 | 1.202 |
| 217 | 0.871 |
| 218 | >10 |
| 219 | ~2.691 |
| 220 | ~4.466 |
| 221 | 2.042 |
| 222 | 9.120 |
| 223 | >10 |
| 224 | >10 |
| 225 | 2.512 |
| 226 | 0.115 |
| 227 | 1.175 |
| 228 | 2.291 |

TABLE 1-continued

| Example | IC$_{50}$ (μM) |
|---|---|
| 229 | 1.585 |
| 230 | 1.288 |
| 231 | 2.754 |
| 232 | 1.122 |
| 233 | ~0.372 |
| 234 | >10 |
| 235 | 5.888 |
| 236 | >10 |
| 237 | >10 |
| 238 | 1.288 |
| 239 | 5.012 |
| 240 | ~0.933 |
| 241 | 0.417 |
| 242 | ~1.096 |
| 243 | 3.802 |
| 244 | >10 |
| 245 | 2.455 |
| 246 | 1.995 |
| 247 | ~1.445 |
| 248 | ~0.676 |
| 249 | 1.585 |
| 250 | 0.851 |
| 251 | 2.512 |
| 252 | >10 |
| 253 | >10 |
| 254 | >10 |
| 255 | >10 |
| 256 | >10 |
| 257 | >10 |
| 258 | 0.324 |
| 259 | 3.548 |
| 260 | >10 |
| 261 | 2.692 |
| 262 | >10 |
| 263 | 0.191 |
| 264 | ~0.933 |
| 265 | >10 |
| 266 | >10 |
| 267 | 7.943 |
| 268 | >10 |
| 269 | 0.229 |
| 270 | 0.692 |
| 271 | >10 |
| 272 | ~0.436 |
| 273 | >10 |
| 274 | >10 |
| 275 | >10 |
| 276 | 6.166 |
| 277 | >10 |
| 278 | >10 |
| 279 | >10 |
| 280 | >10 |
| 281 | 5.495 |
| 282 | >10 |
| 283 | ~0.724 |
| 284 | ~1.071 |
| 285 | 0.022 |
| 286 | ~0.158 |
| 287 | 3.715 |
| 288 | >10 |
| 289 | ~3.467 |
| 290 | ~0.708 |
| 291 | ~0.407 |
| 292 | >10 |
| 293 | 2.692 |
| 294 | ~1 |
| 295 | 1.738 |
| 296 | 4.467 |
| 297 | 0.355 |
| 298 | 4.677 |
| 299 | ~1.585 |
| 300 | 2.512 |
| 301 | 5.623 |
| 302 | 8.710 |
| 303 | ~2.818 |
| 304 | 0.331 |
| 305 | ~5.888 |
| 306 | ~2.089 |

TABLE 1-continued

| Example | IC$_{50}$ (μM) |
|---|---|
| 307 | ~0.354 |
| 308 | 1.778 |
| 309 | 1.175 |
| 310 | 0.407 |
| 311 | ~1.513 |
| 312 | 0.295 |
| 313 | ~0.489 |
| 314 | ~1.318 |
| 315 | ~0.45 |
| 316 | 1.450 |
| 317 | 0.016 |
| 318 | 0.029 |
| 319 | 0.021 |
| 320 | 0.745 |
| 321 | 1.016 |
| 322 | 1.179 |
| 323 | 0.510 |
| 324 | 0.412 |
| 325 | 0.845 |
| 326 | 5.970 |
| 327 | 0.587 |
| 328 | 0.682 |
| 329 | 1.756 |
| 330 | 0.604 |
| 331 | 0.176 |
| 332 | 0.058 |
| 333 | 0.073 |
| 334 | 2.633 |
| 335 | 0.179 |
| 336 | 0.113 |
| 337 | 1.005 |
| 338 | 0.382 |
| 339 | 0.251 |
| 340 | 0.210 |
| 341 | 0.693 |
| 342 | 0.296 |
| 343 | 1.057 |
| 344 | >10 |
| 345 | 2.497 |
| 346 | >10 |
| 347 | 0.518 |
| 348 | 1.626 |
| 349 | 1.694 |
| 350 | 7.261 |
| 351 | >10 |
| 352 | 7.088 |
| 353 | 2.754 |
| 354 | 1.070 |
| 355 | 0.891 |
| 356 | >10 |
| 357 | >10 |
| 358 | >10 |
| 359 | 1.190 |
| 360 | 2.275 |
| 361 | 0.452 |
| 362 | 19.953 |
| 363 | 4.870 |
| 364 | 2.726 |
| 365 | 1.687 |
| 366 | 1.650 |
| 367 | 0.018 |
| 368 | 0.418 |
| 369 | 0.079 |
| 370 | 0.115 |
| 371 | 2.061 |
| 372 | 1.614 |
| 373 | 0.043 |
| 374 | 2.092 |
| 375 | 1.943 |
| 376 | 0.241 |
| 377 | 4.710 |
| 378 | 19.953 |
| 379 | 0.380 |
| 380 | 0.523 |
| 381 | 0.729 |
| 382 | 5.093 |
| 383 | 0.488 |
| 384 | 2.218 |

TABLE 1-continued

| Example | IC$_{50}$ (μM) |
|---|---|
| 385 | 0.978 |
| 386 | 0.311 |
| 387 | 3.048 |
| 388 | 3.524 |
| 389 | 0.095 |
| 390 | 0.382 |
| 391 | 0.797 |
| 392 | 0.414 |
| 393 | 0.461 |
| 394 | 0.598 |
| 395 | 2.975 |
| 396 | 1.793 |
| 397 | 2.951 |
| 398 | 7.088 |
| 399 | 2.612 |
| 400 | 1.832 |
| 401 | 2.521 |
| 402 | 0.594 |
| 403 | 0.466 |
| 404 | 1.910 |
| 405 | 0.481 |
| 406 | 0.833 |
| 407 | 0.185 |
| 408 | 0.054 |
| 409 | 0.064 |
| 410 | 1.260 |
| 411 | 1.426 |
| 412 | 1.269 |
| 413 | 0.269 |
| 414 | 0.057 |
| 415 | 0.570 |
| 416 | 1.056 |
| 417 | 0.082 |

While the invention has been illustrated by reference to examples, it is understood that the invention is intended not to be limited to the foregoing detailed description.

What is claimed is:

1. A compound of Formula (I), pharmaceutically acceptable salt of a compound of Formula (I), or a pharmaceutically acceptable prodrug of a compound of Formula (I),

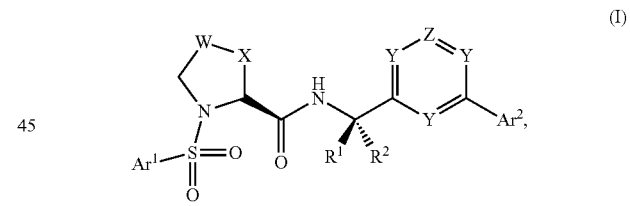

wherein,
Ar$^1$ is:
  iii) phenyl substituted with 0, 1, 2 or 3 substituents R$^a$; or
  iv) a 5- or 6-membered monocyclic aromatic heterocycle ring optionally substituted with one or two substituents R$^a$;
    where each R$^a$ is independently halo, —C$_{1-4}$alkyl, —OC$_{1-4}$alkyl, —CN, —CF$_3$, —OCF$_3$, —NO$_2$, —C(O)C$_{1-4}$alkyl or —CO$_2$H;
Ar$^2$ is:
  i) phenyl substituted with 0, 1, 2 or 3 substituents R$^b$;
    where each R$^b$ is independently halo, —C$_{1-4}$alkyl, —C(O)NR$^c$R$^d$, —OC$_{1-4}$alkyl, —OC$_{1-4}$alkylCF$_3$, —CN, —CF$_3$, —OCF$_2$H, —NO$_2$, —NR$^c$R$^d$, —S(O)$_{0-2}$C$_{1-4}$alkyl, —C(O)C$_{1-4}$alkyl, —S(O)(O)NH$_2$, —(CH$_2$)$_{0-2}$-morpholinyl, piperidin-1-yl or piperazinyl, said piperazinyl optionally substituted with a methyl;

ii) pyridyl substituted with 0, 1 or 2 substituents $R^e$,
where each $R^e$ is independently selected from halo, —$C_{1-4}$alkyl, —$OC_{1-4}$alkyl, —$CF_3$, —$NR^cR^d$ or 4-morpholinyl; or iii) a bicyclic 9- or 10-membered aromatic heterocycle optionally substituted with 1 substituent $R^f$;
where $R^f$ is —$C_{1-4}$alkyl;

$R^c$ and $R^d$ are each independently selected from H or —$C_{1-4}$alkyl;

W is —$CR''H$— or —$CF_2$—;

X is —$CR''H$—;

or W and X may each be a CH group linked together by a double bond;

$R''$ is H or —OH; or two adjacent $R''$ moieties taken together form —$CH_2$—;

$R^1$ and $R^2$ are each independently H or —$C_{1-4}$alkyl;

each Y is independently CH or N;

Z is $CR^g$;

$R^g$ is
i) H, —$C_{1-4}$alkyl, —$CF_3$, —$OR^z$, —$N(CH_3)_2$ or —$NR^hR^i$;
where $R^h$ is selected from H, 2-hydroxy-propyl, 2-hydroxy-2-methyl-propyl, —$C_{1-4}$alkyl-$N(CH_3)_2$, —$C_{1-4}$alkyl-pyridyl, —$C_{1-4}$alkyl-phenyl, 1-pyridinyl-ethyl, 1-methyl-pyrrolidin-3-ylmethyl or —$C_{1-4}$alkyl-piperidinyl, said piperidinyl optionally substituted with —$C_{1-4}$alkyl;
where $R^z$ is —$C_{1-4}$alkyl, —$C_{1-4}$alkyl$CF_3$ or —$C_{1-4}$alkyl-heterocycloalkyl;

ii) 1-pyrrolidinyl optionally substituted with —$C_{1-4}$alkyl or —$NR^kR^l$;

iii) piperazinyl optionally substituted with —$C_{2-5}$alkyl, —$OC_{1-4}$alkyl, —$C_{1-4}$-alkyl-pyridyl, —$C_{0-4}$alkyl-1-methyl-piperidin-4-yl, —$C_{0-4}$alkyl$NR^kR^i$ or —$C_{0-4}$-alkyl-phenyl, said phenyl optionally substituted with one or two substituents selected from the group consisting of Cl, Br, I, —$OCF_3$, and —$C_{1-4}$alkyl or said one substituent is F bound at the 2-position;

iv) phenyl optionally substituted with —$CF_3$; or vii) pyridyl;

viii) 1-piperidinyl;

$R^k$ is H, —$C_{1-4}$alkyl or —$C(O)_{1-2}C_{1-4}$alkyl; and $R^i$ is H or $CH_3$;

with the proviso that when $Ar^1$ is 4-fluoro-phenyl;

$Ar^2$ is 4-trifluoromethyl-phenyl;

$R^1$ and $R^2$ are each H;

W and X are each —$CH_2$—;

and the two Y's adjacent to Z are N with the third being C;

then $R^g$ cannot be [4-(2-fluoro-phenyl)-piperazin-1-yl].

2. A compound according to claim 1 selected from the group consisting of: (a) the compounds of Formula (I) wherein each instance of Y and Z is CH; and (b) pharmaceutically acceptable salts of said compounds.

3. A compound according to claim 1, wherein Z is $CR^g$ and two instances of Y are N.

4. A compound according to claim 1, wherein Z is $CR^g$ and one instance of Y is N.

5. A compound according to claim 1, wherein W and X are CH.

6. A compound according to claim 1, wherein W is —$CF_2$—.

7. A compound according to claim 1, wherein W and X are —$CH_2$—.

8. A compound according to claim 1, wherein $R^1$ and $R^2$ are H.

9. A compound according to claim 3, wherein $R^g$ is $NR^hR^i$.

10. A compound according to claim 4, wherein $R^g$ is $NR^hR^i$.

11. A compound according to claim 1, wherein $R^b$ is selected from —$CF_3$, —$OCF_3$, F, Cl, Br, —$NO_2$, —$SO_2Me$, —$SCH_3$, —$OCH_3$, —$N(CH_3)_2$, —$SO_2NH_2$, —CN, —$CONH_2$, —$OCH_2CF_3$, —$(CH_2)_{0-1}$morpholinyl, piperazinyl, or N-methylpiperazinyl.

12. A compound according to claim 1, wherein $Ar^1$ is phenyl with 0, 1, 2 or 3 substituents $R^a$.

13. A compound according to claim 1, wherein $Ar^1$ is thiophen-yl with 0, 1, 2 or 3 substituents $R^a$.

14. A compound according to claim 1, wherein $Ar^2$ is phenyl with 0, 1, 2 or 3 substituents $R^b$.

15. A compound according to claim 1, wherein $Ar^2$ is pyridyl.

16. A compound selected from the group consisting of:
1-(4-Fluoro-benzenesulfonyl)-pyrrolidine-2S-carboxylic acid [2-(4-isobutyl-piperazin-1-yl)-6-(4-trifluoromethyl-phenyl)-pyrimidin-4-ylmethyl]-amide;
1-(4-Fluoro-benzenesulfonyl)-pyrrolidine-2S-carboxylic acid [2-methoxy-6-(4-trifluoromethyl-phenyl)-pyrimidin-4-ylmethyl]-amide;
1-(4-Fluoro-benzenesulfonyl)-pyrrolidine-2S-carboxylic acid [2-pyridin-3-yl-6-(4-trifluoromethyl-phenyl)-pyrimidin-4-ylmethyl]-amide;
1-(4-Fluoro-benzenesulfonyl)-pyrrolidine-2S-carboxylic acid [2,6-bis-(4-trifluoromethyl-phenyl)-pyrimidin-4-ylmethyl]-amide;
1-(4-Fluoro-benzenesulfonyl)-pyrrolidine-2S-carboxylic acid [2-(3-trifluoromethyl-phenyl)-6-(4-trifluoromethyl-phenyl)-pyrimidin-4-ylmethyl]-amide;
1-(4-Fluoro-benzenesulfonyl)-pyrrolidine-2S-carboxylic acid [2-(2-trifluoromethyl-phenyl)-6-(4-trifluoromethyl-phenyl)-pyrimidin-4-ylmethyl]-amide;
1-(4-Fluoro-benzenesulfonyl)-pyrrolidine-2S-carboxylic acid [2-pyridin-4-yl-6-(4-trifluoromethyl-phenyl)-pyrimidin-4-ylmethyl]-amide;
1-(4-Fluoro-benzenesulfonyl)-pyrrolidine-2S-carboxylic acid [2-amino-6-(4-trifluoromethyl-phenyl)-pyrimidin-4-ylmethyl]-amide;
1-(4-Fluoro-benzenesulfonyl)-pyrrolidine-2S-carboxylic acid [2-(4-isopropyl-piperazin-1-yl)-6-(4-trifluoromethyl-phenyl)-pyrimidin-4-ylmethyl]-amide;
1-(4-Fluoro-benzenesulfonyl)-pyrrolidine-2S-carboxylic acid [2-dimethylamino-6-(4-trifluoromethyl-phenyl)-pyrimidin-4-ylmethyl]-amide;
1-(4-Fluoro-benzenesulfonyl)-pyrrolidine-2S-carboxylic acid [6-(4-trifluoromethyl-phenyl)-pyrimidin-4-ylmethyl]-amide;
1-(4-Fluoro-benzenesulfonyl)-pyrrolidine-2S-carboxylic acid [2-[(1-methyl-pyrrolidin-3-ylmethyl)-amino]-6-(4-trifluoromethyl-phenyl)-pyrimidin-4-ylmethyl]-amide;
1-(4-Fluoro-benzenesulfonyl)-pyrrolidine-2S-carboxylic acid [2-[4-(1-ethyl-propyl)-piperazin-1-yl]-6-(4-trifluoromethyl-phenyl)-pyrimidin-4-ylmethyl]-amide;
1-(4-Fluoro-benzenesulfonyl)-pyrrolidine-2S-carboxylic acid [2-methylamino-6-(4-trifluoromethyl-phenyl)-pyrimidin-4-ylmethyl]-amide;
1-(4-Fluoro-benzenesulfonyl)-pyrrolidine-2S-carboxylic acid [2-(4-ethyl-piperain-1-yl)-6-(4-trifluoromethyl-phenyl)-pyrimidin-4-ylmethyl]-amide;
1-(4-Fluoro-benzenesulfonyl)-pyrrolidine-2S-carboxylic acid [2-(1-pyridin-2-yl-ethylamino)-6-(4-trifluoromethyl-phenyl)-pyrimidin-4-ylmethyl]-amide;

1-(4-Fluoro-benzenesulfonyl)-pyrrolidine-2S-carboxylic acid [2-[4-(2-dimethylamino-ethyl)-piperazin-1-yl]-6-(4-trifluoromethyl-phenyl)-pyrimidin-4-ylmethyl]-amide;

1-(4-Fluoro-benzenesulfonyl)-pyrrolidine-2S-carboxylic acid [2-[(2-dimethylamino-ethyl)-methyl-amino]-6-(4-trifluoromethyl-phenyl)-pyrimidin-4-ylmethyl]-amide;

1-(4-Fluoro-benzenesulfonyl)-pyrrolidine-2S-carboxylic acid [2-(4-pyridin-3-ylmethyl-piperazin-1-yl)-6-(4-trifluoromethyl-phenyl)-pyrimidin-4-ylmethyl]-amide;

1-(4-Fluoro-benzenesulfonyl)-pyrrolidine-2S-carboxylic acid [2-[4-(1-methyl-piperidin-4-ylmethyl)-piperazin-1-yl]-6-(4-trifluoromethyl-phenyl)-pyrimidin-4-ylmethyl]-amide;

1-(4-Fluoro-benzenesulfonyl)-pyrrolidine-2S-carboxylic acid [2-(4-pyridin-4-ylmethyl-piperazin-1-yl)-6-(4-trifluoromethyl-phenyl)-pyrimidin-4-ylmethyl]-amide;

1-(4-Fluoro-benzenesulfonyl)-pyrrolidine-2S-carboxylic acid [2-(4-pyridin-2-ylmethyl-piperazin-1-yl)-6-(4-trifluoromethyl-phenyl)-pyrimidin-4-ylmethyl]-amide;

1-(4-Fluoro-benzenesulfonyl)-pyrrolidine-2S-carboxylic acid [2-piperazin-1-yl-6-(4-trifluoromethyl-phenyl)-pyrimidin-4-ylmethyl]-amide;

1-(5-Chloro-thiophene-2-sulfonyl)-pyrrolidine-2S-carboxylic acid [2-(4-isobutyl-piperazin-1-yl)-6-(4-trifluoromethyl-phenyl)-pyrimidin-4-ylmethyl]-amide;

1-(4-Fluoro-benzenesulfonyl)-pyrrolidine-2-carboxylic acid [2-(2-methyl-pyrrolidin-1-yl)-6-(4-trifluoromethyl-phenyl)-pyrimidin-4-ylmethyl]-amide;

1-(4-Fluoro-benzenesulfonyl)-pyrrolidine-2S-carboxylic acid [2-(2S-methyl-pyrrolidin-1-yl)-6-(4-trifluoromethyl-phenyl)-pyrimidin-4-ylmethyl]-amide;

1-(4-Fluoro-benzenesulfonyl)-pyrrolidine-2S-carboxylic acid [2-(2R-methyl-pyrrolidin-1-yl)-6-(4-trifluoromethyl-phenyl)-pyrimidin-4-ylmethyl]-amide;

1-(5-Chloro-thiophene-2-sulfonyl)-pyrrolidine-2S-carboxylic acid [2-methylamino-6-(4-trifluoromethyl-phenyl)-pyrimidin-4-ylmethyl]-amide;

1-(5-Chloro-thiophene-2-sulfonyl)-pyrrolidine-2S-carboxylic acid [2-dimethylamino-6-(4-trifluoromethyl-phenyl)-pyrimidin-4-ylmethyl]-amide;

1-(5-Chloro-thiophene-2-sulfonyl)-pyrrolidine-2(S)-carboxylic acid [2-(2R-methyl-pyrrolidin-1-yl)-6-(4-trifluoromethyl-phenyl)-pyrimidin-4-ylmethyl]-amide;

1-(5-Chloro-thiophene-2-sulfonyl)-pyrrolidine-2S-carboxylic acid [2-(2S-methyl-pyrrolidin-1-yl)-6-(4-trifluoromethyl-phenyl)-pyrimidin-4-ylmethyl]-amide;

1-(5-Chloro-thiophene-2-sulfonyl)-pyrrolidine-2S-carboxylic acid [2-(3R-dimethylamino-pyrrolidin-1-yl)-6-(4-trifluoromethyl-phenyl)-pyrimidin-4-ylmethyl]-amide;

1-(5-Chloro-thiophene-2-sulfonyl)-pyrrolidine-2S-carboxylic acid [2-(3S-dimethylamino-pyrrolidin-1-yl)-6-(4-trifluoromethyl-phenyl)-pyrimidin-4-ylmethyl]-amide;

{1-[4-({[1-(5-Chloro-thiophene-2-sulfonyl)-pyrrolidine-2S-carbonyl]-amino}-methyl)-6-(4-trifluoromethyl-phenyl)-pyrimidin-2-yl]-pyrrolidin-3S-yl}-carbamic acid tert-butyl ester;

{1-[4-({[1-(5-Chloro-thiophene-2-sulfonyl)-pyrrolidine-2S-carbonyl]-amino}-methyl)-6-(4-trifluoromethyl-phenyl)-pyrimidin-2-yl]-pyrrolidin-3R-yl}-carbamic acid tert-butyl ester;

1-(5-Chloro-thiophene-2-sulfonyl)-pyrrolidine-2S-carboxylic acid [2-(1-pyridin-2-yl-ethylamino)-6-(4-trifluoromethyl-phenyl)-pyrimidin-4S-ylmethyl]-amide;

1-(5-Chloro-thiophene-2-sulfonyl)-pyrrolidine-2S-carboxylic acid [2-(1-pyridin-2-yl-ethylamino)-6-(4-trifluoromethyl-phenyl)-pyrimidin-4R-ylmethyl]-amide;

{1-[4-({[1-(5-Chloro-thiophene-2-sulfonyl)-pyrrolidine-2S-carbonyl]-amino}-methyl)-6-(4-trifluoromethyl-phenyl)-pyrimidin-2-yl]-pyrrolidin-3-yl}-methyl-carbamic acid tert-butyl ester;

1-(5-Chloro-thiophene-2-sulfonyl)-pyrrolidine-2S-carboxylic acid [2-(3S-amino-pyrrolidin-1-yl)-6-(4-trifluoromethyl-phenyl)-pyrimidin-4-ylmethyl]-amide;

1-(5-Chloro-thiophene-2-sulfonyl)-pyrrolidine-2S-carboxylic acid [2-(3R-amino-pyrrolidin-1-yl)-6-(4-trifluoromethyl-phenyl)-pyrimidin-4-ylmethyl]-amide;

1-(5-Chloro-thiophene-2-sulfonyl)-pyrrolidine-2S-carboxylic acid [2-(3-methylamino-pyrrolidin-1-yl)-6-(4-trifluoromethyl-phenyl)-pyrimidin-4-ylmethyl]-amide;

1-(4-Fluoro-benzenesulfonyl)-pyrrolidine-2-carboxylic acid [2-isobutoxy-6-(4-trifluoromethyl-phenyl)-pyrimidin-4-ylmethyl]-amide;

1-(5-Chloro-thiophene-2-sulfonyl)-pyrrolidine-2S-carboxylic acid [2-isobutoxy-6-(4-trifluoromethyl-phenyl)-pyrimidin-4-ylmethyl]-amide;

1-(5-Chloro-thiophene-2-sulfonyl)-pyrrolidine-2S-carboxylic acid [2-(2-isopropyl-pyrrolidin-1-yl)-6-(4-trifluoromethyl-phenyl)-pyrimidin-4-ylmethyl]-amide;

1-(5-Chloro-thiophene-2-sulfonyl)-pyrrolidine-2S-carboxylic acid [2-(2-hydroxy-propylamino)-6-(4-trifluoromethyl-phenyl)-pyrimidin-4-ylmethyl]-amide;

1-(5-Chloro-thiophene-2-sulfonyl)-pyrrolidine-2S-carboxylic acid [2-(2-hydroxy-2-methyl-propylamino)-6-(4-trifluoromethyl-phenyl)-pyrimidin-4-ylmethyl]-amide;

1-(5-Chloro-thiophene-2-sulfonyl)-pyrrolidine-2S-carboxylic acid [2-methoxy-6-(4-trifluoromethyl-phenyl)-pyrimidin-4-ylmethyl]-amide;

1-(5-Chloro-thiophene-2-sulfonyl)-pyrrolidine-2S-carboxylic acid [2-(2-methyl-pyrrolidin-1-yl)-6-(4-trifluoromethyl-phenyl)-pyrimidin-4-ylmethyl]-amide;

1-(5-Chloro-thiophene-2-sulfonyl)-pyrrolidine-2S-carboxylic acid [2-ethoxy-6-(4-trifluoromethyl-phenyl)-pyrimidin-4-ylmethyl]-amide;

1-(4-Fluoro-benzenesulfonyl)-pyrrolidine-2S-carboxylic acid [2-[4-(2-chloro-benzyl)-piperazin-1-yl]-6-(4-trifluoromethyl-phenyl)-pyrimidin-4-ylmethyl]-amide;

1-(4-Fluoro-benzenesulfonyl)-pyrrolidine-2S-carboxylic acid [2-[4-(2-trifluoromethoxy-benzyl)-piperazin-1-yl]-6-(4-trifluoromethyl-phenyl)-pyrimidin-4-ylmethyl]-amide;

1-(4-Fluoro-benzenesulfonyl)-pyrrolidine-2S-carboxylic acid [2-[4-(2-ethyl-benzyl)-piperazin-1-yl]-6-(4-trifluoromethyl-phenyl)-pyrimidin-4-ylmethyl]-amide;

1-(5-Chloro-thiophene-2-sulfonyl)-pyrrolidine-2S-carboxylic acid [2-[(3-(acetyl-methyl-amino)-pyrrolidin-1-yl]-6-(4-trifluoromethyl-phenyl)-pyrimidin-4-ylmethyl]-amide;

1-(5-Chloro-thiophene-2-sulfonyl)-pyrrolidine-2S-carboxylic acid [2-(3-diethylamino-pyrrolidin-1-yl)-6-(4-trifluoromethyl-phenyl)-pyrimidin-4-ylmethyl]-amide;

1-(5-Chloro-thiophene-2S-sulfonyl)-pyrrolidine-2S-carboxylic acid [2-[(1-isopropyl-piperidin-4-ylmethyl)-methyl-amino]-6-(4-trifluoromethyl-phenyl)-pyrimidin-4-ylmethyl]-amide;

1-(5-Chloro-thiophene-2-sulfonyl)-2,5-dihydro-1H-pyrrole-2S-carboxylic acid [2-(4-isobutyl-piperazin-1-yl)-6-(4-trifluoromethyl-phenyl)-pyrimidin-4-ylmethyl]-amide;

1-(5-Chloro-thiophene-2-sulfonyl)-4,4-difluoro-pyrrolidine-2S-carboxylic acid [2-(4-isobutyl-piperazin-1-yl)-6-(4-trifluoromethyl-phenyl)-pyrimidin-4-ylmethyl]-amide;

1-(5-Chloro-thiophene-2-sulfonyl)-pyrrolidine-2S-carboxylic acid [2-(2,2,2-trifluoro-ethoxy)-6-(4-trifluoromethyl-phenyl)-pyrimidin-4-ylmethyl]-amide;

1-(5-Chloro-thiophene-2-sulfonyl)-pyrrolidine-2S-carboxylic acid [2-dimethylamino-6-(4-trifluoromethyl-phenyl)-pyrimidin-4-ylmethyl]-amide;

1-(5-Chloro-thiophene-2-sulfonyl)-4,4-difluoro-pyrrolidine-2S-carboxylic acid [2-(2-methyl-pyrrolidin-1-yl)-6-(4-trifluoromethyl-phenyl)-pyrimidin-4-ylmethyl]-amide;

1-(5-Chloro-thiophene-2-sulfonyl)-4,4-difluoro-pyrrolidine-2S-carboxylic acid [2-(2,2,2-trifluoro-ethoxy)-6-(4-trifluoromethyl-phenyl)-pyrimidin-4-ylmethyl]-amide;

1-(5-Chloro-thiophene-2-sulfonyl)-pyrrolidine-2S-carboxylic acid [2-(2-pyrrolidin-1-yl-ethoxy)-6-(4-trifluoromethyl-phenyl)-pyrimidin-4-ylmethyl]-amide;

1-(5-Chloro-thiophene-2-sulfonyl)-pyrrolidine-2S-carboxylic acid [2-(2-piperidin-1-yl-ethoxy)-6-(4-trifluoromethyl-phenyl)-pyrimidin-4-ylmethyl]-amide;

1-(5-Chloro-thiophene-2-sulfonyl)-pyrrolidine-2S-carboxylic acid [2-(2-morpholin-4-yl-ethoxy)-6-(4-trifluoromethyl-phenyl)-pyrimidin-4-ylmethyl]-amide;

1-(4-Fluorobenzenesulfonyl)-pyrrolidine-2S-carboxylic acid (4'-trifluoromethylbiphenyl-3-ylmethyl)-amide;

1-(4-Fluorobenzenesulfonyl)-pyrrolidine-2S-carboxylic acid (3'-trifluoromethylbiphenyl-3-ylmethyl)-amide;

1-(4-Fluorobenzenesulfonyl)-pyrrolidine-2S-carboxylic acid (2'-trifluoromethylbiphenyl-3-ylmethyl)-amide;

1-(4-Fluorobenzenesulfonyl)-pyrrolidine-2S-carboxylic acid (4'-trifluoromethoxybiphenyl-3-ylmethyl)-amide;

1-(4-Fluorobenzenesulfonyl)-pyrrolidine-2S-carboxylic acid (3'-trifluoromethoxybiphenyl-3-ylmethyl)-amide;

1-(4-Fluorobenzenesulfonyl)-pyrrolidine-2S-carboxylic acid (2'-trifluoromethoxybiphenyl-3-ylmethyl)-amide;

1-(4-Fluorobenzenesulfonyl)-pyrrolidine-2S-carboxylic acid (3'-fluoro-4'-trifluoromethylbiphenyl-3-ylmethyl)-amide;

1-(4-Fluoro-benzenesulfonyl)-pyrrolidine-2S-carboxylic acid (3'-chloro-4'-trifluoromethyl-biphenyl-3-ylmethyl)-amide;

1-(4-Fluorobenzenesulfonyl)-pyrrolidine-2S-carboxylic acid (3'-fluoro-4'-trifluoromethoxybiphenyl-3-ylmethyl)-amide;

1-(4-Fluorobenzenesulfonyl)-pyrrolidine-2-carboxylic acid (4'-difluoromethoxy-3',5'-difluorobiphenyl-3-ylmethyl)-amide;

1-(4-Fluorobenzenesulfonyl)-pyrrolidine-2S-carboxylic acid (4'-methanesulfonylbiphenyl-3-ylmethyl)-amide;

1-(4-Fluorobenzenesulfonyl)-pyrrolidine-2S-carboxylic acid (4'-nitrobiphenyl-3-ylmethyl)-amide;

1-(4-Fluoro-benzenesulfonyl)-pyrrolidine-2S-carboxylic acid (4'-bromo-biphenyl-3-ylmethyl)-amide;

1-(4-Fluorobenzenesulfonyl)-pyrrolidine-2S-carboxylic acid (4'-sulfamoyl-biphenyl-3-ylmethyl)-amide;

1-(4-Fluoro-benzenesulfonyl)-pyrrolidine-2S-carboxylic acid (4'-methyl-biphenyl-3-ylmethyl)-amide;

1-(4-Fluorobenzenesulfonyl)-pyrrolidine-2S-carboxylic acid (4'-methoxybiphenyl-3-ylmethyl)-amide;

1-(4-Fluorobenzenesulfonyl)-pyrrolidine-2S-carboxylic acid [4'-(2,2,2-trifluoroethoxy)-biphenyl-3-ylmethyl]-amide;

1-(4-Fluoro-benzenesulfonyl)-pyrrolidine-2S-carboxylic acid (4'-methylsulfanyl-biphenyl-3-ylmethyl)-amide;

1-(4-Fluoro-benzenesulfonyl)-pyrrolidine-2S-carboxylic acid 3-(6-chloro-pyridin-3-yl)-benzylamide;

1-(4-Fluorobenzenesulfonyl)-pyrrolidine-2S-carboxylic acid 3-(6-methoxypyridin-3-yl)-benzylamide;

1-(4-Fluorobenzenesulfonyl)-pyrrolidine-2S-carboxylic acid (4'-carbamoylbiphenyl-3-ylmethyl)-amide;

1-(4-Fluoro-benzenesulfonyl)-pyrrolidine-2S-carboxylic acid (4'-cyano-biphenyl-3-ylmethyl)-amide;

1-(4-Fluorobenzenesulfonyl)-pyrrolidine-2S-carboxylic acid 3-(6-methylpyridin-3-yl)-benzyl amide;

1-(4-Fluorobenzenesulfonyl)-pyrrolidine-2S-carboxylic acid 3-(6-trifluoromethylpyridin-3-yl)-benzyl amide;

1-(4-Fluorobenzenesulfonyl)-pyrrolidine-2S-carboxylic acid (4'-acetylbiphenyl-3-ylmethyl)-amide;

1-(4-Fluorobenzenesulfonyl)-pyrrolidine-2S-carboxylic acid 3-(5-methoxypyridin-2-yl)-benzylamide;

1-(4-Fluorobenzenesulfonyl)-pyrrolidine-2S-carboxylic acid 3-(5-chloropyridin-2-yl)-benzylamide;

1-(4-Fluorobenzenesulfonyl)-pyrrolidine-2S-carboxylic acid 3-(5-trifluoromethylpyridin-2-yl)-benzylamide;

1-(4-Fluorobenzenesulfonyl)-pyrrolidine-2S-carboxylic acid (4'-dimethylaminobiphenyl-3-ylmethyl)-amide;

1-(4-Fluorobenzenesulfonyl)-pyrrolidine-2S-carboxylic acid (4'-morpholin-4-yl-biphenyl-3-ylmethyl)-amide;

1-(4-Fluoro-benzenesulfonyl)-pyrrolidine-2S-carboxylic acid 3-(1H-indol-5-yl)-benzylamide;

1-(4-Fluoro-benzenesulfonyl)-pyrrolidine-2S-carboxylic acid 3-(1-methyl-1H-indol-5-yl)-benzylamide;

1-(4-Fluorobenzenesulfonyl)-pyrrolidine-2S-carboxylic acid 3-(6-morpholin-4-yl-pyridin-3-yl)-benzylamide;

1-(4-Fluorobenzenesulfonyl)-pyrrolidine-2S-carboxylic acid (biphenyl-3-ylmethyl)-amide;

1-(4-Fluorobenzenesulfonyl)-pyrrolidine-2S-carboxylic acid (4'-amino-biphenyl-3-ylmethyl)-amide;

1-(4-Fluorobenzenesulfonyl)-pyrrolidine-2S-carboxylic acid [4'-(4-methylpiperazin-1-yl)-biphenyl-3-ylmethyl]-amide;

1-(4-Fluorobenzenesulfonyl)-pyrrolidine-2S-carboxylic acid 3-(1H-indol-6-yl)-benzylamide;

1-(4-Fluorobenzenesulfonyl)-pyrrolidine-2S-carboxylic acid (4'-morpholin-4-ylmethylbiphenyl-3-ylmethyl)-amide;

1-(4-Fluoro-benzenesulfonyl)-pyrrolidine-2S-carboxylic acid (4'-piperidin-1-yl-biphenyl-3-ylmethyl)-amide;

1-(4-Fluorobenzenesulfonyl)-pyrrolidine-2S-carboxylic acid 3-(6-dimethylaminopyridin-3-yl)-benzylamide;

1-(4-Fluorobenzenesulfonyl)-pyrrolidine-2S-carboxylic acid (2-methylene-4-quinolin-3-yl-pent-3-enyl)-amide;

1-(4-Fluoro-benzenesulfonyl)-pyrrolidine-2S-carboxylic acid 3-quinolin-6-yl-benzylamide;

1-(4-Fluoro-benzenesulfonyl)-pyrrolidine-2S-carboxylic acid 3-quinolin-2-yl-benzylamide;

1-(4-Fluorobenzenesulfonyl)-pyrrolidine-2S-carboxylic acid 3-(1-methyl-1H-indol-6-yl)-benzylamide;

3-(4-Fluorobenzenesulfonyl)-3-aza-1S,5R-bicyclo[3;1;0]hexane-2S-carboxylic acid (4'-trifluoromethylbiphenyl-3-ylmethyl)-amide;

3-(5-Chlorothiophene-2-sulfonyl)-3-aza-1S,5R-bicyclo[3;1;0]hexane-2S-carboxylic acid (4'-trifluoromethylbiphenyl-3-ylmethyl)-amide;

1-(4-Fluorobenzenesulfonyl)-2,5-dihydro-1H-pyrrole-2S-carboxylic acid (4'-trifluoromethylbiphenyl-3-ylmethyl)-amide;

1-(5-Chlorothiophene-2-sulfonyl)-2,5-dihydro-1H-pyrrole-2S-carboxylic acid (4'-trifluoromethylbiphenyl-3-ylmethyl)-amide;

(1S,2S)-1-(4-Fluoro-benzenesulfonyl)-pyrrolidine-2-carboxylic acid [1-(4'-trifluoromethyl-biphenyl-3-yl)-ethyl]-amide;

(1R,2S)-1-(4-Fluoro-benzenesulfonyl)-pyrrolidine-2-carboxylic acid [1-(4'-trifluoromethyl-biphenyl-3-yl)-ethyl]-amide;

(1S,2S)-1-(5-Chloro-thiophene-2-sulfonyl)-pyrrolidine-2-carboxylic acid [1-(4'-trifluoromethylbiphenyl-3-yl)-ethyl]-amide;

(1R,2S)-1-(5-Chloro-thiophene-2-sulfonyl)-pyrrolidine-2-carboxylic acid [1-(4'-trifluoromethylbiphenyl-3-yl)-ethyl]-amide;

(2S)-1-(4-Fluoro-benzenesulfonyl)-pyrrolidine-2-carboxylic acid [1-methyl-1-(4'-trifluoromethyl-biphenyl-3-yl)-ethyl]-amide;

(2S)-1-(5-Chloro-thiophene-2-sulfonyl)-pyrrolidine-2-carboxylic acid [1-methyl-1-(4'-trifluoromethyl-biphenyl-3-yl)-ethyl]-amide;

(2S)-4,4-Difluoro-1-(4-fluoro-benzenesulfonyl)-pyrrolidine-2-carboxylic acid (4'-trifluoromethyl-biphenyl-3-ylmethyl)-amide;

(2S)-1-(5-Chloro-thiophene-2-sulfonyl)-4,4-difluoro-pyrrolidine-2-carboxylic acid (4'-trifluoromethyl-biphenyl-3-ylmethyl)-amide;

(2S,4S)-1-(4-Fluoro-benzenesulfonyl)-4-hydroxy-pyrrolidine-2-carboxylic acid (4'-trifluoromethyl-biphenyl-3-ylmethyl)-amide;

(2S,4R)-1-(4-Fluoro-benzenesulfonyl)-4-hydroxy-pyrrolidine-2-carboxylic acid (4'-trifluoromethyl-biphenyl-3-ylmethyl)-amide;

1-(4-Fluoro-benzenesulfonyl)-pyrrolidine-2S-carboxylic acid [2-(4-trifluoromethyl-phenyl)-pyridin-4-ylmethyl]-amide;

1-(5-Chlorothiophene-2-sulfonyl)-pyrrolidine-2S-carboxylic acid [2-(4-trifluoromethylphenyl)-pyridin-4-ylmethyl]-amide;

4,4-Difluoro-1-(4-fluorobenzenesulfonyl)-pyrrolidine-2S-carboxylic acid [2-(4-trifluoromethylphenyl)-pyridin-4-ylmethyl]-amide;

1-(5-Chlorothiophene-2-sulfonyl)-4,4-difluoropyrrolidine-2S-carboxylic acid [2-(4-trifluoromethylphenyl)-pyridin-4-ylmethyl]-amide;

1-(4-Fluorobenzenesulfonyl)-2,5-dihydro-1H-pyrrole-2S-carboxylic acid [2-(4-trifluoromethylphenyl)-pyridin-4-ylmethyl]-amide;

1-(5-Chlorothiophene-2-sulfonyl)-2,5-dihydro-1H-pyrrole-2S-carboxylic acid [2-(4-trifluoromethylphenyl)-pyridin-4-ylmethyl]-amide;

1-(4-Fluoro-benzenesulfonyl)-pyrrolidine-2S-carboxylic acid [2-(4-trifluoromethoxy-phenyl)-pyridin-4-ylmethyl]-amide;

1-(5-Chloro-thiophene-2-sulfonyl)-pyrrolidine-2S-carboxylic acid [2-(4-trifluoromethoxy-phenyl)-pyridin-4-ylmethyl]-amide;

4,4-Difluoro-1-(4-fluoro-benzenesulfonyl)-pyrrolidine-2S-carboxylic acid [2-(4-trifluoromethoxy-phenyl)-pyridin-4-ylmethyl]-amide;

1-(5-Chloro-thiophene-2-sulfonyl)-4,4-difluoro-pyrrolidine-2S-carboxylic acid [2-(4-trifluoromethoxy-phenyl)-pyridin-4-ylmethyl]-amide;

1-(4-Fluoro-benzenesulfonyl)-2,5-dihydro-1H-pyrrole-2S-carboxylic acid [2-(4-trifluoromethoxy-phenyl)-pyridin-4-ylmethyl]-amide;

1-(5-Chloro-thiophene-2-sulfonyl)-2,5-dihydro-1H-pyrrole-2S-carboxylic acid [2-(4-trifluoromethoxy-phenyl)-pyridin-4-ylmethyl]-amide;

1-(4-Fluoro-benzenesulfonyl)-pyrrolidine-2S-carboxylic acid [4-(4-trifluoromethyl-phenyl)-pyridin-2-ylmethyl]-amide;

1-(5-Chloro-thiophene-2-sulfonyl)-pyrrolidine-2S-carboxylic acid [4-(4-trifluoromethyl-phenyl)-pyridin-2-ylmethyl]-amide;

1-(4-Fluoro-benzenesulfonyl)-pyrrolidine-2S-carboxylic acid [4-(4-trifluoromethoxy-phenyl)-pyridin-2-ylmethyl]-amide;

1-(5-Chloro-thiophene-2-sulfonyl)-pyrrolidine-2S-carboxylic acid [4-(4-trifluoromethoxy-phenyl)-pyridin-2-ylmethyl]-amide;

4,4-Difluoro-1-(4-fluoro-benzenesulfonyl)-pyrrolidine-2S-carboxylic acid [4-(4-trifluoromethyl-phenyl)-pyridin-2-ylmethyl]-amide;

1-(5-Chloro-thiophene-2-sulfonyl)-4,4-difluoro-pyrrolidine-2S-carboxylic acid [4-(4-trifluoromethyl-phenyl)-pyridin-2-ylmethyl]-amide;

4,4-Difluoro-1-(4-fluoro-benzenesulfonyl)-pyrrolidine-2S-carboxylic acid [4-(4-trifluoromethoxy-phenyl)-pyridin-2-ylmethyl]-amide;

1-(5-Chloro-thiophene-2-sulfonyl)-4,4-difluoro-pyrrolidine-2S-carboxylic acid [4-(4-trifluoromethoxy-phenyl)-pyridin-2-ylmethyl]-amide;

1-(4-Fluoro-benzenesulfonyl)-2,5-dihydro-1H-pyrrole-2S-carboxylic acid [4-(4-trifluoromethyl-phenyl)-pyridin-2-ylmethyl]-amide;

1-(5-Chloro-thiophene-2-sulfonyl)-2,5-dihydro-1H-pyrrole-2S-carboxylic acid [4-(4-trifluoromethyl-phenyl)-pyridin-2-ylmethyl]-amide;

1-(4-Fluoro-benzenesulfonyl)-2,5-dihydro-1H-pyrrole-2S-carboxylic acid [4-(4-trifluoromethoxy-phenyl)-pyridin-2-ylmethyl]-amide;

1-(5-Chloro-thiophene-2-sulfonyl)-2,5-dihydro-1H-pyrrole-2S-carboxylic acid [4-(4-trifluoromethoxy-phenyl)-pyridin-2-ylmethyl]-amide;

1-(4-Bromobenzenesulfonyl)-pyrrolidine-2S-carboxylic acid [6-(4-trifluoromethylphenyl)-pyrimidin-4-ylmethyl]-amide;

1-(3,4-Difluorobenzenesulfonyl)-pyrrolidine-2S-carboxylic acid [6-(4-trifluoromethylphenyl)-pyrimidin-4-ylmethyl]-amide;

1-(4-Trifluoromethoxybenzenesulfonyl)-pyrrolidine-2S-carboxylic acid [6-(4-trifluoromethylphenyl)-pyrimidin-4-ylmethyl]-amide;

1-(4-Methoxybenzenesulfonyl)-pyrrolidine-2S-carboxylic acid [6-(4-trifluoromethylphenyl)-pyrimidin-4-ylmethyl]-amide;

1-(1,2-Dimethyl-1H-imidazole-4-sulfonyl)-pyrrolidine-2S-carboxylic acid [6-(4-trifluoromethylphenyl)-pyrimidin-4-ylmethyl]-amide;

1-(4-Chlorobenzenesulfonyl)-pyrrolidine-2S-carboxylic acid [6-(4-trifluoromethyl-phenyl)-pyrimidin-4-ylmethyl]-amide;

1-(2-Fluorobenzenesulfonyl)-pyrrolidine-2S-carboxylic acid [6-(4-trifluoromethylphenyl)-pyrimidin-4-ylmethyl]-amide;

1-(3-Fluorobenzenesulfonyl)-pyrrolidine-2S-carboxylic acid [6-(4-trifluoromethylphenyl)-pyrimidin-4-ylmethyl]-amide;

1-(Toluene-2-sulfonyl)-pyrrolidine-2S-carboxylic acid [6-(4-trifluoromethylphenyl)-pyrimidin-4-ylmethyl]-amide;

1-(Toluene-3-sulfonyl)-pyrrolidine-2S-carboxylic acid [6-(4-trifluoromethylphenyl)-pyrimidin-4-ylmethyl]-amide;
1-(3-Trifluoromethylbenzenesulfonyl)-pyrrolidine-2S-carboxylic acid [6-(4-trifluoromethylphenyl)-pyrimidin-4-ylmethyl]-amide;
1-(4-Trifluoromethylbenzenesulfonyl)-pyrrolidine-2S-carboxylic acid [6-(4-trifluoromethylphenyl)-pyrimidin-4-ylmethyl]-amide;
1-(4-Cyanobenzenesulfonyl)-pyrrolidine-2S-carboxylic acid [6-(4-trifluoromethylphenyl)-pyrimidin-4-ylmethyl]-amide;
1-Benzenesulfonylpyrrolidine-2S-carboxylic acid [6-(4-trifluoromethylphenyl)-pyrimidin-4-ylmethyl]-amide;
1-(Toluene-4-sulfonyl)-pyrrolidine-2S-carboxylic acid [6-(4-trifluoromethylphenyl)-pyrimidin-4-ylmethyl]-amide;
1-(4-Acetylbenzenesulfonyl)-pyrrolidine-2S-carboxylic acid [6-(4-trifluoromethylphenyl)-pyrimidin-4-ylmethyl]-amide;
1-(4-Nitrobenzenesulfonyl)-pyrrolidine-2S-carboxylic acid [6-(4-trifluoromethylphenyl)-pyrimidin-4-ylmethyl]-amide;
1-(1-Methyl-1H-imidazole-4-sulfonyl)-pyrrolidine-2S-carboxylic acid [6-(4-trifluoromethylphenyl)-pyrimidin-4-ylmethyl]-amide;
1-(4,5-Dichlorothiophene-2-sulfonyl)-pyrrolidine-2S-carboxylic acid [6-(4-trifluoromethylphenyl)-pyrimidin-4-ylmethyl]-amide;
1-(5-Chlorothiophene-2-sulfonyl)pyrrolidine-2S-carboxylic acid [6-(4-trifluoromethylphenyl)-pyrimidin-4-ylmethyl]-amide;
1-(Furan-2-sulfonyl)-pyrrolidine-2S-carboxylic acid [6-(4-trifluoromethylphenyl)-pyrimidin-4-ylmethyl]-amide;
1-(2-Trifluoromethylbenzenesulfonyl)-pyrrolidine-2S-carboxylic acid [6-(4-trifluoromethylphenyl)-pyrimidin-4-ylmethyl]-amide;
1-(3,5-Difluorobenzenesulfonyl)-pyrrolidine-2S-carboxylic acid [6-(4-trifluoromethylphenyl)-pyrimidin-4-ylmethyl]-amide;
1-(Thiophene-2-sulfonyl)-pyrrolidine-2S-carboxylic acid [6-(4-trifluoromethylphenyl)-pyrimidin-4-ylmethyl]-amide;
1-(4-Fluorobenzenesulfonyl)-pyrrolidine-2S-carboxylic acid (4'-chlorobiphenyl-3-ylmethyl)-amide;
1-(Thiophene-3-sulfonyl)-pyrrolidine-2S-carboxylic acid [6-(4-trifluoromethyl-phenyl)-pyrimidin-4-ylmethyl]-amide;
1-(2,5-Dichlorothiophene-3-sulfonyl)-pyrrolidine-2S-carboxylic acid [6-(4-trifluoromethylphenyl)-pyrimidin-4-ylmethyl]-amide;
1-(6-Chloropyridine-3-sulfonyl)-pyrrolidine-2S-carboxylic acid [6-(4-trifluoromethylphenyl)-pyrimidin-4-ylmethyl]-amide;
4-(2S-{[6-(4-Trifluoromethylphenyl)-pyrimidin-4-ylmethyl]-carbamoyl}-pyrrolidine-1-sulfonyl)-benzoic acid;
1-(Furan-3-sulfonyl)-pyrrolidine-2S-carboxylic acid [6-(4-trifluoromethylphenyl)-pyrimidin-4-ylmethyl]-amide;
1-(4-Fluorobenzenesulfonyl)-pyrrolidine-2S-carboxylic acid [6-(4-trifluoromethoxyphenyl)-pyrimidin-4-ylmethyl]-amide;
1-(4-Fluoro-benzenesulfonyl)-pyrrolidine-2S-carboxylic acid [6-(6-trifluoromethyl-pyridin-3-yl)-pyrimidin-4-ylmethyl]-amide;
(2S)-4,4-Difluoro-1-(4-fluoro-benzenesulfonyl)-pyrrolidine-2-carboxylic acid [6-(4-trifluoromethyl-phenyl)-pyrimidin-4-ylmethyl]-amide;
(2S)-1-(5-Chloro-thiophene-2-sulfonyl)-4,4-difluoro-pyrrolidine-2-carboxylic acid [6-(4-trifluoromethyl-phenyl)-pyrimidin-4-ylmethyl]-amide;
(1S*,2S)-1-(4-Fluoro-benzenesulfonyl)-pyrrolidine-2-carboxylic acid {1-[6-(4-trifluoromethyl-phenyl)-pyrimidin-4-yl]-ethyl}-amide;
(1R*,2S)-1-(4-Fluoro-benzenesulfonyl)-pyrrolidine-2-carboxylic acid {1-[6-(4-trifluoromethyl-phenyl)-pyrimidin-4-yl]-ethyl}-amide;
1-(4-Fluoro-benzenesulfonyl)-pyrrolidine-2S-carboxylic acid [2-methyl-6-(4-trifluoromethyl-phenyl)-pyrimidin-4-ylmethyl]-amide;
1-(4-Fluoro-benzenesulfonyl)-pyrrolidine-2S-carboxylic acid [2-trifluoromethyl-6-(4-trifluoromethyl-phenyl)-pyrimidin-4-ylmethyl]-amide;
(2S)-1-(4-Fluoro-benzenesulfonyl)-pyrrolidine-2-carboxylic acid [4-(4-trifluoromethyl-phenyl)-pyrimidin-2-ylmethyl]-amide;
(2S)-1-(4-Fluoro-benzenesulfonyl)-pyrrolidine-2-carboxylic acid [4-(4-trifluoromethyl-phenyl)-pyrimidin-2-ylmethyl]-amide;
(2S)-1-(4-Fluoro-benzenesulfonyl)-pyrrolidine-2-carboxylic acid [2-(4-trifluoromethyl-phenyl)-pyrimidin-4-ylmethyl]-amide;
(2S)-1-(5-Chloro-thiophene-2-sulfonyl)-pyrrolidine-2-carboxylic acid [4-(4-trifluoromethyl-phenyl)-pyrimidin-2-ylmethyl]-amide;
1-(4-Fluoro-benzenesulfonyl)-pyrrolidine-2S-carboxylic acid [2-[4-(2-fluoro-phenyl)-piperazin-1-yl]-6-(4-trifluoromethoxy-phenyl)-pyrimidin-4-ylmethyl]-amide;
1-(4-Fluoro-benzenesulfonyl)-pyrrolidine-2S-carboxylic acid {6-(4-fluoro-phenyl)-2-[4-(2-fluoro-phenyl)-piperazin-1-yl]-pyrimidin-4-ylmethyl}-amide;
1-(4-Fluoro-benzenesulfonyl)-pyrrolidine-2S-carboxylic acid {6-(2,6-dimethoxy-phenyl)-2-[4-(2-fluoro-phenyl)-piperazin-1-yl]-pyrimidin-4-ylmethyl}-amide;
1-(4-Fluoro-benzenesulfonyl)-pyrrolidine-2-carboxylic acid {6-(4-cyano-phenyl)-2-[4-(2-fluoro-phenyl)-piperazin-1-yl]-pyrimidin-4-ylmethyl}-amide;
1-(4-Fluoro-benzenesulfonyl)-pyrrolidine-2S-carboxylic acid {6-(5-fluoro-2-methoxy-phenyl)-2-[4-(2-fluoro-phenyl)-piperazin-1-yl]-pyrimidin-4-ylmethyl}-amide;
1-(4-Fluoro-benzenesulfonyl)-pyrrolidine-2-carboxylic acid {6-(5-fluoro-2-methoxy-phenyl)-2-[4-(2-fluoro-phenyl)-piperazin-1-yl]-pyrimidin-4-ylmethyl}-amide;
1-(4-Fluoro-benzenesulfonyl)-pyrrolidine-2S-carboxylic acid {6-(2,5-dimethyl-phenyl)-2-[4-(2-fluoro-phenyl)-piperazin-1-yl]-pyrimidin-4-ylmethyl}-amide;
1-(4-Fluoro-benzenesulfonyl)-pyrrolidine-2S-carboxylic acid {6-(2,4-difluoro-phenyl)-2-[4-(2-fluoro-phenyl)-piperazin-1-yl]-pyrimidin-4-ylmethyl}-amide;
1-(4-Fluoro-benzenesulfonyl)-pyrrolidine-2S-carboxylic acid [2-[4-(2-fluoro-phenyl)-piperazin-1-yl]-6-(3-trifluoromethoxy-phenyl)-pyrimidin-4-ylmethyl]-amide;
1-(4-Fluoro-benzenesulfonyl)-pyrrolidine-2S-carboxylic acid {6-(3-cyano-phenyl)-2-[4-(2-fluoro-phenyl)-piperazin-1-yl]-pyrimidin-4-ylmethyl}-amide;
1-(4-Fluoro-benzenesulfonyl)-pyrrolidine-2S-carboxylic acid {6-(3,5-dimethyl-phenyl)-2-[4-(2-fluoro-phenyl)-piperazin-1-yl]-pyrimidin-4-ylmethyl}-amide;
1-(4-Fluoro-benzenesulfonyl)-pyrrolidine-2S-carboxylic acid {6-(3-dimethylamino-phenyl)-2-[4-(2-fluoro-phenyl)-piperazin-1-yl]-pyrimidin-4-ylmethyl}-amide;

1-(4-Fluoro-benzenesulfonyl)-pyrrolidine-2S-carboxylic acid {6-benzo[1,3]dioxol-5-yl-2-[4-(2-fluoro-phenyl)-piperazin-1-yl]-pyrimidin-4-ylmethyl}-amide;
1-(4-Fluoro-benzenesulfonyl)-pyrrolidine-2S-carboxylic acid {6-(3-chloro-phenyl)-2-[4-(2-fluoro-phenyl)-piperazin-1-yl]-pyrimidin-4-ylmethyl}-amide;
1-(4-Fluoro-benzenesulfonyl)-pyrrolidine-2S-carboxylic acid {6-(2,6-dimethyl-phenyl)-2-[4-(2-fluoro-phenyl)-piperazin-1-yl]-pyrimidin-4-ylmethyl}-amide;
1-(4-Fluoro-benzenesulfonyl)-pyrrolidine-2-carboxylic acid {6-(4-chloro-phenyl)-2-[4-(2-fluoro-phenyl)-piperazin-1-yl]-pyrimidin-4-ylmethyl}-amide;
1-(4-Fluoro-benzenesulfonyl)-pyrrolidine-2-carboxylic acid {6-(2-chloro-phenyl)-2-[4-(2-fluoro-phenyl)-piperazin-1-yl]-pyrimidin-4-ylmethyl}-amide;
1-(4-Fluoro-benzenesulfonyl)-pyrrolidine-2S-carboxylic acid [2-[4-(2-fluoro-phenyl)-piperazin-1-yl]-6-(3-trifluoromethyl-phenyl)-pyrimidin-4-ylmethyl]-amide;
1-(4-Fluoro-benzenesulfonyl)-pyrrolidine-2-carboxylic acid {6-(3-chloro-4-fluoro-phenyl)-2-[4-(2-fluoro-phenyl)-piperazin-1-yl]-pyrimidin-4-ylmethyl}-amide;
1-(4-Fluoro-benzenesulfonyl)-pyrrolidine-2S-carboxylic acid {6-(2-fluoro-phenyl)-2-[4-(2-fluoro-phenyl)-piperazin-1-yl]-pyrimidin-4-ylmethyl}-amide;
1-(4-Fluoro-benzenesulfonyl)-pyrrolidine-2S-carboxylic acid {6-(3-fluoro-phenyl)-2-[4-(2-fluoro-phenyl)-piperazin-1-yl]-pyrimidin-4-ylmethyl}-amide;
1-(4-Fluoro-benzenesulfonyl)-pyrrolidine-2S-carboxylic acid {2-[4-(2-fluoro-phenyl)-piperazin-1-yl]-6-o-tolyl-pyrimidin-4-ylmethyl}-amide;
1-(4-Fluoro-benzenesulfonyl)-pyrrolidine-2S-carboxylic acid {6-(3,4-dichloro-phenyl)-2-[4-(2-fluoro-phenyl)-piperazin-1-yl]-pyrimidin-4-ylmethyl}-amide;
1-(4-Fluoro-benzenesulfonyl)-pyrrolidine-2S-carboxylic acid {6-(3,5-difluoro-phenyl)-2-[4-(2-fluoro-phenyl)-piperazin-1-yl]-pyrimidin-4-ylmethyl}-amide;
1-(4-Fluoro-benzenesulfonyl)-pyrrolidine-2S-carboxylic acid {6-(2,4-dichloro-phenyl)-2-[4-(2-fluoro-phenyl)-piperazin-1-yl]-pyrimidin-4-ylmethyl}-amide;
1-(4-Fluoro-benzenesulfonyl)-pyrrolidine-2S-carboxylic acid {2-[4-(2-fluoro-phenyl)-piperazin-1-yl]-6-phenyl-pyrimidin-4-ylmethyl}-amide;
1-(2-Chloro-4-fluoro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;
1-(3-Methoxy-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;
1-(3-Chloro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;
1-(4-Methoxy-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;
1-(5-Fluoro-2-methyl-benzenesulfonyl)-pyrrolidine-2-carboxylic acid [2-[4-(2-fluoro-phenyl)-piperazin-1-yl]-6-(4-trifluoromethyl-phenyl)-pyrimidin-4-ylmethyl]-amide;
1-(5-Chloro-2-fluoro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;
1-(3,4-Difluoro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;
1-(3-Chloro-4-fluoro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;
1-(4-Isopropyl-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;
1-(2,3,4-Trifluoro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;
1-(3-Chloro-2-methyl-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;
1-(5-Chloro-thiophene-2-sulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;
1-(Thiophene-2-sulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;
1-(4-Propyl-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;
1-(2,5-Dimethyl-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;
1-(2,4-Difluoro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;
1-(2-Chloro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;
1-(4-Chloro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;
1-(3-Fluoro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;
1-(Toluene-3-sulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;
1-Benzenesulfonyl-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;
1-(3-Chloro-2-fluoro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;
1-(4-Acetyl-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;
1-(2,4,6-Trimethyl-benzenesulfonyl)-pyrrolidine-2-carboxylic acid [2-[4-(2-fluoro-phenyl)-piperazin-1-yl]-6-(4-trifluoromethyl-phenyl)-pyrimidin-4-ylmethyl]-amide;
1-(2-Fluoro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;
1-(2-Chloro-6-methyl-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;

1-(4-Chloro-2-fluoro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;

1-(Toluene-2-sulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;

1-(3-Chloro-4-methyl-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;

1-(3,5-Difluoro-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;

1-(4-tert-Butyl-benzenesulfonyl)-pyrrolidine-2S-carboxylic acid [2-[4-(2-fluoro-phenyl)-piperazin-1-yl]-6-(4-trifluoromethyl-phenyl)-pyrimidin-4-ylmethyl]-amide;

1-(4-Fluoro-benzenesulfonyl)-pyrrolidine-2S-carboxylic acid [6-(4-trifluoromethyl-phenyl)-pyridin-2-ylmethyl]-amide;

1-(5-Chloro-thiophene-2-sulfonyl)-pyrrolidine-2S-carboxylic acid [6-(4-trifluoromethyl-phenyl)-pyridin-2-ylmethyl]-amide;

1-(4-Fluoro-benzenesulfonyl)-pyrrolidine-2S-carboxylic acid [2,6-bis-(4-trifluoromethyl-phenyl)-pyrimidin-4-ylmethyl]-amide;

1-(4-Fluoro-benzenesulfonyl)-pyrrolidine-S2-carboxylic acid [2-pyrrolidin-1-yl-6-(4-trifluoromethyl-phenyl)-pyridin-4-ylmethyl]-amide;

1-(4-Fluoro-benzenesulfonyl)-pyrrolidine-S2-carboxylic acid [6'-(4-trifluoromethyl-phenyl)-3,4,5,6-tetrahydro-2H-[1,2']bipyridinyl-4'-ylmethyl]-amide;

1-(5-Chloro-thiophene-2-sulfonyl)-pyrrolidine-S2-carboxylic acid [6'-(4-trifluoromethyl-phenyl)-3,4,5,6-tetrahydro-2H-[1,2']bipyridinyl-4'-ylmethyl]-amide;

(2S)—N-({2-(Benzylamino)-6-[4-(trifluoromethyl)phenyl]pyridin-4-yl}methyl)-1-[(5-chlorothiophen-2-yl)sulfonyl]-2,5-dihydro-1H-pyrrole-2-carboxamide;

(2S)—N-({2-(Benzylamino)-6-[4-(trifluoromethyl)phenyl]pyridin-4-yl}methyl)-1-[(4-fluorophenyl)sulfonyl]-2,5-dihydro-1H-pyrrole-2-carboxamide;

N-({2-(Benzylamino)-6-[4-(trifluoromethyl)phenyl]pyridin-4-yl}methyl)-1-[(4-fluorophenyl)sulfonyl]-L-prolinamide;

N-({2-(Benzylamino)-6-[4-(trifluoromethyl)phenyl]pyridin-4-yl}methyl)-1-[(5-chlorothiophen-2-yl)sulfonyl]-L-prolinamide;

1-[(5-Chlorothiophen-2-yl)sulfonyl]-N-({2-[4-(2-fluorophenyl)piperazin-1-yl]-6-[4-(trifluoromethyl)phenyl]pyridin-4-yl}methyl)-L-prolinamide;

N-({2-[4-(2-Fluorophenyl)piperazin-1-yl]-6-[4-(trifluoromethyl)phenyl]pyridin-4-yl}methyl)-1-[(4-fluorophenyl)sulfonyl]-L-prolinamide;

(2S)—N-({2-[4-(2-Fluorophenyl)piperazin-1-yl]-6-[4-(trifluoromethyl)phenyl]pyridin-4-yl}methyl)-1-[(4-fluorophenyl)sulfonyl]-2,5-dihydro-1H-pyrrole-2-carboxamide;

1-[(5-Chlorothiophen-2-yl)sulfonyl]-N-({2-[4-(pyridin-4-ylmethyl)piperazin-1-yl]-6-[4-(trifluoromethyl)phenyl]pyridin-4-yl}methyl)-L-prolinamide;

1-[(4-Fluorophenyl)sulfonyl]-N-({2-[4-(pyridin-3-ylmethyl)piperazin-1-yl]-6-[4-(trifluoromethyl)phenyl]pyridin-4-yl}methyl)-L-prolinamide;

(2S)-1-[(4-Fluorophenyl)sulfonyl]-N-({2-[4-(pyridin-4-ylmethyl)piperazin-1-yl]-6-[4-(trifluoromethyl)phenyl]pyridin-4-yl}methyl)-2,5-dihydro-1H-pyrrole-2-carboxamide;

(2S)-1-[(5-Chlorothiophen-2-yl)sulfonyl]-N-({2-[(pyridin-2-ylmethyl)amino]-6-[4-(trifluoromethyl)phenyl]pyridin-4-yl}methyl)-2,5-dihydro-1H-pyrrole-2-carboxamide;

N-({2-(Dimethylamino)-6-[4-(trifluoromethyl)phenyl]pyridin-4-yl}methyl)-1-[(4-fluorophenyl)sulfonyl]-L-prolinamide;

1-[(5-Chlorothiophen-2-yl)sulfonyl]-N-({2-(dimethylamino)-6-[4-(trifluoromethyl)phenyl]pyridin-4-yl}methyl)-L-prolinamide;

1-[(5-Chlorothiophen-2-yl)sulfonyl]-N-({2-(2-methylpyrrolidin-1-yl)-6-[4-(trifluoromethyl)phenyl]pyridin-4-yl}methyl)-L-prolinamide;

(2S)-1-[(5-Chlorothiophen-2-yl)sulfonyl]-N-({2-(dimethylamino)-6-[4-(trifluoromethyl)phenyl]pyridin-4-yl}methyl)-2,5-dihydro-1H-pyrrole-2-carboxamide;

1-[(5-Chlorothiophen-2-yl)sulfonyl]-N-({2-(methylamino)-6-[4-(trifluoromethyl)phenyl]pyridin-4-yl}methyl)-L-prolinamide;

1-[(4-Fluorophenyl)sulfonyl]-N-({2-(2-methylpyrrolidin-1-yl)-6-[4-(trifluoromethyl)phenyl]pyridin-4-yl}methyl)-L-prolinamide;

1-[(4-Fluorophenyl)sulfonyl]-N-({2-(methylamino)-6-[4-(trifluoromethyl)phenyl]pyridin-4-yl}methyl)-L-prolinamide;

(2S)—N-({2-(Dimethylamino)-6-[4-(trifluoromethyl)phenyl]pyridin-4-yl}methyl)-1-[(4-fluorophenyl)sulfonyl]-2,5-dihydro-1H-pyrrole-2-carboxamide;

1-[(5-Chlorothiophen-2-yl)sulfonyl]-N-({2-[4-(pyridin-2-ylmethyl)piperazin-1-yl]-6-[4-(trifluoromethyl)phenyl]pyridin-4-yl}methyl)-L-prolinamide;

(2S)-1-[(5-Chlorothiophen-2-yl)sulfonyl]-N-({2-[4-(pyridin-4-ylmethyl)piperazin-1-yl]-6-[4-(trifluoromethyl)phenyl]pyridin-4-yl}methyl)-2,5-dihydro-1H-pyrrole-2-carboxamide;

1-[(5-Chlorothiophen-2-yl)sulfonyl]-N-({2-[4-(pyridin-3-ylmethyl)piperazin-1-yl]-6-[4-(trifluoromethyl)phenyl]pyridin-4-yl}methyl)-L-prolinamide;

1-[(4-Fluorophenyl)sulfonyl]-N-({2-[4-(pyridin-4-ylmethyl)piperazin-1-yl]-6-[4-(trifluoromethyl)phenyl]pyridin-4-yl}methyl)-L-prolinamide;

4,4-Difluoro-1-[(4-fluorophenyl)sulfonyl]-N-({2-[(pyridin-4-ylmethyl)amino]-6-[4-(trifluoromethyl)phenyl]pyridin-4-yl}methyl)-L-prolinamide;

(2S)-1-[(4-Fluorophenyl)sulfonyl]-N-({2-[(pyridin-4-ylmethyl)amino]-6-[4-(trifluoromethyl)phenyl]pyridin-4-yl}methyl)-2,5-dihydro-1H-pyrrole-2-carboxamide;

(2S)-1-[(5-Chlorothiophen-2-yl)sulfonyl]-N-({2-[(pyridin-3-ylmethyl)amino]-6-[4-(trifluoromethyl)phenyl]pyridin-4-yl}methyl)-2,5-dihydro-1H-pyrrole-2-carboxamide;

(2S)-1-[(4-Fluorophenyl)sulfonyl]-N-({2-[(pyridin-3-ylmethyl)amino]-6-[4-(trifluoromethyl)phenyl]pyridin-4-yl}methyl)-2,5-dihydro-1H-pyrrole-2-carboxamide;

1-[(5-Chlorothiophen-2-yl)sulfonyl]-N-({2-[(pyridin-2-ylmethyl)amino]-6-[4-(trifluoromethyl)phenyl]pyridin-4-yl}methyl)-L-prolinamide;

1-[(4-Fluorophenyl)sulfonyl]-N-({2-[4-(pyridin-2-ylmethyl)piperazin-1-yl]-6-[4-(trifluoromethyl)phenyl]pyridin-4-yl}methyl)-L-prolinamide;

1-[(4-Fluorophenyl)sulfonyl]-N-({2-[(1-pyridin-3-yl-ethyl)amino]-6-[4-(trifluoromethyl)phenyl]pyridin-4-yl}methyl)-L-prolinamide;

(2S)-1-[(4-Fluorophenyl)sulfonyl]-N-({2-[(1-pyridin-3-ylethyl)amino]-6-[4-(trifluoromethyl)phenyl]pyridin-4-yl}methyl)-2,5-dihydro-1H-pyrrole-2-carboxamide;

(2S)-1-[(5-Chlorothiophen-2-yl)sulfonyl]-N-({2-[(1-pyridin-3-ylethyl)amino]-6-[4-(trifluoromethyl)phenyl]pyridin-4-yl}methyl)-2,5-dihydro-1H-pyrrole-2-carboxamide;

N-({2-(Benzylamino)-6-[4-(trifluoromethyl)phenyl]pyridin-4-yl}methyl)-1-[(5-chlorothiophen-2-yl)sulfonyl]-4,4-difluoro-L-prolinamide;

(2S)-1-[(4-Fluorophenyl)sulfonyl]-N-({2-[4-(pyridin-2-ylmethyl)piperazin-1-yl]-6-[4-(trifluoromethyl)phenyl]pyridin-4-yl}methyl)-2,5-dihydro-1H-pyrrole-2-carboxamide;

(2S)-1-[(5-Chlorothiophen-2-yl)sulfonyl]-N-({2-[4-(pyridin-2-ylmethyl)piperazin-1-yl]-6-[4-(trifluoromethyl)phenyl]pyridin-4-yl}methyl)-2,5-dihydro-1H-pyrrole-2-carboxamide;

(2S)-1-[(5-Chlorothiophen-2-yl)sulfonyl]-N-({2-[4-(pyridin-3-ylmethyl)piperazin-1-yl]-6-[4-(trifluoromethyl)phenyl]pyridin-4-yl}methyl)-2,5-dihydro-1H-pyrrole-2-carboxamide;

4,4-Difluoro-1-[(4-fluorophenyl)sulfonyl]-N-({2-[4-(pyridin-4-ylmethyl)piperazin-1-yl]-6-[4-(trifluoromethyl)phenyl]pyridin-4-yl}methyl)-L-prolinamide;

4,4-Difluoro-N-({2-[4-(2-fluorophenyl)piperazin-1-yl]-6-[4-(trifluoromethyl)phenyl]pyridin-4-yl}methyl)-1-[(4-fluorophenyl)sulfonyl]-L-prolinamide;

1-[(5-Chlorothiophen-2-yl)sulfonyl]-4,4-difluoro-N-({2-[4-(2-fluorophenyl)piperazin-1-yl]-6-[4-(trifluoromethyl)phenyl]pyridin-4-yl}methyl)-L-prolinamide;

(2S)-1-[(5-Chlorothiophen-2-yl)sulfonyl]-N-({2-[4-(2-fluorophenyl)piperazin-1-yl]-6-[4-(trifluoromethyl)phenyl]pyridin-4-yl}methyl)-2,5-dihydro-1H-pyrrole-2-carboxamide;

4,4-Difluoro-1-[(4-fluorophenyl)sulfonyl]-N-({2-(methylamino)-6-[4-(trifluoromethyl)phenyl]pyridin-4-yl}methyl)-L-prolinamide;

(2S)—N-({2-(4-Benzylpiperazin-1-yl)-6-[4-(trifluoromethyl)phenyl]pyridin-4-yl}methyl)-1-[(4-fluorophenyl)sulfonyl]-2,5-dihydro-1H-pyrrole-2-carboxamide;

4,4-Difluoro-1-[(4-fluorophenyl)sulfonyl]-N-({2-[(pyridin-3-ylmethyl)amino]-6-[4-(trifluoromethyl)phenyl]pyridin-4-yl}methyl)-L-prolinamide;

4,4-Difluoro-1-[(4-fluorophenyl)sulfonyl]-N-({2-[4-(pyridin-3-ylmethyl)piperazin-1-yl]-6-[4-(trifluoromethyl)phenyl]pyridin-4-yl}methyl)-L-prolinamide;

1-[(5-Chlorothiophen-2-yl)sulfonyl]-N-({2-[(pyridin-4-ylmethyl)amino]-6-[4-(trifluoromethyl)phenyl]pyridin-4-yl}methyl)-L-prolinamide;

(2S)-1-[(4-Fluorophenyl)sulfonyl]-N-({2-[4-(pyridin-3-ylmethyl)piperazin-1-yl]-6-[4-(trifluoromethyl)phenyl]pyridin-4-yl}methyl)-2,5-dihydro-1H-pyrrole-2-carboxamide;

1-[(5-Chlorothiophen-2-yl)sulfonyl]-4,4-difluoro-N-({2-[4-(pyridin-3-ylmethyl)piperazin-1-yl]-6-[4-(trifluoromethyl)phenyl]pyridin-4-yl}methyl)-L-prolinamide;

N-({2-(4-Benzylpiperazin-1-yl)-6-[4-(trifluoromethyl)phenyl]pyridin-4-yl}methyl)-1-[(5-chlorothiophen-2-yl)sulfonyl]-L-prolinamide;

(2S)—N-({2-(4-Benzylpiperazin-1-yl)-6-[4-(trifluoromethyl)phenyl]pyridin-4-yl}methyl)-1-[(5-chlorothiophen-2-yl)sulfonyl]-2,5-dihydro-1H-pyrrole-2-carboxamide;

1-[(5-Chlorothiophen-2-yl)sulfonyl]-N-({2-[4-(2-methylpropyl)piperazin-1-yl]-6-[4-(trifluoromethyl)phenyl]pyridin-4-yl}methyl)-L-prolinamide;

1-[(4-Fluorophenyl)sulfonyl]-N-({2-[4-(2-methylpropyl)piperazin-1-yl]-6-[4-(trifluoromethyl)phenyl]pyridin-4-yl}methyl)-L-prolinamide;

1-[(5-Chlorothiophen-2-yl)sulfonyl]-N-({2-[(pyridin-3-ylmethyl)amino]-6-[4-(trifluoromethyl)phenyl]pyridin-4-yl}methyl)-L-prolinamide;

(2S)-1-[(4-Fluorophenyl)sulfonyl]-N-({2-(methylamino)-6-[4-(trifluoromethyl)phenyl]pyridin-4-yl}methyl)-2,5-dihydro-1H-pyrrole-2-carboxamide;

N-({2-(4-Benzylpiperazin-1-yl)-6-[4-(trifluoromethyl)phenyl]pyridin-4-yl}methyl)-1-[(4-fluorophenyl)sulfonyl]-L-prolinamide;

4,4-Difluoro-1-[(4-fluorophenyl)sulfonyl]-N-({2-[(pyridin-2-ylmethyl)amino]-6-[4-(trifluoromethyl)phenyl]pyridin-4-yl}methyl)-L-prolinamide;

1-[(5-Chlorothiophen-2-yl)sulfonyl]-4,4-difluoro-N-({2-[4-(pyridin-2-ylmethyl)piperazin-1-yl]-6-[4-(trifluoromethyl)phenyl]pyridin-4-yl}methyl)-L-prolinamide;

1-[(5-Chlorothiophen-2-yl)sulfonyl]-N-({2-(dimethylamino)-6-[4-(trifluoromethyl)phenyl]pyridin-4-yl}methyl)-4,4-difluoro-L-prolinamide;

N-({2-(4-Benzylpiperazin-1-yl)-6-[4-(trifluoromethyl)phenyl]pyridin-4-yl}methyl)-1-[(5-chlorothiophen-2-yl)sulfonyl]-4,4-difluoro-L-prolinamide;

1-[(5-Chlorothiophen-2-yl)sulfonyl]-4,4-difluoro-N-({2-[(pyridin-4-ylmethyl)amino]-6-[4-(trifluoromethyl)phenyl]pyridin-4-yl}methyl)-L-prolinamide;

(2S)-1-[(5-Chlorothiophen-2-yl)sulfonyl]-N-({2-(methylamino)-6-[4-(trifluoromethyl)phenyl]pyridin-4-yl}methyl)-2,5-dihydro-1H-pyrrole-2-carboxamide;

(2S)-1-[(4-Fluorophenyl)sulfonyl]-N-({2-[(pyridin-2-ylmethyl)amino]-6-[4-(trifluoromethyl)phenyl]pyridin-4-yl}methyl)-2,5-dihydro-1H-pyrrole-2-carboxamide;

1-[(5-Chlorothiophen-2-yl)sulfonyl]-4,4-difluoro-N-({2-[4-(pyridin-4-ylmethyl)piperazin-1-yl]-6-[4-(trifluoromethyl)phenyl]pyridin-4-yl}methyl)-L-prolinamide;

1-[(5-Chlorothiophen-2-yl)sulfonyl]-4,4-difluoro-N-({2-[(pyridin-2-ylmethyl)amino]-6-[4-(trifluoromethyl)phenyl]pyridin-4-yl}methyl)-L-prolinamide;

1-[(5-Chlorothiophen-2-yl)sulfonyl]-4,4-difluoro-N-({2-[4-(2-methylpropyl)piperazin-1-yl]-6-[4-(trifluoromethyl)phenyl]pyridin-4-yl}methyl)-L-prolinamide;

1-[(5-Chlorothiophen-2-yl)sulfonyl]-4,4-difluoro-N-({2-(methylamino)-6-[4-(trifluoromethyl)phenyl]pyridin-4-yl}methyl)-L-prolinamide;

1-[(4-Fluorophenyl)sulfonyl]-N-({2-[(pyridin-4-ylmethyl)amino]-6-[4-(trifluoromethyl)phenyl]pyridin-4-yl}methyl)-L-prolinamide;

4,4-Difluoro-1-[(4-fluorophenyl)sulfonyl]-N-({2-[4-(2-methylpropyl)piperazin-1-yl]-6-[4-(trifluoromethyl)phenyl]pyridin-4-yl}methyl)-L-prolinamide;

4,4-Difluoro-1-[(4-fluorophenyl)sulfonyl]-N-({2-[4-(pyridin-2-ylmethyl)piperazin-1-yl]-6-[4-(trifluoromethyl)phenyl]pyridin-4-yl}methyl)-L-prolinamide;

N-({2-(4-Benzylpiperazin-1-yl)-6-[4-(trifluoromethyl)phenyl]pyridin-4-yl}methyl)-4,4-difluoro-1-[(4-fluorophenyl)sulfonyl]-L-prolinamide;

(2S)-1-[(5-Chlorothiophen-2-yl)sulfonyl]-N-({2-[4-(2-methylpropyl)piperazin-1-yl]-6-[4-(trifluoromethyl)phenyl]pyridin-4-yl}methyl)-2,5-dihydro-1H-pyrrole-2-carboxamide;

(2S)-1-[(4-Fluorophenyl)sulfonyl]-N-({2-[4-(2-methylpropyl)piperazin-1-yl]-6-[4-(trifluoromethyl)phenyl]pyridin-4-yl}methyl)-2,5-dihydro-1H-pyrrole-2-carboxamide;

(2S)-1-[(5-Chlorothiophen-2-yl)sulfonyl]-N-({2-[(pyridin-4-ylmethyl)amino]-6-[4-(trifluoromethyl)phenyl]pyridin-4-yl}methyl)-2,5-dihydro-1H-pyrrole-2-carboxamide;

1-[(4-Fluorophenyl)sulfonyl]-N-({2-[(pyridin-2-ylmethyl)amino]-6-[4-(trifluoromethyl)phenyl]pyridin-4-yl}methyl)-L-prolinamide;

N-({2-(Dimethylamino)-6-[4-(trifluoromethyl)phenyl]pyridin-4-yl}methyl)-4,4-difluoro-1-[(4-fluorophenyl)sulfonyl]-L-prolinamide;

N-({2-(Benzylamino)-6-[4-(trifluoromethyl)phenyl]pyridin-4-yl}methyl)-4,4-difluoro-1-[(4-fluorophenyl)sulfonyl]-L-prolinamide;

1-[(4-Fluorophenyl)sulfonyl]-N-({2-[(pyridin-3-ylmethyl)amino]-6-[4-(trifluoromethyl)phenyl]pyridin-4-yl}methyl)-L-prolinamide;

4,4-Difluoro-1-[(4-fluorophenyl)sulfonyl]-N-({2-(2-methylpyrrolidin-1-yl)-6-[4-(trifluoromethyl)phenyl]pyridin-4-yl}methyl)-L-prolinamide;

1-[(5-Chlorothiophen-2-yl)sulfonyl]-4,4-difluoro-N-({2-(2-methylpyrrolidin-1-yl)-6-[4-(trifluoromethyl)phenyl]pyridin-4-yl}methyl)-L-prolinamide;

4,4-Difluoro-1-[(4-fluorophenyl)sulfonyl]-N-({2-[(1-pyridin-3-ylethyl)amino]-6-[4-(trifluoromethyl)phenyl]pyridin-4-yl}methyl)-L-prolinamide;

1-[(5-Chlorothiophen-2-yl)sulfonyl]-4,4-difluoro-N-({2-[(1-pyridin-3-ylethyl)amino]-6-[4-(trifluoromethyl)phenyl]pyridin-4-yl}methyl)-L-prolinamide;

1-[(5-Chlorothiophen-2-yl)sulfonyl]-4,4-difluoro-N-({2-[(1-pyridin-4-ylethyl)amino]-6-[4-(trifluoromethyl)phenyl]pyridin-4-yl}methyl)-L-prolinamide;

4,4-Difluoro-1-[(4-fluorophenyl)sulfonyl]-N-({2-[(1-pyridin-4-ylethyl)amino]-6-[4-(trifluoromethyl)phenyl]pyridin-4-yl}methyl)-L-prolinamide;

1-[(4-Fluorophenyl)sulfonyl]-N-({2-[(1-pyridin-4-ylethyl)amino]-6-[4-(trifluoromethyl)phenyl]pyridin-4-yl}methyl)-L-prolinamide;

1-[(5-Chlorothiophen-2-yl)sulfonyl]-N-({2-[(1-pyridin-4-ylethyl)amino]-6-[4-(trifluoromethyl)phenyl]pyridin-4-yl}methyl)-L-prolinamide;

(2S)-1-[(5-Chlorothiophen-2-yl)sulfonyl]-N-({2-[(1-pyridin-4-ylethyl)amino]-6-[4-(trifluoromethyl)phenyl]pyridin-4-yl}methyl)-2,5-dihydro-1H-pyrrole-2-carboxamide;

1-[(5-Chlorothiophen-2-yl)sulfonyl]-N-({2-[(1-pyridin-3-ylethyl)amino]-6-[4-(trifluoromethyl)phenyl]pyridin-4-yl}methyl)-L-prolinamide;

(2S)-1-[(4-Fluorophenyl)sulfonyl]-N-({2-[(1-phenylethyl)amino]-6-[4-(trifluoromethyl)phenyl]pyridin-4-yl}methyl)-2,5-dihydro-1H-pyrrole-2-carboxamide;

(2S)-1-[(5-Chlorothiophen-2-yl)sulfonyl]-N-({2-[(1-phenylethyl)amino]-6-[4-(trifluoromethyl)phenyl]pyridin-4-yl}methyl)-2,5-dihydro-1H-pyrrole-2-carboxamide;

1-[(4-Fluorophenyl)sulfonyl]-N-({2-[(1-pyridin-2-yl-ethyl)amino]-6-[4-(trifluoromethyl)phenyl]pyridin-4-yl}methyl)-L-prolinamide;

1-[(5-Chlorothiophen-2-yl)sulfonyl]-N-({2-[(1-pyridin-2-ylethyl)amino]-6-[4-(trifluoromethyl)phenyl]pyridin-4-yl}methyl)-L-prolinamide;

4,4-Difluoro-1-[(4-fluorophenyl)sulfonyl]-N-({2-[(1-phenylethyl)amino]-6-[4-(trifluoromethyl)phenyl]pyridin-4-yl}methyl)-L-prolinamide;

1-[(5-Chlorothiophen-2-yl)sulfonyl]-4,4-difluoro-N-({2-[(1-phenylethyl)amino]-6-[4-(trifluoromethyl)phenyl]pyridin-4-yl}methyl)-L-prolinamide;

(2S)-1-[(4-Fluorophenyl)sulfonyl]-N-({2-[(1-pyridin-4-ylethyl)amino]-6-[4-(trifluoromethyl)phenyl]pyridin-4-yl}methyl)-2,5-dihydro-1H-pyrrole-2-carboxamide;

1-[(4-Fluorophenyl)sulfonyl]-N-({2-[(1-phenylethyl)amino]-6-[4-(trifluoromethyl)phenyl]pyridin-4-yl}methyl)-L-prolinamide;

1-[(5-Chlorothiophen-2-yl)sulfonyl]-N-({2-[(1-phenylethyl)amino]-6-[4-(trifluoromethyl)phenyl]pyridin-4-yl}methyl)-L-prolinamide;

1-[(5-Chlorothiophen-2-yl)sulfonyl]-4,4-difluoro-N-({2-[(1-pyridin-2-ylethyl)amino]-6-[4-(trifluoromethyl)phenyl]pyridin-4-yl}methyl)-L-prolinamide;

4,4-Difluoro-1-[(4-fluorophenyl)sulfonyl]-N-({2-[(1-pyridin-2-ylethyl)amino]-6-[4-(trifluoromethyl)phenyl]pyridin-4-yl}methyl)-L-prolinamide;

(2S)-1-[(5-Chlorothiophen-2-yl)sulfonyl]-N-({2-(2-methylpyrrolidin-1-yl)-6-[4-(trifluoromethyl)phenyl]pyridin-4-yl}methyl)-2,5-dihydro-1H-pyrrole-2-carboxamide;

and pharmaceutically acceptable salts and prodrugs thereof.

17. A pharmaceutical composition, comprising:
(a) a therapeutically effective amount of at least one chemical entity selected from the group consisting of compounds of Formula (II):

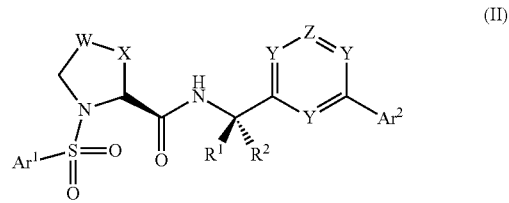

(II)

wherein,
Ar$^1$ is:
  i) phenyl substituted with 0, 1, 2 or 3 substituents R$^a$; or
  ii) a 5- or 6-membered monocyclic aromatic heterocycle ring optionally substituted with one or two substituents R$^a$;
    where each R$^a$ is independently halo, —C$_{1-4}$alkyl, —OC$_{1-4}$alkyl, —CN, —CF$_3$, —OCF$_3$, —NO$_2$, —C(O)C$_{1-4}$alkyl or —CO$_2$H;

Ar$^2$ is:
  i) phenyl substituted with 0, 1, 2 or 3 substituents R$^b$;
    where each R$^b$ is independently halo, —C$_{1-4}$alkyl, —C(O)NR$^c$R$^d$, —OC$_{1-4}$alkyl, —OC$_{0-4}$alkylCF$_3$, —CN, —CF$_3$, —OCF$_2$H, —NO$_2$, —NR$^c$R$^d$, —S(O)$_{0-2}$C$_{1-4}$alkyl, —C(O)C$_{1-4}$alkyl, S(O)(O)NH$_2$, —(CH$_2$)$_{0-2}$-morpholinyl, piperidin-1-yl, piperazinyl, said piperazinyl optionally substituted with a methyl, or two R$^b$ substituents on adjacent carbon atoms taken together form —O(CH$_2$)$_{1-2}$O—;
  ii) pyridyl substituted with 0, 1 or 2 substituents R$^e$;
    where each R$^e$ is independently selected from halo, —C$_{1-4}$alkyl, —OC$_{1-4}$alkyl, —CF$_3$, —NR$^c$R$^d$ or 4-morpholinyl; or
  iii) a bicyclic 9- or 10-membered aromatic heterocycle optionally substituted with 1 substituent R$^f$;
    where R$^f$ is —C$_{1-4}$alkyl;

R$^c$ and R$^d$ are each independently selected from H or —C$_{1-4}$ alkyl;
W is —CR″H— or —CF$_2$—;
X is —CR″H—;

or W and X may each be a CH group linked together by a double bond;

$R^n$ is H or —OH; or two adjacent $R^n$ moieties taken together form —CH$_2$—;

$R^1$ and $R^2$ are each independently H or —C$_{1-4}$alkyl;

each Y is independently CH or N;

Z is CR$^g$;

$R^g$ is
  i) H, —CF$_{1-4}$alkyl, —CF$_3$, —OR$^z$ or —NR$^h$R$^i$;
    where $R^h$ is selected from
      a) H, —C$_{0-4}$alkylCF$_3$, —C$_{1-4}$alkyl-N(CH$_3$)$_2$, 1-hydroxymethyl-2-phenyl-ethyl, —C$_{1-4}$alkyl-3H-indol-3yl, indan-1yl, saturated cycloalkyl or —C$_{1-4}$alkyl-monocyclic heteroaryl ring;
      b) —C$_{1-5}$alkyl optionally substituted with OH;
      c) —C$_{1-4}$alkyl-heterocycloalkyl, said heterocycloalkyl optionally substituted with —C$_{1-4}$alkyl; or
      d) —C$_{0-4}$alkyl-phenyl, said phenyl optionally substituted with one or two R$^j$ moieties;
        where each R$^j$ is independently halo, —OC$_{1-4}$alkyl, —S(O)(O)NH$_2$ or 4-methyl-piperazine-1-carbonyl;
    $R^z$ is —C$_{1-4}$alkyl, —C$_{1-4}$alkylCF$_3$ or —C$_{1-4}$alkyl-heterocycloalkyl;
  ii) 1-pyrrolidinyl optionally substituted with a moiety selected from the group consisting of —NR$^k$R$^i$ and —C$_{1-4}$alkyl, said —C$_{1-4}$alkyl optionally substituted with —OH;
  iii) 1-piperidinyl optionally substituted with —C$_{1-4}$alkyl, —C(O)NH$_2$, —CO$_2$C$_{1-4}$alkyl or —C$_{0-4}$alkyl-phenyl;
  iv) piperazinyl optionally substituted with —C$_{1-5}$alkyl, —OC$_{1-4}$alkyl, —C$_{0-4}$-alkylpyridyl, —C$_{0-4}$alkyl-1-methyl-piperidin-4-yl, —C$_{0-4}$alkylNR$^k$R$^i$ or —C$_{0-4}$alkyl-phenyl, said phenyl optionally substituted with one or two R$^T$ substituents;
    where each R$^T$ substituent is selected from the group consisting of halo, —OCF$_3$, —C$_{1-4}$alkyl, —OC$_{1-4}$alkyl, —CO$_2$C$_{1-4}$alkyl, —C(O)CH$_3$ and —C$_{0-4}$alkylNR$^k$R$^i$, or two R$^T$ substituents on adjacent carbon atoms taken together form —O(CH$_2$)$_{1-2}$O—;
  v) phenyl optionally substituted with CF$_3$, pyridyl or 3,4-dihydro-1H-isoquinolin-2-yl;
  vi) pyridyl;
  vii) 3,4-dihydro-1H-isoquinolin-2-yl;
  viii) [1,4]diazepane-yl optionally substituted with —C$_{1-4}$alkyl; or
  ix) morpholin-yl;

$R^k$ is H, —C$_{1-4}$alkyl or —C(O)$_{1-2}$C$_{1-4}$alkyl;

$R^i$ is H or C$_{1-4}$alkyl;

a pharmaceutically acceptable salt of a compound of Formula (II), or a pharmaceutically acceptable prodrug of a compound of Formula (II); and (b) a pharmaceutically acceptable excipient.

\* \* \* \* \*